US011402384B2

(12) United States Patent
Hellinga et al.

(10) Patent No.: US 11,402,384 B2
(45) Date of Patent: Aug. 2, 2022

(54) THERMOSTABLE GLUCOSE BIOSENSORS AND USES THEREOF

(71) Applicant: Duke University, Durham, NC (US)

(72) Inventors: Homme W. Hellinga, Durham, NC (US); Malin J. Allert, Raleigh, NC (US)

(73) Assignee: Duke University, Durham, NC (US)

( * ) Notice: Subject to any disclaimer, the term of this patent is extended or adjusted under 35 U.S.C. 154(b) by 632 days.

(21) Appl. No.: 15/776,747

(22) PCT Filed: Nov. 19, 2016

(86) PCT No.: PCT/US2016/062962
§ 371 (c)(1),
(2) Date: May 16, 2018

(87) PCT Pub. No.: WO2017/087916
PCT Pub. Date: May 26, 2017

(65) Prior Publication Data

US 2020/0271659 A1 Aug. 27, 2020

Related U.S. Application Data

(60) Provisional application No. 62/257,800, filed on Nov. 20, 2015, provisional application No. 62/257,796, filed on Nov. 20, 2015.

(51) Int. Cl.

| | |
|---|---|
| ***G01N 33/66*** | (2006.01) |
| ***C07K 14/245*** | (2006.01) |
| ***G01N 33/542*** | (2006.01) |

(52) U.S. Cl.
CPC ........... *G01N 33/66* (2013.01); *C07K 14/245* (2013.01); *G01N 33/542* (2013.01); *G01N 2800/042* (2013.01)

(58) Field of Classification Search
None
See application file for complete search history.

(56) References Cited

U.S. PATENT DOCUMENTS

| | | | | |
|---|---|---|---|---|
| 6,428,797 | B2 | 8/2002 | Fishman | |
| 8,608,310 | B2 | 12/2013 | Otis et al. | |
| 2002/0004217 | A1* | 1/2002 | Hellinga | G01N 33/66 435/14 |
| 2004/0118681 | A1 | 6/2004 | Hellinga et al. | |
| 2009/0325221 | A1 | 12/2009 | Long et al. | |
| 2011/0171737 | A1 | 7/2011 | Hellinga et al. | |
| 2015/0111222 | A1 | 4/2015 | Marvin et al. | |
| 2016/0220686 | A1 | 8/2016 | Brudno et al. | |

FOREIGN PATENT DOCUMENTS

| | | | |
|---|---|---|---|
| WO | 2013/052946 | A2 | 4/2013 |
| WO | 2017/087912 | A2 | 5/2017 |
| WO | 2017/087916 | A2 | 5/2017 |

OTHER PUBLICATIONS

Drake, S. K. et al. "Molecular tuning of an EF-hand-like calcium binding loop. Contributions of the coordinating side chain at loop position 3." 1997, The Journal of General Physiology vol. 110, 2. (Year: 1997).*
NCBI BLAST Alignment of Seq ID 48 vs. T. thermophilus GBP, generated Jan. 20, 2021 (Year: 2021).*
UniProt (Jan. 7, 2015) "UniProtKB/TrEMBL Accession No. Q3MED5".
Abouhamad et al. (Jun. 1991) "Peptide Transport and Chemotaxis in *Escherichia coli*and *Salmonella typhimurium*: Characterization of the Dipeptide Permease (Dpp) and the Dipeptide-Binding Protein", Molecular Microbiology, 5(5):1035-1047.
Adewoye et al. (Aug. 8, 2000) "Identification and Characterization of the Gltk Gene Encoding a Membrane-Associated Glucose Transport Protein of Pseudomonas Aeruginosa", Gene, 253(2):323-330.
Adey et al. (Apr. 14, 1995) "Characterization of Phage that Bind Plastic from Phage-Displayed Random Peptide Libraries", Gene, 156(1):27-31.
Adhikari et al. (Oct. 20, 1995) "Biochemical Characterization of a Haemophilus Influenzae Periplasmic Iran Transport Operon", The Journal of Biological Chemistry, 270(42):25142-25149.
Allert et al. (Oct. 8, 2010) "Multifactorial Determinants of Protein Expression in Prokaryotic Open Reading Frames", Journal of Molecular Biology, 402(5):905-918.
Altschul et al. (Oct. 1990) "Basic Local Alignment Search Tool", Journal of Molecular Biology, 215(3):403-410.
Andersen et al. (2003) "Secondary Structure Assignment", Structural Bioinformatics, 341-363.
Anraku (Jun. 10, 1968) "Transport of Sugars and Amino Acids in Bacteria", Journal of Biological Chemistry, 243(11):3116-3122.
Artimo et al. (May 2012) "ExPASy: SIB Bioinformatics Resource Portal", Nucleic Acids Research, 40:W597-W603.
Avvakumova et al. (Jan. 2014) "Biotechnological Approaches Toward Nanoparticle Biofunctionalization", Trends in Biotechnology, 32(1):11-20.
Baneyx et al. (Jul. 5, 2007) "Selection and Analysis of Solid-Binding Peptides", Current Opinion in Biotechnology, 8(4):312-317.
Barash et al. (Mar. 28, 1975) "Purification and Properties of Glutamate Binding Protein from the Periplasmic Space of *Escherichia coli* K-12", Biochimica et Biophysica Acta (BBA)—Protein Structure, 386(1):168-180.
Baskin et al. (Oct. 23, 2007) "Copper-Free Click Chemistry for Dynamic in Vivo Imaging", PNAS, 104(43):16793-16797.
Benedetti et al. (Jul. 13, 2012) "Synthesis and Photophysical Properties of a Series of Cyclopenta[b]naphthalene Solvatochromic Fluorophores", Journal of the American Chemical Society, 134(30):12418-12421.
Berman et al. (2000) "The Protein Data Bank", Nucleic Acids Research, 28(1):235-242.

(Continued)

*Primary Examiner* — Robert J Yamasaki
(74) *Attorney, Agent, or Firm* — Mintz Levin Cohn Ferris Glovsky and Popeo, P.C.; Ingrid A. Beattie

(57) ABSTRACT

The present subject matter provides glucose biosensors as well as compositions, devices, and methods comprising such biosensors.

17 Claims, 109 Drawing Sheets

Specification includes a Sequence Listing.

(56) References Cited

OTHER PUBLICATIONS

Biju et al. (Feb. 7, 2014) "Chemical Modifications and Bioconjugate Reactions of Nanomaterials for Sensing, Imaging, Drug Delivery and Therapy", Chemical Society Reviews, 43(3):744-764.
Bjorkman et al. (Jun. 12, 1998) "Multiple Open Forms of Ribose-Binding Protein Trace the Path of its Conformational Change", Journal of Molecular Biology, 279(3):651-664.
Bruns et al. (2001) "Crystallographic and Biochemical Analyses of the Metal-Free Haemophilus influenzae Fe3+-Binding Protein", Biochemistry, 40(51):15631-15637.
Bruns et al. (Nov. 1997) "Structure of Haemophilus Infuenzae Fe+3-Binding Protein Reveals Convergent Evolution within a Superfamily", Nature Structural Biology, 4(11):919-924.
Care et al. (May 2015) "Solid-Binding Peptides: Smart Tools for Nanobiotechnology", Trends in Biotechnology, 33(5):259-268.
CAS Database "Bicyclo(2.2.1)Hept-2-ene, Polymer with Ethene", CAS No. 26007-43-2.
Chen et al. (Feb. 2011) "Binding Analysis of Peptides That Recognize Preferentially Cis-Azobenzene Groups of Synthetic Polymers", Journal of Peptide Science, 17(2):163-168.
Chenna et al. (Jul. 2003) "Multiple Sequence Alignment with the Clustal Series of Programs", Nucleic Acids Research, 31(13):3497-3500.
Cheung (1991) "Resonance Energy Transfer", Topics in Fluorescence Spectroscopy, 2:127-176.
Chothia et al. (1986) "The Relation Between the Divergence of Sequence and Structure in Proteins", The EMBO Journal, 5(4):823-826.
Clark et al. (Apr. 27, 1982) "Proton Nuclear Magnetic Resonance Spectroscopy and Ligand Binding Dynamics of the *Escherichia coli* L-Arabinose Binding Protein", 21(9):2227-2233.
Clegg (1995) "Fluorescence Resonance Energy Transfer", Current Opinion in Biotechnology, 6(1):103-110.
Cox et al. (Mar. 2007) "Protein Fabrication Automation", Protein Science, 16(3):379-390.
Cuneo et al. (Nov. 27, 2009) "Structural Analysis of Semi-specific Oligosaccharide Recognition by a Cellulose-binding Protein of Thermotoga maritima Reveals Adaptations for Functional Diversification of the Oligopeptide Periplasmic Binding Protein Fold", The Journal of Biological chemistry, 284(48):33217-33223.
Database Genbank "*Arthrobacter* Sp. FB24, Complete Genome", Accession No. NC_008541.1.
Database Genbank "Bacillus Halodurans C-125 DNA, Complete Genome", Accession No. NC_002570.2.
Database Genbank "Deinococcus Maricopensis DSM 21211, Complete Fenome", Accession No. NC_014958.1.
Database Genbank (Dec. 16, 2014) "Glucose-Binding Protein [Thermus Thermophilus HB27]", Accession No. YP_004303.1, 2 pages.
Database Genbank "Kosmotoga Olearia TBF 19.5.1, Complete Genome", Accession No. NC_012785.1.
Database Genbank (Dec. 17, 2014) "Methyl-Galactoside ABC Transporter Substrate Binding Component [*Escherichia coli* Se15]", Accession No. YP_003350022.1, 2 pages.
Database Genbank (Aug. 21, 2015) "Staphylothermus Marinus F1, Complete Genome", Accession No. NC_009033.1, 2 pages.
Database Genbank "Thermotoga Neapolitana DSM 4359, Complete Genome", Accession No. NC_011978.1.
Database Genbank "Thermus Scotoductus SA-01, Complete Genome", Accession No. NC_014974.1.
Database Genbank "Thermus Thermophilus HB27, Complete Genome", Accession No. NC_005835.1.
Date et al. (Feb. 2, 2011) "Polymer-Binding Peptides for the Noncovalent Modification of Polymer Surfaces: Effects of Peptide Density on the Subsequent Immobilization of Functional Proteins", ACS Applied Materials & Interfaces, 3(2):351-359.
De Lorimier et al. (Aug. 1, 2006) "Binding and Signaling of Surface-Immobilized Reagentless Fluorescent Biosensors Derived from Periplasmic Binding Proteins", Protein Science, 15(8):1936-1944.
De Lorimier et al. (2002) "Construction of a Fluorescent Biosensor Family", Protein Science, 11:2655-2575.
Demchenko (Dec. 5, 2014) "Practical Aspects of Wavelength Ratiometry in the Studies of Intermolecular Interactions", Journal of Molecular Structure, 1077:51-67.
Demchenko (Sep. 2010) "The Concept of λ-Ratiometry in Fluorescence Sensing and Imaging", Journal of Fluorescence, 20(5):1099-1128.
Dunten (Nov. 1995) "Crystal Structure of the Dipeptide Binding Protein From *Escherichia coli* Involved in Active Transport and Chemotaxis", Protein Science, 4(11):2327-2334.
Duplay et al. (Aug. 25, 1984) "Sequences of the malE Gene and of its Product, the Maltose-binding Protein of *Escherichia coli* K12", The Journal of Biological Chemistry, 259(16):10606-10613.
Dwyer et al. (2004) "Periplasmic Binding Proteins: A Versatile Superfamily for Protein Engineering", Current Opinion in Structural Biology, 14:495-504.
Ejima et al. (Oct. 15, 2010) "Biological Identification of Peptides that Specifically Bind to Poly(phenylene vinylene) Surfaces: Recognition of the Branched or Linear Structure of the Conjugated Polymer", Langmuir, 26(22):17278-17285.
Falke et al. (Sep. 3, 1991) "Quantitating and Engineering the Ion Specificity of an EF-Hand-Like Ca2+ Binding", Biochemistry, 30(35):8690-8697.
George et al. (Aug. 30, 2005) "Effective Function Annotation Through Catalytic Residue Conservation", PNAS, 102(35):12299-12304.
Gifford et al. (Jul. 15, 2007) "Structures and Metal-Ion-Binding Properties of the Ca2+-Binding Helix-Loop-Helix EF-Hand Motifs", Biochemical Journal, 405(2):199-221.
Gill et al. (Nov. 1, 1989) "Calculation of Protein Extinction Coefficients from Amino Acid Sequence Data", Analytical Biochemistry, 182(2):319-326.
Gough et al. (Sep. 1995) "Development of the Implantable Glucose Sensor: What Are the Prospects and Why Is It Taking So Long?", Diabetes, 44(9):1005-1009.
Groarke et al. (Nov. 1983) "The Amino Acid Sequence of D-Ribose-binding Protein from *Escherichia coli* K12", Journal of Biological Chemistry, 258(21):12952-12956.
Group (Sep. 30, 1993) "The Effect of Intensive Treatment of Diabetes on the Development and Progression of Long-Term Complications in Insulin-Dependent Diabetes Mellitus", The New England Journal of Medicine, 329:977-986.
Gunay et al. (Oct. 21, 2015) "Identification of Soft Matter Binding Peptide Ligands Using Phage Display", Bioconjugate Chemistry, 26(10):2002-2015.
Guo et al. (Jun. 10, 2013) "Identification and Characterization of a Cellulose Binding Heptapeptide Revealed by Phage Display", Biomacromolecules, 14(6):1795-1805.
Guyer et al. (Nov. 1986) "Binding Specificity of the Periplasmic Oligopeptide-Binding Protein from *Escherichia coli*", Journal of Bacteriology, 168(2):775-779.
He et al. (1993) "Dominant Role of Local Dipoles in Stabilizing Uncompensated Charges on a Sulfate Sequestered in a Periplasmic Active Transport Protein", Protein Science, 2:1643-1647.
Hellinga et al. (Jul. 1985) "Nucleotide Sequence and High-Level Expression of the Major *Escherichia coli* Phosphofructokinase", European Journal of Biochemistry, 149(2)363-373.
Hengen (Jul. 1995) "Purification of His-Tag Fusion Proteins from *Escherichia coli*", Trends in Biochemical Sciences, 20(7):285-286.
Heo et al. (Jan. 2013) "Towards Smart Tattoos: Implantable Biosensors for Continuous Glucose Monitoring", Advanced Healthcare Materials, 2(1):43-56.
Hnilova et al. (2012) "Peptide-Directed Co-Assembly of Nanoprobes on Multimaterial Patterned Solid Surfaces", Soft Matter, 8(16):4327-4334.
Hsiao et al. (Sep. 20, 1996) "The Crystal Structure of Glutamine-binding Protein from *Escherichia coli*", Journal of Molecular Biology, 262(2):225-242.
Jacobson et al. (Dec. 5, 1998) "Sulfate-Binding Protein Dislikes Protonated Oxyacids. A Molecular Explanation", Journal of Molecular Biology, 204(3):783-787.

(56) References Cited

OTHER PUBLICATIONS

Joshi et al. (Jan. 29, 1998) "*Escherichia coli* Lysine-Arginine-Omithine(LAO)-Binding Periplasmic Protein Argt (Argt) Gene, Partial Cds, Histidine-Binding Periplasmic Protein Hisj (Hisj) And Histidine Transport System Permease Protein Hisq (Hisq) Genes, Complete Cds, And Histidine Tran", GenBank: U47027.1, 2 pages.
Judge et al. (Feb. 27, 2011) "Continuous Glucose Monitoring Using a Novel Glucose/Galactose Binding Protein: Results of a 12-Hour Feasibility Study with the Becton Dickinson Glucose/Galactose Binding Protein Sensor", Diabetes Technology & Therapeutics, 13(3):309-317.
Klymchenko et al. (Jan. 1, 2013) "Fluorescent Environment-Sensitive Dyes as Reporters of Biomolecular Interactions", Progress in Molecular Biology and Translational Science, 113:35-58.
Kolb et al. (Jun. 1, 2001) "Click Chemistry: Diverse Chemical Function from a Few Good Reactions", Angewandte Chemie International Edition, 40(11):2004-2021.
Koo et al. (Nov. 19, 2012) "Bioorthogonal Copper-Free Click Chemistry In Vivo for Tumor-Targeted Delivery of Nanoparticles", Angewandte Chemie, 51(47):11836-11840.
Kucherak et al. (Jan. 12, 2010) "Fluorene Analogues of Prodan with Superior Fluorescence Brightness and Solvatochromism", The Journal of Physical Chemistry Letters, 1(3):616-620.
Kumada et al. (Dec. 14, 2009) "Characterization of Polystyrene-Binding Peptides (PS-tags) for Site-Specific Immobilization of Proteins", Journal of Bioscience and Bioengineering, 109(6):583-587.
Kumada et al. (Aug. 31, 2012) "Screening of PC and PMMA-Binding Peptides for Site-Specific Immobilization of Proteins", Journal of Biotechnology, 160(3-4):222-228.
Kumada (Nov. 2014) "Site-Specific Immobilization of Recombinant Antibody Fragments Through Material-binding Peptides for the Sensitive Detection of Antigens in Enzyme Immunoassays", Biochimica et Biophysica Acta (BBA)—Proteins and Proteomics, 1844(11):1960-1969.
Zeng et al. (2014) "Nanomaterials Enhanced Surface Plasmon Resonance for Biological and Chemical Sensing Applications", Chemical Society Reviews, 43(10):3426-3452.
Layton et al. (Nov. 4, 2010) "Thermodynamic Analysis of Ligand-Induced Changes in Protein Thermal Unfolding Applied to High-Throughput Determination of Ligand Affinities with Extrinsic Fluorescent Dyes", Biochemistry, 49(51):10831-10841.
Ledvina et al. (Jun. 1996) "Negative Electrostatic Surface Potential of Protein Sites Specific for Anionic Ligands", Proceedings of the National Academy of Sciences, 93:6786-6791.
Lee et al. (Jun. 2002) "Ordering of Quantum Dots Using Genetically Engineered Viruses", Science, 296(5569):892-895.
Lu et al. (Nov. 23, 2006) "Long-Wavelength Analogue of PRODAN: Synthesis and Properties of Anthradan, a Fluorophore with a 2,6-Donor-Acceptor Anthracene Structure", The Journal of Organic Chemistry, 71(26):9651-9657.
Luecke et al. (Sep. 27, 1990) "High Specificity of a Phosphate Transport Protein Determined by Hydrogen Bonds", Nature, 347:402-406.
Magota et al. (Mar. 1984) "Nucleotide Sequence of the phoS Gene, the Structural Gene for the Phosphate-Binding Protein of *Escherichia coli*", Journal of Bacteriology, 157(3):909-917.
Marvin et al. (1998) "Engineering Biosensors by Introducing Fluorescent Allosteric Signal Transducers: Construction of a Novel Glucose Sensor", Journal of the American Chemical Society, 120:7-11.
Marvin et al. (Apr. 1997) "The Rational Design of Allosteric Interactions in a Monomeric Protein and its Applications to the Construction of Biosensors", Proceedings of the National Academy of Sciences, 94:4366-4371.
Matsuno et al. (May 24, 2008) "Biological Selection of Peptides for Poly(l-lactide) Substrates", Langmuir, 24(13):6399-6403.
McDonagh et al. (Jan. 30, 2008) "Optical Chemical Sensors", Chemical Reviews, 108(2):400-422.
Medintz et al. (Jun. 1, 2005) "Quantum Dot Bioconjugates for Imaging, Labelling and Sensing", Nature Materials, 4:435-446.
Medveczky et al. (Nov. 18, 1969) "The Binding and Release of Phosphate by a Protein Isolated from *Escherichia coli*", Biochimica et Biophysica Acta (BBA)—General Subjects, 192(2):369-371.
Meyerhoff et al. (1966) "Current Status of the Glucose Sensor", Endricon, 6(1):51-58.
Miller et al. (Nov. 25, 1983) "Rates of Ligand Binding to Periplasmic Proteins Involved in Bacterial Transport and Chemotaxis", The Journal of Biological Chemistry, 258(22)13665-13672.
Mowbray et al. (May 5, 1992) "1.7 A X-Ray Structure of the Periplasmic Ribose Receptor from *Escherichia coli*", Journal of Molecular Biology, 225(1):155-175.
Neves et al. (Jun. 19, 2013) "Imaging Cell Surface Glycosylation in Vivo Using "Double Click" Chemistry", Bioconjugate Chemistry, 24(6):934-941.
Nickitenko (Dec. 1995) "2 A Resolution Structure of DppA, a Periplasmic Dipeptide Transport/Chemosensory Receptor", Biochemistry, 34(51):16585-16595.
Niko et al. (Jul. 22, 2013) "Solvatochromic Pyrene Analogues of Prodan Exhibiting Extremely High Fluorescence Quantum Yields in Apolar and Polar Solvents", Chemistry, 19(30):9760-9765.
Nohno et al. (1986) "Cloning and Complete Nucleotide Sequence of the *Escherichia coli* Glutamine Permease Operon (Glnhpq)", Molecular Genetics and Genomics, 205:260-269.
Nwe et al. (2009) "Growing Applications of "Click Chemistry" for Bioconjugation in Contemporary Biomedical Research", Cancer Biotherapy and Radiopharmaceuticals, 24(3):289-302.
Oliveira et al. (May-Aug. 2015) "Recombinant CBM-Fusion Technology—Applications Overview", Biotechnology Advances, 33(3-4):358-369.
Oneto et al. (2014) "Implantable Biomaterial Based on Click Chemistry for Targeting Small Molecules", Acta Biomaterilia, 10:5099-5105.
Pasquel et al. (Nov. 2014) "Hyperosmolar Hyperglycemic State: A Historic Review of the Clinical Presentation, Diagnosis, and Treatment", Diabetes Care, 37(11):3124-3131.
Pflugrath et al. (Mar. 21, 1985) "Sulphate Sequestered in the Sulphate-Binding Protein of *Salmonella typhimurium* is Bound Solely by Hydrogen Bonds", Nature, 314:257-260.
E8PK67, UniProtKB/TrEMBL Accession No. E8PK67, Jan. 7, 2015, (online), Retrieved from the internet, < URL: www.uniprot.org/uniprot/E8PK67.txt?version=16>.
W2U7T7, UniProtKB/TrEMBL Accession No. W2U7T7, Jan. 7, 2015 (online), Retrieved from the internet: < URL: www.uniprot.org/uniprot/W2U7T7.txt?version=5>.
G8NCM6, UniProtKB/TrEMBL Accession No. G8NCM6, Jan. 7, 2015(online), Retrieved from the internet: < URL: www.uniprot.org/uniprot/G8NCM6.txt?version=12>.
Hibbs et al., Acrylodan-Conjugated Cysteine Side Chains Reveal Conformational State and Ligand Site Locations of the Acetylcholine-Binding Protein, J. Biol Chem., Jul. 2, 2004, pp. 28483-28491.
Tam et al., Structural, Functional, and Evolutionary Relationships Among Extracelullar Solute-Binding Receptors of Bacteria, Microbiol Rev. Jun. 1993, vol. 57, No. 2, pp. 320?346.
Pickup (1993) "Developing Glucose Sensors for In Vivo Use", Tibtech, 11:285-291.
Quiocho et al. (Aug. 15, 1997) "Extensive Features of Tight Oligosaccharide Binding Revealed in High-Resolution Structures of the Maltodextrin Transport/Chemosensory Receptor", Structure, 5(8):997-1015.
Quiocho et al. (Aug. 2, 1984) "Novel Stereospecificity of the L-Arabinose-Binding Protein", Nature, 310:381-386.
Resch-Genger et al. (Oct. 2008) "Quantum Dots Versus Organic Dyes as Fluorescent Labels", Nature Methods, 5(9):763-775.
Riklin et al. (Aug. 24, 1995) "Improving Enzyme-Electrode Contacts by Redox Modification of Cofactors", Nature, 376:672-675.
Rossin et al. (Apr. 10, 2010) "In Vivo Chemistry for Pretargeted Tumor Imaging in Live Mice", Angewandte Chemie, 49(19):3375-3378.
Sanders et al. (Oct. 1994) "Identification of a Locus Involved in the Utilization of Iron by Haemophilus influenzae". Infection and Immunity, 62(10):4515-4525.

(56) References Cited

OTHER PUBLICATIONS

Sapsford et al. (Jul. 10, 2006) "Materials for Fluorescence Resonance Energy Transfer Analysis: Beyond Traditional Donor-Acceptor Combinations", Angew Chem Int Ed Engl, 45(28):4562-4589.
Scholle et al. (Jun. 1987) "Sequence of the Mglb Gene from *Escherichia coli* K12: Comparison of Wild-Type and Mutant Galactose Chemoreceptors", Molecular and General Genetics MGG, 208(1-2):247-253.
Schwartz et al. (1976) "Further Studies on the Binding of Maltose to the Maltose-Binding Protein of *Escherichia coli*", European Journal of Biochemistry, 71:167-170.
Scripture et al. (Sep. 5, 1987) "High-Affinity L-Arabinose Transport Operon. Nucleotide Sequence and Analysis of Gene Products", Journal of Molecular Biology, 197(1):37-46.
Serizawa et al. (Sep. 15, 2005) "A Peptide Motif Recognizing a Polymer Stereoregularity", Journal of the American Chemical Society, 127(40):13780-13781.
Serizawa et al. (Oct. 23, 2007) "Highly Specific Affinities of Short Peptides Against Synthetic Polymers", Langmuir, 23(22):11127-11133.
Serizawa et al. (Jun. 18, 2007) "Isolation of Peptides that Can Recognize Syndiotactic Polystyrene", Chembiochem, 8(9):989-993.
Serizawa et al. (2007) "Peptide Motifs that Recognize Differences in Polymer-Film Surfaces", Angew Chem Int Ed Engl, 46(5):723-726.
Sharff et al. (Nov. 10, 1992) "Crystallographic Evidence of a Large Ligand-Induced Hinge-Twist Motion between the two Domains of the Maltodextrin Binding Protein Involved in Active Transport and Chemotaxis", Biochemistry, 31(44):10657-10663.
Shen et al. (Dec. 21, 2015) "Fluorescence Enhancement on Silver Nanoplates at the Single- and Sub-Nanoparticle Level", Nanoscale, 7(47):20132-20141.
Shin et al. (2005) "Chemical Structure and Physical Properties of Cyclic Olefin Copolymers (IUPAC Technical Report)", Pure and Applied Chemistry, 77(5):801-814.
Shoseyov et al. (Jun. 2006) "Carbohydrate Binding Modules: Biochemical Properties and Novel Applications", Microbiology and Molecular Biology Reviews, 70(2):283-295.
Smith et al. (2005) "Orthogonal Site-Specific Protein Modification by Engineering Reversible Thiol Protection Mechanisms", Protein Science, 14:64-73.
Smith et al. (1999) "Substrate Specificity of the Periplasmic Dipeptide-Binding Protein from *Escherichia coli*: Experimental Basis for the Design of Peptide Prodrugs", Microbiology, 145:2891-2901.
Snyder et al. (Apr. 24, 1990) "Calcium(II) Site Specificity: Effect of Size and Charge on Metal Ion Binding to an Ef-Hand-Like Site", Biochemistry, 29(16):3937-3943.
Spurlino et al. (Mar. 15, 1991) "The 2.3-A Resolution Structure of the Maltose- or Maltodextrinbinding Protein, A Primary Receptor of Bacterial Active Transport and Chemotaxis", Journal of Biological Chemistry, 266(8):5202-5219.
Suleiman et al. (Oct. 23, 1992) "Biosensors for Food Analysis", Biosensor Design and Application, 511:26-40.
Sun et al. (Apr. 24, 1998) "The Structure of Glutamine-Binding Protein Complexed With Glutamine at 1.94 A Resolution: Comparisons with Other Amino Acid Binding Proteins", Journal of Molecular Biology, 278(1):219-229.
Tian et al. (Oct. 1, 2003) "How Well is Enzyme Function Conserved as a Function of Pairwise Sequence Identity?", Journal of Molecular Biology, 333(4):863-882.
Todd (Apr. 1, 2001) "Evolution of Function in Protein Superfamilies, from a Structural Perspective", Journal of Molecular Biology, 307(4):1113-1143.
Vodnik et al. (May 15, 2012) "HWGMWSY, An Unanticipated Polystyrene Binding Peptide from Random Phage Display Libraries", Analytical Biochemistry, 424(2):83-86.
Vyas et al. (Apr. 26, 1994) "Crystallographic Analysis of the Epimeric and Anomeric Specificity of the Periplasmic Transport/Chemosensory Protein Receptor for D-Glucose and D-Galactose", Biochemistry, 33(16):4762-4768.
Vyas et al. (Dec. 2, 1988) "Sugar and Signal-Transducer Binding Sites of the *Escherichia coli* Galactose Chemoreceptor Protein", Science, 242(4883):1290-1295.
Weidemaier et al. (Jun. 15, 2011) "Multi-Day Pre-Clinical Demonstration of Glucose/Galactose Binding Protein-Based Fiber Optic Sensor", Biosensorsand Bioelectronics, 26(10):4117-4123.
Weiner et al. (1971) "A Binding Protein for L-Glutamine and its Relation to Active Transport in *E. coli*", Archives of Biochemistry and Biophysics, 124:715-717.
Wilkins et al. (Jun. 1996) "Glucose Monitoring: State of Art and Future Possibilities", Medical Engineering & Physics, 18:273-288.
Willis et al. (Apr. 10, 1975) "Purification and Properties of a Periplasmic Glutamate-Aspartate Binding Protein from *Escherichkz coli* K12 Strain W3092", The Journal of Biological Chemistry, 250(7):2574-2580.
Willis et al. (Nov. 10, 1974) "Purification and Properties of a Ribose-binding Protein from *Escherichia coli*", Journal of Biological Chemistry, 249(21):6926-6929.
Willner et al. (Oct. 23, 1996) "Electrical Wiring of Glucose Oxidase by Reconstitution of FAD-Modified Monolayers Assembled onto Au-Electrodes", Journal of the American Chemical Society, 118(42):10321-10322.
Yao et al. (Apr. 26, 1994) "Refined 1.89-A Structure of the Histidine-Binding Protein Complexed with Histidine and its Relationship with Many Other Active Transport/Chemosensory Proteins", Biochemistry, 33(16):4769-4779.
Vallee-Belisle and Plaxco, "Structure-switching biosensors: inspired by Nature", Current Opinion in Structural Biology 2010, 20:518-526.
Grünewald, F.S. "Periplasmic Binding Proteins in Biosensing Applications", BIOREV 2014, 1: 205-236.

* cited by examiner

| Position | Allowed residues |
|---|---|
| 8 | W, H, N, Q |
| 9 | W, F, Y |
| 13 | E, D, N, Q |
| 64 | Q, N |
| 66 | H, N, Q, W, K |
| 119 | H, N, Q, W |
| 224 | W, F, Y |
| 244 | W, F, Y |
| 278 | D, E, N, Q |
| 312 | K, R |
| 348 | H, N, Q, W |

FIG. 7 - ttGBP1

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                          10
                                                                          M  K  L  E  I  F  S  W  W  A  G  D  E  G  P  A  L  E  A  L
GGAGACCACAACGGTTTCCCTCTAGAAATAATTTTGTTTAACTTTAAGAAGGAGATATACCATGAAATTAGAAATTTTTTCTTGGTGGGCAGGTGATGAAGGCCCGGCCTTAGAGGCCTT
CCTCTGGTGTTGCCAAAGGGAGATCTTTATTAAAACAAATTGAAATTCTTCCTCTATATGGTACTTTAATCTTTAAAAAAGAACCACCCGTCCACTACTTCCGGGCCGGAATCTCCGGAA
       130       140       150       160       170       180       190       200       210       220       230       240

                              30                            40                            50
 I  R  L  Y  K  Q  K  Y  P  G  V  E  V  I  N  A  T  V  T  G  G  A  G  V  N  A  R  A  V  L  K  T  R  M  L  G  G  D  P  P
GATCCGCTTATATAAACAAAAATACCCGGGTGTAGAAGTGATTAATGCAACCGTGACAGGCGGTGCAGGCGTCAATGCGCGGGCAGTTCTCAAAACCCGTATGTTAGGCGGTGATCCACC
CTAGGCGAATATATTTGTTTTTATGGGCCCACATCTTCACTAATTACGTTGGCACTGTCCGCCACGTCCGCAGTTACGCGCCCGTCAAGAGTTTTGGGCATACAATCCGCCACTAGGTGG
       250       260       270       280       290       300       310       320       330       340       350       360

                              70                            80                            90
 D  T  F  Q  V  H  A  G  M  E  L  I  G  T  W  V  V  A  N  R  M  E  D  L  S  A  L  F  R  Q  E  G  W  L  Q  A  F  P  K  G
AGACACCTTCCAAGTCCATGCTGGGATGGAATTAATCGGCACATGGGTCGTCGCGAACCGCATGGAGGACCTCTCGGCGCTGTTTCGGCAGGAAGGCTGGCTTCAGGCATTCCCTAAAGG
TCTGTGGAAGGTTCAGGTACGACCCTACCTTAATTAGCCGTGTACCCAGCAGCGCTTGGCGTACCTCCTGGAGAGCCGCGACAAAGCCGTCCTTCCGACCGAAGTCCGTAAGGGATTTCC
       370       380       390       400       410       420       430       440       450       460       470       480

                             110                           120                           130
 L  I  D  L  I  S  Y  K  G  G  I  W  S  V  P  V  N  I  H  R  S  N  V  M  W  Y  L  P  A  K  L  K  G  W  G  V  N  P  P  R
CCTCATCGACCTGATTTCTTATAAGGGCGGGATTTGGTCCGTACCTGTAAATATCCACCGGAGTAACGTAATGTGGTATCTGCCGGCAAAATTAAAAGGCTGGGGCGTAAACCCACCACG
GGAGTAGCTGGACTAAAGAATATTCCCGCCCTAAACCAGGCATGGACATTTATAGGTGGCCTCATTGCATTACACCATAGACGGCCGTTTTAATTTTCCGACCCCGCATTTGGGTGGTGC
       490       500       510       520       530       540       550       560       570       580       590       600

                             150                           160                           170
 T  W  D  K  F  L  A  T  A  Q  T  L  K  Q  K  G  L  E  A  P  L  A  L  G  E  N  W  T  Q  Q  H  L  W  E  S  V  A  L  A  V
TACTTGGGACAAATTTCTTGCGACGGCGCAGACCTTAAAGCAAAAAGGTTTAGAGGCACCACTGGCCCTCGGGGAAAATTGGACACAGCAGCACTTGTGGGAGTCGGTCGCCTTGGCAGT
ATGAACCCTGTTTAAAGAACGCTGCCGCGTCTGGAATTTCGTTTTTCCAAATCTCCGTGGTGACCGGGAGCCCCTTTTAACCTGTGTCGTCGTGAACACCCTCAGCCAGCGGAACCGTCA
       610       620       630       640       650       660       670       680       690       700       710       720

                             190                           200                           210
 L  G  P  D  D  W  N  N  L  W  N  G  K  L  K  F  T  D  P  K  A  V  R  A  W  E  V  F  G  R  V  L  D  A  A  N  K  D  A  A
ATTGGGTCCAGATGATTGGAATAACTTATGGAACGGCAAACTCAAGTTTACTGATCCAAAAGCCGTCCGTGCATGGGAGGTGTTCGGCCGCGTCCTCGACGCAGCTAATAAAGATGCAGC
TAACCCAGGTCTACTAACCTTATTGAATACCTTGCCGTTTGAGTTCAAATGACTAGGTTTTCGGCAGGCACGTACCCTCCACAAGCCGGCGCAGGAGCTGCGTCGATTATTTCTACGTCG
       730       740       750       760       770       780       790       800       810       820       830       840

                             230                           240                           250
 G  L  S  W  Q  Q  A  V  D  R  V  V  Q  G  K  A  A  F  N  I  M  G  D  W  A  A  G  Y  M  T  T  T  L  K  L  K  P  G  T  D
AGGCTTGAGCTGGCAGCAAGCCGTCGATCGCGTCGTACAGGGGAAAGCCGCATTCAACATTATGGGGGATTGGGCGGCTGGGTACATGACTACGACGTTAAAATTAAAACCAGGTACAGA
TCCGAACTCGACCGTCGTTCGGCAGCTAGCGCAGCATGTCCCCTTTCGGCGTAAGTTGTAATACCCCCTAACCCGCCGACCCATGTACTGATGCTGCAATTTTAATTTTGGTCCATGTCT
       850       860       870       880       890       900       910       920       930       940       950       960

                             270                           280                           290
 F  A  W  A  P  S  P  G  T  Q  G  V  F  M  M  L  S  D  S  F  G  L  P  K  G  A  K  N  R  Q  N  A  I  N  W  L  R  L  V  G
```

```
TTTCGCTTGGGCCCCATCACCAGGTACCCAAGGCGTATTCATGATGTTAAGTGACTCATTCGGTCTCCCTAAAGGTGCCAAAAATCGTCAGAATGCTATTAACTGGCTGCGTCTCGTAGG
AAAGCGAACCCGGGGTAGTGGTCCATGGGTTCCGCATAAGTACTACAATTCACTGAGTAAGCCAGAGGGATTTCCACGGTTTTTAGCAGTCTTACGATAATTGACCGACGCAGAGCATCC
       970       980       990      1000      1010      1020      1030      1040      1050      1060      1070      1080

                   310                           320                           330
 S  K  E  G  Q  D  T  S  N  P  L  K  G  S  I  A  A  R  L  D  S  D  P  S  K  Y  N  A  Y  G  Q  S  A  M  R  D  W  R  S  N
TTCAAAGGAAGGGCAAGATACATCTAACCCTCTCAAAGGTAGTATTGCAGCACGTCTTGACAGCGACCCTTCGAAGTATAACGCCTATGGCCAATCGGCAATGCGTGACTGGCGCAGTAA
AAGTTTCCTTCCCGTTCTATGTAGATTGGGAGAGTTTCCATCATAACGTCGTGCAGAACTGTCGCTGGGAAGCTTCATATTGCGGATACCGGTTAGCCGTTACGCACTGACCGCGTCATT
      1090      1100      1110      1120      1130      1140      1150      1160      1170      1180      1190      1200

                   350                           360                           370
 R  I  V  G  S  L  V  H  G  A  V  A  P  E  S  F  M  S  Q  F  G  T  V  M  E  I  F  L  Q  T  R  N  P  Q  A  A  A  N  A  A
CCGTATCGTAGGGTCCCTCGTTCACGGCGCCGTTGCACCAGAATCGTTTATGAGTCAATTCGGTACCGTAATGGAAATCTTCCTCCAAACCCGCAATCCACAAGCAGCTGCTAATGCAGC
GGCATAGCATCCCAGGGAGCAAGTGCCGCGGCAACGTGGTCTTAGCAAATACTCAGTTAAGCCATGGCATTACCTTTAGAAGGAGGTTTGGGCGTTAGGTGTTCGTCGACGATTACGTCG
      1210      1220      1230      1240      1250      1260      1270      1280      1290      1300      1310      1320

                   390                           400
 Q  A  I  A  D  Q  V  G  L  G  R  L  G  Q  H  H  H  H  H  H  *  *
ACAGGCCATCGCCGACCAAGTAGGCCTCGGTCGTTTAGGTCAACATCATCATCATCATCATTAATGAAAGGGCGATATCCAGCACACTGGCGGCCGTTACTAGTGGATCCGGCTGCTAAC
TGTCCGGTAGCGGCTGGTTCATCCGGAGCCAGCAAATCCAGTTGTAGTAGTAGTAGTAGTAATTACTTTCCCGCTATAGGTCGTGTGACCGCCGGCAATGATCACCTAGGCCGACGATTG
      1330      1340      1350      1360      1370      1380      1390      1400      1410      1420      1430      1440


AAAGCCCGAAAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGA
TTTCGGGCTTTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCT
      1450      1460      1470      1480      1490      1500      1510      1520      1530      1540      1550      1560


GCGACTCCCACGGCACGTTGGCAAGCTCGGAATTCGGCGTAATC
CGCTGAGGGTGCCGTGCAACCGTTCGAGCCTTAAGCCGCATTAG
      1570      1580      1590      1600
```

FIG. 7 (Continued)

FIG. 8 - tsGBP2.0

```
CGGTCACGCTTGGGACTGCCATAGGCTGGCCCGGTGATGCCGGCCACGATGCGTCCGGCGTAGAGGATCGAGATCTCGATCCCGCGAAATTAATACGACT
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGA
        10        20        30        40        50        60        70        80        90       100

                                                                                                 10
                                                                      M  K  L  E  I  F  S  W  W  A  G
CACTATAGGGAGACCACAACGGTTTCCCTCTAGAAATAATTTTGTTTAACTTTAAGAAGGAGATATACCATGAAATTAGAAATTTTTTCTTGGTGGGCAG
GTGATATCCCTCTGGTGTTGCCAAAGGGAGATCTTTATTAAAACAAATTGAAATTCTTCCTCTATATGGTACTTTAATCTTTAAAAAAGAACCACCCGTC
       110       120       130       140       150       160       170       180       190       200

                          20                            30                            40
 D  E  G  P  A  L  E  A  L  I  R  L  Y  K  Q  K  Y  P  G  V  E  V  I  N  A  T  V  T  G  G  A  G  V
GTGATGAAGGCCCAGCTCTCGAAGCCTTGATCCGGTTGTATAAACAGAAATACCCAGGTGTAGAGGTCATTAATGCTACCGTCACCGGGGGTGCCGGTGT
CACTACTTCCGGGTCGAGAGCTTCGGAACTAGGCCAACATATTTGTCTTTATGGGTCCACATCTCCAGTAATTACGATGGCAGTGGCCCCCACGGCCACA
       210       220       230       240       250       260       270       280       290       300

                50                            60                            70
 N  A  K  A  V  L  K  T  R  M  L  G  G  D  P  P  D  T  F  Q  V  H  A  G  Q  E  L  I  G  T  W  V  V
CAACGCCAAAGCCGTCCTTAAAACGCGTATGCTCGGCGGGGACCCACCAGATACCTTTCAAGTACATGCAGGGCAGGAGCTGATCGGCACATGGGTCGTC
GTTGCGGTTTCGGCAGGAATTTTGCGCATACGAGCCGCCCCTGGGTGGTCTATGGAAAGTTCATGTACGTCCCGTCCTCGACTAGCCGTGTACCCAGCAG
       310       320       330       340       350       360       370       380       390       400

    80                            90                           100                           110
A  D  R  M  E  D  L  T  S  L  F  R  Q  E  G  W  L  Q  A  F  P  K  G  L  I  D  L  L  S  Y  K  G  G  I
GCCGACCGTATGGAAGATCTTACCTCATTGTTTCGGCAGGAGGGCTGGCTTCAAGCGTTCCCAAAAGGTTTAATCGATCTCCTCAGTTACAAAGGTGGCA
CGGCTGGCATACCTTCTAGAATGGAGTAACAAAGCCGTCCTCCCGACCGAAGTTCGCAAGGGTTTTCCAAATTAGCTAGAGGAGTCAATGTTTCCACCGT
       410       420       430       440       450       460       470       480       490       500

                         120                           130                           140
 W  S  V  P  V  N  I  H  R  S  N  V  M  W  Y  I  P  A  K  L  K  E  W  G  V  T  P  P  K  T  W  A  E
TTTGGTCAGTCCCAGTCAACATCCACCGTTCTAACGTAATGTGGTACATCCCGGCAAAATTAAAAGAATGGGGCGTGACCCCGCCAAAAACATGGGCAGA
AAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       510       520       530       540       550       560       570       580       590       600

             150                           160                           170
 F  L  A  T  A  Q  T  L  K  R  K  G  L  E  A  P  L  A  L  G  E  N  W  T  Q  Q  H  L  W  E  S  V  A
ATTTTTAGCGACAGCGCAAACATTAAAGCGGAAAGGCCTTGAGGCACCATTGGCACTCGGTGAGAATTGGACACAGCAACATCTCTGGGAAAGCGTCGCC
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGG
       610       620       630       640       650       660       670       680       690       700

   180                           190                           200                           210
L  A  T  L  G  A  D  G  W  N  N  L  W  S  G  K  L  K  F  T  D  P  K  A  V  A  V  W  E  T  F  G  K  V
CTCGCCACACTGGGTGCCGATGGTTGGAATAATCTCTGGAGTGGTAAGCTCAAATTCACGGATCCAAAAGCAGTCGCCGTATGGGAAACATTCGGTAAGG
GAGCGGTGTGACCCACGGCTACCAACCTTATTAGAGACCTCACCATTCGAGTTTAAGTGCCTAGGTTTTCGTCAGCGGCATACCCTTTGTAAGCCATTCC
       710       720       730       740       750       760       770       780       790       800
```

```
                                220                                     230                                     240
  L  D  A  A  N  K  D  A  A  G  L  S  W  Q  Q  A  V  D  R  V  V  Q  G  K  A  A  F  N  I  M  G  D  W
TATTAGATGCAGCGAACAAGGATGCAGCCGGGCTTTCATGGCAACAAGCAGTAGACCGTGTAGTACAGGGGAAAGCTGCATTCAATATCATGGGGGACTG
ATAATCTACGTCGCTTGTTCCTACGTCGGCCCGAAAGTACCGTTGTTCGTCATCTGGCACATCATGTCCCCTTTCGACGTAAGTTATAGTACCCCCTGAC
       810       820       830       840       850       860       870       880       890       900

                    250                                     260                                     270
  A  A  G  Y  M  S  T  T  L  K  L  K  P  G  T  D  F  A  W  T  P  S  P  G  T  S  G  I  F  M  M  L  S
GGCAGCAGGTTACATGAGTACGACCTTAAAACTGAAGCCAGGTACCGACTTCGCATGGACACCTTCTCCGGGCACTTCAGGGATCTTTATGATGCTGTCT
CCGTCGTCCAATGTACTCATGCTGGAATTTTGACTTCGGTCCATGGCTGAAGCGTACCTGTGGAAGAGGCCCGTGAAGTCCCTAGAAATACTACGACAGA
       910       920       930       940       950       960       970       980       990      1000

    280                                     290                                     300                                     310
D  S  F  G  L  P  K  G  A  K  N  R  Q  N  A  I  N  W  L  K  L  V  G  S  K  E  G  Q  D  T  F  N  P  L
GATAGTTTCGGCTTGCCAAAGGGGGCGAAGAATCGTCAAAATGCTATTAACTGGTTGAAACTCGTCGGGTCAAAAGAGGGGCAGGACACCTTCAACCCGC
CTATCAAAGCCGAACGGTTTCCCCCGCTTCTTAGCAGTTTTACGATAATTGACCAACTTTGAGCAGCCCAGTTTTCTCCCCGTCCTGTGGAAGTTGGGCG
      1010      1020      1030      1040      1050      1060      1070      1080      1090      1100

                                320                                     330                                     340
  K  G  S  I  A  A  R  L  D  S  D  P  A  K  Y  N  A  Y  G  Q  S  A  M  K  D  W  K  S  N  R  I  V  G
TCAAAGGTTCCATCGCTGCTCGTCTCGATTCTGATCCTGCCAAATATAATGCATACGGCCAAAGTGCAATGAAGGACTGGAAGTCAAATCGGATCGTAGG
AGTTTCCAAGGTAGCGACGAGCAGAGCTAAGACTAGGACGGTTTATATTACGTATGCCGGTTTCACGTTACTTCCTGACCTTCAGTTTAGCCTAGCATCC
      1110      1120      1130      1140      1150      1160      1170      1180      1190      1200

                    350                                     360                                     370
  S  L  V  H  G  A  V  A  P  E  S  F  M  S  Q  F  G  T  V  M  E  I  F  L  Q  S  R  N  P  Q  A  A  A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCT
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGA
      1210      1220      1230      1240      1250      1260      1270      1280      1290      1300

    380                                     390                                     400
N  A  A  Q  A  I  A  N  Q  V  G  L  G  R  G  G  S  H  H  H  H  H  H  *  *
AATGCCGCACAAGCTATCGCCAATCAGGTCGGTTTAGGTCGTGGGGGTTCACATCATCATCATCATCATTAATGAAAGGGCGATATCCAGCACACTGGCG
TTACGGCGTGTTCGATAGCGGTTAGTCCAGCCAAATCCAGCACCCCCAAGTGTAGTAGTAGTAGTAGTAATTACTTTCCCGCTATAGGTCGTGTGACCGC
      1310      1320      1330      1340      1350      1360      1370      1380      1390      1400


GCCGTTACTAGTGGATCCGGCTGCTAACAAAGCCCGAAAGGAAGCTGAGTTGGCTGCTGCCACCGCTGAGCAATAACTAGCATAACCCCTTGGGGCCTCT
CGGCAATGATCACCTAGGCCGACGATTGTTTCGGGCTTTCCTTCGACTCAACCGACGACGGTGGCGACTCGTTATTGATCGTATTGGGGAACCCCGGAGA
      1410      1420      1430      1440      1450      1460      1470      1480      1490      1500


AAACGGGTCTTGAGGGGTTTTTTGCTGAAAGGAGGAACTATATCCGGAGCGACTCCCACGGCACGTTGGCAAGCTCG
TTTGCCCAGAACTCCCCAAAAAACGACTTTCCTCCTTGATATAGGCCTCGCTGAGGGTGCCGTGCAACCGTTCGAGC
      1510      1520      1530      1540      1550      1560      1570
```

FIG. 8 (Continued)

FIG. 9 - dmGBP3

```
CGGTCACGCTTGGGACTGCCATAGGCTGGCCCGGTGATGCCGGCCACGATGCGTCCGGCGTAGAGGATCGAGATCTCGATCCCGCGAAATTAATACGACT
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGA
        10        20        30        40        50        60        70        80        90       100

                                                                                             10
                                                                      M  K  L  E  I  F  S  W  W  S  G
CACTATAGGGAGACCACAACGGTTTCCCTCTAGAAATAATTTTGTTTAACTTTAAGAAGGAGATATACCATGAAACTCGAAATTTTTAGTTGGTGGTCAG
GTGATATCCCTCTGGTGTTGCCAAAGGGAGATCTTTATTAAAACAAATTGAAATTCTTCCTCTATATGGTACTTTGAGCTTTAAAAATCAACCACCAGTC
       110       120       130       140       150       160       170       180       190       200

                        20                            30                            40
  D  E  G  P  A  L  E  A  L  V  K  L  Y  K  Q  K  Y  P  S  V  D  V  V  N  A  T  V  A  G  G  A  G  T
GTGACGAAGGCCCAGCACTCGAGGCACTCGTGAAGTTATATAAGCAAAAGTATCCATCGGTAGACGTGGTCAATGCGACGGTAGCAGGGGGCGCAGGGAC
CACTGCTTCCGGGTCGTGAGCTCCGTGAGCACTTCAATATATTCGTTTTCATAGGTAGCCATCTGCACCAGTTACGCTGCCATCGTCCCCCGCGTCCCTG
       210       220       230       240       250       260       270       280       290       300

               50                            60                            70
 N  A  K  A  V  L  K  T  R  M  L  G  G  D  P  P  D  S  F  Q  A  H  A  G  Q  E  L  I  G  T  W  V  V
AAATGCAAAAGCGGTGCTGAAAACTCGTATGCTCGGGGGCGACCCACCGGATTCATTCCAGGCCCACGCCGGCCAAGAATTGATCGGGACATGGGTAGTG
TTTACGTTTTCGCCACGACTTTTGAGCATACGAGCCCCCGCTGGGTGGCCTAAGTAAGGTCCGGGTGCGGCCGGTTCTTAACTAGCCCTGTACCCATCAC
       310       320       330       340       350       360       370       380       390       400

    80                            90                           100                           110
A  N  R  M  E  D  L  S  S  L  F  K  S  E  G  W  T  T  K  F  P  K  D  L  L  P  L  I  S  S  K  G  G  I
GCAAATCGTATGGAAGATTTAAGTTCCCTGTTCAAATCCGAAGGTTGGACCACAAAATTCCCAAAAGATTTATTACCACTTATCTCTTCGAAAGGGGGCA
CGTTTAGCATACCTTCTAAATTCAAGGGACAAGTTTAGGCTTCCAACCTGGTGTTTTAAGGGTTTTCTAAATAATGGTGAATAGAGAAGCTTTCCCCCGT
       410       420       430       440       450       460       470       480       490       500

                       120                           130                           140
  W  S  V  P  V  N  V  H  R  S  N  V  M  W  Y  I  P  A  N  L  K  K  W  G  V  T  A  P  K  T  W  D  Q
TCTGGTCAGTCCCAGTAAACGTCCATCGCAGTAACGTCATGTGGTACATCCCGGCTAATCTGAAGAAATGGGGCGTGACCGCACCTAAAACCTGGGACCA
AGACCAGTCAGGGTCATTTGCAGGTAGCGTCATTGCAGTACACCATGTAGGGCCGATTAGACTTCTTTACCCCGCACTGGCGTGGATTTTGGACCCTGGT
       510       520       530       540       550       560       570       580       590       600

              150                           160                           170
 F  L  T  T  A  K  T  L  K  T  K  N  V  T  P  L  A  L  G  E  N  W  T  Q  Q  H  L  W  E  S  V  A  V
GTTCTTAACTACCGCGAAGACCTTGAAGACCAAGAACGTAACTCCATTAGCACTCGGGGAAAACTGGACTCAACAACACTTATGGGAATCAGTGGCGGTC
CAAGAATTGATGGCGCTTCTGGAACTTCTGGTTCTTGCATTGAGGTAATCGTGAGCCCCTTTTGACCTGAGTTGTTGTGAATACCCTTAGTCACCGCCAG
       610       620       630       640       650       660       670       680       690       700

    180                           190                           200                           210
G  T  L  G  A  Q  G  W  Q  N  L  W  S  G  K  L  K  F  T  D  P  K  V  V  K  V  W  D  T  F  G  K  V  L
GGTACATTAGGGGCCCAGGGTTGGCAGAACTTATGGTCGGGGAAGTTAAAGTTTACAGACCCAAAGGTGGTGAAAGTATGGGACACATTCGGCAAGGTCT
CCATGTAATCCCCGGGTCCCAACCGTCTTGAATACCAGCCCCTTCAATTTCAAATGTCTGGGTTTCCACCACTTTCATACCCTGTGTAAGCCGTTCCAGA
       710       720       730       740       750       760       770       780       790       800
```

```
                       220                                 230                                 240
  D  A  T  N  K  D  A  S  G  L  S  W  Q  Q  A  T  D  R  V  V  N  G  Q  A  A  F  N  I  M  G  D  W  A
TGGATGCAACAAACAAGGATGCATCGGGTCTCAGTTGGCAGCAGGCGACGGACCGTGTAGTAAATGGCCAGGCAGCGTTTAACATTATGGGGGATTGGGC
ACCTACGTTGTTTGTTCCTACGTAGCCCAGAGTCAACCGTCGTCCGCTGCCTGGCACATCATTTACCGGTCCGTCGCAAATTGTAATACCCCCTAACCCG
       810       820       830       840       850       860       870       880       890       900

             250                                 260                                 270
 A  G  Y  L  S  T  T  K  K  L  K  P  G  T  G  F  G  W  A  P  S  P  S  T  S  G  T  F  I  F  L  A  D
CGCAGGTTATCTCAGTACGACCAAGAAATTGAAACCGGGGACAGGCTTCGGCTGGGCGCCGTCCCCATCAACATCAGGCACGTTCATTTTCTTGGCTGAT
GCGTCCAATAGAGTCATGCTGGTTCTTTAACTTTGGCCCCTGTCCGAAGCCGACCCGCGGCAGGGGTAGTTGTAGTCCGTGCAAGTAAAAGAACCGACTA
       910       920       930       940       950       960       970       980       990      1000

   280                                 290                                 300                                 310
S  F  G  L  P  K  G  A  K  D  R  A  E  A  L  S  W  L  K  L  L  G  S  K  Q  G  Q  D  T  F  N  P  L  K
AGCTTTGGGTTGCCGAAAGGTGCCAAGGATCGCGCGGAAGCCCTCTCATGGTTAAAACTTTTAGGCTCAAAACAGGGTCAGGACACATTTAATCCTTTAA
TCGAAACCCAACGGCTTTCCACGGTTCCTAGCGCGCCTTCGGGAGAGTACCAATTTTGAAAATCCGAGTTTTGTCCCAGTCCTGTGTAAATTAGGAAATT
      1010      1020      1030      1040      1050      1060      1070      1080      1090      1100

                       320                                 330                                 340
  G  S  I  A  A  R  V  D  S  D  L  S  K  Y  S  T  Y  S  Q  S  A  A  K  D  W  K  S  N  K  I  V  G  S
AGGGCAGTATCGCGGCTCGGGTCGACAGTGATTTATCTAAATACTCCACATATAGCCAATCGGCAGCCAAGGACTGGAAGAGCAATAAAATTGTGGGGTC
TCCCGTCATAGCGCCGAGCCCAGCTGTCACTAAATAGATTTATGAGGTGTATATCGGTTAGCCGTCGGTTCCTGACCTTCTCGTTATTTTAACACCCCAG
      1110      1120      1130      1140      1150      1160      1170      1180      1190      1200

             350                                 360                                 370
 L  T  H  G  A  V  A  P  E  S  F  T  S  T  F  G  T  V  I  D  A  F  V  A  S  R  N  A  Q  V  A  A  A
GTTGACGCATGGGGCAGTCGCACCAGAATCCTTTACTTCTACCTTTGGCACCGTAATCGATGCCTTTGTAGCAAGTCGGAATGCTCAGGTCGCAGCCGCT
CAACTGCGTACCCCGTCAGCGTGGTCTTAGGAAATGAAGATGGAAACCGTGGCATTAGCTACGGAAACATCGTTCAGCCTTACGAGTCCAGCGTCGGCGA
      1210      1220      1230      1240      1250      1260      1270      1280      1290      1300

   380                                 390                                 400
T  T  Q  Q  L  A  D  K  A  G  L  G  K  G  G  S  H  H  H  H  H  H  *  *
ACTACACAACAGCTCGCAGATAAAGCCGGTCTGGGCAAAGGTGGTAGTCATCATCATCATCATCATTAATGAAAGGGCGATATCCAGCACACTGGCGGCC
TGATGTGTTGTCGAGCGTCTATTTCGGCCAGACCCGTTTCCACCATCAGTAGTAGTAGTAGTAGTAATTACTTTCCCGCTATAGGTCGTGTGACCGCCGG
      1310      1320      1330      1340      1350      1360      1370      1380      1390      1400


GTTACTAGTGGATCCGGCTGCTAACAAAGCCCGAAAGGAAGCTGAGTTGGCTGCTGCCACCGCTGAGCAATAACTAGCATAACCCCTTGGGGCCTCTAAA
CAATGATCACCTAGGCCGACGATTGTTTCGGGCTTTCCTTCGACTCAACCGACGACGGTGGCGACTCGTTATTGATCGTATTGGGGAACCCCGGAGATTT
      1410      1420      1430      1440      1450      1460      1470      1480      1490      1500


CGGGTCTTGAGGGGTTTTTTGCTGAAAGGAGGAACTATATCCGGAGCGACTCCCACGGCACGTTGGCAAGCTCG
GCCCAGAACTCCCCAAAAAACGACTTTCCTCCTTGATATAGGCCTCGCTGAGGGTGCCGTGCAACCGTTCGAGC
      1510      1520      1530      1540      1550      1560      1570
```

FIG. 9 (Continued)

FIG. 10 - tnGBP4

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAACGGTTTCCCTCTAGAAATAATTTTGTTTAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTGCCAAAGGGAGATCTTTATTAAAACAAATTG
        10         20         30         40         50         60         70         80         90        100        110        120        130        140        150

                                      10                             20                             30                             40
                       M  L  E  I  F  S  W  W  T  A  G  G  E  A  E  A  L  E  A  L  I  K  V  F  N  K  Y  Y  P  D  V  E  V  I  N  A  T  V  A  G  G  A  G  T
TTTAAGAAGGAGATATACCATGTTAGAAATTTTTTCTTGGTGGACAGCAGGTGGCGAAGCCGAAGCCTTAGAAGCACTCATTAAAGTCTTCAATAAGTACTATCCGGATGTAGAGGTCATCAATGCGACAGTCGCAGGCGGTGCTGGTAC
AAATTCTTCCTCTATATGGTACAATCTTTAAAAAAGAACCACCTGTCGTCCACCGCTTCGGCTTCGGAATCTTCGTGAGTAATTTCAGAAGTTATTCATGATAGGCCTACATCTCCAGTAGTTACGCTGTCAGCGTCCGCCACGACCATG
       160        170        180        190        200        210        220        230        240        250        260        270        280        290        300

            50                             60                             70                             80                             90
 N  A  K  A  V  L  K  T  R  I  L  G  G  N  P  P  D  S  F  Q  V  H  A  G  M  E  L  I  D  T  Y  V  I  P  G  Y  M  T  P  I  T  N  L  L  E  Q  W  G  V  M
TAACGCCAAAGCAGTCTTAAAGACCCGCATTCTTGGTGGTAACCCTCCGGATTCATTCCAAGTTCACGCTGGCATGGAACTCATCGACACATACGTTATTCCAGGTTACATGACACCAATCACCAATCTCTTAGAGCAATGGGGCGTCAT
ATTGCGGTTTCGTCAGAATTTCTGGGCGTAAGAACCACCATTGGGAGGCCTAAGTAAGGTTCAAGTGCGACCGTACCTTGAGTAGCTGTGTATGCAATAAGGTCCAATGTACTGTGGTTAGTGGTTAGAGAATCTCGTTACCCCGCAGTA
       310        320        330        340        350        360        370        380        390        400        410        420        430        440        450

           100                            110                            120                            130                            140
 D  K  F  P  K  G  I  L  E  M  A  S  Y  E  G  E  I  Y  S  I  P  V  N  V  H  R  G  N  V  V  F  Y  N  K  K  I  A  E  E  I  G  M  N  E  P  P  K  T  W  D
GGACAAGTTTCCGAAAGGCATTCTCGAGATGGCTTCCTATGAAGGCGAAATTTACTCAATTCCGGTAAATGTACATCGCGGTAATGTGGTCTTTTACAATAAGAAAATTGCAGAGGAAATTGGCATGAACGAACCACCAAAAACGTGGGA
CCTGTTCAAAGGCTTTCCGTAAGAGCTCTACCGAAGGATACTTCCGCTTTAAATGAGTTAAGGCCATTTACATGTAGCGCCATTACACCAGAAAATGTTATTCTTTTAACGTCTCCTTTAACCGTACTTGCTTGGTGGTTTTTGCACCCT
       460        470        480        490        500        510        520        530        540        550        560        570        580        590        600

           150                            160                            170                            180                            190
 E  F  I  M  Y  L  Q  K  A  K  E  K  G  Y  V  G  L  A  L  G  D  K  N  K  W  T  A  L  H  L  F  E  T  I  L  L  G  V  L  G  P  N  D  Y  N  G  L  W  K  G
CGAATTTATCATGTATCTCCAGAAAGCCAAAGAGAAAGGCTATGTAGGGCTTGCACTGGGTGACAAGAATAAGTGGACAGCCCTCCACCTGTTCGAAACAATCCTCTTAGGCGTGTTAGGCCCAAATGATTATAATGGTCTTTGGAAAGG
GCTTAAATAGTACATAGAGGTCTTTCGGTTTCTCTTTCCGATACATCCCGAACGTGACCCACTGTTCTTATTCACCTGTCGGGAGGTGGACAAGCTTTGTTAGGAGAATCCGCACAATCCGGGTTTACTAATATTACCAGAAACCTTTCC
       610        620        630        640        650        660        670        680        690        700        710        720        730        740        750

           200                            210                            220                            230                            240
 E  V  S  F  N  D  P  R  I  R  R  A  F  E  I  M  N  K  L  L  D  Y  V  N  E  D  H  A  A  L  A  W  Q  D  A  T  R  L  V  Y  E  G  K  A  L  A  N  V  M  G
GGAAGTTAGCTTTAACGACCCTCGTATTCGCCGCGCATTCGAAATTATGAACAAGTTGTTGGACTACGTAAACGAAGATCATGCAGCACTCGCCTGGCAGGATGCAACTCGTTTAGTATACGAAGGCAAAGCCTTGGCTAACGTCATGGG
CCTTCAATCGAAATTGCTGGGAGCATAAGCGGCGCGTAAGCTTTAATACTTGTTCAACAACCTGATGCATTTGCTTCTAGTACGTCGTGAGCGGACCGTCCTACGTTGAGCAAATCATATGCTTCCGTTTCGGAACCGATTGCAGTACCC
       760        770        780        790        800        810        820        830        840        850        860        870        880        890        900

           250                            260                            270                            280                            290
 D  W  A  E  G  Y  L  K  S  V  G  W  E  P  G  K  D  F  G  W  F  A  V  P  E  T  Q  N  A  F  M  V  V  S  D  T  F  G  L  P  K  N  A  P  H  K  E  N  A  V
TGATTGGGCGGAGGGGTACTTAAAAAGCGTCGGGTGGGAACCGGGTAAAGATTTCGGGTGGTTCGCCGTGCCAGAAACCCAAAACGCTTTCATGGTAGTCTCCGATACGTTTGGTCTCCCGAAAAACGCACCTCATAAAGAAAATGCAGT
ACTAACCCGCCTCCCCATGAATTTTTCGCAGCCCACCCTTGGCCCATTTCTAAAGCCCACCAAGCGGCACGGTCTTTGGGTTTTGCGAAAGTACCATCAGAGGCTATGCAAACCAGAGGGCTTTTTGCGTGGAGTATTTCTTTTACGTCA
       910        920        930        940        950        960        970        980        990       1000       1010       1020       1030       1040       1050

           300                            310                            320                            330                            340
 K  W  L  K  V  V  A  S  V  E  G  Q  D  A  F  N  P  I  K  G  S  I  P  A  R  L  D  A  D  R  S  K  Y  D  I  Y  L  Q  W  S  M  E  D  F  A  T  K  A  L  T
AAAATGGTTAAAGGTGGTAGCCTCAGTAGAGGGCCAGGATGCATTTAATCCTATCAAGGGCTCAATTCCGGCCCGTCTCGACGCAGACCGCTCAAAATATGATATCTACTTGCAATGGTCCATGGAAGATTTTGCCACGAAGGCACTCAC
TTTTACCAATTTCCACCATCGGAGTCATCTCCCGGTCCTACGTAAATTAGGATAGTTCCCGAGTTAAGGCCGGGCAGAGCTGCGTCTGGCGAGTTTTATACTATAGATGAACGTTACCAGGTACCTTCTAAAACGGTGCTTCCGTGAGTG
      1060       1070       1080       1090       1100       1110       1120       1130       1140       1150       1160       1170       1180       1190       1200

           350                            360                            370                            380                            390
 P  S  I  A  K  G  S  A  A  P  K  G  F  V  T  T  L  N  D  I  I  N  R  F  V  T  T  R  D  I  D  S  A  L  E  E  L  L  M  A  A  E  D  E  G  Y  L  V  E  G
CCCAAGCATCGCCCATGGAGAGTGCAGCCCCGGAAGGTTTTGTAACAACATTAAATGACATTATTAACCGGTTTGTAACCACCCGCGATATCGACTCCGCCCTGGAAGAACTGCTCATGGCAGCCGAGGACGAAGGGTACTTGGTAGAAGG
GGGTTCGTAGCGGGTACCCTCACGTCGGGGCCTTCCAAAACATTGTTGTAATTTACTGTAATAATTGGCCAAACATTGGTGGGCGCTATAGCTGAGGCGGGACCTTCTTGACGAGTACCGTCGGCTCCTGCTTCCCATGAACCATCTTCC
      1210       1220       1230       1240       1250       1260       1270       1280       1290       1300       1310       1320       1330       1340       1350

           400
 G  S  H  H  H  H  H  H  *  *
```

```
TGGTAGTCATCATCATCATCATCATTAATGAAAGGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGG
ACCATCAGTAGTAGTAGTAGTAGTAATTACTTTCCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCC
       1360      1370      1380      1390      1400      1410      1420      1430      1440      1450      1460      1470      1480      1490      1500

GCCTCTAAACGGGTCTTGAGGGGTTTTTTGCTGAAAGGAGGAACTATATCCGGAGCGACTCCCACGGCACGTTGGCAAGCTCG
CGGAGATTTGCCCAGAACTCCCCAAAAAACGACTTTCCTCCTTGATATAGGCCTCGCTGAGGGTGCCGTGCAACCGTTCGAGC
       1510      1520      1530      1540      1550      1560      1570      1580
```

FIG. 10 (Continued)

FIG. 11 - koGBP5

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAACGGTTTCCCTCTAGAAATAATTTTGTTTAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTGCCAAAGGGAGATCTTTATTAAAACAAATTG
        10         20         30         40         50         60         70         80         90        100        110        120        130        140        150

                              10                                      20                                      30                                      40
                     M  L  E  I  F  S  W  W  T  G  G  G  E  E  E  G  L  L  A  L  F  D  V  F  H  K  Y  Y  P  D  V  E  I  I  N  A  T  V  A  G  G  A  G  T
TTTAAGAAGGAGATATACCATGTTAGAAATTTTTAGTTGGTGGACAGGTGGTGGCGAAGAAGAAGGGCTCTTGGCTTTATTCGACGTATTCCACAAATACTACCCAGATGTCGAGATCATCAACGCCACCGTCGCTGGGGGTGCAGGGAC
AAATTCTTCCTCTATATGGTACAATCTTTAAAAATCAACCACCTGTCCACCACCGCTTCTTCTTCCCGAGAACCGAAATAAGCTGCATAAGGTGTTTATGATGGGTCTACAGCTCTAGTAGTTGCGGTGGCAGCGACCCCCACGTCCCTG
       160        170        180        190        200        210        220        230        240        250        260        270        280        290        300

              50                                      60                                      70                                      80                                      90
 N  A  K  A  V  L  K  T  R  M  L  G  G  N  P  P  D  S  F  Q  V  H  G  G  M  E  L  I  D  T  Y  V  V  T  G  M  M  E  P  I  T  D  L  L  E  E  W  G  I  I
TAACGCCAAGGCAGTATTGAAGACTCGTATGTTAGGGGGGAACCCGCCAGACAGCTTTCAGGTACACGGCGGCATGGAACTCATCGATACCTACGTAGTAACAGGGATGATGGAGCCAATTACAGACTTATTAGAGGAATGGGGTATTAT
ATTGCGGTTCCGTCATAACTTCTGAGCATACAATCCCCCCTTGGGCGGTCTGTCGAAAGTCCATGTGCCGCCGTACCTTGAGTAGCTATGGATGCATCATTGTCCCTACTACCTCGGTTAATGTCTGAATAATCTCCTTACCCCATAATA
       310        320        330        340        350        360        370        380        390        400        410        420        430        440        450

             100                                     110                                     120                                     130                                     140
 D  K  F  P  E  D  I  L  K  I  A  S  Y  K  G  E  V  Y  S  I  P  V  N  V  H  R  G  N  V  V  F  Y  N  K  A  I  L  E  E  V  G  I  E  K  V  P  S  T  W  P
TGACAAATTTCCAGAGGATATCTTGAAAATTGCGTCCTATAAAGGGGAAGTGTACAGTATTCCAGTCAACGTCCATCGTGGTAACGTCGTCTTCTACAATAAAGCTATCCTCGAAGAGGTCGGGATCGAAAAGGTGCCTAGTACATGGCC
ACTGTTTAAAGGTCTCCTATAGAACTTTTAACGCAGGATATTTCCCCTTCACATGTCATAAGGTCAGTTGCAGGTAGCACCATTGCAGCAGAAGATGTTATTTCGATAGGAGCTTCTCCAGCCCTAGCTTTTCCACGGATCATGTACCGG
       460        470        480        490        500        510        520        530        540        550        560        570        580        590        600

             150                                     160                                     170                                     180                                     190
 E  F  I  E  V  L  K  K  I  K  K  A  G  Y  I  P  L  A  L  G  D  K  N  K  W  T  A  T  H  L  F  E  D  I  L  L  S  T  L  G  P  Y  N  Y  N  G  L  W  N  G
GGAATTTATTGAAGTCCTCAAAAAAATCAAGAAGGCAGGTTATATCCCTCTTGCATTGGGTGATAAGAATAAATGGACTGCGACGCACCTGTTCGAGGACATTTTACTGTCAACTCTCGGTCCATACAATTACAACGGCCTGTGGAACGG
CCTTAAATAACTTCAGGAGTTTTTTTAGTTCTTCCGTCCAATATAGGGAGAACGTAACCCACTATTCTTATTTACCTGACGCTGCGTGGACAAGCTCCTGTAAAATGACAGTTGAGAGCCAGGTATGTTAATGTTGCCGGACACCTTGCC
       610        620        630        640        650        660        670        680        690        700        710        720        730        740        750

             200                                     210                                     220                                     230                                     240
 R  T  S  F  E  H  Q  G  V  K  E  A  L  E  I  F  K  E  L  M  N  Y  V  N  P  N  H  A  S  L  T  W  Q  D  A  T  L  L  V  F  E  G  K  A  A  F  N  V  M  G
TCGTACGTCATTTGAACATCAGGGCGTGAAGGAGGCCTTAGAGATCTTCAAAGAATTGATGAACTACGTAAACCCAAATCATGCTTCGCTGACATGGCAAGACGCCACGCTCTTGGTATTTGAAGGTAAAGCAGCATTCAACGTTATGGG
AGCATGCAGTAAACTTGTAGTCCCGCACTTCCTCCGGAATCTCTAGAAGTTTCTTAACTACTTGATGCATTTGGGTTTAGTACGAAGCGACTGTACCGTTCTGCGGTGCGAGAACCATAAACTTCCATTTCGTCGTAAGTTGCAATACCC
       760        770        780        790        800        810        820        830        840        850        860        870        880        890        900

             250                                     260                                     270                                     280                                     290
 D  W  A  E  G  Y  L  K  T  L  G  W  T  P  G  K  E  F  G  W  M  V  V  P  G  T  K  G  S  F  M  V  V  T  D  T  F  G  L  P  K  N  A  P  H  R  E  N  A  I
CGATTGGGCCGAGGGTTATCTTAAAACATTAGGGTGGACCCCAGGCAAAGAGTTCGGTTGGATGGTAGTCCCGGGTACGAAAGGTTCTTTCATGGTAGTCACCGACACCTTCGGTCTGCCTAAAAATGCGCCACACCGCGAGAACGCAAT
GCTAACCCGGCTCCCAATAGAATTTTGTAATCCCACCTGGGGTCCGTTTCTCAAGCCAACCTACCATCAGGGCCCATGCTTTCCAAGAAAGTACCATCAGTGGCTGTGGAAGCCAGACGGATTTTTACGCGGTGTGGCGCTCTTGCGTTA
       910        920        930        940        950        960        970        980        990       1000       1010       1020       1030       1040       1050

             300                                     310                                     320                                     330                                     340
 K  W  L  K  I  I  S  S  V  E  G  Q  D  T  F  N  P  I  K  G  S  I  P  A  R  I  D  A  D  R  S  L  Y  D  D  Y  L  I  W  S  M  D  D  F  A  T  N  A  L  C
CAAATGGTTAAAGATCATCAGTTCCGTGGAAGGCCAAGACACATTCAACCCTATCAAGGGTTCAATTCCAGCACGTATTGACGCCGATCGCAGCTTGTACGATGACTATCTGATCTGGTCTATGGACGATTTCGCTACAAATGCGTTGTG
GTTTACCAATTTCTAGTAGTCAAGGCACCTTCCGGTTCTGTGTAAGTTGGGATAGTTCCCAAGTTAAGGTCGTGCATAACTGCGGCTAGCGTCGAACATGCTACTGATAGACTAGACCAGATACCTGCTAAAGCGATGTTTACGCAACAC
      1060       1070       1080       1090       1100       1110       1120       1130       1140       1150       1160       1170       1180       1190       1200

             350                                     360                                     370                                     380                                     390
 P  S  I  I  H  G  S  A  A  P  E  A  F  V  T  A  L  N  D  T  I  N  M  F  I  T  R  K  D  V  K  K  A  L  K  E  I  I  Y  A  A  E  D  Y  L  E  G  G  S  H
TCCTAGCATTATCCACGGGTCCGCTGCCCCAGAAGCCTTCGTTACTGCGCTCAACGATACGATTAATATGTTCATCACACGCAAGGACGTTAAAAAAGCATTAAAGGAAATTATCTATGCAGCAGAAGATTATTTAGAAGGTGGTAGTCA
AGGATCGTAATAGGTGCCCAGGCGACGGGGTCTTCGGAAGCAATGACGCGAGTTGCTATGCTAATTATACAAGTAGTGTGCGTTCCTGCAATTTTTTCGTAATTTCCTTTAATAGATACGTCGTCTTCTAATAAATCTTCCACCATCAGT
      1210       1220       1230       1240       1250       1260       1270       1280       1290       1300       1310       1320       1330       1340       1350

             400
 H  H  H  H  H  *  *
```

```
TCATCATCATCATCATTAATGAAAGGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCCTCTAAA
AGTAGTAGTAGTAGTAATTACTTTCCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGGAGATTT
       1360      1370      1380      1390      1400      1410      1420      1430      1440      1450      1460      1470      1480      1490      1500

CGGGTCTTGAGGGGTTTTTTGCTGAAAGGAGGAACTATATCCGGAGCGACTCCCACGGCACGTTGGCAAGCTCG
GCCCAGAACTCCCCAAAAAACGACTTTCCTCCTTGATATAGGCCTCGCTGAGGGTGCCGTGCAACCGTTCGAGC
       1510      1520      1530      1540      1550      1560      1570
```

FIG. 11 (Continued)

FIG. 12 - bhGBP6

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAACGGTTTCCCTCTAGAAATAATTTTGTTTAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTGCCAAAGGGAGATCTTTATTAAAACAAATTG
10 20 30 40 50 60 70 80 90 100 110 120 130 140 150

10 20 30 40
M L E I F S W W T G A G E E D G L L A L I E L F E E K H P E I E V D N A A V A G G A G T
TTTAAGAAGGAGATATACCATGTTAGAAATTTTTAGTTGGTGGACAGGTGCAGGCGAGGAAGACGGGCTCTTAGCCCTCATTGAATTATTCGAGGAGAAGCACCCAGAGATTGAGGTCGACAACGCCGCGGTAGCCGGTGGGGCCGGGAC
AAATTCTTCCTCTATATGGTACAATCTTTAAAAATCAACCACCTGTCCACGTCCGCTCCTTCTGCCCGAGAATCGGGAGTAACTTAATAAGCTCCTCTTCGTGGGTCTCTAACTCCAGCTGTTGCGGCGCCATCGGCCACCCCGGCCCTG
160 170 180 190 200 210 220 230 240 250 260 270 280 290 300

50 60 70 80 90
N A K A V L T S R M Q G N D P P G T F Q V H G G A E L N D S W V A A G Q M D P L N D L F E A E G W A
CAATGCAAAAGCCGTACTGACATCGCGGATGCAAGGTAATGATCCACCAGGCACGTTTCAGGTTCACGGTGGCGCCGAGCTCAACGACAGCTGGGTAGCGGCCGGCCAAATGGACCCATTGAACGATTTATTCGAAGCCGAGGGGTGGGC
GTTACGTTTTCGGCATGACTGTAGCGCCTACGTTCCATTACTAGGTGGTCCGTGCAAAGTCCAAGTGCCACCGCGGCTCGAGTTGCTGTCGACCCATCGCCGGCCGGTTTACCTGGGTAACTTGCTAAATAAGCTTCGGCTCCCCACCCG
310 320 330 340 350 360 370 380 390 400 410 420 430 440 450

100 110 120 130 140
D K F P E E L I E L V S K D G N I Y S V P V N I H R G N V L W Y N T E I F E E H G L E V P T T F E E
GGACAAGTTCCCTGAGGAGCTTATCGAATTGGTCTCCAAGGATGGCAACATTTATAGCGTCCCAGTGAACATTCACCGGGGTAACGTTCTCTGGTATAACACTGAAATTTTCGAGGAGCATGGCTTAGAAGTACCGACGACATTTGAAGA
CCTGTTCAAGGGACTCCTCGAATAGCTTAACCAGAGGTTCCTACCGTTGTAAATATCGCAGGGTCACTTGTAAGTGGCCCCATTGCAAGAGACCATATTGTGACTTTAAAAGCTCCTCGTACCGAATCTTCATGGCTGCTGTAAACTTCT
460 470 480 490 500 510 520 530 540 550 560 570 580 590 600

150 160 170 180 190
F F D V A D A L Q E A G V T P L A L G D R E P W A A T H L F E T V L L G T L G A D D Y N K L W S G E
ATTTTTCGATGTAGCGGACGCCTTACAAGAAGCAGGTGTAACCCCTCTGGCCTTAGGCGACCGCGAACCATGGGCCGCCACACATTTGTTCGAGACCGTATTACTCGGCACACTCGGTGCAGATGATTATAACAAGCTGTGGAGTGGTGA
TAAAAAGCTACATCGCCTGCGGAATGTTCTTCGTCCACATTGGGGAGACCGGAATCCGCTGGCGCTTGGTACCCGGCGGTGTGTAAACAAGCTCTGGCATAATGAGCCGTGTGAGCCACGTCTACTAATATTGTTCGACACCTCACCACT
610 620 630 640 650 660 670 680 690 700 710 720 730 740 750

200 210 220 230 240
V G M D D P R V E E A A E I F I R M L D Y V N E D H S S R N W Q D A S Q L V A Q G E A A M N V M G D
AGTAGGCATGGATGACCCGCGTGTAGAAGAGGCAGCAGAGATTTTCATCCGTATGCTCGATTATGTTAATGAGGACCACAGTAGTCGTAACTGGCAAGACGCTTCACAACTCGTGGCACAGGGGGAAGCAGCCATGAATGTGATGGGCGA
TCATCCGTACCTACTGGGCGCACATCTTCTCCGTCGTCTCTAAAAGTAGGCATACGAGCTAATACAATTACTCCTGGTGTCATCAGCATTGACCGTTCTGCGAAGTGTTGAGCACCGTGTCCCCCTTCGTCGGTACTTACACTACCCGCT
760 770 780 790 800 810 820 830 840 850 860 870 880 890 900

250 260 270 280 290
W A K G Y F V N D L N L A V K E D F G W A A T P G T E G T F M V I T D T F G L P T G V E N P E V V K
TTGGGCGAAAGGCTACTTTGTTAACGACCTGAATCTCGCGGTAAAAGAGGATTTTGGTTGGGCGGCCACTCCAGGTACAGAGGGGACATTCATGGTGATCACAGACACATTCGGTTTGCCGACCGGTGTAGAGAACCCAGAGGTCGTCAA
AACCCGCTTTCCGATGAAACAATTGCTGGACTTAGAGCGCCATTTTCTCCTAAAACCAACCCGCCGGTGAGGTCCATGTCTCCCCTGTAAGTACCACTAGTGTCTGTGTAAGCCAAACGGCTGGCCACATCTCTTGGGTCTCCAGCAGTT
910 920 930 940 950 960 970 980 990 1000 1010 1020 1030 1040 1050

300 310 320 330 340
S F L A V L G S Q E G Q D A F N P L K G S I P A R V D A D V S K Y D E Y G Q E T I E D F K S A E L S
AAGTTTCCTCGCGGTCTTAGGCTCACAAGAAGGCCAGGATGCCTTCAATCCATTAAAAGGTTCCATTCCAGCTCGTGTTGACGCAGATGTTTCCAAGTACGACGAATATGGTCAAGAAACCATTGAAGATTTTAAGTCCGCGGAGCTGTC
TTCAAAGGAGCGCCAGAATCCGAGTGTTCTTCCGGTCCTACGGAAGTTAGGTAATTTTCCAAGGTAAGGTCGAGCACAACTGCGTCTACAAAGGTTCATGCTGCTTATACCAGTTCTTTGGTAACTTCTAAAATTCAGGCGCCTCGACAG
1060 1070 1080 1090 1100 1110 1120 1130 1140 1150 1160 1170 1180 1190 1200

350 360 370 380 390
P S L A H G S A A N E G F L T Q V N Q A I N I F V T Q K D V D S F V D S L K Q Y Q P G G S H H H H H
ACCATCGCTCGCGCACGGCAGTGCAGCAAACGAGGGGTTCTTGACCCAAGTGAATCAGGCTATCAACATTTTTGTAACACAGAAGGACGTAGATTCATTCGTAGACTCGTTGAAACAATATCAACCAGGTGGTAGTCATCATCATCATCA
TGGTAGCGAGCGCGTGCCGTCACGTCGTTTGCTCCCCAAGAACTGGGTTCACTTAGTCCGATAGTTGTAAAAACATTGTGTCTTCCTGCATCTAAGTAAGCATCTGAGCAACTTTGTTATAGTTGGTCCACCATCAGTAGTAGTAGTAGT
1210 1220 1230 1240 1250 1260 1270 1280 1290 1300 1310 1320 1330 1340 1350

H * *
```

```
TCATTAATGAAAGGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCCTCTAAACGGGTCTTGAGG
AGTAATTACTTTCCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGGAGATTTGCCCAGAACTCC
       1360      1370      1380      1390      1400      1410      1420      1430      1440      1450      1460      1470      1480      1490      1500

GGTTTTTTGCTGAAAGGAGGAACTATATCCGGAGCGACTCCCACGGCACGTTGGCAAGCTCG
CCAAAAAACGACTTTCCTCCTTGATATAGGCCTCGCTGAGGGTGCCGTGCAACCGTTCGAGC
       1510      1520      1530      1540      1550      1560
```

FIG. 12 (Continued)

FIG. 13 - smGBP7

CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAACGGTTTCCCTCTAGAAATAATTTTGTTTAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTGCCAAAGGGAGATCTTTATTAAAACAAATTG
10 20 30 40 50 60 70 80 90 100 110 120 130 140 150

10 20 30 40
M E L V I Y H W W T A G G E R E A I N A V F Q V F K Q K Y P N I Q I V E N P V A G G A G
TTTAAGAAGGAGATATACCATGGAATTAGTAATTTATCATTGGTGGACAGCAGGCGGGGAACGTGAGGCAATCAACGCCGTCTTCCAGGTCTTTAAGCAAAAGTACCCGAACATTCAAATCGTGGAAAATCCAGTAGCCGGCGGTGCAGG
AAATTCTTCCTCTATATGGTACCTTAATCATTAAATAGTAACCACCTGTCGTCCGCCCCTTGCACTCCGTTAGTTGCGGCAGAAGGTCCAGAAATTCGTTTTCATGGGCTTGTAAGTTTAGCACCTTTTAGGTCATCGGCCGCCACGTCC
160 170 180 190 200 210 220 230 240 250 260 270 280 290 300

50 60 70 80 90
S V M K S V I I G L L A A G T P P D T F Q V H A G A E L K E Y V D A G Y L A P I D D I W S K L G L D
CTCGGTCATGAAGAGTGTAATTATCGGCCTCCTCGCCGCAGGTACCCCACCAGACACATTTCAGGTACACGCAGGTGCAGAGTTAAAAGAGTATGTGGACGCCGGTTATCTCGCCCCAATCGACGACATTTGGTCGAAGCTGGGTCTGGA
GAGCCAGTACTTCTCACATTAATAGCCGGAGGAGCGGCGTCCATGGGGTGGTCTGTGTAAAGTCCATGTGCGTCCACGTCTCAATTTTCTCATACACCTGCGGCCAATAGAGCGGGGTTAGCTGCTGTAAACCAGCTTCGACCCAGACCT
310 320 330 340 350 360 370 380 390 400 410 420 430 440 450

100 110 120 130 140
K V I P S T L Q V M A K F N G H Y Y A V P I D V H R S N V L W Y N P K I F N E L G I I N K F G D P R
CAAGGTAATCCCGAGTACCCTCCAAGTCATGGCAAAATTTAACGGGCATTACTATGCAGTCCCAATTGACGTGCACCGGTCCAATGTACTCTGGTACAACCCTAAGATCTTCAACGAACTCGGTATCATCAACAAATTCGGTGACCCTCG
GTTCCATTAGGGCTCATGGGAGGTTCAGTACCGTTTTAAATTGCCCGTAATGATACGTCAGGGTTAACTGCACGTGGCCAGGTTACATGAGACCATGTTGGGATTCTAGAAGTTGCTTGAGCCATAGTAGTTGTTTAAGCCACTGGGAGC
460 470 480 490 500 510 520 530 540 550 560 570 580 590 600

150 160 170 180 190
N W S V D T L L Q V A R Y I K Q Q R P D I A P I A L A S R N K W P V T H L F E V L L A N A G G P E T
TAACTGGTCTGTAGATACGCTCCTCCAAGTAGCACGTTACATTAAGCAACAACGCCCTGACATCGCACCAATTGCACTGGCGTCGCGTAATAAGTGGCCAGTAACGCATCTCTTCGAGGTCCTTTTAGCCAACGCAGGCGGTCCAGAGAC
ATTGACCAGACATCTATGCGAGGAGGTTCATCGTGCAATGTAATTCGTTGTTGCGGGACTGTAGCGTGGTTAACGTGACCGCAGCGCATTATTCACCGGTCATTGCGTAGAGAAGCTCCAGGAAAATCGGTTGCGTCCGCCAGGTCTCTG
610 620 630 640 650 660 670 680 690 700 710 720 730 740 750

200 210 220 230 240
Y V K F F T G K F N Y N D P N D P V V Q T V K K V L T V M A T M A K E G L F N S N H P E L T W D Q A
TTACGTCAAATTCTTTACCGGTAAATTTAATTACAATGACCCTAATGACCCAGTTGTACAGACAGTAAAGAAAGTCCTCACCGTGATGGCGACCATGGCAAAGGAAGGTTTGTTTAACAGCAACCATCCGGAACTCACCTGGGATCAAGC
AATGCAGTTTAAGAAATGGCCATTTAAATTAATGTTACTGGGATTACTGGGTCAACATGTCTGTCATTTCTTTCAGGAGTGGCACTACCGCTGGTACCGTTTCCTTCCAAACAAATTGTCGTTGGTAGGCCTTGAGTGGACCCTAGTTCG
760 770 780 790 800 810 820 830 840 850 860 870 880 890 900

250 260 270 280 290
A A L V A E G K A A M F I H G D W V A G Y Y I A N N Y K Y G K D W A A A P F P K N I F I L L S D A F
AGCAGCGCTTGTAGCTGAAGGCAAGGCAGCAATGTTCATTCACGGGGATTGGGTCGCCGGCTACTATATCGCCAATAACTATAAATACGGTAAGGATTGGGCTGCGGCACCGTTCCCGAAAAACATCTTCATCCTGCTTTCAGATGCCTT
TCGTCGCGAACATCGACTTCCGTTCCGTCGTTACAAGTAAGTGCCCCTAACCCAGCGGCCGATGATATAGCGGTTATTGATATTTATGCCATTCCTAACCCGACGCCGTGGCAAGGGCTTTTTGTAGAAGTAGGACGAAAGTCTACGGAA
910 920 930 940 950 960 970 980 990 1000 1010 1020 1030 1040 1050

300 310 320 330 340
E L P K N A P H P E A A K D W L M V V G S K E A Q E K F N L I K G S I P A R T D V S P K Y P D P Y R
CGAATTGCCAAAAAACGCCCCTCACCCTGAGGCCGCCAAGGATTGGCTCATGGTTGTCGGTAGTAAGGAAGCACAAGAGAAATTCAATCTCATCAAGGGGTCGATCCCAGCACGCACTGACGTCTCCCCAAAATACCCAGATCCGTACCG
GCTTAACGGTTTTTTGCGGGGAGTGGGACTCCGGCGGTTCCTAACCGAGTACCAACAGCCATCATTCCTTCGTGTTCTCTTTAAGTTAGAGTAGTTCCCCAGCTAGGGTCGTGCGTGACTGCAGAGGGGTTTTATGGGTCTAGGCATGGC
1060 1070 1080 1090 1100 1110 1120 1130 1140 1150 1160 1170 1180 1190 1200

350 360 370 380 390
P E T A E D F Q K S T L I P S A V H G G I A K E A F M T D L H N I L T S M L T A V S V G T P V D N A
GCCAGAGACAGCGGAAGACTTCCAGAAATCAACATTGATTCCTTCAGCTGTTCACGGCGGTATCGCTAAAGAAGCCTTTATGACAGATTTACACAACATTTTGACATCGATGCTGACGGCCGTCTCGGTAGGTACTCCGGTGGACAATGC
CGGTCTCTGTCGCCTTCTGAAGGTCTTTAGTTGTAACTAAGGAAGTCGACAAGTGCCGCCATAGCGATTTCTTCGGAAATACTGTCTAAATGTGTTGTAAAACTGTAGCTACGACTGCCGGCAGAGCCATCCATGAGGCCACCTGTTACG
1210 1220 1230 1240 1250 1260 1270 1280 1290 1300 1310 1320 1330 1340 1350

400 410 420 430
V N T A L A Q I L Q S V K T S G L A S F W K G Y T I D Y F I T K R G G S H H H H H H * *

```
GGTGAATACAGCATTAGCCCAAATCCTTCAGTCAGTAAAAACGTCCGGCTTGGCGTCGTTTTGGAAAGGTTACACAATTGACTACTTTATCACAAAGCGTGGCGGTTCTCATCATCATCATCATCATTAATGAAAGGGCGATATCCAGCA
CCACTTATGTCGTAATCGGGTTTAGGAAGTCAGTCATTTTTGCAGGCCGAACCGCAGCAAAACCTTTCCAATGTGTTAACTGATGAAATAGTGTTTCGCACCGCCAAGAGTAGTAGTAGTAGTAGTAATTACTTTCCCGCTATAGGTCGT
       1360      1370      1380      1390      1400      1410      1420      1430      1440      1450      1460      1470      1480      1490      1500

CACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATA
GTGACCGCCGGCAATGATCACCTAGGCCGACGATTGTTTCGGGCTTTCCTTCGACTCAACCGACGACGGTGGCGACTCGTTATTGATCGTATTGGGGAACCCCGGAGATTTGCCCAGAACTCCCCAAAAAACGACTTTCCTCCTTGATAT
       1510      1520      1530      1540      1550      1560      1570      1580      1590      1600      1610      1620      1630      1640      1650

TCCGGAGCGACTCCCACGGCACGTTGGCAAGCTCG
AGGCCTCGCTGAGGGTGCCGTGCAACCGTTCGAGC
       1660      1670      1680
```

FIG. 13 (Continued)

FIG. 14 - asGBP8

CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAACGGTTTCCCTCTAGAAATAATTTTGTTTAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTGCCAAAGGGAGATCTTTATTAAAACAAATTG
10 20 30 40 50 60 70 80 90 100 110 120 130 140 150

10 20 30 40
M K L E I T S W W T S G S E A D A L N V L I D G V K A A K P G L S V D N A A V S G G G G
TTTAAGAAGGAGATATACCATGAAATTAGAAATTACAAGTTGGTGGACTTCCGGGAGTGAGGCAGATGCCCTTAACGTACTCATCGACGGTGTCAAAGCCGCAAAACCGGGTCTCAGCGTAGACAACGCAGCGGTCTCAGGGGGCGGCGG
AAATTCTTCCTCTATATGGTACTTTAATCTTTAATGTTCAACCACCTGAAGGCCCTCACTCCGTCTACGGGAATTGCATGAGTAGCTGCCACAGTTTCGGCGTTTTGGCCCAGAGTCGCATCTGTTGCGTCGCCAGAGTCCCCCGCCGCC
160 170 180 190 200 210 220 230 240 250 260 270 280 290 300

50 60 70 80 90
A N A R Q A L A A R L Q A G S P P D A W Q V H P A G Q L K S Y V D G G Q V A D L T D L W T E G D W A
CGCCAACGCCCGCCAGGCACTCGCAGCACGTCTCCAAGCAGGCAGTCCACCTGACGCCTGGCAAGTTCATCCAGCAGGTCAATTAAAGTCCTATGTAGACGGGGGCCAGGTGGCCGACCTCACTGATTTATGGACTGAAGGCGATTGGGC
GCGGTTGCGGGCGGTCCGTGAGCGTCGTGCAGAGGTTCGTCCGTCAGGTGGACTGCGGACCGTTCAAGTAGGTCGTCCAGTTAATTTCAGGATACATCTGCCCCCGGTCCACCGGCTGGAGTGACTAAATACCTGACTTCCGCTAACCCG
310 320 330 340 350 360 370 380 390 400 410 420 430 440 450

100 110 120 130 140
S Q M P K D V A E A Q Q V D G K Y Y T V P I G V H R G N V L W T N P A V L S K A N V T I D A D A G I
CTCGCAAATGCCGAAAGACGTAGCCGAGGCGCAACAGGTAGACGGTAAATACTACACAGTACCAATCGGTGTGCACCGCGGTAATGTACTCTGGACAAATCCAGCCGTACTCAGCAAAGCGAATGTAACCATTGACGCAGACGCGGGTAT
GAGCGTTTACGGCTTTCTGCATCGGCTCCGCGTTGTCCATCTGCCATTTATGATGTGTCATGGTTAGCCACACGTGGCGCCATTACATGAGACCTGTTTAGGTCGGCATGAGTCGTTTCGCTTACATTGGTAACTGCGTCTGCGCCCATA
460 470 480 490 500 510 520 530 540 550 560 570 580 590 600

150 160 170 180 190
D G L I S S L E Q V Q A S G T T P L A L G D K D I F A S S Q L L E S L I M S R A G A D N W T K L F T
CGACGGGCTCATCTCTTCATTGGAACAAGTACAAGCAAGTGGGACTACCCCGTTGGCTTTAGGTGACAAAGACATTTTCGCAAGTTCCCAGCTGTTAGAGTCCCTGATTATGTCGCGGGCTGGTGCCGATAACTGGACAAAACTCTTTAC
GCTGCCCGAGTAGAGAAGTAACCTTGTTCATGTTCGTTCACCCTGATGGGGCAACCGAAATCCACTGTTTCTGTAAAAGCGTTCAAGGGTCGACAATCTCAGGGACTAATACAGCGCCCGACCACGGCTATTGACCTGTTTTGAGAAATG
610 620 630 640 650 660 670 680 690 700 710 720 730 740 750

200 210 220 230 240
S E Y S F D A P E V K Q A L E D Y K T I L S F A N K D H S A I T W D E A A K K M A D G E A A V N L N
AAGTGAGTATTCCTTCGATGCACCAGAAGTCAAACAAGCCCTTGAAGACTATAAAACGATCCTCAGCTTTGCAAATAAGGACCATAGCGCCATCACCTGGGACGAGGCAGCTAAGAAGATGGCCGACGGTGAAGCCGCAGTAAACTTGAT
TTCACTCATAAGGAAGCTACGTGGTCTTCAGTTTGTTCGGGAACTTCTGATATTTTGCTAGGAGTCGAAACGTTTATTCCTGGTATCGCGGTAGTGGACCCTGCTCCGTCGATTCTTCTACCGGCTGCCACTTCGGCGTCATTTGAACTA
760 770 780 790 800 810 820 830 840 850 860 870 880 890 900

250 260 270 280 290
G D W A Y G E L L N A G K K P G T D F A W V A F P G K E D I F D Y V G D G F S I P A N N I P H A E A
GGGCGATTGGGCGTACGGCGAACTCTTGAACGCAGGGAAGAAACCAGGGACCGATTTCGCATGGGTGGCATTTCCGGGCAAAGAGGACATCTTCGATTATGTAGGTGACGGTTTTAGTATCCCGGCAAACAATATTCCACACGCGGAGGC
CCCGCTAACCCGCATGCCGCTTGAGAACTTGCGTCCCTTCTTTGGTCCCTGGCTAAAGCGTACCCACCGTAAAGGCCCGTTTCTCCTGTAGAAGCTAATACATCCACTGCCAAAATCATAGGGCCGTTTGTTATAAGGTGTGCGCCTCCG
910 920 930 940 950 960 970 980 990 1000 1010 1020 1030 1040 1050

300 310 320 330 340
A R A W L K T L M D P K I Q T E F A A K K G S I P A V T S A D I S G L S E Y Q Q E A A K S L A S G A
AGCTCGGGCGTGGCTGAAGACCTTAATGGATCCAAAAATCCAAACCGAATTTGCCGCCAAAAAAGGGTCGATTCCAGCCGTCACAAGTGCCGACATTTCCGGCCTGAGTGAATACCAGCAGGAAGCTGCCAAATCTCTCGCCAGTGGTGC
TCGAGCCCGCACCGACTTCTGGAATTACCTAGGTTTTTAGGTTTGGCTTAAACGGCGGTTTTTTCCCAGCTAAGGTCGGCAGTGTTCACGGCTGTAAAGGCCGGACTCACTTATGGTCGTCCTTCGACGGTTTAGAGAGCGGTCACCACG
1060 1070 1080 1090 1100 1110 1120 1130 1140 1150 1160 1170 1180 1190 1200

350 360 370 380 390
V V S S L A H A Q A A G A E F A Q T Y A D A V S T F N G S G N T D A F I A S M T Q A Q K T Q L G G S
CGTAGTCAGTTCTTTAGCGCATGCACAAGCAGCCGGTGCAGAGTTCGCCCAAACATACGCAGATGCAGTAAGCACTTTCAACGGTAGCGGCAATACTGACGCGTTCATCGCTTCCATGACCCAGGCCCAGAAAACACAGTTAGGTGGTTC
GCATCAGTCAAGAAATCGCGTACGTGTTCGTCGGCCACGTCTCAAGCGGGTTTGTATGCGTCTACGTCATTCGTGAAAGTTGCCATCGCCGTTATGACTGCGCAAGTAGCGAAGGTACTGGGTCCGGGTCTTTTGTGTCAATCCACCAAG
1210 1220 1230 1240 1250 1260 1270 1280 1290 1300 1310 1320 1330 1340 1350

400
H H H H H H * *

```
ACATCATCATCATCATCATTAATGAAAGGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCCTCT
TGTAGTAGTAGTAGTAGTAATTACTTTCCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGGAGA
       1360      1370      1380      1390      1400      1410      1420      1430      1440      1450      1460      1470      1480      1490      1500

AAACGGGTCTTGAGGGGTTTTTTGCTGAAAGGAGGAACTATATCCGGAGCGACTCCCACGGCACGTTGGCAAGCTCG
TTTGCCCAGAACTCCCCAAAAAACGACTTTCCTCCTTGATATAGGCCTCGCTGAGGGTGCCGTGCAACCGTTCGAGC
       1510      1520      1530      1540      1550      1560      1570
```

FIG. 14 (Continued)

FIG. 15 - tsGBP2_C8

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                          10                  20
                                                        M  K  L  E  I  F  S  C  W  A  G  D  E  G  P  A  L  E  A  L  I  R  L  Y
GGTTTCCCTCTAGAAATAATTTTGTTTAACTTTAAGAAGGAGATATACCATGAAATTAGAAATTTTTTCTTGCTGGGCAGGTGATGAAGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACGACCCGTCCACTACTTCCGGGTCGAGAGCTTCGGAACTAGGCCAACAT
       130       140       150       160       170       180       190       200       210       220       230       240

           30                  40                  50                  60
 K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
       250       260       270       280       290       300       310       320       330       340       350       360

           70                  80                  90                 100
 V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

          110                 120                 130                 140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

          150                 160                 170                 180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

          190                 200                 210                 220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

          230                 240                 250                 260
 Q  Q  A  V  D  R  V  V  Q  G  K  A  A  F  N  I  M  G  D  W  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850       860       870       880       890       900       910       920       930       940       950       960
```

```
               270                                     280                                     290                                     300
 P  S  P  G  T  S  G  I  F  M  M  L  S  D  S  F  G  L  P  K  G  A  K  N  R  Q  N  A  I  N  W  L  K  L  V  G  S  K  E  G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
        970       980       990      1000      1010      1020      1030      1040      1050      1060      1070      1080

               310                                     320                                     330                                     340
 Q  D  T  F  N  P  L  K  G  S  I  A  A  R  L  D  S  D  P  A  K  Y  N  A  Y  G  Q  S  A  M  K  D  W  K  S  N  R  I  V  G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
       1090      1100      1110      1120      1130      1140      1150      1160      1170      1180      1190      1200

               350                                     360                                     370                                     380
 S  L  V  H  G  A  V  A  P  E  S  F  M  S  Q  F  G  T  V  M  E  I  F  L  Q  S  R  N  P  Q  A  A  A  N  A  A  Q  A  I  A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
       1210      1220      1230      1240      1250      1260      1270      1280      1290      1300      1310      1320

               390                                     400
 N  Q  V  G  L  G  R  G  G  S  H  H  H  H  H  H  *  *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
       1330      1340      1350      1360      1370      1380      1390      1400      1410      1420      1430      1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
       1450      1460      1470      1480      1490      1500      1510      1520      1530      1540      1550      1560


GCACGTTGGCAAGCTCG
CGTGCAACCGTTCGAGC
       1570
```

FIG. 15 (Continued)

FIG. 16 - tsGBP2_C9

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10         20         30         40         50         60         70         80         90        100        110        120

                                                                                          10                            20
                                                                      M  K  L  E  I  F  S  W  C  A  G  D  E  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGCGCAGGTGATGAAGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACGCGTCCACTACTTCCGGGTCGAGAGCTTCGGAACTAGGCCAACAT
       130        140        150        160        170        180        190        200        210        220        230        240

              30                             40                             50                            60
 K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
       250        260        270        280        290        300        310        320        330        340        350        360

              70                             80                             90                           100
 V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370        380        390        400        410        420        430        440        450        460        470        480

             110                            120                            130                           140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490        500        510        520        530        540        550        560        570        580        590        600

             150                            160                            170                           180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610        620        630        640        650        660        670        680        690        700        710        720

             190                            200                            210                           220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730        740        750        760        770        780        790        800        810        820        830        840

             230                            240                            250                           260
 Q  Q  A  V  D  R  V  V  Q  G  K  A  A  F  N  I  M  G  D  W  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850        860        870        880        890        900        910        920        930        940        950        960
```

```
               270                                     280                                     290                                     300
 P  S  P  G  T  S  G  I  F  M  M  L  S  D  S  F  G  L  P  K  G  A  K  N  R  Q  N  A  I  N  W  L  K  L  V  G  S  K  E  G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
         970         980         990        1000        1010        1020        1030        1040        1050        1060        1070        1080

               310                                     320                                     330                                     340
 Q  D  T  F  N  P  L  K  G  S  I  A  A  R  L  D  S  D  P  A  K  Y  N  A  Y  G  Q  S  A  M  K  D  W  K  S  N  R  I  V  G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
        1090        1100        1110        1120        1130        1140        1150        1160        1170        1180        1190        1200

               350                                     360                                     370                                     380
 S  L  V  H  G  A  V  A  P  E  S  F  M  S  Q  F  G  T  V  M  E  I  F  L  Q  S  R  N  P  Q  A  A  A  N  A  A  Q  A  I  A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
        1210        1220        1230        1240        1250        1260        1270        1280        1290        1300        1310        1320

               390                                     400
 N  Q  V  G  L  G  R  G  G  S  H  H  H  H  H  H  *  *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
        1330        1340        1350        1360        1370        1380        1390        1400        1410        1420        1430        1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
        1450        1460        1470        1480        1490        1500        1510        1520        1530        1540        1550        1560


GCACGTTGGCAAGCTCG
CGTGCAACCGTTCGAGC
        1570
```

FIG. 16 (Continued)

FIG. 17 - tsGBP2_C12

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                   10                            20
                                                               M  K  L  E  I  F  S  W  W  A  G  C  E  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGGGCAGGTTGCGAAGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACCCGTCCAACGCTTCCGGGTCGAGAGCTTCGGAACTAGGCCAACAT
       130       140       150       160       170       180       190       200       210       220       230       240

          30                            40                            50                            60
 K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
       250       260       270       280       290       300       310       320       330       340       350       360

          70                            80                            90                           100
 V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

         110                           120                           130                           140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

         150                           160                           170                           180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

         190                           200                           210                           220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

         230                           240                           250                           260
 Q  Q  A  V  D  R  V  V  Q  G  K  A  A  F  N  I  M  G  D  W  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850       860       870       880       890       900       910       920       930       940       950       960
```

```
                270                           280                           290                           300
 P  S  P  G  T  S  G  I  F  M  M  L  S  D  S  F  G  L  P  K  G  A  K  N  R  Q  N  A  I  N  W  L  K  L  V  G  S  K  E  G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
        970       980       990      1000      1010      1020      1030      1040      1050      1060      1070      1080

                310                           320                           330                           340
 Q  D  T  F  N  P  L  K  G  S  I  A  A  R  L  D  S  D  P  A  K  Y  N  A  Y  G  Q  S  A  M  K  D  W  K  S  N  R  I  V  G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
       1090      1100      1110      1120      1130      1140      1150      1160      1170      1180      1190      1200

                350                           360                           370                           380
 S  L  V  H  G  A  V  A  P  E  S  F  M  S  Q  F  G  T  V  M  E  I  F  L  Q  S  R  N  P  Q  A  A  A  N  A  A  Q  A  I  A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
       1210      1220      1230      1240      1250      1260      1270      1280      1290      1300      1310      1320

                390                           400
 N  Q  V  G  L  G  R  G  G  S  H  H  H  H  H  H  *  *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
       1330      1340      1350      1360      1370      1380      1390      1400      1410      1420      1430      1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
       1450      1460      1470      1480      1490      1500      1510      1520      1530      1540      1550      1560


GCACGTTGGCAAGCTCG
CGTGCAACCGTTCGAGC
       1570
```

FIG. 17 (Continued)

FIG. 18 - tsGBP2_C13

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                 10                            20
                                                        M  K  L  E  I  F  S  W  W  A  G  D  C  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGGGCAGGTGATTGCGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACCCGTCCACTAACGCCGGGTCGAGAGCTTCGGAACTAGGCCAACAT
       130       140       150       160       170       180       190       200       210       220       230       240

          30                            40                            50                            60
 K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
       250       260       270       280       290       300       310       320       330       340       350       360

          70                            80                            90                           100
 V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

         110                           120                           130                           140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

         150                           160                           170                           180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

         190                           200                           210                           220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

         230                           240                           250                           260
 Q  Q  A  V  D  R  V  V  Q  G  K  A  A  F  N  I  M  G  D  W  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850       860       870       880       890       900       910       920       930       940       950       960
```

```
              270                                280                                290                                300
 P  S  P  G  T  S  G  I  F  M  M  L  S  D  S  F  G  L  P  K  G  A  K  N  R  Q  N  A  I  N  W  L  K  L  V  G  S  K  E  G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
        970       980       990      1000      1010      1020      1030      1040      1050      1060      1070      1080

              310                                320                                330                                340
 Q  D  T  F  N  P  L  K  G  S  I  A  A  R  L  D  S  D  P  A  K  Y  N  A  Y  G  Q  S  A  M  K  D  W  K  S  N  R  I  V  G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
       1090      1100      1110      1120      1130      1140      1150      1160      1170      1180      1190      1200

              350                                360                                370                                380
 S  L  V  H  G  A  V  A  P  E  S  F  M  S  Q  F  G  T  V  M  E  I  F  L  Q  S  R  N  P  Q  A  A  A  N  A  A  Q  A  I  A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
       1210      1220      1230      1240      1250      1260      1270      1280      1290      1300      1310      1320

              390                                400
 N  Q  V  G  L  G  R  G  G  S  H  H  H  H  H  H  *  *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
       1330      1340      1350      1360      1370      1380      1390      1400      1410      1420      1430      1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
       1450      1460      1470      1480      1490      1500      1510      1520      1530      1540      1550      1560


GCACGTTGGCAAGCTCG
CGTGCAACCGTTCGAGC
       1570
```

FIG. 18 (Continued)

FIG. 19 - tsGBP2_C41

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                 10                  20
                                                  M  K  L  E  I  F  S  W  W  A  G  D  E  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGGGCAGGTGATGAAGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACCCGTCCACTACTTCCGGGTCGAGAGCTTCGGAACTAGGCCAACAT
       130       140       150       160       170       180       190       200       210       220       230       240

          30                  40                  50                  60
 K  Q  K  Y  P  G  V  E  V  I  N  A  T  V  T  G  C  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGTGCGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCACGCGGCCACAGTTGCGGTTTCGGCAGGAATTTTGCGCATACGAGCCGCCCCTGGGTGGTCTATGGAAAGT
       250       260       270       280       290       300       310       320       330       340       350       360

          70                  80                  90                 100
 V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

         110                 120                 130                 140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

         150                 160                 170                 180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

         190                 200                 210                 220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

         230                 240                 250                 260
 Q  Q  A  V  D  R  V  V  Q  G  K  A  A  F  N  I  M  G  D  W  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850       860       870       880       890       900       910       920       930       940       950       960
```

```
            270                                280                                290                                300
 P  S  P  G  T  S  G  I  F  M  M  L  S  D  S  F  G  L  P  K  G  A  K  N  R  Q  N  A  I  N  W  L  K  L  V  G  S  K  E  G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
       970       980       990      1000      1010      1020      1030      1040      1050      1060      1070      1080

            310                                320                                330                                340
 Q  D  T  F  N  P  L  K  G  S  I  A  A  R  L  D  S  D  P  A  K  Y  N  A  Y  G  Q  S  A  M  K  D  W  K  S  N  R  I  V  G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
      1090      1100      1110      1120      1130      1140      1150      1160      1170      1180      1190      1200

            350                                360                                370                                380
 S  L  V  H  G  A  V  A  P  E  S  F  M  S  Q  F  G  T  V  M  E  I  F  L  Q  S  R  N  P  Q  A  A  A  N  A  A  Q  A  I  A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
      1210      1220      1230      1240      1250      1260      1270      1280      1290      1300      1310      1320

            390                                400
 N  Q  V  G  L  G  R  G  G  S  H  H  H  H  H  H  *  *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
      1330      1340      1350      1360      1370      1380      1390      1400      1410      1420      1430      1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
      1450      1460      1470      1480      1490      1500      1510      1520      1530      1540      1550      1560


GCACGTTGGCAAGCTCG
CGTGCAACCGTTCGAGC
      1570
```

FIG. 19 (Continued)

FIG. 20 - tsGBP2_C42

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                          10                            20
                                                 M  K  L  E  I  F  S  W  W  A  G  D  E  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGGGCAGGTGATGAAGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACCCGTCCACTACTTCCGGGTCGAGAGCTTCGGAACTAGGCCAACAT
       130       140       150       160       170       180       190       200       210       220       230       240

      30                            40                            50                            60
K  Q  K  Y  P  G  V  E  V  I  N  A  T  V  T  G  G  C  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTTGCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCAACGCCACAGTTGCGGTTTCGGCAGGAATTTTGCGCATACGAGCCGCCCCTGGGTGGTCTATGGAAAGT
       250       260       270       280       290       300       310       320       330       340       350       360

      70                            80                            90                           100
V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

     110                           120                           130                           140
L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

     150                           160                           170                           180
F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

     190                           200                           210                           220
G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

     230                           240                           250                           260
Q  Q  A  V  D  R  V  V  Q  G  K  A  A  F  N  I  M  G  D  W  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850       860       870       880       890       900       910       920       930       940       950       960
```

```
        270                                280                                290                                300
P  S  P  G  T  S  G  I  F  M  M  L  S  D  S  F  G  L  P  K  G  A  K  N  R  Q  N  A  I  N  W  L  K  L  V  G  S  K  E  G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
      970       980       990      1000      1010      1020      1030      1040      1050      1060      1070      1080

        310                                320                                330                                340
Q  D  T  F  N  P  L  K  G  S  I  A  A  R  L  D  S  D  P  A  K  Y  N  A  Y  G  Q  S  A  M  K  D  W  K  S  N  R  I  V  G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
     1090      1100      1110      1120      1130      1140      1150      1160      1170      1180      1190      1200

        350                                360                                370                                380
S  L  V  H  G  A  V  A  P  E  S  F  M  S  Q  F  G  T  V  M  E  I  F  L  Q  S  R  N  P  Q  A  A  A  N  A  A  Q  A  I  A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
     1210      1220      1230      1240      1250      1260      1270      1280      1290      1300      1310      1320

        390                                400
N  Q  V  G  L  G  R  G  G  S  H  H  H  H  H  H  *  *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
     1330      1340      1350      1360      1370      1380      1390      1400      1410      1420      1430      1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
     1450      1460      1470      1480      1490      1500      1510      1520      1530      1540      1550      1560


GCACGTTGGCAAGCTCG
CGTGCAACCGTTCGAGC
     1570
```

FIG. 20 (Continued)

FIG. 21 - tsGBP2_C64

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                  10                            20
                                                        M  K  L  E  I  F  S  W  W  A  G  D  E  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGGGCAGGTGATGAAGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACCCGTCCACTACTTCCGGGTCGAGAGCTTCGGAACTAGGCCAACAT
       130       140       150       160       170       180       190       200       210       220       230       240

              30                            40                            50                            60
 K  Q  K  Y  P  G  V  E  V  I  N  A  T  V  T  G  G  A  G  V  N  A  K  A  V  L  K  T  R  M  L  G  G  D  P  P  D  T  F  C
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTTG
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAAC
       250       260       270       280       290       300       310       320       330       340       350       360

              70                            80                            90                           100
 V  H  A  G  Q  E  L  I  G  T  W  V  V  A  D  R  M  E  D  L  T  S  L  F  R  Q  E  G  W  L  Q  A  F  P  K  G  L  I  D  L
CGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
GCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

             110                           120                           130                           140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

             150                           160                           170                           180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

             190                           200                           210                           220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

             230                           240                           250                           260
 Q  Q  A  V  D  R  V  V  Q  G  K  A  A  F  N  I  M  G  D  W  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850       860       870       880       890       900       910       920       930       940       950       960
```

```
                270                                     280                                     290                                     300
 P   S   P   G   T   S   G   I   F   M   M   L   S   D   S   F   G   L   P   K   G   A   K   N   R   Q   N   A   I   N   W   L   K   L   V   G   S   K   E   G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
       970       980       990      1000      1010      1020      1030      1040      1050      1060      1070      1080

                310                                     320                                     330                                     340
 Q   D   T   F   N   P   L   K   G   S   I   A   A   R   L   D   S   D   P   A   K   Y   N   A   Y   G   Q   S   A   M   K   D   W   K   S   N   R   I   V   G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
      1090      1100      1110      1120      1130      1140      1150      1160      1170      1180      1190      1200

                350                                     360                                     370                                     380
 S   L   V   H   G   A   V   A   P   E   S   F   M   S   Q   F   G   T   V   M   E   I   F   L   Q   S   R   N   P   Q   A   A   A   N   A   A   Q   A   I   A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
      1210      1220      1230      1240      1250      1260      1270      1280      1290      1300      1310      1320

                390                                     400
 N   Q   V   G   L   G   R   G   G   S   H   H   H   H   H   H   *   *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
      1330      1340      1350      1360      1370      1380      1390      1400      1410      1420      1430      1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
      1450      1460      1470      1480      1490      1500      1510      1520      1530      1540      1550      1560


GCACGTTGGCAAGCTCG
CGTGCAACCGTTCGAGC
      1570
```

FIG. 21 (Continued)

FIG. 22 - tsGBP2_C66

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                   10                            20
                                                   M  K  L  E  I  F  S  W  W  A  G  D  E  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGGGCAGGTGATGAAGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACCCGTCCACTACTTCCGGGTCGAGAGCTTCGGAACTAGGCCAACAT
       130       140       150       160       170       180       190       200       210       220       230       240

          30                            40                            50                            60
 K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
       250       260       270       280       290       300       310       320       330       340       350       360

          70                            80                            90                           100
 V  C  A  G  Q  E  L  I  G  T  W  V  V  A  D  R  M  E  D  L  T  S  L  F  R  Q  E  G  W  L  Q  A  F  P  K  G  L  I  D  L
AGTATGCGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATACGCGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

         110                           120                           130                           140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

         150                           160                           170                           180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

         190                           200                           210                           220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

         230                           240                           250                           260
 Q  Q  A  V  D  R  V  V  Q  G  K  A  A  F  N  I  M  G  D  W  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850       860       870       880       890       900       910       920       930       940       950       960
```

```
          270                 280                 290                 300
 P  S  P  G  T  S  G  I  F  M  M  L  S  D  S  F  G  L  P  K  G  A  K  N  R  Q  N  A  I  N  W  L  K  L  V  G  S  K  E  G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
       970       980       990      1000      1010      1020      1030      1040      1050      1060      1070      1080

          310                 320                 330                 340
 Q  D  T  F  N  P  L  K  G  S  I  A  A  R  L  D  S  D  P  A  K  Y  N  A  Y  G  Q  S  A  M  K  D  W  K  S  N  R  I  V  G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
      1090      1100      1110      1120      1130      1140      1150      1160      1170      1180      1190      1200

          350                 360                 370                 380
 S  L  V  H  G  A  V  A  P  E  S  F  M  S  Q  F  G  T  V  M  E  I  F  L  Q  S  R  N  P  Q  A  A  A  N  A  A  Q  A  I  A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
      1210      1220      1230      1240      1250      1260      1270      1280      1290      1300      1310      1320

          390                 400
 N  Q  V  G  L  G  R  G  G  S  H  H  H  H  H  H  *  *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
      1330      1340      1350      1360      1370      1380      1390      1400      1410      1420      1430      1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
      1450      1460      1470      1480      1490      1500      1510      1520      1530      1540      1550      1560


GCACGTTGGCAAGCTCG
CGTGCAACCGTTCGAGC
      1570
```

FIG. 22 (Continued)

FIG. 23 - tsGBP2_C119

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                   10                            20
                                                       M  K  L  E  I  F  S  W  W  A  G  D  E  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGGGCAGGTGATGAAGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACCCGTCCACTACTTCCGGGTCGAGAGCTTCGGAACTAGGCCAACAT
       130       140       150       160       170       180       190       200       210       220       230       240

                    30                            40                            50                            60
 K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
       250       260       270       280       290       300       310       320       330       340       350       360

                    70                            80                            90                           100
 V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

                   110                           120                           130                           140
 L  S  Y  K  G  G  I  W  S  V  P  V  N  I  C  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCTGCCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGACGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

                   150                           160                           170                           180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

                   190                           200                           210                           220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

                   230                           240                           250                           260
 Q  Q  A  V  D  R  V  V  Q  G  K  A  A  F  N  I  M  G  D  W  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850       860       870       880       890       900       910       920       930       940       950       960
```

```
            270                       280                       290                       300
 P  S  P  G  T  S  G  I  F  M  M  L  S  D  S  F  G  L  P  K  G  A  K  N  R  Q  N  A  I  N  W  L  K  L  V  G  S  K  E  G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
       970       980       990      1000      1010      1020      1030      1040      1050      1060      1070      1080

            310                       320                       330                       340
 Q  D  T  F  N  P  L  K  G  S  I  A  A  R  L  D  S  D  P  A  K  Y  N  A  Y  G  Q  S  A  M  K  D  W  K  S  N  R  I  V  G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
      1090      1100      1110      1120      1130      1140      1150      1160      1170      1180      1190      1200

            350                       360                       370                       380
 S  L  V  H  G  A  V  A  P  E  S  F  M  S  Q  F  G  T  V  M  E  I  F  L  Q  S  R  N  P  Q  A  A  A  N  A  A  Q  A  I  A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
      1210      1220      1230      1240      1250      1260      1270      1280      1290      1300      1310      1320

            390                       400
 N  Q  V  G  L  G  R  G  G  S  H  H  H  H  H  H  *  *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
      1330      1340      1350      1360      1370      1380      1390      1400      1410      1420      1430      1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
      1450      1460      1470      1480      1490      1500      1510      1520      1530      1540      1550      1560


GCACGTTGGCAAGCTCG
CGTGCAACCGTTCGAGC
      1570
```

FIG. 23 (Continued)

FIG. 24 - tsGBP2_C167

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10         20         30         40         50         60         70         80         90        100        110        120

                                                                                    10                            20
                                                  M  K  L  E  I  F  S  W  W  A  G  D  E  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGGGCAGGTGATGAAGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACCCGTCCACTACTTCCGGGTCGAGAGCTTCGGAACTAGGCCAACAT
       130        140        150        160        170        180        190        200        210        220        230        240

          30                            40                            50                            60
 K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
       250        260        270        280        290        300        310        320        330        340        350        360

          70                            80                            90                           100
 V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370        380        390        400        410        420        430        440        450        460        470        480

         110                           120                           130                           140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490        500        510        520        530        540        550        560        570        580        590        600

         150                           160                           170                           180
 F  L  A  T  A  Q  T  L  K  R  K  G  L  E  A  P  L  A  L  G  E  N  C  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGCACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACGTGTGTCGTTGTAGAGACCCTTTCGCAGCGGGAGCGGTGTGACCCACGGCT
       610        620        630        640        650        660        670        680        690        700        710        720

         190                           200                           210                           220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730        740        750        760        770        780        790        800        810        820        830        840

         230                           240                           250                           260
 Q  Q  A  V  D  R  V  V  Q  G  K  A  A  F  N  I  M  G  D  W  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850        860        870        880        890        900        910        920        930        940        950        960
```

```
                270                                     280                                     290                                     300
 P   S   P   G   T   S   G   I   F   M   M   L   S   D   S   F   G   L   P   K   G   A   K   N   R   Q   N   A   I   N   W   L   K   L   V   G   S   K   E   G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
        970       980       990      1000      1010      1020      1030      1040      1050      1060      1070      1080

                310                                     320                                     330                                     340
 Q   D   T   F   N   P   L   K   G   S   I   A   A   R   L   D   S   D   P   A   K   Y   N   A   Y   G   Q   S   A   M   K   D   W   K   S   N   R   I   V   G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
       1090      1100      1110      1120      1130      1140      1150      1160      1170      1180      1190      1200

                350                                     360                                     370                                     380
 S   L   V   H   G   A   V   A   P   E   S   F   M   S   Q   F   G   T   V   M   E   I   F   L   Q   S   R   N   P   Q   A   A   A   N   A   A   Q   A   I   A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
       1210      1220      1230      1240      1250      1260      1270      1280      1290      1300      1310      1320

                390                                     400
 N   Q   V   G   L   G   R   G   G   S   H   H   H   H   H   H   *   *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
       1330      1340      1350      1360      1370      1380      1390      1400      1410      1420      1430      1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
       1450      1460      1470      1480      1490      1500      1510      1520      1530      1540      1550      1560


GCACGTTGGCAAGCTCG
CGTGCAACCGTTCGAGC
       1570
```

FIG. 24 (Continued)

FIG. 25 - tsGBP2_C223

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                            10                            20
                                                                      M  K  L  E  I  F  S  W  W  A  G  D  E  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGGGCAGGTGATGAAGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACCCGTCCACTACTTCCGGGTCGAGAGCTTCGGAACTAGGCCAACAT
       130       140       150       160       170       180       190       200       210       220       230       240

          30                            40                            50                            60
 K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
       250       260       270       280       290       300       310       320       330       340       350       360

          70                            80                            90                           100
 V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

         110                           120                           130                           140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

         150                           160                           170                           180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

         190                           200                           210                           220
 G  W  N  N  L  W  S  G  K  L  K  F  T  D  P  K  A  V  A  V  W  E  T  F  G  K  V  L  D  A  A  N  K  D  A  A  G  L  C  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTGCTG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAACGAC
       730       740       750       760       770       780       790       800       810       820       830       840

         230                           240                           250                           260
 Q  Q  A  V  D  R  V  V  Q  G  K  A  A  F  N  I  M  G  D  W  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850       860       870       880       890       900       910       920       930       940       950       960
```

```
          270                           280                           290                           300
 P  S  P  G  T  S  G  I  F  M  M  L  S  D  S  F  G  L  P  K  G  A  K  N  R  Q  N  A  I  N  W  L  K  L  V  G  S  K  E  G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
       970       980       990      1000      1010      1020      1030      1040      1050      1060      1070      1080

          310                           320                           330                           340
 Q  D  T  F  N  P  L  K  G  S  I  A  A  R  L  D  S  D  P  A  K  Y  N  A  Y  G  Q  S  A  M  K  D  W  K  S  N  R  I  V  G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
      1090      1100      1110      1120      1130      1140      1150      1160      1170      1180      1190      1200

          350                           360                           370                           380
 S  L  V  H  G  A  V  A  P  E  S  F  M  S  Q  F  G  T  V  M  E  I  F  L  Q  S  R  N  P  Q  A  A  A  N  A  A  Q  A  I  A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
      1210      1220      1230      1240      1250      1260      1270      1280      1290      1300      1310      1320

          390                           400
 N  Q  V  G  L  G  R  G  G  S  H  H  H  H  H  H  *  *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
      1330      1340      1350      1360      1370      1380      1390      1400      1410      1420      1430      1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
      1450      1460      1470      1480      1490      1500      1510      1520      1530      1540      1550      1560


GCACGTTGGCAAGCTCG
CGTGCAACCGTTCGAGC
      1570
```

FIG. 25 (Continued)

FIG. 26 - tsGBP2_C224

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                          10                            20
                                                  M  K  L  E  I  F  S  W  W  A  G  D  E  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGGGCAGGTGATGAAGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACCCGTCCACTACTTCCGGGTCGAGAGCTTCGGAACTAGGCCAACAT
       130       140       150       160       170       180       190       200       210       220       230       240

           30                            40                            50                            60
 K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
       250       260       270       280       290       300       310       320       330       340       350       360

           70                            80                            90                           100
 V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

          110                           120                           130                           140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

          150                           160                           170                           180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

          190                           200                           210                           220
 G  W  N  N  L  W  S  G  K  L  K  F  T  D  P  K  A  V  A  V  W  E  T  F  G  K  V  L  D  A  A  N  K  D  A  A  G  L  S  C
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

          230                           240                           250                           260
 Q  Q  A  V  D  R  V  V  Q  G  K  A  A  F  N  I  M  G  D  W  A  A  G  Y  M  S  T  T  L  K  L  K  P  G  T  D  F  A  W  T
CCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
GGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850       860       870       880       890       900       910       920       930       940       950       960
```

```
              270                                     280                                     290                                     300
 P    S    P    G    T    S    G    I    F    M    M    L    S    D    S    F    G    L    P    K    G    A    K    N    R    Q    N    A    I    N    W    L    K    L    V    G    S    K    E    G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
       970       980       990      1000      1010      1020      1030      1040      1050      1060      1070      1080

              310                                     320                                     330                                     340
 Q    D    T    F    N    P    L    K    G    S    I    A    A    R    L    D    S    D    P    A    K    Y    N    A    Y    G    Q    S    A    M    K    D    W    K    S    N    R    I    V    G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
      1090      1100      1110      1120      1130      1140      1150      1160      1170      1180      1190      1200

              350                                     360                                     370                                     380
 S    L    V    H    G    A    V    A    P    E    S    F    M    S    Q    F    G    T    V    M    E    I    F    L    Q    S    R    N    P    Q    A    A    A    N    A    A    Q    A    I    A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
      1210      1220      1230      1240      1250      1260      1270      1280      1290      1300      1310      1320

              390                                     400
 N    Q    V    G    L    G    R    G    G    S    H    H    H    H    H    H    *    *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
      1330      1340      1350      1360      1370      1380      1390      1400      1410      1420      1430      1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
      1450      1460      1470      1480      1490      1500      1510      1520      1530      1540      1550      1560


GCACGTTGGCAAGCTCG
CGTGCAACCGTTCGAGC
      1570
```

FIG. 26 (Continued)

Figure 27:
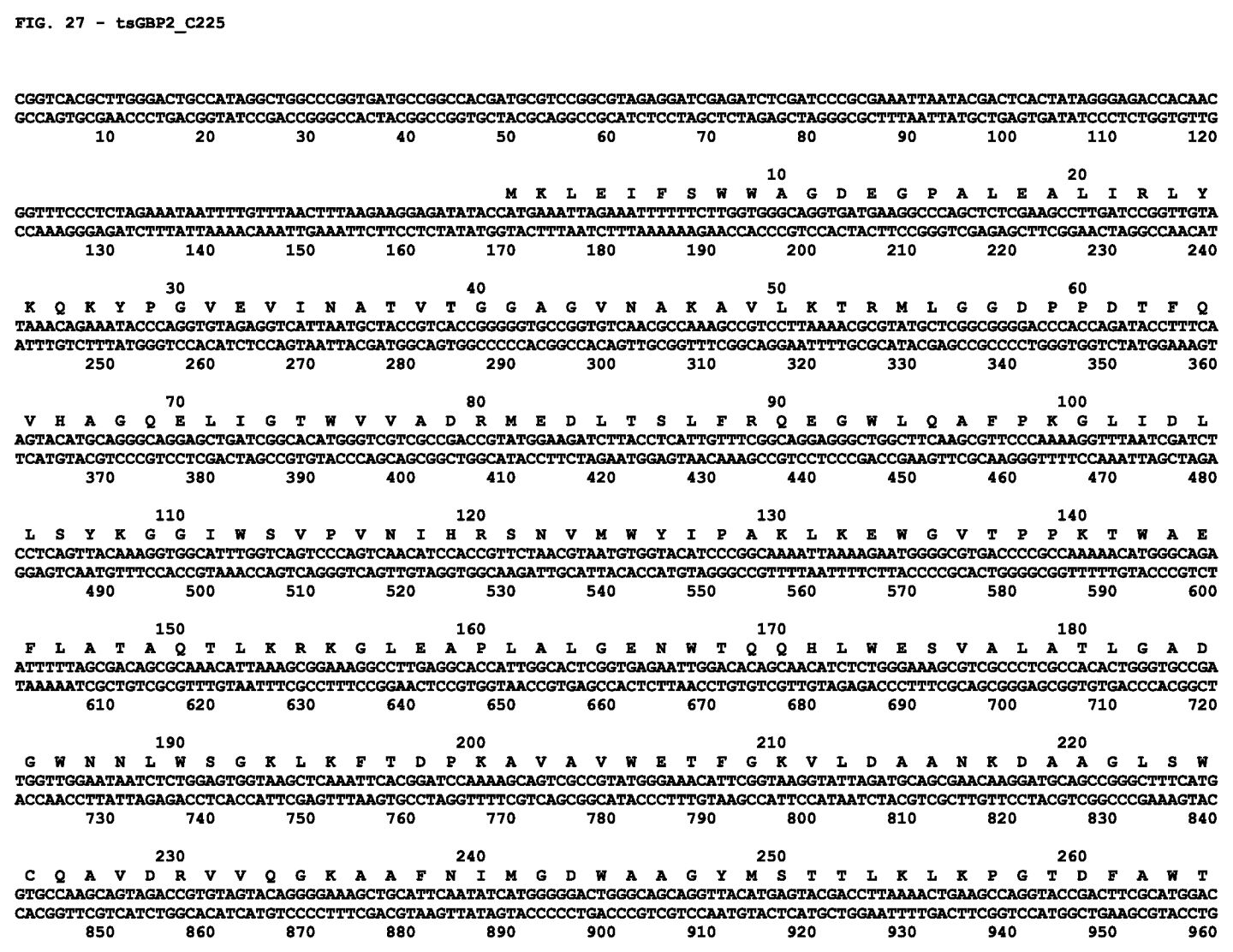

FIG. 27 - tsGBP2_C225

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                   10                            20
                                                     M  K  L  E  I  F  S  W  W  A  G  D  E  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGGGCAGGTGATGAAGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACCCGTCCACTACTTCCGGGTCGAGAGCTTCGGAACTAGGCCAACAT
       130       140       150       160       170       180       190       200       210       220       230       240

         30                            40                            50                            60
 K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
       250       260       270       280       290       300       310       320       330       340       350       360

         70                            80                            90                           100
 V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

        110                           120                           130                           140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

        150                           160                           170                           180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

        190                           200                           210                           220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

        230                           240                           250                           260
 C  Q  A  V  D  R  V  V  Q  G  K  A  A  F  N  I  M  G  D  W  A  A  G  Y  M  S  T  T  L  K  L  K  P  G  T  D  F  A  W  T
GTGCCAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CACGGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850       860       870       880       890       900       910       920       930       940       950       960
```

```
              270                                     280                                     290                                     300
 P  S  P  G  T  S  G  I  F  M  M  L  S  D  S  F  G  L  P  K  G  A  K  N  R  Q  N  A  I  N  W  L  K  L  V  G  S  K  E  G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
       970       980       990      1000      1010      1020      1030      1040      1050      1060      1070      1080

              310                                     320                                     330                                     340
 Q  D  T  F  N  P  L  K  G  S  I  A  A  R  L  D  S  D  P  A  K  Y  N  A  Y  G  Q  S  A  M  K  D  W  K  S  N  R  I  V  G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
      1090      1100      1110      1120      1130      1140      1150      1160      1170      1180      1190      1200

              350                                     360                                     370                                     380
 S  L  V  H  G  A  V  A  P  E  S  F  M  S  Q  F  G  T  V  M  E  I  F  L  Q  S  R  N  P  Q  A  A  A  N  A  A  Q  A  I  A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
      1210      1220      1230      1240      1250      1260      1270      1280      1290      1300      1310      1320

              390                                     400
 N  Q  V  G  L  G  R  G  G  S  H  H  H  H  H  H  *  *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
      1330      1340      1350      1360      1370      1380      1390      1400      1410      1420      1430      1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
      1450      1460      1470      1480      1490      1500      1510      1520      1530      1540      1550      1560


GCACGTTGGCAAGCTCG
CGTGCAACCGTTCGAGC
      1570
```

FIG. 27 (Continued)

FIG. 28 - tsGBP2_C244

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                          10                            20
                                                                      M  K  L  E  I  F  S  W  W  A  G  D  E  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGGGCAGGTGATGAAGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACCCGTCCACTACTTCCGGGTCGAGAGCTTCGGAACTAGGCCAACAT
       130       140       150       160       170       180       190       200       210       220       230       240

             30                            40                            50                            60
 K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
       250       260       270       280       290       300       310       320       330       340       350       360

             70                            80                            90                           100
 V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

            110                           120                           130                           140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

            150                           160                           170                           180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

            190                           200                           210                           220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

            230                           240                           250                           260
 Q  Q  A  V  D  R  V  V  Q  G  K  A  A  F  N  I  M  G  D  C  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGCGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACGCGTCGTCCAATGTACTCATGCTGGAATTTTGACTTCGGTCCATGGCTGAAGCGTACCTG
       850       860       870       880       890       900       910       920       930       940       950       960
```

```
                 270                                     280                                     290                                     300
  P   S   P   G   T   S   G   I   F   M   M   L   S   D   S   F   G   L   P   K   G   A   K   N   R   Q   N   A   I   N   W   L   K   L   V   G   S   K   E   G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
        970       980       990      1000      1010      1020      1030      1040      1050      1060      1070      1080

                 310                                     320                                     330                                     340
  Q   D   T   F   N   P   L   K   G   S   I   A   A   R   L   D   S   D   P   A   K   Y   N   A   Y   G   Q   S   A   M   K   D   W   K   S   N   R   I   V   G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
       1090      1100      1110      1120      1130      1140      1150      1160      1170      1180      1190      1200

                 350                                     360                                     370                                     380
  S   L   V   H   G   A   V   A   P   E   S   F   M   S   Q   F   G   T   V   M   E   I   F   L   Q   S   R   N   P   Q   A   A   A   N   A   A   Q   A   I   A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
       1210      1220      1230      1240      1250      1260      1270      1280      1290      1300      1310      1320

                 390                                     400
  N   Q   V   G   L   G   R   G   G   S   H   H   H   H   H   H   *   *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
       1330      1340      1350      1360      1370      1380      1390      1400      1410      1420      1430      1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
       1450      1460      1470      1480      1490      1500      1510      1520      1530      1540      1550      1560


GCACGTTGGCAAGCTCG
CGTGCAACCGTTCGAGC
       1570
```

FIG. 28 (Continued)

FIG. 29 - tsGBP2_C277

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                   10                            20
                                                M  K  L  E  I  F  S  W  W  A  G  D  E  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGGGCAGGTGATGAAGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACCCGTCCACTACTTCCGGGTCGAGAGCTTCGGAACTAGGCCAACAT
       130       140       150       160       170       180       190       200       210       220       230       240

             30                            40                            50                            60
 K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
       250       260       270       280       290       300       310       320       330       340       350       360

             70                            80                            90                           100
 V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

            110                           120                           130                           140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

            150                           160                           170                           180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

            190                           200                           210                           220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

            230                           240                           250                           260
 Q  Q  A  V  D  R  V  V  Q  G  K  A  A  F  N  I  M  G  D  W  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850       860       870       880       890       900       910       920       930       940       950       960
```

```
                270                                     280                                     290                                     300
 P   S   P   G   T   S   G   I   F   M   M   L   C   D   S   F   G   L   P   K   G   A   K   N   R   Q   N   A   I   N   W   L   K   L   V   G   S   K   E   G
ACCTTCTCCGGGCACTTCAGGGATCTTTATGATGCTGTGCGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACACGCTATCAAAGCCGAACGGTTTCCCCCGCTTCTTAGCAGTTTTACGATAATTGACCAACTTTGAGCAGCCCAGTTTTCTCCC
         970         980         990        1000        1010        1020        1030        1040        1050        1060        1070        1080

                310                                     320                                     330                                     340
 Q   D   T   F   N   P   L   K   G   S   I   A   A   R   L   D   S   D   P   A   K   Y   N   A   Y   G   Q   S   A   M   K   D   W   K   S   N   R   I   V   G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
        1090        1100        1110        1120        1130        1140        1150        1160        1170        1180        1190        1200

                350                                     360                                     370                                     380
 S   L   V   H   G   A   V   A   P   E   S   F   M   S   Q   F   G   T   V   M   E   I   F   L   Q   S   R   N   P   Q   A   A   A   N   A   A   Q   A   I   A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
        1210        1220        1230        1240        1250        1260        1270        1280        1290        1300        1310        1320

                390                                     400
 N   Q   V   G   L   G   R   G   G   S   H   H   H   H   H   H   *   *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
        1330        1340        1350        1360        1370        1380        1390        1400        1410        1420        1430        1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
        1450        1460        1470        1480        1490        1500        1510        1520        1530        1540        1550        1560


GCACGTTGGCAAGCTCG
CGTGCAACCGTTCGAGC
        1570
```

FIG. 29 (Continued)

FIG. 30 - tsGBP2_C278

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                          10                                          20
                                                           M  K  L  E  I  F  S  W  W  A  G  D  E  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGGGCAGGTGATGAAGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACCCGTCCACTACTTCCGGGTCGAGAGCTTCGGAACTAGGCCAACAT
       130       140       150       160       170       180       190       200       210       220       230       240

          30                            40                            50                            60
 K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
       250       260       270       280       290       300       310       320       330       340       350       360

          70                            80                            90                           100
 V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

         110                           120                           130                           140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

         150                           160                           170                           180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

         190                           200                           210                           220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

         230                           240                           250                           260
 Q  Q  A  V  D  R  V  V  Q  G  K  A  A  F  N  I  M  G  D  W  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850       860       870       880       890       900       910       920       930       940       950       960
```

```
                 270                                     280                                     290                                     300
 P  S  P  G  T  S  G  I  F  M  M  L  S  C  S  F  G  L  P  K  G  A  K  N  R  Q  N  A  I  N  W  L  K  L  V  G  S  K  E  G
ACCTTCTCCGGGCACTTCAGGGATCTTTATGATGCTGTCTTGCAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGAACGTCAAAGCCGAACGGTTTCCCCCGCTTCTTAGCAGTTTTACGATAATTGACCAACTTTGAGCAGCCCAGTTTTCTCCC
       970       980       990      1000      1010      1020      1030      1040      1050      1060      1070      1080

                 310                                     320                                     330                                     340
 Q  D  T  F  N  P  L  K  G  S  I  A  A  R  L  D  S  D  P  A  K  Y  N  A  Y  G  Q  S  A  M  K  D  W  K  S  N  R  I  V  G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
      1090      1100      1110      1120      1130      1140      1150      1160      1170      1180      1190      1200

                 350                                     360                                     370                                     380
 S  L  V  H  G  A  V  A  P  E  S  F  M  S  Q  F  G  T  V  M  E  I  F  L  Q  S  R  N  P  Q  A  A  A  N  A  A  Q  A  I  A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
      1210      1220      1230      1240      1250      1260      1270      1280      1290      1300      1310      1320

                 390                                     400
 N  Q  V  G  L  G  R  G  G  S  H  H  H  H  H  H  *  *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
      1330      1340      1350      1360      1370      1380      1390      1400      1410      1420      1430      1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
      1450      1460      1470      1480      1490      1500      1510      1520      1530      1540      1550      1560


GCACGTTGGCAAGCTCG
CGTGCAACCGTTCGAGC
      1570
```

FIG. 30 (Continued)

FIG. 31 - tsGBP2_C312

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                      10                            20
                                                        M  K  L  E  I  F  S  W  W  A  G  D  E  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGGGCAGGTGATGAAGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACCCGTCCACTACTTCCGGGTCGAGAGCTTCGGAACTAGGCCAACAT
       130       140       150       160       170       180       190       200       210       220       230       240

             30                            40                            50                            60
 K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
       250       260       270       280       290       300       310       320       330       340       350       360

             70                            80                            90                           100
 V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

            110                           120                           130                           140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

            150                           160                           170                           180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

            190                           200                           210                           220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

            230                           240                           250                           260
 Q  Q  A  V  D  R  V  V  Q  G  K  A  A  F  N  I  M  G  D  W  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850       860       870       880       890       900       910       920       930       940       950       960
```

```
                 270                                     280                                     290                                     300
 P   S   P   G   T   S   G   I   F   M   M   L   S   D   S   F   G   L   P   K   G   A   K   N   R   Q   N   A   I   N   W   L   K   L   V   G   S   K   E   G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
        970       980       990      1000      1010      1020      1030      1040      1050      1060      1070      1080

                 310                                     320                                     330                                     340
 Q   D   T   F   N   P   L   C   G   S   I   A   A   R   L   D   S   D   P   A   K   Y   N   A   Y   G   Q   S   A   M   K   D   W   K   S   N   R   I   V   G
GCAGGACACCTTCAACCCGCTCTGCGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGACGCCAAGGTAGCGACGAGCAGAGCTAAGACTAGGACGGTTTATATTACGTATGCCGGTTTCACGTTACTTCCTGACCTTCAGTTTAGCCTAGCATCC
       1090      1100      1110      1120      1130      1140      1150      1160      1170      1180      1190      1200

                 350                                     360                                     370                                     380
 S   L   V   H   G   A   V   A   P   E   S   F   M   S   Q   F   G   T   V   M   E   I   F   L   Q   S   R   N   P   Q   A   A   A   N   A   A   Q   A   I   A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
       1210      1220      1230      1240      1250      1260      1270      1280      1290      1300      1310      1320

                 390                                     400
 N   Q   V   G   L   G   R   G   G   S   H   H   H   H   H   H   *   *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
       1330      1340      1350      1360      1370      1380      1390      1400      1410      1420      1430      1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
       1450      1460      1470      1480      1490      1500      1510      1520      1530      1540      1550      1560


GCACGTTGGCAAGCTCG
CGTGCAACCGTTCGAGC
       1570
```

FIG. 31 (Continued)

FIG. 32 - tsGBP2_C337

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10          20          30          40          50          60          70          80          90         100         110         120

                                                                                         10                                    20
                                                                   M  K  L  E  I  F  S  W  W  A  G  D  E  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGGGCAGGTGATGAAGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACCCGTCCACTACTTCCGGGTCGAGAGCTTCGGAACTAGGCCAACAT
       130         140         150         160         170         180         190         200         210         220         230         240

               30                                    40                                    50                                    60
 K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
       250         260         270         280         290         300         310         320         330         340         350         360

               70                                    80                                    90                                   100
 V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370         380         390         400         410         420         430         440         450         460         470         480

              110                                   120                                   130                                   140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490         500         510         520         530         540         550         560         570         580         590         600

              150                                   160                                   170                                   180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610         620         630         640         650         660         670         680         690         700         710         720

              190                                   200                                   210                                   220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730         740         750         760         770         780         790         800         810         820         830         840

              230                                   240                                   250                                   260
 Q  Q  A  V  D  R  V  V  Q  G  K  A  A  F  N  I  M  G  D  W  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850         860         870         880         890         900         910         920         930         940         950         960
```

```
              270                                     280                                     290                                     300
  P   S   P   G   T   S   G   I   F   M   M   L   S   D   S   F   G   L   P   K   G   A   K   N   R   Q   N   A   I   N   W   L   K   L   V   G   S   K   E   G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
          970       980       990      1000      1010      1020      1030      1040      1050      1060      1070      1080

              310                                     320                                     330                                     340
  Q   D   T   F   N   P   L   K   G   S   I   A   A   R   L   D   S   D   P   A   K   Y   N   A   Y   G   Q   S   A   M   K   D   C   K   S   N   R   I   V   G
GCAGGACACCTTCAACCCGCTCAAAGGTTCCATCGCTGCTCGTCTCGATTCTGATCCTGCCAAATATAATGCATACGGCCAAAGTGCAATGAAGGACTGCAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACGTTCAGTTTAGCCTAGCATCC
        1090      1100      1110      1120      1130      1140      1150      1160      1170      1180      1190      1200

              350                                     360                                     370                                     380
  S   L   V   H   G   A   V   A   P   E   S   F   M   S   Q   F   G   T   V   M   E   I   F   L   Q   S   R   N   P   Q   A   A   A   N   A   A   Q   A   I   A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
        1210      1220      1230      1240      1250      1260      1270      1280      1290      1300      1310      1320

              390                                     400
  N   Q   V   G   L   G   R   G   G   S   H   H   H   H   H   H   *   *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
        1330      1340      1350      1360      1370      1380      1390      1400      1410      1420      1430      1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
        1450      1460      1470      1480      1490      1500      1510      1520      1530      1540      1550      1560


GCACGTTGGCAAGCTCG
CGTGCAACCGTTCGAGC
        1570
```

FIG. 32 (Continued)

FIG. 33 - tsGBP2_C348

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                  10                            20
                                                          M  K  L  E  I  F  S  W  W  A  G  D  E  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGGGCAGGTGATGAAGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACCCGTCCACTACTTCCGGGTCGAGAGCTTCGGAACTAGGCCAACAT
       130       140       150       160       170       180       190       200       210       220       230       240

              30                                      40                                      50                                      60
 K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
       250       260       270       280       290       300       310       320       330       340       350       360

              70                                      80                                      90                                     100
 V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

             110                                     120                                     130                                     140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

             150                                     160                                     170                                     180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

             190                                     200                                     210                                     220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

             230                                     240                                     250                                     260
 Q  Q  A  V  D  R  V  V  Q  G  K  A  A  F  N  I  M  G  D  W  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850       860       870       880       890       900       910       920       930       940       950       960
```

```
            270                                280                                290                                300
 P  S  P  G  T  S  G  I  F  M  M  L  S  D  S  F  G  L  P  K  G  A  K  N  R  Q  N  A  I  N  W  L  K  L  V  G  S  K  E  G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
       970       980       990      1000      1010      1020      1030      1040      1050      1060      1070      1080

            310                                320                                330                                340
 Q  D  T  F  N  P  L  K  G  S  I  A  A  R  L  D  S  D  P  A  K  Y  N  A  Y  G  Q  S  A  M  K  D  W  K  S  N  R  I  V  G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
      1090      1100      1110      1120      1130      1140      1150      1160      1170      1180      1190      1200

            350                                360                                370                                380
 S  L  V  C  G  A  V  A  P  E  S  F  M  S  Q  F  G  T  V  M  E  I  F  L  Q  S  R  N  P  Q  A  A  A  N  A  A  Q  A  I  A
CTCCCTCGTCTGCGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGACGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
      1210      1220      1230      1240      1250      1260      1270      1280      1290      1300      1310      1320

            390                                400
 N  Q  V  G  L  G  R  G  G  S  H  H  H  H  H  H  *  *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
      1330      1340      1350      1360      1370      1380      1390      1400      1410      1420      1430      1440

GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
      1450      1460      1470      1480      1490      1500      1510      1520      1530      1540      1550      1560

GCACGTTGGCAAGCTCG
CGTGCAACCGTTCGAGC
      1570
```

FIG. 33 (Continued)

FIG. 34 - tsGBP2_C357

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                   10                            20
                                                         M  K  L  E  I  F  S  W  W  A  G  D  E  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGGGCAGGTGATGAAGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACCCGTCCACTACTTCCGGGTCGAGAGCTTCGGAACTAGGCCAACAT
       130       140       150       160       170       180       190       200       210       220       230       240

           30                            40                            50                            60
 K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
       250       260       270       280       290       300       310       320       330       340       350       360

           70                            80                            90                           100
 V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

          110                           120                           130                           140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

          150                           160                           170                           180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

          190                           200                           210                           220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

          230                           240                           250                           260
 Q  Q  A  V  D  R  V  V  Q  G  K  A  A  F  N  I  M  G  D  W  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850       860       870       880       890       900       910       920       930       940       950       960
```

```
                270                                     280                                     290                                     300
  P   S   P   G   T   S   G   I   F   M   M   L   S   D   S   F   G   L   P   K   G   A   K   N   R   Q   N   A   I   N   W   L   K   L   V   G   S   K   E   G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
       970       980       990      1000      1010      1020      1030      1040      1050      1060      1070      1080

                310                                     320                                     330                                     340
  Q   D   T   F   N   P   L   K   G   S   I   A   A   R   L   D   S   D   P   A   K   Y   N   A   Y   G   Q   S   A   M   K   D   W   K   S   N   R   I   V   G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
      1090      1100      1110      1120      1130      1140      1150      1160      1170      1180      1190      1200

                350                                     360                                     370                                     380
  S   L   V   H   G   A   V   A   P   E   S   F   C   S   Q   F   G   T   V   M   E   I   F   L   Q   S   R   N   P   Q   A   A   A   N   A   A   Q   A   I   A
CTCCCTCGTCCACGGCGCAGTCGCGCCAGAATCCTTCTGCTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGACGAGCGTCAAACCCTGCCATTACCTCTAAAAGAACGTTAGGGCATTGGGCGTCCGTCGGCGATTACGGCGTGTTCGATAGCG
      1210      1220      1230      1240      1250      1260      1270      1280      1290      1300      1310      1320

                390                                     400
  N   Q   V   G   L   G   R   G   G   S   H   H   H   H   H   H   *   *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
      1330      1340      1350      1360      1370      1380      1390      1400      1410      1420      1430      1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
      1450      1460      1470      1480      1490      1500      1510      1520      1530      1540      1550      1560


GCACGTTGGCAAGCTCG
CGTGCAACCGTTCGAGC
      1570
```

FIG. 34 (Continued)

FIG. 35 - tsGBP2.13C.W8F

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                           10                            20
                                                M  K  L  E  I  F  S  F  W  A  G  D  C  G  P  A  L  E  A  L  I  R  L  Y
GGTTTCCCTCTAGAAATAATTTTGTTTAACTTTAAGAAGGAGATATACCATGAAATTAGAAATTTTTTCTTTTTGGGCAGGTGATTGTGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAAAAACCCGTCCACTAACACCGGGTCGAGAGCTTCGGAACTAGGCCAACAT
       130       140       150       160       170       180       190       200       210       220       230       240

               30                            40                            50                            60
 K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
       250       260       270       280       290       300       310       320       330       340       350       360

               70                            80                            90                           100
 V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

              110                           120                           130                           140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

              150                           160                           170                           180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

              190                           200                           210                           220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

              230                           240                           250                           260
 Q  Q  A  V  D  R  V  V  Q  G  K  A  A  F  N  I  M  G  D  W  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850       860       870       880       890       900       910       920       930       940       950       960
```

```
          270                 280                 290                 300
 P  S  P  G  T  S  G  I  F  M  M  L  S  D  S  F  G  L  P  K  G  A  K  N  R  Q  N  A  I  N  W  L  K  L  V  G  S  K  E  G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
     970       980       990      1000      1010      1020      1030      1040      1050      1060      1070      1080

          310                 320                 330                 340
 Q  D  T  F  N  P  L  K  G  S  I  A  A  R  L  D  S  D  P  A  K  Y  N  A  Y  G  Q  S  A  M  K  D  W  K  S  N  R  I  V  G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
    1090      1100      1110      1120      1130      1140      1150      1160      1170      1180      1190      1200

          350                 360                 370                 380
 S  L  V  H  G  A  V  A  P  E  S  F  M  S  Q  F  G  T  V  M  E  I  F  L  Q  S  R  N  P  Q  A  A  A  N  A  A  Q  A  I  A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
    1210      1220      1230      1240      1250      1260      1270      1280      1290      1300      1310      1320

          390                 400
 N  Q  V  G  L  G  R  G  G  S  H  H  H  H  H  H  *  *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
    1330      1340      1350      1360      1370      1380      1390      1400      1410      1420      1430      1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
    1450      1460      1470      1480      1490      1500      1510      1520      1530      1540      1550      1560


GCACGTTGGCAAGCTCG
CGTGCAACCGTTCGAGC
    1570
```

FIG. 35 (Continued)

FIG. 36 - tsGBP2.13C.W8M

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                   10                            20
                                                  M  K  L  E  I  F  S  M  W  A  G  D  C  G  P  A  L  E  A  L  I  R  L  Y
GGTTTCCCTCTAGAAATAATTTTGTTTAACTTTAAGAAGGAGATATACCATGAAATTAGAAATTTTTTCTATGTGGGCAGGTGATTGTGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGATACACCCGTCCACTAACACCGGGTCGAGAGCTTCGGAACTAGGCCAACAT
       130       140       150       160       170       180       190       200       210       220       230       240

        30                            40                            50                            60
 K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
       250       260       270       280       290       300       310       320       330       340       350       360

        70                            80                            90                           100
 V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

       110                           120                           130                           140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

       150                           160                           170                           180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

       190                           200                           210                           220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

       230                           240                           250                           260
 Q  Q  A  V  D  R  V  V  Q  G  K  A  A  F  N  I  M  G  D  W  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850       860       870       880       890       900       910       920       930       940       950       960
```

```
                 270                                     280                                     290                                     300
 P   S   P   G   T   S   G   I   F   M   M   L   S   D   S   F   G   L   P   K   G   A   K   N   R   Q   N   A   I   N   W   L   K   L   V   G   S   K   E   G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
        970       980       990      1000      1010      1020      1030      1040      1050      1060      1070      1080

                 310                                     320                                     330                                     340
 Q   D   T   F   N   P   L   K   G   S   I   A   A   R   L   D   S   D   P   A   K   Y   N   A   Y   G   Q   S   A   M   K   D   W   K   S   N   R   I   V   G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
       1090      1100      1110      1120      1130      1140      1150      1160      1170      1180      1190      1200

                 350                                     360                                     370                                     380
 S   L   V   H   G   A   V   A   P   E   S   F   M   S   Q   F   G   T   V   M   E   I   F   L   Q   S   R   N   P   Q   A   A   A   N   A   A   Q   A   I   A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
       1210      1220      1230      1240      1250      1260      1270      1280      1290      1300      1310      1320

                 390                                     400
 N   Q   V   G   L   G   R   G   G   S   H   H   H   H   H   H   *   *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
       1330      1340      1350      1360      1370      1380      1390      1400      1410      1420      1430      1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
       1450      1460      1470      1480      1490      1500      1510      1520      1530      1540      1550      1560


GCACGTTGGCAAGCTCG
CGTGCAACCGTTCGAGC
       1570
```

FIG. 36 (Continued)

FIG. 37 - tsGBP2.13C.W8Y

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                              10                            20
                                                      M  K  L  E  I  F  S  Y  W  A  G  D  C  G  P  A  L  E  A  L  I  R  L  Y
GGTTTCCCTCTAGAAATAATTTTGTTTAACTTTAAGAAGGAGATATACCATGAAATTAGAAATTTTTTCTTATTGGGCAGGTGATTGTGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAATAACCCGTCCACTAACACCGGGTCGAGAGCTTCGGAACTAGGCCAACAT
       130       140       150       160       170       180       190       200       210       220       230       240

         30                            40                            50                            60
 K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
       250       260       270       280       290       300       310       320       330       340       350       360

         70                            80                            90                           100
 V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

        110                           120                           130                           140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

        150                           160                           170                           180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

        190                           200                           210                           220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

        230                           240                           250                           260
 Q  Q  A  V  D  R  V  V  Q  G  K  A  A  F  N  I  M  G  D  W  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850       860       870       880       890       900       910       920       930       940       950       960
```

```
                 270                                280                                290                                300
 P  S  P  G  T  S  G  I  F  M  M  L  S  D  S  F  G  L  P  K  G  A  K  N  R  Q  N  A  I  N  W  L  K  L  V  G  S  K  E  G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
       970       980       990      1000      1010      1020      1030      1040      1050      1060      1070      1080

                 310                                320                                330                                340
 Q  D  T  F  N  P  L  K  G  S  I  A  A  R  L  D  S  D  P  A  K  Y  N  A  Y  G  Q  S  A  M  K  D  W  K  S  N  R  I  V  G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
      1090      1100      1110      1120      1130      1140      1150      1160      1170      1180      1190      1200

                 350                                360                                370                                380
 S  L  V  H  G  A  V  A  P  E  S  F  M  S  Q  F  G  T  V  M  E  I  F  L  Q  S  R  N  P  Q  A  A  A  N  A  A  Q  A  I  A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
      1210      1220      1230      1240      1250      1260      1270      1280      1290      1300      1310      1320

                 390                                400
 N  Q  V  G  L  G  R  G  G  S  H  H  H  H  H  H  *  *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
      1330      1340      1350      1360      1370      1380      1390      1400      1410      1420      1430      1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
      1450      1460      1470      1480      1490      1500      1510      1520      1530      1540      1550      1560


GCACGTTGGCAAGCTCG
CGTGCAACCGTTCGAGC
      1570
```

FIG. 37 (Continued)

FIG. 38 - tsGBP2.13C.W9F

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                  10                            20
                                                     M  K  L  E  I  F  S  W  F  A  G  D  C  G  P  A  L  E  A  L  I  R  L  Y
GGTTTCCCTCTAGAAATAATTTTGTTTAACTTTAAGAAGGAGATATACCATGAAATTAGAAATTTTTTCTTGGTTTGCAGGTGATTGTGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCAAACGTCCACTAACACCGGGTCGAGAGCTTCGGAACTAGGCCAACAT
       130       140       150       160       170       180       190       200       210       220       230       240

           30                            40                            50                            60
 K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
       250       260       270       280       290       300       310       320       330       340       350       360

           70                            80                            90                           100
 V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

          110                           120                           130                           140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

          150                           160                           170                           180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

          190                           200                           210                           220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

          230                           240                           250                           260
 Q  Q  A  V  D  R  V  V  Q  G  K  A  A  F  N  I  M  G  D  W  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850       860       870       880       890       900       910       920       930       940       950       960
```

```
                  270                                     280                                     290                                     300
 P  S  P  G  T  S  G  I  F  M  M  L  S  D  S  F  G  L  P  K  G  A  K  N  R  Q  N  A  I  N  W  L  K  L  V  G  S  K  E  G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
        970          980          990         1000         1010         1020         1030         1040         1050         1060         1070         1080

                  310                                     320                                     330                                     340
 Q  D  T  F  N  P  L  K  G  S  I  A  A  R  L  D  S  D  P  A  K  Y  N  A  Y  G  Q  S  A  M  K  D  W  K  S  N  R  I  V  G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
       1090         1100         1110         1120         1130         1140         1150         1160         1170         1180         1190         1200

                  350                                     360                                     370                                     380
 S  L  V  H  G  A  V  A  P  E  S  F  M  S  Q  F  G  T  V  M  E  I  F  L  Q  S  R  N  P  Q  A  A  A  N  A  A  Q  A  I  A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
       1210         1220         1230         1240         1250         1260         1270         1280         1290         1300         1310         1320

                  390                                     400
 N  Q  V  G  L  G  R  G  G  S  H  H  H  H  H  H  *  *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
       1330         1340         1350         1360         1370         1380         1390         1400         1410         1420         1430         1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
       1450         1460         1470         1480         1490         1500         1510         1520         1530         1540         1550         1560


GCACGTTGGCAAGCTCG
CGTGCAACCGTTCGAGC
       1570
```

FIG. 38 (Continued)

FIG. 39 - tsGBP2.13C.W9M

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                           10                            20
                                                      M  K  L  E  I  F  S  W  M  A  G  D  C  G  P  A  L  E  A  L  I  R  L  Y
GGTTTCCCTCTAGAAATAATTTTGTTTAACTTTAAGAAGGAGATATACCATGAAATTAGAAATTTTTTCTTGGATGGCAGGTGATTGTGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCTACCGTCCACTAACACCGGGTCGAGAGCTTCGGAACTAGGCCAACAT
       130       140       150       160       170       180       190       200       210       220       230       240

         30                            40                            50                            60
K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
       250       260       270       280       290       300       310       320       330       340       350       360

         70                            80                            90                           100
V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

        110                           120                           130                           140
L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

        150                           160                           170                           180
F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

        190                           200                           210                           220
G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

        230                           240                           250                           260
Q  Q  A  V  D  R  V  V  Q  G  K  A  A  F  N  I  M  G  D  W  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850       860       870       880       890       900       910       920       930       940       950       960
```

```
             270                                280                                290                                300
 P   S   P   G   T   S   G   I   F   M   M   L   S   D   S   F   G   L   P   K   G   A   K   N   R   Q   N   A   I   N   W   L   K   L   V   G   S   K   E   G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
       970       980       990      1000      1010      1020      1030      1040      1050      1060      1070      1080

             310                                320                                330                                340
 Q   D   T   F   N   P   L   K   G   S   I   A   A   R   L   D   S   D   P   A   K   Y   N   A   Y   G   Q   S   A   M   K   D   W   K   S   N   R   I   V   G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
      1090      1100      1110      1120      1130      1140      1150      1160      1170      1180      1190      1200

             350                                360                                370                                380
 S   L   V   H   G   A   V   A   P   E   S   F   M   S   Q   F   G   T   V   M   E   I   F   L   Q   S   R   N   P   Q   A   A   A   N   A   A   Q   A   I   A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
      1210      1220      1230      1240      1250      1260      1270      1280      1290      1300      1310      1320

             390                                400
 N   Q   V   G   L   G   R   G   G   S   H   H   H   H   H   H   *   *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
      1330      1340      1350      1360      1370      1380      1390      1400      1410      1420      1430      1440

GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
      1450      1460      1470      1480      1490      1500      1510      1520      1530      1540      1550      1560

GCACGTTGGCAAGCTCG
CGTGCAACCGTTCGAGC
      1570
```

FIG. 39 (Continued)

FIG. 40 - tsGBP2.13C.W9Y

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                 10                                      20
                                                             M  K  L  E  I  F  S  W  Y  A  G  D  C  G  P  A  L  E  A  L  I  R  L  Y
GGTTTCCCTCTAGAAATAATTTTGTTTAACTTTAAGAAGGAGATATACCATGAAATTAGAAATTTTTTCTTGGTATGCAGGTGATTGTGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCATACGTCCACTAACACCGGGTCGAGAGCTTCGGAACTAGGCCAACAT
       130       140       150       160       170       180       190       200       210       220       230       240

       30                                      40                                      50                                      60
 K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
       250       260       270       280       290       300       310       320       330       340       350       360

       70                                      80                                      90                                     100
 V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

      110                                     120                                     130                                     140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

      150                                     160                                     170                                     180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

      190                                     200                                     210                                     220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

      230                                     240                                     250                                     260
 Q  Q  A  V  D  R  V  V  Q  G  K  A  A  F  N  I  M  G  D  W  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850       860       870       880       890       900       910       920       930       940       950       960
```

```
              270                       280                       290                       300
 P  S  P  G  T  S  G  I  F  M  M  L  S  D  S  F  G  L  P  K  G  A  K  N  R  Q  N  A  I  N  W  L  K  L  V  G  S  K  E  G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
       970       980       990      1000      1010      1020      1030      1040      1050      1060      1070      1080

              310                       320                       330                       340
 Q  D  T  F  N  P  L  K  G  S  I  A  A  R  L  D  S  D  P  A  K  Y  N  A  Y  G  Q  S  A  M  K  D  W  K  S  N  R  I  V  G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
      1090      1100      1110      1120      1130      1140      1150      1160      1170      1180      1190      1200

              350                       360                       370                       380
 S  L  V  H  G  A  V  A  P  E  S  F  M  S  Q  F  G  T  V  M  E  I  F  L  Q  S  R  N  P  Q  A  A  A  N  A  A  Q  A  I  A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
      1210      1220      1230      1240      1250      1260      1270      1280      1290      1300      1310      1320

              390                       400
 N  Q  V  G  L  G  R  G  G  S  H  H  H  H  H  H  *  *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
      1330      1340      1350      1360      1370      1380      1390      1400      1410      1420      1430      1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
      1450      1460      1470      1480      1490      1500      1510      1520      1530      1540      1550      1560


GCACGTTGGCAAGCTCG
CGTGCAACCGTTCGAGC
      1570
```

FIG. 40 (Continued)

FIG. 41 - tsGBP2.13C.Q64N

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                                  10                            20
                                                           M  K  L  E  I  F  S  W  W  A  G  D  C  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGGGCAGGTGATTGTGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACCCGTCCACTAACACCGGGTCGAGAGCTTCGGAACTAGGCCAACAT
       130       140       150       160       170       180       190       200       210       220       230       240

          30                            40                            50                            60
 K  Q  K  Y  P  G  V  E  V  I  N  A  T  V  T  G  G  A  G  V  N  A  K  A  V  L  K  T  R  M  L  G  G  D  P  P  D  T  F  N
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTAA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAATT
       250       260       270       280       290       300       310       320       330       340       350       360

          70                            80                            90                           100
 V  H  A  G  Q  E  L  I  G  T  W  V  V  A  D  R  M  E  D  L  T  S  L  F  R  Q  E  G  W  L  Q  A  F  P  K  G  L  I  D  L
CGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
GCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

         110                           120                           130                           140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

         150                           160                           170                           180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

         190                           200                           210                           220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

         230                           240                           250                           260
 Q  Q  A  V  D  R  V  V  Q  G  K  A  A  F  N  I  M  G  D  W  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850       860       870       880       890       900       910       920       930       940       950       960
```

```
              270                           280                           290                           300
 P  S  P  G  T  S  G  I  F  M  M  L  S  D  S  F  G  L  P  K  G  A  K  N  R  Q  N  A  I  N  W  L  K  L  V  G  S  K  E  G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
       970       980       990      1000      1010      1020      1030      1040      1050      1060      1070      1080

              310                           320                           330                           340
 Q  D  T  F  N  P  L  K  G  S  I  A  A  R  L  D  S  D  P  A  K  Y  N  A  Y  G  Q  S  A  M  K  D  W  K  S  N  R  I  V  G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
      1090      1100      1110      1120      1130      1140      1150      1160      1170      1180      1190      1200

              350                           360                           370                           380
 S  L  V  H  G  A  V  A  P  E  S  F  M  S  Q  F  G  T  V  M  E  I  F  L  Q  S  R  N  P  Q  A  A  A  N  A  A  Q  A  I  A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
      1210      1220      1230      1240      1250      1260      1270      1280      1290      1300      1310      1320

              390                           400
 N  Q  V  G  L  G  R  G  G  S  H  H  H  H  H  H  *  *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
      1330      1340      1350      1360      1370      1380      1390      1400      1410      1420      1430      1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
      1450      1460      1470      1480      1490      1500      1510      1520      1530      1540      1550      1560


GCACGTTGGCAAGCTCG
CGTGCAACCGTTCGAGC
      1570
```

FIG. 41 (Continued)

FIG. 42 - tsGBP2.13C.Q64E

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                      10                  20
                                                       M  K  L  E  I  F  S  W  W  A  G  D  C  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGGGCAGGTGATTGTGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACCCGTCCACTAACACCGGGTCGAGAGCTTCGGAACTAGGCCAACAT
       130       140       150       160       170       180       190       200       210       220       230       240

          30                            40                            50                            60
 K  Q  K  Y  P  G  V  E  V  I  N  A  T  V  T  G  G  A  G  V  N  A  K  A  V  L  K  T  R  M  L  G  G  D  P  P  D  T  F  E
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTGA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAACT
       250       260       270       280       290       300       310       320       330       340       350       360

          70                            80                            90                           100
 V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

         110                           120                           130                           140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

         150                           160                           170                           180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

         190                           200                           210                           220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

         230                           240                           250                           260
 Q  Q  A  V  D  R  V  V  Q  G  K  A  A  F  N  I  M  G  D  W  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850       860       870       880       890       900       910       920       930       940       950       960
```

```
              270                                     280                                     290                                     300
  P   S   P   G   T   S   G   I   F   M   M   L   S   D   S   F   G   L   P   K   G   A   K   N   R   Q   N   A   I   N   W   L   K   L   V   G   S   K   E   G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
        970       980       990      1000      1010      1020      1030      1040      1050      1060      1070      1080

              310                                     320                                     330                                     340
  Q   D   T   F   N   P   L   K   G   S   I   A   A   R   L   D   S   D   P   A   K   Y   N   A   Y   G   Q   S   A   M   K   D   W   K   S   N   R   I   V   G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
       1090      1100      1110      1120      1130      1140      1150      1160      1170      1180      1190      1200

              350                                     360                                     370                                     380
  S   L   V   H   G   A   V   A   P   E   S   F   M   S   Q   F   G   T   V   M   E   I   F   L   Q   S   R   N   P   Q   A   A   A   N   A   A   Q   A   I   A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
       1210      1220      1230      1240      1250      1260      1270      1280      1290      1300      1310      1320

              390                                     400
  N   Q   V   G   L   G   R   G   G   S   H   H   H   H   H   H   *   *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
       1330      1340      1350      1360      1370      1380      1390      1400      1410      1420      1430      1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
       1450      1460      1470      1480      1490      1500      1510      1520      1530      1540      1550      1560


GCACGTTGGCAAGCTCG
CGTGCAACCGTTCGAGC
       1570
```

FIG. 42 (Continued)

FIG. 43 - tsGBP2.13C.Q64M

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                              10                            20
                                                  M  K  L  E  I  F  S  W  W  A  G  D  C  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGGGCAGGTGATTGTGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACCCGTCCACTAACACCGGGTCGAGAGCTTCGGAACTAGGCCAACAT
       130       140       150       160       170       180       190       200       210       220       230       240

             30                            40                            50                            60
 K  Q  K  Y  P  G  V  E  V  I  N  A  T  V  T  G  G  A  G  V  N  A  K  A  V  L  K  T  R  M  L  G  G  D  P  P  D  T  F  M
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTAT
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAATA
       250       260       270       280       290       300       310       320       330       340       350       360

             70                            80                            90                           100
 V  H  A  G  Q  E  L  I  G  T  W  V  V  A  D  R  M  E  D  L  T  S  L  F  R  Q  E  G  W  L  Q  A  F  P  K  G  L  I  D  L
GGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
CCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

            110                           120                           130                           140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

            150                           160                           170                           180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

            190                           200                           210                           220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

            230                           240                           250                           260
 Q  Q  A  V  D  R  V  V  Q  G  K  A  A  F  N  I  M  G  D  W  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850       860       870       880       890       900       910       920       930       940       950       960
```

```
                 270                                    280                                    290                                    300
  P   S   P   G   T   S   G   I   F   M   M   L   S   D   S   F   G   L   P   K   G   A   K   N   R   Q   N   A   I   N   W   L   K   L   V   G   S   K   E   G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
         970          980          990         1000         1010         1020         1030         1040         1050         1060         1070         1080

                 310                                    320                                    330                                    340
  Q   D   T   F   N   P   L   K   G   S   I   A   A   R   L   D   S   D   P   A   K   Y   N   A   Y   G   Q   S   A   M   K   D   W   K   S   N   R   I   V   G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
        1090         1100         1110         1120         1130         1140         1150         1160         1170         1180         1190         1200

                 350                                    360                                    370                                    380
  S   L   V   H   G   A   V   A   P   E   S   F   M   S   Q   F   G   T   V   M   E   I   F   L   Q   S   R   N   P   Q   A   A   A   N   A   A   Q   A   I   A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
        1210         1220         1230         1240         1250         1260         1270         1280         1290         1300         1310         1320

                 390                                    400
  N   Q   V   G   L   G   R   G   G   S   H   H   H   H   H   H   *   *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
        1330         1340         1350         1360         1370         1380         1390         1400         1410         1420         1430         1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
        1450         1460         1470         1480         1490         1500         1510         1520         1530         1540         1550         1560


GCACGTTGGCAAGCTCG
CGTGCAACCGTTCGAGC
        1570
```

FIG. 43 (Continued)

FIG. 44 - tsGBP2.13C.H66Q

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                      10                            20
                                                  M  K  L  E  I  F  S  W  W  A  G  D  C  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGGGCAGGTGATTGTGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACCCGTCCACTAACACCGGGTCGAGAGCTTCGGAACTAGGCCAACAT
       130       140       150       160       170       180       190       200       210       220       230       240

          30                            40                            50                            60
 K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
       250       260       270       280       290       300       310       320       330       340       350       360

          70                            80                            90                           100
 V  Q  A  G  Q  E  L  I  G  T  W  V  V  A  D  R  M  E  D  L  T  S  L  F  R  Q  E  G  W  L  Q  A  F  P  K  G  L  I  D  L
AGTACAGGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTCCGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

         110                           120                           130                           140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

         150                           160                           170                           180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

         190                           200                           210                           220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

         230                           240                           250                           260
 Q  Q  A  V  D  R  V  V  Q  G  K  A  A  F  N  I  M  G  D  W  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850       860       870       880       890       900       910       920       930       940       950       960
```

```
              270                                     280                                     290                                     300
 P  S  P  G  T  S  G  I  F  M  M  L  S  D  S  F  G  L  P  K  G  A  K  N  R  Q  N  A  I  N  W  L  K  L  V  G  S  K  E  G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
       970       980       990      1000      1010      1020      1030      1040      1050      1060      1070      1080

              310                                     320                                     330                                     340
 Q  D  T  F  N  P  L  K  G  S  I  A  A  R  L  D  S  D  P  A  K  Y  N  A  Y  G  Q  S  A  M  K  D  W  K  S  N  R  I  V  G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
      1090      1100      1110      1120      1130      1140      1150      1160      1170      1180      1190      1200

              350                                     360                                     370                                     380
 S  L  V  H  G  A  V  A  P  E  S  F  M  S  Q  F  G  T  V  M  E  I  F  L  Q  S  R  N  P  Q  A  A  A  N  A  A  Q  A  I  A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
      1210      1220      1230      1240      1250      1260      1270      1280      1290      1300      1310      1320

              390                                     400
 N  Q  V  G  L  G  R  G  G  S  H  H  H  H  H  H  *  *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
      1330      1340      1350      1360      1370      1380      1390      1400      1410      1420      1430      1440

GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
      1450      1460      1470      1480      1490      1500      1510      1520      1530      1540      1550      1560

GCACGTTGGCAAGCTCG
CGTGCAACCGTTCGAGC
      1570
```

FIG. 44 (Continued)

FIG. 45 - tsGBP2.13C.W244M

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                              10                            20
                                                        M  K  L  E  I  F  S  W  W  A  G  D  C  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGGGCAGGTGATTGTGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACCCGTCCACTAACACCGGGTCGAGAGCTTCGGAACTAGGCCAACAT
       130       140       150       160       170       180       190       200       210       220       230       240

         30                            40                            50                            60
 K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
       250       260       270       280       290       300       310       320       330       340       350       360

         70                            80                            90                           100
 V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

        110                           120                           130                           140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

        150                           160                           170                           180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

        190                           200                           210                           220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

        230                           240                           250                           260
 Q  Q  A  V  D  R  V  V  Q  G  K  A  A  F  N  I  M  G  D  M  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACATGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGTACCGTCGTCCAATGTACTCATGCTGGAATTTTGACTTCGGTCCATGGCTGAAGCGTACCTG
       850       860       870       880       890       900       910       920       930       940       950       960
```

```
                 270                                     280                                     290                                     300
 P  S  P  G  T  S  G  I  F  M  M  L  S  D  S  F  G  L  P  K  G  A  K  N  R  Q  N  A  I  N  W  L  K  L  V  G  S  K  E  G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
        970       980       990      1000      1010      1020      1030      1040      1050      1060      1070      1080

                 310                                     320                                     330                                     340
 Q  D  T  F  N  P  L  K  G  S  I  A  A  R  L  D  S  D  P  A  K  Y  N  A  Y  G  Q  S  A  M  K  D  W  K  S  N  R  I  V  G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
       1090      1100      1110      1120      1130      1140      1150      1160      1170      1180      1190      1200

                 350                                     360                                     370                                     380
 S  L  V  H  G  A  V  A  P  E  S  F  M  S  Q  F  G  T  V  M  E  I  F  L  Q  S  R  N  P  Q  A  A  A  N  A  A  Q  A  I  A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
       1210      1220      1230      1240      1250      1260      1270      1280      1290      1300      1310      1320

                 390                                     400
 N  Q  V  G  L  G  R  G  G  S  H  H  H  H  H  H  *  *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
       1330      1340      1350      1360      1370      1380      1390      1400      1410      1420      1430      1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
       1450      1460      1470      1480      1490      1500      1510      1520      1530      1540      1550      1560


GCACGTTGGCAAGCTCG
CGTGCAACCGTTCGAGC
       1570
```

FIG. 45 (Continued)

FIG. 46 - tsGBP2.13C.W244F

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                   10                            20
                                                          M  K  L  E  I  F  S  W  W  A  G  D  C  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGGGCAGGTGATTGTGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACCCGTCCACTAACACCGGGTCGAGAGCTTCGGAACTAGGCCAACAT
       130       140       150       160       170       180       190       200       210       220       230       240

           30                            40                            50                            60
 K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
       250       260       270       280       290       300       310       320       330       340       350       360

           70                            80                            90                           100
 V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

          110                           120                           130                           140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

          150                           160                           170                           180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

          190                           200                           210                           220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

          230                           240                           250                           260
 Q  Q  A  V  D  R  V  V  Q  G  K  A  A  F  N  I  M  G  D  F  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTTTGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGAAACGTCGTCCAATGTACTCATGCTGGAATTTTGACTTCGGTCCATGGCTGAAGCGTACCTG
       850       860       870       880       890       900       910       920       930       940       950       960
```

```
                 270                                     280                                     290                                     300
 P  S  P  G  T  S  G  I  F  M  M  L  S  D  S  F  G  L  P  K  G  A  K  N  R  Q  N  A  I  N  W  L  K  L  V  G  S  K  E  G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
       970       980       990      1000      1010      1020      1030      1040      1050      1060      1070      1080

                 310                                     320                                     330                                     340
 Q  D  T  F  N  P  L  K  G  S  I  A  A  R  L  D  S  D  P  A  K  Y  N  A  Y  G  Q  S  A  M  K  D  W  K  S  N  R  I  V  G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
      1090      1100      1110      1120      1130      1140      1150      1160      1170      1180      1190      1200

                 350                                     360                                     370                                     380
 S  L  V  H  G  A  V  A  P  E  S  F  M  S  Q  F  G  T  V  M  E  I  F  L  Q  S  R  N  P  Q  A  A  A  N  A  A  Q  A  I  A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
      1210      1220      1230      1240      1250      1260      1270      1280      1290      1300      1310      1320

                 390                                     400
 N  Q  V  G  L  G  R  G  G  S  H  H  H  H  H  H  *  *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
      1330      1340      1350      1360      1370      1380      1390      1400      1410      1420      1430      1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
      1450      1460      1470      1480      1490      1500      1510      1520      1530      1540      1550      1560


GCACGTTGGCAAGCTCG
CGTGCAACCGTTCGAGC
      1570
```

FIG. 46 (Continued)

FIG. 47 - tsGBP2.13C.W244Y

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                            10                            20
                                                      M  K  L  E  I  F  S  W  W  A  G  D  C  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGGGCAGGTGATTGTGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACCCGTCCACTAACACCGGGTCGAGAGCTTCGGAACTAGGCCAACAT
       130       140       150       160       170       180       190       200       210       220       230       240

              30                            40                            50                            60
 K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
       250       260       270       280       290       300       310       320       330       340       350       360

              70                            80                            90                           100
 V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

             110                           120                           130                           140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

             150                           160                           170                           180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

             190                           200                           210                           220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

             230                           240                           250                           260
 Q  Q  A  V  D  R  V  V  Q  G  K  A  A  F  N  I  M  G  D  Y  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTATGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGATACGTCGTCCAATGTACTCATGCTGGAATTTTGACTTCGGTCCATGGCTGAAGCGTACCTG
       850       860       870       880       890       900       910       920       930       940       950       960
```

```
              270                                280                                290                                300
 P  S  P  G  T  S  G  I  F  M  M  L  S  D  S  F  G  L  P  K  G  A  K  N  R  Q  N  A  I  N  W  L  K  L  V  G  S  K  E  G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
       970       980       990      1000      1010      1020      1030      1040      1050      1060      1070      1080

              310                                320                                330                                340
 Q  D  T  F  N  P  L  K  G  S  I  A  A  R  L  D  S  D  P  A  K  Y  N  A  Y  G  Q  S  A  M  K  D  W  K  S  N  R  I  V  G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
      1090      1100      1110      1120      1130      1140      1150      1160      1170      1180      1190      1200

              350                                360                                370                                380
 S  L  V  H  G  A  V  A  P  E  S  F  M  S  Q  F  G  T  V  M  E  I  F  L  Q  S  R  N  P  Q  A  A  A  N  A  A  Q  A  I  A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
      1210      1220      1230      1240      1250      1260      1270      1280      1290      1300      1310      1320

              390                                400
 N  Q  V  G  L  G  R  G  G  S  H  H  H  H  H  H  *  *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
      1330      1340      1350      1360      1370      1380      1390      1400      1410      1420      1430      1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
      1450      1460      1470      1480      1490      1500      1510      1520      1530      1540      1550      1560


GCACGTTGGCAAGCTCG
CGTGCAACCGTTCGAGC
      1570
```

FIG. 47 (Continued)

FIG. 48 - tsGBP2.13C.D278N

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                     10                            20
                                                                 M  K  L  E  I  F  S  W  W  A  G  D  C  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGGGCAGGTGATTGTGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACCCGTCCACTAACACCGGGTCGAGAGCTTCGGAACTAGGCCAACAT
       130       140       150       160       170       180       190       200       210       220       230       240

         30                            40                            50                            60
K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
       250       260       270       280       290       300       310       320       330       340       350       360

         70                            80                            90                           100
V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

        110                           120                           130                           140
L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

        150                           160                           170                           180
F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

        190                           200                           210                           220
G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

        230                           240                           250                           260
Q  Q  A  V  D  R  V  V  Q  G  K  A  A  F  N  I  M  G  D  W  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850       860       870       880       890       900       910       920       930       940       950       960
```

```
              270                                     280                                     290                                     300
 P   S   P   G   T   S   G   I   F   M   M   L   S   N   S   F   G   L   P   K   G   A   K   N   R   Q   N   A   I   N   W   L   K   L   V   G   S   K   E   G
ACCTTCTCCGGGCACTTCAGGGATCTTTATGATGCTGTCTAACAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGATTGTCAAAGCCGAACGGTTTCCCCCGCTTCTTAGCAGTTTTACGATAATTGACCAACTTTGAGCAGCCCAGTTTTCTCCC
        970       980       990      1000      1010      1020      1030      1040      1050      1060      1070      1080

              310                                     320                                     330                                     340
 Q   D   T   F   N   P   L   K   G   S   I   A   A   R   L   D   S   D   P   A   K   Y   N   A   Y   G   Q   S   A   M   K   D   W   K   S   N   R   I   V   G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
       1090      1100      1110      1120      1130      1140      1150      1160      1170      1180      1190      1200

              350                                     360                                     370                                     380
 S   L   V   H   G   A   V   A   P   E   S   F   M   S   Q   F   G   T   V   M   E   I   F   L   Q   S   R   N   P   Q   A   A   A   N   A   A   Q   A   I   A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
       1210      1220      1230      1240      1250      1260      1270      1280      1290      1300      1310      1320

              390                                     400
 N   Q   V   G   L   G   R   G   G   S   H   H   H   H   H   H   *   *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
       1330      1340      1350      1360      1370      1380      1390      1400      1410      1420      1430      1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
       1450      1460      1470      1480      1490      1500      1510      1520      1530      1540      1550      1560


GCACGTTGGCAAGCTCG
CGTGCAACCGTTCGAGC
       1570
```

FIG. 48 (Continued)

FIG. 49 - tsGBP2.13C.D278S

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                          10                            20
                                                                       M  K  L  E  I  F  S  W  W  A  G  D  C  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGGGCAGGTGATTGTGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACCCGTCCACTAACACCGGGTCGAGAGCTTCGGAACTAGGCCAACAT
       130       140       150       160       170       180       190       200       210       220       230       240

       30                            40                            50                            60
 K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
       250       260       270       280       290       300       310       320       330       340       350       360

       70                            80                            90                           100
 V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

      110                           120                           130                           140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

      150                           160                           170                           180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

      190                           200                           210                           220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

      230                           240                           250                           260
 Q  Q  A  V  D  R  V  V  Q  G  K  A  A  F  N  I  M  G  D  W  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850       860       870       880       890       900       910       920       930       940       950       960
```

```
                 270                                     280                                     290                                     300
  P   S   P   G   T   S   G   I   F   M   M   L   S   S   S   F   G   L   P   K   G   A   K   N   R   Q   N   A   I   N   W   L   K   L   V   G   S   K   E   G
ACCTTCTCCGGGCACTTCAGGGATCTTTATGATGCTGTCTAGCAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGATCGTCAAAGCCGAACGGTTTCCCCCGCTTCTTAGCAGTTTTACGATAATTGACCAACTTTGAGCAGCCCAGTTTTCTCCC
        970       980       990      1000      1010      1020      1030      1040      1050      1060      1070      1080

                 310                                     320                                     330                                     340
  Q   D   T   F   N   P   L   K   G   S   I   A   A   R   L   D   S   D   P   A   K   Y   N   A   Y   G   Q   S   A   M   K   D   W   K   S   N   R   I   V   G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
       1090      1100      1110      1120      1130      1140      1150      1160      1170      1180      1190      1200

                 350                                     360                                     370                                     380
  S   L   V   H   G   A   V   A   P   E   S   F   M   S   Q   F   G   T   V   M   E   I   F   L   Q   S   R   N   P   Q   A   A   A   N   A   A   Q   A   I   A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
       1210      1220      1230      1240      1250      1260      1270      1280      1290      1300      1310      1320

                 390                                     400
  N   Q   V   G   L   G   R   G   G   S   H   H   H   H   H   H   *   *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
       1330      1340      1350      1360      1370      1380      1390      1400      1410      1420      1430      1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
       1450      1460      1470      1480      1490      1500      1510      1520      1530      1540      1550      1560


GCACGTTGGCAAGCTCG
CGTGCAACCGTTCGAGC
       1570
```

FIG. 49 (Continued)

FIG. 50 - tsGBP2.13C.D278L

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                           10                  20
                                                  M  K  L  E  I  F  S  W  W  A  G  D  C  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGGGCAGGTGATTGTGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACCCGTCCACTAACACCGGGTCGAGAGCTTCGGAACTAGGCCAACAT
       130       140       150       160       170       180       190       200       210       220       230       240

         30                  40                  50                  60
 K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
       250       260       270       280       290       300       310       320       330       340       350       360

         70                  80                  90                 100
 V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

        110                 120                 130                 140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

        150                 160                 170                 180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

        190                 200                 210                 220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

        230                 240                 250                 260
 Q  Q  A  V  D  R  V  V  Q  G  K  A  A  F  N  I  M  G  D  W  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850       860       870       880       890       900       910       920       930       940       950       960
```

```
              270                                280                                290                                300
 P   S   P   G   T   S   G   I   F   M   M   L   S   L   S   F   G   L   P   K   G   A   K   N   R   Q   N   A   I   N   W   L   K   L   V   G   S   K   E   G
ACCTTCTCCGGGCACTTCAGGGATCTTTATGATGCTGTCTCTGAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGAGACTCAAAGCCGAACGGTTTCCCCCGCTTCTTAGCAGTTTTACGATAATTGACCAACTTTGAGCAGCCCAGTTTTCTCCC
        970       980       990      1000      1010      1020      1030      1040      1050      1060      1070      1080

              310                                320                                330                                340
 Q   D   T   F   N   P   L   K   G   S   I   A   A   R   L   D   S   D   P   A   K   Y   N   A   Y   G   Q   S   A   M   K   D   W   K   S   N   R   I   V   G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
       1090      1100      1110      1120      1130      1140      1150      1160      1170      1180      1190      1200

              350                                360                                370                                380
 S   L   V   H   G   A   V   A   P   E   S   F   M   S   Q   F   G   T   V   M   E   I   F   L   Q   S   R   N   P   Q   A   A   A   N   A   A   Q   A   I   A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
       1210      1220      1230      1240      1250      1260      1270      1280      1290      1300      1310      1320

              390                                400
 N   Q   V   G   L   G   R   G   G   S   H   H   H   H   H   H   *   *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
       1330      1340      1350      1360      1370      1380      1390      1400      1410      1420      1430      1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
       1450      1460      1470      1480      1490      1500      1510      1520      1530      1540      1550      1560


GCACGTTGGCAAGCTCG
CGTGCAACCGTTCGAGC
       1570
```

FIG. 50 (Continued)

FIG. 51 - tsGBP2.13C.K312M

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
         10        20        30        40        50        60        70        80        90       100       110       120

                                                                                          10                            20
                                                      M  K  L  E  I  F  S  W  W  A  G  D  C  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGGGCAGGTGATTGTGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACCCGTCCACTAACACCGGGTCGAGAGCTTCGGAACTAGGCCAACAT
        130       140       150       160       170       180       190       200       210       220       230       240

          30                            40                            50                            60
 K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
        250       260       270       280       290       300       310       320       330       340       350       360

          70                            80                            90                           100
 V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
        370       380       390       400       410       420       430       440       450       460       470       480

         110                           120                           130                           140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
        490       500       510       520       530       540       550       560       570       580       590       600

         150                           160                           170                           180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
        610       620       630       640       650       660       670       680       690       700       710       720

         190                           200                           210                           220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
        730       740       750       760       770       780       790       800       810       820       830       840

         230                           240                           250                           260
 Q  Q  A  V  D  R  V  V  Q  G  K  A  A  F  N  I  M  G  D  W  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
        850       860       870       880       890       900       910       920       930       940       950       960
```

```
                 270                                     280                                     290                                     300
  P   S   P   G   T   S   G   I   F   M   M   L   S   D   S   F   G   L   P   K   G   A   K   N   R   Q   N   A   I   N   W   L   K   L   V   G   S   K   E   G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
         970          980          990         1000         1010         1020         1030         1040         1050         1060         1070         1080

                 310                                     320                                     330                                     340
  Q   D   T   F   N   P   L   M   G   S   I   A   A   R   L   D   S   D   P   A   K   Y   N   A   Y   G   Q   S   A   M   K   D   W   K   S   N   R   I   V   G
GCAGGACACCTTCAACCCGCTCATGGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTACCCAAGGTAGCGACGAGCAGAGCTAAGACTAGGACGGTTTATATTACGTATGCCGGTTTCACGTTACTTCCTGACCTTCAGTTTAGCCTAGCATCC
        1090         1100         1110         1120         1130         1140         1150         1160         1170         1180         1190         1200

                 350                                     360                                     370                                     380
  S   L   V   H   G   A   V   A   P   E   S   F   M   S   Q   F   G   T   V   M   E   I   F   L   Q   S   R   N   P   Q   A   A   A   N   A   A   Q   A   I   A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
        1210         1220         1230         1240         1250         1260         1270         1280         1290         1300         1310         1320

                 390                                     400
  N   Q   V   G   L   G   R   G   G   S   H   H   H   H   H   H   *   *
CAATCAGGTCGGTTTAGGTCGTGGGGGTTCACATCATCATCATCATCATTAATGAAAGGGCGATATCCAGCACACTGGCGGCCGTTACTAGTGGATCCGGCTGCTAACAAAGCCCGAAAG
GTTAGTCCAGCCAAATCCAGCACCCCCAAGTGTAGTAGTAGTAGTAGTAATTACTTTCCCGCTATAGGTCGTGTGACCGCCGGCAATGATCACCTAGGCCGACGATTGTTTCGGGCTTTC
        1330         1340         1350         1360         1370         1380         1390         1400         1410         1420         1430         1440


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
        1450         1460         1470         1480         1490         1500         1510         1520         1530         1540         1550         1560


GCACGTTGGCAAGCTCG
CGTGCAACCGTTCGAGC
        1570
```

FIG. 51 (Continued)

FIG. 52 - tsGBP2.13C.bZif

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                  10                            20
                                                              M  K  L  E  I  F  S  W  W  A  G  D  C  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGGGCAGGTGATTGCGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACCCGTCCACTAACGCCGGGTCGAGAGCTTCGGAACTAGGCCAACAT
       130       140       150       160       170       180       190       200       210       220       230       240

            30                            40                            50                            60
 K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
       250       260       270       280       290       300       310       320       330       340       350       360

            70                            80                            90                           100
 V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

           110                           120                           130                           140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
       490       500       510       520       530       540       550       560       570       580       590       600

           150                           160                           170                           180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

           190                           200                           210                           220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

           230                           240                           250                           260
 Q  Q  A  V  D  R  V  V  Q  G  K  A  A  F  N  I  M  G  D  W  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGGGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACCCGTCGTCCAATGTACTCATGCTGGAATTTTGACTTCGGTCCATGGCTGAAGCGTACCTG
       850       860       870       880       890       900       910       920       930       940       950       960
```

```
               270                                280                                290                                300
 P  S  P  G  T  S  G  I  F  M  M  L  S  D  S  F  G  L  P  K  G  A  K  N  R  Q  N  A  I  N  W  L  K  L  V  G  S  K  E  G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
       970       980       990      1000      1010      1020      1030      1040      1050      1060      1070      1080

               310                                320                                330                                340
 Q  D  T  F  N  P  L  K  G  S  I  A  A  R  L  D  S  D  P  A  K  Y  N  A  Y  G  Q  S  A  M  K  D  W  K  S  N  R  I  V  G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
      1090      1100      1110      1120      1130      1140      1150      1160      1170      1180      1190      1200

               350                                360                                370                                380
 S  L  V  H  G  A  V  A  P  E  S  F  M  S  Q  F  G  T  V  M  E  I  F  L  Q  S  R  N  P  Q  A  A  A  N  A  A  Q  A  I  A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
      1210      1220      1230      1240      1250      1260      1270      1280      1290      1300      1310      1320

               390                                400                                410                                420
 N  Q  V  G  L  G  R  G  G  S  G  G  S  T  G  E  K  P  Y  K  C  P  E  C  G  K  S  F  S  R  S  G  G  S  H  H  H  H  H  H
CAATCAGGTCGGTTTAGGTCGTGGCGGCAGCGGCGGCAGCACCGGCGAAAAACCGTATAAATGCCCGGAATGCGGCAAAAGCTTTAGCCGCAGCGGGGGTTCACATCATCATCATCATCA
GTTAGTCCAGCCAAATCCAGCACCGCCGTCGCCGCCGTCGTGGCCGCTTTTTGGCATATTTACGGGCCTTACGCCGTTTTCGAAATCGGCGTCGCCCCCAAGTGTAGTAGTAGTAGTAGT
      1330      1340      1350      1360      1370      1380      1390      1400      1410      1420      1430      1440

 *  *
TTAATGAAAGGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCC
AATTACTTTCCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGG
      1450      1460      1470      1480      1490      1500      1510      1520      1530      1540      1550      1560

CTTGGGGCCTCTAAACGGGTCTTGAGGGGTTTTTTGCTGAAAGGAGGAACTATATCCGGAGCGACTCCCACGGCACGTTGGCAAGCTCG
GAACCCCGGAGATTTGCCCAGAACTCCCCAAAAAACGACTTTCCTCCTTGATATAGGCCTCGCTGAGGGTGCCGTGCAACCGTTCGAGC
      1570      1580      1590      1600      1610      1620      1630      1640
```

FIG. 52 (Continued)

FIG. 53 - tsGBP2.244C.bZif

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
         10        20        30        40        50        60        70        80        90       100       110       120

                                                                                               10                  20
                                                  M  K  L  E  I  F  S  W  W  A  G  D  E  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGGGCAGGTGATGAAGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACCCGTCCACTACTTCCGGGTCGAGAGCTTCGGAACTAGGCCAACAT
        130       140       150       160       170       180       190       200       210       220       230       240

          30                  40                  50                  60
 K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
        250       260       270       280       290       300       310       320       330       340       350       360

          70                  80                  90                 100
 V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
        370       380       390       400       410       420       430       440       450       460       470       480

         110                 120                 130                 140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTTCTTACCCCGCACTGGGGCGGTTTTTGTACCCGTCT
        490       500       510       520       530       540       550       560       570       580       590       600

         150                 160                 170                 180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
        610       620       630       640       650       660       670       680       690       700       710       720

         190                 200                 210                 220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
        730       740       750       760       770       780       790       800       810       820       830       840

         230                 240                 250                 260
 Q  Q  A  V  D  R  V  V  Q  G  K  A  A  F  N  I  M  G  D  C  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTGCGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGACGCGTCGTCCAATGTACTCATGCTGGAATTTTGACTTCGGTCCATGGCTGAAGCGTACCTG
        850       860       870       880       890       900       910       920       930       940       950       960
```

```
          270                           280                           290                           300
 P  S  P  G  T  S  G  I  F  M  M  L  S  D  S  F  G  L  P  K  G  A  K  N  R  Q  N  A  I  N  W  L  K  L  V  G  S  K  E  G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
      970       980       990      1000      1010      1020      1030      1040      1050      1060      1070      1080

          310                           320                           330                           340
 Q  D  T  F  N  P  L  K  G  S  I  A  A  R  L  D  S  D  P  A  K  Y  N  A  Y  G  Q  S  A  M  K  D  W  K  S  N  R  I  V  G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
     1090      1100      1110      1120      1130      1140      1150      1160      1170      1180      1190      1200

          350                           360                           370                           380
 S  L  V  H  G  A  V  A  P  E  S  F  M  S  Q  F  G  T  V  M  E  I  F  L  Q  S  R  N  P  Q  A  A  A  N  A  A  Q  A  I  A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
     1210      1220      1230      1240      1250      1260      1270      1280      1290      1300      1310      1320

          390                           400                           410                           420
 N  Q  V  G  L  G  R  G  G  S  G  G  S  T  G  E  K  P  Y  K  C  P  E  C  G  K  S  F  S  R  S  G  G  S  H  H  H  H  H  H
CAATCAGGTCGGTTTAGGTCGTGGCGGCAGCGGCGGCAGCACCGGCGAAAAACCGTATAAATGCCCGGAATGCGGCAAAAGCTTTAGCCGCAGCGGGGGTTCACATCATCATCATCATCA
GTTAGTCCAGCCAAATCCAGCACCGCCGTCGCCGCCGTCGTGGCCGCTTTTTGGCATATTTACGGGCCTTACGCCGTTTTCGAAATCGGCGTCGCCCCCAAGTGTAGTAGTAGTAGTAGT
     1330      1340      1350      1360      1370      1380      1390      1400      1410      1420      1430      1440


 *  *
TTAATGAAAGGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCC
AATTACTTTCCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGG
     1450      1460      1470      1480      1490      1500      1510      1520      1530      1540      1550      1560


CTTGGGGCCTCTAAACGGGTCTTGAGGGGTTTTTTGCTGAAAGGAGGAACTATATCCGGAGCGACTCCCACGGCACGTTGGCAAGCTCG
GAACCCCGGAGATTTGCCCAGAACTCCCCAAAAAACGACTTTCCTCCTTGATATAGGCCTCGCTGAGGGTGCCGTGCAACCGTTCGAGC
     1570      1580      1590      1600      1610      1620      1630      1640
```

FIG. 53 (Continued)

FIG. 54 - tsGBP2.13C_244F.bZif

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                              10                  20
                                                    M  K  L  E  I  F  S  W  W  A  G  D  C  G  P  A  L  E  A  L  I  R  L  Y
GGTTTCCCTCTAGAAATAATTTTGTTTAACTTTAAGAAGGAGATATACCATGAAATTAGAAATTTTTTCTTGGTGGGCAGGTGATTGCGGCCCAGCTCTCGAAGCCTTGATCCGGTTGTA
CCAAAGGGAGATCTTTATTAAAACAAATTGAAATTCTTCCTCTATATGGTACTTTAATCTTTAAAAAAGAACCACCCGTCCACTAACGCCGGGTCGAGAGCTTCGGAACTAGGCCAACAT
       130       140       150       160       170       180       190       200       210       220       230       240

          30                            40                            50                            60
 K  Q  K  Y  P  G  V  E  V  I  N  A  T  V  T  G  G  A  G  V  N  A  K  A  V  L  K  T  R  M  L  G  G  D  P  P  D  T  F  Q
TAAACAGAAATACCCAGGTGTAGAGGTCATTAATGCTACCGTCACCGGGGGTGCCGGTGTCAACGCCAAAGCCGTCCTTAAAACGCGTATGCTCGGCGGGGACCCACCAGATACCTTTCA
ATTTGTCTTTATGGGTCCACATCTCCAGTAATTACGATGGCAGTGGCCCCCACGGCCACAGTTGCGGTTTCGGCAGGAATTTTGCGCATACGAGCCGCCCCTGGGTGGTCTATGGAAAGT
       250       260       270       280       290       300       310       320       330       340       350       360

          70                            80                            90                           100
 V  H  A  G  Q  E  L  I  G  T  W  V  V  A  D  R  M  E  D  L  T  S  L  F  R  Q  E  G  W  L  Q  A  F  P  K  G  L  I  D  L
AGTACATGCAGGGCAGGAGCTGATCGGCACATGGGTCGTCGCCGACCGTATGGAAGATCTTACCTCATTGTTTCGGCAGGAGGGCTGGCTTCAAGCGTTCCCAAAAGGTTTAATCGATCT
TCATGTACGTCCCGTCCTCGACTAGCCGTGTACCCAGCAGCGGCTGGCATACCTTCTAGAATGGAGTAACAAAGCCGTCCTCCCGACCGAAGTTCGCAAGGGTTTTCCAAATTAGCTAGA
       370       380       390       400       410       420       430       440       450       460       470       480

         110                           120                           130                           140
 L  S  Y  K  G  G  I  W  S  V  P  V  N  I  H  R  S  N  V  M  W  Y  I  P  A  K  L  K  E  W  G  V  T  P  P  K  T  W  A  E
CCTCAGTTACAAAGGTGGCATTTGGTCAGTCCCAGTCAACATCCACCGTTCTAACGTAATGTGGTACATCCCGGCAAAATTAAAAGAATGGGGCGTGACCCCGCCAAAAACATGGGCAGA
GGAGTCAATGTTTCCACCGTAAACCAGTCAGGGTCAGTTGTAGGTGGCAAGATTGCATTACACCATGTAGGGCCGTTTTAATTTCTTACCCCGCACTGGGGCGGTTTTTGTACCCGTCT
       490       500       510       520       530       540       550       560       570       580       590       600

         150                           160                           170                           180
 F  L  A  T  A  Q  T  L  K  R  K  G  L  E  A  P  L  A  L  G  E  N  W  T  Q  Q  H  L  W  E  S  V  A  L  A  T  L  G  A  D
ATTTTTAGCGACAGCGCAAACATTAAAGCGGAAAGGCCTTGAGGCACCATTGGCACTCGGTGAGAATTGGACACAGCAACATCTCTGGGAAAGCGTCGCCCTCGCCACACTGGGTGCCGA
TAAAAATCGCTGTCGCGTTTGTAATTTCGCCTTTCCGGAACTCCGTGGTAACCGTGAGCCACTCTTAACCTGTGTCGTTGTAGAGACCCTTTCGCAGCGGGAGCGGTGTGACCCACGGCT
       610       620       630       640       650       660       670       680       690       700       710       720

         190                           200                           210                           220
 G  W  N  N  L  W  S  G  K  L  K  F  T  D  P  K  A  V  A  V  W  E  T  F  G  K  V  L  D  A  A  N  K  D  A  A  G  L  S  W
TGGTTGGAATAATCTCTGGAGTGGTAAGCTCAAATTCACGGATCCAAAAGCAGTCGCCGTATGGGAAACATTCGGTAAGGTATTAGATGCAGCGAACAAGGATGCAGCCGGGCTTTCATG
ACCAACCTTATTAGAGACCTCACCATTCGAGTTTAAGTGCCTAGGTTTTCGTCAGCGGCATACCCTTTGTAAGCCATTCCATAATCTACGTCGCTTGTTCCTACGTCGGCCCGAAAGTAC
       730       740       750       760       770       780       790       800       810       820       830       840

         230                           240                           250                           260
 Q  Q  A  V  D  R  V  V  Q  G  K  A  A  F  N  I  M  G  D  F  A  A  G  Y  M  S  T  T  L  K  L  K  P  G  T  D  F  A  W  T
GCAACAAGCAGTAGACCGTGTAGTACAGGGGAAAGCTGCATTCAATATCATGGGGGACTTTGCAGCAGGTTACATGAGTACGACCTTAAAACTGAAGCCAGGTACCGACTTCGCATGGAC
CGTTGTTCGTCATCTGGCACATCATGTCCCCTTTCGACGTAAGTTATAGTACCCCCTGAAACGTCGTCCAATGTACTCATGCTGGAATTTTGACTTCGGTCCATGGCTGAAGCGTACCTG
       850       860       870       880       890       900       910       920       930       940       950       960
```

```
                270                                     280                                     290                                     300
P   S   P   G   T   S   G   I   F   M   M   L   S   D   S   F   G   L   P   K   G   A   K   N   R   Q   N   A   I   N   W   L   K   L   V   G   S   K   E   G
ACCTTCTCCGGGCACTTCAGGGATCTTTATGATGCTGTCTGATAGTTTCGGCTTGCCAAAGGGGGCGAAGAATCGTCAAAATGCTATTAACTGGTTGAAACTCGTCGGGTCAAAAGAGGG
TGGAAGAGGCCCGTGAAGTCCCTAGAAATACTACGACAGACTATCAAAGCCGAACGGTTTCCCCCGCTTCTTAGCAGTTTTACGATAATTGACCAACTTTGAGCAGCCCAGTTTTCTCCC
         970          980          990         1000         1010         1020         1030         1040         1050         1060         1070         1080

                310                                     320                                     330                                     340
Q   D   T   F   N   P   L   K   G   S   I   A   A   R   L   D   S   D   P   A   K   Y   N   A   Y   G   Q   S   A   M   K   D   W   K   S   N   R   I   V   G
GCAGGACACCTTCAACCCGCTCAAAGGTTCCATCGCTGCTCGTCTCGATTCTGATCCTGCCAAATATAATGCATACGGCCAAAGTGCAATGAAGGACTGGAAGTCAAATCGGATCGTAGG
CGTCCTGTGGAAGTTGGGCGAGTTTCCAAGGTAGCGACGAGCAGAGCTAAGACTAGGACGGTTTATATTACGTATGCCGGTTTCACGTTACTTCCTGACCTTCAGTTTAGCCTAGCATCC
        1090         1100         1110         1120         1130         1140         1150         1160         1170         1180         1190         1200

                350                                     360                                     370                                     380
S   L   V   H   G   A   V   A   P   E   S   F   M   S   Q   F   G   T   V   M   E   I   F   L   Q   S   R   N   P   Q   A   A   A   N   A   A   Q   A   I   A
CTCCCTCGTCCACGGCGCAGTCGCGCCAGAATCCTTCATGTCGCAGTTTGGGACGGTAATGGAGATTTTCTTGCAATCCCGTAACCCGCAGGCAGCCGCTAATGCCGCACAAGCTATCGC
GAGGGAGCAGGTGCCGCGTCAGCGCGGTCTTAGGAAGTACAGCGTCAAACCCTGCCATTACCTCTAAAAGAACGTTAGGGCATTGGGCGTCCGTCGGCGATTACGGCGTGTTCGATAGCG
        1210         1220         1230         1240         1250         1260         1270         1280         1290         1300         1310         1320

                390                                     400                                     410                                     420
N   Q   V   G   L   G   R   G   G   S   G   G   S   T   G   E   K   P   Y   K   C   P   E   C   G   K   S   F   S   R   S   G   G   S   H   H   H   H   H   H
CAATCAGGTCGGTTTAGGTCGTGGCGGCAGCGGCGGCAGCACCGGCGAAAAACCGTATAAATGCCCGGAATGCGGCAAAAGCTTTAGCCGCAGCGGGGGTTCACATCATCATCATCATCA
GTTAGTCCAGCCAAATCCAGCACCGCCGTCGCCGCCGTCGTGGCCGCTTTTTGGCATATTTACGGGCCTTACGCCGTTTTCGAAATCGGCGTCGCCCCCAAGTGTAGTAGTAGTAGTAGT
        1330         1340         1350         1360         1370         1380         1390         1400         1410         1420         1430         1440

*   *
TTAATGAAAGGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCC
AATTACTTTCCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGG
        1450         1460         1470         1480         1490         1500         1510         1520         1530         1540         1550         1560

CTTGGGGCCTCTAAACGGGTCTTGAGGGGTTTTTTGCTGAAAGGAGGAACTATATCCGGAGCGACTCCCACGGCACGTTGGCAAGCTCG
GAACCCCGGAGATTTGCCCAGAACTCCCCAAAAAACGACTTTCCTCCTTGATATAGGCCTCGCTGAGGGTGCCGTGCAACCGTTCGAGC
        1570         1580         1590         1600         1610         1620         1630         1640
```

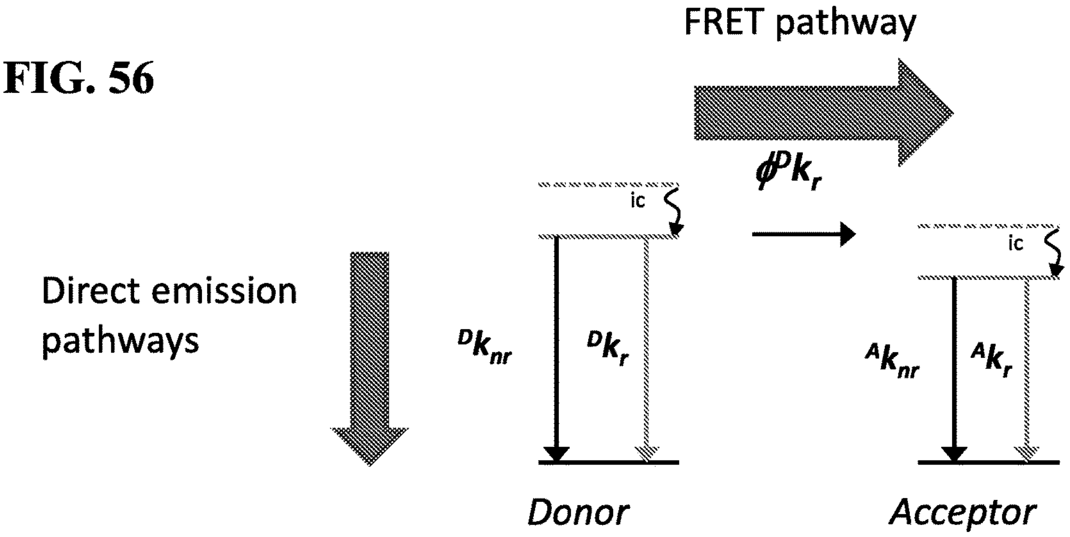

*Directly responsive partner*

- Responds directly to ligand-induced protein conformational changes
- Binds ligand (chemosensor)

Changes due to balance on photon flow in FRET and/or direct emission pathways

*Indirectly responsive partner*

No interactions with ligand of protein conformational changes
Changes only due photon flow in FRET pathway

Effects depend on role of directly responsive partner

*Donor:* Photon flow through competing output pathways
*Outputs*: Direct emission pathway (quenching) and FRET (spectral overlap) pathway

*Acceptor*
Balance of photon flow through input and output pathways
*Input:* FRET pathway (spectral overlap only)
*Output:* Direct emission pathway (quenching)

```
                         SEQUENCE LISTING


<160> NUMBER OF SEQ ID NOS: 158

<210> SEQ ID NO 1
<211> LENGTH: 414
<212> TYPE: PRT
<213> ORGANISM: Thermus thermophilus

<400> SEQUENCE: 1

Met Arg Lys Trp Leu Leu Ala Ile Gly Met Val Leu Gly Leu Ser Ala
1               5                   10                  15

Leu Ala Gln Gly Gly Lys Leu Glu Ile Phe Ser Trp Trp Ala Gly Asp
            20                  25                  30

Glu Gly Pro Ala Leu Glu Ala Leu Ile Arg Leu Tyr Lys Gln Lys Tyr
        35                  40                  45

Pro Gly Val Glu Val Ile Asn Ala Thr Val Thr Gly Gly Ala Gly Val
    50                  55                  60

Asn Ala Arg Ala Val Leu Lys Thr Arg Met Leu Gly Gly Asp Pro Pro
65                  70                  75                  80

Asp Thr Phe Gln Val His Ala Gly Met Glu Leu Ile Gly Thr Trp Val
                85                  90                  95

Val Ala Asn Arg Met Glu Asp Leu Ser Ala Leu Phe Arg Gln Glu Gly
            100                 105                 110

Trp Leu Gln Ala Phe Pro Lys Gly Leu Ile Asp Leu Ile Ser Tyr Lys
        115                 120                 125

Gly Gly Ile Trp Ser Val Pro Val Asn Ile His Arg Ser Asn Val Met
    130                 135                 140

Trp Tyr Leu Pro Ala Lys Leu Lys Glu Trp Gly Val Asn Pro Pro Arg
145                 150                 155                 160

Thr Trp Asp Glu Phe Leu Ala Thr Cys Gln Thr Leu Lys Gln Lys Gly
                165                 170                 175

Leu Glu Ala Pro Leu Ala Leu Gly Glu Asn Trp Thr Gln Gln His Leu
            180                 185                 190

Trp Glu Ser Val Ala Leu Ala Val Leu Gly Pro Asp Asp Trp Asn Asn
        195                 200                 205

Leu Trp Asn Gly Lys Leu Lys Phe Thr Asp Pro Lys Ala Val Arg Ala
    210                 215                 220

Trp Glu Val Phe Gly Arg Val Leu Asp Cys Ala Asn Lys Asp Ala Ala
225                 230                 235                 240

Gly Leu Ser Trp Gln Gln Ala Val Asp Arg Val Val Gln Gly Lys Ala
                245                 250                 255

Ala Phe Asn Val Met Gly Asp Trp Ala Ala Gly Tyr Met Thr Thr Thr
            260                 265                 270

Leu Lys Leu Lys Pro Gly Thr Asp Phe Ala Trp Ala Pro Ser Pro Gly
        275                 280                 285

Thr Gln Gly Val Phe Met Met Leu Ser Asp Ser Phe Gly Leu Pro Lys
    290                 295                 300

Gly Ala Lys Asn Arg Gln Asn Ala Ile Asn Trp Leu Arg Leu Val Gly
305                 310                 315                 320

Ser Lys Glu Gly Gln Asp Thr Phe Asn Pro Leu Lys Gly Ser Ile Ala
                325                 330                 335

Ala Arg Leu Asp Ser Asp Pro Ser Lys Tyr Asn Ala Tyr Gly Gln Ser
```

```
            340                 345                 350

Ala Met Arg Asp Trp Arg Ser Asn Arg Ile Val Gly Ser Leu Val His
        355                 360                 365

Gly Ala Val Ala Pro Glu Ser Phe Met Ser Gln Phe Gly Thr Val Met
    370                 375                 380

Glu Ile Phe Leu Gln Thr Arg Asn Pro Gln Ala Ala Ala Asn Ala Ala
385                 390                 395                 400

Gln Ala Ile Ala Asp Gln Val Gly Leu Gly Arg Leu Gly Gln
                405                 410


<210> SEQ ID NO 2
<211> LENGTH: 411
<212> TYPE: PRT
<213> ORGANISM: Thermus scotoductus

<400> SEQUENCE: 2

Met Arg Lys Trp Leu Leu Ala Ile Gly Val Ala Leu Gly Leu Ser Ala
1               5                   10                  15

Leu Ala Gln Thr Gly Lys Leu Glu Ile Phe Ser Trp Trp Ala Gly Asp
            20                  25                  30

Glu Gly Pro Ala Leu Glu Ala Leu Ile Arg Leu Tyr Lys Gln Lys Tyr
        35                  40                  45

Pro Gly Val Glu Val Ile Asn Ala Thr Val Thr Gly Gly Ala Gly Val
    50                  55                  60

Asn Ala Lys Ala Val Leu Lys Thr Arg Met Leu Gly Gly Asp Pro Pro
65                  70                  75                  80

Asp Thr Phe Gln Val His Ala Gly Gln Glu Leu Ile Gly Thr Trp Val
                85                  90                  95

Val Ala Asp Arg Met Glu Asp Leu Thr Ser Leu Phe Arg Gln Glu Gly
            100                 105                 110

Trp Leu Gln Ala Phe Pro Lys Gly Leu Ile Asp Leu Leu Ser Tyr Lys
        115                 120                 125

Gly Gly Ile Trp Ser Val Pro Val Asn Ile His Arg Ser Asn Val Met
    130                 135                 140

Trp Tyr Ile Pro Ala Lys Leu Lys Glu Trp Gly Val Thr Pro Pro Lys
145                 150                 155                 160

Thr Trp Ala Glu Phe Leu Ala Thr Cys Gln Thr Leu Lys Arg Lys Gly
                165                 170                 175

Leu Glu Ala Pro Leu Ala Leu Gly Glu Asn Trp Thr Gln Gln His Leu
            180                 185                 190

Trp Glu Ser Val Ala Leu Ala Thr Leu Gly Ala Asp Gly Trp Asn Asn
        195                 200                 205

Leu Trp Ser Gly Lys Leu Lys Phe Thr Asp Pro Lys Ala Val Ala Val
    210                 215                 220

Trp Glu Thr Phe Gly Lys Val Leu Asp Cys Ala Asn Lys Asp Ala Ala
225                 230                 235                 240

Gly Leu Ser Trp Gln Gln Ala Val Asp Arg Val Val Gln Gly Lys Ala
                245                 250                 255

Ala Phe Asn Ile Met Gly Asp Trp Ala Ala Gly Tyr Met Ser Thr Thr
            260                 265                 270

Leu Lys Leu Lys Pro Gly Thr Asp Phe Ala Trp Thr Pro Ser Pro Gly
        275                 280                 285

Thr Ser Gly Ile Phe Met Met Leu Ser Asp Ser Phe Gly Leu Pro Lys
    290                 295                 300
```

-continued

```
Gly Ala Lys Asn Arg Gln Asn Ala Ile Asn Trp Leu Lys Leu Val Gly
305                 310                 315                 320

Ser Lys Glu Gly Gln Asp Thr Phe Asn Pro Leu Lys Gly Ser Ile Ala
                325                 330                 335

Ala Arg Leu Asp Ser Asp Pro Ala Lys Tyr Asn Ala Tyr Gly Gln Ser
            340                 345                 350

Ala Met Lys Asp Trp Lys Ser Asn Arg Ile Val Gly Ser Leu Val His
        355                 360                 365

Gly Ala Val Ala Pro Glu Ser Phe Met Ser Gln Phe Gly Thr Val Met
    370                 375                 380

Glu Ile Phe Leu Gln Ser Arg Asn Pro Gln Ala Ala Ala Asn Ala Ala
385                 390                 395                 400

Gln Ala Ile Ala Asn Gln Val Gly Leu Gly Arg
                405                 410


<210> SEQ ID NO 3
<211> LENGTH: 413
<212> TYPE: PRT
<213> ORGANISM: Deinococcus maricopensis

<400> SEQUENCE: 3

Met Lys Arg Ile Lys Ala Ala Leu Leu Val Thr Thr Ala Ala Leu Leu
1               5                   10                  15

Ala Ser Ser Ala Ser Ala Ala Gly Lys Leu Glu Ile Phe Ser Trp Trp
            20                  25                  30

Ser Gly Asp Glu Gly Pro Ala Leu Glu Ala Leu Val Lys Leu Tyr Lys
        35                  40                  45

Gln Lys Tyr Pro Ser Val Asp Val Val Asn Ala Thr Val Ala Gly Gly
    50                  55                  60

Ala Gly Thr Asn Ala Lys Ala Val Leu Lys Thr Arg Met Leu Gly Gly
65                  70                  75                  80

Asp Pro Pro Asp Ser Phe Gln Ala His Ala Gly Gln Glu Leu Ile Gly
                85                  90                  95

Thr Trp Val Val Ala Asn Arg Met Glu Asp Leu Ser Ser Leu Phe Lys
            100                 105                 110

Ser Glu Gly Trp Thr Thr Lys Phe Pro Lys Asp Leu Leu Pro Leu Ile
        115                 120                 125

Ser Ser Lys Gly Gly Ile Trp Ser Val Pro Val Asn Val His Arg Ser
    130                 135                 140

Asn Val Met Trp Tyr Ile Pro Ala Asn Leu Lys Lys Trp Gly Val Thr
145                 150                 155                 160

Ala Pro Lys Thr Trp Asp Gln Phe Leu Thr Thr Cys Lys Thr Leu Lys
                165                 170                 175

Thr Lys Asn Val Thr Pro Leu Ala Leu Gly Glu Asn Trp Thr Gln Gln
            180                 185                 190

His Leu Trp Glu Ser Val Ala Val Gly Thr Leu Gly Ala Gln Gly Trp
        195                 200                 205

Gln Asn Leu Trp Ser Gly Lys Leu Lys Phe Thr Asp Pro Lys Val Val
    210                 215                 220

Lys Val Trp Asp Thr Phe Gly Lys Val Leu Asp Cys Thr Asn Lys Asp
225                 230                 235                 240

Ala Ser Gly Leu Ser Trp Gln Gln Ala Thr Asp Arg Val Val Asn Gly
                245                 250                 255

Gln Ala Ala Phe Asn Ile Met Gly Asp Trp Ala Ala Gly Tyr Leu Ser
            260                 265                 270
```

Thr Thr Lys Lys Leu Lys Pro Gly Thr Gly Phe Gly Trp Ala Pro Ser
275 280 285

Pro Ser Thr Ser Gly Thr Phe Ile Phe Leu Ala Asp Ser Phe Gly Leu
290 295 300

Pro Lys Gly Ala Lys Asp Arg Ala Glu Ala Leu Ser Trp Leu Lys Leu
305 310 315 320

Leu Gly Ser Lys Gln Gly Gln Asp Thr Phe Asn Pro Leu Lys Gly Ser
325 330 335

Ile Ala Ala Arg Val Asp Ser Asp Leu Ser Lys Tyr Ser Thr Tyr Ser
340 345 350

Gln Ser Ala Ala Lys Asp Trp Lys Ser Asn Lys Ile Val Gly Ser Leu
355 360 365

Thr His Gly Ala Val Ala Pro Glu Ser Phe Thr Ser Thr Phe Gly Thr
370 375 380

Val Ile Asp Ala Phe Val Ala Ser Arg Asn Ala Gln Val Ala Ala Ala
385 390 395 400

Thr Thr Gln Gln Leu Ala Asp Lys Ala Gly Leu Gly Lys
405 410

<210> SEQ ID NO 4
<211> LENGTH: 417
<212> TYPE: PRT
<213> ORGANISM: Thermotoga neapolitana

<400> SEQUENCE: 4

Met Phe Phe Met Arg Arg Phe Val Gly Leu Phe Leu Met Val Val Leu
1 5 10 15

Leu Ser Ala Val Val Thr Ala Ser Gln Leu Glu Ile Phe Ser Trp Trp
20 25 30

Thr Ala Gly Gly Glu Ala Glu Ala Leu Glu Ala Leu Ile Lys Val Phe
35 40 45

Asn Lys Tyr Tyr Pro Asp Val Glu Val Ile Asn Ala Thr Val Ala Gly
50 55 60

Gly Ala Gly Thr Asn Ala Lys Ala Val Leu Lys Thr Arg Ile Leu Gly
65 70 75 80

Gly Asn Pro Pro Asp Ser Phe Gln Val His Ala Gly Met Glu Leu Ile
85 90 95

Asp Thr Tyr Val Ile Pro Gly Tyr Met Thr Pro Ile Thr Asn Leu Leu
100 105 110

Glu Gln Trp Gly Val Met Asp Lys Phe Pro Lys Gly Ile Leu Glu Met
115 120 125

Cys Ser Tyr Glu Gly Glu Ile Tyr Ser Ile Pro Val Asn Val His Arg
130 135 140

Gly Asn Val Val Phe Tyr Asn Lys Lys Ile Ala Glu Glu Ile Gly Met
145 150 155 160

Asn Glu Pro Pro Lys Thr Trp Asp Glu Phe Ile Met Tyr Leu Gln Lys
165 170 175

Ala Lys Glu Lys Gly Tyr Val Gly Leu Ala Leu Gly Asp Lys Asn Lys
180 185 190

Trp Thr Ala Leu His Leu Phe Glu Thr Ile Leu Leu Gly Val Leu Gly
195 200 205

Pro Asn Asp Tyr Asn Gly Leu Trp Lys Gly Glu Val Ser Phe Asn Asp
210 215 220

Pro Arg Ile Arg Arg Ala Phe Glu Ile Met Asn Lys Leu Leu Asp Tyr

```
225                 230                 235                 240

Val Asn Glu Asp His Ala Ala Leu Ala Trp Gln Asp Ala Thr Arg Leu
                245                 250                 255

Val Tyr Glu Gly Lys Ala Leu Ala Asn Val Met Gly Asp Trp Ala Glu
            260                 265                 270

Gly Tyr Leu Lys Ser Val Gly Trp Glu Pro Gly Lys Asp Phe Gly Trp
        275                 280                 285

Phe Ala Val Pro Glu Thr Gln Asn Ala Phe Met Val Val Ser Asp Thr
    290                 295                 300

Phe Gly Leu Pro Lys Asn Ala Pro His Lys Glu Asn Ala Val Lys Trp
305                 310                 315                 320

Leu Lys Val Val Ala Ser Val Glu Gly Gln Asp Ala Phe Asn Pro Ile
                325                 330                 335

Lys Gly Ser Ile Pro Ala Arg Leu Asp Ala Asp Arg Ser Lys Tyr Asp
            340                 345                 350

Ile Tyr Leu Gln Trp Ser Met Glu Asp Phe Ala Thr Lys Ala Leu Thr
        355                 360                 365

Pro Ser Ile Ala His Gly Ser Ala Ala Pro Glu Gly Phe Val Thr Thr
    370                 375                 380

Leu Asn Asp Ile Ile Asn Arg Phe Val Thr Thr Arg Asp Ile Asp Ser
385                 390                 395                 400

Ala Leu Glu Glu Leu Leu Met Ala Ala Glu Asp Glu Gly Tyr Leu Val
                405                 410                 415

Glu


<210> SEQ ID NO 5
<211> LENGTH: 411
<212> TYPE: PRT
<213> ORGANISM: Kosmotoga olearia

<400> SEQUENCE: 5

Met Arg Lys Phe Phe Val Leu Leu Met Ile Leu Ser Met Ala Phe Val
1               5                   10                  15

Ala Phe Ser Ala Asn Gln Leu Glu Ile Phe Ser Trp Trp Thr Gly Gly
            20                  25                  30

Gly Glu Glu Glu Gly Leu Leu Ala Leu Phe Asp Val Phe His Lys Tyr
        35                  40                  45

Tyr Pro Asp Val Glu Ile Ile Asn Ala Thr Val Ala Gly Gly Ala Gly
    50                  55                  60

Thr Asn Ala Lys Ala Val Leu Lys Thr Arg Met Leu Gly Gly Asn Pro
65                  70                  75                  80

Pro Asp Ser Phe Gln Val His Gly Gly Met Glu Leu Ile Asp Thr Tyr
                85                  90                  95

Val Val Thr Gly Met Met Glu Pro Ile Thr Asp Leu Leu Glu Glu Trp
            100                 105                 110

Gly Ile Ile Asp Lys Phe Pro Glu Asp Ile Leu Lys Ile Cys Ser Tyr
        115                 120                 125

Lys Gly Glu Val Tyr Ser Ile Pro Val Asn Val His Arg Gly Asn Val
    130                 135                 140

Val Phe Tyr Asn Lys Ala Ile Leu Glu Glu Val Gly Ile Glu Lys Val
145                 150                 155                 160

Pro Ser Thr Trp Pro Glu Phe Ile Glu Val Leu Lys Lys Ile Lys Lys
                165                 170                 175

Ala Gly Tyr Ile Pro Leu Ala Leu Gly Asp Lys Asn Lys Trp Thr Ala
```

-continued

```
            180                 185                 190

Thr His Leu Phe Glu Asp Ile Leu Leu Ser Thr Leu Gly Pro Tyr Asn
        195                 200                 205

Tyr Asn Gly Leu Trp Asn Gly Arg Thr Ser Phe Glu His Gln Gly Val
    210                 215                 220

Lys Glu Ala Leu Glu Ile Phe Lys Glu Leu Met Asn Tyr Val Asn Pro
225                 230                 235                 240

Asn His Ala Ser Leu Thr Trp Gln Asp Ala Thr Leu Leu Val Phe Glu
                245                 250                 255

Gly Lys Ala Ala Phe Asn Val Met Gly Asp Trp Ala Glu Gly Tyr Leu
            260                 265                 270

Lys Thr Leu Gly Trp Thr Pro Gly Lys Glu Phe Gly Trp Met Val Val
        275                 280                 285

Pro Gly Thr Lys Gly Ser Phe Met Val Val Thr Asp Thr Phe Gly Leu
    290                 295                 300

Pro Lys Asn Ala Pro His Arg Glu Asn Ala Ile Lys Trp Leu Lys Ile
305                 310                 315                 320

Ile Ser Ser Val Glu Gly Gln Asp Thr Phe Asn Pro Ile Lys Gly Ser
                325                 330                 335

Ile Pro Ala Arg Ile Asp Ala Asp Arg Ser Leu Tyr Asp Asp Tyr Leu
            340                 345                 350

Ile Trp Ser Met Asp Asp Phe Ala Thr Asn Ala Leu Cys Pro Ser Ile
        355                 360                 365

Ile His Gly Ser Ala Ala Pro Glu Ala Phe Val Thr Ala Leu Asn Asp
    370                 375                 380

Thr Ile Asn Met Phe Ile Thr Arg Lys Asp Val Lys Lys Ala Leu Lys
385                 390                 395                 400

Glu Ile Ile Tyr Ala Ala Glu Asp Tyr Leu Glu
                405                 410


<210> SEQ ID NO 6
<211> LENGTH: 436
<212> TYPE: PRT
<213> ORGANISM: Xanthomonas campestris

<400> SEQUENCE: 6

Met Val Lys Lys Trp Phe Ala Leu Met Ile Ala Leu Ser Val Leu Val
1               5                   10                  15

Ile Gly Leu Val Ala Cys Gly Ser Ser Glu Asp Ser Ser Asn Glu Pro
            20                  25                  30

Ser Glu Glu Pro Glu Thr Ser Asp Ser Glu Glu Ala Thr Gly Glu Ala
        35                  40                  45

Ser Gly Thr Leu Glu Ile Phe Ser Trp Trp Thr Gly Ala Gly Glu Glu
    50                  55                  60

Asp Gly Leu Leu Ala Leu Ile Glu Leu Phe Glu Glu Lys His Pro Glu
65                  70                  75                  80

Ile Glu Val Asp Asn Ala Ala Val Ala Gly Gly Ala Gly Thr Asn Ala
                85                  90                  95

Lys Ala Val Leu Thr Ser Arg Met Gln Gly Asn Asp Pro Pro Gly Thr
            100                 105                 110

Phe Gln Val His Gly Gly Ala Glu Leu Asn Asp Ser Trp Val Ala Ala
        115                 120                 125

Gly Gln Met Asp Pro Leu Asn Asp Leu Phe Glu Ala Glu Gly Trp Ala
    130                 135                 140
```

-continued

Asp Lys Phe Pro Glu Glu Leu Ile Glu Leu Val Ser Lys Asp Gly Asn
145 150 155 160

Ile Tyr Ser Val Pro Val Asn Ile His Arg Gly Asn Val Leu Trp Tyr
165 170 175

Asn Thr Glu Ile Phe Glu Glu His Gly Leu Glu Val Pro Thr Thr Phe
180 185 190

Glu Glu Phe Phe Asp Val Ala Asp Ala Leu Gln Glu Ala Gly Val Thr
195 200 205

Pro Leu Ala Leu Gly Asp Arg Glu Pro Trp Ala Ala Thr His Leu Phe
210 215 220

Glu Thr Val Leu Leu Gly Thr Leu Gly Ala Asp Asp Tyr Asn Lys Leu
225 230 235 240

Trp Ser Gly Glu Val Gly Met Asp Asp Pro Arg Val Glu Glu Ala Ala
245 250 255

Glu Ile Phe Ile Arg Met Leu Asp Tyr Val Asn Glu Asp His Ser Ser
260 265 270

Arg Asn Trp Gln Asp Ala Ser Gln Leu Val Ala Gln Gly Glu Ala Ala
275 280 285

Met Asn Val Met Gly Asp Trp Ala Lys Gly Tyr Phe Val Asn Asp Leu
290 295 300

Asn Leu Ala Val Lys Glu Asp Phe Gly Trp Ala Ala Thr Pro Gly Thr
305 310 315 320

Glu Gly Thr Phe Met Val Ile Thr Asp Thr Phe Gly Leu Pro Thr Gly
325 330 335

Val Glu Asn Pro Glu Val Val Lys Ser Phe Leu Ala Val Leu Gly Ser
340 345 350

Gln Glu Gly Gln Asp Ala Phe Asn Pro Leu Lys Gly Ser Ile Pro Ala
355 360 365

Arg Val Asp Ala Asp Val Ser Lys Tyr Asp Glu Tyr Gly Gln Glu Thr
370 375 380

Ile Glu Asp Phe Lys Ser Ala Glu Leu Ser Pro Ser Leu Ala His Gly
385 390 395 400

Ser Ala Ala Asn Glu Gly Phe Leu Thr Gln Val Asn Gln Ala Ile Asn
405 410 415

Ile Phe Val Thr Gln Lys Asp Val Asp Ser Phe Val Asp Ser Leu Lys
420 425 430

Gln Tyr Gln Pro
435

<210> SEQ ID NO 7
<211> LENGTH: 487
<212> TYPE: PRT
<213> ORGANISM: Staphylothermus marinus

<400> SEQUENCE: 7

Met Ser Tyr Ser Ala Ile Thr Lys Ser Thr Ala Ile Ile Ile Thr Leu
1 5 10 15

Leu Val Ile Ile Gly Ile Leu Ala Gly Ile Ala Trp Trp Gly Trp Ser
20 25 30

Arg Thr Pro Ala Pro Ala Thr Thr Ile Thr Thr Pro Pro Thr Thr Pro
35 40 45

Thr Thr Thr Thr Thr Thr Thr Ala Thr Pro Pro Gln Ala Glu Leu Val
50 55 60

Ile Tyr His Trp Trp Thr Ala Gly Gly Glu Arg Glu Ala Ile Asn Ala
65 70 75 80

-continued

```
Val Phe Gln Val Phe Lys Gln Lys Tyr Pro Asn Ile Gln Ile Val Glu
                85                  90                  95

Asn Pro Val Ala Gly Gly Ala Gly Ser Val Met Lys Ser Val Ile Ile
            100                 105                 110

Gly Leu Leu Ala Ala Gly Thr Pro Pro Asp Thr Phe Gln Val His Ala
        115                 120                 125

Gly Ala Glu Leu Lys Glu Tyr Val Asp Ala Gly Tyr Leu Ala Pro Ile
    130                 135                 140

Asp Asp Ile Trp Ser Lys Leu Gly Leu Asp Lys Val Ile Pro Ser Thr
145                 150                 155                 160

Leu Gln Val Met Cys Lys Phe Asn Gly His Tyr Tyr Ala Val Pro Ile
                165                 170                 175

Asp Val His Arg Ser Asn Val Leu Trp Tyr Asn Pro Lys Ile Phe Asn
            180                 185                 190

Glu Leu Gly Ile Ile Asn Lys Phe Gly Asp Pro Arg Asn Trp Ser Val
        195                 200                 205

Asp Thr Leu Leu Gln Val Ala Arg Tyr Ile Lys Gln Gln Arg Pro Asp
    210                 215                 220

Ile Ala Pro Ile Ala Leu Ala Ser Arg Asn Lys Trp Pro Val Thr His
225                 230                 235                 240

Leu Phe Glu Val Leu Leu Ala Asn Ala Gly Gly Pro Glu Thr Tyr Val
                245                 250                 255

Lys Phe Phe Thr Gly Lys Phe Asn Tyr Asn Asp Pro Asn Asp Pro Val
            260                 265                 270

Val Gln Thr Val Lys Lys Val Leu Thr Val Met Ala Thr Met Ala Lys
        275                 280                 285

Glu Gly Leu Phe Asn Ser Asn His Pro Glu Leu Thr Trp Asp Gln Ala
    290                 295                 300

Ala Ala Leu Val Ala Glu Gly Lys Ala Ala Met Phe Ile His Gly Asp
305                 310                 315                 320

Trp Val Ala Gly Tyr Tyr Ile Ala Asn Asn Tyr Lys Tyr Gly Lys Asp
                325                 330                 335

Trp Ala Ala Ala Pro Phe Pro Lys Asn Ile Phe Ile Leu Leu Ser Asp
            340                 345                 350

Ala Phe Glu Leu Pro Lys Asn Ala Pro His Pro Glu Ala Ala Lys Asp
        355                 360                 365

Trp Leu Met Val Val Gly Ser Lys Glu Ala Gln Glu Lys Phe Asn Leu
    370                 375                 380

Ile Lys Gly Ser Ile Pro Ala Arg Thr Asp Val Ser Pro Lys Tyr Pro
385                 390                 395                 400

Asp Pro Tyr Arg Pro Glu Thr Ala Glu Asp Phe Gln Lys Ser Thr Leu
                405                 410                 415

Ile Pro Ser Ala Val His Gly Gly Ile Ala Lys Glu Ala Phe Met Thr
            420                 425                 430

Asp Leu His Asn Ile Leu Thr Ser Met Leu Thr Ala Val Ser Val Gly
        435                 440                 445

Thr Pro Val Asp Asn Ala Val Asn Thr Ala Leu Ala Gln Ile Leu Gln
    450                 455                 460

Ser Val Lys Thr Ser Gly Leu Ala Ser Phe Trp Lys Gly Tyr Thr Ile
465                 470                 475                 480

Asp Tyr Phe Ile Thr Lys Arg
                485
```

<210> SEQ ID NO 8
<211> LENGTH: 430
<212> TYPE: PRT
<213> ORGANISM: Arthrobacter sp.

<400> SEQUENCE: 8

```
Met Arg Ala Pro Asn Lys Leu Arg Ile Ser Leu Ala Val Thr Ala Ala
1               5                   10                  15

Ala Ser Leu Ile Ala Val Ser Gly Cys Ala Ala Asn Thr Pro Ala Gly
            20                  25                  30

Ser Ser Ser Gly Gly Gly Thr Asp Lys Leu Glu Ile Thr Ser Trp Trp
        35                  40                  45

Thr Ser Gly Ser Glu Ala Asp Ala Leu Asn Val Leu Ile Asp Gly Val
    50                  55                  60

Lys Ala Ala Lys Pro Gly Leu Ser Val Asp Asn Ala Ala Val Ser Gly
65                  70                  75                  80

Gly Gly Gly Ala Asn Ala Arg Gln Ala Leu Ala Ala Arg Leu Gln Ala
                85                  90                  95

Gly Ser Pro Pro Asp Ala Trp Gln Val His Pro Ala Gly Gln Leu Lys
            100                 105                 110

Ser Tyr Val Asp Gly Gly Gln Val Ala Asp Leu Thr Asp Leu Trp Thr
        115                 120                 125

Glu Gly Asp Trp Ala Ser Gln Met Pro Lys Asp Val Ala Glu Ala Gln
    130                 135                 140

Gln Val Asp Gly Lys Tyr Tyr Thr Val Pro Ile Gly Val His Arg Gly
145                 150                 155                 160

Asn Val Leu Trp Thr Asn Pro Ala Val Leu Ser Lys Ala Asn Val Thr
                165                 170                 175

Ile Asp Ala Asp Ala Gly Ile Asp Gly Leu Ile Ser Ser Leu Glu Gln
            180                 185                 190

Val Gln Ala Ser Gly Thr Thr Pro Leu Cys Leu Gly Asp Lys Asp Ile
        195                 200                 205

Phe Ala Ser Ser Gln Leu Leu Glu Ser Leu Ile Met Ser Arg Ala Gly
    210                 215                 220

Ala Asp Asn Trp Thr Lys Leu Phe Thr Ser Glu Tyr Ser Phe Asp Ala
225                 230                 235                 240

Pro Glu Val Lys Gln Ala Leu Glu Asp Tyr Lys Thr Ile Leu Ser Phe
                245                 250                 255

Ala Asn Lys Asp His Ser Ala Ile Thr Trp Asp Glu Ala Ala Lys Lys
            260                 265                 270

Met Ala Asp Gly Glu Cys Ala Val Asn Leu Met Gly Asp Trp Ala Tyr
        275                 280                 285

Gly Glu Leu Leu Asn Ala Gly Lys Lys Pro Gly Thr Asp Phe Ala Trp
    290                 295                 300

Val Ala Phe Pro Gly Lys Glu Asp Ile Phe Asp Tyr Val Gly Asp Gly
305                 310                 315                 320

Phe Ser Ile Pro Ala Asn Asn Ile Pro His Ala Glu Ala Ala Arg Ala
                325                 330                 335

Trp Leu Lys Thr Leu Met Asp Pro Lys Ile Gln Thr Glu Phe Ala Ala
            340                 345                 350

Lys Lys Gly Ser Ile Pro Ala Val Thr Ser Ala Asp Ile Ser Gly Leu
        355                 360                 365

Ser Glu Tyr Gln Gln Glu Ala Ala Lys Ser Leu Ala Ser Gly Ala Val
    370                 375                 380
```

```
Val Ser Ser Leu Ala His Ala Gln Ala Ala Gly Ala Glu Phe Ala Gln
385                 390                 395                 400

Thr Tyr Ala Asp Ala Val Ser Thr Phe Asn Gly Ser Gly Asn Thr Asp
                405                 410                 415

Ala Phe Ile Ala Ser Met Thr Gln Ala Gln Lys Thr Gln Leu
            420                 425                 430


<210> SEQ ID NO 9
<211> LENGTH: 400
<212> TYPE: PRT
<213> ORGANISM: Artificial Sequence
<220> FEATURE:
<223> OTHER INFORMATION: ttGBP1 (with signal peptide replaced with M and
      a HHHHHH at C-terminus)

<400> SEQUENCE: 9

Met Lys Leu Glu Ile Phe Ser Trp Trp Ala Gly Asp Glu Gly Pro Ala
1               5                   10                  15

Leu Glu Ala Leu Ile Arg Leu Tyr Lys Gln Lys Tyr Pro Gly Val Glu
            20                  25                  30

Val Ile Asn Ala Thr Val Thr Gly Gly Ala Gly Val Asn Ala Arg Ala
        35                  40                  45

Val Leu Lys Thr Arg Met Leu Gly Gly Asp Pro Pro Asp Thr Phe Gln
    50                  55                  60

Val His Ala Gly Met Glu Leu Ile Gly Thr Trp Val Val Ala Asn Arg
65                  70                  75                  80

Met Glu Asp Leu Ser Ala Leu Phe Arg Gln Glu Gly Trp Leu Gln Ala
                85                  90                  95

Phe Pro Lys Gly Leu Ile Asp Leu Ile Ser Tyr Lys Gly Gly Ile Trp
            100                 105                 110

Ser Val Pro Val Asn Ile His Arg Ser Asn Val Met Trp Tyr Leu Pro
        115                 120                 125

Ala Lys Leu Lys Gly Trp Gly Val Asn Pro Pro Arg Thr Trp Asp Lys
    130                 135                 140

Phe Leu Ala Thr Ala Gln Thr Leu Lys Gln Lys Gly Leu Glu Ala Pro
145                 150                 155                 160

Leu Ala Leu Gly Glu Asn Trp Thr Gln Gln His Leu Trp Glu Ser Val
                165                 170                 175

Ala Leu Ala Val Leu Gly Pro Asp Asp Trp Asn Asn Leu Trp Asn Gly
            180                 185                 190

Lys Leu Lys Phe Thr Asp Pro Lys Ala Val Arg Ala Trp Glu Val Phe
        195                 200                 205

Gly Arg Val Leu Asp Ala Ala Asn Lys Asp Ala Ala Gly Leu Ser Trp
    210                 215                 220

Gln Gln Ala Val Asp Arg Val Val Gln Gly Lys Ala Ala Phe Asn Ile
225                 230                 235                 240

Met Gly Asp Trp Ala Ala Gly Tyr Met Thr Thr Thr Leu Lys Leu Lys
                245                 250                 255

Pro Gly Thr Asp Phe Ala Trp Ala Pro Ser Pro Gly Thr Gln Gly Val
            260                 265                 270

Phe Met Met Leu Ser Asp Ser Phe Gly Leu Pro Lys Gly Ala Lys Asn
        275                 280                 285

Arg Gln Asn Ala Ile Asn Trp Leu Arg Leu Val Gly Ser Lys Glu Gly
    290                 295                 300

Gln Asp Thr Ser Asn Pro Leu Lys Gly Ser Ile Ala Ala Arg Leu Asp
```

305 310 315 320

Ser Asp Pro Ser Lys Tyr Asn Ala Tyr Gly Gln Ser Ala Met Arg Asp
325 330 335

Trp Arg Ser Asn Arg Ile Val Gly Ser Leu Val His Gly Ala Val Ala
340 345 350

Pro Glu Ser Phe Met Ser Gln Phe Gly Thr Val Met Glu Ile Phe Leu
355 360 365

Gln Thr Arg Asn Pro Gln Ala Ala Ala Asn Ala Ala Gln Ala Ile Ala
370 375 380

Asp Gln Val Gly Leu Gly Arg Leu Gly Gln His His His His His His
385 390 395 400

<210> SEQ ID NO 10
<211> LENGTH: 400
<212> TYPE: PRT
<213> ORGANISM: Artificial Sequence
<220> FEATURE:
<223> OTHER INFORMATION: tsGBP2 (with signal peptide replaced with M and a GGSHHHHHH at C-terminus)

<400> SEQUENCE: 10

Met Lys Leu Glu Ile Phe Ser Trp Trp Ala Gly Asp Glu Gly Pro Ala
1 5 10 15

Leu Glu Ala Leu Ile Arg Leu Tyr Lys Gln Lys Tyr Pro Gly Val Glu
20 25 30

Val Ile Asn Ala Thr Val Thr Gly Gly Ala Gly Val Asn Ala Lys Ala
35 40 45

Val Leu Lys Thr Arg Met Leu Gly Gly Asp Pro Pro Asp Thr Phe Gln
50 55 60

Val His Ala Gly Gln Glu Leu Ile Gly Thr Trp Val Val Ala Asp Arg
65 70 75 80

Met Glu Asp Leu Thr Ser Leu Phe Arg Gln Glu Gly Trp Leu Gln Ala
85 90 95

Phe Pro Lys Gly Leu Ile Asp Leu Leu Ser Tyr Lys Gly Gly Ile Trp
100 105 110

Ser Val Pro Val Asn Ile His Arg Ser Asn Val Met Trp Tyr Ile Pro
115 120 125

Ala Lys Leu Lys Glu Trp Gly Val Thr Pro Pro Lys Thr Trp Ala Glu
130 135 140

Phe Leu Ala Thr Ala Gln Thr Leu Lys Arg Lys Gly Leu Glu Ala Pro
145 150 155 160

Leu Ala Leu Gly Glu Asn Trp Thr Gln Gln His Leu Trp Glu Ser Val
165 170 175

Ala Leu Ala Thr Leu Gly Ala Asp Gly Trp Asn Asn Leu Trp Ser Gly
180 185 190

Lys Leu Lys Phe Thr Asp Pro Lys Ala Val Ala Val Trp Glu Thr Phe
195 200 205

Gly Lys Val Leu Asp Ala Ala Asn Lys Asp Ala Ala Gly Leu Ser Trp
210 215 220

Gln Gln Ala Val Asp Arg Val Val Gln Gly Lys Ala Ala Phe Asn Ile
225 230 235 240

Met Gly Asp Trp Ala Ala Gly Tyr Met Ser Thr Thr Leu Lys Leu Lys
245 250 255

Pro Gly Thr Asp Phe Ala Trp Thr Pro Ser Pro Gly Thr Ser Gly Ile
260 265 270

```
Phe Met Met Leu Ser Asp Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300

Gln Asp Thr Phe Asn Pro Leu Lys Gly Ser Ile Ala Ala Arg Leu Asp
305                 310                 315                 320

Ser Asp Pro Ala Lys Tyr Asn Ala Tyr Gly Gln Ser Ala Met Lys Asp
                325                 330                 335

Trp Lys Ser Asn Arg Ile Val Gly Ser Leu Val His Gly Ala Val Ala
            340                 345                 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380

Asn Gln Val Gly Leu Gly Arg Gly Gly Ser His His His His His His
385                 390                 395                 400


<210> SEQ ID NO 11
<211> LENGTH: 399
<212> TYPE: PRT
<213> ORGANISM: Artificial Sequence
<220> FEATURE:
<223> OTHER INFORMATION: dmGBP3 (with signal peptide replaced with M and
      a GGSHHHHHH at C-terminus)

<400> SEQUENCE: 11

Met Lys Leu Glu Ile Phe Ser Trp Trp Ser Gly Asp Glu Gly Pro Ala
1               5                   10                  15

Leu Glu Ala Leu Val Lys Leu Tyr Lys Gln Lys Tyr Pro Ser Val Asp
            20                  25                  30

Val Val Asn Ala Thr Val Ala Gly Gly Ala Gly Thr Asn Ala Lys Ala
        35                  40                  45

Val Leu Lys Thr Arg Met Leu Gly Gly Asp Pro Pro Asp Ser Phe Gln
    50                  55                  60

Ala His Ala Gly Gln Glu Leu Ile Gly Thr Trp Val Val Ala Asn Arg
65                  70                  75                  80

Met Glu Asp Leu Ser Ser Leu Phe Lys Ser Glu Gly Trp Thr Thr Lys
                85                  90                  95

Phe Pro Lys Asp Leu Leu Pro Leu Ile Ser Ser Lys Gly Gly Ile Trp
            100                 105                 110

Ser Val Pro Val Asn Val His Arg Ser Asn Val Met Trp Tyr Ile Pro
        115                 120                 125

Ala Asn Leu Lys Lys Trp Gly Val Thr Ala Pro Lys Thr Trp Asp Gln
    130                 135                 140

Phe Leu Thr Thr Ala Lys Thr Leu Lys Thr Lys Asn Val Thr Pro Leu
145                 150                 155                 160

Ala Leu Gly Glu Asn Trp Thr Gln Gln His Leu Trp Glu Ser Val Ala
                165                 170                 175

Val Gly Thr Leu Gly Ala Gln Gly Trp Gln Asn Leu Trp Ser Gly Lys
            180                 185                 190

Leu Lys Phe Thr Asp Pro Lys Val Val Lys Val Trp Asp Thr Phe Gly
        195                 200                 205

Lys Val Leu Asp Ala Thr Asn Lys Asp Ala Ser Gly Leu Ser Trp Gln
    210                 215                 220

Gln Ala Thr Asp Arg Val Val Asn Gly Gln Ala Ala Phe Asn Ile Met
225                 230                 235                 240
```

Gly Asp Trp Ala Ala Gly Tyr Leu Ser Thr Thr Lys Lys Leu Lys Pro
245 250 255

Gly Thr Gly Phe Gly Trp Ala Pro Ser Pro Ser Thr Ser Gly Thr Phe
260 265 270

Ile Phe Leu Ala Asp Ser Phe Gly Leu Pro Lys Gly Ala Lys Asp Arg
275 280 285

Ala Glu Ala Leu Ser Trp Leu Lys Leu Leu Gly Ser Lys Gln Gly Gln
290 295 300

Asp Thr Phe Asn Pro Leu Lys Gly Ser Ile Ala Ala Arg Val Asp Ser
305 310 315 320

Asp Leu Ser Lys Tyr Ser Thr Tyr Ser Gln Ser Ala Ala Lys Asp Trp
325 330 335

Lys Ser Asn Lys Ile Val Gly Ser Leu Thr His Gly Ala Val Ala Pro
340 345 350

Glu Ser Phe Thr Ser Thr Phe Gly Thr Val Ile Asp Ala Phe Val Ala
355 360 365

Ser Arg Asn Ala Gln Val Ala Ala Ala Thr Thr Gln Gln Leu Ala Asp
370 375 380

Lys Ala Gly Leu Gly Lys Gly Gly Ser His His His His His His
385 390 395

<210> SEQ ID NO 12
<211> LENGTH: 402
<212> TYPE: PRT
<213> ORGANISM: Artificial Sequence
<220> FEATURE:
<223> OTHER INFORMATION: tnGBP4 (with signal peptide replaced with M and a GGSHHHHHH at C-terminus)

<400> SEQUENCE: 12

Met Leu Glu Ile Phe Ser Trp Trp Thr Ala Gly Gly Glu Ala Glu Ala
1 5 10 15

Leu Glu Ala Leu Ile Lys Val Phe Asn Lys Tyr Tyr Pro Asp Val Glu
20 25 30

Val Ile Asn Ala Thr Val Ala Gly Gly Ala Gly Thr Asn Ala Lys Ala
35 40 45

Val Leu Lys Thr Arg Ile Leu Gly Gly Asn Pro Pro Asp Ser Phe Gln
50 55 60

Val His Ala Gly Met Glu Leu Ile Asp Thr Tyr Val Ile Pro Gly Tyr
65 70 75 80

Met Thr Pro Ile Thr Asn Leu Leu Glu Gln Trp Gly Val Met Asp Lys
85 90 95

Phe Pro Lys Gly Ile Leu Glu Met Ala Ser Tyr Glu Gly Glu Ile Tyr
100 105 110

Ser Ile Pro Val Asn Val His Arg Gly Asn Val Val Phe Tyr Asn Lys
115 120 125

Lys Ile Ala Glu Glu Ile Gly Met Asn Glu Pro Pro Lys Thr Trp Asp
130 135 140

Glu Phe Ile Met Tyr Leu Gln Lys Ala Lys Glu Lys Gly Tyr Val Gly
145 150 155 160

Leu Ala Leu Gly Asp Lys Asn Lys Trp Thr Ala Leu His Leu Phe Glu
165 170 175

Thr Ile Leu Leu Gly Val Leu Gly Pro Asn Asp Tyr Asn Gly Leu Trp
180 185 190

Lys Gly Glu Val Ser Phe Asn Asp Pro Arg Ile Arg Arg Ala Phe Glu

```
        195                 200                 205

Ile Met Asn Lys Leu Leu Asp Tyr Val Asn Glu Asp His Ala Ala Leu
    210                 215                 220

Ala Trp Gln Asp Ala Thr Arg Leu Val Tyr Glu Gly Lys Ala Leu Ala
225                 230                 235                 240

Asn Val Met Gly Asp Trp Ala Glu Gly Tyr Leu Lys Ser Val Gly Trp
                245                 250                 255

Glu Pro Gly Lys Asp Phe Gly Trp Phe Ala Val Pro Glu Thr Gln Asn
            260                 265                 270

Ala Phe Met Val Val Ser Asp Thr Phe Gly Leu Pro Lys Asn Ala Pro
        275                 280                 285

His Lys Glu Asn Ala Val Lys Trp Leu Lys Val Val Ala Ser Val Glu
    290                 295                 300

Gly Gln Asp Ala Phe Asn Pro Ile Lys Gly Ser Ile Pro Ala Arg Leu
305                 310                 315                 320

Asp Ala Asp Arg Ser Lys Tyr Asp Ile Tyr Leu Gln Trp Ser Met Glu
                325                 330                 335

Asp Phe Ala Thr Lys Ala Leu Thr Pro Ser Ile Ala His Gly Ser Ala
            340                 345                 350

Ala Pro Glu Gly Phe Val Thr Thr Leu Asn Asp Ile Ile Asn Arg Phe
        355                 360                 365

Val Thr Thr Arg Asp Ile Asp Ser Ala Leu Glu Glu Leu Leu Met Ala
    370                 375                 380

Ala Glu Asp Glu Gly Tyr Leu Val Glu Gly Gly Ser His His His His
385                 390                 395                 400

His His


<210> SEQ ID NO 13
<211> LENGTH: 399
<212> TYPE: PRT
<213> ORGANISM: Artificial Sequence
<220> FEATURE:
<223> OTHER INFORMATION: koGBP5 (with signal peptide replaced with M and
      a GGSHHHHHH at C-terminus)

<400> SEQUENCE: 13

Met Leu Glu Ile Phe Ser Trp Trp Thr Gly Gly Gly Glu Glu Glu Gly
1               5                   10                  15

Leu Leu Ala Leu Phe Asp Val Phe His Lys Tyr Tyr Pro Asp Val Glu
            20                  25                  30

Ile Ile Asn Ala Thr Val Ala Gly Gly Ala Gly Thr Asn Ala Lys Ala
        35                  40                  45

Val Leu Lys Thr Arg Met Leu Gly Gly Asn Pro Pro Asp Ser Phe Gln
    50                  55                  60

Val His Gly Gly Met Glu Leu Ile Asp Thr Tyr Val Val Thr Gly Met
65                  70                  75                  80

Met Glu Pro Ile Thr Asp Leu Leu Glu Glu Trp Gly Ile Ile Asp Lys
                85                  90                  95

Phe Pro Glu Asp Ile Leu Lys Ile Ala Ser Tyr Lys Gly Glu Val Tyr
            100                 105                 110

Ser Ile Pro Val Asn Val His Arg Gly Asn Val Val Phe Tyr Asn Lys
        115                 120                 125

Ala Ile Leu Glu Glu Val Gly Ile Glu Lys Val Pro Ser Thr Trp Pro
    130                 135                 140

Glu Phe Ile Glu Val Leu Lys Lys Ile Lys Lys Ala Gly Tyr Ile Pro
```

```
145                 150                 155                 160

Leu Ala Leu Gly Asp Lys Asn Lys Trp Thr Ala Thr His Leu Phe Glu
                165                 170                 175

Asp Ile Leu Leu Ser Thr Leu Gly Pro Tyr Asn Tyr Asn Gly Leu Trp
            180                 185                 190

Asn Gly Arg Thr Ser Phe Glu His Gln Gly Val Lys Glu Ala Leu Glu
        195                 200                 205

Ile Phe Lys Glu Leu Met Asn Tyr Val Asn Pro Asn His Ala Ser Leu
    210                 215                 220

Thr Trp Gln Asp Ala Thr Leu Leu Val Phe Glu Gly Lys Ala Ala Phe
225                 230                 235                 240

Asn Val Met Gly Asp Trp Ala Glu Gly Tyr Leu Lys Thr Leu Gly Trp
                245                 250                 255

Thr Pro Gly Lys Glu Phe Gly Trp Met Val Val Pro Gly Thr Lys Gly
            260                 265                 270

Ser Phe Met Val Val Thr Asp Thr Phe Gly Leu Pro Lys Asn Ala Pro
        275                 280                 285

His Arg Glu Asn Ala Ile Lys Trp Leu Lys Ile Ile Ser Ser Val Glu
    290                 295                 300

Gly Gln Asp Thr Phe Asn Pro Ile Lys Gly Ser Ile Pro Ala Arg Ile
305                 310                 315                 320

Asp Ala Asp Arg Ser Leu Tyr Asp Asp Tyr Leu Ile Trp Ser Met Asp
                325                 330                 335

Asp Phe Ala Thr Asn Ala Leu Cys Pro Ser Ile Ile His Gly Ser Ala
            340                 345                 350

Ala Pro Glu Ala Phe Val Thr Ala Leu Asn Asp Thr Ile Asn Met Phe
        355                 360                 365

Ile Thr Arg Lys Asp Val Lys Lys Ala Leu Lys Glu Ile Ile Tyr Ala
    370                 375                 380

Ala Glu Asp Tyr Leu Glu Gly Gly Ser His His His His His His
385                 390                 395


<210> SEQ ID NO 14
<211> LENGTH: 395
<212> TYPE: PRT
<213> ORGANISM: Artificial Sequence
<220> FEATURE:
<223> OTHER INFORMATION: bhGBP6 (with signal peptide replaced with M and
      a GGSHHHHHH at C-terminus)

<400> SEQUENCE: 14

Met Leu Glu Ile Phe Ser Trp Trp Thr Gly Ala Gly Glu Glu Asp Gly
1               5                   10                  15

Leu Leu Ala Leu Ile Glu Leu Phe Glu Glu Lys His Pro Glu Ile Glu
            20                  25                  30

Val Asp Asn Ala Ala Val Ala Gly Gly Ala Gly Thr Asn Ala Lys Ala
        35                  40                  45

Val Leu Thr Ser Arg Met Gln Gly Asn Asp Pro Pro Gly Thr Phe Gln
    50                  55                  60

Val His Gly Gly Ala Glu Leu Asn Asp Ser Trp Val Ala Ala Gly Gln
65                  70                  75                  80

Met Asp Pro Leu Asn Asp Leu Phe Glu Ala Glu Gly Trp Ala Asp Lys
                85                  90                  95

Phe Pro Glu Glu Leu Ile Glu Leu Val Ser Lys Asp Gly Asn Ile Tyr
            100                 105                 110
```

```
Ser Val Pro Val Asn Ile His Arg Gly Asn Val Leu Trp Tyr Asn Thr
        115                 120                 125

Glu Ile Phe Glu Glu His Gly Leu Glu Val Pro Thr Thr Phe Glu Glu
    130                 135                 140

Phe Phe Asp Val Ala Asp Ala Leu Gln Glu Ala Gly Val Thr Pro Leu
145                 150                 155                 160

Ala Leu Gly Asp Arg Glu Pro Trp Ala Ala Thr His Leu Phe Glu Thr
                165                 170                 175

Val Leu Leu Gly Thr Leu Gly Ala Asp Asp Tyr Asn Lys Leu Trp Ser
            180                 185                 190

Gly Glu Val Gly Met Asp Asp Pro Arg Val Glu Glu Ala Ala Glu Ile
        195                 200                 205

Phe Ile Arg Met Leu Asp Tyr Val Asn Glu Asp His Ser Ser Arg Asn
    210                 215                 220

Trp Gln Asp Ala Ser Gln Leu Val Ala Gln Gly Glu Ala Ala Met Asn
225                 230                 235                 240

Val Met Gly Asp Trp Ala Lys Gly Tyr Phe Val Asn Asp Leu Asn Leu
                245                 250                 255

Ala Val Lys Glu Asp Phe Gly Trp Ala Ala Thr Pro Gly Thr Glu Gly
            260                 265                 270

Thr Phe Met Val Ile Thr Asp Thr Phe Gly Leu Pro Thr Gly Val Glu
        275                 280                 285

Asn Pro Glu Val Val Lys Ser Phe Leu Ala Val Leu Gly Ser Gln Glu
    290                 295                 300

Gly Gln Asp Ala Phe Asn Pro Leu Lys Gly Ser Ile Pro Ala Arg Val
305                 310                 315                 320

Asp Ala Asp Val Ser Lys Tyr Asp Glu Tyr Gly Gln Glu Thr Ile Glu
                325                 330                 335

Asp Phe Lys Ser Ala Glu Leu Ser Pro Ser Leu Ala His Gly Ser Ala
            340                 345                 350

Ala Asn Glu Gly Phe Leu Thr Gln Val Asn Gln Ala Ile Asn Ile Phe
        355                 360                 365

Val Thr Gln Lys Asp Val Asp Ser Phe Val Asp Ser Leu Lys Gln Tyr
    370                 375                 380

Gln Pro Gly Gly Ser His His His His His His
385                 390                 395
```

<210> SEQ ID NO 15
<211> LENGTH: 436
<212> TYPE: PRT
<213> ORGANISM: Artificial Sequence
<220> FEATURE:
<223> OTHER INFORMATION: smGBP7 (with signal peptide replaced with M and a GGSHHHHHH at C-terminus)

<400> SEQUENCE: 15

```
Met Glu Leu Val Ile Tyr His Trp Trp Thr Ala Gly Gly Glu Arg Glu
1               5                   10                  15

Ala Ile Asn Ala Val Phe Gln Val Phe Lys Gln Lys Tyr Pro Asn Ile
            20                  25                  30

Gln Ile Val Glu Asn Pro Val Ala Gly Gly Ala Gly Ser Val Met Lys
        35                  40                  45

Ser Val Ile Ile Gly Leu Leu Ala Ala Gly Thr Pro Pro Asp Thr Phe
    50                  55                  60

Gln Val His Ala Gly Ala Glu Leu Lys Glu Tyr Val Asp Ala Gly Tyr
65                  70                  75                  80
```

```
Leu Ala Pro Ile Asp Asp Ile Trp Ser Lys Leu Gly Leu Asp Lys Val
                85                  90                  95

Ile Pro Ser Thr Leu Gln Val Met Ala Lys Phe Asn Gly His Tyr Tyr
            100                 105                 110

Ala Val Pro Ile Asp Val His Arg Ser Asn Val Leu Trp Tyr Asn Pro
        115                 120                 125

Lys Ile Phe Asn Glu Leu Gly Ile Ile Asn Lys Phe Gly Asp Pro Arg
    130                 135                 140

Asn Trp Ser Val Asp Thr Leu Leu Gln Val Ala Arg Tyr Ile Lys Gln
145                 150                 155                 160

Gln Arg Pro Asp Ile Ala Pro Ile Ala Leu Ala Ser Arg Asn Lys Trp
                165                 170                 175

Pro Val Thr His Leu Phe Glu Val Leu Leu Ala Asn Ala Gly Gly Pro
            180                 185                 190

Glu Thr Tyr Val Lys Phe Phe Thr Gly Lys Phe Asn Tyr Asn Asp Pro
        195                 200                 205

Asn Asp Pro Val Val Gln Thr Val Lys Lys Val Leu Thr Val Met Ala
    210                 215                 220

Thr Met Ala Lys Glu Gly Leu Phe Asn Ser Asn His Pro Glu Leu Thr
225                 230                 235                 240

Trp Asp Gln Ala Ala Ala Leu Val Ala Glu Gly Lys Ala Ala Met Phe
                245                 250                 255

Ile His Gly Asp Trp Val Ala Gly Tyr Tyr Ile Ala Asn Asn Tyr Lys
            260                 265                 270

Tyr Gly Lys Asp Trp Ala Ala Ala Pro Phe Pro Lys Asn Ile Phe Ile
        275                 280                 285

Leu Leu Ser Asp Ala Phe Glu Leu Pro Lys Asn Ala Pro His Pro Glu
    290                 295                 300

Ala Ala Lys Asp Trp Leu Met Val Val Gly Ser Lys Glu Ala Gln Glu
305                 310                 315                 320

Lys Phe Asn Leu Ile Lys Gly Ser Ile Pro Ala Arg Thr Asp Val Ser
                325                 330                 335

Pro Lys Tyr Pro Asp Pro Tyr Arg Pro Glu Thr Ala Glu Asp Phe Gln
            340                 345                 350

Lys Ser Thr Leu Ile Pro Ser Ala Val His Gly Gly Ile Ala Lys Glu
        355                 360                 365

Ala Phe Met Thr Asp Leu His Asn Ile Leu Thr Ser Met Leu Thr Ala
    370                 375                 380

Val Ser Val Gly Thr Pro Val Asp Asn Ala Val Asn Thr Ala Leu Ala
385                 390                 395                 400

Gln Ile Leu Gln Ser Val Lys Thr Ser Gly Leu Ala Ser Phe Trp Lys
                405                 410                 415

Gly Tyr Thr Ile Asp Tyr Phe Ile Thr Lys Arg Gly Gly Ser His His
            420                 425                 430

His His His His
        435
```

<210> SEQ ID NO 16
<211> LENGTH: 400
<212> TYPE: PRT
<213> ORGANISM: Artificial Sequence
<220> FEATURE:
<223> OTHER INFORMATION: asGBP8 (with signal peptide replaced with M and
a GGSHHHHHH at C-terminus)

<400> SEQUENCE: 16

```
Met Lys Leu Glu Ile Thr Ser Trp Trp Thr Ser Gly Ser Glu Ala Asp
1               5                   10                  15

Ala Leu Asn Val Leu Ile Asp Gly Val Lys Ala Ala Lys Pro Gly Leu
            20                  25                  30

Ser Val Asp Asn Ala Ala Val Ser Gly Gly Gly Gly Ala Asn Ala Arg
        35                  40                  45

Gln Ala Leu Ala Ala Arg Leu Gln Ala Gly Ser Pro Pro Asp Ala Trp
    50                  55                  60

Gln Val His Pro Ala Gly Gln Leu Lys Ser Tyr Val Asp Gly Gly Gln
65                  70                  75                  80

Val Ala Asp Leu Thr Asp Leu Trp Thr Glu Gly Asp Trp Ala Ser Gln
                85                  90                  95

Met Pro Lys Asp Val Ala Glu Ala Gln Gln Val Asp Gly Lys Tyr Tyr
            100                 105                 110

Thr Val Pro Ile Gly Val His Arg Gly Asn Val Leu Trp Thr Asn Pro
        115                 120                 125

Ala Val Leu Ser Lys Ala Asn Val Thr Ile Asp Ala Asp Ala Gly Ile
    130                 135                 140

Asp Gly Leu Ile Ser Ser Leu Glu Gln Val Gln Ala Ser Gly Thr Thr
145                 150                 155                 160

Pro Leu Ala Leu Gly Asp Lys Asp Ile Phe Ala Ser Ser Gln Leu Leu
                165                 170                 175

Glu Ser Leu Ile Met Ser Arg Ala Gly Ala Asp Asn Trp Thr Lys Leu
            180                 185                 190

Phe Thr Ser Glu Tyr Ser Phe Asp Ala Pro Glu Val Lys Gln Ala Leu
        195                 200                 205

Glu Asp Tyr Lys Thr Ile Leu Ser Phe Ala Asn Lys Asp His Ser Ala
    210                 215                 220

Ile Thr Trp Asp Glu Ala Ala Lys Lys Met Ala Asp Gly Glu Ala Ala
225                 230                 235                 240

Val Asn Leu Met Gly Asp Trp Ala Tyr Gly Glu Leu Leu Asn Ala Gly
                245                 250                 255

Lys Lys Pro Gly Thr Asp Phe Ala Trp Val Ala Phe Pro Gly Lys Glu
            260                 265                 270

Asp Ile Phe Asp Tyr Val Gly Asp Gly Phe Ser Ile Pro Ala Asn Asn
        275                 280                 285

Ile Pro His Ala Glu Ala Ala Arg Ala Trp Leu Lys Thr Leu Met Asp
    290                 295                 300

Pro Lys Ile Gln Thr Glu Phe Ala Ala Lys Lys Gly Ser Ile Pro Ala
305                 310                 315                 320

Val Thr Ser Ala Asp Ile Ser Gly Leu Ser Glu Tyr Gln Gln Glu Ala
                325                 330                 335

Ala Lys Ser Leu Ala Ser Gly Ala Val Val Ser Ser Leu Ala His Ala
            340                 345                 350

Gln Ala Ala Gly Ala Glu Phe Ala Gln Thr Tyr Ala Asp Ala Val Ser
        355                 360                 365

Thr Phe Asn Gly Ser Gly Asn Thr Asp Ala Phe Ile Ala Ser Met Thr
    370                 375                 380

Gln Ala Gln Lys Thr Gln Leu Gly Gly Ser His His His His His His
385                 390                 395                 400
```

<210> SEQ ID NO 17

```
<211> LENGTH: 400
<212> TYPE: PRT
<213> ORGANISM: Artificial Sequence
<220> FEATURE:
<223> OTHER INFORMATION: tsGBP2_C8 (8C substitution mutant with signal
      peptide replaced with M and a GGSHHHHHH at C-terminus)

<400> SEQUENCE: 17

Met Lys Leu Glu Ile Phe Ser Cys Trp Ala Gly Asp Glu Gly Pro Ala
1               5                   10                  15

Leu Glu Ala Leu Ile Arg Leu Tyr Lys Gln Lys Tyr Pro Gly Val Glu
            20                  25                  30

Val Ile Asn Ala Thr Val Thr Gly Gly Ala Gly Val Asn Ala Lys Ala
        35                  40                  45

Val Leu Lys Thr Arg Met Leu Gly Gly Asp Pro Pro Asp Thr Phe Gln
    50                  55                  60

Val His Ala Gly Gln Glu Leu Ile Gly Thr Trp Val Val Ala Asp Arg
65                  70                  75                  80

Met Glu Asp Leu Thr Ser Leu Phe Arg Gln Glu Gly Trp Leu Gln Ala
                85                  90                  95

Phe Pro Lys Gly Leu Ile Asp Leu Leu Ser Tyr Lys Gly Gly Ile Trp
            100                 105                 110

Ser Val Pro Val Asn Ile His Arg Ser Asn Val Met Trp Tyr Ile Pro
        115                 120                 125

Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
145                 150                 155                 160

Leu Ala Leu Gly Glu Asn Trp Thr Gln Gln His Leu Trp Glu Ser Val
                165                 170                 175

Ala Leu Ala Thr Leu Gly Ala Asp Gly Trp Asn Asn Leu Trp Ser Gly
            180                 185                 190

Lys Leu Lys Phe Thr Asp Pro Lys Ala Val Ala Val Trp Glu Thr Phe
        195                 200                 205

Gly Lys Val Leu Asp Ala Ala Asn Lys Asp Ala Ala Gly Leu Ser Trp
    210                 215                 220

Gln Gln Ala Val Asp Arg Val Val Gln Gly Lys Ala Ala Phe Asn Ile
225                 230                 235                 240

Met Gly Asp Trp Ala Ala Gly Tyr Met Ser Thr Thr Leu Lys Leu Lys
                245                 250                 255

Pro Gly Thr Asp Phe Ala Trp Thr Pro Ser Pro Gly Thr Ser Gly Ile
            260                 265                 270

Phe Met Met Leu Ser Asp Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300

Gln Asp Thr Phe Asn Pro Leu Lys Gly Ser Ile Ala Ala Arg Leu Asp
305                 310                 315                 320

Ser Asp Pro Ala Lys Tyr Asn Ala Tyr Gly Gln Ser Ala Met Lys Asp
                325                 330                 335

Trp Lys Ser Asn Arg Ile Val Gly Ser Leu Val His Gly Ala Val Ala
            340                 345                 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
```

```
    370                 375                 380

Asn Gln Val Gly Leu Gly Arg Gly Gly Ser His His His His His His
385                 390                 395                 400


<210> SEQ ID NO 18
<211> LENGTH: 400
<212> TYPE: PRT
<213> ORGANISM: Artificial Sequence
<220> FEATURE:
<223> OTHER INFORMATION: tsGBP2_C9 (9C substitution mutant with signal
      peptide replaced with M and a GGSHHHHHH at C-terminus)

<400> SEQUENCE: 18

Met Lys Leu Glu Ile Phe Ser Trp Cys Ala Gly Asp Glu Gly Pro Ala
1               5                   10                  15

Leu Glu Ala Leu Ile Arg Leu Tyr Lys Gln Lys Tyr Pro Gly Val Glu
            20                  25                  30

Val Ile Asn Ala Thr Val Thr Gly Gly Ala Gly Val Asn Ala Lys Ala
        35                  40                  45

Val Leu Lys Thr Arg Met Leu Gly Gly Asp Pro Pro Asp Thr Phe Gln
    50                  55                  60

Val His Ala Gly Gln Glu Leu Ile Gly Thr Trp Val Val Ala Asp Arg
65                  70                  75                  80

Met Glu Asp Leu Thr Ser Leu Phe Arg Gln Glu Gly Trp Leu Gln Ala
                85                  90                  95

Phe Pro Lys Gly Leu Ile Asp Leu Leu Ser Tyr Lys Gly Gly Ile Trp
            100                 105                 110

Ser Val Pro Val Asn Ile His Arg Ser Asn Val Met Trp Tyr Ile Pro
        115                 120                 125

Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
145                 150                 155                 160

Leu Ala Leu Gly Glu Asn Trp Thr Gln Gln His Leu Trp Glu Ser Val
                165                 170                 175

Ala Leu Ala Thr Leu Gly Ala Asp Gly Trp Asn Asn Leu Trp Ser Gly
            180                 185                 190

Lys Leu Lys Phe Thr Asp Pro Lys Ala Val Ala Val Trp Glu Thr Phe
        195                 200                 205

Gly Lys Val Leu Asp Ala Ala Asn Lys Asp Ala Ala Gly Leu Ser Trp
    210                 215                 220

Gln Gln Ala Val Asp Arg Val Val Gln Gly Lys Ala Ala Phe Asn Ile
225                 230                 235                 240

Met Gly Asp Trp Ala Ala Gly Tyr Met Ser Thr Thr Leu Lys Leu Lys
                245                 250                 255

Pro Gly Thr Asp Phe Ala Trp Thr Pro Ser Pro Gly Thr Ser Gly Ile
            260                 265                 270

Phe Met Met Leu Ser Asp Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300

Gln Asp Thr Phe Asn Pro Leu Lys Gly Ser Ile Ala Ala Arg Leu Asp
305                 310                 315                 320

Ser Asp Pro Ala Lys Tyr Asn Ala Tyr Gly Gln Ser Ala Met Lys Asp
                325                 330                 335
```

-continued

```
Trp Lys Ser Asn Arg Ile Val Gly Ser Leu Val His Gly Ala Val Ala
            340                 345                 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380

Asn Gln Val Gly Leu Gly Arg Gly Gly Ser His His His His His His
385                 390                 395                 400


<210> SEQ ID NO 19
<211> LENGTH: 400
<212> TYPE: PRT
<213> ORGANISM: Artificial Sequence
<220> FEATURE:
<223> OTHER INFORMATION: tsGBP2_C12 (12C substitution mutant with signal
      peptide replaced with M and a GGSHHHHHH at C-terminus)

<400> SEQUENCE: 19

Met Lys Leu Glu Ile Phe Ser Trp Trp Ala Gly Cys Glu Gly Pro Ala
1               5                   10                  15

Leu Glu Ala Leu Ile Arg Leu Tyr Lys Gln Lys Tyr Pro Gly Val Glu
            20                  25                  30

Val Ile Asn Ala Thr Val Thr Gly Gly Ala Gly Val Asn Ala Lys Ala
        35                  40                  45

Val Leu Lys Thr Arg Met Leu Gly Gly Asp Pro Pro Asp Thr Phe Gln
    50                  55                  60

Val His Ala Gly Gln Glu Leu Ile Gly Thr Trp Val Val Ala Asp Arg
65                  70                  75                  80

Met Glu Asp Leu Thr Ser Leu Phe Arg Gln Glu Gly Trp Leu Gln Ala
                85                  90                  95

Phe Pro Lys Gly Leu Ile Asp Leu Leu Ser Tyr Lys Gly Gly Ile Trp
            100                 105                 110

Ser Val Pro Val Asn Ile His Arg Ser Asn Val Met Trp Tyr Ile Pro
        115                 120                 125

Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
145                 150                 155                 160

Leu Ala Leu Gly Glu Asn Trp Thr Gln Gln His Leu Trp Glu Ser Val
                165                 170                 175

Ala Leu Ala Thr Leu Gly Ala Asp Gly Trp Asn Asn Leu Trp Ser Gly
            180                 185                 190

Lys Leu Lys Phe Thr Asp Pro Lys Ala Val Ala Val Trp Glu Thr Phe
        195                 200                 205

Gly Lys Val Leu Asp Ala Ala Asn Lys Asp Ala Ala Gly Leu Ser Trp
    210                 215                 220

Gln Gln Ala Val Asp Arg Val Val Gln Gly Lys Ala Ala Phe Asn Ile
225                 230                 235                 240

Met Gly Asp Trp Ala Ala Gly Tyr Met Ser Thr Thr Leu Lys Leu Lys
                245                 250                 255

Pro Gly Thr Asp Phe Ala Trp Thr Pro Ser Pro Gly Thr Ser Gly Ile
            260                 265                 270

Phe Met Met Leu Ser Asp Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300
```

Gln Asp Thr Phe Asn Pro Leu Lys Gly Ser Ile Ala Ala Arg Leu Asp
305 310 315 320

Ser Asp Pro Ala Lys Tyr Asn Ala Tyr Gly Gln Ser Ala Met Lys Asp
325 330 335

Trp Lys Ser Asn Arg Ile Val Gly Ser Leu Val His Gly Ala Val Ala
340 345 350

Pro Glu Ser Phe Met Ser Gln Phe Gly Thr Val Met Glu Ile Phe Leu
355 360 365

Gln Ser Arg Asn Pro Gln Ala Ala Ala Asn Ala Ala Gln Ala Ile Ala
370 375 380

Asn Gln Val Gly Leu Gly Arg Gly Gly Ser His His His His His His
385 390 395 400

<210> SEQ ID NO 20
<211> LENGTH: 400
<212> TYPE: PRT
<213> ORGANISM: Artificial Sequence
<220> FEATURE:
<223> OTHER INFORMATION: tsGBP2_C13 (13C substitution mutant with signal peptide replaced with M and a GGSHHHHHH at C-terminus)

<400> SEQUENCE: 20

Met Lys Leu Glu Ile Phe Ser Trp Trp Ala Gly Asp Cys Gly Pro Ala
1 5 10 15

Leu Glu Ala Leu Ile Arg Leu Tyr Lys Gln Lys Tyr Pro Gly Val Glu
20 25 30

Val Ile Asn Ala Thr Val Thr Gly Gly Ala Gly Val Asn Ala Lys Ala
35 40 45

Val Leu Lys Thr Arg Met Leu Gly Gly Asp Pro Pro Asp Thr Phe Gln
50 55 60

Val His Ala Gly Gln Glu Leu Ile Gly Thr Trp Val Val Ala Asp Arg
65 70 75 80

Met Glu Asp Leu Thr Ser Leu Phe Arg Gln Glu Gly Trp Leu Gln Ala
85 90 95

Phe Pro Lys Gly Leu Ile Asp Leu Leu Ser Tyr Lys Gly Gly Ile Trp
100 105 110

Ser Val Pro Val Asn Ile His Arg Ser Asn Val Met Trp Tyr Ile Pro
115 120 125

Ala Lys Leu Lys Glu Trp Gly Val Thr Pro Pro Lys Thr Trp Ala Glu
130 135 140

Phe Leu Ala Thr Ala Gln Thr Leu Lys Arg Lys Gly Leu Glu Ala Pro
145 150 155 160

Leu Ala Leu Gly Glu Asn Trp Thr Gln Gln His Leu Trp Glu Ser Val
165 170 175

Ala Leu Ala Thr Leu Gly Ala Asp Gly Trp Asn Asn Leu Trp Ser Gly
180 185 190

Lys Leu Lys Phe Thr Asp Pro Lys Ala Val Ala Val Trp Glu Thr Phe
195 200 205

Gly Lys Val Leu Asp Ala Ala Asn Lys Asp Ala Ala Gly Leu Ser Trp
210 215 220

Gln Gln Ala Val Asp Arg Val Val Gln Gly Lys Ala Ala Phe Asn Ile
225 230 235 240

Met Gly Asp Trp Ala Ala Gly Tyr Met Ser Thr Thr Leu Lys Leu Lys
245 250 255

Pro Gly Thr Asp Phe Ala Trp Thr Pro Ser Pro Gly Thr Ser Gly Ile

-continued

```
            260                 265                 270

Phe Met Met Leu Ser Asp Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300

Gln Asp Thr Phe Asn Pro Leu Lys Gly Ser Ile Ala Ala Arg Leu Asp
305                 310                 315                 320

Ser Asp Pro Ala Lys Tyr Asn Ala Tyr Gly Gln Ser Ala Met Lys Asp
                325                 330                 335

Trp Lys Ser Asn Arg Ile Val Gly Ser Leu Val His Gly Ala Val Ala
            340                 345                 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380

Asn Gln Val Gly Leu Gly Arg Gly Gly Ser His His His His His His
385                 390                 395                 400


<210> SEQ ID NO 21
<211> LENGTH: 400
<212> TYPE: PRT
<213> ORGANISM: Artificial Sequence
<220> FEATURE:
<223> OTHER INFORMATION: tsGBP2_C41 (41C substitution mutant with signal
      peptide replaced with M and a GGSHHHHHH at C-terminus)

<400> SEQUENCE: 21

Met Lys Leu Glu Ile Phe Ser Trp Trp Ala Gly Asp Glu Gly Pro Ala
1               5                   10                  15

Leu Glu Ala Leu Ile Arg Leu Tyr Lys Gln Lys Tyr Pro Gly Val Glu
            20                  25                  30

Val Ile Asn Ala Thr Val Thr Gly Cys Ala Gly Val Asn Ala Lys Ala
        35                  40                  45

Val Leu Lys Thr Arg Met Leu Gly Gly Asp Pro Pro Asp Thr Phe Gln
    50                  55                  60

Val His Ala Gly Gln Glu Leu Ile Gly Thr Trp Val Val Ala Asp Arg
65                  70                  75                  80

Met Glu Asp Leu Thr Ser Leu Phe Arg Gln Glu Gly Trp Leu Gln Ala
                85                  90                  95

Phe Pro Lys Gly Leu Ile Asp Leu Leu Ser Tyr Lys Gly Gly Ile Trp
            100                 105                 110

Ser Val Pro Val Asn Ile His Arg Ser Asn Val Met Trp Tyr Ile Pro
        115                 120                 125

Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
145                 150                 155                 160

Leu Ala Leu Gly Glu Asn Trp Thr Gln Gln His Leu Trp Glu Ser Val
                165                 170                 175

Ala Leu Ala Thr Leu Gly Ala Asp Gly Trp Asn Asn Leu Trp Ser Gly
            180                 185                 190

Lys Leu Lys Phe Thr Asp Pro Lys Ala Val Ala Val Trp Glu Thr Phe
        195                 200                 205

Gly Lys Val Leu Asp Ala Ala Asn Lys Asp Ala Ala Gly Leu Ser Trp
    210                 215                 220
```

Gln Gln Ala Val Asp Arg Val Val Gln Gly Lys Ala Ala Phe Asn Ile
225 230 235 240

Met Gly Asp Trp Ala Ala Gly Tyr Met Ser Thr Thr Leu Lys Leu Lys
245 250 255

Pro Gly Thr Asp Phe Ala Trp Thr Pro Ser Pro Gly Thr Ser Gly Ile
260 265 270

Phe Met Met Leu Ser Asp Ser Phe Gly Leu Pro Lys Gly Ala Lys Asn
275 280 285

Arg Gln Asn Ala Ile Asn Trp Leu Lys Leu Val Gly Ser Lys Glu Gly
290 295 300

Gln Asp Thr Phe Asn Pro Leu Lys Gly Ser Ile Ala Ala Arg Leu Asp
305 310 315 320

Ser Asp Pro Ala Lys Tyr Asn Ala Tyr Gly Gln Ser Ala Met Lys Asp
325 330 335

Trp Lys Ser Asn Arg Ile Val Gly Ser Leu Val His Gly Ala Val Ala
340 345 350

Pro Glu Ser Phe Met Ser Gln Phe Gly Thr Val Met Glu Ile Phe Leu
355 360 365

Gln Ser Arg Asn Pro Gln Ala Ala Ala Asn Ala Ala Gln Ala Ile Ala
370 375 380

Asn Gln Val Gly Leu Gly Arg Gly Gly Ser His His His His His His
385 390 395 400

<210> SEQ ID NO 22
<211> LENGTH: 400
<212> TYPE: PRT
<213> ORGANISM: Artificial Sequence
<220> FEATURE:
<223> OTHER INFORMATION: tsGBP2_C42 (42C substitution mutant with signal peptide replaced with M and a GGSHHHHHH at C-terminus)

<400> SEQUENCE: 22

Met Lys Leu Glu Ile Phe Ser Trp Trp Ala Gly Asp Glu Gly Pro Ala
1 5 10 15

Leu Glu Ala Leu Ile Arg Leu Tyr Lys Gln Lys Tyr Pro Gly Val Glu
20 25 30

Val Ile Asn Ala Thr Val Thr Gly Gly Cys Gly Val Asn Ala Lys Ala
35 40 45

Val Leu Lys Thr Arg Met Leu Gly Gly Asp Pro Pro Asp Thr Phe Gln
50 55 60

Val His Ala Gly Gln Glu Leu Ile Gly Thr Trp Val Val Ala Asp Arg
65 70 75 80

Met Glu Asp Leu Thr Ser Leu Phe Arg Gln Glu Gly Trp Leu Gln Ala
85 90 95

Phe Pro Lys Gly Leu Ile Asp Leu Leu Ser Tyr Lys Gly Gly Ile Trp
100 105 110

Ser Val Pro Val Asn Ile His Arg Ser Asn Val Met Trp Tyr Ile Pro
115 120 125

Ala Lys Leu Lys Glu Trp Gly Val Thr Pro Pro Lys Thr Trp Ala Glu
130 135 140

Phe Leu Ala Thr Ala Gln Thr Leu Lys Arg Lys Gly Leu Glu Ala Pro
145 150 155 160

Leu Ala Leu Gly Glu Asn Trp Thr Gln Gln His Leu Trp Glu Ser Val
165 170 175

Ala Leu Ala Thr Leu Gly Ala Asp Gly Trp Asn Asn Leu Trp Ser Gly
180 185 190

-continued

```
Lys Leu Lys Phe Thr Asp Pro Lys Ala Val Ala Val Trp Glu Thr Phe
        195                 200                 205

Gly Lys Val Leu Asp Ala Ala Asn Lys Asp Ala Ala Gly Leu Ser Trp
    210                 215                 220

Gln Gln Ala Val Asp Arg Val Val Gln Gly Lys Ala Ala Phe Asn Ile
225                 230                 235                 240

Met Gly Asp Trp Ala Ala Gly Tyr Met Ser Thr Thr Leu Lys Leu Lys
                245                 250                 255

Pro Gly Thr Asp Phe Ala Trp Thr Pro Ser Pro Gly Thr Ser Gly Ile
            260                 265                 270

Phe Met Met Leu Ser Asp Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300

Gln Asp Thr Phe Asn Pro Leu Lys Gly Ser Ile Ala Ala Arg Leu Asp
305                 310                 315                 320

Ser Asp Pro Ala Lys Tyr Asn Ala Tyr Gly Gln Ser Ala Met Lys Asp
                325                 330                 335

Trp Lys Ser Asn Arg Ile Val Gly Ser Leu Val His Gly Ala Val Ala
            340                 345                 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380

Asn Gln Val Gly Leu Gly Arg Gly Gly Ser His His His His His His
385                 390                 395                 400


<210> SEQ ID NO 23
<211> LENGTH: 400
<212> TYPE: PRT
<213> ORGANISM: Artificial Sequence
<220> FEATURE:
<223> OTHER INFORMATION: tsGBP2_C64 (64C substitution mutant with signal
      peptide replaced with M and a GGSHHHHHH at C-terminus)

<400> SEQUENCE: 23

Met Lys Leu Glu Ile Phe Ser Trp Trp Ala Gly Asp Glu Gly Pro Ala
1               5                   10                  15

Leu Glu Ala Leu Ile Arg Leu Tyr Lys Gln Lys Tyr Pro Gly Val Glu
            20                  25                  30

Val Ile Asn Ala Thr Val Thr Gly Gly Ala Gly Val Asn Ala Lys Ala
        35                  40                  45

Val Leu Lys Thr Arg Met Leu Gly Gly Asp Pro Pro Asp Thr Phe Cys
    50                  55                  60

Val His Ala Gly Gln Glu Leu Ile Gly Thr Trp Val Val Ala Asp Arg
65                  70                  75                  80

Met Glu Asp Leu Thr Ser Leu Phe Arg Gln Glu Gly Trp Leu Gln Ala
                85                  90                  95

Phe Pro Lys Gly Leu Ile Asp Leu Leu Ser Tyr Lys Gly Gly Ile Trp
            100                 105                 110

Ser Val Pro Val Asn Ile His Arg Ser Asn Val Met Trp Tyr Ile Pro
        115                 120                 125

Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
```

-continued

```
145                 150                 155                 160

Leu Ala Leu Gly Glu Asn Trp Thr Gln Gln His Leu Trp Glu Ser Val
                165                 170                 175

Ala Leu Ala Thr Leu Gly Ala Asp Gly Trp Asn Asn Leu Trp Ser Gly
            180                 185                 190

Lys Leu Lys Phe Thr Asp Pro Lys Ala Val Ala Val Trp Glu Thr Phe
        195                 200                 205

Gly Lys Val Leu Asp Ala Ala Asn Lys Asp Ala Ala Gly Leu Ser Trp
    210                 215                 220

Gln Gln Ala Val Asp Arg Val Val Gln Gly Lys Ala Ala Phe Asn Ile
225                 230                 235                 240

Met Gly Asp Trp Ala Ala Gly Tyr Met Ser Thr Thr Leu Lys Leu Lys
                245                 250                 255

Pro Gly Thr Asp Phe Ala Trp Thr Pro Ser Pro Gly Thr Ser Gly Ile
            260                 265                 270

Phe Met Met Leu Ser Asp Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300

Gln Asp Thr Phe Asn Pro Leu Lys Gly Ser Ile Ala Ala Arg Leu Asp
305                 310                 315                 320

Ser Asp Pro Ala Lys Tyr Asn Ala Tyr Gly Gln Ser Ala Met Lys Asp
                325                 330                 335

Trp Lys Ser Asn Arg Ile Val Gly Ser Leu Val His Gly Ala Val Ala
            340                 345                 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380

Asn Gln Val Gly Leu Gly Arg Gly Gly Ser His His His His His His
385                 390                 395                 400


<210> SEQ ID NO 24
<211> LENGTH: 400
<212> TYPE: PRT
<213> ORGANISM: Artificial Sequence
<220> FEATURE:
<223> OTHER INFORMATION: tsGBP2_C66 (66C substitution mutant with signal
      peptide replaced with M and a GGSHHHHHH at C-terminus)

<400> SEQUENCE: 24

Met Lys Leu Glu Ile Phe Ser Trp Trp Ala Gly Asp Glu Gly Pro Ala
1               5                   10                  15

Leu Glu Ala Leu Ile Arg Leu Tyr Lys Gln Lys Tyr Pro Gly Val Glu
            20                  25                  30

Val Ile Asn Ala Thr Val Thr Gly Gly Ala Gly Val Asn Ala Lys Ala
        35                  40                  45

Val Leu Lys Thr Arg Met Leu Gly Gly Asp Pro Pro Asp Thr Phe Gln
    50                  55                  60

Val Cys Ala Gly Gln Glu Leu Ile Gly Thr Trp Val Val Ala Asp Arg
65                  70                  75                  80

Met Glu Asp Leu Thr Ser Leu Phe Arg Gln Glu Gly Trp Leu Gln Ala
                85                  90                  95

Phe Pro Lys Gly Leu Ile Asp Leu Leu Ser Tyr Lys Gly Gly Ile Trp
            100                 105                 110
```

-continued

Ser Val Pro Val Asn Ile His Arg Ser Asn Val Met Trp Tyr Ile Pro
115 120 125

Ala Lys Leu Lys Glu Trp Gly Val Thr Pro Pro Lys Thr Trp Ala Glu
130 135 140

Phe Leu Ala Thr Ala Gln Thr Leu Lys Arg Lys Gly Leu Glu Ala Pro
145 150 155 160

Leu Ala Leu Gly Glu Asn Trp Thr Gln Gln His Leu Trp Glu Ser Val
165 170 175

Ala Leu Ala Thr Leu Gly Ala Asp Gly Trp Asn Asn Leu Trp Ser Gly
180 185 190

Lys Leu Lys Phe Thr Asp Pro Lys Ala Val Ala Val Trp Glu Thr Phe
195 200 205

Gly Lys Val Leu Asp Ala Ala Asn Lys Asp Ala Ala Gly Leu Ser Trp
210 215 220

Gln Gln Ala Val Asp Arg Val Val Gln Gly Lys Ala Ala Phe Asn Ile
225 230 235 240

Met Gly Asp Trp Ala Ala Gly Tyr Met Ser Thr Thr Leu Lys Leu Lys
245 250 255

Pro Gly Thr Asp Phe Ala Trp Thr Pro Ser Pro Gly Thr Ser Gly Ile
260 265 270

Phe Met Met Leu Ser Asp Ser Phe Gly Leu Pro Lys Gly Ala Lys Asn
275 280 285

Arg Gln Asn Ala Ile Asn Trp Leu Lys Leu Val Gly Ser Lys Glu Gly
290 295 300

Gln Asp Thr Phe Asn Pro Leu Lys Gly Ser Ile Ala Ala Arg Leu Asp
305 310 315 320

Ser Asp Pro Ala Lys Tyr Asn Ala Tyr Gly Gln Ser Ala Met Lys Asp
325 330 335

Trp Lys Ser Asn Arg Ile Val Gly Ser Leu Val His Gly Ala Val Ala
340 345 350

Pro Glu Ser Phe Met Ser Gln Phe Gly Thr Val Met Glu Ile Phe Leu
355 360 365

Gln Ser Arg Asn Pro Gln Ala Ala Ala Asn Ala Ala Gln Ala Ile Ala
370 375 380

Asn Gln Val Gly Leu Gly Arg Gly Gly Ser His His His His His His
385 390 395 400

<210> SEQ ID NO 25
<211> LENGTH: 400
<212> TYPE: PRT
<213> ORGANISM: Artificial Sequence
<220> FEATURE:
<223> OTHER INFORMATION: tsGBP2_C119 (119C substitution mutant with signal peptide replaced with M and a GGSHHHHHH at C-terminus)

<400> SEQUENCE: 25

Met Lys Leu Glu Ile Phe Ser Trp Trp Ala Gly Asp Glu Gly Pro Ala
1 5 10 15

Leu Glu Ala Leu Ile Arg Leu Tyr Lys Gln Lys Tyr Pro Gly Val Glu
20 25 30

Val Ile Asn Ala Thr Val Thr Gly Gly Ala Gly Val Asn Ala Lys Ala
35 40 45

Val Leu Lys Thr Arg Met Leu Gly Gly Asp Pro Pro Asp Thr Phe Gln
50 55 60

Val His Ala Gly Gln Glu Leu Ile Gly Thr Trp Val Val Ala Asp Arg
65 70 75 80

```
Met Glu Asp Leu Thr Ser Leu Phe Arg Gln Glu Gly Trp Leu Gln Ala
                85                  90                  95

Phe Pro Lys Gly Leu Ile Asp Leu Leu Ser Tyr Lys Gly Gly Ile Trp
            100                 105                 110

Ser Val Pro Val Asn Ile Cys Arg Ser Asn Val Met Trp Tyr Ile Pro
        115                 120                 125

Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
145                 150                 155                 160

Leu Ala Leu Gly Glu Asn Trp Thr Gln Gln His Leu Trp Glu Ser Val
                165                 170                 175

Ala Leu Ala Thr Leu Gly Ala Asp Gly Trp Asn Asn Leu Trp Ser Gly
            180                 185                 190

Lys Leu Lys Phe Thr Asp Pro Lys Ala Val Ala Val Trp Glu Thr Phe
        195                 200                 205

Gly Lys Val Leu Asp Ala Ala Asn Lys Asp Ala Ala Gly Leu Ser Trp
    210                 215                 220

Gln Gln Ala Val Asp Arg Val Val Gln Gly Lys Ala Ala Phe Asn Ile
225                 230                 235                 240

Met Gly Asp Trp Ala Ala Gly Tyr Met Ser Thr Thr Leu Lys Leu Lys
                245                 250                 255

Pro Gly Thr Asp Phe Ala Trp Thr Pro Ser Pro Gly Thr Ser Gly Ile
            260                 265                 270

Phe Met Met Leu Ser Asp Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300

Gln Asp Thr Phe Asn Pro Leu Lys Gly Ser Ile Ala Ala Arg Leu Asp
305                 310                 315                 320

Ser Asp Pro Ala Lys Tyr Asn Ala Tyr Gly Gln Ser Ala Met Lys Asp
                325                 330                 335

Trp Lys Ser Asn Arg Ile Val Gly Ser Leu Val His Gly Ala Val Ala
            340                 345                 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380

Asn Gln Val Gly Leu Gly Arg Gly Gly Ser His His His His His His
385                 390                 395                 400


<210> SEQ ID NO 26
<211> LENGTH: 400
<212> TYPE: PRT
<213> ORGANISM: Artificial Sequence
<220> FEATURE:
<223> OTHER INFORMATION: tsGBP2_C167 (167C substitution mutant with
      signal peptide replaced with M and a GGSHHHHHH at C-terminus)

<400> SEQUENCE: 26

Met Lys Leu Glu Ile Phe Ser Trp Trp Ala Gly Asp Glu Gly Pro Ala
1               5                   10                  15

Leu Glu Ala Leu Ile Arg Leu Tyr Lys Gln Lys Tyr Pro Gly Val Glu
            20                  25                  30

Val Ile Asn Ala Thr Val Thr Gly Gly Ala Gly Val Asn Ala Lys Ala
```

```
        35                  40                  45

Val Leu Lys Thr Arg Met Leu Gly Gly Asp Pro Pro Asp Thr Phe Gln
    50                  55                  60

Val His Ala Gly Gln Glu Leu Ile Gly Thr Trp Val Val Ala Asp Arg
65                  70                  75                  80

Met Glu Asp Leu Thr Ser Leu Phe Arg Gln Glu Gly Trp Leu Gln Ala
                85                  90                  95

Phe Pro Lys Gly Leu Ile Asp Leu Leu Ser Tyr Lys Gly Gly Ile Trp
            100                 105                 110

Ser Val Pro Val Asn Ile His Arg Ser Asn Val Met Trp Tyr Ile Pro
        115                 120                 125

Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
145                 150                 155                 160

Leu Ala Leu Gly Glu Asn Cys Thr Gln Gln His Leu Trp Glu Ser Val
                165                 170                 175

Ala Leu Ala Thr Leu Gly Ala Asp Gly Trp Asn Asn Leu Trp Ser Gly
            180                 185                 190

Lys Leu Lys Phe Thr Asp Pro Lys Ala Val Ala Val Trp Glu Thr Phe
        195                 200                 205

Gly Lys Val Leu Asp Ala Ala Asn Lys Asp Ala Ala Gly Leu Ser Trp
    210                 215                 220

Gln Gln Ala Val Asp Arg Val Val Gln Gly Lys Ala Ala Phe Asn Ile
225                 230                 235                 240

Met Gly Asp Trp Ala Ala Gly Tyr Met Ser Thr Thr Leu Lys Leu Lys
                245                 250                 255

Pro Gly Thr Asp Phe Ala Trp Thr Pro Ser Pro Gly Thr Ser Gly Ile
            260                 265                 270

Phe Met Met Leu Ser Asp Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300

Gln Asp Thr Phe Asn Pro Leu Lys Gly Ser Ile Ala Ala Arg Leu Asp
305                 310                 315                 320

Ser Asp Pro Ala Lys Tyr Asn Ala Tyr Gly Gln Ser Ala Met Lys Asp
                325                 330                 335

Trp Lys Ser Asn Arg Ile Val Gly Ser Leu Val His Gly Ala Val Ala
            340                 345                 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380

Asn Gln Val Gly Leu Gly Arg Gly Gly Ser His His His His His His
385                 390                 395                 400


<210> SEQ ID NO 27
<211> LENGTH: 400
<212> TYPE: PRT
<213> ORGANISM: Artificial Sequence
<220> FEATURE:
<223> OTHER INFORMATION: tsGBP2_C223 (223C substitution mutant with
      signal peptide replaced with M and a GGSHHHHHH at C-terminus)

<400> SEQUENCE: 27
```

-continued

```
Met Lys Leu Glu Ile Phe Ser Trp Trp Ala Gly Asp Glu Gly Pro Ala
1               5                   10                  15

Leu Glu Ala Leu Ile Arg Leu Tyr Lys Gln Lys Tyr Pro Gly Val Glu
            20                  25                  30

Val Ile Asn Ala Thr Val Thr Gly Gly Ala Gly Val Asn Ala Lys Ala
        35                  40                  45

Val Leu Lys Thr Arg Met Leu Gly Gly Asp Pro Pro Asp Thr Phe Gln
    50                  55                  60

Val His Ala Gly Gln Glu Leu Ile Gly Thr Trp Val Val Ala Asp Arg
65                  70                  75                  80

Met Glu Asp Leu Thr Ser Leu Phe Arg Gln Glu Gly Trp Leu Gln Ala
                85                  90                  95

Phe Pro Lys Gly Leu Ile Asp Leu Leu Ser Tyr Lys Gly Gly Ile Trp
            100                 105                 110

Ser Val Pro Val Asn Ile His Arg Ser Asn Val Met Trp Tyr Ile Pro
        115                 120                 125

Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
145                 150                 155                 160

Leu Ala Leu Gly Glu Asn Trp Thr Gln Gln His Leu Trp Glu Ser Val
                165                 170                 175

Ala Leu Ala Thr Leu Gly Ala Asp Gly Trp Asn Asn Leu Trp Ser Gly
            180                 185                 190

Lys Leu Lys Phe Thr Asp Pro Lys Ala Val Ala Val Trp Glu Thr Phe
        195                 200                 205

Gly Lys Val Leu Asp Ala Ala Asn Lys Asp Ala Ala Gly Leu Cys Trp
    210                 215                 220

Gln Gln Ala Val Asp Arg Val Val Gln Gly Lys Ala Ala Phe Asn Ile
225                 230                 235                 240

Met Gly Asp Trp Ala Ala Gly Tyr Met Ser Thr Thr Leu Lys Leu Lys
                245                 250                 255

Pro Gly Thr Asp Phe Ala Trp Thr Pro Ser Pro Gly Thr Ser Gly Ile
            260                 265                 270

Phe Met Met Leu Ser Asp Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300

Gln Asp Thr Phe Asn Pro Leu Lys Gly Ser Ile Ala Ala Arg Leu Asp
305                 310                 315                 320

Ser Asp Pro Ala Lys Tyr Asn Ala Tyr Gly Gln Ser Ala Met Lys Asp
                325                 330                 335

Trp Lys Ser Asn Arg Ile Val Gly Ser Leu Val His Gly Ala Val Ala
            340                 345                 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380

Asn Gln Val Gly Leu Gly Arg Gly Gly Ser His His His His His His
385                 390                 395                 400
```

<210> SEQ ID NO 28
<211> LENGTH: 400
<212> TYPE: PRT

<213> ORGANISM: Artificial Sequence
<220> FEATURE:
<223> OTHER INFORMATION: tsGBP2_C224 (224C substitution mutant with
signal peptide replaced with M and a GGSHHHHHH at C-terminus)

<400> SEQUENCE: 28

```
Met Lys Leu Glu Ile Phe Ser Trp Trp Ala Gly Asp Glu Gly Pro Ala
1               5                   10                  15

Leu Glu Ala Leu Ile Arg Leu Tyr Lys Gln Lys Tyr Pro Gly Val Glu
            20                  25                  30

Val Ile Asn Ala Thr Val Thr Gly Gly Ala Gly Val Asn Ala Lys Ala
        35                  40                  45

Val Leu Lys Thr Arg Met Leu Gly Gly Asp Pro Pro Asp Thr Phe Gln
    50                  55                  60

Val His Ala Gly Gln Glu Leu Ile Gly Thr Trp Val Val Ala Asp Arg
65                  70                  75                  80

Met Glu Asp Leu Thr Ser Leu Phe Arg Gln Glu Gly Trp Leu Gln Ala
                85                  90                  95

Phe Pro Lys Gly Leu Ile Asp Leu Leu Ser Tyr Lys Gly Gly Ile Trp
            100                 105                 110

Ser Val Pro Val Asn Ile His Arg Ser Asn Val Met Trp Tyr Ile Pro
        115                 120                 125

Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
145                 150                 155                 160

Leu Ala Leu Gly Glu Asn Trp Thr Gln Gln His Leu Trp Glu Ser Val
                165                 170                 175

Ala Leu Ala Thr Leu Gly Ala Asp Gly Trp Asn Asn Leu Trp Ser Gly
            180                 185                 190

Lys Leu Lys Phe Thr Asp Pro Lys Ala Val Ala Val Trp Glu Thr Phe
        195                 200                 205

Gly Lys Val Leu Asp Ala Ala Asn Lys Asp Ala Ala Gly Leu Ser Cys
    210                 215                 220

Gln Gln Ala Val Asp Arg Val Val Gln Gly Lys Ala Ala Phe Asn Ile
225                 230                 235                 240

Met Gly Asp Trp Ala Ala Gly Tyr Met Ser Thr Thr Leu Lys Leu Lys
                245                 250                 255

Pro Gly Thr Asp Phe Ala Trp Thr Pro Ser Pro Gly Thr Ser Gly Ile
            260                 265                 270

Phe Met Met Leu Ser Asp Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300

Gln Asp Thr Phe Asn Pro Leu Lys Gly Ser Ile Ala Ala Arg Leu Asp
305                 310                 315                 320

Ser Asp Pro Ala Lys Tyr Asn Ala Tyr Gly Gln Ser Ala Met Lys Asp
                325                 330                 335

Trp Lys Ser Asn Arg Ile Val Gly Ser Leu Val His Gly Ala Val Ala
            340                 345                 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380
```

Asn Gln Val Gly Leu Gly Arg Gly Gly Ser His His His His His His
385 390 395 400

<210> SEQ ID NO 29
<211> LENGTH: 400
<212> TYPE: PRT
<213> ORGANISM: Artificial Sequence
<220> FEATURE:
<223> OTHER INFORMATION: tsGBP2_C225 (225C substitution mutant with signal peptide replaced with M and a GGSHHHHHH at C-terminus)

<400> SEQUENCE: 29

Met Lys Leu Glu Ile Phe Ser Trp Trp Ala Gly Asp Glu Gly Pro Ala
1 5 10 15

Leu Glu Ala Leu Ile Arg Leu Tyr Lys Gln Lys Tyr Pro Gly Val Glu
20 25 30

Val Ile Asn Ala Thr Val Thr Gly Gly Ala Gly Val Asn Ala Lys Ala
35 40 45

Val Leu Lys Thr Arg Met Leu Gly Gly Asp Pro Pro Asp Thr Phe Gln
50 55 60

Val His Ala Gly Gln Glu Leu Ile Gly Thr Trp Val Val Ala Asp Arg
65 70 75 80

Met Glu Asp Leu Thr Ser Leu Phe Arg Gln Glu Gly Trp Leu Gln Ala
85 90 95

Phe Pro Lys Gly Leu Ile Asp Leu Leu Ser Tyr Lys Gly Gly Ile Trp
100 105 110

Ser Val Pro Val Asn Ile His Arg Ser Asn Val Met Trp Tyr Ile Pro
115 120 125

Ala Lys Leu Lys Glu Trp Gly Val Thr Pro Pro Lys Thr Trp Ala Glu
130 135 140

Phe Leu Ala Thr Ala Gln Thr Leu Lys Arg Lys Gly Leu Glu Ala Pro
145 150 155 160

Leu Ala Leu Gly Glu Asn Trp Thr Gln Gln His Leu Trp Glu Ser Val
165 170 175

Ala Leu Ala Thr Leu Gly Ala Asp Gly Trp Asn Asn Leu Trp Ser Gly
180 185 190

Lys Leu Lys Phe Thr Asp Pro Lys Ala Val Ala Val Trp Glu Thr Phe
195 200 205

Gly Lys Val Leu Asp Ala Ala Asn Lys Asp Ala Ala Gly Leu Ser Trp
210 215 220

Cys Gln Ala Val Asp Arg Val Val Gln Gly Lys Ala Ala Phe Asn Ile
225 230 235 240

Met Gly Asp Trp Ala Ala Gly Tyr Met Ser Thr Thr Leu Lys Leu Lys
245 250 255

Pro Gly Thr Asp Phe Ala Trp Thr Pro Ser Pro Gly Thr Ser Gly Ile
260 265 270

Phe Met Met Leu Ser Asp Ser Phe Gly Leu Pro Lys Gly Ala Lys Asn
275 280 285

Arg Gln Asn Ala Ile Asn Trp Leu Lys Leu Val Gly Ser Lys Glu Gly
290 295 300

Gln Asp Thr Phe Asn Pro Leu Lys Gly Ser Ile Ala Ala Arg Leu Asp
305 310 315 320

Ser Asp Pro Ala Lys Tyr Asn Ala Tyr Gly Gln Ser Ala Met Lys Asp
325 330 335

Trp Lys Ser Asn Arg Ile Val Gly Ser Leu Val His Gly Ala Val Ala
340 345 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380

Asn Gln Val Gly Leu Gly Arg Gly Gly Ser His His His His His His
385                 390                 395                 400

<210> SEQ ID NO 30
<211> LENGTH: 400
<212> TYPE: PRT
<213> ORGANISM: Artificial Sequence
<220> FEATURE:
<223> OTHER INFORMATION: tsGBP2_C244 (244C substitution mutant with signal peptide replaced with M and a GGSHHHHHH at C-terminus)

<400> SEQUENCE: 30

Met Lys Leu Glu Ile Phe Ser Trp Trp Ala Gly Asp Glu Gly Pro Ala
1               5                   10                  15

Leu Glu Ala Leu Ile Arg Leu Tyr Lys Gln Lys Tyr Pro Gly Val Glu
            20                  25                  30

Val Ile Asn Ala Thr Val Thr Gly Gly Ala Gly Val Asn Ala Lys Ala
        35                  40                  45

Val Leu Lys Thr Arg Met Leu Gly Gly Asp Pro Pro Asp Thr Phe Gln
    50                  55                  60

Val His Ala Gly Gln Glu Leu Ile Gly Thr Trp Val Val Ala Asp Arg
65                  70                  75                  80

Met Glu Asp Leu Thr Ser Leu Phe Arg Gln Glu Gly Trp Leu Gln Ala
                85                  90                  95

Phe Pro Lys Gly Leu Ile Asp Leu Leu Ser Tyr Lys Gly Gly Ile Trp
            100                 105                 110

Ser Val Pro Val Asn Ile His Arg Ser Asn Val Met Trp Tyr Ile Pro
        115                 120                 125

Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
145                 150                 155                 160

Leu Ala Leu Gly Glu Asn Trp Thr Gln Gln His Leu Trp Glu Ser Val
                165                 170                 175

Ala Leu Ala Thr Leu Gly Ala Asp Gly Trp Asn Asn Leu Trp Ser Gly
            180                 185                 190

Lys Leu Lys Phe Thr Asp Pro Lys Ala Val Ala Val Trp Glu Thr Phe
        195                 200                 205

Gly Lys Val Leu Asp Ala Ala Asn Lys Asp Ala Ala Gly Leu Ser Trp
    210                 215                 220

Gln Gln Ala Val Asp Arg Val Val Gln Gly Lys Ala Ala Phe Asn Ile
225                 230                 235                 240

Met Gly Asp Cys Ala Ala Gly Tyr Met Ser Thr Thr Leu Lys Leu Lys
                245                 250                 255

Pro Gly Thr Asp Phe Ala Trp Thr Pro Ser Pro Gly Thr Ser Gly Ile
            260                 265                 270

Phe Met Met Leu Ser Asp Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300

Gln Asp Thr Phe Asn Pro Leu Lys Gly Ser Ile Ala Ala Arg Leu Asp 305 310 315 320

Ser Asp Pro Ala Lys Tyr Asn Ala Tyr Gly Gln Ser Ala Met Lys Asp
325 330 335

Trp Lys Ser Asn Arg Ile Val Gly Ser Leu Val His Gly Ala Val Ala
340 345 350

Pro Glu Ser Phe Met Ser Gln Phe Gly Thr Val Met Glu Ile Phe Leu
355 360 365

Gln Ser Arg Asn Pro Gln Ala Ala Ala Asn Ala Ala Gln Ala Ile Ala
370 375 380

Asn Gln Val Gly Leu Gly Arg Gly Gly Ser His His His His His His
385 390 395 400

<210> SEQ ID NO 31
<211> LENGTH: 400
<212> TYPE: PRT
<213> ORGANISM: Artificial Sequence
<220> FEATURE:
<223> OTHER INFORMATION: tsGBP2_C277 (cysteine substitution mutant with signal peptide replaced with M and a GGSHHHHHH at C-terminus)

<400> SEQUENCE: 31

Met Lys Leu Glu Ile Phe Ser Trp Trp Ala Gly Asp Glu Gly Pro Ala
1 5 10 15

Leu Glu Ala Leu Ile Arg Leu Tyr Lys Gln Lys Tyr Pro Gly Val Glu
20 25 30

Val Ile Asn Ala Thr Val Thr Gly Gly Ala Gly Val Asn Ala Lys Ala
35 40 45

Val Leu Lys Thr Arg Met Leu Gly Gly Asp Pro Pro Asp Thr Phe Gln
50 55 60

Val His Ala Gly Gln Glu Leu Ile Gly Thr Trp Val Val Ala Asp Arg
65 70 75 80

Met Glu Asp Leu Thr Ser Leu Phe Arg Gln Glu Gly Trp Leu Gln Ala
85 90 95

Phe Pro Lys Gly Leu Ile Asp Leu Leu Ser Tyr Lys Gly Gly Ile Trp
100 105 110

Ser Val Pro Val Asn Ile His Arg Ser Asn Val Met Trp Tyr Ile Pro
115 120 125

Ala Lys Leu Lys Glu Trp Gly Val Thr Pro Pro Lys Thr Trp Ala Glu
130 135 140

Phe Leu Ala Thr Ala Gln Thr Leu Lys Arg Lys Gly Leu Glu Ala Pro
145 150 155 160

Leu Ala Leu Gly Glu Asn Trp Thr Gln Gln His Leu Trp Glu Ser Val
165 170 175

Ala Leu Ala Thr Leu Gly Ala Asp Gly Trp Asn Asn Leu Trp Ser Gly
180 185 190

Lys Leu Lys Phe Thr Asp Pro Lys Ala Val Ala Val Trp Glu Thr Phe
195 200 205

Gly Lys Val Leu Asp Ala Ala Asn Lys Asp Ala Ala Gly Leu Ser Trp
210 215 220

Gln Gln Ala Val Asp Arg Val Val Gln Gly Lys Ala Ala Phe Asn Ile
225 230 235 240

Met Gly Asp Trp Ala Ala Gly Tyr Met Ser Thr Thr Leu Lys Leu Lys
245 250 255

Pro Gly Thr Asp Phe Ala Trp Thr Pro Ser Pro Gly Thr Ser Gly Ile
260 265 270

```
Phe Met Met Leu Cys Asp Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300

Gln Asp Thr Phe Asn Pro Leu Lys Gly Ser Ile Ala Ala Arg Leu Asp
305                 310                 315                 320

Ser Asp Pro Ala Lys Tyr Asn Ala Tyr Gly Gln Ser Ala Met Lys Asp
                325                 330                 335

Trp Lys Ser Asn Arg Ile Val Gly Ser Leu Val His Gly Ala Val Ala
            340                 345                 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380

Asn Gln Val Gly Leu Gly Arg Gly Gly Ser His His His His His His
385                 390                 395                 400


<210> SEQ ID NO 32
<211> LENGTH: 400
<212> TYPE: PRT
<213> ORGANISM: Artificial Sequence
<220> FEATURE:
<223> OTHER INFORMATION: tsGBP2_C278 (278C substitution mutant with
      signal peptide replaced with M and a GGSHHHHHH at C-terminus)

<400> SEQUENCE: 32

Met Lys Leu Glu Ile Phe Ser Trp Trp Ala Gly Asp Glu Gly Pro Ala
1               5                   10                  15

Leu Glu Ala Leu Ile Arg Leu Tyr Lys Gln Lys Tyr Pro Gly Val Glu
            20                  25                  30

Val Ile Asn Ala Thr Val Thr Gly Gly Ala Gly Val Asn Ala Lys Ala
        35                  40                  45

Val Leu Lys Thr Arg Met Leu Gly Gly Asp Pro Pro Asp Thr Phe Gln
    50                  55                  60

Val His Ala Gly Gln Glu Leu Ile Gly Thr Trp Val Val Ala Asp Arg
65                  70                  75                  80

Met Glu Asp Leu Thr Ser Leu Phe Arg Gln Glu Gly Trp Leu Gln Ala
                85                  90                  95

Phe Pro Lys Gly Leu Ile Asp Leu Leu Ser Tyr Lys Gly Gly Ile Trp
            100                 105                 110

Ser Val Pro Val Asn Ile His Arg Ser Asn Val Met Trp Tyr Ile Pro
        115                 120                 125

Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
145                 150                 155                 160

Leu Ala Leu Gly Glu Asn Trp Thr Gln Gln His Leu Trp Glu Ser Val
                165                 170                 175

Ala Leu Ala Thr Leu Gly Ala Asp Gly Trp Asn Asn Leu Trp Ser Gly
            180                 185                 190

Lys Leu Lys Phe Thr Asp Pro Lys Ala Val Ala Val Trp Glu Thr Phe
        195                 200                 205

Gly Lys Val Leu Asp Ala Ala Asn Lys Asp Ala Ala Gly Leu Ser Trp
    210                 215                 220

Gln Gln Ala Val Asp Arg Val Val Gln Gly Lys Ala Ala Phe Asn Ile
225                 230                 235                 240
```

```
Met Gly Asp Trp Ala Ala Gly Tyr Met Ser Thr Thr Leu Lys Leu Lys
                245                 250                 255

Pro Gly Thr Asp Phe Ala Trp Thr Pro Ser Pro Gly Thr Ser Gly Ile
            260                 265                 270

Phe Met Met Leu Ser Cys Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300

Gln Asp Thr Phe Asn Pro Leu Lys Gly Ser Ile Ala Ala Arg Leu Asp
305                 310                 315                 320

Ser Asp Pro Ala Lys Tyr Asn Ala Tyr Gly Gln Ser Ala Met Lys Asp
                325                 330                 335

Trp Lys Ser Asn Arg Ile Val Gly Ser Leu Val His Gly Ala Val Ala
            340                 345                 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380

Asn Gln Val Gly Leu Gly Arg Gly Gly Ser His His His His His His
385                 390                 395                 400


<210> SEQ ID NO 33
<211> LENGTH: 400
<212> TYPE: PRT
<213> ORGANISM: Artificial Sequence
<220> FEATURE:
<223> OTHER INFORMATION: tsGBP2_C312 (312C substitution mutant with
      signal peptide replaced with M and a GGSHHHHHH at C-terminus)

<400> SEQUENCE: 33

Met Lys Leu Glu Ile Phe Ser Trp Trp Ala Gly Asp Glu Gly Pro Ala
1               5                   10                  15

Leu Glu Ala Leu Ile Arg Leu Tyr Lys Gln Lys Tyr Pro Gly Val Glu
            20                  25                  30

Val Ile Asn Ala Thr Val Thr Gly Gly Ala Gly Val Asn Ala Lys Ala
        35                  40                  45

Val Leu Lys Thr Arg Met Leu Gly Gly Asp Pro Pro Asp Thr Phe Gln
    50                  55                  60

Val His Ala Gly Gln Glu Leu Ile Gly Thr Trp Val Val Ala Asp Arg
65                  70                  75                  80

Met Glu Asp Leu Thr Ser Leu Phe Arg Gln Glu Gly Trp Leu Gln Ala
                85                  90                  95

Phe Pro Lys Gly Leu Ile Asp Leu Leu Ser Tyr Lys Gly Gly Ile Trp
            100                 105                 110

Ser Val Pro Val Asn Ile His Arg Ser Asn Val Met Trp Tyr Ile Pro
        115                 120                 125

Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
145                 150                 155                 160

Leu Ala Leu Gly Glu Asn Trp Thr Gln Gln His Leu Trp Glu Ser Val
                165                 170                 175

Ala Leu Ala Thr Leu Gly Ala Asp Gly Trp Asn Asn Leu Trp Ser Gly
            180                 185                 190

Lys Leu Lys Phe Thr Asp Pro Lys Ala Val Ala Val Trp Glu Thr Phe
```

```
        195                 200                 205

Gly Lys Val Leu Asp Ala Ala Asn Lys Asp Ala Ala Gly Leu Ser Trp
    210                 215                 220

Gln Gln Ala Val Asp Arg Val Val Gln Gly Lys Ala Ala Phe Asn Ile
225                 230                 235                 240

Met Gly Asp Trp Ala Ala Gly Tyr Met Ser Thr Thr Leu Lys Leu Lys
                245                 250                 255

Pro Gly Thr Asp Phe Ala Trp Thr Pro Ser Pro Gly Thr Ser Gly Ile
            260                 265                 270

Phe Met Met Leu Ser Asp Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300

Gln Asp Thr Phe Asn Pro Leu Cys Gly Ser Ile Ala Ala Arg Leu Asp
305                 310                 315                 320

Ser Asp Pro Ala Lys Tyr Asn Ala Tyr Gly Gln Ser Ala Met Lys Asp
                325                 330                 335

Trp Lys Ser Asn Arg Ile Val Gly Ser Leu Val His Gly Ala Val Ala
            340                 345                 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380

Asn Gln Val Gly Leu Gly Arg Gly Gly Ser His His His His His His
385                 390                 395                 400


<210> SEQ ID NO 34
<211> LENGTH: 400
<212> TYPE: PRT
<213> ORGANISM: Artificial Sequence
<220> FEATURE:
<223> OTHER INFORMATION: tsGBP2_C337 (337C substitution mutant with
      signal peptide replaced with M and a GGSHHHHHH at C-terminus)

<400> SEQUENCE: 34

Met Lys Leu Glu Ile Phe Ser Trp Trp Ala Gly Asp Glu Gly Pro Ala
1               5                   10                  15

Leu Glu Ala Leu Ile Arg Leu Tyr Lys Gln Lys Tyr Pro Gly Val Glu
            20                  25                  30

Val Ile Asn Ala Thr Val Thr Gly Gly Ala Gly Val Asn Ala Lys Ala
        35                  40                  45

Val Leu Lys Thr Arg Met Leu Gly Gly Asp Pro Pro Asp Thr Phe Gln
    50                  55                  60

Val His Ala Gly Gln Glu Leu Ile Gly Thr Trp Val Val Ala Asp Arg
65                  70                  75                  80

Met Glu Asp Leu Thr Ser Leu Phe Arg Gln Glu Gly Trp Leu Gln Ala
                85                  90                  95

Phe Pro Lys Gly Leu Ile Asp Leu Leu Ser Tyr Lys Gly Gly Ile Trp
            100                 105                 110

Ser Val Pro Val Asn Ile His Arg Ser Asn Val Met Trp Tyr Ile Pro
        115                 120                 125

Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
145                 150                 155                 160
```

Leu Ala Leu Gly Glu Asn Trp Thr Gln Gln His Leu Trp Glu Ser Val
165 170 175

Ala Leu Ala Thr Leu Gly Ala Asp Gly Trp Asn Asn Leu Trp Ser Gly
180 185 190

Lys Leu Lys Phe Thr Asp Pro Lys Ala Val Ala Val Trp Glu Thr Phe
195 200 205

Gly Lys Val Leu Asp Ala Ala Asn Lys Asp Ala Ala Gly Leu Ser Trp
210 215 220

Gln Gln Ala Val Asp Arg Val Val Gln Gly Lys Ala Ala Phe Asn Ile
225 230 235 240

Met Gly Asp Trp Ala Ala Gly Tyr Met Ser Thr Thr Leu Lys Leu Lys
245 250 255

Pro Gly Thr Asp Phe Ala Trp Thr Pro Ser Pro Gly Thr Ser Gly Ile
260 265 270

Phe Met Met Leu Ser Asp Ser Phe Gly Leu Pro Lys Gly Ala Lys Asn
275 280 285

Arg Gln Asn Ala Ile Asn Trp Leu Lys Leu Val Gly Ser Lys Glu Gly
290 295 300

Gln Asp Thr Phe Asn Pro Leu Lys Gly Ser Ile Ala Ala Arg Leu Asp
305 310 315 320

Ser Asp Pro Ala Lys Tyr Asn Ala Tyr Gly Gln Ser Ala Met Lys Asp
325 330 335

Cys Lys Ser Asn Arg Ile Val Gly Ser Leu Val His Gly Ala Val Ala
340 345 350

Pro Glu Ser Phe Met Ser Gln Phe Gly Thr Val Met Glu Ile Phe Leu
355 360 365

Gln Ser Arg Asn Pro Gln Ala Ala Ala Asn Ala Ala Gln Ala Ile Ala
370 375 380

Asn Gln Val Gly Leu Gly Arg Gly Gly Ser His His His His His His
385 390 395 400

<210> SEQ ID NO 35
<211> LENGTH: 400
<212> TYPE: PRT
<213> ORGANISM: Artificial Sequence
<220> FEATURE:
<223> OTHER INFORMATION: tsGBP2_C348 (348C substitution mutant with signal peptide replaced with M and a GGSHHHHHH at C-terminus)

<400> SEQUENCE: 35

Met Lys Leu Glu Ile Phe Ser Trp Trp Ala Gly Asp Glu Gly Pro Ala
1 5 10 15

Leu Glu Ala Leu Ile Arg Leu Tyr Lys Gln Lys Tyr Pro Gly Val Glu
20 25 30

Val Ile Asn Ala Thr Val Thr Gly Gly Ala Gly Val Asn Ala Lys Ala
35 40 45

Val Leu Lys Thr Arg Met Leu Gly Gly Asp Pro Pro Asp Thr Phe Gln
50 55 60

Val His Ala Gly Gln Glu Leu Ile Gly Thr Trp Val Val Ala Asp Arg
65 70 75 80

Met Glu Asp Leu Thr Ser Leu Phe Arg Gln Glu Gly Trp Leu Gln Ala
85 90 95

Phe Pro Lys Gly Leu Ile Asp Leu Leu Ser Tyr Lys Gly Gly Ile Trp
100 105 110

Ser Val Pro Val Asn Ile His Arg Ser Asn Val Met Trp Tyr Ile Pro
115 120 125

-continued

Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
145                 150                 155                 160

Leu Ala Leu Gly Glu Asn Trp Thr Gln Gln His Leu Trp Glu Ser Val
                165                 170                 175

Ala Leu Ala Thr Leu Gly Ala Asp Gly Trp Asn Asn Leu Trp Ser Gly
            180                 185                 190

Lys Leu Lys Phe Thr Asp Pro Lys Ala Val Ala Val Trp Glu Thr Phe
        195                 200                 205

Gly Lys Val Leu Asp Ala Ala Asn Lys Asp Ala Ala Gly Leu Ser Trp
    210                 215                 220

Gln Gln Ala Val Asp Arg Val Val Gln Gly Lys Ala Ala Phe Asn Ile
225                 230                 235                 240

Met Gly Asp Trp Ala Ala Gly Tyr Met Ser Thr Thr Leu Lys Leu Lys
                245                 250                 255

Pro Gly Thr Asp Phe Ala Trp Thr Pro Ser Pro Gly Thr Ser Gly Ile
            260                 265                 270

Phe Met Met Leu Ser Asp Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300

Gln Asp Thr Phe Asn Pro Leu Lys Gly Ser Ile Ala Ala Arg Leu Asp
305                 310                 315                 320

Ser Asp Pro Ala Lys Tyr Asn Ala Tyr Gly Gln Ser Ala Met Lys Asp
                325                 330                 335

Trp Lys Ser Asn Arg Ile Val Gly Ser Leu Val Cys Gly Ala Val Ala
            340                 345                 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380

Asn Gln Val Gly Leu Gly Arg Gly Gly Ser His His His His His His
385                 390                 395                 400

<210> SEQ ID NO 36
<211> LENGTH: 400
<212> TYPE: PRT
<213> ORGANISM: Artificial Sequence
<220> FEATURE:
<223> OTHER INFORMATION: tsGBP2_C357 (357C substitution mutant with
      signal peptide replaced with M and a GGSHHHHHH at C-terminus)

<400> SEQUENCE: 36

Met Lys Leu Glu Ile Phe Ser Trp Trp Ala Gly Asp Glu Gly Pro Ala
1               5                   10                  15

Leu Glu Ala Leu Ile Arg Leu Tyr Lys Gln Lys Tyr Pro Gly Val Glu
            20                  25                  30

Val Ile Asn Ala Thr Val Thr Gly Gly Ala Gly Val Asn Ala Lys Ala
        35                  40                  45

Val Leu Lys Thr Arg Met Leu Gly Gly Asp Pro Pro Asp Thr Phe Gln
    50                  55                  60

Val His Ala Gly Gln Glu Leu Ile Gly Thr Trp Val Val Ala Asp Arg
65                  70                  75                  80

Met Glu Asp Leu Thr Ser Leu Phe Arg Gln Glu Gly Trp Leu Gln Ala

```
                85                  90                  95

Phe Pro Lys Gly Leu Ile Asp Leu Leu Ser Tyr Lys Gly Gly Ile Trp
            100                 105                 110

Ser Val Pro Val Asn Ile His Arg Ser Asn Val Met Trp Tyr Ile Pro
        115                 120                 125

Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
145                 150                 155                 160

Leu Ala Leu Gly Glu Asn Trp Thr Gln Gln His Leu Trp Glu Ser Val
                165                 170                 175

Ala Leu Ala Thr Leu Gly Ala Asp Gly Trp Asn Asn Leu Trp Ser Gly
            180                 185                 190

Lys Leu Lys Phe Thr Asp Pro Lys Ala Val Ala Val Trp Glu Thr Phe
        195                 200                 205

Gly Lys Val Leu Asp Ala Ala Asn Lys Asp Ala Ala Gly Leu Ser Trp
    210                 215                 220

Gln Gln Ala Val Asp Arg Val Val Gln Gly Lys Ala Ala Phe Asn Ile
225                 230                 235                 240

Met Gly Asp Trp Ala Ala Gly Tyr Met Ser Thr Thr Leu Lys Leu Lys
                245                 250                 255

Pro Gly Thr Asp Phe Ala Trp Thr Pro Ser Pro Gly Thr Ser Gly Ile
            260                 265                 270

Phe Met Met Leu Ser Asp Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300

Gln Asp Thr Phe Asn Pro Leu Lys Gly Ser Ile Ala Ala Arg Leu Asp
305                 310                 315                 320

Ser Asp Pro Ala Lys Tyr Asn Ala Tyr Gly Gln Ser Ala Met Lys Asp
                325                 330                 335

Trp Lys Ser Asn Arg Ile Val Gly Ser Leu Val His Gly Ala Val Ala
            340                 345                 350

Pro Glu Ser Phe Cys Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380

Asn Gln Val Gly Leu Gly Arg Gly Gly Ser His His His His His His
385                 390                 395                 400


<210> SEQ ID NO 37
<211> LENGTH: 400
<212> TYPE: PRT
<213> ORGANISM: Artificial Sequence
<220> FEATURE:
<223> OTHER INFORMATION: tsGBP2.13C.W8F (13C, 8F double substitution
      mutant)

<400> SEQUENCE: 37

Met Lys Leu Glu Ile Phe Ser Phe Trp Ala Gly Asp Cys Gly Pro Ala
1               5                   10                  15

Leu Glu Ala Leu Ile Arg Leu Tyr Lys Gln Lys Tyr Pro Gly Val Glu
            20                  25                  30

Val Ile Asn Ala Thr Val Thr Gly Gly Ala Gly Val Asn Ala Lys Ala
        35                  40                  45
```

```
Val Leu Lys Thr Arg Met Leu Gly Gly Asp Pro Pro Asp Thr Phe Gln
    50                  55                  60

Val His Ala Gly Gln Glu Leu Ile Gly Thr Trp Val Val Ala Asp Arg
65                  70                  75                  80

Met Glu Asp Leu Thr Ser Leu Phe Arg Gln Glu Gly Trp Leu Gln Ala
                85                  90                  95

Phe Pro Lys Gly Leu Ile Asp Leu Leu Ser Tyr Lys Gly Gly Ile Trp
            100                 105                 110

Ser Val Pro Val Asn Ile His Arg Ser Asn Val Met Trp Tyr Ile Pro
        115                 120                 125

Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
145                 150                 155                 160

Leu Ala Leu Gly Glu Asn Trp Thr Gln Gln His Leu Trp Glu Ser Val
                165                 170                 175

Ala Leu Ala Thr Leu Gly Ala Asp Gly Trp Asn Asn Leu Trp Ser Gly
            180                 185                 190

Lys Leu Lys Phe Thr Asp Pro Lys Ala Val Ala Val Trp Glu Thr Phe
        195                 200                 205

Gly Lys Val Leu Asp Ala Ala Asn Lys Asp Ala Ala Gly Leu Ser Trp
    210                 215                 220

Gln Gln Ala Val Asp Arg Val Val Gln Gly Lys Ala Ala Phe Asn Ile
225                 230                 235                 240

Met Gly Asp Trp Ala Ala Gly Tyr Met Ser Thr Thr Leu Lys Leu Lys
                245                 250                 255

Pro Gly Thr Asp Phe Ala Trp Thr Pro Ser Pro Gly Thr Ser Gly Ile
            260                 265                 270

Phe Met Met Leu Ser Asp Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300

Gln Asp Thr Phe Asn Pro Leu Lys Gly Ser Ile Ala Ala Arg Leu Asp
305                 310                 315                 320

Ser Asp Pro Ala Lys Tyr Asn Ala Tyr Gly Gln Ser Ala Met Lys Asp
                325                 330                 335

Trp Lys Ser Asn Arg Ile Val Gly Ser Leu Val His Gly Ala Val Ala
            340                 345                 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380

Asn Gln Val Gly Leu Gly Arg Gly Gly Ser His His His His His His
385                 390                 395                 400


<210> SEQ ID NO 38
<211> LENGTH: 400
<212> TYPE: PRT
<213> ORGANISM: Artificial Sequence
<220> FEATURE:
<223> OTHER INFORMATION: tsGBP2.13C.W8M (13C, 8M double substitution
      mutant with signal peptide replaced with M and a GGSHHHHHH at
      C-terminus)

<400> SEQUENCE: 38

Met Lys Leu Glu Ile Phe Ser Met Trp Ala Gly Asp Cys Gly Pro Ala
```

-continued

```
1               5                   10                  15

Leu Glu Ala Leu Ile Arg Leu Tyr Lys Gln Lys Tyr Pro Gly Val Glu
            20                  25                  30

Val Ile Asn Ala Thr Val Thr Gly Gly Ala Gly Val Asn Ala Lys Ala
        35                  40                  45

Val Leu Lys Thr Arg Met Leu Gly Gly Asp Pro Pro Asp Thr Phe Gln
    50                  55                  60

Val His Ala Gly Gln Glu Leu Ile Gly Thr Trp Val Val Ala Asp Arg
65                  70                  75                  80

Met Glu Asp Leu Thr Ser Leu Phe Arg Gln Glu Gly Trp Leu Gln Ala
                85                  90                  95

Phe Pro Lys Gly Leu Ile Asp Leu Leu Ser Tyr Lys Gly Gly Ile Trp
            100                 105                 110

Ser Val Pro Val Asn Ile His Arg Ser Asn Val Met Trp Tyr Ile Pro
        115                 120                 125

Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
145                 150                 155                 160

Leu Ala Leu Gly Glu Asn Trp Thr Gln Gln His Leu Trp Glu Ser Val
                165                 170                 175

Ala Leu Ala Thr Leu Gly Ala Asp Gly Trp Asn Asn Leu Trp Ser Gly
            180                 185                 190

Lys Leu Lys Phe Thr Asp Pro Lys Ala Val Ala Val Trp Glu Thr Phe
        195                 200                 205

Gly Lys Val Leu Asp Ala Ala Asn Lys Asp Ala Ala Gly Leu Ser Trp
    210                 215                 220

Gln Gln Ala Val Asp Arg Val Val Gln Gly Lys Ala Ala Phe Asn Ile
225                 230                 235                 240

Met Gly Asp Trp Ala Ala Gly Tyr Met Ser Thr Thr Leu Lys Leu Lys
                245                 250                 255

Pro Gly Thr Asp Phe Ala Trp Thr Pro Ser Pro Gly Thr Ser Gly Ile
            260                 265                 270

Phe Met Met Leu Ser Asp Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300

Gln Asp Thr Phe Asn Pro Leu Lys Gly Ser Ile Ala Ala Arg Leu Asp
305                 310                 315                 320

Ser Asp Pro Ala Lys Tyr Asn Ala Tyr Gly Gln Ser Ala Met Lys Asp
                325                 330                 335

Trp Lys Ser Asn Arg Ile Val Gly Ser Leu Val His Gly Ala Val Ala
            340                 345                 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380

Asn Gln Val Gly Leu Gly Arg Gly Gly Ser His His His His His His
385                 390                 395                 400
```

<210> SEQ ID NO 39
<211> LENGTH: 400
<212> TYPE: PRT
<213> ORGANISM: Artificial Sequence -continued
<220> FEATURE:
<223> OTHER INFORMATION: tsGBP2.13C.W8Y (13C, 8Y double substitution
      mutant with signal peptide replaced with M and a GGSHHHHHH at
      C-terminus)

<400> SEQUENCE: 39

```
Met Lys Leu Glu Ile Phe Ser Tyr Trp Ala Gly Asp Cys Gly Pro Ala
1               5                   10                  15

Leu Glu Ala Leu Ile Arg Leu Tyr Lys Gln Lys Tyr Pro Gly Val Glu
            20                  25                  30

Val Ile Asn Ala Thr Val Thr Gly Gly Ala Gly Val Asn Ala Lys Ala
        35                  40                  45

Val Leu Lys Thr Arg Met Leu Gly Gly Asp Pro Pro Asp Thr Phe Gln
    50                  55                  60

Val His Ala Gly Gln Glu Leu Ile Gly Thr Trp Val Val Ala Asp Arg
65                  70                  75                  80

Met Glu Asp Leu Thr Ser Leu Phe Arg Gln Glu Gly Trp Leu Gln Ala
                85                  90                  95

Phe Pro Lys Gly Leu Ile Asp Leu Leu Ser Tyr Lys Gly Gly Ile Trp
            100                 105                 110

Ser Val Pro Val Asn Ile His Arg Ser Asn Val Met Trp Tyr Ile Pro
        115                 120                 125

Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
145                 150                 155                 160

Leu Ala Leu Gly Glu Asn Trp Thr Gln Gln His Leu Trp Glu Ser Val
                165                 170                 175

Ala Leu Ala Thr Leu Gly Ala Asp Gly Trp Asn Asn Leu Trp Ser Gly
            180                 185                 190

Lys Leu Lys Phe Thr Asp Pro Lys Ala Val Ala Val Trp Glu Thr Phe
        195                 200                 205

Gly Lys Val Leu Asp Ala Ala Asn Lys Asp Ala Ala Gly Leu Ser Trp
    210                 215                 220

Gln Gln Ala Val Asp Arg Val Val Gln Gly Lys Ala Ala Phe Asn Ile
225                 230                 235                 240

Met Gly Asp Trp Ala Ala Gly Tyr Met Ser Thr Thr Leu Lys Leu Lys
                245                 250                 255

Pro Gly Thr Asp Phe Ala Trp Thr Pro Ser Pro Gly Thr Ser Gly Ile
            260                 265                 270

Phe Met Met Leu Ser Asp Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300

Gln Asp Thr Phe Asn Pro Leu Lys Gly Ser Ile Ala Ala Arg Leu Asp
305                 310                 315                 320

Ser Asp Pro Ala Lys Tyr Asn Ala Tyr Gly Gln Ser Ala Met Lys Asp
                325                 330                 335

Trp Lys Ser Asn Arg Ile Val Gly Ser Leu Val His Gly Ala Val Ala
            340                 345                 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380
```

```
Asn Gln Val Gly Leu Gly Arg Gly Gly Ser His His His His His His
385                 390                 395                 400


<210> SEQ ID NO 40
<211> LENGTH: 400
<212> TYPE: PRT
<213> ORGANISM: Artificial Sequence
<220> FEATURE:
<223> OTHER INFORMATION: tsGBP2.13C.W9F (13C 9F double substitution
      mutant with signal peptide replaced with M and a GGSHHHHHH at
      C-terminus)

<400> SEQUENCE: 40

Met Lys Leu Glu Ile Phe Ser Trp Phe Ala Gly Asp Cys Gly Pro Ala
1               5                   10                  15

Leu Glu Ala Leu Ile Arg Leu Tyr Lys Gln Lys Tyr Pro Gly Val Glu
            20                  25                  30

Val Ile Asn Ala Thr Val Thr Gly Gly Ala Gly Val Asn Ala Lys Ala
        35                  40                  45

Val Leu Lys Thr Arg Met Leu Gly Gly Asp Pro Pro Asp Thr Phe Gln
    50                  55                  60

Val His Ala Gly Gln Glu Leu Ile Gly Thr Trp Val Val Ala Asp Arg
65                  70                  75                  80

Met Glu Asp Leu Thr Ser Leu Phe Arg Gln Glu Gly Trp Leu Gln Ala
                85                  90                  95

Phe Pro Lys Gly Leu Ile Asp Leu Leu Ser Tyr Lys Gly Gly Ile Trp
            100                 105                 110

Ser Val Pro Val Asn Ile His Arg Ser Asn Val Met Trp Tyr Ile Pro
        115                 120                 125

Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
145                 150                 155                 160

Leu Ala Leu Gly Glu Asn Trp Thr Gln Gln His Leu Trp Glu Ser Val
                165                 170                 175

Ala Leu Ala Thr Leu Gly Ala Asp Gly Trp Asn Asn Leu Trp Ser Gly
            180                 185                 190

Lys Leu Lys Phe Thr Asp Pro Lys Ala Val Ala Val Trp Glu Thr Phe
        195                 200                 205

Gly Lys Val Leu Asp Ala Ala Asn Lys Asp Ala Ala Gly Leu Ser Trp
    210                 215                 220

Gln Gln Ala Val Asp Arg Val Val Gln Gly Lys Ala Ala Phe Asn Ile
225                 230                 235                 240

Met Gly Asp Trp Ala Ala Gly Tyr Met Ser Thr Thr Leu Lys Leu Lys
                245                 250                 255

Pro Gly Thr Asp Phe Ala Trp Thr Pro Ser Pro Gly Thr Ser Gly Ile
            260                 265                 270

Phe Met Met Leu Ser Asp Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300

Gln Asp Thr Phe Asn Pro Leu Lys Gly Ser Ile Ala Ala Arg Leu Asp
305                 310                 315                 320

Ser Asp Pro Ala Lys Tyr Asn Ala Tyr Gly Gln Ser Ala Met Lys Asp
                325                 330                 335

Trp Lys Ser Asn Arg Ile Val Gly Ser Leu Val His Gly Ala Val Ala
```

```
            340                 345                 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380

Asn Gln Val Gly Leu Gly Arg Gly Gly Ser His His His His His His
385                 390                 395                 400


<210> SEQ ID NO 41
<211> LENGTH: 400
<212> TYPE: PRT
<213> ORGANISM: Artificial Sequence
<220> FEATURE:
<223> OTHER INFORMATION: tsGBP2.13C.W9M (13C 9M double substitution
      mutant with signal peptide replaced with M and a GGSHHHHHH at
      C-terminus)

<400> SEQUENCE: 41

Met Lys Leu Glu Ile Phe Ser Trp Met Ala Gly Asp Cys Gly Pro Ala
1               5                   10                  15

Leu Glu Ala Leu Ile Arg Leu Tyr Lys Gln Lys Tyr Pro Gly Val Glu
            20                  25                  30

Val Ile Asn Ala Thr Val Thr Gly Gly Ala Gly Val Asn Ala Lys Ala
        35                  40                  45

Val Leu Lys Thr Arg Met Leu Gly Gly Asp Pro Pro Asp Thr Phe Gln
    50                  55                  60

Val His Ala Gly Gln Glu Leu Ile Gly Thr Trp Val Val Ala Asp Arg
65                  70                  75                  80

Met Glu Asp Leu Thr Ser Leu Phe Arg Gln Glu Gly Trp Leu Gln Ala
                85                  90                  95

Phe Pro Lys Gly Leu Ile Asp Leu Leu Ser Tyr Lys Gly Gly Ile Trp
            100                 105                 110

Ser Val Pro Val Asn Ile His Arg Ser Asn Val Met Trp Tyr Ile Pro
        115                 120                 125

Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
145                 150                 155                 160

Leu Ala Leu Gly Glu Asn Trp Thr Gln Gln His Leu Trp Glu Ser Val
                165                 170                 175

Ala Leu Ala Thr Leu Gly Ala Asp Gly Trp Asn Asn Leu Trp Ser Gly
            180                 185                 190

Lys Leu Lys Phe Thr Asp Pro Lys Ala Val Ala Val Trp Glu Thr Phe
        195                 200                 205

Gly Lys Val Leu Asp Ala Ala Asn Lys Asp Ala Ala Gly Leu Ser Trp
    210                 215                 220

Gln Gln Ala Val Asp Arg Val Val Gln Gly Lys Ala Ala Phe Asn Ile
225                 230                 235                 240

Met Gly Asp Trp Ala Ala Gly Tyr Met Ser Thr Thr Leu Lys Leu Lys
                245                 250                 255

Pro Gly Thr Asp Phe Ala Trp Thr Pro Ser Pro Gly Thr Ser Gly Ile
            260                 265                 270

Phe Met Met Leu Ser Asp Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300
```

```
Gln Asp Thr Phe Asn Pro Leu Lys Gly Ser Ile Ala Ala Arg Leu Asp
305                 310                 315                 320

Ser Asp Pro Ala Lys Tyr Asn Ala Tyr Gly Gln Ser Ala Met Lys Asp
                325                 330                 335

Trp Lys Ser Asn Arg Ile Val Gly Ser Leu Val His Gly Ala Val Ala
            340                 345                 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380

Asn Gln Val Gly Leu Gly Arg Gly Gly Ser His His His His His His
385                 390                 395                 400


<210> SEQ ID NO 42
<211> LENGTH: 400
<212> TYPE: PRT
<213> ORGANISM: Artificial Sequence
<220> FEATURE:
<223> OTHER INFORMATION: tsGBP2.13C.W9Y (13C, 9Y double substitution
      mutant with signal peptide replaced with M and a GGSHHHHHH at
      C-terminus)

<400> SEQUENCE: 42

Met Lys Leu Glu Ile Phe Ser Trp Tyr Ala Gly Asp Cys Gly Pro Ala
1               5                   10                  15

Leu Glu Ala Leu Ile Arg Leu Tyr Lys Gln Lys Tyr Pro Gly Val Glu
            20                  25                  30

Val Ile Asn Ala Thr Val Thr Gly Gly Ala Gly Val Asn Ala Lys Ala
        35                  40                  45

Val Leu Lys Thr Arg Met Leu Gly Gly Asp Pro Pro Asp Thr Phe Gln
    50                  55                  60

Val His Ala Gly Gln Glu Leu Ile Gly Thr Trp Val Val Ala Asp Arg
65                  70                  75                  80

Met Glu Asp Leu Thr Ser Leu Phe Arg Gln Glu Gly Trp Leu Gln Ala
                85                  90                  95

Phe Pro Lys Gly Leu Ile Asp Leu Leu Ser Tyr Lys Gly Gly Ile Trp
            100                 105                 110

Ser Val Pro Val Asn Ile His Arg Ser Asn Val Met Trp Tyr Ile Pro
        115                 120                 125

Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
145                 150                 155                 160

Leu Ala Leu Gly Glu Asn Trp Thr Gln Gln His Leu Trp Glu Ser Val
                165                 170                 175

Ala Leu Ala Thr Leu Gly Ala Asp Gly Trp Asn Asn Leu Trp Ser Gly
            180                 185                 190

Lys Leu Lys Phe Thr Asp Pro Lys Ala Val Ala Val Trp Glu Thr Phe
        195                 200                 205

Gly Lys Val Leu Asp Ala Ala Asn Lys Asp Ala Ala Gly Leu Ser Trp
    210                 215                 220

Gln Gln Ala Val Asp Arg Val Val Gln Gly Lys Ala Ala Phe Asn Ile
225                 230                 235                 240

Met Gly Asp Trp Ala Ala Gly Tyr Met Ser Thr Thr Leu Lys Leu Lys
                245                 250                 255
```

```
Pro Gly Thr Asp Phe Ala Trp Thr Pro Ser Pro Gly Thr Ser Gly Ile
            260                 265                 270

Phe Met Met Leu Ser Asp Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300

Gln Asp Thr Phe Asn Pro Leu Lys Gly Ser Ile Ala Ala Arg Leu Asp
305                 310                 315                 320

Ser Asp Pro Ala Lys Tyr Asn Ala Tyr Gly Gln Ser Ala Met Lys Asp
                325                 330                 335

Trp Lys Ser Asn Arg Ile Val Gly Ser Leu Val His Gly Ala Val Ala
            340                 345                 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380

Asn Gln Val Gly Leu Gly Arg Gly Gly Ser His His His His His His
385                 390                 395                 400


<210> SEQ ID NO 43
<211> LENGTH: 400
<212> TYPE: PRT
<213> ORGANISM: Artificial Sequence
<220> FEATURE:
<223> OTHER INFORMATION: tsGBP2.13C.Q64N (13C, 64N double substitution
      mutant with signal peptide replaced with M and a GGSHHHHHH at
      C-terminus)

<400> SEQUENCE: 43

Met Lys Leu Glu Ile Phe Ser Trp Trp Ala Gly Asp Cys Gly Pro Ala
1               5                   10                  15

Leu Glu Ala Leu Ile Arg Leu Tyr Lys Gln Lys Tyr Pro Gly Val Glu
            20                  25                  30

Val Ile Asn Ala Thr Val Thr Gly Gly Ala Gly Val Asn Ala Lys Ala
        35                  40                  45

Val Leu Lys Thr Arg Met Leu Gly Gly Asp Pro Pro Asp Thr Phe Asn
    50                  55                  60

Val His Ala Gly Gln Glu Leu Ile Gly Thr Trp Val Val Ala Asp Arg
65                  70                  75                  80

Met Glu Asp Leu Thr Ser Leu Phe Arg Gln Glu Gly Trp Leu Gln Ala
                85                  90                  95

Phe Pro Lys Gly Leu Ile Asp Leu Leu Ser Tyr Lys Gly Gly Ile Trp
            100                 105                 110

Ser Val Pro Val Asn Ile His Arg Ser Asn Val Met Trp Tyr Ile Pro
        115                 120                 125

Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
145                 150                 155                 160

Leu Ala Leu Gly Glu Asn Trp Thr Gln Gln His Leu Trp Glu Ser Val
                165                 170                 175

Ala Leu Ala Thr Leu Gly Ala Asp Gly Trp Asn Asn Leu Trp Ser Gly
            180                 185                 190

Lys Leu Lys Phe Thr Asp Pro Lys Ala Val Ala Val Trp Glu Thr Phe
        195                 200                 205

Gly Lys Val Leu Asp Ala Ala Asn Lys Asp Ala Ala Gly Leu Ser Trp
```

```
    210                 215                 220

Gln Gln Ala Val Asp Arg Val Val Gln Gly Lys Ala Ala Phe Asn Ile
225                 230                 235                 240

Met Gly Asp Trp Ala Ala Gly Tyr Met Ser Thr Thr Leu Lys Leu Lys
                245                 250                 255

Pro Gly Thr Asp Phe Ala Trp Thr Pro Ser Pro Gly Thr Ser Gly Ile
            260                 265                 270

Phe Met Met Leu Ser Asp Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300

Gln Asp Thr Phe Asn Pro Leu Lys Gly Ser Ile Ala Ala Arg Leu Asp
305                 310                 315                 320

Ser Asp Pro Ala Lys Tyr Asn Ala Tyr Gly Gln Ser Ala Met Lys Asp
                325                 330                 335

Trp Lys Ser Asn Arg Ile Val Gly Ser Leu Val His Gly Ala Val Ala
            340                 345                 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380

Asn Gln Val Gly Leu Gly Arg Gly Gly Ser His His His His His His
385                 390                 395                 400


<210> SEQ ID NO 44
<211> LENGTH: 400
<212> TYPE: PRT
<213> ORGANISM: Artificial Sequence
<220> FEATURE:
<223> OTHER INFORMATION: tsGBP2.13C.Q64E (13C, 64E double substitution
      mutant with signal peptide replaced with M and a GGSHHHHHH at
      C-terminus)

<400> SEQUENCE: 44

Met Lys Leu Glu Ile Phe Ser Trp Trp Ala Gly Asp Cys Gly Pro Ala
1               5                   10                  15

Leu Glu Ala Leu Ile Arg Leu Tyr Lys Gln Lys Tyr Pro Gly Val Glu
            20                  25                  30

Val Ile Asn Ala Thr Val Thr Gly Gly Ala Gly Val Asn Ala Lys Ala
        35                  40                  45

Val Leu Lys Thr Arg Met Leu Gly Gly Asp Pro Pro Asp Thr Phe Glu
    50                  55                  60

Val His Ala Gly Gln Glu Leu Ile Gly Thr Trp Val Val Ala Asp Arg
65                  70                  75                  80

Met Glu Asp Leu Thr Ser Leu Phe Arg Gln Glu Gly Trp Leu Gln Ala
                85                  90                  95

Phe Pro Lys Gly Leu Ile Asp Leu Leu Ser Tyr Lys Gly Gly Ile Trp
            100                 105                 110

Ser Val Pro Val Asn Ile His Arg Ser Asn Val Met Trp Tyr Ile Pro
        115                 120                 125

Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
145                 150                 155                 160

Leu Ala Leu Gly Glu Asn Trp Thr Gln Gln His Leu Trp Glu Ser Val
                165                 170                 175
```

Ala Leu Ala Thr Leu Gly Ala Asp Gly Trp Asn Asn Leu Trp Ser Gly
180 185 190

Lys Leu Lys Phe Thr Asp Pro Lys Ala Val Ala Val Trp Glu Thr Phe
195 200 205

Gly Lys Val Leu Asp Ala Ala Asn Lys Asp Ala Ala Gly Leu Ser Trp
210 215 220

Gln Gln Ala Val Asp Arg Val Val Gln Gly Lys Ala Ala Phe Asn Ile
225 230 235 240

Met Gly Asp Trp Ala Ala Gly Tyr Met Ser Thr Thr Leu Lys Leu Lys
245 250 255

Pro Gly Thr Asp Phe Ala Trp Thr Pro Ser Pro Gly Thr Ser Gly Ile
260 265 270

Phe Met Met Leu Ser Asp Ser Phe Gly Leu Pro Lys Gly Ala Lys Asn
275 280 285

Arg Gln Asn Ala Ile Asn Trp Leu Lys Leu Val Gly Ser Lys Glu Gly
290 295 300

Gln Asp Thr Phe Asn Pro Leu Lys Gly Ser Ile Ala Ala Arg Leu Asp
305 310 315 320

Ser Asp Pro Ala Lys Tyr Asn Ala Tyr Gly Gln Ser Ala Met Lys Asp
325 330 335

Trp Lys Ser Asn Arg Ile Val Gly Ser Leu Val His Gly Ala Val Ala
340 345 350

Pro Glu Ser Phe Met Ser Gln Phe Gly Thr Val Met Glu Ile Phe Leu
355 360 365

Gln Ser Arg Asn Pro Gln Ala Ala Ala Asn Ala Ala Gln Ala Ile Ala
370 375 380

Asn Gln Val Gly Leu Gly Arg Gly Gly Ser His His His His His His
385 390 395 400

<210> SEQ ID NO 45
<211> LENGTH: 400
<212> TYPE: PRT
<213> ORGANISM: Artificial Sequence
<220> FEATURE:
<223> OTHER INFORMATION: tsGBP2.13C.Q64M (13C, 64M double substitution mutant with signal peptide replaced with M and a GGSHHHHHH at C-terminus)

<400> SEQUENCE: 45

Met Lys Leu Glu Ile Phe Ser Trp Trp Ala Gly Asp Cys Gly Pro Ala
1 5 10 15

Leu Glu Ala Leu Ile Arg Leu Tyr Lys Gln Lys Tyr Pro Gly Val Glu
20 25 30

Val Ile Asn Ala Thr Val Thr Gly Gly Ala Gly Val Asn Ala Lys Ala
35 40 45

Val Leu Lys Thr Arg Met Leu Gly Gly Asp Pro Pro Asp Thr Phe Met
50 55 60

Val His Ala Gly Gln Glu Leu Ile Gly Thr Trp Val Val Ala Asp Arg
65 70 75 80

Met Glu Asp Leu Thr Ser Leu Phe Arg Gln Glu Gly Trp Leu Gln Ala
85 90 95

Phe Pro Lys Gly Leu Ile Asp Leu Leu Ser Tyr Lys Gly Gly Ile Trp
100 105 110

Ser Val Pro Val Asn Ile His Arg Ser Asn Val Met Trp Tyr Ile Pro
115 120 125

-continued

```
Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
145                 150                 155                 160

Leu Ala Leu Gly Glu Asn Trp Thr Gln Gln His Leu Trp Glu Ser Val
                165                 170                 175

Ala Leu Ala Thr Leu Gly Ala Asp Gly Trp Asn Asn Leu Trp Ser Gly
            180                 185                 190

Lys Leu Lys Phe Thr Asp Pro Lys Ala Val Ala Val Trp Glu Thr Phe
        195                 200                 205

Gly Lys Val Leu Asp Ala Ala Asn Lys Asp Ala Ala Gly Leu Ser Trp
    210                 215                 220

Gln Gln Ala Val Asp Arg Val Val Gln Gly Lys Ala Ala Phe Asn Ile
225                 230                 235                 240

Met Gly Asp Trp Ala Ala Gly Tyr Met Ser Thr Thr Leu Lys Leu Lys
                245                 250                 255

Pro Gly Thr Asp Phe Ala Trp Thr Pro Ser Pro Gly Thr Ser Gly Ile
            260                 265                 270

Phe Met Met Leu Ser Asp Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300

Gln Asp Thr Phe Asn Pro Leu Lys Gly Ser Ile Ala Ala Arg Leu Asp
305                 310                 315                 320

Ser Asp Pro Ala Lys Tyr Asn Ala Tyr Gly Gln Ser Ala Met Lys Asp
                325                 330                 335

Trp Lys Ser Asn Arg Ile Val Gly Ser Leu Val His Gly Ala Val Ala
            340                 345                 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380

Asn Gln Val Gly Leu Gly Arg Gly Gly Ser His His His His His His
385                 390                 395                 400


<210> SEQ ID NO 46
<211> LENGTH: 400
<212> TYPE: PRT
<213> ORGANISM: Artificial Sequence
<220> FEATURE:
<223> OTHER INFORMATION: tsGBP2.13C.H66Q (13C, 66Q double substitution
      mutant with signal peptide replaced with M and a GGSHHHHHH at
      C-terminus)

<400> SEQUENCE: 46

Met Lys Leu Glu Ile Phe Ser Trp Trp Ala Gly Asp Cys Gly Pro Ala
1               5                   10                  15

Leu Glu Ala Leu Ile Arg Leu Tyr Lys Gln Lys Tyr Pro Gly Val Glu
            20                  25                  30

Val Ile Asn Ala Thr Val Thr Gly Gly Ala Gly Val Asn Ala Lys Ala
        35                  40                  45

Val Leu Lys Thr Arg Met Leu Gly Gly Asp Pro Pro Asp Thr Phe Gln
    50                  55                  60

Val Gln Ala Gly Gln Glu Leu Ile Gly Thr Trp Val Val Ala Asp Arg
65                  70                  75                  80

Met Glu Asp Leu Thr Ser Leu Phe Arg Gln Glu Gly Trp Leu Gln Ala
```

-continued

```
                85                  90                  95

Phe Pro Lys Gly Leu Ile Asp Leu Leu Ser Tyr Lys Gly Gly Ile Trp
            100                 105                 110

Ser Val Pro Val Asn Ile His Arg Ser Asn Val Met Trp Tyr Ile Pro
        115                 120                 125

Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
145                 150                 155                 160

Leu Ala Leu Gly Glu Asn Trp Thr Gln Gln His Leu Trp Glu Ser Val
                165                 170                 175

Ala Leu Ala Thr Leu Gly Ala Asp Gly Trp Asn Asn Leu Trp Ser Gly
            180                 185                 190

Lys Leu Lys Phe Thr Asp Pro Lys Ala Val Ala Val Trp Glu Thr Phe
        195                 200                 205

Gly Lys Val Leu Asp Ala Ala Asn Lys Asp Ala Ala Gly Leu Ser Trp
    210                 215                 220

Gln Gln Ala Val Asp Arg Val Val Gln Gly Lys Ala Ala Phe Asn Ile
225                 230                 235                 240

Met Gly Asp Trp Ala Ala Gly Tyr Met Ser Thr Thr Leu Lys Leu Lys
                245                 250                 255

Pro Gly Thr Asp Phe Ala Trp Thr Pro Ser Pro Gly Thr Ser Gly Ile
            260                 265                 270

Phe Met Met Leu Ser Asp Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300

Gln Asp Thr Phe Asn Pro Leu Lys Gly Ser Ile Ala Ala Arg Leu Asp
305                 310                 315                 320

Ser Asp Pro Ala Lys Tyr Asn Ala Tyr Gly Gln Ser Ala Met Lys Asp
                325                 330                 335

Trp Lys Ser Asn Arg Ile Val Gly Ser Leu Val His Gly Ala Val Ala
            340                 345                 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380

Asn Gln Val Gly Leu Gly Arg Gly Gly Ser His His His His His His
385                 390                 395                 400


<210> SEQ ID NO 47
<211> LENGTH: 400
<212> TYPE: PRT
<213> ORGANISM: Artificial Sequence
<220> FEATURE:
<223> OTHER INFORMATION: tsGBP2.13C.W244M (13C, 244M double substitution
      mutant with signal peptide replaced with M and a GGSHHHHHH at
      C-terminus)

<400> SEQUENCE: 47

Met Lys Leu Glu Ile Phe Ser Trp Trp Ala Gly Asp Cys Gly Pro Ala
1               5                   10                  15

Leu Glu Ala Leu Ile Arg Leu Tyr Lys Gln Lys Tyr Pro Gly Val Glu
            20                  25                  30

Val Ile Asn Ala Thr Val Thr Gly Gly Ala Gly Val Asn Ala Lys Ala
        35                  40                  45
```

```
Val Leu Lys Thr Arg Met Leu Gly Gly Asp Pro Pro Asp Thr Phe Gln
    50                  55                  60

Val His Ala Gly Gln Glu Leu Ile Gly Thr Trp Val Val Ala Asp Arg
65                  70                  75                  80

Met Glu Asp Leu Thr Ser Leu Phe Arg Gln Glu Gly Trp Leu Gln Ala
                85                  90                  95

Phe Pro Lys Gly Leu Ile Asp Leu Leu Ser Tyr Lys Gly Gly Ile Trp
            100                 105                 110

Ser Val Pro Val Asn Ile His Arg Ser Asn Val Met Trp Tyr Ile Pro
        115                 120                 125

Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
145                 150                 155                 160

Leu Ala Leu Gly Glu Asn Trp Thr Gln Gln His Leu Trp Glu Ser Val
                165                 170                 175

Ala Leu Ala Thr Leu Gly Ala Asp Gly Trp Asn Asn Leu Trp Ser Gly
            180                 185                 190

Lys Leu Lys Phe Thr Asp Pro Lys Ala Val Ala Val Trp Glu Thr Phe
        195                 200                 205

Gly Lys Val Leu Asp Ala Ala Asn Lys Asp Ala Ala Gly Leu Ser Trp
    210                 215                 220

Gln Gln Ala Val Asp Arg Val Val Gln Gly Lys Ala Ala Phe Asn Ile
225                 230                 235                 240

Met Gly Asp Met Ala Ala Gly Tyr Met Ser Thr Thr Leu Lys Leu Lys
                245                 250                 255

Pro Gly Thr Asp Phe Ala Trp Thr Pro Ser Pro Gly Thr Ser Gly Ile
            260                 265                 270

Phe Met Met Leu Ser Asp Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300

Gln Asp Thr Phe Asn Pro Leu Lys Gly Ser Ile Ala Ala Arg Leu Asp
305                 310                 315                 320

Ser Asp Pro Ala Lys Tyr Asn Ala Tyr Gly Gln Ser Ala Met Lys Asp
                325                 330                 335

Trp Lys Ser Asn Arg Ile Val Gly Ser Leu Val His Gly Ala Val Ala
            340                 345                 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380

Asn Gln Val Gly Leu Gly Arg Gly Gly Ser His His His His His His
385                 390                 395                 400
```

<210> SEQ ID NO 48
<211> LENGTH: 400
<212> TYPE: PRT
<213> ORGANISM: Artificial Sequence
<220> FEATURE:
<223> OTHER INFORMATION: tsGBP2.13C.W244F (13C, 244F double substitution mutant with signal peptide replaced with M and a GGSHHHHHH at C-terminus)

<400> SEQUENCE: 48

-continued

```
Met Lys Leu Glu Ile Phe Ser Trp Trp Ala Gly Asp Cys Gly Pro Ala
1               5                   10                  15

Leu Glu Ala Leu Ile Arg Leu Tyr Lys Gln Lys Tyr Pro Gly Val Glu
            20                  25                  30

Val Ile Asn Ala Thr Val Thr Gly Gly Ala Gly Val Asn Ala Lys Ala
        35                  40                  45

Val Leu Lys Thr Arg Met Leu Gly Gly Asp Pro Pro Asp Thr Phe Gln
    50                  55                  60

Val His Ala Gly Gln Glu Leu Ile Gly Thr Trp Val Val Ala Asp Arg
65                  70                  75                  80

Met Glu Asp Leu Thr Ser Leu Phe Arg Gln Glu Gly Trp Leu Gln Ala
                85                  90                  95

Phe Pro Lys Gly Leu Ile Asp Leu Leu Ser Tyr Lys Gly Gly Ile Trp
            100                 105                 110

Ser Val Pro Val Asn Ile His Arg Ser Asn Val Met Trp Tyr Ile Pro
        115                 120                 125

Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
145                 150                 155                 160

Leu Ala Leu Gly Glu Asn Trp Thr Gln Gln His Leu Trp Glu Ser Val
                165                 170                 175

Ala Leu Ala Thr Leu Gly Ala Asp Gly Trp Asn Asn Leu Trp Ser Gly
            180                 185                 190

Lys Leu Lys Phe Thr Asp Pro Lys Ala Val Ala Val Trp Glu Thr Phe
        195                 200                 205

Gly Lys Val Leu Asp Ala Ala Asn Lys Asp Ala Ala Gly Leu Ser Trp
    210                 215                 220

Gln Gln Ala Val Asp Arg Val Val Gln Gly Lys Ala Ala Phe Asn Ile
225                 230                 235                 240

Met Gly Asp Phe Ala Ala Gly Tyr Met Ser Thr Thr Leu Lys Leu Lys
                245                 250                 255

Pro Gly Thr Asp Phe Ala Trp Thr Pro Ser Pro Gly Thr Ser Gly Ile
            260                 265                 270

Phe Met Met Leu Ser Asp Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300

Gln Asp Thr Phe Asn Pro Leu Lys Gly Ser Ile Ala Ala Arg Leu Asp
305                 310                 315                 320

Ser Asp Pro Ala Lys Tyr Asn Ala Tyr Gly Gln Ser Ala Met Lys Asp
                325                 330                 335

Trp Lys Ser Asn Arg Ile Val Gly Ser Leu Val His Gly Ala Val Ala
            340                 345                 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380

Asn Gln Val Gly Leu Gly Arg Gly Gly Ser His His His His His His
385                 390                 395                 400
```

<210> SEQ ID NO 49
<211> LENGTH: 400
<212> TYPE: PRT

```
<213> ORGANISM: Artificial Sequence
<220> FEATURE:
<223> OTHER INFORMATION: tsGBP2.13C.W244Y (13C, 244Y double substitution
      mutant with signal peptide replaced with M and a GGSHHHHHH at
      C-terminus)

<400> SEQUENCE: 49

Met Lys Leu Glu Ile Phe Ser Trp Trp Ala Gly Asp Cys Gly Pro Ala
1               5                   10                  15

Leu Glu Ala Leu Ile Arg Leu Tyr Lys Gln Lys Tyr Pro Gly Val Glu
            20                  25                  30

Val Ile Asn Ala Thr Val Thr Gly Gly Ala Gly Val Asn Ala Lys Ala
        35                  40                  45

Val Leu Lys Thr Arg Met Leu Gly Gly Asp Pro Pro Asp Thr Phe Gln
    50                  55                  60

Val His Ala Gly Gln Glu Leu Ile Gly Thr Trp Val Val Ala Asp Arg
65                  70                  75                  80

Met Glu Asp Leu Thr Ser Leu Phe Arg Gln Glu Gly Trp Leu Gln Ala
                85                  90                  95

Phe Pro Lys Gly Leu Ile Asp Leu Leu Ser Tyr Lys Gly Gly Ile Trp
            100                 105                 110

Ser Val Pro Val Asn Ile His Arg Ser Asn Val Met Trp Tyr Ile Pro
        115                 120                 125

Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
145                 150                 155                 160

Leu Ala Leu Gly Glu Asn Trp Thr Gln Gln His Leu Trp Glu Ser Val
                165                 170                 175

Ala Leu Ala Thr Leu Gly Ala Asp Gly Trp Asn Asn Leu Trp Ser Gly
            180                 185                 190

Lys Leu Lys Phe Thr Asp Pro Lys Ala Val Ala Val Trp Glu Thr Phe
        195                 200                 205

Gly Lys Val Leu Asp Ala Ala Asn Lys Asp Ala Ala Gly Leu Ser Trp
    210                 215                 220

Gln Gln Ala Val Asp Arg Val Val Gln Gly Lys Ala Ala Phe Asn Ile
225                 230                 235                 240

Met Gly Asp Tyr Ala Ala Gly Tyr Met Ser Thr Thr Leu Lys Leu Lys
                245                 250                 255

Pro Gly Thr Asp Phe Ala Trp Thr Pro Ser Pro Gly Thr Ser Gly Ile
            260                 265                 270

Phe Met Met Leu Ser Asp Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300

Gln Asp Thr Phe Asn Pro Leu Lys Gly Ser Ile Ala Ala Arg Leu Asp
305                 310                 315                 320

Ser Asp Pro Ala Lys Tyr Asn Ala Tyr Gly Gln Ser Ala Met Lys Asp
                325                 330                 335

Trp Lys Ser Asn Arg Ile Val Gly Ser Leu Val His Gly Ala Val Ala
            340                 345                 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380
```

Asn Gln Val Gly Leu Gly Arg Gly Gly Ser His His His His His His
385 390 395 400

<210> SEQ ID NO 50
<211> LENGTH: 400
<212> TYPE: PRT
<213> ORGANISM: Artificial Sequence
<220> FEATURE:
<223> OTHER INFORMATION: tsGBP2.13C.D278N (13C, 278N double substitution mutant with signal peptide replaced with M and a GGSHHHHHH at C-terminus)

<400> SEQUENCE: 50

Met Lys Leu Glu Ile Phe Ser Trp Trp Ala Gly Asp Cys Gly Pro Ala
1 5 10 15

Leu Glu Ala Leu Ile Arg Leu Tyr Lys Gln Lys Tyr Pro Gly Val Glu
20 25 30

Val Ile Asn Ala Thr Val Thr Gly Gly Ala Gly Val Asn Ala Lys Ala
35 40 45

Val Leu Lys Thr Arg Met Leu Gly Gly Asp Pro Pro Asp Thr Phe Gln
50 55 60

Val His Ala Gly Gln Glu Leu Ile Gly Thr Trp Val Val Ala Asp Arg
65 70 75 80

Met Glu Asp Leu Thr Ser Leu Phe Arg Gln Glu Gly Trp Leu Gln Ala
85 90 95

Phe Pro Lys Gly Leu Ile Asp Leu Leu Ser Tyr Lys Gly Gly Ile Trp
100 105 110

Ser Val Pro Val Asn Ile His Arg Ser Asn Val Met Trp Tyr Ile Pro
115 120 125

Ala Lys Leu Lys Glu Trp Gly Val Thr Pro Pro Lys Thr Trp Ala Glu
130 135 140

Phe Leu Ala Thr Ala Gln Thr Leu Lys Arg Lys Gly Leu Glu Ala Pro
145 150 155 160

Leu Ala Leu Gly Glu Asn Trp Thr Gln Gln His Leu Trp Glu Ser Val
165 170 175

Ala Leu Ala Thr Leu Gly Ala Asp Gly Trp Asn Asn Leu Trp Ser Gly
180 185 190

Lys Leu Lys Phe Thr Asp Pro Lys Ala Val Ala Val Trp Glu Thr Phe
195 200 205

Gly Lys Val Leu Asp Ala Ala Asn Lys Asp Ala Ala Gly Leu Ser Trp
210 215 220

Gln Gln Ala Val Asp Arg Val Val Gln Gly Lys Ala Ala Phe Asn Ile
225 230 235 240

Met Gly Asp Trp Ala Ala Gly Tyr Met Ser Thr Thr Leu Lys Leu Lys
245 250 255

Pro Gly Thr Asp Phe Ala Trp Thr Pro Ser Pro Gly Thr Ser Gly Ile
260 265 270

Phe Met Met Leu Ser Asn Ser Phe Gly Leu Pro Lys Gly Ala Lys Asn
275 280 285

Arg Gln Asn Ala Ile Asn Trp Leu Lys Leu Val Gly Ser Lys Glu Gly
290 295 300

Gln Asp Thr Phe Asn Pro Leu Lys Gly Ser Ile Ala Ala Arg Leu Asp
305 310 315 320

Ser Asp Pro Ala Lys Tyr Asn Ala Tyr Gly Gln Ser Ala Met Lys Asp
325 330 335

-continued

```
Trp Lys Ser Asn Arg Ile Val Gly Ser Leu Val His Gly Ala Val Ala
            340                 345                 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380

Asn Gln Val Gly Leu Gly Arg Gly Gly Ser His His His His His His
385                 390                 395                 400


<210> SEQ ID NO 51
<211> LENGTH: 400
<212> TYPE: PRT
<213> ORGANISM: Artificial Sequence
<220> FEATURE:
<223> OTHER INFORMATION: tsGBP2.13C.D278S (13C, 278S double substitution
      mutant with signal peptide replaced with M and a GGSHHHHHH at
      C-terminus)

<400> SEQUENCE: 51

Met Lys Leu Glu Ile Phe Ser Trp Trp Ala Gly Asp Cys Gly Pro Ala
1               5                   10                  15

Leu Glu Ala Leu Ile Arg Leu Tyr Lys Gln Lys Tyr Pro Gly Val Glu
            20                  25                  30

Val Ile Asn Ala Thr Val Thr Gly Gly Ala Gly Val Asn Ala Lys Ala
        35                  40                  45

Val Leu Lys Thr Arg Met Leu Gly Gly Asp Pro Pro Asp Thr Phe Gln
    50                  55                  60

Val His Ala Gly Gln Glu Leu Ile Gly Thr Trp Val Val Ala Asp Arg
65                  70                  75                  80

Met Glu Asp Leu Thr Ser Leu Phe Arg Gln Glu Gly Trp Leu Gln Ala
                85                  90                  95

Phe Pro Lys Gly Leu Ile Asp Leu Leu Ser Tyr Lys Gly Gly Ile Trp
            100                 105                 110

Ser Val Pro Val Asn Ile His Arg Ser Asn Val Met Trp Tyr Ile Pro
        115                 120                 125

Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
145                 150                 155                 160

Leu Ala Leu Gly Glu Asn Trp Thr Gln Gln His Leu Trp Glu Ser Val
                165                 170                 175

Ala Leu Ala Thr Leu Gly Ala Asp Gly Trp Asn Asn Leu Trp Ser Gly
            180                 185                 190

Lys Leu Lys Phe Thr Asp Pro Lys Ala Val Ala Val Trp Glu Thr Phe
        195                 200                 205

Gly Lys Val Leu Asp Ala Ala Asn Lys Asp Ala Ala Gly Leu Ser Trp
    210                 215                 220

Gln Gln Ala Val Asp Arg Val Val Gln Gly Lys Ala Ala Phe Asn Ile
225                 230                 235                 240

Met Gly Asp Trp Ala Ala Gly Tyr Met Ser Thr Thr Leu Lys Leu Lys
                245                 250                 255

Pro Gly Thr Asp Phe Ala Trp Thr Pro Ser Pro Gly Thr Ser Gly Ile
            260                 265                 270

Phe Met Met Leu Ser Ser Ser Phe Gly Leu Pro Lys Gly Ala Lys Asn
        275                 280                 285

Arg Gln Asn Ala Ile Asn Trp Leu Lys Leu Val Gly Ser Lys Glu Gly
```

```
    290                 295                 300

Gln Asp Thr Phe Asn Pro Leu Lys Gly Ser Ile Ala Ala Arg Leu Asp
305                 310                 315                 320

Ser Asp Pro Ala Lys Tyr Asn Ala Tyr Gly Gln Ser Ala Met Lys Asp
                325                 330                 335

Trp Lys Ser Asn Arg Ile Val Gly Ser Leu Val His Gly Ala Val Ala
            340                 345                 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380

Asn Gln Val Gly Leu Gly Arg Gly Gly Ser His His His His His His
385                 390                 395                 400


<210> SEQ ID NO 52
<211> LENGTH: 400
<212> TYPE: PRT
<213> ORGANISM: Artificial Sequence
<220> FEATURE:
<223> OTHER INFORMATION: tsGBP2.13C.D278L (13C, 278L double substitution
      mutant with signal peptide replaced with M and a GGSHHHHHH at
      C-terminus)

<400> SEQUENCE: 52

Met Lys Leu Glu Ile Phe Ser Trp Trp Ala Gly Asp Cys Gly Pro Ala
1               5                   10                  15

Leu Glu Ala Leu Ile Arg Leu Tyr Lys Gln Lys Tyr Pro Gly Val Glu
            20                  25                  30

Val Ile Asn Ala Thr Val Thr Gly Gly Ala Gly Val Asn Ala Lys Ala
        35                  40                  45

Val Leu Lys Thr Arg Met Leu Gly Gly Asp Pro Pro Asp Thr Phe Gln
    50                  55                  60

Val His Ala Gly Gln Glu Leu Ile Gly Thr Trp Val Val Ala Asp Arg
65                  70                  75                  80

Met Glu Asp Leu Thr Ser Leu Phe Arg Gln Glu Gly Trp Leu Gln Ala
                85                  90                  95

Phe Pro Lys Gly Leu Ile Asp Leu Leu Ser Tyr Lys Gly Gly Ile Trp
            100                 105                 110

Ser Val Pro Val Asn Ile His Arg Ser Asn Val Met Trp Tyr Ile Pro
        115                 120                 125

Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
145                 150                 155                 160

Leu Ala Leu Gly Glu Asn Trp Thr Gln Gln His Leu Trp Glu Ser Val
                165                 170                 175

Ala Leu Ala Thr Leu Gly Ala Asp Gly Trp Asn Asn Leu Trp Ser Gly
            180                 185                 190

Lys Leu Lys Phe Thr Asp Pro Lys Ala Val Ala Val Trp Glu Thr Phe
        195                 200                 205

Gly Lys Val Leu Asp Ala Ala Asn Lys Asp Ala Ala Gly Leu Ser Trp
    210                 215                 220

Gln Gln Ala Val Asp Arg Val Val Gln Gly Lys Ala Ala Phe Asn Ile
225                 230                 235                 240

Met Gly Asp Trp Ala Ala Gly Tyr Met Ser Thr Thr Leu Lys Leu Lys
                245                 250                 255
```

```
Pro Gly Thr Asp Phe Ala Trp Thr Pro Ser Pro Gly Thr Ser Gly Ile
            260                 265                 270

Phe Met Met Leu Ser Leu Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300

Gln Asp Thr Phe Asn Pro Leu Lys Gly Ser Ile Ala Ala Arg Leu Asp
305                 310                 315                 320

Ser Asp Pro Ala Lys Tyr Asn Ala Tyr Gly Gln Ser Ala Met Lys Asp
                325                 330                 335

Trp Lys Ser Asn Arg Ile Val Gly Ser Leu Val His Gly Ala Val Ala
            340                 345                 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380

Asn Gln Val Gly Leu Gly Arg Gly Gly Ser His His His His His His
385                 390                 395                 400


<210> SEQ ID NO 53
<211> LENGTH: 400
<212> TYPE: PRT
<213> ORGANISM: Artificial Sequence
<220> FEATURE:
<223> OTHER INFORMATION: tsGBP2.13C.K312M (13C, 312M double substitution
      mutant with signal peptide replaced with M and a GGSHHHHHH at
      C-terminus)

<400> SEQUENCE: 53

Met Lys Leu Glu Ile Phe Ser Trp Trp Ala Gly Asp Cys Gly Pro Ala
1               5                   10                  15

Leu Glu Ala Leu Ile Arg Leu Tyr Lys Gln Lys Tyr Pro Gly Val Glu
            20                  25                  30

Val Ile Asn Ala Thr Val Thr Gly Gly Ala Gly Val Asn Ala Lys Ala
        35                  40                  45

Val Leu Lys Thr Arg Met Leu Gly Gly Asp Pro Pro Asp Thr Phe Gln
    50                  55                  60

Val His Ala Gly Gln Glu Leu Ile Gly Thr Trp Val Val Ala Asp Arg
65                  70                  75                  80

Met Glu Asp Leu Thr Ser Leu Phe Arg Gln Glu Gly Trp Leu Gln Ala
                85                  90                  95

Phe Pro Lys Gly Leu Ile Asp Leu Leu Ser Tyr Lys Gly Gly Ile Trp
            100                 105                 110

Ser Val Pro Val Asn Ile His Arg Ser Asn Val Met Trp Tyr Ile Pro
        115                 120                 125

Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
145                 150                 155                 160

Leu Ala Leu Gly Glu Asn Trp Thr Gln Gln His Leu Trp Glu Ser Val
                165                 170                 175

Ala Leu Ala Thr Leu Gly Ala Asp Gly Trp Asn Asn Leu Trp Ser Gly
            180                 185                 190

Lys Leu Lys Phe Thr Asp Pro Lys Ala Val Ala Val Trp Glu Thr Phe
        195                 200                 205
```

-continued

Gly Lys Val Leu Asp Ala Ala Asn Lys Asp Ala Ala Gly Leu Ser Trp
210 215 220

Gln Gln Ala Val Asp Arg Val Val Gln Gly Lys Ala Ala Phe Asn Ile
225 230 235 240

Met Gly Asp Trp Ala Ala Gly Tyr Met Ser Thr Thr Leu Lys Leu Lys
245 250 255

Pro Gly Thr Asp Phe Ala Trp Thr Pro Ser Pro Gly Thr Ser Gly Ile
260 265 270

Phe Met Met Leu Ser Asp Ser Phe Gly Leu Pro Lys Gly Ala Lys Asn
275 280 285

Arg Gln Asn Ala Ile Asn Trp Leu Lys Leu Val Gly Ser Lys Glu Gly
290 295 300

Gln Asp Thr Phe Asn Pro Leu Met Gly Ser Ile Ala Ala Arg Leu Asp
305 310 315 320

Ser Asp Pro Ala Lys Tyr Asn Ala Tyr Gly Gln Ser Ala Met Lys Asp
325 330 335

Trp Lys Ser Asn Arg Ile Val Gly Ser Leu Val His Gly Ala Val Ala
340 345 350

Pro Glu Ser Phe Met Ser Gln Phe Gly Thr Val Met Glu Ile Phe Leu
355 360 365

Gln Ser Arg Asn Pro Gln Ala Ala Ala Asn Ala Ala Gln Ala Ile Ala
370 375 380

Asn Gln Val Gly Leu Gly Arg Gly Gly Ser His His His His His His
385 390 395 400

<210> SEQ ID NO 54
<211> LENGTH: 424
<212> TYPE: PRT
<213> ORGANISM: Artificial Sequence
<220> FEATURE:
<223> OTHER INFORMATION: tsGBP2.13C.bZif (13C substitution mutant, with bZif fusion, signal peptide replaced with M and a GGSHHHHHH at C-terminus)

<400> SEQUENCE: 54

Met Lys Leu Glu Ile Phe Ser Trp Trp Ala Gly Asp Cys Gly Pro Ala
1 5 10 15

Leu Glu Ala Leu Ile Arg Leu Tyr Lys Gln Lys Tyr Pro Gly Val Glu
20 25 30

Val Ile Asn Ala Thr Val Thr Gly Gly Ala Gly Val Asn Ala Lys Ala
35 40 45

Val Leu Lys Thr Arg Met Leu Gly Gly Asp Pro Pro Asp Thr Phe Gln
50 55 60

Val His Ala Gly Gln Glu Leu Ile Gly Thr Trp Val Val Ala Asp Arg
65 70 75 80

Met Glu Asp Leu Thr Ser Leu Phe Arg Gln Glu Gly Trp Leu Gln Ala
85 90 95

Phe Pro Lys Gly Leu Ile Asp Leu Leu Ser Tyr Lys Gly Gly Ile Trp
100 105 110

Ser Val Pro Val Asn Ile His Arg Ser Asn Val Met Trp Tyr Ile Pro
115 120 125

Ala Lys Leu Lys Glu Trp Gly Val Thr Pro Pro Lys Thr Trp Ala Glu
130 135 140

Phe Leu Ala Thr Ala Gln Thr Leu Lys Arg Lys Gly Leu Glu Ala Pro
145 150 155 160

Leu Ala Leu Gly Glu Asn Trp Thr Gln Gln His Leu Trp Glu Ser Val 165 170 175

Ala Leu Ala Thr Leu Gly Ala Asp Gly Trp Asn Asn Leu Trp Ser Gly
180 185 190

Lys Leu Lys Phe Thr Asp Pro Lys Ala Val Ala Val Trp Glu Thr Phe
195 200 205

Gly Lys Val Leu Asp Ala Ala Asn Lys Asp Ala Ala Gly Leu Ser Trp
210 215 220

Gln Gln Ala Val Asp Arg Val Val Gln Gly Lys Ala Ala Phe Asn Ile
225 230 235 240

Met Gly Asp Trp Ala Ala Gly Tyr Met Ser Thr Thr Leu Lys Leu Lys
245 250 255

Pro Gly Thr Asp Phe Ala Trp Thr Pro Ser Pro Gly Thr Ser Gly Ile
260 265 270

Phe Met Met Leu Ser Asp Ser Phe Gly Leu Pro Lys Gly Ala Lys Asn
275 280 285

Arg Gln Asn Ala Ile Asn Trp Leu Lys Leu Val Gly Ser Lys Glu Gly
290 295 300

Gln Asp Thr Phe Asn Pro Leu Lys Gly Ser Ile Ala Ala Arg Leu Asp
305 310 315 320

Ser Asp Pro Ala Lys Tyr Asn Ala Tyr Gly Gln Ser Ala Met Lys Asp
325 330 335

Trp Lys Ser Asn Arg Ile Val Gly Ser Leu Val His Gly Ala Val Ala
340 345 350

Pro Glu Ser Phe Met Ser Gln Phe Gly Thr Val Met Glu Ile Phe Leu
355 360 365

Gln Ser Arg Asn Pro Gln Ala Ala Ala Asn Ala Ala Gln Ala Ile Ala
370 375 380

Asn Gln Val Gly Leu Gly Arg Gly Gly Ser Gly Gly Ser Thr Gly Glu
385 390 395 400

Lys Pro Tyr Lys Cys Pro Glu Cys Gly Lys Ser Phe Ser Arg Ser Gly
405 410 415

Gly Ser His His His His His His
420

<210> SEQ ID NO 55
<211> LENGTH: 424
<212> TYPE: PRT
<213> ORGANISM: Artificial Sequence
<220> FEATURE:
<223> OTHER INFORMATION: tsGBP2.244C.bZif (244C substitution mutant, with bZif fusion with signal peptide replaced with M and a GGSHHHHHH at C-terminus)

<400> SEQUENCE: 55

Met Lys Leu Glu Ile Phe Ser Trp Trp Ala Gly Asp Glu Gly Pro Ala
1 5 10 15

Leu Glu Ala Leu Ile Arg Leu Tyr Lys Gln Lys Tyr Pro Gly Val Glu
20 25 30

Val Ile Asn Ala Thr Val Thr Gly Gly Ala Gly Val Asn Ala Lys Ala
35 40 45

Val Leu Lys Thr Arg Met Leu Gly Gly Asp Pro Pro Asp Thr Phe Gln
50 55 60

Val His Ala Gly Gln Glu Leu Ile Gly Thr Trp Val Val Ala Asp Arg
65 70 75 80

Met Glu Asp Leu Thr Ser Leu Phe Arg Gln Glu Gly Trp Leu Gln Ala
85 90 95

Phe Pro Lys Gly Leu Ile Asp Leu Leu Ser Tyr Lys Gly Gly Ile Trp
            100                 105                 110

Ser Val Pro Val Asn Ile His Arg Ser Asn Val Met Trp Tyr Ile Pro
        115                 120                 125

Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
145                 150                 155                 160

Leu Ala Leu Gly Glu Asn Trp Thr Gln Gln His Leu Trp Glu Ser Val
                165                 170                 175

Ala Leu Ala Thr Leu Gly Ala Asp Gly Trp Asn Asn Leu Trp Ser Gly
            180                 185                 190

Lys Leu Lys Phe Thr Asp Pro Lys Ala Val Ala Val Trp Glu Thr Phe
        195                 200                 205

Gly Lys Val Leu Asp Ala Ala Asn Lys Asp Ala Ala Gly Leu Ser Trp
    210                 215                 220

Gln Gln Ala Val Asp Arg Val Val Gln Gly Lys Ala Ala Phe Asn Ile
225                 230                 235                 240

Met Gly Asp Cys Ala Ala Gly Tyr Met Ser Thr Thr Leu Lys Leu Lys
                245                 250                 255

Pro Gly Thr Asp Phe Ala Trp Thr Pro Ser Pro Gly Thr Ser Gly Ile
            260                 265                 270

Phe Met Met Leu Ser Asp Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300

Gln Asp Thr Phe Asn Pro Leu Lys Gly Ser Ile Ala Ala Arg Leu Asp
305                 310                 315                 320

Ser Asp Pro Ala Lys Tyr Asn Ala Tyr Gly Gln Ser Ala Met Lys Asp
                325                 330                 335

Trp Lys Ser Asn Arg Ile Val Gly Ser Leu Val His Gly Ala Val Ala
            340                 345                 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380

Asn Gln Val Gly Leu Gly Arg Gly Gly Ser Gly Gly Ser Thr Gly Glu
385                 390                 395                 400

Lys Pro Tyr Lys Cys Pro Glu Cys Gly Lys Ser Phe Ser Arg Ser Gly
                405                 410                 415

Gly Ser His His His His His His
            420

<210> SEQ ID NO 56
<211> LENGTH: 424
<212> TYPE: PRT
<213> ORGANISM: Artificial Sequence
<220> FEATURE:
<223> OTHER INFORMATION: tsGBP2.13C_244F.bZif (13C, 244F double substitution mutant, with bZif fusion, signal peptide replaced with M and a GGSHHHHHH at C-terminus)

<400> SEQUENCE: 56

Met Lys Leu Glu Ile Phe Ser Trp Trp Ala Gly Asp Cys Gly Pro Ala
1               5                   10                  15

-continued

```
Leu Glu Ala Leu Ile Arg Leu Tyr Lys Gln Lys Tyr Pro Gly Val Glu
            20                  25                  30

Val Ile Asn Ala Thr Val Thr Gly Gly Ala Gly Val Asn Ala Lys Ala
        35                  40                  45

Val Leu Lys Thr Arg Met Leu Gly Gly Asp Pro Pro Asp Thr Phe Gln
    50                  55                  60

Val His Ala Gly Gln Glu Leu Ile Gly Thr Trp Val Val Ala Asp Arg
65                  70                  75                  80

Met Glu Asp Leu Thr Ser Leu Phe Arg Gln Glu Gly Trp Leu Gln Ala
                85                  90                  95

Phe Pro Lys Gly Leu Ile Asp Leu Leu Ser Tyr Lys Gly Gly Ile Trp
            100                 105                 110

Ser Val Pro Val Asn Ile His Arg Ser Asn Val Met Trp Tyr Ile Pro
        115                 120                 125

Ala Lys Leu Lys Glu Trp Gly Val Thr Pro Pro Lys Thr Trp Ala Glu
    130                 135                 140

Phe Leu Ala Thr Ala Gln Thr Leu Lys Arg Lys Gly Leu Glu Ala Pro
145                 150                 155                 160

Leu Ala Leu Gly Glu Asn Trp Thr Gln Gln His Leu Trp Glu Ser Val
                165                 170                 175

Ala Leu Ala Thr Leu Gly Ala Asp Gly Trp Asn Asn Leu Trp Ser Gly
            180                 185                 190

Lys Leu Lys Phe Thr Asp Pro Lys Ala Val Ala Val Trp Glu Thr Phe
        195                 200                 205

Gly Lys Val Leu Asp Ala Ala Asn Lys Asp Ala Ala Gly Leu Ser Trp
    210                 215                 220

Gln Gln Ala Val Asp Arg Val Val Gln Gly Lys Ala Ala Phe Asn Ile
225                 230                 235                 240

Met Gly Asp Phe Ala Ala Gly Tyr Met Ser Thr Thr Leu Lys Leu Lys
                245                 250                 255

Pro Gly Thr Asp Phe Ala Trp Thr Pro Ser Pro Gly Thr Ser Gly Ile
            260                 265                 270

Phe Met Met Leu Ser Asp Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300

Gln Asp Thr Phe Asn Pro Leu Lys Gly Ser Ile Ala Ala Arg Leu Asp
305                 310                 315                 320

Ser Asp Pro Ala Lys Tyr Asn Ala Tyr Gly Gln Ser Ala Met Lys Asp
                325                 330                 335

Trp Lys Ser Asn Arg Ile Val Gly Ser Leu Val His Gly Ala Val Ala
            340                 345                 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380

Asn Gln Val Gly Leu Gly Arg Gly Gly Ser Gly Gly Ser Thr Gly Glu
385                 390                 395                 400

Lys Pro Tyr Lys Cys Pro Glu Cys Gly Lys Ser Phe Ser Arg Ser Gly
                405                 410                 415

Gly Ser His His His His His His
            420
```

<210> SEQ ID NO 57
<211> LENGTH: 1604
<212> TYPE: DNA
<213> ORGANISM: Artificial Sequence
<220> FEATURE:
<223> OTHER INFORMATION: Exemplary ttGBP1 expression sequence, optimized using OrfOpt

<400> SEQUENCE: 57

```
gccagtaagc ttcggtcacg cttgggactg ccataggctg gcccggtgat gccggccacg     60

atgcgtccgg cgtagaggat cgagatctcg atcccgcgaa attaatacga ctcactatag    120

ggagaccaca acggtttccc tctagaaata attttgttta actttaagaa ggagatatac    180

catgaaatta gaaatttttt cttggtgggc aggtgatgaa ggcccggcct tagaggcctt    240

gatccgctta tataaacaaa aatacccggg tgtagaagtg attaatgcaa ccgtgacagg    300

cggtgcaggc gtcaatgcgc gggcagttct caaaacccgt atgttaggcg gtgatccacc    360

agacaccttc caagtccatg ctgggatgga attaatcggc acatgggtcg tcgcgaaccg    420

catggaggac ctctcggcgc tgtttcggca ggaaggctgg cttcaggcat tccctaaagg    480

cctcatcgac ctgatttctt ataagggcgg gatttggtcc gtacctgtaa atatccaccg    540

gagtaacgta atgtggtatc tgccggcaaa attaaaaggc tggggcgtaa acccaccacg    600

tacttgggac aaatttcttg cgacggcgca gaccttaaag caaaaaggtt tagaggcacc    660

actggccctc ggggaaaatt ggacacagca gcacttgtgg gagtcggtcg ccttggcagt    720

attgggtcca gatgattgga ataacttatg gaacggcaaa ctcaagttta ctgatccaaa    780

agccgtccgt gcatgggagg tgttcggccg cgtcctcgac gcagctaata aagatgcagc    840

aggcttgagc tggcagcaag ccgtcgatcg cgtcgtacag gggaaagccg cattcaacat    900

tatgggggat tgggcggctg ggtacatgac tacgacgtta aaattaaaac caggtacaga    960

tttcgcttgg gccccatcac caggtaccca aggcgtattc atgatgttaa gtgactcatt   1020

cggtctccct aaaggtgcca aaaatcgtca gaatgctatt aactggctgc gtctcgtagg   1080

ttcaaaggaa gggcaagata catctaaccc tctcaaaggt agtattgcag cacgtcttga   1140

cagcgaccct tcgaagtata acgcctatgg ccaatcggca atgcgtgact ggcgcagtaa   1200

ccgtatcgta gggtccctcg ttcacggcgc cgttgcacca gaatcgttta tgagtcaatt   1260

cggtaccgta atggaaatct tcctccaaac ccgcaatcca caagcagctg ctaatgcagc   1320

acaggccatc gccgaccaag taggcctcgg tcgtttaggt caacatcatc atcatcatca   1380

ttaatgaaag ggcgatatcc agcacactgg cggccgttac tagtggatcc ggctgctaac   1440

aaagcccgaa aggaagctga gttggctgct gccaccgctg agcaataact agcataaccc   1500

cttggggcct ctaaacgggt cttgaggggt tttttgctga aaggaggaac tatatccgga   1560

gcgactccca cggcacgttg gcaagctcgg aattcggcgt aatc                    1604
```

<210> SEQ ID NO 58
<211> LENGTH: 1577
<212> TYPE: DNA
<213> ORGANISM: Artificial Sequence
<220> FEATURE:
<223> OTHER INFORMATION: Exemplary tsGBP2 expression sequence, optimized using OrfOpt

<400> SEQUENCE: 58

```
cggtcacgct tgggactgcc ataggctggc ccggtgatgc cggccacgat gcgtccggcg     60

tagaggatcg agatctcgat cccgcgaaat taatacgact cactataggg agaccacaac    120
```

-continued

```
ggtttccctc tagaaataat tttgtttaac tttaagaagg agatatacca tgaaattaga    180

aatttttttct tggtgggcag gtgatgaagg cccagctctc gaagccttga tccggttgta    240

taaacagaaa tacccaggtg tagaggtcat taatgctacc gtcaccgggg gtgccggtgt    300

caacgccaaa gccgtcctta aaacgcgtat gctcggcggg gacccaccag atacctttca    360

agtacatgca gggcaggagc tgatcggcac atgggtcgtc gccgaccgta tggaagatct    420

tacctcattg tttcggcagg agggctggct tcaagcgttc ccaaaaggtt taatcgatct    480

cctcagttac aaaggtggca tttggtcagt cccagtcaac atccaccgtt ctaacgtaat    540

gtggtacatc ccggcaaaat taaaagaatg gggcgtgacc ccgccaaaaa catgggcaga    600

atttttagcg acagcgcaaa cattaaagcg gaaaggcctt gaggcaccat tggcactcgg    660

tgagaattgg acacagcaac atctctggga aagcgtcgcc ctcgccacac tgggtgccga    720

tggttggaat aatctctgga gtggtaagct caaattcacg gatccaaaag cagtcgccgt    780

atgggaaaca ttcggtaagg tattagatgc agcgaacaag gatgcagccg ggctttcatg    840

gcaacaagca gtagaccgtg tagtacaggg gaaagctgca ttcaatatca tgggggactg    900

ggcagcaggt tacatgagta cgaccttaaa actgaagcca ggtaccgact tcgcatggac    960

accttctccg ggcacttcag ggatctttat gatgctgtct gatagtttcg gcttgccaaa   1020

gggggcgaag aatcgtcaaa atgctattaa ctggttgaaa ctcgtcgggt caaaagaggg   1080

gcaggacacc ttcaacccgc tcaaaggttc catcgctgct cgtctcgatt ctgatcctgc   1140

caaatataat gcatacggcc aaagtgcaat gaaggactgg aagtcaaatc ggatcgtagg   1200

ctccctcgtc cacggcgcag tcgcgccaga atccttcatg tcgcagtttg ggacggtaat   1260

ggagattttc ttgcaatccc gtaacccgca ggcagccgct aatgccgcac aagctatcgc   1320

caatcaggtc ggtttaggtc gtgggggttc acatcatcat catcatcatt aatgaaaggg   1380

cgatatccag cacactggcg gccgttacta gtggatccgg ctgctaacaa agcccgaaag   1440

gaagctgagt tggctgctgc caccgctgag caataactag cataacccct tggggcctct   1500

aaacgggtct tgaggggttt tttgctgaaa ggaggaacta tatccggagc gactcccacg   1560

gcacgttggc aagctcg                                                  1577
```

```
<210> SEQ ID NO 59
<211> LENGTH: 1574
<212> TYPE: DNA
<213> ORGANISM: Artificial Sequence
<220> FEATURE:
<223> OTHER INFORMATION: Exemplary dmGBP3 expression sequence, optimized
      using OrfOpt

<400> SEQUENCE: 59
```

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaactcga    180

aatttttagt tggtggtcag gtgacgaagg cccagcactc gaggcactcg tgaagttata    240

taagcaaaag tatccatcgg tagacgtggt caatgcgacg gtagcagggg gcgcagggac    300

aaatgcaaaa gcggtgctga aaactcgtat gctcgggggc gacccaccgg attcattcca    360

ggcccacgcc ggccaagaat tgatcgggac atgggtagtg gcaaatcgta tggaagattt    420

aagttccctg ttcaaatccg aaggttggac cacaaaattc ccaaaagatt tattaccact    480

tatctcttcg aaagggggca tctggtcagt cccagtaaac gtccatcgca gtaacgtcat    540
```

-continued gtggtacatc ccggctaatc tgaagaaatg gggcgtgacc gcacctaaaa cctgggacca 600
gttcttaact accgcgaaga ccttgaagac caagaacgta actccattag cactcgggga 660
aaactggact caacaacact tatgggaatc agtggcggtc ggtacattag gggcccaggg 720
ttggcagaac ttatggtcgg ggaagttaaa gtttacagac ccaaaggtgg tgaaagtatg 780
ggacacattc ggcaaggtct tggatgcaac aaacaaggat gcatcgggtc tcagttggca 840
gcaggcgacg gaccgtgtag taaatggcca ggcagcgttt aacattatgg gggattgggc 900
cgcaggttat ctcagtacga ccaagaaatt gaaaccgggg acaggcttcg gctgggcgcc 960
gtccccatca acatcaggca cgttcatttt cttggctgat agctttgggt tgccgaaagg 1020
tgccaaggat cgcgcggaag ccctctcatg gttaaaactt ttaggctcaa aacagggtca 1080
ggacacattt aatcctttaa agggcagtat cgcggctcgg gtcgacagtg atttatctaa 1140
atactccaca tatagccaat cggcagccaa ggactggaag agcaataaaa ttgtggggtc 1200
gttgacgcat ggggcagtcg caccagaatc ctttacttct acctttggca ccgtaatcga 1260
tgcctttgta gcaagtcgga atgctcaggt cgcagccgct actacacaac agctcgcaga 1320
taaagccggt ctgggcaaag gtggtagtca tcatcatcat catcattaat gaaagggcga 1380
tatccagcac actggcggcc gttactagtg gatccggctg ctaacaaagc ccgaaaggaa 1440
gctgagttgg ctgctgccac cgctgagcaa taactagcat aaccccttgg ggcctctaaa 1500
cgggtcttga ggggtttttt gctgaaagga ggaactatat ccggagcgac tcccacggca 1560
cgttggcaag ctcg 1574

<210> SEQ ID NO 60
<211> LENGTH: 1583
<212> TYPE: DNA
<213> ORGANISM: Artificial Sequence
<220> FEATURE:
<223> OTHER INFORMATION: Exemplary tnGBP4 expression sequence, optimized using OrfOpt

<400> SEQUENCE: 60
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgttagaaat 180
tttttcttgg tggacagcag gtggcgaagc cgaagcctta gaagcactca ttaaagtctt 240
caataagtac tatccggatg tagaggtcat caatgcgaca gtcgcaggcg gtgctggtac 300
taacgccaaa gcagtcttaa agacccgcat tcttggtggt aaccctccgg attcattcca 360
agttcacgct ggcatggaac tcatcgacac atacgttatt ccaggttaca tgacaccaat 420
caccaatctc ttagagcaat ggggcgtcat ggacaagttt ccgaaaggca ttctcgagat 480
ggcttcctat gaaggcgaaa tttactcaat tccggtaaat gtacatcgcg gtaatgtggt 540
cttttacaat aagaaaattg cagaggaaat tggcatgaac gaaccaccaa aaacgtggga 600
cgaatttatc atgtatctcc agaaagccaa agagaaaggc tatgtagggc ttgcactggg 660
tgacaagaat aagtggacag ccctccacct gttcgaaaca atcctcttag gcgtgttagg 720
cccaaatgat tataatggtc tttggaaagg ggaagttagc tttaacgacc ctcgtattcg 780
ccgcgcattc gaaattatga acaagttgtt ggactacgta aacgaagatc atgcagcact 840
cgcctggcag gatgcaactc gtttagtata cgaaggcaaa gccttggcta acgtcatggg 900
tgattgggcg gaggggtact taaaaagcgt cgggtgggaa ccgggtaaag atttcgggtg 960
gttcgccgtg ccagaaaccc aaaacgcttt catggtagtc tccgatacgt ttggtctccc 1020
gaaaaacgca cctcataaag aaaatgcagt aaaatggtta aaggtggtag cctcagtaga 1080
gggccaggat gcatttaatc ctatcaaggg ctcaattccg gcccgtctcg acgcagaccg 1140
ctcaaaatat gatatctact tgcaatggtc catggaagat tttgccacga aggcactcac 1200
cccaagcatc gcccatggga gtgcagcccc ggaaggtttt gtaacaacat taaatgacat 1260
tattaaccgg tttgtaacca cccgcgatat cgactccgcc ctggaagaac tgctcatggc 1320
agccgaggac gaagggtact tggtagaagg tggtagtcat catcatcatc atcattaatg 1380
aaagggcgat atccagcaca ctggcggccg ttactagtgg atccggctgc taacaaagcc 1440
cgaaaggaag ctgagttggc tgctgccacc gctgagcaat aactagcata accccttggg 1500
gcctctaaac gggtcttgag gggttttttg ctgaaaggag gaactatatc cggagcgact 1560
cccacggcac gttggcaagc tcg 1583

<210> SEQ ID NO 61
<211> LENGTH: 1574
<212> TYPE: DNA
<213> ORGANISM: Artificial Sequence
<220> FEATURE:
<223> OTHER INFORMATION: Exemplary koGBP5 expression sequence, optimized using OrfOpt

<400> SEQUENCE: 61
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgttagaaat 180
ttttagttgg tggacaggtg gtggcgaaga agaagggctc ttggctttat tcgacgtatt 240
ccacaaatac tacccagatg tcgagatcat caacgccacc gtcgctgggg gtgcagggac 300
taacgccaag gcagtattga agactcgtat gttagggggg aacccgccag acagctttca 360
ggtacacggc ggcatggaac tcatcgatac ctacgtagta acagggatga tggagccaat 420
tacagactta ttagaggaat ggggtattat tgacaaattt ccagaggata tcttgaaaat 480
tgcgtcctat aaaggggaag tgtacagtat tccagtcaac gtccatcgtg gtaacgtcgt 540
cttctacaat aaagctatcc tcgaagaggt cgggatcgaa aaggtgccta gtacatggcc 600
ggaatttatt gaagtcctca aaaaaatcaa gaaggcaggt tatatccctc ttgcattggg 660
tgataagaat aaatggactg cgacgcacct gttcgaggac attttactgt caactctcgg 720
tccatacaat tacaacggcc tgtggaacgg tcgtacgtca tttgaacatc agggcgtgaa 780
ggaggcctta gagatcttca aagaattgat gaactacgta aacccaaatc atgcttcgct 840
gacatggcaa gacgccacgc tcttggtatt tgaaggtaaa gcagcattca acgttatggg 900
cgattgggcc gagggttatc ttaaaacatt agggtggacc ccaggcaaag agttcggttg 960
gatggtagtc ccgggtacga aaggttcttt catggtagtc accgacacct tcggtctgcc 1020
taaaaatgcg ccacaccgcg agaacgcaat caaatggtta aagatcatca gttccgtgga 1080
aggccaagac acattcaacc ctatcaaggg ttcaattcca gcacgtattg acgccgatcg 1140
cagcttgtac gatgactatc tgatctggtc tatggacgat ttcgctacaa atgcgttgtg 1200
tcctagcatt atccacgggt ccgctgcccc agaagccttc gttactgcgc tcaacgatac 1260
gattaatatg ttcatcacac gcaaggacgt taaaaaagca ttaaaggaaa ttatctatgc 1320
agcagaagat tatttagaag gtggtagtca tcatcatcat catcattaat gaaagggcga 1380

-continued

```
tatccagcac actggcggcc gttactagtg gatccggctg ctaacaaagc ccgaaaggaa   1440

gctgagttgg ctgctgccac cgctgagcaa taactagcat aaccccttgg ggcctctaaa   1500

cgggtcttga ggggtttttt gctgaaagga ggaactatat ccggagcgac tcccacggca   1560

cgttggcaag ctcg                                                     1574
```

<210> SEQ ID NO 62
<211> LENGTH: 1562
<212> TYPE: DNA
<213> ORGANISM: Artificial Sequence
<220> FEATURE:
<223> OTHER INFORMATION: Exemplary bhGBP6 expression sequence, optimized using OrfOpt

<400> SEQUENCE: 62

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgttagaaat    180

ttttagttgg tggacaggtg caggcgagga agacgggctc ttagccctca ttgaattatt    240

cgaggagaag cacccagaga ttgaggtcga caacgccgcg gtagccggtg gggccgggac    300

caatgcaaaa gccgtactga catcgcggat gcaaggtaat gatccaccag gcacgtttca    360

ggttcacggt ggcgccgagc tcaacgacag ctgggtagcg gccggccaaa tggacccatt    420

gaacgattta ttcgaagccg aggggtgggc ggacaagttc cctgaggagc ttatcgaatt    480

ggtctccaag gatggcaaca tttatagcgt cccagtgaac attcaccggg gtaacgttct    540

ctggtataac actgaaattt tcgaggagca tggcttagaa gtaccgacga catttgaaga    600

atttttcgat gtagcggacg ccttacaaga agcaggtgta acccctctgg ccttaggcga    660

ccgcgaacca tgggccgcca cacatttgtt cgagaccgta ttactcggca cactcggtgc    720

agatgattat aacaagctgt ggagtggtga agtaggcatg gatgacccgc gtgtagaaga    780

ggcagcagag attttcatcc gtatgctcga ttatgttaat gaggaccaca gtagtcgtaa    840

ctggcaagac gcttcacaac tcgtggcaca gggggaagca gccatgaatg tgatgggcga    900

ttgggcgaaa ggctactttg ttaacgacct gaatctcgcg gtaaaagagg attttggttg    960

ggcggccact ccaggtacag aggggacatt catggtgatc acagacacat tcggtttgcc   1020

gaccggtgta gagaacccag aggtcgtcaa aagtttcctc gcggtcttag gctcacaaga   1080

aggccaggat gccttcaatc cattaaaagg ttccattcca gctcgtgttg acgcagatgt   1140

ttccaagtac gacgaatatg gtcaagaaac cattgaagat tttaagtccg cggagctgtc   1200

accatcgctc gcgcacggca gtgcagcaaa cgaggggttc ttgacccaag tgaatcaggc   1260

tatcaacatt tttgtaacac agaaggacgt agattcattc gtagactcgt tgaaacaata   1320

tcaaccaggt ggtagtcatc atcatcatca tcattaatga aagggcgata tccagcacac   1380

tggcggccgt tactagtgga tccggctgct aacaaagccc gaaaggaagc tgagttggct   1440

gctgccaccg ctgagcaata actagcataa ccccttgggg cctctaaacg ggtcttgagg   1500

ggtttttgc tgaaaggagg aactatatcc ggagcgactc ccacggcacg ttggcaagct    1560

cg                                                                  1562
```

<210> SEQ ID NO 63
<211> LENGTH: 1685
<212> TYPE: DNA
<213> ORGANISM: Artificial Sequence
<220> FEATURE:

-continued

<223> OTHER INFORMATION: Exemplary smGBP7 expression sequence, optimized
      using OrfOpt

<400> SEQUENCE: 63

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tggaattagt    180

aatttatcat tggtggacag caggcgggga acgtgaggca atcaacgccg tcttccaggt    240

ctttaagcaa aagtacccga acattcaaat cgtggaaaat ccagtagccg gcggtgcagg    300

ctcggtcatg aagagtgtaa ttatcggcct cctcgccgca ggtaccccac cagacacatt    360

tcaggtacac gcaggtgcag agttaaaaga gtatgtggac gccggttatc tcgccccaat    420

cgacgacatt tggtcgaagc tgggtctgga caaggtaatc ccgagtaccc tccaagtcat    480

ggcaaaattt aacgggcatt actatgcagt cccaattgac gtgcaccggt ccaatgtact    540

ctggtacaac cctaagatct tcaacgaact cggtatcatc aacaaattcg gtgaccctcg    600

taactggtct gtagatacgc tcctccaagt agcacgttac attaagcaac aacgccctga    660

catcgcacca attgcactgg cgtcgcgtaa taagtggcca gtaacgcatc tcttcgaggt    720

ccttttagcc aacgcaggcg gtccagagac ttacgtcaaa ttctttaccg gtaaatttaa    780

ttacaatgac cctaatgacc cagttgtaca gacagtaaag aaagtcctca ccgtgatggc    840

gaccatggca aaggaaggtt tgtttaacag caaccatccg gaactcacct gggatcaagc    900

agcagcgctt gtagctgaag gcaaggcagc aatgttcatt cacggggatt gggtcgccgg    960

ctactatatc gccaataact ataaatacgg taaggattgg gctgcggcac cgttcccgaa   1020

aaacatcttc atcctgcttt cagatgcctt cgaattgcca aaaaacgccc ctcaccctga   1080

ggccgccaag gattggctca tggttgtcgg tagtaaggaa gcacaagaga aattcaatct   1140

catcaagggg tcgatcccag cacgcactga cgtctcccca aaatacccag atccgtaccg   1200

gccagagaca gcggaagact tccagaaatc aacattgatt ccttcagctg ttcacggcgg   1260

tatcgctaaa gaagccttta tgacagattt acacaacatt ttgacatcga tgctgacggc   1320

cgtctcggta ggtactccgg tggacaatgc ggtgaataca gcattagccc aaatccttca   1380

gtcagtaaaa acgtccggct tggcgtcgtt ttggaaaggt tacacaattg actactttat   1440

cacaaagcgt ggcggttctc atcatcatca tcatcattaa tgaaagggcg atatccagca   1500

cactggcggc cgttactagt ggatccggct gctaacaaag cccgaaagga agctgagttg   1560

gctgctgcca ccgctgagca ataactagca taaccccttg gggcctctaa acgggtcttg   1620

aggggttttt tgctgaaagg aggaactata tccggagcga ctcccacggc acgttggcaa   1680

gctcg                                                               1685
```

<210> SEQ ID NO 64
<211> LENGTH: 1577
<212> TYPE: DNA
<213> ORGANISM: Artificial Sequence
<220> FEATURE:
<223> OTHER INFORMATION: Exemplary asGBP8 expression sequence, optimized
      using OrfOpt

<400> SEQUENCE: 64

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaattaga    180
```

```
aattacaagt tggtggactt ccgggagtga ggcagatgcc cttaacgtac tcatcgacgg    240
tgtcaaagcc gcaaaaccgg gtctcagcgt agacaacgca gcggtctcag gggcggcgg     300
cgccaacgcc cgccaggcac tcgcagcacg tctccaagca ggcagtccac ctgacgcctg    360
gcaagttcat ccagcaggtc aattaaagtc ctatgtagac gggggccagg tggccgacct    420
cactgattta tggactgaag gcgattgggc ctcgcaaatg ccgaaagacg tagccgaggc    480
gcaacaggta gacggtaaat actacacagt accaatcggt gtgcaccgcg gtaatgtact    540
ctggacaaat ccagccgtac tcagcaaagc gaatgtaacc attgacgcag acgcgggtat    600
cgacgggctc atctcttcat tggaacaagt acaagcaagt gggactaccc cgttggcttt    660
aggtgacaaa gacattttcg caagttccca gctgttagag tccctgatta tgtcgcgggc    720
tggtgccgat aactggacaa aactctttac aagtgagtat tccttcgatg caccagaagt    780
caaacaagcc cttgaagact ataaaacgat cctcagcttt gcaaataagg accatagcgc    840
catcacctgg gacgaggcag ctaagaagat ggccgacggt gaagccgcag taaacttgat    900
gggcgattgg gcgtacggcg aactcttgaa cgcagggaag aaaccaggga ccgatttcgc    960
atgggtggca tttccgggca aagaggacat cttcgattat gtaggtgacg gttttagtat   1020
cccggcaaac aatattccac acgcggaggc agctcgggcg tggctgaaga ccttaatgga   1080
tccaaaaatc caaaccgaat ttgccgccaa aaaagggtcg attccagccg tcacaagtgc   1140
cgacatttcc ggcctgagtg aataccagca ggaagctgcc aaatctctcg ccagtggtgc   1200
cgtagtcagt tctttagcgc atgcacaagc agccggtgca gagttcgccc aaacatacgc   1260
agatgcagta agcactttca acggtagcgg caatactgac gcgttcatcg cttccatgac   1320
ccaggcccag aaaacacagt taggtggttc acatcatcat catcatcatt aatgaaaggg   1380
cgatatccag cacactggcg gccgttacta gtggatccgg ctgctaacaa agcccgaaag   1440
gaagctgagt tggctgctgc caccgctgag caataactag cataacccct tggggcctct   1500
aaacgggtct tgaggggttt tttgctgaaa ggaggaacta tatccggagc gactcccacg   1560
gcacgttggc aagctcg                                                  1577
```

<210> SEQ ID NO 65
<211> LENGTH: 1577
<212> TYPE: DNA
<213> ORGANISM: Artificial Sequence
<220> FEATURE:
<223> OTHER INFORMATION: Exemplary tsGBP2_C8 expression sequence, optimized using OrfOpt

<400> SEQUENCE: 65

```
cggtcacgct tgggactgcc ataggctggc ccggtgatgc cggccacgat gcgtccggcg     60
tagaggatcg agatctcgat cccgcgaaat taatacgact cactataggg agaccacaac    120
ggtttccctc tagaaataat tttgtttaac tttaagaagg agatatacca tgaaattaga    180
aattttttct tgctgggcag gtgatgaagg cccagctctc gaagccttga tccggttgta    240
taaacagaaa tacccaggtg tagaggtcat taatgctacc gtcaccgggg gtgccggtgt    300
caacgccaaa gccgtcctta aaacgcgtat gctcggcggg gacccaccag atacctttca    360
agtacatgca gggcaggagc tgatcggcac atgggtcgtc gccgaccgta tggaagatct    420
tacctcattg tttcggcagg agggctggct tcaagcgttc ccaaaaggtt taatcgatct    480
cctcagttac aaaggtggca tttggtcagt cccagtcaac atccaccgtt ctaacgtaat    540
gtggtacatc ccggcaaaat taaaagaatg gggcgtgacc ccgccaaaaa catgggcaga    600
```

atttttagcg acagcgcaaa cattaaagcg gaaaggcctt gaggcaccat tggcactcgg 660
tgagaattgg acacagcaac atctctggga aagcgtcgcc ctcgccacac tgggtgccga 720
tggttggaat aatctctgga gtggtaagct caaattcacg gatccaaaag cagtcgccgt 780
atgggaaaca ttcggtaagg tattagatgc agcgaacaag gatgcagccg ggctttcatg 840
gcaacaagca gtagaccgtg tagtacaggg gaaagctgca ttcaatatca tgggggactg 900
ggcagcaggt tacatgagta cgaccttaaa actgaagcca ggtaccgact tcgcatggac 960
accttctccg ggcacttcag ggatctttat gatgctgtct gatagtttcg gcttgccaaa 1020
gggggcgaag aatcgtcaaa atgctattaa ctggttgaaa ctcgtcgggt caaaagaggg 1080
gcaggacacc ttcaacccgc tcaaaggttc catcgctgct cgtctcgatt ctgatcctgc 1140
caaatataat gcatacggcc aaagtgcaat gaaggactgg aagtcaaatc ggatcgtagg 1200
ctccctcgtc cacggcgcag tcgcgccaga atccttcatg tcgcagtttg ggacggtaat 1260 ggagatttc ttgcaatccc gtaacccgca ggcagccgct aatgccgcac aagctatcgc 1320
caatcaggtc ggtttaggtc gtgggggttc acatcatcat catcatcatt aatgaaaggg 1380
cgatatccag cacactggcg gccgttacta gtggatccgg ctgctaacaa agcccgaaag 1440
gaagctgagt tggctgctgc caccgctgag caataactag cataacccct tggggcctct 1500
aaacgggtct tgaggggttt tttgctgaaa ggaggaacta tatccggagc gactcccacg 1560
gcacgttggc aagctcg 1577

<210> SEQ ID NO 66
<211> LENGTH: 1577
<212> TYPE: DNA
<213> ORGANISM: Artificial Sequence
<220> FEATURE:
<223> OTHER INFORMATION: Exemplary tsGBP2_C9 expression sequence, optimized using OrfOpt

<400> SEQUENCE: 66
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaattaga 180 aatttttct tggtgcgcag gtgatgaagg cccagctctc gaagccttga tccggttgta 240
taaacagaaa tacccaggtg tagaggtcat taatgctacc gtcaccgggg gtgccggtgt 300
caacgccaaa gccgtcctta aaacgcgtat gctcggcggg gacccaccag ataccttca 360 agtacatgca gggcaggagc tgatcggcac atgggtcgtc gccgaccgta tggaagatct 420
tacctcattg tttcggcagg agggctggct tcaagcgttc ccaaaaggtt taatcgatct 480
cctcagttac aaaggtggca tttggtcagt cccagtcaac atccaccgtt ctaacgtaat 540
gtggtacatc ccggcaaaat taaaagaatg ggcgtgacc ccgccaaaaa catgggcaga 600
atttttagcg acagcgcaaa cattaaagcg gaaaggcctt gaggcaccat tggcactcgg 660
tgagaattgg acacagcaac atctctggga aagcgtcgcc ctcgccacac tgggtgccga 720
tggttggaat aatctctgga gtggtaagct caaattcacg gatccaaaag cagtcgccgt 780
atgggaaaca ttcggtaagg tattagatgc agcgaacaag gatgcagccg ggctttcatg 840
gcaacaagca gtagaccgtg tagtacaggg gaaagctgca ttcaatatca tgggggactg 900
ggcagcaggt tacatgagta cgaccttaaa actgaagcca ggtaccgact tcgcatggac 960
accttctccg ggcacttcag ggatctttat gatgctgtct gatagtttcg gcttgccaaa 1020
gggggcgaag aatcgtcaaa atgctattaa ctggttgaaa ctcgtcgggt caaaagaggg 1080
gcaggacacc ttcaacccgc tcaaaggttc catcgctgct cgtctcgatt ctgatcctgc 1140
caaatataat gcatacggcc aaagtgcaat gaaggactgg aagtcaaatc ggatcgtagg 1200
ctccctcgtc cacggcgcag tcgcgccaga atccttcatg tcgcagtttg ggacggtaat 1260
ggagattttc ttgcaatccc gtaacccgca ggcagccgct aatgccgcac aagctatcgc 1320
caatcaggtc ggtttaggtc gtgggggttc acatcatcat catcatcatt aatgaaaggg 1380
cgatatccag cacactggcg gccgttacta gtggatccgg ctgctaacaa agcccgaaag 1440
gaagctgagt tggctgctgc caccgctgag caataactag cataacccct tggggcctct 1500
aaacgggtct tgaggggttt tttgctgaaa ggaggaacta tatccggagc gactcccacg 1560
gcacgttggc aagctcg 1577

<210> SEQ ID NO 67
<211> LENGTH: 1577
<212> TYPE: DNA
<213> ORGANISM: Artificial Sequence
<220> FEATURE:
<223> OTHER INFORMATION: Exemplary tsGBP2_C12 expression sequence, optimized using OrfOpt

<400> SEQUENCE: 67
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaattaga 180
aatttttctt tggtgggcag gttgcgaagg cccagctctc gaagccttga tccggttgta 240
taaacagaaa tacccaggtg tagaggtcat taatgctacc gtcaccgggg gtgccggtgt 300
caacgccaaa gccgtcctta aaacgcgtat gctcggcggg gacccaccag ataccttcca 360
agtacatgca gggcaggagc tgatcggcac atgggtcgtc gccgaccgta tggaagatct 420
tacctcattg tttcggcagg agggctggct tcaagcgttc ccaaaaggtt taatcgatct 480
cctcagttac aaaggtggca tttggtcagt cccagtcaac atccaccgtt ctaacgtaat 540
gtggtacatc ccggcaaaat taaaagaatg gggcgtgacc ccgccaaaaa catgggcaga 600
atttttagcg acagcgcaaa cattaaagcg gaaaggcctt gaggcaccat tggcactcgg 660
tgagaattgg acacagcaac atctctggga aagcgtcgcc ctcgccacac tgggtgccga 720
tggttggaat aatctctgga gtggtaagct caaattcacg gatccaaaag cagtcgccgt 780
atgggaaaca ttcggtaagg tattagatgc agcgaacaag gatgcagccg ggctttcatg 840
gcaacaagca gtagaccgtg tagtacaggg gaaagctgca ttcaatatca tgggggactg 900
ggcagcaggt tacatgagta cgaccttaaa actgaagcca ggtaccgact tcgcatggac 960
accttctccg ggcacttcag ggatctttat gatgctgtct gatagtttcg gcttgccaaa 1020
gggggcgaag aatcgtcaaa atgctattaa ctggttgaaa ctcgtcgggt caaaagaggg 1080
gcaggacacc ttcaacccgc tcaaaggttc catcgctgct cgtctcgatt ctgatcctgc 1140
caaatataat gcatacggcc aaagtgcaat gaaggactgg aagtcaaatc ggatcgtagg 1200
ctccctcgtc cacggcgcag tcgcgccaga atccttcatg tcgcagtttg ggacggtaat 1260
ggagattttc ttgcaatccc gtaacccgca ggcagccgct aatgccgcac aagctatcgc 1320
caatcaggtc ggtttaggtc gtgggggttc acatcatcat catcatcatt aatgaaaggg 1380
cgatatccag cacactggcg gccgttacta gtggatccgg ctgctaacaa agcccgaaag 1440
gaagctgagt tggctgctgc caccgctgag caataactag cataacccct tggggcctct 1500
aaacgggtct tgaggggttt tttgctgaaa ggaggaacta tatccggagc gactcccacg 1560
gcacgttggc aagctcg 1577

<210> SEQ ID NO 68
<211> LENGTH: 1577
<212> TYPE: DNA
<213> ORGANISM: Artificial Sequence
<220> FEATURE:
<223> OTHER INFORMATION: Exemplary tsGBP2_C13 expression sequence, optimized using OrfOpt

<400> SEQUENCE: 68
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaattaga 180 aatttttttct tggtgggcag gtgattgcgg cccagctctc gaagccttga tccggttgta 240
taaacagaaa tacccaggtg tagaggtcat taatgctacc gtcaccgggg gtgccggtgt 300
caacgccaaa gccgtcctta aaacgcgtat gctcggcggg gacccaccag ataccttttca 360 agtacatgca gggcaggagc tgatcggcac atgggtcgtc gccgaccgta tggaagatct 420
tacctcattg tttcggcagg agggctggct tcaagcgttc ccaaaaggtt taatcgatct 480
cctcagttac aaaggtggca tttggtcagt cccagtcaac atccaccgtt ctaacgtaat 540
gtggtacatc ccggcaaaat taaaagaatg gggcgtgacc ccgccaaaaa catgggcaga 600
atttttagcg acagcgcaaa cattaaagcg gaaaggcctt gaggcaccat tggcactcgg 660
tgagaattgg acacagcaac atctctggga aagcgtcgcc ctcgccacac tgggtgccga 720
tggttggaat aatctctgga gtggtaagct caaattcacg gatccaaaag cagtcgccgt 780
atgggaaaca ttcggtaagg tattagatgc agcgaacaag gatgcagccg ggctttcatg 840
gcaacaagca gtagaccgtg tagtacaggg gaaagctgca ttcaatatca tgggggactg 900
ggcagcaggt tacatgagta cgaccttaaa actgaagcca ggtaccgact tcgcatggac 960
accttctccg ggcacttcag ggatctttat gatgctgtct gatagtttcg gcttgccaaa 1020
gggggcgaag aatcgtcaaa atgctattaa ctggttgaaa ctcgtcgggt caaaagaggg 1080
gcaggacacc ttcaacccgc tcaaaggttc catcgctgct cgtctcgatt ctgatcctgc 1140
caaatataat gcatacggcc aaagtgcaat gaaggactgg aagtcaaatc ggatcgtagg 1200
ctccctcgtc cacggcgcag tcgcgccaga atccttcatg tcgcagtttg ggacggtaat 1260
ggagattttc ttgcaatccc gtaacccgca ggcagccgct aatgccgcac aagctatcgc 1320
caatcaggtc ggtttaggtc gtgggggttc acatcatcat catcatcatt aatgaaaggg 1380
cgatatccag cacactggcg gccgttacta gtggatccgg ctgctaacaa agcccgaaag 1440
gaagctgagt tggctgctgc caccgctgag caataactag cataacccct tggggcctct 1500
aaacgggtct tgaggggttt tttgctgaaa ggaggaacta tatccggagc gactcccacg 1560
gcacgttggc aagctcg 1577

<210> SEQ ID NO 69
<211> LENGTH: 1577
<212> TYPE: DNA
<213> ORGANISM: Artificial Sequence
<220> FEATURE:
<223> OTHER INFORMATION: Exemplary tsGBP2_C41 expression sequence, optimized using OrfOpt

<400> SEQUENCE: 69

```
cggtcacgct tgggactgcc ataggctggc ccggtgatgc cggccacgat gcgtccggcg     60
tagaggatcg agatctcgat cccgcgaaat taatacgact cactataggg agaccacaac    120
ggtttccctc tagaaataat tttgtttaac tttaagaagg agatatacca tgaaattaga    180
aatttttcct tggtgggcag gtgatgaagg cccagctctc gaagccttga tccggttgta    240
taaacagaaa tacccaggtg tagaggtcat taatgctacc gtcaccgggt gcgccggtgt    300
caacgccaaa gccgtcctta aaacgcgtat gctcggcggg gacccaccag ataccttca     360
agtacatgca gggcaggagc tgatcggcac atgggtcgtc gccgaccgta tggaagatct    420
tacctcattg tttcggcagg agggctggct tcaagcgttc ccaaaaggtt taatcgatct    480
cctcagttac aaaggtggca tttggtcagt cccagtcaac atccaccgtt ctaacgtaat    540
gtggtacatc ccggcaaaat taaaagaatg gggcgtgacc ccgccaaaaa catgggcaga    600
atttttagcg acagcgcaaa cattaaagcg gaaaggcctt gaggcaccat tggcactcgg    660
tgagaattgg acacagcaac atctctggga aagcgtcgcc ctcgccacac tgggtgccga    720
tggttggaat aatctctgga gtggtaagct caaattcacg gatccaaaag cagtcgccgt    780
atgggaaaca ttcggtaagg tattagatgc agcgaacaag gatgcagccg ggctttcatg    840
gcaacaagca gtagaccgtg tagtacaggg gaaagctgca ttcaatatca tgggggactg    900
ggcagcaggt tacatgagta cgaccttaaa actgaagcca ggtaccgact tcgcatggac    960
accttctccg ggcacttcag ggatctttat gatgctgtct gatagtttcg gcttgccaaa   1020
gggggcgaag aatcgtcaaa atgctattaa ctggttgaaa ctcgtcgggt caaaagaggg   1080
gcaggacacc ttcaacccgc tcaaaggttc catcgctgct cgtctcgatt ctgatcctgc   1140
caaatataat gcatacggcc aaagtgcaat gaaggactgg aagtcaaatc ggatcgtagg   1200
ctccctcgtc cacggcgcag tcgcgccaga atccttcatg tcgcagtttg ggacggtaat   1260
ggagattttc ttgcaatccc gtaacccgca ggcagccgct aatgccgcac aagctatcgc   1320
caatcaggtc ggtttaggtc gtgggggttc acatcatcat catcatcatt aatgaaaggg   1380
cgatatccag cacactggcg gccgttacta gtggatccgg ctgctaacaa agcccgaaag   1440
gaagctgagt tggctgctgc caccgctgag caataactag cataacccct tggggcctct   1500
aaacgggtct tgaggggttt tttgctgaaa ggaggaacta tatccggagc gactcccacg   1560
gcacgttggc aagctcg                                                  1577
```

<210> SEQ ID NO 70
<211> LENGTH: 1577
<212> TYPE: DNA
<213> ORGANISM: Artificial Sequence
<220> FEATURE:
<223> OTHER INFORMATION: Exemplary tsGBP2_C42 expression sequence, optimized using OrfOpt

<400> SEQUENCE: 70

```
cggtcacgct tgggactgcc ataggctggc ccggtgatgc cggccacgat gcgtccggcg     60
tagaggatcg agatctcgat cccgcgaaat taatacgact cactataggg agaccacaac    120
ggtttccctc tagaaataat tttgtttaac tttaagaagg agatatacca tgaaattaga    180
aatttttcct tggtgggcag gtgatgaagg cccagctctc gaagccttga tccggttgta    240
taaacagaaa tacccaggtg tagaggtcat taatgctacc gtcaccgggg gttgcggtgt    300
```

```
caacgccaaa gccgtcctta aaacgcgtat gctcggcggg gacccaccag atacctttca    360
agtacatgca gggcaggagc tgatcggcac atgggtcgtc gccgaccgta tggaagatct    420
tacctcattg tttcggcagg agggctggct tcaagcgttc ccaaaaggtt taatcgatct    480
cctcagttac aaaggtggca tttggtcagt cccagtcaac atccaccgtt ctaacgtaat    540
gtggtacatc ccggcaaaat taaaagaatg gggcgtgacc ccgccaaaaa catgggcaga    600
atttttagcg acagcgcaaa cattaaagcg gaaaggcctt gaggcaccat tggcactcgg    660
tgagaattgg acacagcaac atctctggga aagcgtcgcc ctcgccacac tgggtgccga    720
tggttggaat aatctctgga gtggtaagct caaattcacg gatccaaaag cagtcgccgt    780
atgggaaaca ttcggtaagg tattagatgc agcgaacaag gatgcagccg ggctttcatg    840
gcaacaagca gtagaccgtg tagtacaggg gaaagctgca ttcaatatca tgggggactg    900
ggcagcaggt tacatgagta cgaccttaaa actgaagcca ggtaccgact tcgcatggac    960
accttctccg ggcacttcag ggatctttat gatgctgtct gatagtttcg gcttgccaaa   1020
gggggcgaag aatcgtcaaa atgctattaa ctggttgaaa ctcgtcgggt caaaagaggg   1080
gcaggacacc ttcaacccgc tcaaaggttc catcgctgct cgtctcgatt ctgatcctgc   1140
caaatataat gcatacggcc aaagtgcaat gaaggactgg aagtcaaatc ggatcgtagg   1200
ctccctcgtc cacggcgcag tcgcgccaga atccttcatg tcgcagtttg ggacggtaat   1260
ggagattttc ttgcaatccc gtaacccgca ggcagccgct aatgccgcac aagctatcgc   1320
caatcaggtc ggtttaggtc gtgggggttc acatcatcat catcatcatt aatgaaaggg   1380
cgatatccag cacactggcg gccgttacta gtggatccgg ctgctaacaa agcccgaaag   1440
gaagctgagt tggctgctgc caccgctgag caataactag cataacccct tggggcctct   1500
aaacgggtct tgaggggttt tttgctgaaa ggaggaacta tatccggagc gactcccacg   1560
gcacgttggc aagctcg                                                  1577

<210> SEQ ID NO 71
<211> LENGTH: 1577
<212> TYPE: DNA
<213> ORGANISM: Artificial Sequence
<220> FEATURE:
<223> OTHER INFORMATION: Exemplary tsGBP2_C64 expression sequence,
      optimized using OrfOpt

<400> SEQUENCE: 71

cggtcacgct tgggactgcc ataggctggc ccggtgatgc cggccacgat gcgtccggcg     60
tagaggatcg agatctcgat cccgcgaaat taatacgact cactataggg agaccacaac    120
ggtttccctc tagaaataat tttgtttaac tttaagaagg agatatacca tgaaattaga    180
aatttttctt tggtgggcag gtgatgaagg cccagctctc gaagccttga tccggttgta    240
taaacagaaa tacccaggtg tagaggtcat taatgctacc gtcaccgggg gtgccggtgt    300
caacgccaaa gccgtcctta aaacgcgtat gctcggcggg gacccaccag atacctttg     360
cgtacatgca gggcaggagc tgatcggcac atgggtcgtc gccgaccgta tggaagatct    420
tacctcattg tttcggcagg agggctggct tcaagcgttc ccaaaaggtt taatcgatct    480
cctcagttac aaaggtggca tttggtcagt cccagtcaac atccaccgtt ctaacgtaat    540
gtggtacatc ccggcaaaat taaaagaatg gggcgtgacc ccgccaaaaa catgggcaga    600
atttttagcg acagcgcaaa cattaaagcg gaaaggcctt gaggcaccat tggcactcgg    660
tgagaattgg acacagcaac atctctggga aagcgtcgcc ctcgccacac tgggtgccga    720
```

-continued

```
tggttggaat aatctctgga gtggtaagct caaattcacg gatccaaaag cagtcgccgt    780

atgggaaaca ttcggtaagg tattagatgc agcgaacaag gatgcagccg ggctttcatg    840

gcaacaagca gtagaccgtg tagtacaggg gaaagctgca ttcaatatca tgggggactg    900

ggcagcaggt tacatgagta cgaccttaaa actgaagcca ggtaccgact tcgcatggac    960

accttctccg ggcacttcag ggatctttat gatgctgtct gatagtttcg gcttgccaaa   1020

gggggcgaag aatcgtcaaa atgctattaa ctggttgaaa ctcgtcgggt caaaagaggg   1080

gcaggacacc ttcaacccgc tcaaaggttc catcgctgct cgtctcgatt ctgatcctgc   1140

caaatataat gcatacggcc aaagtgcaat gaaggactgg aagtcaaatc ggatcgtagg   1200

ctccctcgtc cacggcgcag tcgcgccaga atccttcatg tcgcagtttg ggacggtaat   1260

ggagattttc ttgcaatccc gtaacccgca ggcagccgct aatgccgcac aagctatcgc   1320

caatcaggtc ggtttaggtc gtgggggttc acatcatcat catcatcatt aatgaaaggg   1380

cgatatccag cacactggcg gccgttacta gtggatccgg ctgctaacaa agcccgaaag   1440

gaagctgagt tggctgctgc caccgctgag caataactag cataacccct tggggcctct   1500

aaacgggtct tgaggggttt tttgctgaaa ggaggaacta tatccggagc gactcccacg   1560

gcacgttggc aagctcg                                                  1577
```

```
<210> SEQ ID NO 72
<211> LENGTH: 1577
<212> TYPE: DNA
<213> ORGANISM: Artificial Sequence
<220> FEATURE:
<223> OTHER INFORMATION: Exemplary tsGBP2_C66 expression sequence,
      optimized using OrfOpt

<400> SEQUENCE: 72
```

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaattaga    180

aatttttttct tggtgggcag gtgatgaagg cccagctctc gaagccttga tccggttgta    240

taaacagaaa tacccaggtg tagaggtcat taatgctacc gtcaccgggg gtgccggtgt    300

caacgccaaa gccgtcctta aaacgcgtat gctcggcggg gacccaccag ataccttca     360

agtatgcgca gggcaggagc tgatcggcac atgggtcgtc gccgaccgta tggaagatct    420

tacctcattg tttcggcagg agggctggct tcaagcgttc ccaaaaggtt taatcgatct    480

cctcagttac aaaggtggca tttggtcagt cccagtcaac atccaccgtt ctaacgtaat    540

gtggtacatc ccggcaaaat taaaagaatg gggcgtgacc ccgccaaaaa catgggcaga    600

atttttagcg acagcgcaaa cattaaagcg gaaaggcctt gaggcaccat tggcactcgg    660

tgagaattgg acacagcaac atctctggga aagcgtcgcc ctcgccacac tgggtgccga    720

tggttggaat aatctctgga gtggtaagct caaattcacg gatccaaaag cagtcgccgt    780

atgggaaaca ttcggtaagg tattagatgc agcgaacaag gatgcagccg ggctttcatg    840

gcaacaagca gtagaccgtg tagtacaggg gaaagctgca ttcaatatca tgggggactg    900

ggcagcaggt tacatgagta cgaccttaaa actgaagcca ggtaccgact tcgcatggac    960

accttctccg ggcacttcag ggatctttat gatgctgtct gatagtttcg gcttgccaaa   1020

gggggcgaag aatcgtcaaa atgctattaa ctggttgaaa ctcgtcgggt caaaagaggg   1080

gcaggacacc ttcaacccgc tcaaaggttc catcgctgct cgtctcgatt ctgatcctgc   1140
```

-continued

```
caaatataat gcatacggcc aaagtgcaat gaaggactgg aagtcaaatc ggatcgtagg   1200

ctccctcgtc cacggcgcag tcgcgccaga atccttcatg tcgcagtttg ggacggtaat   1260

ggagattttc ttgcaatccc gtaacccgca ggcagccgct aatgccgcac aagctatcgc   1320

caatcaggtc ggtttaggtc gtgggggttc acatcatcat catcatcatt aatgaaaggg   1380

cgatatccag cacactggcg gccgttacta gtggatccgg ctgctaacaa agcccgaaag   1440

gaagctgagt tggctgctgc caccgctgag caataactag cataacccct tggggcctct   1500

aaacgggtct tgaggggttt tttgctgaaa ggaggaacta tatccggagc gactcccacg   1560

gcacgttggc aagctcg                                                  1577
```

```
<210> SEQ ID NO 73
<211> LENGTH: 1577
<212> TYPE: DNA
<213> ORGANISM: Artificial Sequence
<220> FEATURE:
<223> OTHER INFORMATION: Exemplary tsGBP2_C119 expression sequence,
      optimized using OrfOpt

<400> SEQUENCE: 73

cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaattaga    180

aatttttctt tggtgggcag gtgatgaagg cccagctctc gaagccttga tccggttgta    240

taaacagaaa tacccaggtg tagaggtcat taatgctacc gtcaccgggg gtgccggtgt    300

caacgccaaa gccgtcctta aaacgcgtat gctcggcggg gacccaccag ataccttca    360

agtacatgca gggcaggagc tgatcggcac atgggtcgtc gccgaccgta tggaagatct    420

tacctcattg tttcggcagg agggctggct tcaagcgttc ccaaaaggtt taatcgatct    480

cctcagttac aaaggtggca tttggtcagt cccagtcaac atctgccgtt ctaacgtaat    540

gtggtacatc ccggcaaaat taaaagaatg gggcgtgacc ccgccaaaaa catgggcaga    600

atttttagcg acagcgcaaa cattaaagcg gaaaggcctt gaggcaccat tggcactcgg    660

tgagaattgg acacagcaac atctctggga aagcgtcgcc ctcgccacac tgggtgccga    720

tggttggaat aatctctgga gtggtaagct caaattcacg gatccaaaag cagtcgccgt    780

atgggaaaca ttcggtaagg tattagatgc agcgaacaag gatgcagccg ggctttcatg    840

gcaacaagca gtagaccgtg tagtacaggg gaaagctgca ttcaatatca tgggggactg    900

ggcagcaggt tacatgagta cgaccttaaa actgaagcca ggtaccgact tcgcatggac    960

accttctccg ggcacttcag ggatctttat gatgctgtct gatagtttcg gcttgccaaa   1020

gggggcgaag aatcgtcaaa atgctattaa ctggttgaaa ctcgtcgggt caaaagaggg   1080

gcaggacacc ttcaacccgc tcaaaggttc catcgctgct cgtctcgatt ctgatcctgc   1140

caaatataat gcatacggcc aaagtgcaat gaaggactgg aagtcaaatc ggatcgtagg   1200

ctccctcgtc cacggcgcag tcgcgccaga atccttcatg tcgcagtttg ggacggtaat   1260

ggagattttc ttgcaatccc gtaacccgca ggcagccgct aatgccgcac aagctatcgc   1320

caatcaggtc ggtttaggtc gtgggggttc acatcatcat catcatcatt aatgaaaggg   1380

cgatatccag cacactggcg gccgttacta gtggatccgg ctgctaacaa agcccgaaag   1440

gaagctgagt tggctgctgc caccgctgag caataactag cataacccct tggggcctct   1500

aaacgggtct tgaggggttt tttgctgaaa ggaggaacta tatccggagc gactcccacg   1560
```

```
gcacgttggc aagctcg                                                1577


<210> SEQ ID NO 74
<211> LENGTH: 1577
<212> TYPE: DNA
<213> ORGANISM: Artificial Sequence
<220> FEATURE:
<223> OTHER INFORMATION: Exemplary tsGBP2_C167 expression sequence,
      optimized using OrfOpt

<400> SEQUENCE: 74

cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaattaga    180

aatttttctt tggtgggcag gtgatgaagg cccagctctc gaagccttga tccggttgta    240

taaacagaaa tacccaggtg tagaggtcat taatgctacc gtcaccgggg gtgccggtgt    300

caacgccaaa gccgtcctta aaacgcgtat gctcggcggg gacccaccag atacctttca    360

agtacatgca gggcaggagc tgatcggcac atgggtcgtc gccgaccgta tggaagatct    420

tacctcattg tttcggcagg agggctggct tcaagcgttc ccaaaaggtt taatcgatct    480

cctcagttac aaaggtggca tttggtcagt cccagtcaac atccaccgtt ctaacgtaat    540

gtggtacatc ccggcaaaat taaaagaatg ggcgtgacc ccgccaaaaa catgggcaga    600

atttttagcg acagcgcaaa cattaaagcg gaaaggcctt gaggcaccat tggcactcgg    660

tgagaattgc acacagcaac atctctggga aagcgtcgcc ctcgccacac tgggtgccga    720

tggttggaat aatctctgga gtggtaagct caaattcacg gatccaaaag cagtcgccgt    780

atgggaaaca ttcggtaagg tattagatgc agcgaacaag gatgcagccg ggctttcatg    840

gcaacaagca gtagaccgtg tagtacaggg gaaagctgca ttcaatatca tgggggactg    900

ggcagcaggt tacatgagta cgaccttaaa actgaagcca ggtaccgact tcgcatggac    960

accttctccg ggcacttcag ggatctttat gatgctgtct gatagtttcg gcttgccaaa   1020

gggggcgaag aatcgtcaaa atgctattaa ctggttgaaa ctcgtcgggt caaaagaggg   1080

gcaggacacc ttcaacccgc tcaaaggttc catcgctgct cgtctcgatt ctgatcctgc   1140

caaatataat gcatacggcc aaagtgcaat gaaggactgg aagtcaaatc ggatcgtagg   1200

ctccctcgtc cacggcgcag tcgcgccaga atccttcatg tcgcagtttg ggacggtaat   1260

ggagatttc ttgcaatccc gtaacccgca ggcagccgct aatgccgcac aagctatcgc   1320

caatcaggtc ggtttaggtc gtgggggttc acatcatcat catcatcatt aatgaaaggg   1380

cgatatccag cacactggcg gccgttacta gtggatccgg ctgctaacaa agcccgaaag   1440

gaagctgagt tggctgctgc caccgctgag caataactag cataacccct tggggcctct   1500

aaacgggtct tgaggggttt tttgctgaaa ggaggaacta tatccggagc gactcccacg   1560

gcacgttggc aagctcg                                                1577


<210> SEQ ID NO 75
<211> LENGTH: 1577
<212> TYPE: DNA
<213> ORGANISM: Artificial Sequence
<220> FEATURE:
<223> OTHER INFORMATION: Exemplary tsGBP2_C223 expression sequence,
      optimized using OrfOpt

<400> SEQUENCE: 75

cggtcacgct tgggactgcc ataggctggc ccggtgatgc cggccacgat gcgtccggcg     60
```

```
tagaggatcg agatctcgat cccgcgaaat taatacgact cactataggg agaccacaac    120
ggtttccctc tagaaataat tttgtttaac tttaagaagg agatatacca tgaaattaga    180
aatttttct tggtgggcag gtgatgaagg cccagctctc gaagccttga tccggttgta    240
taaacagaaa tacccaggtg tagaggtcat taatgctacc gtcaccgggg gtgccggtgt    300
caacgccaaa gccgtcctta aaacgcgtat gctcggcggg gacccaccag ataccttca    360
agtacatgca gggcaggagc tgatcggcac atgggtcgtc gccgaccgta tggaagatct    420
tacctcattg tttcggcagg agggctggct tcaagcgttc ccaaaaggtt taatcgatct    480
cctcagttac aaaggtggca tttggtcagt cccagtcaac atccaccgtt ctaacgtaat    540
gtggtacatc ccggcaaaat taaaagaatg ggcgtgacc ccgccaaaaa catgggcaga    600
atttttagcg acagcgcaaa cattaaagcg gaaaggcctt gaggcaccat tggcactcgg    660
tgagaattgg acacagcaac atctctggga aagcgtcgcc ctcgccacac tgggtgccga    720
tggttggaat aatctctgga gtggtaagct caaattcacg gatccaaaag cagtcgccgt    780
atgggaaaca ttcggtaagg tattagatgc agcgaacaag gatgcagccg ggctttgctg    840
gcaacaagca gtagaccgtg tagtacaggg gaaagctgca ttcaatatca tgggggactg    900
ggcagcaggt tacatgagta cgaccttaaa actgaagcca ggtaccgact tcgcatggac    960
accttctccg ggcacttcag ggatctttat gatgctgtct gatagtttcg gcttgccaaa   1020
gggggcgaag aatcgtcaaa atgctattaa ctggttgaaa ctcgtcgggt caaaagaggg   1080
gcaggacacc ttcaacccgc tcaaaggttc catcgctgct cgtctcgatt ctgatcctgc   1140
caaatataat gcatacggcc aaagtgcaat gaaggactgg aagtcaaatc ggatcgtagg   1200
ctccctcgtc cacggcgcag tcgcgccaga atccttcatg tcgcagtttg ggacggtaat   1260
ggagatttc ttgcaatccc gtaacccgca ggcagccgct aatgccgcac aagctatcgc   1320
caatcaggtc ggtttaggtc gtgggggttc acatcatcat catcatcatt aatgaaaggg   1380
cgatatccag cacactggcg gccgttacta gtggatccgg ctgctaacaa agcccgaaag   1440
gaagctgagt tggctgctgc caccgctgag caataactag cataacccct tggggcctct   1500
aaacgggtct tgaggggttt tttgctgaaa ggaggaacta tatccggagc gactcccacg   1560
gcacgttggc aagctcg                                                  1577
```

```
<210> SEQ ID NO 76
<211> LENGTH: 1577
<212> TYPE: DNA
<213> ORGANISM: Artificial Sequence
<220> FEATURE:
<223> OTHER INFORMATION: Exemplary tsGBP2_C224 expression sequence,
      optimized using OrfOpt

<400> SEQUENCE: 76
```

```
cggtcacgct tgggactgcc ataggctggc ccggtgatgc cggccacgat gcgtccggcg     60
tagaggatcg agatctcgat cccgcgaaat taatacgact cactataggg agaccacaac    120
ggtttccctc tagaaataat tttgtttaac tttaagaagg agatatacca tgaaattaga    180
aatttttct tggtgggcag gtgatgaagg cccagctctc gaagccttga tccggttgta    240
taaacagaaa tacccaggtg tagaggtcat taatgctacc gtcaccgggg gtgccggtgt    300
caacgccaaa gccgtcctta aaacgcgtat gctcggcggg gacccaccag ataccttca    360
agtacatgca gggcaggagc tgatcggcac atgggtcgtc gccgaccgta tggaagatct    420
tacctcattg tttcggcagg agggctggct tcaagcgttc ccaaaaggtt taatcgatct    480
```

-continued cctcagttac aaaggtggca tttggtcagt cccagtcaac atccaccgtt ctaacgtaat 540
gtggtacatc ccggcaaaat taaaagaatg gggcgtgacc ccgccaaaaa catgggcaga 600
atttttagcg acagcgcaaa cattaaagcg gaaaggcctt gaggcaccat tggcactcgg 660
tgagaattgg acacagcaac atctctggga aagcgtcgcc ctcgccacac tgggtgccga 720
tggttggaat aatctctgga gtggtaagct caaattcacg gatccaaaag cagtcgccgt 780
atgggaaaca ttcggtaagg tattagatgc agcgaacaag gatgcagccg ggctttcatg 840
ccaacaagca gtagaccgtg tagtacaggg gaaagctgca ttcaatatca tgggggactg 900
ggcagcaggt tacatgagta cgaccttaaa actgaagcca ggtaccgact tcgcatggac 960
accttctccg ggcacttcag ggatctttat gatgctgtct gatagtttcg gcttgccaaa 1020
gggggcgaag aatcgtcaaa atgctattaa ctggttgaaa ctcgtcgggt caaaagaggg 1080
gcaggacacc ttcaacccgc tcaaaggttc catcgctgct cgtctcgatt ctgatcctgc 1140
caaatataat gcatacggcc aaagtgcaat gaaggactgg aagtcaaatc ggatcgtagg 1200
ctccctcgtc cacggcgcag tcgcgccaga atccttcatg tcgcagtttg ggacggtaat 1260 ggagatttc ttgcaatccc gtaacccgca ggcagccgct aatgccgcac aagctatcgc 1320
caatcaggtc ggtttaggtc gtgggggttc acatcatcat catcatcatt aatgaaaggg 1380
cgatatccag cacactggcg gccgttacta gtggatccgg ctgctaacaa agcccgaaag 1440
gaagctgagt tggctgctgc caccgctgag caataactag cataacccct tggggcctct 1500
aaacgggtct tgaggggttt tttgctgaaa ggaggaacta tatccggagc gactcccacg 1560
gcacgttggc aagctcg 1577

<210> SEQ ID NO 77
<211> LENGTH: 1577
<212> TYPE: DNA
<213> ORGANISM: Artificial Sequence
<220> FEATURE:
<223> OTHER INFORMATION: Exemplary tsGBP2_C225 expression sequence, optimized using OrfOpt

<400> SEQUENCE: 77
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaattaga 180
aattttttct tggtgggcag gtgatgaagg cccagctctc gaagccttga tccggttgta 240
taaacagaaa tacccaggtg tagaggtcat taatgctacc gtcaccgggg gtgccggtgt 300
caacgccaaa gccgtcctta aaacgcgtat gctcggcggg gacccaccag ataccttca 360 agtacatgca gggcaggagc tgatcggcac atgggtcgtc gccgaccgta tggaagatct 420
tacctcattg tttcggcagg agggctggct tcaagcgttc ccaaaaggtt taatcgatct 480
cctcagttac aaaggtggca tttggtcagt cccagtcaac atccaccgtt ctaacgtaat 540
gtggtacatc ccggcaaaat taaaagaatg gggcgtgacc ccgccaaaaa catgggcaga 600
atttttagcg acagcgcaaa cattaaagcg gaaaggcctt gaggcaccat tggcactcgg 660
tgagaattgg acacagcaac atctctggga aagcgtcgcc ctcgccacac tgggtgccga 720
tggttggaat aatctctgga gtggtaagct caaattcacg gatccaaaag cagtcgccgt 780
atgggaaaca ttcggtaagg tattagatgc agcgaacaag gatgcagccg ggctttcatg 840
gtgccaagca gtagaccgtg tagtacaggg gaaagctgca ttcaatatca tgggggactg 900

```
ggcagcaggt tacatgagta cgaccttaaa actgaagcca ggtaccgact tcgcatggac    960

accttctccg ggcacttcag ggatctttat gatgctgtct gatagtttcg gcttgccaaa   1020

gggggcgaag aatcgtcaaa atgctattaa ctggttgaaa ctcgtcgggt caaaagaggg   1080

gcaggacacc ttcaacccgc tcaaaggttc catcgctgct cgtctcgatt ctgatcctgc   1140

caaatataat gcatacggcc aaagtgcaat gaaggactgg aagtcaaatc ggatcgtagg   1200

ctccctcgtc cacggcgcag tcgcgccaga atccttcatg tcgcagtttg ggacggtaat   1260

ggagattttc ttgcaatccc gtaacccgca ggcagccgct aatgccgcac aagctatcgc   1320

caatcaggtc ggtttaggtc gtgggggttc acatcatcat catcatcatt aatgaaaggg   1380

cgatatccag cacactggcg gccgttacta gtggatccgg ctgctaacaa agcccgaaag   1440

gaagctgagt tggctgctgc caccgctgag caataactag cataacccct tggggcctct   1500

aaacgggtct tgaggggttt tttgctgaaa ggaggaacta tatccggagc gactcccacg   1560

gcacgttggc aagctcg                                                  1577
```

```
<210> SEQ ID NO 78
<211> LENGTH: 1577
<212> TYPE: DNA
<213> ORGANISM: Artificial Sequence
<220> FEATURE:
<223> OTHER INFORMATION: Exemplary tsGBP2_C244 expression sequence,
      optimized using OrfOpt

<400> SEQUENCE: 78
```

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaattaga    180

aatttttttct tggtgggcag gtgatgaagg cccagctctc gaagccttga tccggttgta    240

taaacagaaa tacccaggtg tagaggtcat taatgctacc gtcaccgggg gtgccggtgt    300

caacgccaaa gccgtcctta aaacgcgtat gctcggcggg gacccaccag ataccttttca    360

agtacatgca gggcaggagc tgatcggcac atgggtcgtc gccgaccgta tggaagatct    420

tacctcattg tttcggcagg agggctggct tcaagcgttc ccaaaaggtt taatcgatct    480

cctcagttac aaaggtggca tttggtcagt cccagtcaac atccaccgtt ctaacgtaat    540

gtggtacatc ccggcaaaat taaaagaatg gggcgtgacc ccgccaaaaa catgggcaga    600

atttttagcg acagcgcaaa cattaaagcg gaaaggcctt gaggcaccat tggcactcgg    660

tgagaattgg acacagcaac atctctggga aagcgtcgcc ctcgccacac tgggtgccga    720

tggttggaat aatctctgga gtggtaagct caaattcacg gatccaaaag cagtcgccgt    780

atgggaaaca ttcggtaagg tattagatgc agcgaacaag gatgcagccg ggctttcatg    840

gcaacaagca gtagaccgtg tagtacaggg gaaagctgca ttcaatatca tgggggactg    900

cgcagcaggt tacatgagta cgaccttaaa actgaagcca ggtaccgact tcgcatggac    960

accttctccg ggcacttcag ggatctttat gatgctgtct gatagtttcg gcttgccaaa   1020

gggggcgaag aatcgtcaaa atgctattaa ctggttgaaa ctcgtcgggt caaaagaggg   1080

gcaggacacc ttcaacccgc tcaaaggttc catcgctgct cgtctcgatt ctgatcctgc   1140

caaatataat gcatacggcc aaagtgcaat gaaggactgg aagtcaaatc ggatcgtagg   1200

ctccctcgtc cacggcgcag tcgcgccaga atccttcatg tcgcagtttg ggacggtaat   1260

ggagattttc ttgcaatccc gtaacccgca ggcagccgct aatgccgcac aagctatcgc   1320
```

caatcaggtc ggtttaggtc gtgggggttc acatcatcat catcatcatt aatgaaaggg 1380
cgatatccag cacactggcg gccgttacta gtggatccgg ctgctaacaa agcccgaaag 1440
gaagctgagt tggctgctgc caccgctgag caataactag cataacccct tggggcctct 1500
aaacgggtct tgaggggttt tttgctgaaa ggaggaacta tatccggagc gactcccacg 1560
gcacgttggc aagctcg 1577

<210> SEQ ID NO 79
<211> LENGTH: 1577
<212> TYPE: DNA
<213> ORGANISM: Artificial Sequence
<220> FEATURE:
<223> OTHER INFORMATION: Exemplary tsGBP2_C277 expression sequence, optimized using OrfOpt

<400> SEQUENCE: 79
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaattaga 180 aatttttct tggtgggcag gtgatgaagg cccagctctc gaagccttga tccggttgta 240
taaacagaaa tacccaggtg tagaggtcat taatgctacc gtcaccgggg gtgccggtgt 300
caacgccaaa gccgtcctta aaacgcgtat gctcggcggg gacccaccag atacctttca 360
agtacatgca gggcaggagc tgatcggcac atgggtcgtc gccgaccgta tggaagatct 420
tacctcattg tttcggcagg agggctggct tcaagcgttc ccaaaaggtt taatcgatct 480
cctcagttac aaaggtggca tttggtcagt cccagtcaac atccaccgtt ctaacgtaat 540
gtggtacatc ccggcaaaat taaaagaatg gggcgtgacc ccgccaaaaa catgggcaga 600
atttttagcg acagcgcaaa cattaaagcg gaaaggcctt gaggcaccat tggcactcgg 660
tgagaattgg acacagcaac atctctggga aagcgtcgcc ctcgccacac tgggtgccga 720
tggttggaat aatctctgga gtggtaagct caaattcacg gatccaaaag cagtcgccgt 780
atgggaaaca ttcggtaagg tattagatgc agcgaacaag gatgcagccg ggctttcatg 840
gcaacaagca gtagaccgtg tagtacaggg gaaagctgca ttcaatatca tgggggactg 900
ggcagcaggt tacatgagta cgaccttaaa actgaagcca ggtaccgact tcgcatggac 960
accttctccg ggcacttcag ggatctttat gatgctgtgc gatagtttcg gcttgccaaa 1020
gggggcgaag aatcgtcaaa atgctattaa ctggttgaaa ctcgtcgggt caaaagaggg 1080
gcaggacacc ttcaacccgc tcaaaggttc catcgctgct cgtctcgatt ctgatcctgc 1140
caaatataat gcatacggcc aaagtgcaat gaaggactgg aagtcaaatc ggatcgtagg 1200
ctccctcgtc cacggcgcag tcgcgccaga atccttcatg tcgcagtttg ggacggtaat 1260 ggagatttc ttgcaatccc gtaacccgca ggcagccgct aatgccgcac aagctatcgc 1320
caatcaggtc ggtttaggtc gtgggggttc acatcatcat catcatcatt aatgaaaggg 1380
cgatatccag cacactggcg gccgttacta gtggatccgg ctgctaacaa agcccgaaag 1440
gaagctgagt tggctgctgc caccgctgag caataactag cataacccct tggggcctct 1500
aaacgggtct tgaggggttt tttgctgaaa ggaggaacta tatccggagc gactcccacg 1560
gcacgttggc aagctcg 1577

<210> SEQ ID NO 80
<211> LENGTH: 1577

<212> TYPE: DNA
<213> ORGANISM: Artificial Sequence
<220> FEATURE:
<223> OTHER INFORMATION: Exemplary tsGBP2_C278 expression sequence,
optimized using OrfOpt

<400> SEQUENCE: 80

```
cggtcacgct tgggactgcc ataggctggc ccggtgatgc cggccacgat gcgtccggcg     60
tagaggatcg agatctcgat cccgcgaaat taatacgact cactataggg agaccacaac    120
ggtttccctc tagaaataat tttgtttaac tttaagaagg agatatacca tgaaattaga    180
aattttttct tggtgggcag gtgatgaagg cccagctctc gaagccttga tccggttgta    240
taaacagaaa tacccaggtg tagaggtcat taatgctacc gtcaccgggg gtgccggtgt    300
caacgccaaa gccgtcctta aaacgcgtat gctcggcggg gacccaccag atacctttca    360
agtacatgca gggcaggagc tgatcggcac atgggtcgtc gccgaccgta tggaagatct    420
tacctcattg tttcggcagg agggctggct tcaagcgttc ccaaaaggtt taatcgatct    480
cctcagttac aaaggtggca tttggtcagt cccagtcaac atccaccgtt ctaacgtaat    540
gtggtacatc ccggcaaaat taaaagaatg gggcgtgacc ccgccaaaaa catgggcaga    600
atttttagcg acagcgcaaa cattaaagcg gaaaggcctt gaggcaccat tggcactcgg    660
tgagaattgg acacagcaac atctctggga aagcgtcgcc ctcgccacac tgggtgccga    720
tggttggaat aatctctgga gtggtaagct caaattcacg gatccaaaag cagtcgccgt    780
atgggaaaca ttcggtaagg tattagatgc agcgaacaag gatgcagccg ggctttcatg    840
gcaacaagca gtagaccgtg tagtacaggg gaaagctgca ttcaatatca tgggggactg    900
ggcagcaggt tacatgagta cgaccttaaa actgaagcca ggtaccgact tcgcatggac    960
accttctccg ggcacttcag ggatctttat gatgctgtct tgcagtttcg gcttgccaaa   1020
gggggcgaag aatcgtcaaa atgctattaa ctggttgaaa ctcgtcgggt caaaagaggg   1080
gcaggacacc ttcaacccgc tcaaaggttc catcgctgct cgtctcgatt ctgatcctgc   1140
caaatataat gcatacggcc aaagtgcaat gaaggactgg aagtcaaatc ggatcgtagg   1200
ctccctcgtc cacggcgcag tcgcgccaga atccttcatg tcgcagtttg ggacggtaat   1260
ggagattttc ttgcaatccc gtaacccgca ggcagccgct aatgccgcac aagctatcgc   1320
caatcaggtc ggtttaggtc gtgggggttc acatcatcat catcatcatt aatgaaaggg   1380
cgatatccag cacactggcg gccgttacta gtggatccgg ctgctaacaa agcccgaaag   1440
gaagctgagt tggctgctgc caccgctgag caataactag cataacccct tggggcctct   1500
aaacgggtct tgaggggttt tttgctgaaa ggaggaacta tatccggagc gactcccacg   1560
gcacgttggc aagctcg                                                  1577
```

<210> SEQ ID NO 81
<211> LENGTH: 1577
<212> TYPE: DNA
<213> ORGANISM: Artificial Sequence
<220> FEATURE:
<223> OTHER INFORMATION: Exemplary tsGBP2_C312 expression sequence,
optimized using OrfOpt

<400> SEQUENCE: 81

```
cggtcacgct tgggactgcc ataggctggc ccggtgatgc cggccacgat gcgtccggcg     60
tagaggatcg agatctcgat cccgcgaaat taatacgact cactataggg agaccacaac    120
ggtttccctc tagaaataat tttgtttaac tttaagaagg agatatacca tgaaattaga    180
```

-continued

```
aatttttct tggtgggcag gtgatgaagg cccagctctc gaagccttga tccggttgta    240

taaacagaaa tacccaggtg tagaggtcat taatgctacc gtcaccgggg gtgccggtgt    300

caacgccaaa gccgtcctta aaacgcgtat gctcggcggg gacccaccag atacctttca    360

agtacatgca gggcaggagc tgatcggcac atgggtcgtc gccgaccgta tggaagatct    420

tacctcattg tttcggcagg agggctggct tcaagcgttc ccaaaaggtt taatcgatct    480

cctcagttac aaaggtggca tttggtcagt cccagtcaac atccaccgtt ctaacgtaat    540

gtggtacatc ccggcaaaat taaaagaatg gggcgtgacc ccgccaaaaa catgggcaga    600

atttttagcg acagcgcaaa cattaaagcg gaaaggcctt gaggcaccat tggcactcgg    660

tgagaattgg acacagcaac atctctggga aagcgtcgcc ctcgccacac tgggtgccga    720

tggttggaat aatctctgga gtggtaagct caaattcacg gatccaaaag cagtcgccgt    780

atgggaaaca ttcggtaagg tattagatgc agcgaacaag gatgcagccg ggctttcatg    840

gcaacaagca gtagaccgtg tagtacaggg gaaagctgca ttcaatatca tgggggactg    900

ggcagcaggt tacatgagta cgaccttaaa actgaagcca ggtaccgact tcgcatggac    960

accttctccg ggcacttcag ggatctttat gatgctgtct gatagtttcg gcttgccaaa   1020

gggggcgaag aatcgtcaaa atgctattaa ctggttgaaa ctcgtcgggt caaaagaggg   1080

gcaggacacc ttcaacccgc tctgcggttc catcgctgct cgtctcgatt ctgatcctgc   1140

caaatataat gcatacggcc aaagtgcaat gaaggactgg aagtcaaatc ggatcgtagg   1200

ctccctcgtc cacggcgcag tcgcgccaga atccttcatg tcgcagtttg ggacggtaat   1260

ggagatttc ttgcaatccc gtaacccgca ggcagccgct aatgccgcac aagctatcgc   1320

caatcaggtc ggtttaggtc gtgggggttc acatcatcat catcatcatt aatgaaaggg   1380

cgatatccag cacactggcg gccgttacta gtggatccgg ctgctaacaa agcccgaaag   1440

gaagctgagt tggctgctgc caccgctgag caataactag cataacccct tggggcctct   1500

aaacgggtct tgaggggttt tttgctgaaa ggaggaacta tatccggagc gactcccacg   1560

gcacgttggc aagctcg                                                  1577
```

<210> SEQ ID NO 82
<211> LENGTH: 1577
<212> TYPE: DNA
<213> ORGANISM: Artificial Sequence
<220> FEATURE:
<223> OTHER INFORMATION: Exemplary tsGBP2_C337 expression sequence, optimized using OrfOpt

<400> SEQUENCE: 82

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaattaga    180

aatttttct tggtgggcag gtgatgaagg cccagctctc gaagccttga tccggttgta    240

taaacagaaa tacccaggtg tagaggtcat taatgctacc gtcaccgggg gtgccggtgt    300

caacgccaaa gccgtcctta aaacgcgtat gctcggcggg gacccaccag atacctttca    360

agtacatgca gggcaggagc tgatcggcac atgggtcgtc gccgaccgta tggaagatct    420

tacctcattg tttcggcagg agggctggct tcaagcgttc ccaaaaggtt taatcgatct    480

cctcagttac aaaggtggca tttggtcagt cccagtcaac atccaccgtt ctaacgtaat    540

gtggtacatc ccggcaaaat taaaagaatg gggcgtgacc ccgccaaaaa catgggcaga    600
```

-continued

```
atttttagcg acagcgcaaa cattaaagcg gaaaggcctt gaggcaccat tggcactcgg    660

tgagaattgg acacagcaac atctctggga aagcgtcgcc ctcgccacac tgggtgccga    720

tggttggaat aatctctgga gtggtaagct caaattcacg gatccaaaag cagtcgccgt    780

atgggaaaca ttcggtaagg tattagatgc agcgaacaag gatgcagccg ggctttcatg    840

gcaacaagca gtagaccgtg tagtacaggg gaaagctgca ttcaatatca tgggggactg    900

ggcagcaggt tacatgagta cgaccttaaa actgaagcca ggtaccgact tcgcatggac    960

accttctccg ggcacttcag ggatctttat gatgctgtct gatagtttcg gcttgccaaa   1020

gggggcgaag aatcgtcaaa atgctattaa ctggttgaaa ctcgtcgggt caaaagaggg   1080

gcaggacacc ttcaacccgc tcaaaggttc catcgctgct cgtctcgatt ctgatcctgc   1140

caaatataat gcatacggcc aaagtgcaat gaaggactgc aagtcaaatc ggatcgtagg   1200

ctccctcgtc cacggcgcag tcgcgccaga atccttcatg tcgcagtttg ggacggtaat   1260

ggagattttc ttgcaatccc gtaacccgca ggcagccgct aatgccgcac aagctatcgc   1320

caatcaggtc ggtttaggtc gtgggggttc acatcatcat catcatcatt aatgaaaggg   1380

cgatatccag cacactggcg gccgttacta gtggatccgg ctgctaacaa agcccgaaag   1440

gaagctgagt tggctgctgc caccgctgag caataactag cataacccct tggggcctct   1500

aaacgggtct tgaggggttt tttgctgaaa ggaggaacta tatccggagc gactcccacg   1560

gcacgttggc aagctcg                                                  1577
```

```
<210> SEQ ID NO 83
<211> LENGTH: 1577
<212> TYPE: DNA
<213> ORGANISM: Artificial Sequence
<220> FEATURE:
<223> OTHER INFORMATION: Exemplary tsGBP2_C348 expression sequence,
      optimized using OrfOpt

<400> SEQUENCE: 83
```

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaattaga    180

aatttttctt tggtgggcag gtgatgaagg cccagctctc gaagccttga tccggttgta    240

taaacagaaa tacccaggtg tagaggtcat taatgctacc gtcaccgggg gtgccggtgt    300

caacgccaaa gccgtcctta aaacgcgtat gctcggcggg gacccaccag ataccttca    360

agtacatgca gggcaggagc tgatcggcac atgggtcgtc gccgaccgta tggaagatct    420

tacctcattg tttcggcagg agggctggct tcaagcgttc ccaaaaggtt taatcgatct    480

cctcagttac aaaggtggca tttggtcagt cccagtcaac atccaccgtt ctaacgtaat    540

gtggtacatc ccggcaaaat taaaagaatg ggcgtgacc ccgccaaaaa catgggcaga    600

atttttagcg acagcgcaaa cattaaagcg gaaaggcctt gaggcaccat tggcactcgg    660

tgagaattgg acacagcaac atctctggga aagcgtcgcc ctcgccacac tgggtgccga    720

tggttggaat aatctctgga gtggtaagct caaattcacg gatccaaaag cagtcgccgt    780

atgggaaaca ttcggtaagg tattagatgc agcgaacaag gatgcagccg ggctttcatg    840

gcaacaagca gtagaccgtg tagtacaggg gaaagctgca ttcaatatca tgggggactg    900

ggcagcaggt tacatgagta cgaccttaaa actgaagcca ggtaccgact tcgcatggac    960

accttctccg ggcacttcag ggatctttat gatgctgtct gatagtttcg gcttgccaaa   1020
```

```
gggggcgaag aatcgtcaaa atgctattaa ctggttgaaa ctcgtcgggt caaaagaggg   1080

gcaggacacc ttcaacccgc tcaaaggttc catcgctgct cgtctcgatt ctgatcctgc   1140

caaatataat gcatacggcc aaagtgcaat gaaggactgg aagtcaaatc ggatcgtagg   1200

ctccctcgtc tgcggcgcag tcgcgccaga atccttcatg tcgcagtttg ggacggtaat   1260

ggagattttc ttgcaatccc gtaacccgca ggcagccgct aatgccgcac aagctatcgc   1320

caatcaggtc ggtttaggtc gtgggggttc acatcatcat catcatcatt aatgaaaggg   1380

cgatatccag cacactggcg gccgttacta gtggatccgg ctgctaacaa agcccgaaag   1440

gaagctgagt tggctgctgc caccgctgag caataactag cataacccct tggggcctct   1500

aaacgggtct tgaggggttt tttgctgaaa ggaggaacta tatccggagc gactcccacg   1560

gcacgttggc aagctcg                                                  1577
```

<210> SEQ ID NO 84
<211> LENGTH: 1577
<212> TYPE: DNA
<213> ORGANISM: Artificial Sequence
<220> FEATURE:
<223> OTHER INFORMATION: Exemplary tsGBP2_C357 expression sequence, optimized using OrfOpt

<400> SEQUENCE: 84

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaattaga    180

aatttttttct tggtgggcag gtgatgaagg cccagctctc gaagccttga tccggttgta   240

taaacagaaa tacccaggtg tagaggtcat taatgctacc gtcaccgggg gtgccggtgt    300

caacgccaaa gccgtcctta aaacgcgtat gctcggcggg gacccaccag ataccttca     360

agtacatgca gggcaggagc tgatcggcac atgggtcgtc gccgaccgta tggaagatct    420

tacctcattg tttcggcagg agggctggct tcaagcgttc ccaaaaggtt taatcgatct    480

cctcagttac aaaggtggca tttggtcagt cccagtcaac atccaccgtt ctaacgtaat    540

gtggtacatc ccggcaaaat taaaagaatg ggcgtgacc ccgccaaaaa catgggcaga     600

atttttagcg acagcgcaaa cattaaagcg gaaaggcctt gaggcaccat tggcactcgg    660

tgagaattgg acacagcaac atctctggga aagcgtcgcc ctcgccacac tgggtgccga    720

tggttggaat aatctctgga gtggtaagct caaattcacg gatccaaaag cagtcgccgt    780

atgggaaaca ttcggtaagg tattagatgc agcgaacaag gatgcagccg ggctttcatg    840

gcaacaagca gtagaccgtg tagtacaggg gaaagctgca ttcaatatca tgggggactg    900

ggcagcaggt tacatgagta cgaccttaaa actgaagcca ggtaccgact tcgcatggac    960

accttctccg ggcacttcag ggatctttat gatgctgtct gatagtttcg gcttgccaaa   1020

gggggcgaag aatcgtcaaa atgctattaa ctggttgaaa ctcgtcgggt caaaagaggg   1080

gcaggacacc ttcaacccgc tcaaaggttc catcgctgct cgtctcgatt ctgatcctgc   1140

caaatataat gcatacggcc aaagtgcaat gaaggactgg aagtcaaatc ggatcgtagg   1200

ctccctcgtc cacggcgcag tcgcgccaga atccttctgc tcgcagtttg ggacggtaat   1260

ggagattttc ttgcaatccc gtaacccgca ggcagccgct aatgccgcac aagctatcgc   1320

caatcaggtc ggtttaggtc gtgggggttc acatcatcat catcatcatt aatgaaaggg   1380

cgatatccag cacactggcg gccgttacta gtggatccgg ctgctaacaa agcccgaaag   1440
```

gaagctgagt tggctgctgc caccgctgag caataactag cataacccct tggggcctct 1500
aaacgggtct tgaggggttt tttgctgaaa ggaggaacta tatccggagc gactcccacg 1560
gcacgttggc aagctcg 1577

<210> SEQ ID NO 85
<211> LENGTH: 1577
<212> TYPE: DNA
<213> ORGANISM: Artificial Sequence
<220> FEATURE:
<223> OTHER INFORMATION: Exemplary tsGBP2.13C.W8F expression sequence, optimized using OrfOpt

<400> SEQUENCE: 85
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaattaga 180 aatttttct ttttgggcag gtgattgtgg cccagctctc gaagccttga tccggttgta 240
taaacagaaa tacccaggtg tagaggtcat taatgctacc gtcaccgggg gtgccggtgt 300
caacgccaaa gccgtcctta aaacgcgtat gctcggcggg gacccaccag atacctttca 360
agtacatgca gggcaggagc tgatcggcac atgggtcgtc gccgaccgta tggaagatct 420
tacctcattg tttcggcagg agggctggct tcaagcgttc ccaaaaggtt taatcgatct 480
cctcagttac aaaggtggca tttggtcagt cccagtcaac atccaccgtt ctaacgtaat 540
gtggtacatc ccggcaaaat taaaagaatg gggcgtgacc ccgccaaaaa catgggcaga 600
atttttagcg acagcgcaaa cattaaagcg gaaaggcctt gaggcaccat tggcactcgg 660
tgagaattgg acacagcaac atctctggga aagcgtcgcc ctcgccacac tgggtgccga 720
tggttggaat aatctctgga gtggtaagct caaattcacg gatccaaaag cagtcgccgt 780
atgggaaaca ttcggtaagg tattagatgc agcgaacaag gatgcagccg ggctttcatg 840
gcaacaagca gtagaccgtg tagtacaggg gaaagctgca ttcaatatca tgggggactg 900
ggcagcaggt tacatgagta cgaccttaaa actgaagcca ggtaccgact tcgcatggac 960
accttctccg ggcacttcag ggatctttat gatgctgtct gatagtttcg gcttgccaaa 1020
gggggcgaag aatcgtcaaa atgctattaa ctggttgaaa ctcgtcgggt caaaagaggg 1080
gcaggacacc ttcaacccgc tcaaaggttc catcgctgct cgtctcgatt ctgatcctgc 1140
caaatataat gcatacggcc aaagtgcaat gaaggactgg aagtcaaatc ggatcgtagg 1200
ctccctcgtc cacggcgcag tcgcgccaga atccttcatg tcgcagtttg ggacggtaat 1260 ggagatttc ttgcaatccc gtaacccgca ggcagccgct aatgccgcac aagctatcgc 1320
caatcaggtc ggtttaggtc gtgggggttc acatcatcat catcatcatt aatgaaaggg 1380
cgatatccag cacactggcg gccgttacta gtggatccgg ctgctaacaa agcccgaaag 1440
gaagctgagt tggctgctgc caccgctgag caataactag cataacccct tggggcctct 1500
aaacgggtct tgaggggttt tttgctgaaa ggaggaacta tatccggagc gactcccacg 1560
gcacgttggc aagctcg 1577

<210> SEQ ID NO 86
<211> LENGTH: 1577
<212> TYPE: DNA
<213> ORGANISM: Artificial Sequence
<220> FEATURE:
<223> OTHER INFORMATION: Exemplary tsGBP2.13C.W8M expression sequence, optimized using OrfOpt

<400> SEQUENCE: 86
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaattaga 180 aatttttct atgtgggcag gtgattgtgg cccagctctc gaagccttga tccggttgta 240
taaacagaaa tacccaggtg tagaggtcat taatgctacc gtcaccgggg gtgccggtgt 300
caacgccaaa gccgtcctta aaacgcgtat gctcggcggg gacccaccag atacctttca 360
agtacatgca gggcaggagc tgatcggcac atgggtcgtc gccgaccgta tggaagatct 420
tacctcattg tttcggcagg agggctggct tcaagcgttc ccaaaaggtt taatcgatct 480
cctcagttac aaaggtggca tttggtcagt cccagtcaac atccaccgtt ctaacgtaat 540
gtggtacatc ccggcaaaat taaaagaatg gggcgtgacc ccgccaaaaa catgggcaga 600
atttttagcg acagcgcaaa cattaaagcg gaaaggcctt gaggcaccat tggcactcgg 660
tgagaattgg acacagcaac atctctggga aagcgtcgcc ctcgccacac tgggtgccga 720
tggttggaat aatctctgga gtggtaagct caaattcacg gatccaaaag cagtcgccgt 780
atgggaaaca ttcggtaagg tattagatgc agcgaacaag gatgcagccg ggctttcatg 840
gcaacaagca gtagaccgtg tagtacaggg gaaagctgca ttcaatatca tgggggactg 900
ggcagcaggt tacatgagta cgaccttaaa actgaagcca ggtaccgact tcgcatggac 960
accttctccg ggcacttcag ggatctttat gatgctgtct gatagtttcg gcttgccaaa 1020
gggggcgaag aatcgtcaaa atgctattaa ctggttgaaa ctcgtcgggt caaaagaggg 1080
gcaggacacc ttcaacccgc tcaaaggttc catcgctgct cgtctcgatt ctgatcctgc 1140
caaatataat gcatacggcc aaagtgcaat gaaggactgg aagtcaaatc ggatcgtagg 1200
ctccctcgtc cacggcgcag tcgcgccaga atccttcatg tcgcagtttg ggacggtaat 1260
ggagattttc ttgcaatccc gtaacccgca ggcagccgct aatgccgcac aagctatcgc 1320
caatcaggtc ggtttaggtc gtgggggttc acatcatcat catcatcatt aatgaaaggg 1380
cgatatccag cacactggcg gccgttacta gtggatccgg ctgctaacaa agcccgaaag 1440
gaagctgagt tggctgctgc caccgctgag caataactag cataacccct tggggcctct 1500
aaacgggtct tgaggggttt tttgctgaaa ggaggaacta tatccggagc gactcccacg 1560
gcacgttggc aagctcg 1577

<210> SEQ ID NO 87
<211> LENGTH: 1577
<212> TYPE: DNA
<213> ORGANISM: Artificial Sequence
<220> FEATURE:
<223> OTHER INFORMATION: Exemplary tsGBP2.13C.W8Y expression sequence, optimized using OrfOpt

<400> SEQUENCE: 87
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaattaga 180 aatttttct tattgggcag gtgattgtgg cccagctctc gaagccttga tccggttgta 240
taaacagaaa tacccaggtg tagaggtcat taatgctacc gtcaccgggg gtgccggtgt 300
caacgccaaa gccgtcctta aaacgcgtat gctcggcggg gacccaccag atacctttca 360
agtacatgca gggcaggagc tgatcggcac atgggtcgtc gccgaccgta tggaagatct 420
tacctcattg tttcggcagg agggctggct tcaagcgttc ccaaaaggtt taatcgatct 480
cctcagttac aaaggtggca tttggtcagt cccagtcaac atccaccgtt ctaacgtaat 540
gtggtacatc ccggcaaaat taaaagaatg gggcgtgacc ccgccaaaaa catgggcaga 600
atttttagcg acagcgcaaa cattaaagcg gaaaggcctt gaggcaccat tggcactcgg 660
tgagaattgg acacagcaac atctctggga aagcgtcgcc ctcgccacac tgggtgccga 720
tggttggaat aatctctgga gtggtaagct caaattcacg gatccaaaag cagtcgccgt 780
atgggaaaca ttcggtaagg tattagatgc agcgaacaag gatgcagccg ggctttcatg 840
gcaacaagca gtagaccgtg tagtacaggg gaaagctgca ttcaatatca tgggggactg 900
ggcagcaggt tacatgagta cgaccttaaa actgaagcca ggtaccgact tcgcatggac 960
accttctccg ggcacttcag ggatctttat gatgctgtct gatagtttcg gcttgccaaa 1020
gggggcgaag aatcgtcaaa atgctattaa ctggttgaaa ctcgtcgggt caaaagaggg 1080
gcaggacacc ttcaacccgc tcaaaggttc catcgctgct cgtctcgatt ctgatcctgc 1140
caaatataat gcatacggcc aaagtgcaat gaaggactgg aagtcaaatc ggatcgtagg 1200
ctccctcgtc cacggcgcag tcgcgccaga atccttcatg tcgcagtttg ggacggtaat 1260
ggagattttc ttgcaatccc gtaacccgca ggcagccgct aatgccgcac aagctatcgc 1320
caatcaggtc ggtttaggtc gtgggggttc acatcatcat catcatcatt aatgaaaggg 1380
cgatatccag cacactggcg gccgttacta gtggatccgg ctgctaacaa agcccgaaag 1440
gaagctgagt tggctgctgc caccgctgag caataactag cataacccct tggggcctct 1500
aaacgggtct tgaggggttt tttgctgaaa ggaggaacta tatccggagc gactcccacg 1560
gcacgttggc aagctcg 1577

<210> SEQ ID NO 88
<211> LENGTH: 1577
<212> TYPE: DNA
<213> ORGANISM: Artificial Sequence
<220> FEATURE:
<223> OTHER INFORMATION: Exemplary tsGBP2.13C.W9F expression sequence, optimized using OrfOpt

<400> SEQUENCE: 88
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaattaga 180
aattttttct tggtttgcag gtgattgtgg cccagctctc gaagccttga tccggttgta 240
taaacagaaa tacccaggtg tagaggtcat taatgctacc gtcaccgggg gtgccggtgt 300
caacgccaaa gccgtcctta aaacgcgtat gctcggcggg gacccaccag ataccttca 360 agtacatgca gggcaggagc tgatcggcac atgggtcgtc gccgaccgta tggaagatct 420
tacctcattg tttcggcagg agggctggct tcaagcgttc ccaaaaggtt taatcgatct 480
cctcagttac aaaggtggca tttggtcagt cccagtcaac atccaccgtt ctaacgtaat 540
gtggtacatc ccggcaaaat taaaagaatg gggcgtgacc ccgccaaaaa catgggcaga 600
atttttagcg acagcgcaaa cattaaagcg gaaaggcctt gaggcaccat tggcactcgg 660
tgagaattgg acacagcaac atctctggga aagcgtcgcc ctcgccacac tgggtgccga 720
tggttggaat aatctctgga gtggtaagct caaattcacg gatccaaaag cagtcgccgt 780

-continued

```
atgggaaaca ttcggtaagg tattagatgc agcgaacaag gatgcagccg ggctttcatg    840

gcaacaagca gtagaccgtg tagtacaggg gaaagctgca ttcaatatca tgggggactg    900

ggcagcaggt tacatgagta cgaccttaaa actgaagcca ggtaccgact tcgcatggac    960

accttctccg ggcacttcag ggatctttat gatgctgtct gatagtttcg gcttgccaaa   1020

gggggcgaag aatcgtcaaa atgctattaa ctggttgaaa ctcgtcgggt caaaagaggg   1080

gcaggacacc ttcaacccgc tcaaaggttc catcgctgct cgtctcgatt ctgatcctgc   1140

caaatataat gcatacggcc aaagtgcaat gaaggactgg aagtcaaatc ggatcgtagg   1200

ctccctcgtc cacggcgcag tcgcgccaga atccttcatg tcgcagtttg ggacggtaat   1260

ggagattttc ttgcaatccc gtaacccgca ggcagccgct aatgccgcac aagctatcgc   1320

caatcaggtc ggtttaggtc gtgggggttc acatcatcat catcatcatt aatgaaaggg   1380

cgatatccag cacactggcg gccgttacta gtggatccgg ctgctaacaa agcccgaaag   1440

gaagctgagt tggctgctgc caccgctgag caataactag cataacccct tggggcctct   1500

aaacgggtct tgaggggttt tttgctgaaa ggaggaacta tatccggagc gactcccacg   1560

gcacgttggc aagctcg                                                  1577
```

<210> SEQ ID NO 89
<211> LENGTH: 1577
<212> TYPE: DNA
<213> ORGANISM: Artificial Sequence
<220> FEATURE:
<223> OTHER INFORMATION: Exemplary tsGBP2.13C.W9M expression sequence, optimized using OrfOpt

<400> SEQUENCE: 89

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaattaga    180

aatttttct tggatggcag gtgattgtgg cccagctctc gaagccttga tccggttgta    240

taaacagaaa tacccaggtg tagaggtcat taatgctacc gtcaccgggg gtgccggtgt    300

caacgccaaa gccgtcctta aaacgcgtat gctcggcggg gacccaccag atacctttca    360

agtacatgca gggcaggagc tgatcggcac atgggtcgtc gccgaccgta tggaagatct    420

tacctcattg tttcggcagg agggctggct tcaagcgttc ccaaaaggtt taatcgatct    480

cctcagttac aaaggtggca tttggtcagt cccagtcaac atccaccgtt ctaacgtaat    540

gtggtacatc ccggcaaaat taaaagaatg gggcgtgacc ccgccaaaaa catgggcaga    600

atttttagcg acagcgcaaa cattaaagcg gaaaggcctt gaggcaccat tggcactcgg    660

tgagaattgg acacagcaac atctctggga aagcgtcgcc ctcgccacac tgggtgccga    720

tggttggaat aatctctgga gtggtaagct caaattcacg gatccaaaag cagtcgccgt    780

atgggaaaca ttcggtaagg tattagatgc agcgaacaag gatgcagccg ggctttcatg    840

gcaacaagca gtagaccgtg tagtacaggg gaaagctgca ttcaatatca tgggggactg    900

ggcagcaggt tacatgagta cgaccttaaa actgaagcca ggtaccgact tcgcatggac    960

accttctccg ggcacttcag ggatctttat gatgctgtct gatagtttcg gcttgccaaa   1020

gggggcgaag aatcgtcaaa atgctattaa ctggttgaaa ctcgtcgggt caaaagaggg   1080

gcaggacacc ttcaacccgc tcaaaggttc catcgctgct cgtctcgatt ctgatcctgc   1140

caaatataat gcatacggcc aaagtgcaat gaaggactgg aagtcaaatc ggatcgtagg   1200
```

```
ctccctcgtc cacggcgcag tcgcgccaga atccttcatg tcgcagtttg ggacggtaat   1260

ggagattttc ttgcaatccc gtaacccgca ggcagccgct aatgccgcac aagctatcgc   1320

caatcaggtc ggtttaggtc gtgggggttc acatcatcat catcatcatt aatgaaaggg   1380

cgatatccag cacactggcg gccgttacta gtggatccgg ctgctaacaa agcccgaaag   1440

gaagctgagt tggctgctgc caccgctgag caataactag cataacccct tggggcctct   1500

aaacgggtct tgaggggttt tttgctgaaa ggaggaacta tatccggagc gactcccacg   1560

gcacgttggc aagctcg                                                  1577
```

```
<210> SEQ ID NO 90
<211> LENGTH: 1577
<212> TYPE: DNA
<213> ORGANISM: Artificial Sequence
<220> FEATURE:
<223> OTHER INFORMATION: Exemplary tsGBP2.13C.W9Y expression sequence,
      optimized using OrfOpt

<400> SEQUENCE: 90
```

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaattaga    180

aatttttttct tggtatgcag gtgattgtgg cccagctctc gaagccttga tccggttgta   240

taaacagaaa tacccaggtg tagaggtcat taatgctacc gtcaccgggg gtgccggtgt    300

caacgccaaa gccgtcctta aaacgcgtat gctcggcggg gacccaccag atacctttca    360

agtacatgca gggcaggagc tgatcggcac atgggtcgtc gccgaccgta tggaagatct    420

tacctcattg tttcggcagg agggctggct tcaagcgttc ccaaaaggtt taatcgatct    480

cctcagttac aaaggtggca tttggtcagt cccagtcaac atccaccgtt ctaacgtaat    540

gtggtacatc ccggcaaaat taaaagaatg gggcgtgacc ccgccaaaaa catgggcaga    600

atttttagcg acagcgcaaa cattaaagcg gaaaggcctt gaggcaccat tggcactcgg    660

tgagaattgg acacagcaac atctctggga aagcgtcgcc ctcgccacac tgggtgccga    720

tggttggaat aatctctgga gtggtaagct caaattcacg gatccaaaag cagtcgccgt    780

atgggaaaca ttcggtaagg tattagatgc agcgaacaag gatgcagccg ggctttcatg    840

gcaacaagca gtagaccgtg tagtacaggg gaaagctgca ttcaatatca tgggggactg    900

ggcagcaggt tacatgagta cgaccttaaa actgaagcca ggtaccgact tcgcatggac    960

accttctccg ggcacttcag ggatctttat gatgctgtct gatagtttcg gcttgccaaa   1020

gggggcgaag aatcgtcaaa atgctattaa ctggttgaaa ctcgtcgggt caaaagaggg   1080

gcaggacacc ttcaacccgc tcaaaggttc catcgctgct cgtctcgatt ctgatcctgc   1140

caaatataat gcatacggcc aaagtgcaat gaaggactgg aagtcaaatc ggatcgtagg   1200

ctccctcgtc cacggcgcag tcgcgccaga atccttcatg tcgcagtttg ggacggtaat   1260

ggagattttc ttgcaatccc gtaacccgca ggcagccgct aatgccgcac aagctatcgc   1320

caatcaggtc ggtttaggtc gtgggggttc acatcatcat catcatcatt aatgaaaggg   1380

cgatatccag cacactggcg gccgttacta gtggatccgg ctgctaacaa agcccgaaag   1440

gaagctgagt tggctgctgc caccgctgag caataactag cataacccct tggggcctct   1500

aaacgggtct tgaggggttt tttgctgaaa ggaggaacta tatccggagc gactcccacg   1560

gcacgttggc aagctcg                                                  1577
```

<210> SEQ ID NO 91
<211> LENGTH: 1577
<212> TYPE: DNA
<213> ORGANISM: Artificial Sequence
<220> FEATURE:
<223> OTHER INFORMATION: Exemplary tsGBP2.13C.Q64N expression sequence, optimized using OrfOpt

<400> SEQUENCE: 91
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaattaga 180
aattttttct tggtgggcag gtgattgtgg cccagctctc gaagccttga tccggttgta 240
taaacagaaa tacccaggtg tagaggtcat taatgctacc gtcaccgggg gtgccggtgt 300
caacgccaaa gccgtcctta aaacgcgtat gctcggcggg gacccaccag atacctttaa 360
cgtacatgca gggcaggagc tgatcggcac atgggtcgtc gccgaccgta tggaagatct 420
tacctcattg tttcggcagg agggctggct tcaagcgttc ccaaaaggtt taatcgatct 480
cctcagttac aaaggtggca tttggtcagt cccagtcaac atccaccgtt ctaacgtaat 540
gtggtacatc ccggcaaaat taaaagaatg ggcgtgacc ccgccaaaaa catgggcaga 600
atttttagcg acagcgcaaa cattaaagcg gaaaggcctt gaggcaccat tggcactcgg 660
tgagaattgg acacagcaac atctctggga aagcgtcgcc ctcgccacac tgggtgccga 720
tggttggaat aatctctgga gtggtaagct caaattcacg gatccaaaag cagtcgccgt 780
atgggaaaca ttcggtaagg tattagatgc agcgaacaag gatgcagccg ggctttcatg 840
gcaacaagca gtagaccgtg tagtacaggg gaaagctgca ttcaatatca tgggggactg 900
ggcagcaggt tacatgagta cgaccttaaa actgaagcca ggtaccgact tcgcatggac 960
accttctccg ggcacttcag ggatctttat gatgctgtct gatagtttcg gcttgccaaa 1020
gggggcgaag aatcgtcaaa atgctattaa ctggttgaaa ctcgtcgggt caaaagaggg 1080
gcaggacacc ttcaacccgc tcaaaggttc catcgctgct cgtctcgatt ctgatcctgc 1140
caaatataat gcatacggcc aaagtgcaat gaaggactgg aagtcaaatc ggatcgtagg 1200
ctccctcgtc cacggcgcag tcgcgccaga atccttcatg tcgcagtttg ggacggtaat 1260
ggagattttc ttgcaatccc gtaacccgca ggcagccgct aatgccgcac aagctatcgc 1320
caatcaggtc ggtttaggtc gtgggggttc acatcatcat catcatcatt aatgaaaggg 1380
cgatatccag cacactggcg gccgttacta gtggatccgg ctgctaacaa agcccgaaag 1440
gaagctgagt tggctgctgc caccgctgag caataactag cataacccct tggggcctct 1500
aaacgggtct tgaggggttt tttgctgaaa ggaggaacta tatccggagc gactcccacg 1560
gcacgttggc aagctcg 1577

<210> SEQ ID NO 92
<211> LENGTH: 1577
<212> TYPE: DNA
<213> ORGANISM: Artificial Sequence
<220> FEATURE:
<223> OTHER INFORMATION: Exemplary tsGBP2.13C.Q64E expression sequence, optimized using OrfOpt

<400> SEQUENCE: 92
cggtcacgct tgggactgcc ataggctggc ccggtgatgc cggccacgat gcgtccggcg 60

```
tagaggatcg agatctcgat cccgcgaaat taatacgact cactataggg agaccacaac    120
ggtttccctc tagaaataat tttgtttaac tttaagaagg agatatacca tgaaattaga    180
aatttttct tggtgggcag gtgattgtgg cccagctctc gaagccttga tccggttgta    240
taaacagaaa tacccaggtg tagaggtcat taatgctacc gtcaccgggg gtgccggtgt    300
caacgccaaa gccgtcctta aaacgcgtat gctcggcggg gacccaccag ataccttga    360
agtacatgca gggcaggagc tgatcggcac atgggtcgtc gccgaccgta tggaagatct    420
tacctcattg tttcggcagg agggctggct tcaagcgttc ccaaaaggtt taatcgatct    480
cctcagttac aaaggtggca tttggtcagt cccagtcaac atccaccgtt ctaacgtaat    540
gtggtacatc ccggcaaaat taaaagaatg gggcgtgacc ccgccaaaaa catgggcaga    600
atttttagcg acagcgcaaa cattaaagcg gaaaggcctt gaggcaccat tggcactcgg    660
tgagaattgg acacagcaac atctctggga aagcgtcgcc ctcgccacac tgggtgccga    720
tggttggaat aatctctgga gtggtaagct caaattcacg gatccaaaag cagtcgccgt    780
atgggaaaca ttcggtaagg tattagatgc agcgaacaag gatgcagccg ggctttcatg    840
gcaacaagca gtagaccgtg tagtacaggg gaaagctgca ttcaatatca tgggggactg    900
ggcagcaggt tacatgagta cgaccttaaa actgaagcca ggtaccgact tcgcatggac    960
accttctccg ggcacttcag ggatctttat gatgctgtct gatagtttcg gcttgccaaa   1020
gggggcgaag aatcgtcaaa atgctattaa ctggttgaaa ctcgtcgggt caaaagaggg   1080
gcaggacacc ttcaacccgc tcaaaggttc catcgctgct cgtctcgatt ctgatcctgc   1140
caaatataat gcatacggcc aaagtgcaat gaaggactgg aagtcaaatc ggatcgtagg   1200
ctccctcgtc cacggcgcag tcgcgccaga atccttcatg tcgcagtttg ggacggtaat   1260
ggagattttc ttgcaatccc gtaacccgca ggcagccgct aatgccgcac aagctatcgc   1320
caatcaggtc ggtttaggtc gtgggggttc acatcatcat catcatcatt aatgaaaggg   1380
cgatatccag cacactggcg gccgttacta gtggatccgg ctgctaacaa agcccgaaag   1440
gaagctgagt tggctgctgc caccgctgag caataactag cataacccct tggggcctct   1500
aaacgggtct tgaggggttt tttgctgaaa ggaggaacta tatccggagc gactcccacg   1560
gcacgttggc aagctcg                                                  1577
```

<210> SEQ ID NO 93
<211> LENGTH: 1577
<212> TYPE: DNA
<213> ORGANISM: Artificial Sequence
<220> FEATURE:
<223> OTHER INFORMATION: Exemplary tsGBP2.13C.Q64M expression sequence, optimized using OrfOpt

<400> SEQUENCE: 93

```
cggtcacgct tgggactgcc ataggctggc ccggtgatgc cggccacgat gcgtccggcg     60
tagaggatcg agatctcgat cccgcgaaat taatacgact cactataggg agaccacaac    120
ggtttccctc tagaaataat tttgtttaac tttaagaagg agatatacca tgaaattaga    180
aatttttct tggtgggcag gtgattgtgg cccagctctc gaagccttga tccggttgta    240
taaacagaaa tacccaggtg tagaggtcat taatgctacc gtcaccgggg gtgccggtgt    300
caacgccaaa gccgtcctta aaacgcgtat gctcggcggg gacccaccag atacctttat    360
ggtacatgca gggcaggagc tgatcggcac atgggtcgtc gccgaccgta tggaagatct    420
tacctcattg tttcggcagg agggctggct tcaagcgttc ccaaaaggtt taatcgatct    480
```

-continued

```
cctcagttac aaaggtggca tttggtcagt cccagtcaac atccaccgtt ctaacgtaat    540

gtggtacatc ccggcaaaat taaaagaatg gggcgtgacc ccgccaaaaa catgggcaga    600

atttttagcg acagcgcaaa cattaaagcg gaaaggcctt gaggcaccat tggcactcgg    660

tgagaattgg acacagcaac atctctggga aagcgtcgcc ctcgccacac tgggtgccga    720

tggttggaat aatctctgga gtggtaagct caaattcacg gatccaaaag cagtcgccgt    780

atgggaaaca ttcggtaagg tattagatgc agcgaacaag gatgcagccg ggctttcatg    840

gcaacaagca gtagaccgtg tagtacaggg gaaagctgca ttcaatatca tgggggactg    900

ggcagcaggt tacatgagta cgaccttaaa actgaagcca ggtaccgact tcgcatggac    960

accttctccg ggcacttcag ggatctttat gatgctgtct gatagtttcg gcttgccaaa   1020

gggggcgaag aatcgtcaaa atgctattaa ctggttgaaa ctcgtcgggt caaaagaggg   1080

gcaggacacc ttcaacccgc tcaaaggttc catcgctgct cgtctcgatt ctgatcctgc   1140

caaatataat gcatacggcc aaagtgcaat gaaggactgg aagtcaaatc ggatcgtagg   1200

ctccctcgtc cacggcgcag tcgcgccaga atccttcatg tcgcagtttg ggacggtaat   1260

ggagattttc ttgcaatccc gtaacccgca ggcagccgct aatgccgcac aagctatcgc   1320

caatcaggtc ggtttaggtc gtgggggttc acatcatcat catcatcatt aatgaaaggg   1380

cgatatccag cacactggcg gccgttacta gtggatccgg ctgctaacaa agcccgaaag   1440

gaagctgagt tggctgctgc caccgctgag caataactag cataacccct tggggcctct   1500

aaacgggtct tgaggggttt tttgctgaaa ggaggaacta tatccggagc gactcccacg   1560

gcacgttggc aagctcg                                                  1577
```

<210> SEQ ID NO 94
<211> LENGTH: 1577
<212> TYPE: DNA
<213> ORGANISM: Artificial Sequence
<220> FEATURE:
<223> OTHER INFORMATION: Exemplary tsGBP2.13C.H66Q expression sequence, optimized using OrfOpt

<400> SEQUENCE: 94

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaattaga    180

aatttttttct tggtgggcag gtgattgtgg cccagctctc gaagccttga tccggttgta    240

taaacagaaa tacccaggtg tagaggtcat taatgctacc gtcaccgggg gtgccggtgt    300

caacgccaaa gccgtcctta aaacgcgtat gctcggcggg gacccaccag ataccttttca    360

agtacaggca gggcaggagc tgatcggcac atgggtcgtc gccgaccgta tggaagatct    420

tacctcattg tttcggcagg agggctggct tcaagcgttc ccaaaaggtt taatcgatct    480

cctcagttac aaaggtggca tttggtcagt cccagtcaac atccaccgtt ctaacgtaat    540

gtggtacatc ccggcaaaat taaaagaatg gggcgtgacc ccgccaaaaa catgggcaga    600

atttttagcg acagcgcaaa cattaaagcg gaaaggcctt gaggcaccat tggcactcgg    660

tgagaattgg acacagcaac atctctggga aagcgtcgcc ctcgccacac tgggtgccga    720

tggttggaat aatctctgga gtggtaagct caaattcacg gatccaaaag cagtcgccgt    780

atgggaaaca ttcggtaagg tattagatgc agcgaacaag gatgcagccg ggctttcatg    840

gcaacaagca gtagaccgtg tagtacaggg gaaagctgca ttcaatatca tgggggactg    900
```

-continued

```
ggcagcaggt tacatgagta cgaccttaaa actgaagcca ggtaccgact tcgcatggac    960

accttctccg ggcacttcag ggatctttat gatgctgtct gatagtttcg gcttgccaaa   1020

gggggcgaag aatcgtcaaa atgctattaa ctggttgaaa ctcgtcgggt caaaagaggg   1080

gcaggacacc ttcaacccgc tcaaaggttc catcgctgct cgtctcgatt ctgatcctgc   1140

caaatataat gcatacggcc aaagtgcaat gaaggactgg aagtcaaatc ggatcgtagg   1200

ctccctcgtc cacggcgcag tcgcgccaga atccttcatg tcgcagtttg ggacggtaat   1260

ggagattttc ttgcaatccc gtaacccgca ggcagccgct aatgccgcac aagctatcgc   1320

caatcaggtc ggtttaggtc gtgggggttc acatcatcat catcatcatt aatgaaaggg   1380

cgatatccag cacactggcg gccgttacta gtggatccgg ctgctaacaa agcccgaaag   1440

gaagctgagt tggctgctgc caccgctgag caataactag cataacccct tggggcctct   1500

aaacgggtct tgaggggttt tttgctgaaa ggaggaacta tatccggagc gactcccacg   1560

gcacgttggc aagctcg                                                  1577
```

<210> SEQ ID NO 95
<211> LENGTH: 1577
<212> TYPE: DNA
<213> ORGANISM: Artificial Sequence
<220> FEATURE:
<223> OTHER INFORMATION: Exemplary tsGBP2.13C.W244M expression sequence, optimized using OrfOpt

<400> SEQUENCE: 95

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaattaga    180

aatttttctt tggtgggcag gtgattgtgg cccagctctc gaagccttga tccggttgta    240

taaacagaaa tacccaggtg tagaggtcat taatgctacc gtcaccgggg gtgccggtgt    300

caacgccaaa gccgtcctta aaacgcgtat gctcggcggg gacccaccag atacctttca    360

agtacatgca gggcaggagc tgatcggcac atgggtcgtc gccgaccgta tggaagatct    420

tacctcattg tttcggcagg agggctggct tcaagcgttc ccaaaaggtt taatcgatct    480

cctcagttac aaaggtggca tttggtcagt cccagtcaac atccaccgtt ctaacgtaat    540

gtggtacatc ccggcaaaat taaaagaatg ggcgtgacc ccgccaaaaa catgggcaga    600

atttttagcg acagcgcaaa cattaaagcg gaaaggcctt gaggcaccat tggcactcgg    660

tgagaattgg acacagcaac atctctggga aagcgtcgcc ctcgccacac tgggtgccga    720

tggttggaat aatctctgga gtggtaagct caaattcacg gatccaaaag cagtcgccgt    780

atgggaaaca ttcggtaagg tattagatgc agcgaacaag gatgcagccg ggctttcatg    840

gcaacaagca gtagaccgtg tagtacaggg gaaagctgca ttcaatatca tgggggacat    900

ggcagcaggt tacatgagta cgaccttaaa actgaagcca ggtaccgact tcgcatggac    960

accttctccg ggcacttcag ggatctttat gatgctgtct gatagtttcg gcttgccaaa   1020

gggggcgaag aatcgtcaaa atgctattaa ctggttgaaa ctcgtcgggt caaaagaggg   1080

gcaggacacc ttcaacccgc tcaaaggttc catcgctgct cgtctcgatt ctgatcctgc   1140

caaatataat gcatacggcc aaagtgcaat gaaggactgg aagtcaaatc ggatcgtagg   1200

ctccctcgtc cacggcgcag tcgcgccaga atccttcatg tcgcagtttg ggacggtaat   1260

ggagattttc ttgcaatccc gtaacccgca ggcagccgct aatgccgcac aagctatcgc   1320
```

caatcaggtc ggtttaggtc gtgggggttc acatcatcat catcatcatt aatgaaaggg 1380
cgatatccag cacactggcg gccgttacta gtggatccgg ctgctaacaa agcccgaaag 1440
gaagctgagt tggctgctgc caccgctgag caataactag cataacccct tggggcctct 1500
aaacgggtct tgaggggttt tttgctgaaa ggaggaacta tatccggagc gactcccacg 1560
gcacgttggc aagctcg 1577

<210> SEQ ID NO 96
<211> LENGTH: 1577
<212> TYPE: DNA
<213> ORGANISM: Artificial Sequence
<220> FEATURE:
<223> OTHER INFORMATION: Exemplary tsGBP2.13C.W244F expression sequence, optimized using OrfOpt

<400> SEQUENCE: 96
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaattaga 180
aatttttctt tggtgggcag gtgattgtgg cccagctctc gaagccttga tccggttgta 240
taaacagaaa tacccaggtg tagaggtcat taatgctacc gtcaccgggg gtgccggtgt 300
caacgccaaa gccgtcctta aaacgcgtat gctcggcggg gacccaccag atacctttca 360
agtacatgca gggcaggagc tgatcggcac atgggtcgtc gccgaccgta tggaagatct 420
tacctcattg tttcggcagg agggctggct tcaagcgttc ccaaaaggtt taatcgatct 480
cctcagttac aaaggtggca tttggtcagt cccagtcaac atccaccgtt ctaacgtaat 540
gtggtacatc ccggcaaaat taaaagaatg gggcgtgacc ccgccaaaaa catgggcaga 600
atttttagcg acagcgcaaa cattaaagcg gaaaggcctt gaggcaccat tggcactcgg 660
tgagaattgg acacagcaac atctctggga aagcgtcgcc ctcgccacac tgggtgccga 720
tggttggaat aatctctgga gtggtaagct caaattcacg gatccaaaag cagtcgccgt 780
atgggaaaca ttcggtaagg tattagatgc agcgaacaag gatgcagccg ggctttcatg 840
gcaacaagca gtagaccgtg tagtacaggg gaaagctgca ttcaatatca tgggggactt 900
tgcagcaggt tacatgagta cgaccttaaa actgaagcca ggtaccgact tcgcatggac 960
accttctccg ggcacttcag ggatctttat gatgctgtct gatagtttcg gcttgccaaa 1020
gggggcgaag aatcgtcaaa atgctattaa ctggttgaaa ctcgtcgggt caaaagaggg 1080
gcaggacacc ttcaacccgc tcaaaggttc catcgctgct cgtctcgatt ctgatcctgc 1140
caaatataat gcatacggcc aaagtgcaat gaaggactgg aagtcaaatc ggatcgtagg 1200
ctccctcgtc cacggcgcag tcgcgccaga atccttcatg tcgcagtttg ggacggtaat 1260
ggagattttc ttgcaatccc gtaacccgca ggcagccgct aatgccgcac aagctatcgc 1320
caatcaggtc ggtttaggtc gtgggggttc acatcatcat catcatcatt aatgaaaggg 1380
cgatatccag cacactggcg gccgttacta gtggatccgg ctgctaacaa agcccgaaag 1440
gaagctgagt tggctgctgc caccgctgag caataactag cataacccct tggggcctct 1500
aaacgggtct tgaggggttt tttgctgaaa ggaggaacta tatccggagc gactcccacg 1560
gcacgttggc aagctcg 1577

<210> SEQ ID NO 97
<211> LENGTH: 1577
<212> TYPE: DNA

<213> ORGANISM: Artificial Sequence
<220> FEATURE:
<223> OTHER INFORMATION: Exemplary tsGBP2.13C.W244Y expression sequence, optimized using OrfOpt

<400> SEQUENCE: 97

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaattaga    180

aatttttct tggtgggcag gtgattgtgg cccagctctc gaagccttga tccggttgta    240

taaacagaaa tacccaggtg tagaggtcat taatgctacc gtcaccgggg gtgccggtgt    300

caacgccaaa gccgtcctta aaacgcgtat gctcggcggg gacccaccag atacctttca    360

agtacatgca gggcaggagc tgatcggcac atgggtcgtc gccgaccgta tggaagatct    420

tacctcattg tttcggcagg agggctggct tcaagcgttc ccaaaaggtt taatcgatct    480

cctcagttac aaaggtggca tttggtcagt cccagtcaac atccaccgtt ctaacgtaat    540

gtggtacatc ccggcaaaat taaaagaatg gggcgtgacc ccgccaaaaa catgggcaga    600

atttttagcg acagcgcaaa cattaaagcg gaaaggcctt gaggcaccat tggcactcgg    660

tgagaattgg acacagcaac atctctggga aagcgtcgcc ctcgccacac tgggtgccga    720

tggttggaat aatctctgga gtggtaagct caaattcacg gatccaaaag cagtcgccgt    780

atgggaaaca ttcggtaagg tattagatgc agcgaacaag gatgcagccg ggctttcatg    840

gcaacaagca gtagaccgtg tagtacaggg gaaagctgca ttcaatatca tgggggacta    900

tgcagcaggt tacatgagta cgaccttaaa actgaagcca ggtaccgact tcgcatggac    960

accttctccg ggcacttcag ggatctttat gatgctgtct gatagtttcg gcttgccaaa   1020

gggggcgaag aatcgtcaaa atgctattaa ctggttgaaa ctcgtcgggt caaaagaggg   1080

gcaggacacc ttcaacccgc tcaaaggttc catcgctgct cgtctcgatt ctgatcctgc   1140

caaatataat gcatacggcc aaagtgcaat gaaggactgg aagtcaaatc ggatcgtagg   1200

ctccctcgtc cacggcgcag tcgcgccaga atccttcatg tcgcagtttg ggacggtaat   1260

ggagattttc ttgcaatccc gtaacccgca ggcagccgct aatgccgcac aagctatcgc   1320

caatcaggtc ggtttaggtc gtgggggttc acatcatcat catcatcatt aatgaaaggg   1380

cgatatccag cacactggcg gccgttacta gtggatccgg ctgctaacaa agcccgaaag   1440

gaagctgagt tggctgctgc caccgctgag caataactag cataacccct tggggcctct   1500

aaacgggtct tgaggggttt tttgctgaaa ggaggaacta tatccggagc gactcccacg   1560

gcacgttggc aagctcg                                                  1577
```

<210> SEQ ID NO 98
<211> LENGTH: 1577
<212> TYPE: DNA
<213> ORGANISM: Artificial Sequence
<220> FEATURE:
<223> OTHER INFORMATION: Exemplary tsGBP2.13C.D278N expression sequence, optimized using OrfOpt

<400> SEQUENCE: 98

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaattaga    180

aatttttct tggtgggcag gtgattgtgg cccagctctc gaagccttga tccggttgta    240
```

-continued

```
taaacagaaa tacccaggtg tagaggtcat taatgctacc gtcaccgggg gtgccggtgt    300

caacgccaaa gccgtcctta aaacgcgtat gctcggcggg gacccaccag atacctttca    360

agtacatgca gggcaggagc tgatcggcac atgggtcgtc gccgaccgta tggaagatct    420

tacctcattg tttcggcagg agggctggct tcaagcgttc ccaaaaggtt taatcgatct    480

cctcagttac aaaggtggca tttggtcagt cccagtcaac atccaccgtt ctaacgtaat    540

gtggtacatc ccggcaaaat taaaagaatg gggcgtgacc ccgccaaaaa catgggcaga    600

atttttagcg acagcgcaaa cattaaagcg gaaaggcctt gaggcaccat tggcactcgg    660

tgagaattgg acacagcaac atctctggga aagcgtcgcc ctcgccacac tgggtgccga    720

tggttggaat aatctctgga gtggtaagct caaattcacg gatccaaaag cagtcgccgt    780

atgggaaaca ttcggtaagg tattagatgc agcgaacaag gatgcagccg ggctttcatg    840

gcaacaagca gtagaccgtg tagtacaggg gaaagctgca ttcaatatca tgggggactg    900

ggcagcaggt tacatgagta cgaccttaaa actgaagcca ggtaccgact tcgcatggac    960

accttctccg ggcacttcag ggatctttat gatgctgtct aacagtttcg gcttgccaaa   1020

gggggcgaag aatcgtcaaa atgctattaa ctggttgaaa ctcgtcgggt caaaagaggg   1080

gcaggacacc ttcaacccgc tcaaaggttc catcgctgct cgtctcgatt ctgatcctgc   1140

caaatataat gcatacggcc aaagtgcaat gaaggactgg aagtcaaatc ggatcgtagg   1200

ctccctcgtc cacggcgcag tcgcgccaga atccttcatg tcgcagtttg ggacggtaat   1260

ggagattttc ttgcaatccc gtaacccgca ggcagccgct aatgccgcac aagctatcgc   1320

caatcaggtc ggtttaggtc gtgggggttc acatcatcat catcatcatt aatgaaaggg   1380

cgatatccag cacactggcg gccgttacta gtggatccgg ctgctaacaa agcccgaaag   1440

gaagctgagt tggctgctgc caccgctgag caataactag cataacccct tggggcctct   1500

aaacgggtct tgaggggttt tttgctgaaa ggaggaacta tatccggagc gactcccacg   1560

gcacgttggc aagctcg                                                  1577
```

```
<210> SEQ ID NO 99
<211> LENGTH: 1577
<212> TYPE: DNA
<213> ORGANISM: Artificial Sequence
<220> FEATURE:
<223> OTHER INFORMATION: Exemplary tsGBP2.13C.D278S expression sequence,
      optimized using OrfOpt

<400> SEQUENCE: 99

cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaattaga    180

aatttttcct tggtgggcag gtgattgtgg cccagctctc gaagccttga tccggttgta    240

taaacagaaa tacccaggtg tagaggtcat taatgctacc gtcaccgggg gtgccggtgt    300

caacgccaaa gccgtcctta aaacgcgtat gctcggcggg gacccaccag atacctttca    360

agtacatgca gggcaggagc tgatcggcac atgggtcgtc gccgaccgta tggaagatct    420

tacctcattg tttcggcagg agggctggct tcaagcgttc ccaaaaggtt taatcgatct    480

cctcagttac aaaggtggca tttggtcagt cccagtcaac atccaccgtt ctaacgtaat    540

gtggtacatc ccggcaaaat taaaagaatg gggcgtgacc ccgccaaaaa catgggcaga    600

atttttagcg acagcgcaaa cattaaagcg gaaaggcctt gaggcaccat tggcactcgg    660
```

```
tgagaattgg acacagcaac atctctggga aagcgtcgcc ctcgccacac tgggtgccga    720

tggttggaat aatctctgga gtggtaagct caaattcacg gatccaaaag cagtcgccgt    780

atgggaaaca ttcggtaagg tattagatgc agcgaacaag gatgcagccg ggctttcatg    840

gcaacaagca gtagaccgtg tagtacaggg gaaagctgca ttcaatatca tgggggactg    900

ggcagcaggt tacatgagta cgaccttaaa actgaagcca ggtaccgact tcgcatggac    960

accttctccg ggcacttcag ggatctttat gatgctgtct agcagtttcg gcttgccaaa   1020

gggggcgaag aatcgtcaaa atgctattaa ctggttgaaa ctcgtcgggt caaaagaggg   1080

gcaggacacc ttcaacccgc tcaaaggttc catcgctgct cgtctcgatt ctgatcctgc   1140

caaatataat gcatacggcc aaagtgcaat gaaggactgg aagtcaaatc ggatcgtagg   1200

ctccctcgtc cacggcgcag tcgcgccaga atccttcatg tcgcagtttg ggacggtaat   1260

ggagattttc ttgcaatccc gtaacccgca ggcagccgct aatgccgcac aagctatcgc   1320

caatcaggtc ggtttaggtc gtgggggttc acatcatcat catcatcatt aatgaaaggg   1380

cgatatccag cacactggcg gccgttacta gtggatccgg ctgctaacaa agcccgaaag   1440

gaagctgagt tggctgctgc caccgctgag caataactag cataacccct tggggcctct   1500

aaacgggtct tgaggggttt tttgctgaaa ggaggaacta tatccggagc gactcccacg   1560

gcacgttggc aagctcg                                                  1577
```

```
<210> SEQ ID NO 100
<211> LENGTH: 1577
<212> TYPE: DNA
<213> ORGANISM: Artificial Sequence
<220> FEATURE:
<223> OTHER INFORMATION: Exemplary tsGBP2.13C.D278L expression sequence,
      optimized using OrfOpt

<400> SEQUENCE: 100

cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaattaga    180

aatttttctt tggtgggcag gtgattgtgg cccagctctc gaagccttga tccggttgta    240

taaacagaaa tacccaggtg tagaggtcat taatgctacc gtcaccgggg gtgccggtgt    300

caacgccaaa gccgtcctta aaacgcgtat gctcggcggg gacccaccag ataccttca    360

agtacatgca gggcaggagc tgatcggcac atgggtcgtc gccgaccgta tggaagatct    420

tacctcattg tttcggcagg agggctggct tcaagcgttc ccaaaaggtt taatcgatct    480

cctcagttac aaaggtggca tttggtcagt cccagtcaac atccaccgtt ctaacgtaat    540

gtggtacatc ccggcaaaat taaaagaatg ggcgtgacc ccgccaaaaa catgggcaga    600

atttttagcg acagcgcaaa cattaaagcg gaaaggcctt gaggcaccat tggcactcgg    660

tgagaattgg acacagcaac atctctggga aagcgtcgcc ctcgccacac tgggtgccga    720

tggttggaat aatctctgga gtggtaagct caaattcacg gatccaaaag cagtcgccgt    780

atgggaaaca ttcggtaagg tattagatgc agcgaacaag gatgcagccg ggctttcatg    840

gcaacaagca gtagaccgtg tagtacaggg gaaagctgca ttcaatatca tgggggactg    900

ggcagcaggt tacatgagta cgaccttaaa actgaagcca ggtaccgact tcgcatggac    960

accttctccg ggcacttcag ggatctttat gatgctgtct ctgagtttcg gcttgccaaa   1020

gggggcgaag aatcgtcaaa atgctattaa ctggttgaaa ctcgtcgggt caaaagaggg   1080
```

-continued

```
gcaggacacc ttcaacccgc tcaaaggttc catcgctgct cgtctcgatt ctgatcctgc   1140

caaatataat gcatacggcc aaagtgcaat gaaggactgg aagtcaaatc ggatcgtagg   1200

ctccctcgtc cacggcgcag tcgcgccaga atccttcatg tcgcagtttg ggacggtaat   1260

ggagattttc ttgcaatccc gtaacccgca ggcagccgct aatgccgcac aagctatcgc   1320

caatcaggtc ggtttaggtc gtgggggttc acatcatcat catcatcatt aatgaaaggg   1380

cgatatccag cacactggcg gccgttacta gtggatccgg ctgctaacaa agcccgaaag   1440

gaagctgagt tggctgctgc caccgctgag caataactag cataacccct tggggcctct   1500

aaacgggtct tgaggggttt tttgctgaaa ggaggaacta tatccggagc gactcccacg   1560

gcacgttggc aagctcg                                                  1577
```

```
<210> SEQ ID NO 101
<211> LENGTH: 1577
<212> TYPE: DNA
<213> ORGANISM: Artificial Sequence
<220> FEATURE:
<223> OTHER INFORMATION: Exemplary tsGBP2.13C.K312M expression sequence,
      optimized using OrfOpt

<400> SEQUENCE: 101

cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaattaga    180

aatttttcct tggtgggcag gtgattgtgg cccagctctc gaagccttga tccggttgta    240

taaacagaaa tacccaggtg tagaggtcat taatgctacc gtcaccgggg gtgccggtgt    300

caacgccaaa gccgtcctta aaacgcgtat gctcggcggg gacccaccag atacctttca    360

agtacatgca gggcaggagc tgatcggcac atgggtcgtc gccgaccgta tggaagatct    420

tacctcattg tttcggcagg agggctggct tcaagcgttc ccaaaaggtt taatcgatct    480

cctcagttac aaaggtggca tttggtcagt cccagtcaac atccaccgtt ctaacgtaat    540

gtggtacatc ccggcaaaat taaaagaatg gggcgtgacc ccgccaaaaa catgggcaga    600

atttttagcg acagcgcaaa cattaaagcg gaaaggcctt gaggcaccat tggcactcgg    660

tgagaattgg acacagcaac atctctggga aagcgtcgcc ctcgccacac tgggtgccga    720

tggttggaat aatctctgga gtggtaagct caaattcacg gatccaaaag cagtcgccgt    780

atgggaaaca ttcggtaagg tattagatgc agcgaacaag gatgcagccg ggctttcatg    840

gcaacaagca gtagaccgtg tagtacaggg gaaagctgca ttcaatatca tgggggactg    900

ggcagcaggt tacatgagta cgaccttaaa actgaagcca ggtaccgact tcgcatggac    960

accttctccg ggcacttcag ggatctttat gatgctgtct gatagtttcg gcttgccaaa   1020

gggggcgaag aatcgtcaaa atgctattaa ctggttgaaa ctcgtcgggt caaaagaggg   1080

gcaggacacc ttcaacccgc tcatgggttc catcgctgct cgtctcgatt ctgatcctgc   1140

caaatataat gcatacggcc aaagtgcaat gaaggactgg aagtcaaatc ggatcgtagg   1200

ctccctcgtc cacggcgcag tcgcgccaga atccttcatg tcgcagtttg ggacggtaat   1260

ggagattttc ttgcaatccc gtaacccgca ggcagccgct aatgccgcac aagctatcgc   1320

caatcaggtc ggtttaggtc gtgggggttc acatcatcat catcatcatt aatgaaaggg   1380

cgatatccag cacactggcg gccgttacta gtggatccgg ctgctaacaa agcccgaaag   1440

gaagctgagt tggctgctgc caccgctgag caataactag cataacccct tggggcctct   1500
```

aaacgggtct tgaggggttt tttgctgaaa ggaggaacta tatccggagc gactcccacg 1560
gcacgttggc aagctcg 1577

<210> SEQ ID NO 102
<211> LENGTH: 1649
<212> TYPE: DNA
<213> ORGANISM: Artificial Sequence
<220> FEATURE:
<223> OTHER INFORMATION: Exemplary tsGBP2.13C.bZif expression sequence,
      optimized using OrfOpt

<400> SEQUENCE: 102
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaattaga 180
aattttttct tggtgggcag gtgattgcgg cccagctctc gaagccttga tccggttgta 240
taaacagaaa tacccaggtg tagaggtcat taatgctacc gtcaccgggg gtgccggtgt 300
caacgccaaa gccgtcctta aaacgcgtat gctcggcggg gacccaccag ataccttca 360 agtacatgca gggcaggagc tgatcggcac atgggtcgtc gccgaccgta tggaagatct 420
tacctcattg tttcggcagg agggctggct tcaagcgttc ccaaaaggtt taatcgatct 480
cctcagttac aaaggtggca tttggtcagt cccagtcaac atccaccgtt ctaacgtaat 540
gtggtacatc ccggcaaaat taaaagaatg gggcgtgacc ccgccaaaaa catgggcaga 600
atttttagcg acagcgcaaa cattaaagcg gaaaggcctt gaggcaccat tggcactcgg 660
tgagaattgg acacagcaac atctctggga aagcgtcgcc ctcgccacac tgggtgccga 720
tggttggaat aatctctgga gtggtaagct caaattcacg gatccaaaag cagtcgccgt 780
atgggaaaca ttcggtaagg tattagatgc agcgaacaag gatgcagccg ggctttcatg 840
gcaacaagca gtagaccgtg tagtacaggg gaaagctgca ttcaatatca tgggggactg 900
ggcagcaggt tacatgagta cgaccttaaa actgaagcca ggtaccgact tcgcatggac 960
accttctccg ggcacttcag ggatctttat gatgctgtct gatagtttcg gcttgccaaa 1020
gggggcgaag aatcgtcaaa atgctattaa ctggttgaaa ctcgtcgggt caaaagaggg 1080
gcaggacacc ttcaacccgc tcaaaggttc catcgctgct cgtctcgatt ctgatcctgc 1140
caaatataat gcatacggcc aaagtgcaat gaaggactgg aagtcaaatc ggatcgtagg 1200
ctccctcgtc cacggcgcag tcgcgccaga atccttcatg tcgcagtttg ggacggtaat 1260
ggagattttc ttgcaatccc gtaacccgca ggcagccgct aatgccgcac aagctatcgc 1320
caatcaggtc ggtttaggtc gtggcggcag cggcggcagc accggcgaaa aaccgtataa 1380
atgcccggaa tgcggcaaaa gctttagccg cagcgggggt tcacatcatc atcatcatca 1440
ttaatgaaag ggcgatatcc agcacactgg cggccgttac tagtggatcc ggctgctaac 1500
aaagcccgaa aggaagctga gttggctgct gccaccgctg agcaataact agcataaccc 1560
cttggggcct ctaaacgggt cttgaggggt tttttgctga aaggaggaac tatatccgga 1620
gcgactccca cggcacgttg gcaagctcg 1649

<210> SEQ ID NO 103
<211> LENGTH: 1649
<212> TYPE: DNA
<213> ORGANISM: Artificial Sequence
<220> FEATURE:
<223> OTHER INFORMATION: Exemplary tsGBP2.244C.bZif expression sequence, optimized using OrfOpt

<400> SEQUENCE: 103
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaattaga 180 aatttttct tggtgggcag gtgatgaagg cccagctctc gaagccttga tccggttgta 240
taaacagaaa tacccaggtg tagaggtcat taatgctacc gtcaccgggg gtgccggtgt 300
caacgccaaa gccgtcctta aaacgcgtat gctcggcggg gacccaccag ataccttca 360 agtacatgca gggcaggagc tgatcggcac atgggtcgtc gccgaccgta tggaagatct 420
tacctcattg tttcggcagg agggctggct tcaagcgttc ccaaaaggtt taatcgatct 480
cctcagttac aaaggtggca tttggtcagt cccagtcaac atccaccgtt ctaacgtaat 540
gtggtacatc ccggcaaaat taaaagaatg gggcgtgacc ccgccaaaaa catgggcaga 600
atttttagcg acagcgcaaa cattaaagcg gaaaggcctt gaggcaccat tggcactcgg 660
tgagaattgg acacagcaac atctctggga aagcgtcgcc ctcgccacac tgggtgccga 720
tggttggaat aatctctgga gtggtaagct caaattcacg gatccaaaag cagtcgccgt 780
atgggaaaca ttcggtaagg tattagatgc agcgaacaag gatgcagccg ggctttcatg 840
gcaacaagca gtagaccgtg tagtacaggg gaaagctgca ttcaatatca tgggggactg 900
cgcagcaggt tacatgagta cgaccttaaa actgaagcca ggtaccgact tcgcatggac 960
accttctccg ggcacttcag ggatctttat gatgctgtct gatagtttcg gcttgccaaa 1020
gggggcgaag aatcgtcaaa atgctattaa ctggttgaaa ctcgtcgggt caaaagaggg 1080
gcaggacacc ttcaacccgc tcaaaggttc catcgctgct cgtctcgatt ctgatcctgc 1140
caaatataat gcatacggcc aaagtgcaat gaaggactgg aagtcaaatc ggatcgtagg 1200
ctccctcgtc cacggcgcag tcgcgccaga atccttcatg tcgcagtttg ggacggtaat 1260 ggagatttc ttgcaatccc gtaacccgca ggcagccgct aatgccgcac aagctatcgc 1320
caatcaggtc ggtttaggtc gtggcggcag cggcggcagc accggcgaaa aaccgtataa 1380
atgcccggaa tgcggcaaaa gctttagccg cagcgggggt tcacatcatc atcatcatca 1440
ttaatgaaag ggcgatatcc agcacactgg cggccgttac tagtggatcc ggctgctaac 1500
aaagcccgaa aggaagctga gttggctgct gccaccgctg agcaataact agcataaccc 1560
cttggggcct ctaaacgggt cttgaggggt tttttgctga aaggaggaac tatatccgga 1620
gcgactccca cggcacgttg gcaagctcg 1649

<210> SEQ ID NO 104
<211> LENGTH: 1649
<212> TYPE: DNA
<213> ORGANISM: Artificial Sequence
<220> FEATURE:
<223> OTHER INFORMATION: Exemplary tsGBP2.13C_244F.bZif expression
sequence, optimized using OrfOpt

<400> SEQUENCE: 104
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaattaga 180 aatttttct tggtgggcag gtgattgcgg cccagctctc gaagccttga tccggttgta 240

-continued

```
taaacagaaa tacccaggtg tagaggtcat taatgctacc gtcaccgggg gtgccggtgt    300
caacgccaaa gccgtcctta aaacgcgtat gctcggcggg gacccaccag ataccttca    360
agtacatgca gggcaggagc tgatcggcac atgggtcgtc gccgaccgta tggaagatct    420
tacctcattg tttcggcagg agggctggct tcaagcgttc ccaaaaggtt taatcgatct    480
cctcagttac aaaggtggca tttggtcagt cccagtcaac atccaccgtt ctaacgtaat    540
gtggtacatc ccggcaaaat taaaagaatg gggcgtgacc ccgccaaaaa catgggcaga    600
atttttagcg acagcgcaaa cattaaagcg gaaaggcctt gaggcaccat tggcactcgg    660
tgagaattgg acacagcaac atctctggga aagcgtcgcc ctcgccacac tgggtgccga    720
tggttggaat aatctctgga gtggtaagct caaattcacg gatccaaaag cagtcgccgt    780
atgggaaaca ttcggtaagg tattagatgc agcgaacaag gatgcagccg ggctttcatg    840
gcaacaagca gtagaccgtg tagtacaggg gaaagctgca ttcaatatca tgggggactt    900
tgcagcaggt tacatgagta cgaccttaaa actgaagcca ggtaccgact tcgcatggac    960
accttctccg ggcacttcag ggatctttat gatgctgtct gatagtttcg gcttgccaaa   1020
gggggcgaag aatcgtcaaa atgctattaa ctggttgaaa ctcgtcgggt caaaagaggg   1080
gcaggacacc ttcaacccgc tcaaaggttc catcgctgct cgtctcgatt ctgatcctgc   1140
caaatataat gcatacggcc aaagtgcaat gaaggactgg aagtcaaatc ggatcgtagg   1200
ctccctcgtc cacggcgcag tcgcgccaga atccttcatg tcgcagtttg ggacggtaat   1260
ggagattttc ttgcaatccc gtaacccgca ggcagccgct aatgccgcac aagctatcgc   1320
caatcaggtc ggtttaggtc gtggcggcag cggcggcagc accggcgaaa aaccgtataa   1380
atgcccggaa tgcggcaaaa gctttagccg cagcgggggt tcacatcatc atcatcatca   1440
ttaatgaaag ggcgatatcc agcacactgg cggccgttac tagtggatcc ggctgctaac   1500
aaagcccgaa aggaagctga gttggctgct gccaccgctg agcaataact agcataaccc   1560
cttggggcct ctaaacgggt cttgaggggt tttttgctga aaggaggaac tatatccgga   1620
gcgactccca cggcacgttg gcaagctcg                                     1649
```

<210> SEQ ID NO 105
<211> LENGTH: 18
<212> TYPE: PRT
<213> ORGANISM: Artificial Sequence
<220> FEATURE:
<223> OTHER INFORMATION: bZif

<400> SEQUENCE: 105

```
Thr Gly Glu Lys Pro Tyr Lys Cys Pro Glu Cys Gly Lys Ser Phe Ser
1               5                   10                  15

Arg Ser
```

<210> SEQ ID NO 106
<211> LENGTH: 32
<212> TYPE: PRT
<213> ORGANISM: Artificial Sequence
<220> FEATURE:
<223> OTHER INFORMATION: ZF-QNK

<400> SEQUENCE: 106

```
Thr Gly Glu Lys Pro Tyr Lys Cys Pro Glu Cys Gly Lys Ser Phe Ser
1               5                   10                  15

Arg Ser Asp His Leu Ser Arg His Gln Arg Thr His Gln Asn Lys Lys
            20                  25                  30
```

-continued

<210> SEQ ID NO 107
<211> LENGTH: 6
<212> TYPE: PRT
<213> ORGANISM: Artificial Sequence
<220> FEATURE:
<223> OTHER INFORMATION: Hexahistidine Tag

<400> SEQUENCE: 107

His His His His His His
1               5

<210> SEQ ID NO 108
<211> LENGTH: 6
<212> TYPE: PRT
<213> ORGANISM: Artificial Sequence
<220> FEATURE:
<223> OTHER INFORMATION: Hexalysine Tag

<400> SEQUENCE: 108

Lys Lys Lys Lys Lys Lys
1               5

<210> SEQ ID NO 109
<211> LENGTH: 394
<212> TYPE: PRT
<213> ORGANISM: Artificial Sequence
<220> FEATURE:
<223> OTHER INFORMATION: ttGBP1 (with signal peptide replaced with M)

<400> SEQUENCE: 109

Met Lys Leu Glu Ile Phe Ser Trp Trp Ala Gly Asp Glu Gly Pro Ala
1               5                   10                  15

Leu Glu Ala Leu Ile Arg Leu Tyr Lys Gln Lys Tyr Pro Gly Val Glu
            20                  25                  30

Val Ile Asn Ala Thr Val Thr Gly Gly Ala Gly Val Asn Ala Arg Ala
        35                  40                  45

Val Leu Lys Thr Arg Met Leu Gly Gly Asp Pro Pro Asp Thr Phe Gln
    50                  55                  60

Val His Ala Gly Met Glu Leu Ile Gly Thr Trp Val Val Ala Asn Arg
65                  70                  75                  80

Met Glu Asp Leu Ser Ala Leu Phe Arg Gln Glu Gly Trp Leu Gln Ala
                85                  90                  95

Phe Pro Lys Gly Leu Ile Asp Leu Ile Ser Tyr Lys Gly Gly Ile Trp
            100                 105                 110

Ser Val Pro Val Asn Ile His Arg Ser Asn Val Met Trp Tyr Leu Pro
        115                 120                 125

Ala Lys Leu Lys Gly Trp Gly Val Asn Pro Pro Arg Thr Trp Asp Lys
    130                 135                 140

Phe Leu Ala Thr Ala Gln Thr Leu Lys Gln Lys Gly Leu Glu Ala Pro
145                 150                 155                 160

Leu Ala Leu Gly Glu Asn Trp Thr Gln Gln His Leu Trp Glu Ser Val
                165                 170                 175

Ala Leu Ala Val Leu Gly Pro Asp Asp Trp Asn Asn Leu Trp Asn Gly
            180                 185                 190

Lys Leu Lys Phe Thr Asp Pro Lys Ala Val Arg Ala Trp Glu Val Phe
        195                 200                 205

Gly Arg Val Leu Asp Ala Ala Asn Lys Asp Ala Ala Gly Leu Ser Trp
    210                 215                 220

Gln Gln Ala Val Asp Arg Val Val Gln Gly Lys Ala Ala Phe Asn Ile 225 230 235 240

Met Gly Asp Trp Ala Ala Gly Tyr Met Thr Thr Thr Leu Lys Leu Lys
245 250 255

Pro Gly Thr Asp Phe Ala Trp Ala Pro Ser Pro Gly Thr Gln Gly Val
260 265 270

Phe Met Met Leu Ser Asp Ser Phe Gly Leu Pro Lys Gly Ala Lys Asn
275 280 285

Arg Gln Asn Ala Ile Asn Trp Leu Arg Leu Val Gly Ser Lys Glu Gly
290 295 300

Gln Asp Thr Ser Asn Pro Leu Lys Gly Ser Ile Ala Ala Arg Leu Asp
305 310 315 320

Ser Asp Pro Ser Lys Tyr Asn Ala Tyr Gly Gln Ser Ala Met Arg Asp
325 330 335

Trp Arg Ser Asn Arg Ile Val Gly Ser Leu Val His Gly Ala Val Ala
340 345 350

Pro Glu Ser Phe Met Ser Gln Phe Gly Thr Val Met Glu Ile Phe Leu
355 360 365

Gln Thr Arg Asn Pro Gln Ala Ala Ala Asn Ala Ala Gln Ala Ile Ala
370 375 380

Asp Gln Val Gly Leu Gly Arg Leu Gly Gln
385 390

<210> SEQ ID NO 110
<211> LENGTH: 391
<212> TYPE: PRT
<213> ORGANISM: Artificial Sequence
<220> FEATURE:
<223> OTHER INFORMATION: tsGBP2 (with signal peptide replaced with M)

<400> SEQUENCE: 110

Met Lys Leu Glu Ile Phe Ser Trp Trp Ala Gly Asp Glu Gly Pro Ala
1 5 10 15

Leu Glu Ala Leu Ile Arg Leu Tyr Lys Gln Lys Tyr Pro Gly Val Glu
20 25 30

Val Ile Asn Ala Thr Val Thr Gly Gly Ala Gly Val Asn Ala Lys Ala
35 40 45

Val Leu Lys Thr Arg Met Leu Gly Gly Asp Pro Pro Asp Thr Phe Gln
50 55 60

Val His Ala Gly Gln Glu Leu Ile Gly Thr Trp Val Val Ala Asp Arg
65 70 75 80

Met Glu Asp Leu Thr Ser Leu Phe Arg Gln Glu Gly Trp Leu Gln Ala
85 90 95

Phe Pro Lys Gly Leu Ile Asp Leu Leu Ser Tyr Lys Gly Gly Ile Trp
100 105 110

Ser Val Pro Val Asn Ile His Arg Ser Asn Val Met Trp Tyr Ile Pro
115 120 125

Ala Lys Leu Lys Glu Trp Gly Val Thr Pro Pro Lys Thr Trp Ala Glu
130 135 140

Phe Leu Ala Thr Ala Gln Thr Leu Lys Arg Lys Gly Leu Glu Ala Pro
145 150 155 160

Leu Ala Leu Gly Glu Asn Trp Thr Gln Gln His Leu Trp Glu Ser Val
165 170 175

Ala Leu Ala Thr Leu Gly Ala Asp Gly Trp Asn Asn Leu Trp Ser Gly
180 185 190

Lys Leu Lys Phe Thr Asp Pro Lys Ala Val Ala Val Trp Glu Thr Phe

```
        195                 200                 205

Gly Lys Val Leu Asp Ala Ala Asn Lys Asp Ala Ala Gly Leu Ser Trp
    210                 215                 220

Gln Gln Ala Val Asp Arg Val Val Gln Gly Lys Ala Ala Phe Asn Ile
225                 230                 235                 240

Met Gly Asp Trp Ala Ala Gly Tyr Met Ser Thr Thr Leu Lys Leu Lys
                245                 250                 255

Pro Gly Thr Asp Phe Ala Trp Thr Pro Ser Pro Gly Thr Ser Gly Ile
            260                 265                 270

Phe Met Met Leu Ser Asp Ser Phe Gly Leu Pro Lys Gly Ala Lys Asn
        275                 280                 285

Arg Gln Asn Ala Ile Asn Trp Leu Lys Leu Val Gly Ser Lys Glu Gly
    290                 295                 300

Gln Asp Thr Phe Asn Pro Leu Lys Gly Ser Ile Ala Ala Arg Leu Asp
305                 310                 315                 320

Ser Asp Pro Ala Lys Tyr Asn Ala Tyr Gly Gln Ser Ala Met Lys Asp
                325                 330                 335

Trp Lys Ser Asn Arg Ile Val Gly Ser Leu Val His Gly Ala Val Ala
            340                 345                 350

Pro Glu Ser Phe Met Ser Gln Phe Gly Thr Val Met Glu Ile Phe Leu
        355                 360                 365

Gln Ser Arg Asn Pro Gln Ala Ala Ala Asn Ala Ala Gln Ala Ile Ala
    370                 375                 380

Asn Gln Val Gly Leu Gly Arg
385                 390


<210> SEQ ID NO 111
<211> LENGTH: 390
<212> TYPE: PRT
<213> ORGANISM: Artificial Sequence
<220> FEATURE:
<223> OTHER INFORMATION: dmGBP3 (with signal peptide replaced with M)

<400> SEQUENCE: 111

Met Lys Leu Glu Ile Phe Ser Trp Trp Ser Gly Asp Glu Gly Pro Ala
1               5                   10                  15

Leu Glu Ala Leu Val Lys Leu Tyr Lys Gln Lys Tyr Pro Ser Val Asp
            20                  25                  30

Val Val Asn Ala Thr Val Ala Gly Gly Ala Gly Thr Asn Ala Lys Ala
        35                  40                  45

Val Leu Lys Thr Arg Met Leu Gly Gly Asp Pro Pro Asp Ser Phe Gln
    50                  55                  60

Ala His Ala Gly Gln Glu Leu Ile Gly Thr Trp Val Val Ala Asn Arg
65                  70                  75                  80

Met Glu Asp Leu Ser Ser Leu Phe Lys Ser Glu Gly Trp Thr Thr Lys
                85                  90                  95

Phe Pro Lys Asp Leu Leu Pro Leu Ile Ser Ser Lys Gly Gly Ile Trp
            100                 105                 110

Ser Val Pro Val Asn Val His Arg Ser Asn Val Met Trp Tyr Ile Pro
        115                 120                 125

Ala Asn Leu Lys Lys Trp Gly Val Thr Ala Pro Lys Thr Trp Asp Gln
    130                 135                 140

Phe Leu Thr Thr Ala Lys Thr Leu Lys Thr Lys Asn Val Thr Pro Leu
145                 150                 155                 160

Ala Leu Gly Glu Asn Trp Thr Gln Gln His Leu Trp Glu Ser Val Ala
```

```
                165                 170                 175

Val Gly Thr Leu Gly Ala Gln Gly Trp Gln Asn Leu Trp Ser Gly Lys
            180                 185                 190

Leu Lys Phe Thr Asp Pro Lys Val Val Lys Val Trp Asp Thr Phe Gly
        195                 200                 205

Lys Val Leu Asp Ala Thr Asn Lys Asp Ala Ser Gly Leu Ser Trp Gln
    210                 215                 220

Gln Ala Thr Asp Arg Val Val Asn Gly Gln Ala Ala Phe Asn Ile Met
225                 230                 235                 240

Gly Asp Trp Ala Ala Gly Tyr Leu Ser Thr Thr Lys Lys Leu Lys Pro
                245                 250                 255

Gly Thr Gly Phe Gly Trp Ala Pro Ser Pro Ser Thr Ser Gly Thr Phe
            260                 265                 270

Ile Phe Leu Ala Asp Ser Phe Gly Leu Pro Lys Gly Ala Lys Asp Arg
        275                 280                 285

Ala Glu Ala Leu Ser Trp Leu Lys Leu Leu Gly Ser Lys Gln Gly Gln
    290                 295                 300

Asp Thr Phe Asn Pro Leu Lys Gly Ser Ile Ala Ala Arg Val Asp Ser
305                 310                 315                 320

Asp Leu Ser Lys Tyr Ser Thr Tyr Ser Gln Ser Ala Ala Lys Asp Trp
                325                 330                 335

Lys Ser Asn Lys Ile Val Gly Ser Leu Thr His Gly Ala Val Ala Pro
            340                 345                 350

Glu Ser Phe Thr Ser Thr Phe Gly Thr Val Ile Asp Ala Phe Val Ala
        355                 360                 365

Ser Arg Asn Ala Gln Val Ala Ala Ala Thr Thr Gln Gln Leu Ala Asp
    370                 375                 380

Lys Ala Gly Leu Gly Lys
385                 390
```

```
<210> SEQ ID NO 112
<211> LENGTH: 393
<212> TYPE: PRT
<213> ORGANISM: Artificial Sequence
<220> FEATURE:
<223> OTHER INFORMATION: tnGBP4 (with signal peptide replaced with M)

<400> SEQUENCE: 112

Met Leu Glu Ile Phe Ser Trp Trp Thr Ala Gly Gly Glu Ala Glu Ala
1               5                   10                  15

Leu Glu Ala Leu Ile Lys Val Phe Asn Lys Tyr Tyr Pro Asp Val Glu
            20                  25                  30

Val Ile Asn Ala Thr Val Ala Gly Gly Ala Gly Thr Asn Ala Lys Ala
        35                  40                  45

Val Leu Lys Thr Arg Ile Leu Gly Gly Asn Pro Pro Asp Ser Phe Gln
    50                  55                  60

Val His Ala Gly Met Glu Leu Ile Asp Thr Tyr Val Ile Pro Gly Tyr
65                  70                  75                  80

Met Thr Pro Ile Thr Asn Leu Leu Glu Gln Trp Gly Val Met Asp Lys
                85                  90                  95

Phe Pro Lys Gly Ile Leu Glu Met Ala Ser Tyr Glu Gly Glu Ile Tyr
            100                 105                 110

Ser Ile Pro Val Asn Val His Arg Gly Asn Val Val Phe Tyr Asn Lys
        115                 120                 125

Lys Ile Ala Glu Glu Ile Gly Met Asn Glu Pro Pro Lys Thr Trp Asp
```

```
    130                 135                 140

Glu Phe Ile Met Tyr Leu Gln Lys Ala Lys Glu Lys Gly Tyr Val Gly
145                 150                 155                 160

Leu Ala Leu Gly Asp Lys Asn Lys Trp Thr Ala Leu His Leu Phe Glu
                165                 170                 175

Thr Ile Leu Leu Gly Val Leu Gly Pro Asn Asp Tyr Asn Gly Leu Trp
            180                 185                 190

Lys Gly Glu Val Ser Phe Asn Asp Pro Arg Ile Arg Arg Ala Phe Glu
        195                 200                 205

Ile Met Asn Lys Leu Leu Asp Tyr Val Asn Glu Asp His Ala Ala Leu
    210                 215                 220

Ala Trp Gln Asp Ala Thr Arg Leu Val Tyr Glu Gly Lys Ala Leu Ala
225                 230                 235                 240

Asn Val Met Gly Asp Trp Ala Glu Gly Tyr Leu Lys Ser Val Gly Trp
                245                 250                 255

Glu Pro Gly Lys Asp Phe Gly Trp Phe Ala Val Pro Glu Thr Gln Asn
            260                 265                 270

Ala Phe Met Val Val Ser Asp Thr Phe Gly Leu Pro Lys Asn Ala Pro
        275                 280                 285

His Lys Glu Asn Ala Val Lys Trp Leu Lys Val Val Ala Ser Val Glu
    290                 295                 300

Gly Gln Asp Ala Phe Asn Pro Ile Lys Gly Ser Ile Pro Ala Arg Leu
305                 310                 315                 320

Asp Ala Asp Arg Ser Lys Tyr Asp Ile Tyr Leu Gln Trp Ser Met Glu
                325                 330                 335

Asp Phe Ala Thr Lys Ala Leu Thr Pro Ser Ile Ala His Gly Ser Ala
            340                 345                 350

Ala Pro Glu Gly Phe Val Thr Thr Leu Asn Asp Ile Ile Asn Arg Phe
        355                 360                 365

Val Thr Thr Arg Asp Ile Asp Ser Ala Leu Glu Glu Leu Leu Met Ala
    370                 375                 380

Ala Glu Asp Glu Gly Tyr Leu Val Glu
385                 390


<210> SEQ ID NO 113
<211> LENGTH: 390
<212> TYPE: PRT
<213> ORGANISM: Artificial Sequence
<220> FEATURE:
<223> OTHER INFORMATION: koGBP5 (with signal peptide replaced with M)

<400> SEQUENCE: 113

Met Leu Glu Ile Phe Ser Trp Trp Thr Gly Gly Gly Glu Glu Glu Gly
1               5                   10                  15

Leu Leu Ala Leu Phe Asp Val Phe His Lys Tyr Tyr Pro Asp Val Glu
            20                  25                  30

Ile Ile Asn Ala Thr Val Ala Gly Gly Ala Gly Thr Asn Ala Lys Ala
        35                  40                  45

Val Leu Lys Thr Arg Met Leu Gly Gly Asn Pro Pro Asp Ser Phe Gln
    50                  55                  60

Val His Gly Gly Met Glu Leu Ile Asp Thr Tyr Val Val Thr Gly Met
65                  70                  75                  80

Met Glu Pro Ile Thr Asp Leu Leu Glu Glu Trp Gly Ile Ile Asp Lys
                85                  90                  95

Phe Pro Glu Asp Ile Leu Lys Ile Ala Ser Tyr Lys Gly Glu Val Tyr
```

```
            100                 105                 110

Ser Ile Pro Val Asn Val His Arg Gly Asn Val Val Phe Tyr Asn Lys
        115                 120                 125

Ala Ile Leu Glu Glu Val Gly Ile Glu Lys Val Pro Ser Thr Trp Pro
    130                 135                 140

Glu Phe Ile Glu Val Leu Lys Lys Ile Lys Lys Ala Gly Tyr Ile Pro
145                 150                 155                 160

Leu Ala Leu Gly Asp Lys Asn Lys Trp Thr Ala Thr His Leu Phe Glu
                165                 170                 175

Asp Ile Leu Leu Ser Thr Leu Gly Pro Tyr Asn Tyr Asn Gly Leu Trp
            180                 185                 190

Asn Gly Arg Thr Ser Phe Glu His Gln Gly Val Lys Glu Ala Leu Glu
        195                 200                 205

Ile Phe Lys Glu Leu Met Asn Tyr Val Asn Pro Asn His Ala Ser Leu
    210                 215                 220

Thr Trp Gln Asp Ala Thr Leu Leu Val Phe Glu Gly Lys Ala Ala Phe
225                 230                 235                 240

Asn Val Met Gly Asp Trp Ala Glu Gly Tyr Leu Lys Thr Leu Gly Trp
                245                 250                 255

Thr Pro Gly Lys Glu Phe Gly Trp Met Val Val Pro Gly Thr Lys Gly
            260                 265                 270

Ser Phe Met Val Val Thr Asp Thr Phe Gly Leu Pro Lys Asn Ala Pro
        275                 280                 285

His Arg Glu Asn Ala Ile Lys Trp Leu Lys Ile Ile Ser Ser Val Glu
    290                 295                 300

Gly Gln Asp Thr Phe Asn Pro Ile Lys Gly Ser Ile Pro Ala Arg Ile
305                 310                 315                 320

Asp Ala Asp Arg Ser Leu Tyr Asp Asp Tyr Leu Ile Trp Ser Met Asp
                325                 330                 335

Asp Phe Ala Thr Asn Ala Leu Cys Pro Ser Ile Ile His Gly Ser Ala
            340                 345                 350

Ala Pro Glu Ala Phe Val Thr Ala Leu Asn Asp Thr Ile Asn Met Phe
        355                 360                 365

Ile Thr Arg Lys Asp Val Lys Lys Ala Leu Lys Glu Ile Ile Tyr Ala
    370                 375                 380

Ala Glu Asp Tyr Leu Glu
385                 390


<210> SEQ ID NO 114
<211> LENGTH: 386
<212> TYPE: PRT
<213> ORGANISM: Artificial Sequence
<220> FEATURE:
<223> OTHER INFORMATION: bhGBP6 (with signal peptide replaced with M)

<400> SEQUENCE: 114

Met Leu Glu Ile Phe Ser Trp Trp Thr Gly Ala Gly Glu Glu Asp Gly
1               5                   10                  15

Leu Leu Ala Leu Ile Glu Leu Phe Glu Glu Lys His Pro Glu Ile Glu
            20                  25                  30

Val Asp Asn Ala Ala Val Ala Gly Gly Ala Gly Thr Asn Ala Lys Ala
        35                  40                  45

Val Leu Thr Ser Arg Met Gln Gly Asn Asp Pro Pro Gly Thr Phe Gln
    50                  55                  60

Val His Gly Gly Ala Glu Leu Asn Asp Ser Trp Val Ala Ala Gly Gln
```

65 70 75 80

Met Asp Pro Leu Asn Asp Leu Phe Glu Ala Glu Gly Trp Ala Asp Lys
85 90 95

Phe Pro Glu Glu Leu Ile Glu Leu Val Ser Lys Asp Gly Asn Ile Tyr
100 105 110

Ser Val Pro Val Asn Ile His Arg Gly Asn Val Leu Trp Tyr Asn Thr
115 120 125

Glu Ile Phe Glu Glu His Gly Leu Glu Val Pro Thr Thr Phe Glu Glu
130 135 140

Phe Phe Asp Val Ala Asp Ala Leu Gln Glu Ala Gly Val Thr Pro Leu
145 150 155 160

Ala Leu Gly Asp Arg Glu Pro Trp Ala Ala Thr His Leu Phe Glu Thr
165 170 175

Val Leu Leu Gly Thr Leu Gly Ala Asp Asp Tyr Asn Lys Leu Trp Ser
180 185 190

Gly Glu Val Gly Met Asp Asp Pro Arg Val Glu Glu Ala Ala Glu Ile
195 200 205

Phe Ile Arg Met Leu Asp Tyr Val Asn Glu Asp His Ser Ser Arg Asn
210 215 220

Trp Gln Asp Ala Ser Gln Leu Val Ala Gln Gly Glu Ala Ala Met Asn
225 230 235 240

Val Met Gly Asp Trp Ala Lys Gly Tyr Phe Val Asn Asp Leu Asn Leu
245 250 255

Ala Val Lys Glu Asp Phe Gly Trp Ala Ala Thr Pro Gly Thr Glu Gly
260 265 270

Thr Phe Met Val Ile Thr Asp Thr Phe Gly Leu Pro Thr Gly Val Glu
275 280 285

Asn Pro Glu Val Val Lys Ser Phe Leu Ala Val Leu Gly Ser Gln Glu
290 295 300

Gly Gln Asp Ala Phe Asn Pro Leu Lys Gly Ser Ile Pro Ala Arg Val
305 310 315 320

Asp Ala Asp Val Ser Lys Tyr Asp Glu Tyr Gly Gln Glu Thr Ile Glu
325 330 335

Asp Phe Lys Ser Ala Glu Leu Ser Pro Ser Leu Ala His Gly Ser Ala
340 345 350

Ala Asn Glu Gly Phe Leu Thr Gln Val Asn Gln Ala Ile Asn Ile Phe
355 360 365

Val Thr Gln Lys Asp Val Asp Ser Phe Val Asp Ser Leu Lys Gln Tyr
370 375 380

Gln Pro
385

<210> SEQ ID NO 115
<211> LENGTH: 427
<212> TYPE: PRT
<213> ORGANISM: Artificial Sequence
<220> FEATURE:
<223> OTHER INFORMATION: smGBP7 (with signal peptide replaced with M)

<400> SEQUENCE: 115

Met Glu Leu Val Ile Tyr His Trp Trp Thr Ala Gly Gly Glu Arg Glu
1 5 10 15

Ala Ile Asn Ala Val Phe Gln Val Phe Lys Gln Lys Tyr Pro Asn Ile
20 25 30

Gln Ile Val Glu Asn Pro Val Ala Gly Gly Ala Gly Ser Val Met Lys

-continued 35 40 45

Ser Val Ile Ile Gly Leu Leu Ala Ala Gly Thr Pro Pro Asp Thr Phe
50 55 60

Gln Val His Ala Gly Ala Glu Leu Lys Glu Tyr Val Asp Ala Gly Tyr
65 70 75 80

Leu Ala Pro Ile Asp Asp Ile Trp Ser Lys Leu Gly Leu Asp Lys Val
85 90 95

Ile Pro Ser Thr Leu Gln Val Met Ala Lys Phe Asn Gly His Tyr Tyr
100 105 110

Ala Val Pro Ile Asp Val His Arg Ser Asn Val Leu Trp Tyr Asn Pro
115 120 125

Lys Ile Phe Asn Glu Leu Gly Ile Ile Asn Lys Phe Gly Asp Pro Arg
130 135 140

Asn Trp Ser Val Asp Thr Leu Leu Gln Val Ala Arg Tyr Ile Lys Gln
145 150 155 160

Gln Arg Pro Asp Ile Ala Pro Ile Ala Leu Ala Ser Arg Asn Lys Trp
165 170 175

Pro Val Thr His Leu Phe Glu Val Leu Leu Ala Asn Ala Gly Gly Pro
180 185 190

Glu Thr Tyr Val Lys Phe Phe Thr Gly Lys Phe Asn Tyr Asn Asp Pro
195 200 205

Asn Asp Pro Val Val Gln Thr Val Lys Lys Val Leu Thr Val Met Ala
210 215 220

Thr Met Ala Lys Glu Gly Leu Phe Asn Ser Asn His Pro Glu Leu Thr
225 230 235 240

Trp Asp Gln Ala Ala Ala Leu Val Ala Glu Gly Lys Ala Ala Met Phe
245 250 255

Ile His Gly Asp Trp Val Ala Gly Tyr Tyr Ile Ala Asn Asn Tyr Lys
260 265 270

Tyr Gly Lys Asp Trp Ala Ala Ala Pro Phe Pro Lys Asn Ile Phe Ile
275 280 285

Leu Leu Ser Asp Ala Phe Glu Leu Pro Lys Asn Ala Pro His Pro Glu
290 295 300

Ala Ala Lys Asp Trp Leu Met Val Val Gly Ser Lys Glu Ala Gln Glu
305 310 315 320

Lys Phe Asn Leu Ile Lys Gly Ser Ile Pro Ala Arg Thr Asp Val Ser
325 330 335

Pro Lys Tyr Pro Asp Pro Tyr Arg Pro Glu Thr Ala Glu Asp Phe Gln
340 345 350

Lys Ser Thr Leu Ile Pro Ser Ala Val His Gly Gly Ile Ala Lys Glu
355 360 365

Ala Phe Met Thr Asp Leu His Asn Ile Leu Thr Ser Met Leu Thr Ala
370 375 380

Val Ser Val Gly Thr Pro Val Asp Asn Ala Val Asn Thr Ala Leu Ala
385 390 395 400

Gln Ile Leu Gln Ser Val Lys Thr Ser Gly Leu Ala Ser Phe Trp Lys
405 410 415

Gly Tyr Thr Ile Asp Tyr Phe Ile Thr Lys Arg
420 425

<210> SEQ ID NO 116
<211> LENGTH: 391
<212> TYPE: PRT
<213> ORGANISM: Artificial Sequence

```
<220> FEATURE:
<223> OTHER INFORMATION: asGBP8 (with signal peptide replaced with M)

<400> SEQUENCE: 116

Met Lys Leu Glu Ile Thr Ser Trp Trp Thr Ser Gly Ser Glu Ala Asp
1               5                   10                  15

Ala Leu Asn Val Leu Ile Asp Gly Val Lys Ala Ala Lys Pro Gly Leu
            20                  25                  30

Ser Val Asp Asn Ala Ala Val Ser Gly Gly Gly Gly Ala Asn Ala Arg
        35                  40                  45

Gln Ala Leu Ala Ala Arg Leu Gln Ala Gly Ser Pro Pro Asp Ala Trp
    50                  55                  60

Gln Val His Pro Ala Gly Gln Leu Lys Ser Tyr Val Asp Gly Gly Gln
65                  70                  75                  80

Val Ala Asp Leu Thr Asp Leu Trp Thr Glu Gly Asp Trp Ala Ser Gln
                85                  90                  95

Met Pro Lys Asp Val Ala Glu Ala Gln Gln Val Asp Gly Lys Tyr Tyr
            100                 105                 110

Thr Val Pro Ile Gly Val His Arg Gly Asn Val Leu Trp Thr Asn Pro
        115                 120                 125

Ala Val Leu Ser Lys Ala Asn Val Thr Ile Asp Ala Asp Ala Gly Ile
    130                 135                 140

Asp Gly Leu Ile Ser Ser Leu Glu Gln Val Gln Ala Ser Gly Thr Thr
145                 150                 155                 160

Pro Leu Ala Leu Gly Asp Lys Asp Ile Phe Ala Ser Ser Gln Leu Leu
                165                 170                 175

Glu Ser Leu Ile Met Ser Arg Ala Gly Ala Asp Asn Trp Thr Lys Leu
            180                 185                 190

Phe Thr Ser Glu Tyr Ser Phe Asp Ala Pro Glu Val Lys Gln Ala Leu
        195                 200                 205

Glu Asp Tyr Lys Thr Ile Leu Ser Phe Ala Asn Lys Asp His Ser Ala
    210                 215                 220

Ile Thr Trp Asp Glu Ala Ala Lys Lys Met Ala Asp Gly Glu Ala Ala
225                 230                 235                 240

Val Asn Leu Met Gly Asp Trp Ala Tyr Gly Glu Leu Leu Asn Ala Gly
                245                 250                 255

Lys Lys Pro Gly Thr Asp Phe Ala Trp Val Ala Phe Pro Gly Lys Glu
            260                 265                 270

Asp Ile Phe Asp Tyr Val Gly Asp Gly Phe Ser Ile Pro Ala Asn Asn
        275                 280                 285

Ile Pro His Ala Glu Ala Ala Arg Ala Trp Leu Lys Thr Leu Met Asp
    290                 295                 300

Pro Lys Ile Gln Thr Glu Phe Ala Ala Lys Lys Gly Ser Ile Pro Ala
305                 310                 315                 320

Val Thr Ser Ala Asp Ile Ser Gly Leu Ser Glu Tyr Gln Gln Glu Ala
                325                 330                 335

Ala Lys Ser Leu Ala Ser Gly Ala Val Val Ser Ser Leu Ala His Ala
            340                 345                 350

Gln Ala Ala Gly Ala Glu Phe Ala Gln Thr Tyr Ala Asp Ala Val Ser
        355                 360                 365

Thr Phe Asn Gly Ser Gly Asn Thr Asp Ala Phe Ile Ala Ser Met Thr
    370                 375                 380

Gln Ala Gln Lys Thr Gln Leu
385                 390
```

<210> SEQ ID NO 117
<211> LENGTH: 309
<212> TYPE: PRT
<213> ORGANISM: Artificial Sequence
<220> FEATURE:
<223> OTHER INFORMATION: ecGGBP (with signal peptide removed)

<400> SEQUENCE: 117

```
Ala Asp Thr Arg Ile Gly Val Thr Ile Tyr Lys Tyr Asp Asp Asn Phe
1               5                   10                  15

Met Ser Val Val Arg Lys Ala Ile Glu Gln Asp Ala Lys Ala Ala Pro
            20                  25                  30

Asp Val Gln Leu Leu Met Asn Asp Ser Gln Asn Asp Gln Ser Lys Gln
        35                  40                  45

Asn Asp Gln Ile Asp Val Leu Leu Ala Lys Gly Val Lys Ala Leu Ala
    50                  55                  60

Ile Asn Leu Val Asp Pro Ala Ala Ala Gly Thr Val Ile Glu Lys Ala
65                  70                  75                  80

Arg Gly Gln Asn Val Pro Val Val Phe Phe Asn Lys Glu Pro Ser Arg
                85                  90                  95

Lys Ala Leu Asp Ser Tyr Asp Lys Ala Tyr Tyr Val Gly Thr Asp Ser
            100                 105                 110

Lys Glu Ser Gly Ile Ile Gln Gly Asp Leu Ile Ala Lys His Trp Ala
        115                 120                 125

Ala Asn Gln Gly Trp Asp Leu Asn Lys Asp Gly Gln Ile Gln Phe Val
    130                 135                 140

Leu Leu Lys Gly Glu Pro Gly His Pro Asp Ala Glu Ala Arg Thr Thr
145                 150                 155                 160

Tyr Val Ile Lys Glu Leu Asn Asp Lys Gly Ile Lys Thr Glu Gln Leu
                165                 170                 175

Gln Leu Asp Thr Ala Met Trp Asp Thr Ala Gln Ala Lys Asp Lys Met
            180                 185                 190

Asp Ala Trp Leu Ser Gly Pro Asn Ala Asn Lys Ile Glu Val Val Ile
        195                 200                 205

Ala Asn Asn Asp Ala Met Ala Met Gly Ala Val Glu Ala Leu Lys Ala
    210                 215                 220

His Asn Lys Ser Ser Ile Pro Val Phe Gly Val Asp Ala Leu Pro Glu
225                 230                 235                 240

Ala Leu Ala Leu Val Lys Ser Gly Ala Leu Ala Gly Thr Val Leu Asn
                245                 250                 255

Asp Ala Asn Asn Gln Ala Lys Ala Thr Phe Asp Leu Ala Lys Asn Gln
            260                 265                 270

Ala Asp Gly Lys Gly Ala Ala Asp Gly Thr Asn Trp Lys Ile Asp Asn
        275                 280                 285

Lys Val Val Arg Val Pro Tyr Val Gly Val Asp Lys Asp Asn Leu Ala
    290                 295                 300

Glu Phe Ser Lys Lys
305
```

<210> SEQ ID NO 118
<211> LENGTH: 360
<212> TYPE: PRT
<213> ORGANISM: Thermoanaerobacterium thermosaccharolyticum

<400> SEQUENCE: 118

-continued

```
Met Lys Lys Ile Leu Thr Tyr Leu Val Leu Val Val Leu Val Leu Ser
1               5                   10                  15

Ala Leu Leu Thr Gly Cys Gly Asn Ser Asn Thr Thr Ser Ser Asn Ser
            20                  25                  30

Ser Ser Ser Ser Ser Gln Gln Ser Asp Lys Thr Ala Ser Ser Asp Ser
        35                  40                  45

Gly Lys Gln Leu Asn Ile Gly Val Ala Ile Tyr Lys Phe Asp Asp Thr
    50                  55                  60

Phe Met Thr Gly Val Arg Asn Ala Met Thr Ala Glu Ala Gln Gly Lys
65                  70                  75                  80

Ala Lys Leu Asn Met Val Asp Ser Gln Asn Ser Gln Pro Thr Gln Asn
                85                  90                  95

Asp Gln Val Asp Leu Phe Ile Thr Lys Lys Met Asn Ala Leu Ala Ile
            100                 105                 110

Asn Pro Val Asp Arg Thr Ala Ala Gly Thr Ile Ile Asp Lys Ala Lys
        115                 120                 125

Gln Ala Asn Ile Pro Val Val Phe Phe Asn Arg Glu Pro Leu Pro Glu
    130                 135                 140

Asp Met Lys Lys Trp Asp Lys Val Tyr Tyr Val Gly Ala Lys Ala Glu
145                 150                 155                 160

Gln Ser Gly Ile Leu Gln Gly Gln Ile Met Ala Asp Tyr Trp Lys Ala
                165                 170                 175

His Pro Glu Ala Asp Lys Asn His Asp Gly Val Met Gln Tyr Val Met
            180                 185                 190

Leu Met Gly Gln Pro Gly His Gln Asp Ala Ile Leu Arg Thr Gln Tyr
        195                 200                 205

Ser Ile Gln Thr Val Lys Asp Ala Gly Ile Lys Val Gln Glu Leu Ala
    210                 215                 220

Lys Asp Tyr Ala Asn Trp Asp Arg Val Thr Ala His Asp Lys Met Ala
225                 230                 235                 240

Ala Trp Leu Ser Ser Phe Gly Asp Lys Ile Glu Ala Val Phe Cys Asn
                245                 250                 255

Asn Asp Asp Met Ala Leu Gly Ala Ile Glu Ala Leu Lys Ser Ala Gly
            260                 265                 270

Tyr Phe Thr Gly Asn Lys Tyr Ile Pro Val Val Gly Val Asp Ala Thr
        275                 280                 285

Ala Pro Gly Ile Gln Ala Ile Lys Asp Gly Thr Leu Leu Gly Thr Val
    290                 295                 300

Leu Asn Asp Ala Lys Asn Gln Ala Lys Ala Thr Phe Asn Ile Ala Tyr
305                 310                 315                 320

Glu Leu Ala Gln Gly Ile Thr Pro Thr Lys Asp Asn Ile Gly Tyr Asp
                325                 330                 335

Ile Thr Asp Gly Lys Tyr Val Trp Ile Pro Tyr Lys Lys Ile Thr Lys
            340                 345                 350

Asp Asn Ile Ser Asp Ala Glu Gln
        355                 360
```

<210> SEQ ID NO 119
<211> LENGTH: 332
<212> TYPE: PRT
<213> ORGANISM: Salmonella typhimurium

<400> SEQUENCE: 119

```
Met Asn Lys Lys Val Leu Thr Leu Ser Ala Val Met Ala Ser Leu Leu
1               5                   10                  15
```

```
Phe Gly Ala His Ala His Ala Ala Asp Thr Arg Ile Gly Val Thr Ile
            20                  25                  30

Tyr Lys Tyr Asp Asp Asn Phe Met Ser Val Val Arg Lys Ala Ile Glu
        35                  40                  45

Lys Asp Gly Lys Ser Ala Pro Asp Val Gln Leu Leu Met Asn Asp Ser
    50                  55                  60

Gln Asn Asp Gln Ser Lys Gln Asn Asp Gln Ile Asp Val Leu Leu Ala
65                  70                  75                  80

Lys Gly Val Lys Ala Leu Ala Ile Asn Leu Val Asp Pro Ala Ala Ala
                85                  90                  95

Gly Thr Val Ile Glu Lys Ala Arg Gly Gln Asn Val Pro Val Val Phe
            100                 105                 110

Phe Asn Lys Glu Pro Ser Arg Lys Ala Leu Asp Ser Tyr Asp Lys Ala
        115                 120                 125

Tyr Tyr Val Gly Thr Asp Ser Lys Glu Ser Gly Val Ile Gln Gly Asp
    130                 135                 140

Leu Ile Ala Lys His Trp Gln Ala Asn Gln Gly Trp Asp Leu Asn Lys
145                 150                 155                 160

Asp Gly Lys Ile Gln Tyr Val Leu Leu Lys Gly Glu Pro Gly His Pro
                165                 170                 175

Asp Ala Glu Ala Arg Thr Thr Tyr Val Val Lys Glu Leu Asn Asp Lys
            180                 185                 190

Gly Ile Gln Thr Glu Gln Leu Ala Leu Asp Thr Ala Met Trp Asp Thr
        195                 200                 205

Ala Gln Ala Lys Asp Lys Met Asp Ala Trp Leu Ser Gly Pro Asn Ala
    210                 215                 220

Asn Lys Ile Glu Val Val Ile Ala Asn Asn Asp Ala Met Ala Met Gly
225                 230                 235                 240

Ala Val Glu Ala Leu Lys Ala His Asn Lys Ser Ser Ile Pro Val Phe
                245                 250                 255

Gly Val Asp Ala Leu Pro Glu Ala Leu Ala Leu Val Lys Ser Gly Ala
            260                 265                 270

Met Ala Gly Thr Val Leu Asn Asp Ala Asn Asn Gln Ala Lys Ala Thr
        275                 280                 285

Phe Asp Leu Ala Lys Asn Leu Ala Glu Gly Lys Gly Ala Ala Asp Gly
    290                 295                 300

Thr Ser Trp Lys Ile Glu Asn Lys Ile Val Arg Val Pro Tyr Val Gly
305                 310                 315                 320

Val Asp Lys Asp Asn Leu Ser Glu Phe Thr Gln Lys
                325                 330
```

<210> SEQ ID NO 120
<211> LENGTH: 356
<212> TYPE: PRT
<213> ORGANISM: Caldicellulosiruptor hydrothermalis

<400> SEQUENCE: 120

```
Met Phe Asn Lys Lys Lys Phe Trp Val Val Leu Val Ser Met Val Leu
1               5                   10                  15

Ile Ile Ser Leu Val Leu Val Gly Cys Gly Lys Lys Ser Thr Asn Asp
            20                  25                  30

Ser Ser Asn Gly Thr Ser Glu Glu Asn Lys Pro Tyr Ile Gly Val Ala
        35                  40                  45

Ile Tyr Lys Phe Asp Asp Thr Phe Met Thr Gly Val Arg Asn Ala Ile
```

-continued

```
    50                  55                  60

Ala Lys Glu Gly Glu Gly Lys Ala Lys Leu Asp Phe Val Asp Cys Gln
65                  70                  75                  80

Asn Ser Gln Ser Thr Gln Asn Asp Lys Ile Asp Leu Phe Ile Thr Lys
                85                  90                  95

Lys Val Asp Ala Leu Ala Ile Asn Pro Val Asp Arg Thr Ala Ala Gly
            100                 105                 110

Val Leu Ile Asp Lys Ala Lys Gln Ala Asn Ile Pro Val Val Phe Phe
        115                 120                 125

Asn Arg Glu Pro Leu Pro Glu Asp Met Lys Lys Trp Asp Lys Val Tyr
    130                 135                 140

Tyr Val Gly Ala Lys Ala Glu Gln Ser Gly Thr Leu Gln Gly Glu Ile
145                 150                 155                 160

Met Ala Glu Tyr Trp Lys Ser His Pro Glu Ala Asp Lys Asn His Asn
                165                 170                 175

Gly Ile Met Glu Tyr Val Met Ile Thr Gly Glu Pro Gly His Gln Asp
            180                 185                 190

Ala Ile Leu Arg Thr Glu Tyr Ser Ile Lys Ala Val Glu Ala Ala Gly
        195                 200                 205

Ile Lys Thr Lys Ala Leu Ala Gln Asp Thr Ala Met Trp Asp Arg Val
    210                 215                 220

Lys Gly Gln Glu Lys Met Gln Ala Phe Leu Ala Ser Phe Gly Asp Arg
225                 230                 235                 240

Ile Glu Ala Val Phe Cys Asn Asn Asp Asp Met Ala Leu Gly Ala Ile
                245                 250                 255

Glu Ala Leu Lys Ala Ala Gly Tyr Phe Lys Asn Gly Lys Tyr Ile Pro
            260                 265                 270

Val Val Gly Val Asp Ala Thr Thr Pro Gly Leu Gln Ala Leu Glu Glu
        275                 280                 285

Gly Thr Leu Leu Gly Thr Val Leu Asn Asp Ala Lys Ala Gln Gly Lys
    290                 295                 300

Ala Thr Phe Asn Leu Ala Tyr Val Leu Ala Lys Gly Glu Lys Pro Thr
305                 310                 315                 320

Lys Glu Asn Val Gly Phe Asp Ile Thr Asp Gly Lys Tyr Ile Trp Val
                325                 330                 335

Pro Tyr Gln Lys Val Thr Lys Asp Asn Leu Glu Glu Met Lys Lys Tyr
            340                 345                 350

Val Asn Glu Gln
        355


<210> SEQ ID NO 121
<211> LENGTH: 356
<212> TYPE: PRT
<213> ORGANISM: Caldicellulosiruptor obsidiansis

<400> SEQUENCE: 121

Met Leu Asn Lys Lys Lys Phe Trp Val Val Leu Val Ser Ile Val Leu
1               5                   10                  15

Ala Ile Ser Leu Val Leu Val Gly Cys Gly Lys Lys Ser Thr Asn Glu
            20                  25                  30

Asn Ser Gly Gly Thr Ser Glu Asp Asn Lys Pro Tyr Ile Gly Val Ala
        35                  40                  45

Ile Tyr Lys Phe Asp Asp Thr Phe Met Thr Gly Val Arg Asn Ala Ile
    50                  55                  60
```

```
Ala Lys Glu Gly Glu Gly Lys Ala Lys Leu Asp Phe Val Asp Cys Gln
65                  70                  75                  80

Asn Ser Gln Ser Thr Gln Asn Asp Lys Ile Asp Leu Phe Ile Thr Lys
                85                  90                  95

Lys Val Asp Ala Leu Ala Ile Asn Pro Val Asp Arg Thr Ala Ala Gly
            100                 105                 110

Val Leu Ile Asp Lys Ala Lys Gln Ala Asn Ile Pro Val Val Phe Phe
        115                 120                 125

Asn Arg Glu Pro Leu Pro Glu Asp Met Lys Lys Trp Asp Lys Val Tyr
    130                 135                 140

Tyr Val Gly Ala Lys Ala Glu Gln Ser Gly Thr Leu Gln Gly Glu Ile
145                 150                 155                 160

Met Ala Glu Tyr Trp Lys Ser His Pro Glu Ala Asp Lys Asn His Asp
                165                 170                 175

Gly Ile Met Gln Tyr Val Met Ile Thr Gly Glu Pro Gly His Gln Asp
            180                 185                 190

Ala Ile Leu Arg Thr Glu Tyr Ser Ile Lys Ala Val Glu Ala Ala Gly
        195                 200                 205

Ile Arg Val Lys Cys Leu Ala Gln Asp Thr Ala Met Trp Asp Arg Val
    210                 215                 220

Lys Gly Gln Glu Lys Met Gln Ala Phe Leu Ala Ser Phe Gly Asp Lys
225                 230                 235                 240

Ile Glu Ala Val Phe Cys Asn Asn Asp Asp Met Ala Leu Gly Ala Ile
                245                 250                 255

Glu Ala Leu Lys Ala Ala Gly Tyr Phe Lys Asp Gly Lys Tyr Val Pro
            260                 265                 270

Val Val Gly Val Asp Ala Thr Thr Pro Gly Leu Gln Ala Leu Glu Glu
        275                 280                 285

Gly Thr Leu Leu Gly Thr Val Leu Asn Asp Ala Lys Ala Gln Gly Lys
    290                 295                 300

Ala Thr Phe Asn Leu Ala Tyr Val Leu Ala Lys Gly Glu Lys Pro Thr
305                 310                 315                 320

Lys Glu Asn Val Gly Phe Glu Ile Thr Asp Gly Lys Tyr Ile Trp Val
                325                 330                 335

Pro Tyr Gln Lys Val Thr Lys Asp Asn Leu Glu Glu Met Lys Lys Tyr
            340                 345                 350

Val Asn Glu Gln
        355


<210> SEQ ID NO 122
<211> LENGTH: 350
<212> TYPE: PRT
<213> ORGANISM: Paenibacillus sp.

<400> SEQUENCE: 122

Met Lys Lys Lys Trp Leu Phe Val Leu Met Ala Gly Met Met Leu Thr
1               5                   10                  15

Thr Ala Ala Cys Asn Asn Gly Gly Ser Ser Ser Thr Gly Ser Asp Ser
            20                  25                  30

Thr Gly Gly Asp Ala Val Gly Gly Ser Thr Pro Gln Val Gly Val Ala
        35                  40                  45

Ile Tyr Lys Phe Asp Asp Thr Phe Met Thr Gly Val Arg Asn Ala Met
    50                  55                  60

Ser Asp Ala Ala Asn Gly Val Ala Lys Leu Asp Ile Val Asp Ser Gln
65                  70                  75                  80
```

Asn Ala Gln Pro Thr Gln Asn Glu Lys Ile Asp Leu Phe Ile Ser Lys
85 90 95

Lys Tyr Ser Ser Met Ile Ile Asn Pro Val Asp Arg Thr Ala Ala Gly
100 105 110

Val Ile Ile Asp Lys Ala Lys Thr Ala Asn Thr Pro Val Val Phe Leu
115 120 125

Asn Arg Glu Pro Ile Ala Glu Asp Met Asn Lys Trp Asp Lys Val Tyr
130 135 140

Tyr Val Gly Ala Lys Ala Glu Glu Ser Gly Thr Ile Ser Gly Gln Leu
145 150 155 160

Ile Val Asp Tyr Trp Lys Ala Asn Pro Lys Ala Asp Lys Asn Gly Asp
165 170 175

Gly Lys Leu Gln Tyr Val Leu Leu Gln Gly Glu Pro Gly His Gln Asp
180 185 190

Ala Glu Leu Arg Thr Lys Phe Ser Val Gln Ala Ile Gln Asp Ala Gly
195 200 205

Ile Glu Val Glu Ala Leu Ala Val Asp Thr Ala Met Trp Asp Arg Val
210 215 220

Lys Gly Gln Glu Lys Met Gln Thr Phe Leu Ala Ser His Gly Asp Lys
225 230 235 240

Ile Glu Ala Val Leu Ala Asn Asn Asp Asp Met Ala Leu Gly Ala Ile
245 250 255

Glu Ala Leu Lys Ala Ala Gly Tyr Phe Ser Gly Asp Lys Tyr Met Pro
260 265 270

Val Val Gly Val Asp Ala Thr Ala Pro Ala Val Gln Ala Leu Glu Asp
275 280 285

Gly Thr Leu Leu Gly Thr Val Leu Asn Asp Ala Lys Ser Gln Gly Lys
290 295 300

Ala Ser Val Ala Ile Ala Ala Ala Leu Ser Lys Gly Glu Ala Pro Asn
305 310 315 320

Lys Glu Asn Thr Gly Phe Asp Ile Thr Asp Gly Lys Tyr Val Trp Ile
325 330 335

Ala Tyr Lys Lys Ile Thr Lys Asp Asn Ile Ala Asp Ala Lys
340 345 350

<210> SEQ ID NO 123
<211> LENGTH: 354
<212> TYPE: PRT
<213> ORGANISM: Clostridium saccharolyticum

<400> SEQUENCE: 123

Met Lys Arg Leu Arg Lys Gly Ile Phe Leu Phe Phe Phe Ile Val Trp
1 5 10 15

Thr Ala Phe Pro Leu Tyr Gly Cys Ala Pro Met Glu Gln Lys Lys Asp
20 25 30

Val Gly Glu Ser Ala Thr Ser Glu Ala Gly Thr Glu Gly Val Pro Glu
35 40 45

Glu Thr Gly Pro Lys Ile Gly Val Ser Ile Tyr Arg Tyr Asp Asp Thr
50 55 60

Phe Met Lys Leu Tyr Arg Gln Glu Leu Lys Gln Tyr Leu Glu Glu Thr
65 70 75 80

Tyr His Ala Glu Val Ile Met Arg Asn Ala Gly Gly Asp Gln Lys Glu
85 90 95

Gln Asp Lys Gln Val Asn Gln Phe Ile Ser Asp Gly Cys Asp Gly Ile 100 105 110

Ile Val Asn Pro Val Glu Ile Pro Ala Ala Gln Glu Leu Ala Asp Ala
115 120 125

Cys Ser Arg Ala Gly Ile Pro Leu Val Phe Ile Asn Arg Glu Pro Lys
130 135 140

Glu Glu Glu Gln Lys Arg Trp Arg Glu Lys Gln Met Ala Val Ser Cys
145 150 155 160

Val Gly Thr Asp Ser Arg Gln Ala Gly Thr Tyr Gln Gly Glu Ile Ile
165 170 175

Leu Glu Thr Leu Asn Lys Gly Asp Phe Asn Gly Asp Gly Val Val Ser
180 185 190

Tyr Val Met Leu Met Gly Glu Lys Gly Asn Glu Asp Ser Gln Tyr Arg
195 200 205

Thr Glu Tyr Ser Ile Lys Ala Leu Glu Glu Gly Gly Met Lys Thr Glu
210 215 220

Glu Leu Phe Ser Gly Asn Gly Asn Trp Asn Lys Asp Glu Gly Lys Lys
225 230 235 240

Leu Ala Lys Gln Ala Leu Ala Ser Trp Gly Asn Arg Ile Glu Val Phe
245 250 255

Phe Cys Asn Asn Asp Ser Met Ala Asn Gly Ala Leu Glu Ala Val Glu
260 265 270

Glu Ala Gly Arg Ile Pro Gly Lys Asp Ile Tyr Leu Val Gly Val Asp
275 280 285

Ala Leu Gln Asp Thr Val Thr Tyr Ile Lys Glu Gly Arg Met Thr Gly
290 295 300

Thr Val Leu Asn Asp His Glu Gly Gln Ser Gln Met Ala Ala Asp Thr
305 310 315 320

Leu Lys Lys Met Ile Asp Gly Glu Ser Val Glu Thr Arg Tyr Gln Val
325 330 335

Asp Tyr Ile Lys Val Thr Ala Ile Ser Thr Phe Gln Thr Leu Lys Gly
340 345 350

Glu Asp

<210> SEQ ID NO 124
<211> LENGTH: 354
<212> TYPE: PRT
<213> ORGANISM: Butyrivibrio proteoclasticus

<400> SEQUENCE: 124

Met Lys Lys Lys Met Ile Cys Tyr Met Ile Ile Ala Ala Leu Ala Leu
1 5 10 15

Ser Leu Met Ala Gly Cys Ser Asn Thr Gln Glu Ser Glu Pro Val Gln
20 25 30

Glu Ser Val Ala Tyr Ser Ser Tyr Ser Asp Ala Lys Val Gly Val Cys
35 40 45

Ile Tyr Gln Lys Ser Asp Asn Phe Met Ser Leu Phe Ser Ser Glu Leu
50 55 60

Val Lys Tyr Leu Val Ser Arg Gly Phe Ser Lys Asp Asn Ile Ile Leu
65 70 75 80

Tyr Asp Ser Asn Asn Asp Glu Asn Val Gln Leu Ser Gln Val Glu Glu
85 90 95

Leu Ile Ala Ser Gly Ile Asn Ala Leu Ile Ile Asn Pro Val Asn Ser
100 105 110

Ser Val Ala His Ser Ile Thr Asp Met Ala Ser Ala Ser Asn Ile Pro

```
        115                 120                 125

Leu Val Tyr Ile Asn Arg Glu Pro Ser Gly Asp Glu Glu Asn Arg Trp
    130                 135                 140

Glu Met Tyr Gln Leu Asn Val Cys Tyr Val Gly Cys Asp Ala Arg Gln
145                 150                 155                 160

Ser Gly Ile Tyr Gln Gly Glu Ile Leu Leu Ser Leu Gly Lys Asn Lys
                165                 170                 175

Leu Asp His Asn Gly Asp Gly Lys Ile Gln Tyr Phe Met Ile Glu Gly
            180                 185                 190

Ala Pro Glu Asn Ile Asp Ala Gly Tyr Arg Thr Leu Tyr Ser Val Ser
        195                 200                 205

Ala Leu Gln Asn Ser Glu Met Glu Met Asp Cys Leu Leu Asp Glu Val
    210                 215                 220

Gly Asn Trp Asp Glu Thr Thr Ala Ser Leu Leu Val Ser Lys Gly Ile
225                 230                 235                 240

Gln Asn Gly Leu Lys Pro Glu Val Ile Ile Cys Asn Asn Asp Ala Met
                245                 250                 255

Ala Leu Gly Ala Ile Lys Ala Ala Glu Lys Ser Gly Leu Val Pro Gly
            260                 265                 270

Glu Asp Val Tyr Ile Val Gly Val Asp Ala Leu Pro Glu Ala Ile Glu
        275                 280                 285

Met Ile Lys Ala Gly Lys Leu Ala Gly Thr Val Tyr Asn Asp Tyr Val
    290                 295                 300

Leu Gln Ser His Lys Ser Ala Asp Ala Val Ile Asn Tyr Leu Lys Gly
305                 310                 315                 320

Ile Asp Asn Glu His Tyr Ile Gly Cys Asp Tyr Val Lys Val Asp Ile
                325                 330                 335

Asp Asn Ala Glu Ser Ile Ala Gly Leu Thr Asn Thr Asp Glu Glu Asp
            340                 345                 350

Ile Asp


<210> SEQ ID NO 125
<211> LENGTH: 383
<212> TYPE: PRT
<213> ORGANISM: Roseburia intestinalis

<400> SEQUENCE: 125

Met Lys Arg Lys Val Val Ser Val Ile Leu Ala Thr Ala Met Val Ala
1               5                   10                  15

Ser Met Val Ala Gly Cys Gly Gly Ser Asn Asn Ala Ser Thr Asn Asn
            20                  25                  30

Ala Gly Thr Thr Thr Asp Ala Ala Ala Ser Asp Ala Ser Ser Asp Thr
        35                  40                  45

Ser Asn Asp Ala Ala Ala Thr Glu Ala Ala Asp Ala Gly Asp Ala Ala
    50                  55                  60

Ala Asp Ala Ala Thr Asp Ala Asp Ala Ser Leu Ala Asp Lys Lys Val
65                  70                  75                  80

Gly Val Cys Ile Tyr Gln Phe Ser Asp Asn Phe Met Thr Leu Phe Arg
                85                  90                  95

Thr Glu Leu Glu Asn Tyr Leu Val Glu Lys Gly Phe Ser Lys Asp Asn
            100                 105                 110

Ile Thr Ile Val Asp Gly Ala Asn Asp Gln Ala Thr Gln Thr Gly Gln
        115                 120                 125

Ile Asp Asn Phe Ile Thr Glu Gly Val Asp Val Leu Ile Ile Asn Pro
```

130 135 140

Val Asn Ser Ser Ser Ala Ala Thr Ile Thr Asp Lys Val Val Ala Ala
145 150 155 160

Gly Ile Pro Leu Val Tyr Ile Asn Arg Glu Pro Asp Glu Glu Glu Gln
165 170 175

Lys Arg Trp Ser Asp Asn Asn Trp Asp Val Thr Tyr Val Gly Cys Asp
180 185 190

Ala Arg Gln Ser Gly Thr Phe Gln Gly Glu Met Ile Ser Asp Leu Gly
195 200 205

Leu Asp Thr Val Asp Leu Asn Gly Asn Gly Lys Ile Asp Tyr Val Met
210 215 220

Val Glu Gly Asp Pro Glu Asn Val Asp Ala Gln Tyr Arg Thr Glu Tyr
225 230 235 240

Ser Val Lys Ala Leu Glu Asp Ala Gly Leu Glu Val Asn Cys Leu Ser
245 250 255

Asp Gln Val Gly Asn Trp Gln Gln Asp Gln Ala Gln Gln Ile Val Ala
260 265 270

Asn Ala Leu Gly Gln Tyr Gly Asn Asp Val Glu Val Val Phe Cys Asn
275 280 285

Asn Asp Ala Met Ala Leu Gly Ala Leu Gln Ala Ile Gln Ser Ala Gly
290 295 300

Arg Thr Val Gly Thr Asp Ile Tyr Leu Val Gly Val Asp Ala Leu Ser
305 310 315 320

Glu Ala Leu Glu Asp Val Leu Ala Gly Thr Met Thr Gly Thr Val Phe
325 330 335

Asn Asp His Phe Ser Gln Ser His Ser Ala Ala Asp Ala Ala Ile Asn
340 345 350

Tyr Ile Thr Gly Ala Gly Asn Asp His Tyr Ile Gly Cys Asp Tyr Val
355 360 365

Lys Val Thr Lys Asp Asn Ala Gln Asp Val Leu Asp Met Val Lys
370 375 380

<210> SEQ ID NO 126
<211> LENGTH: 350
<212> TYPE: PRT
<213> ORGANISM: Faecalibacterium prausnitzii

<400> SEQUENCE: 126

Met Lys Met Ile Ser Arg Arg Asp Phe Leu Lys Ala Ser Ala Val Val
1 5 10 15

Gly Ala Thr Ala Ala Met Thr Ala Cys Gly Gly Ser Ser Ser Thr Ser
20 25 30

Thr Ala Ala Ser Ser Val Ala Ser Ser Thr Ala Ala Ser Ala Ala Ala
35 40 45

Thr Asn Gly Ser Ala Asn Ile Gly Val Cys Ile Tyr Gln Phe Ala Asp
50 55 60

Asn Phe Met Thr Leu Tyr Arg Ala Asp Leu Glu Gly Tyr Leu Lys Asp
65 70 75 80

Met Gly Tyr Ser Val Thr Ile Met Asp Gly Lys Asn Asp Gln Asn Thr
85 90 95

Gln Thr Glu Gln Ile Asn Thr Phe Leu Gln Gln Gly Val Asp Val Leu
100 105 110

Val Ile Asn Pro Val Gln Thr Thr Ser Ala Gln Thr Ile Val Asp Thr
115 120 125

Val Ser Pro Ser Gly Thr Pro Ile Val Phe Ile Asn Arg Glu Pro Glu
    130                 135                 140

Glu Ser Val Leu Asp Ser Tyr Lys Gly Lys Cys Cys Tyr Val Gly Ala
145                 150                 155                 160

Asp Ala Arg Gln Ser Gly Thr Tyr Gln Gly Glu Leu Ile Leu Ala Thr
                165                 170                 175

Asp Thr Gln Gly Asp Ile Asn Gly Asp Gly Lys Ile Thr Tyr Ile Met
            180                 185                 190

Cys Lys Gly Asp Pro Glu Asn Ile Asp Ala Gln Tyr Arg Thr Glu Tyr
        195                 200                 205

Ser Ile Lys Ala Leu Thr Asp Ala Gly Lys Glu Val Glu Cys Leu Tyr
    210                 215                 220

Glu Tyr Leu Asp Asn Trp Asp Gln Thr Thr Ala Gln Gln Asp Val Ala
225                 230                 235                 240

Asn Ala Leu Ser Gln Tyr Gly Glu Lys Ile Glu Val Val Phe Cys Asn
                245                 250                 255

Asn Asp Ala Met Ala Leu Gly Ala Leu Gln Ser Ile Gln Gln Ala Gly
            260                 265                 270

Arg Thr Val Gly Lys Asp Val Tyr Leu Val Gly Val Asp Ala Leu Val
        275                 280                 285

Glu Ala Val Gln Asn Val Val Asp Gly Asn Met Thr Gly Thr Val Leu
    290                 295                 300

Asn Asp Asp Val Gly Gln Ala Thr Lys Ala Ala Glu Ala Thr Lys Leu
305                 310                 315                 320

Phe Val Glu Gly Lys Asp Val Glu Lys Tyr Tyr Trp Val Asp Tyr Val
                325                 330                 335

Lys Val Thr Lys Asp Asn Ala Ser Gln Tyr Leu Lys Glu Asp
            340                 345                 350

<210> SEQ ID NO 127
<211> LENGTH: 338
<212> TYPE: PRT
<213> ORGANISM: Clostridium ljungdahlii

<400> SEQUENCE: 127

Met Ile Val Lys Lys Cys Met Lys Ser Ile Ala Val Thr Gly Leu Leu
1               5                   10                  15

Thr Ile Ile Leu Gly Thr Gly Cys Ser Asn Ser Leu Ser Ser Asn Lys
            20                  25                  30

Asn Glu Pro Val Ile Gly Phe Val Ala Tyr Glu Phe Asn Asn Thr Trp
        35                  40                  45

Ile Thr Glu Leu Lys Asn Glu Ile Tyr Lys Val Ser Ser Gly Lys Ala
    50                  55                  60

Arg Val Asp Ile Trp Asn Gly Asp Asn Ile Gln Thr Val Glu Asn Asp
65                  70                  75                  80

Lys Ile Asn Leu Phe Ile Asn Arg Lys Val Asn Val Leu Asp Ile Asn
                85                  90                  95

Pro Val Asp Val Asn Ala Ala Gly Gln Ile Ile Glu Lys Cys Lys Lys
            100                 105                 110

Ala Asn Ile Pro Thr Val Phe Val Asn Arg Gln Pro Lys Lys Glu Asp
        115                 120                 125

Met Glu Lys Trp Asn Lys Val Tyr Tyr Val Gly Ala Lys Ala Glu Gln
    130                 135                 140

Ser Gly Thr Ile Gln Gly Gln Met Leu Val Asn Tyr Phe Lys Gly His
145                 150                 155                 160

```
Pro Thr Gln Asp Gly Thr Ile Arg Tyr Ile Met Leu Lys Gly Glu Thr
                165                 170                 175

Arg Asn Gln Asp Ala Glu Lys Arg Thr Gln Tyr Ser Ile Lys Ala Leu
            180                 185                 190

Lys Asp Ser Gly Phe Lys Val Gln Lys Val Ala Glu Asp Thr Ala Met
        195                 200                 205

Trp Asp Arg Thr Lys Ala Gln Glu Lys Met Thr Ser Phe Ile Ser Ser
    210                 215                 220

Tyr Gly Pro Asn Phe Asp Cys Val Ile Ala Asn Asn Asp Asp Met Ala
225                 230                 235                 240

Leu Gly Ala Val Asp Ala Leu Lys Ala Ala Gly Tyr Phe Asn Gly Gly
                245                 250                 255

Lys Tyr Val Pro Val Val Gly Val Asp Ala Thr Ala Pro Ala Val Lys
            260                 265                 270

Ala Val Glu Asp Gly Thr Leu Phe Gly Thr Val Leu Asn Asp Ala Ala
        275                 280                 285

Lys Gln Gly Asp Ala Ala Phe Asp Leu Ser Tyr Ile Leu Ser Lys Gly
    290                 295                 300

Lys Ile Pro Asp Glu Ser Asn Phe Lys Tyr Lys Val Thr Asp Gly Lys
305                 310                 315                 320

Tyr Ile Trp Ile Asp Tyr Lys Met Ile Thr Lys Glu Asn Val Gln Asp
                325                 330                 335

Ala Lys


<210> SEQ ID NO 128
<211> LENGTH: 336
<212> TYPE: PRT
<213> ORGANISM: Clostridium autoethanogenum

<400> SEQUENCE: 128

Met Lys Lys Cys Met Lys Ser Ile Ala Val Thr Gly Leu Leu Thr Ile
1               5                   10                  15

Ile Leu Gly Thr Gly Cys Ser Asn Ser Leu Ser Ser Asn Lys Asn Glu
            20                  25                  30

Pro Val Ile Gly Phe Val Ala Tyr Glu Phe Asn Asn Thr Trp Ile Thr
        35                  40                  45

Glu Leu Lys Asn Glu Met Tyr Lys Val Ser Asn Gly Lys Ala Arg Val
    50                  55                  60

Asp Ile Trp Asn Gly Asn Asn Ile Gln Thr Val Glu Asn Asp Lys Ile
65                  70                  75                  80

Ser Leu Phe Ile Asn Arg Lys Val Asp Val Leu Asp Ile Asn Pro Val
                85                  90                  95

Asp Val Asn Ala Ala Gly Gln Ile Ile Glu Lys Cys Lys Lys Ala Asn
            100                 105                 110

Ile Pro Thr Val Phe Val Asn Arg Gln Pro Lys Lys Glu Asp Val Glu
        115                 120                 125

Lys Trp Asn Lys Val Tyr Tyr Val Gly Ala Lys Ala Glu Gln Ser Gly
    130                 135                 140

Thr Ile Gln Gly Gln Met Leu Val Asn Tyr Phe Lys Gly His Pro Thr
145                 150                 155                 160

Gln Asp Gly Thr Ile Arg Tyr Ile Met Leu Lys Gly Glu Met Arg Asn
                165                 170                 175

Gln Asp Ala Glu Lys Arg Thr Gln Tyr Ser Ile Lys Ala Leu Glu Asp
            180                 185                 190
```

```
Ser Gly Phe Lys Val Gln Lys Val Ala Glu Asp Thr Ala Met Trp Asp
        195                 200                 205

Arg Thr Lys Ala Gln Glu Lys Met Thr Ser Phe Ile Ser Ser Tyr Gly
    210                 215                 220

Pro Asn Phe Asp Cys Val Ile Ala Asn Asn Asp Asp Met Ala Leu Gly
225                 230                 235                 240

Ala Val Asp Ala Leu Lys Ala Ala Gly Tyr Phe Asn Gly Gly Lys Tyr
                245                 250                 255

Val Pro Val Val Gly Val Asp Ala Thr Ala Pro Ala Val Lys Ala Val
            260                 265                 270

Glu Asp Gly Thr Leu Phe Gly Thr Val Leu Asn Asp Ala Ala Lys Gln
        275                 280                 285

Gly Asp Ala Ala Phe Asp Leu Ser Tyr Ile Leu Ser Lys Gly Lys Ile
    290                 295                 300

Pro Asp Glu Ser Asn Phe Lys Tyr Lys Ile Thr Asp Gly Lys Tyr Ile
305                 310                 315                 320

Trp Ile Asp Tyr Lys Met Ile Thr Lys Glu Asn Val Gln Asp Ala Lys
                325                 330                 335


<210> SEQ ID NO 129
<211> LENGTH: 367
<212> TYPE: PRT
<213> ORGANISM: Roseburia intestinalis

<400> SEQUENCE: 129

Met Cys Gly Ala Glu Lys Val Arg His Met Leu Met Gly Glu Gln Val
1               5                   10                  15

Leu Lys Lys Trp Lys Lys Ser Lys Lys Met Thr Val Ala Phe Gly Gly
            20                  25                  30

Ile Leu Val Met Ser Val Val Ile Gly Gly Cys Gly Gly Arg Glu Asp
        35                  40                  45

Ala Lys Lys Ser Ile Lys Ile Gly Ile Ser Val Tyr Asp Gln Tyr Asp
    50                  55                  60

Thr Phe Val Ser Glu Met Met Lys Asp Phe Asn Asp Tyr Ala Thr Lys
65                  70                  75                  80

Lys Glu Glu Glu Thr Gly Val Ala Ile Asn Ile Asp Thr Tyr Asn Ala
                85                  90                  95

Ser Ala Ser Gln Ser Thr Gln Asn Ser Gln Val Glu Asn Met Ile Thr
            100                 105                 110

Glu Gly Cys Asp Val Ile Cys Val Asn Leu Val Asp Arg Thr Asp Pro
        115                 120                 125

Thr Ala Ile Ile Asp Leu Ala Glu Lys Asn Asn Ile Pro Val Ile Phe
    130                 135                 140

Phe Asn Arg Glu Leu Val Glu Glu Asp Leu Glu Arg Trp Thr Arg Leu
145                 150                 155                 160

Tyr Tyr Val Gly Ala Gln Ala Phe Glu Ser Gly Ile Met Gln Gly Glu
                165                 170                 175

Leu Ala Ala Glu Ala Phe Leu Thr Asp Gln Ser Leu Asp Lys Asn Gly
            180                 185                 190

Asp Gly Ile Phe Gln Tyr Val Val Leu Glu Gly Glu Ala Gly His Gln
        195                 200                 205

Asp Ala Ile Val Arg Thr Glu Tyr Ser Val Ser Thr Met Ile Asp Ser
    210                 215                 220

Gly Val Glu Val Glu Lys Leu Gly Tyr Ala Ile Ala Asn Trp Asn Arg
```

225 230 235 240

Ala Gln Ala Gln Thr Lys Met Ala Gln Leu Met Ser Gln Phe Gly Asp
245 250 255

Ser Ile Glu Leu Val Ile Ala Asn Asn Asp Asp Met Ala Leu Gly Ala
260 265 270

Ile Asp Ala Leu Lys Ala Ser Gly Leu Thr Lys Asp Glu Trp Pro Ala
275 280 285

Val Ile Gly Ile Asp Gly Thr Asp Val Gly Leu Glu Ala Val Lys Asn
290 295 300

Lys Glu Met Ile Gly Thr Val Tyr Asn Asp Lys Glu Gly Gln Ala Asp
305 310 315 320

Ala Met Leu Asn Leu Ala Tyr Glu Leu Ser Thr Gly Ser Asp Leu Ser
325 330 335

Asp Leu Asn Leu Ile Asp Gly Lys Tyr Ile Arg Leu Pro Tyr Ala Arg
340 345 350

Val Thr Cys Asp Asp Val Asp Ser Tyr Met Glu Gly Asp Thr Glu
355 360 365

<210> SEQ ID NO 130
<211> LENGTH: 360
<212> TYPE: PRT
<213> ORGANISM: Erysipelothrix rhusiopathiae

<400> SEQUENCE: 130

Met Lys Lys Leu Ser Lys Leu Ile Leu Val Ser Leu Leu Ala Leu Thr
1 5 10 15

Leu Phe Gly Cys Ser Ser Lys Gly Gly Ala Glu Gly Asn Ala Asn Glu
20 25 30

Gly Gly Lys Thr Tyr Asn Ile Gly Val Ala Ile Tyr Lys Phe Asp Asp
35 40 45

Asn Phe Met Thr Leu Tyr Arg Glu Glu Leu Ala Ser Tyr Phe Lys Glu
50 55 60

Val Gly Glu Lys Asp Gly Asn Thr Tyr Lys Leu Asp Ile Gln Asp Gly
65 70 75 80

Lys Gln Asp Gln Ala Asn Gln Thr Glu Gln Ile Asn Asn Phe Ile Ala
85 90 95

Gln Gly Lys Asp Leu Ile Ile Ala Asn Met Val Asp Pro Thr Ala Ala
100 105 110

Gly Ser Ile Ile Asn Ser Ala Lys Ala Lys Glu Ile Pro Val Val Phe
115 120 125

Ile Asn Arg Glu Pro Glu Thr Gln Glu Leu Glu Ile Trp Pro Gly Lys
130 135 140

Thr Thr Tyr Val Gly Ala Asp Ala Thr Gln Ser Gly Thr Ile Gln Gly
145 150 155 160

Tyr Met Ile Ala Asn Leu Glu Asn Lys Gly Asp Ile Asp Gly Asp Gly
165 170 175

Ser Val Ser Tyr Ile Thr Leu Met Gly Asp Pro Ala Asn Val Asp Ala
180 185 190

Lys Gln Arg Thr Glu Tyr Ser Val Lys Gly Leu Glu Glu Lys Gly Val
195 200 205

Lys Thr Asn Ala Leu Ala Gln Pro Tyr Gln Ala Asn Trp Asp Thr Ala
210 215 220

Lys Gly Gln Glu Phe Thr Ala Asn Ala Leu Glu Gln Phe Gly Asn Lys
225 230 235 240

Leu Glu Val Val Phe Ala Asn Asn Asp Gly Met Ala Val Gly Ala Val
245 250 255

Thr Ala Ile Glu Ala Ala Gly Arg Lys Val Gly Glu Asp Ile Phe Val
260 265 270

Val Gly Val Asp Ala Ile Pro Asp Ala Ile Glu Leu Leu Lys Gly Gly
275 280 285

Lys Leu Thr Gly Thr Val Leu Asn Asp His Phe Asn Gln Ser His Thr
290 295 300

Ala Val Asp Val Ala Leu Glu Leu Leu Gln Gly Lys Asp Val Ser Ala
305 310 315 320

Tyr Tyr Trp His Asp Tyr Val Gly Val Thr Lys Pro Glu Glu Ala Glu
325 330 335

Leu Lys Arg Ala Glu Ala Arg Lys Glu Thr Val Glu Glu Ala Val Lys
340 345 350

Arg Tyr Ala Glu Arg Asp Ala Gln
355 360

<210> SEQ ID NO 131
<211> LENGTH: 338
<212> TYPE: PRT
<213> ORGANISM: Eubacterium rectale

<400> SEQUENCE: 131

Met Met Ile Leu Cys Phe Ala Leu Ile Leu Ser Phe Val Ser Cys Ser
1 5 10 15

Asn Thr Arg Val Asp Glu Lys Lys Gln Ile Tyr Ile Gly Val Thr Cys
20 25 30

Tyr Asp Gln Lys Asp Thr Phe Ile Gly Glu Leu Ile Glu Thr Phe Lys
35 40 45

Lys Glu Cys Ala Ser Leu Asp Thr Asp Lys Tyr Asp Ile Ser Met Thr
50 55 60

Ile Met Asp Ala Ala Gly Ser Gln Arg Ala Gln Asp Asp Gln Val Gln
65 70 75 80

Glu Met Ile Glu Asp Gly Cys Asn Val Leu Cys Ile Asn Leu Ala Asp
85 90 95

Arg Thr Asp Leu Ser His Ile Ile Asn Ala Ala Met Glu Lys Asp Ile
100 105 110

Pro Ile Ile Phe Phe Asn Arg Glu Pro Val Asp Glu Asp Leu Asn Arg
115 120 125

Trp Asp Lys Leu Tyr Tyr Val Gly Ala Lys Ala Lys Gln Ser Gly Gln
130 135 140

Met Gln Gly Glu Leu Ile Ala Asp Tyr Ile Lys Asn Asn Pro Gly Val
145 150 155 160

Asp Lys Asn Gly Asp Gly Arg Ile Gln Tyr Val Ile Leu Glu Gly Glu
165 170 175

Met Gly His Gln Asp Ala Ile Val Arg Thr Glu Ser Val Thr Glu Ser
180 185 190

Met Lys Asn Asn Gly Leu Gln Ile Glu Lys Leu Ser Cys Gln Ile Ala
195 200 205

Asn Trp Asn Arg Ala Gln Ala Gln Asn Arg Met Thr Gln Leu Ile Gly
210 215 220

Gln Tyr Lys Asn Ser Ile Glu Leu Val Ile Ala Asn Asn Asp Ala Met
225 230 235 240

Ala Leu Gly Ala Ile Asp Ala Tyr Glu Lys Leu Gly Val Thr Glu Ser
245 250 255

```
Asn Val Pro Ala Phe Phe Gly Val Asp Gly Thr Asp Asp Gly Leu Glu
            260                 265                 270

Ala Val Gln Gln Ser Lys Leu Ala Ala Thr Val Tyr Asn Asp Lys Glu
        275                 280                 285

Gly Gln Ala Met Ala Met Ala Gln Leu Ala Tyr Leu Ala Ala Thr Gly
    290                 295                 300

Gly Ser Met Lys Asn Ile Lys Phe Glu Asp Lys Lys Tyr Val Tyr Leu
305                 310                 315                 320

Pro Tyr Glu Lys Val Thr Pro Asp Asn Val Asn Glu Phe Val Lys Asp
                325                 330                 335

Glu Gln


<210> SEQ ID NO 132
<211> LENGTH: 9
<212> TYPE: PRT
<213> ORGANISM: Artificial Sequence
<220> FEATURE:
<223> OTHER INFORMATION: GGSHHHHHH motif

<400> SEQUENCE: 132

Gly Gly Ser His His His His His His
1               5


<210> SEQ ID NO 133
<211> LENGTH: 7
<212> TYPE: PRT
<213> ORGANISM: Artificial Sequence
<220> FEATURE:
<223> OTHER INFORMATION: Conserved sequence
<220> FEATURE:
<221> NAME/KEY: misc_feature
<222> LOCATION: (3)..(6)
<223> OTHER INFORMATION: Xaa can be any naturally occurring amino acid

<400> SEQUENCE: 133

Trp Trp Xaa Xaa Xaa Xaa Glu
1               5


<210> SEQ ID NO 134
<211> LENGTH: 6
<212> TYPE: PRT
<213> ORGANISM: Artificial Sequence
<220> FEATURE:
<223> OTHER INFORMATION: Conserved sequence
<220> FEATURE:
<221> NAME/KEY: misc_feature
<222> LOCATION: (3)..(5)
<223> OTHER INFORMATION: Xaa can be any naturally occurring amino acid

<400> SEQUENCE: 134

Trp Trp Xaa Xaa Xaa Glu
1               5


<210> SEQ ID NO 135
<211> LENGTH: 5
<212> TYPE: PRT
<213> ORGANISM: Artificial Sequence
<220> FEATURE:
<223> OTHER INFORMATION: Conserved sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
```

-continued

<223> OTHER INFORMATION: Xaa can be any naturally occurring amino acid

<400> SEQUENCE: 135

Xaa Gln Val Xaa His
1 5

<210> SEQ ID NO 136
<211> LENGTH: 5
<212> TYPE: PRT
<213> ORGANISM: Artificial Sequence
<220> FEATURE:
<223> OTHER INFORMATION: Conserved sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 136

His Arg Xaa Asn Val
1 5

<210> SEQ ID NO 137
<211> LENGTH: 4
<212> TYPE: PRT
<213> ORGANISM: Artificial Sequence
<220> FEATURE:
<223> OTHER INFORMATION: Conserved sequence
<220> FEATURE:
<221> NAME/KEY: misc_feature
<222> LOCATION: (4)..(4)
<223> OTHER INFORMATION: Xaa can be any naturally occurring amino acid

<400> SEQUENCE: 137

Gly Asp Trp Xaa
1

<210> SEQ ID NO 138
<211> LENGTH: 6
<212> TYPE: PRT
<213> ORGANISM: Artificial Sequence
<220> FEATURE:
<223> OTHER INFORMATION: Conserved sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 138

Asp Xaa Phe Xaa Xaa Pro
1 5

<210> SEQ ID NO 139
<211> LENGTH: 6
<212> TYPE: PRT
<213> ORGANISM: Artificial Sequence
<220> FEATURE:
<223> OTHER INFORMATION: Conserved sequence
<220> FEATURE:
<221> NAME/KEY: misc_feature
<222> LOCATION: (5)..(5)
<223> OTHER INFORMATION: Xaa can be any naturally occurring amino acid

<400> SEQUENCE: 139

Lys Gly Ser Ile Xaa Ala
1 5

<210> SEQ ID NO 140
<211> LENGTH: 109
<212> TYPE: PRT
<213> ORGANISM: Escherichia coli

<400> SEQUENCE: 140

Met Ser Asp Lys Ile Ile His Leu Thr Asp Asp Ser Phe Asp Thr Asp
1 5 10 15

Val Leu Lys Ala Asp Gly Ala Ile Leu Val Asp Phe Trp Ala Glu Trp
20 25 30

Cys Gly Pro Cys Lys Met Ile Ala Pro Ile Leu Asp Glu Ile Ala Asp
35 40 45

Glu Tyr Gln Gly Lys Leu Thr Val Ala Lys Leu Asn Ile Asp Gln Asn
50 55 60

Pro Gly Thr Ala Pro Lys Tyr Gly Ile Arg Gly Ile Pro Thr Leu Leu
65 70 75 80

Leu Phe Lys Asn Gly Glu Val Ala Ala Thr Lys Val Gly Ala Leu Ser
85 90 95

Lys Gly Gln Leu Lys Glu Phe Leu Asp Ala Asn Leu Ala
100 105

<210> SEQ ID NO 141
<211> LENGTH: 118
<212> TYPE: PRT
<213> ORGANISM: Artificial Sequence
<220> FEATURE:
<223> OTHER INFORMATION: Adaptor0

<400> SEQUENCE: 141

Met Ser Ala Lys Ile Ile His Leu Thr Asp Asp Ser Phe Asp Thr Asp
1 5 10 15

Val Leu Lys Ala Asp Gly Ala Ile Leu Val Ala Phe Trp Ala Glu Trp
20 25 30

Cys Gly Pro Cys Lys Met Ile Ala Pro Ile Leu Asp Glu Ile Ala Asp
35 40 45

Glu Tyr Gln Gly Lys Leu Thr Val Ala Met Leu Asn Ile Asp Gln Asn
50 55 60

Pro Gly Thr Ala Pro Lys Tyr Gly Ile Arg Gly Ile Pro Thr Leu Leu
65 70 75 80

Leu Phe Lys Asn Gly Glu Val Ala Ala Thr Lys Val Gly Ala Leu Ser
85 90 95

Lys Gly Gln Leu Lys Glu Phe Leu Asp Ala Asn Leu Ala Gly Gly Ser
100 105 110

His His His His His His
115

<210> SEQ ID NO 142
<211> LENGTH: 118
<212> TYPE: PRT
<213> ORGANISM: Artificial Sequence
<220> FEATURE:
<223> OTHER INFORMATION: Adaptor1.0

<400> SEQUENCE: 142

Met Ser Ala Lys Ile Ile His Leu Thr Asp Asp Ser Phe Asp Thr Asp
1 5 10 15

Val Leu Lys Ala Asp Gly Ala Ile Leu Val Ala Phe Trp Ala Glu Trp
20 25 30

```
Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Cys Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115


<210> SEQ ID NO 143
<211> LENGTH: 118
<212> TYPE: PRT
<213> ORGANISM: Artificial Sequence
<220> FEATURE:
<223> OTHER INFORMATION: Adaptor2.0a

<400> SEQUENCE: 143

Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Cys Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115


<210> SEQ ID NO 144
<211> LENGTH: 118
<212> TYPE: PRT
<213> ORGANISM: Artificial Sequence
<220> FEATURE:
<223> OTHER INFORMATION: Adaptor2.0b

<400> SEQUENCE: 144

Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Cys Gly Ile Pro Thr Leu Leu
65                  70                  75                  80

Leu Phe Lys Asn Gly Glu Val Ala Ala Thr Lys Val Gly Ala Leu Ser
                85                  90                  95
```

```
Lys Gly Gln Leu Lys Glu Phe Leu Asp Ala Asn Leu Ala Gly Gly Ser
            100                 105                 110

His His His His His His
        115


<210> SEQ ID NO 145
<211> LENGTH: 118
<212> TYPE: PRT
<213> ORGANISM: Artificial Sequence
<220> FEATURE:
<223> OTHER INFORMATION: Adaptor3.0

<400> SEQUENCE: 145

Met Ser Ala Lys Ile Ile His Leu Thr Asp Cys Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115


<210> SEQ ID NO 146
<211> LENGTH: 118
<212> TYPE: PRT
<213> ORGANISM: Artificial Sequence
<220> FEATURE:
<223> OTHER INFORMATION: Adaptor4.0

<400> SEQUENCE: 146

Met Ser Ala Lys Ile Ile His Leu Thr Asp Asp Ser Phe Asp Cys Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115


<210> SEQ ID NO 147
<211> LENGTH: 118
<212> TYPE: PRT
```

<213> ORGANISM: Artificial Sequence
<220> FEATURE:
<223> OTHER INFORMATION: Adaptor5.0

<400> SEQUENCE: 147

```
Met Ser Ala Lys Ile Ile His Leu Thr Asp Asp Ser Phe Asp Thr Asp
1               5                   10                  15

Val Leu Lys Ala Cys Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115
```

<210> SEQ ID NO 148
<211> LENGTH: 118
<212> TYPE: PRT
<213> ORGANISM: Artificial Sequence
<220> FEATURE:
<223> OTHER INFORMATION: Adaptor6.0

<400> SEQUENCE: 148

```
Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Cys
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115
```

<210> SEQ ID NO 149
<211> LENGTH: 118
<212> TYPE: PRT
<213> ORGANISM: Artificial Sequence
<220> FEATURE:
<223> OTHER INFORMATION: Adaptor7.0

<400> SEQUENCE: 149

```
Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30
```

```
Cys Gly Pro Cys Lys Cys Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115


<210> SEQ ID NO 150
<211> LENGTH: 118
<212> TYPE: PRT
<213> ORGANISM: Artificial Sequence
<220> FEATURE:
<223> OTHER INFORMATION: Adaptor8.0

<400> SEQUENCE: 150

Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Cys Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115


<210> SEQ ID NO 151
<211> LENGTH: 118
<212> TYPE: PRT
<213> ORGANISM: Artificial Sequence
<220> FEATURE:
<223> OTHER INFORMATION: Adaptor9.0

<400> SEQUENCE: 151

Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Cys Leu Thr Val Ala Met Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
```

```
                85                  90                  95

Lys Gly Gln Leu Lys Glu Phe Leu Asp Ala Asn Leu Ala Gly Gly Ser
            100                 105                 110

His His His His His His
        115


<210> SEQ ID NO 152
<211> LENGTH: 118
<212> TYPE: PRT
<213> ORGANISM: Artificial Sequence
<220> FEATURE:
<223> OTHER INFORMATION: Adaptor10.0

<400> SEQUENCE: 152

Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Cys Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115


<210> SEQ ID NO 153
<211> LENGTH: 118
<212> TYPE: PRT
<213> ORGANISM: Artificial Sequence
<220> FEATURE:
<223> OTHER INFORMATION: Adaptor11.0

<400> SEQUENCE: 153

Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Cys Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115


<210> SEQ ID NO 154
<211> LENGTH: 118
```

<212> TYPE: PRT
<213> ORGANISM: Artificial Sequence
<220> FEATURE:
<223> OTHER INFORMATION: Adaptor12.0

<400> SEQUENCE: 154

```
Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Cys Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115
```

<210> SEQ ID NO 155
<211> LENGTH: 118
<212> TYPE: PRT
<213> ORGANISM: Artificial Sequence
<220> FEATURE:
<223> OTHER INFORMATION: Adaptor13.0

<400> SEQUENCE: 155

```
Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Cys Gly Ala Leu Ser
                85                  90                  95

Lys Gly Gln Leu Lys Glu Phe Leu Asp Ala Asn Leu Ala Gly Gly Ser
            100                 105                 110

His His His His His His
        115
```

<210> SEQ ID NO 156
<211> LENGTH: 118
<212> TYPE: PRT
<213> ORGANISM: Artificial Sequence
<220> FEATURE:
<223> OTHER INFORMATION: Adaptor14.0

<400> SEQUENCE: 156

```
Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
```

```
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Cys Gly Gln Leu Lys Glu Phe Leu Asp Ala Asn Leu Ala Gly Gly Ser
            100                 105                 110

His His His His His His
        115


<210> SEQ ID NO 157
<211> LENGTH: 118
<212> TYPE: PRT
<213> ORGANISM: Artificial Sequence
<220> FEATURE:
<223> OTHER INFORMATION: Adaptor15.0

<400> SEQUENCE: 157

Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Cys Leu Lys Glu Phe Leu Asp Ala Asn Leu Ala Gly Gly Ser
            100                 105                 110

His His His His His His
        115


<210> SEQ ID NO 158
<211> LENGTH: 118
<212> TYPE: PRT
<213> ORGANISM: Artificial Sequence
<220> FEATURE:
<223> OTHER INFORMATION: Adaptor16.0

<400> SEQUENCE: 158

Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Arg Gly Ile Pro Thr Leu Leu
65                  70                  75                  80
```

-continued

```
Leu Phe Lys Asn Gly Glu Val Ala Ala Thr Lys Val Gly Ala Leu Ser
                85                  90                  95

Lys Gly Gln Leu Lys Glu Phe Leu Asp Cys Asn Leu Ala Gly Gly Ser
            100                 105                 110

His His His His His His
        115
```

THERMOSTABLE GLUCOSE BIOSENSORS AND USES THEREOF

RELATED APPLICATIONS

This application is a national stage application, filed under 35 U.S.C. § 371, of International Application No. PCT/US2016/062962 filed Nov. 19, 2016, which claims benefit of priority to U.S. Provisional Application No. 62/257,800, filed Nov. 20, 2015 and U.S. Provisional Application No. 62/257,796, filed Nov. 20, 2015, the entire contents of each of which are incorporated herein by reference.

INCORPORATION-BY-REFERENCE OF SEQUENCE LISTING

The contents of the text file named "35327-527001WO_Sequence_Listing.txt", which was created on Nov. 19, 2016 and is 402 KB in size, is hereby incorporated by reference in its entirety.

FIELD OF THE INVENTION

The present invention relates to compositions and methods for detecting and determining the concentration of glucose.

BACKGROUND

Most current glucose-monitoring technologies rely on enzymes for which glucose is one of the substrates. Glucose concentration measurements are therefore subject to variations in second substrate concentrations consumed in the enzyme reaction, such as oxygen in the case of glucose oxidase. Additional complications arise in systems where reaction rates are measured for enzymes immobilized on electrodes. In such arrangements, accuracy is compromised by factors that alter the rate at which glucose arrives at the electrode surface interfere with accuracy, such as hematocrit levels, or surface "fouling" by deposition of proteins and cells in the foreign body response.

Improved ratiometric fluorescent glucose sensors are needed.

SUMMARY OF THE INVENTION

The compositions and methods described herein provide a solution to these and other disadvantages associated with earlier glucose sensors.

Provided herein are semisynthetic, reagentless, ratiometric fluorescent glucose biosensors based on the hyperthermophilic ttGBP1 and homologues thereof. These engineered compounds include biosensors that respond to glucose concentrations in clinically relevant concentration ranges. Also included are biosensors with thermostability that exceeds 100° C. Unlike biosensors based on GGBPs, biosensors provided herein have a weak affinity for galactose, and lacks a $Ca^{2+}$-binding site, the occupancy of which may affect glucose affinity in GGBPs.

Aspects include a biosensor for the determination of a presence or concentration of glucose, comprising a glucose-binding protein and a reporter group attached to the glucose-binding protein. Binding of glucose to a glucose-binding domain of the glucose-binding protein causes a change in signaling by the reporter group. Preferably, the glucose-binding protein lacks a $Ca^{2+}$ binding site. In certain embodiments, the glucose-binding protein lacks an EF hand $Ca^{2+}$ binding site. In various embodiments, the amino acid sequence of said glucose-binding protein is less than 20%, 19%, 18%, 17%, 16%, 15%, 14%, 13%, 12%, 11%, 10%, 9%, 8%, 7%, 6%, or 5% identical to the amino acid sequence of ecGGBP (SEQ ID NO: 117). In embodiments, the glucose-binding protein and/or a naturally occurring counterpart thereof has a different number and/or arrangement of β-strands (e.g., with respect to α-helices) than ecGGP. In certain embodiments, the glucose-binding protein comprises 7, 6, or 5 β-strands and/or 14, 13, 12, 11, or 10 α-helices. Preferably, the glucose-binding protein has a higher affinity (lower $K_d$) for glucose than for galactose. In various embodiments, the affinity of the glucose-binding protein for glucose is at least about 2-fold, 3-fold, 4-fold, 5-fold, 6-fold, 7-fold, 8-fold, 9-fold, 10-fold, 20-fold, 30-fold, 40-fold, 50-fold, or 100-fold higher than the affinity of the glucose-binding protein for galactose.

In some embodiments, the biosensor proteins include a second fluorophore, thereby permitting ratiometric sensing/detection of an analyte using establishing non-geometrically modulated Förster resonance energy transfer (ngmFRET).

Among the advantages of these fluorophore-containing protein constructs is their high durability. The constructs retain their ability to bind glucose, change shape and thus detect the analyte, glucose, (a) even when immobilized (directly or indirectly) onto a solid surface such as a bead, plate, or sheet; (b) even after desiccation (and subsequent reconstitution in a physiological buffer solution); (c) even when subjected to ambient conditions, e.g., conditions that can be encountered in storage and/or transportation; and (d) even when aged/stored for extended periods of time, e.g., weeks, months, or even years. Thus, the biosensors do not require refrigeration or a cold chain for distribution, permitting a wider range of applicability such as in-the-field use and reducing the cost of the sensor product.

For clinical applications, microliter volumes (e.g., less than 0.1, 0.5, 1, 2, 3, 4, 5, 6, 7, 8, 9, or 10, or less than 10 μl) of a bodily fluid such as blood may be used. Moreover compared to conventional enzyme-based or antibody based assay systems, the results are achieved virtually instantaneously, e.g., 0.1-5 minutes, e.g., 0.1-1 minutes, or within 30-60 seconds. A further advantage is that the sensors consistently and reliably bind to and detect the analyte (glucose) in complex fluids such as whole blood, plasma, serum, saliva, urine, and environmental fluids. Thus in a clinical setting, whole blood need not be processed, thereby reducing time and cost of the diagnostic procedure. Alternatively or in addition, the biosensors provided herein may be used to monitor glucose levels continuously. In a non-limiting example, one or more biosensors is immobilized at the tip of a thin optical fiber to construct a glucose-responsive optode. Such an optode can be introduced into the body (e.g., subcutaneously). The sensor may be in continuous contact with the sample, and excitation and emission light are passed to and from the immobilized sensor, respectively. Fluctuations in the glucose sample alter the dynamic equilibrium between the open and closed states of the glucose-binding protein, which is transduced into fluctuations of the fluorescent emission signal, by virtue of the sensing mechanism of the conjugated fluorophore. The emitted light intensities may be read by a reader connected to the optode.

In non-clinical situations, e.g., food and beverage composition (e.g, meat, canned food, dairy, nondairy, a fermented food, a fruit, a vegetable, a tuber, a starch, a grain, pasta, yogurt, soup, ice cream, a broth, a puree, a shake, a smoothie, a batter, a condiment, a sauce, a soft drink, a fountain beverage, water, coffee, tea, milk, a dairy-based beverages, soy-based beverage, an almond-based beverage, vegetable juice, fruit juice, a fruit juice-flavored drink, an energy drink, or an alcoholic beverage) production and/or storage, industrial, environmental (e.g., wetlands, rivers, streams, ponds, marine environments, wells, aquariums, pools, lakes, rivers, brooks, reservoirs, ground water, residential land, commercial/industrial land, agricultural land, or land abutting agricultural land), or commercial settings such as analysis of waste water, food or beverage production, or bioreactor/fermentation monitoring, the samples to be analyzed can be used directly upon sampling without further purification or processing, similarly reducing time and expense of the test. Moreover, the immobilized sensors need not be washed to remove unbound material following contacting the test sample with the sensors, because the unbound material ("contaminants") do not materially affect the production of a precise, reliable detectable assay signal.

Included herein are glucose biosensors that produce a dichromatic, ratiometric signal, i.e., the signal is defined as the quotient of the intensities at two independent wavelengths. The advantage of such a signal is that it provides an internally consistent reference. The self-calibrating nature of a ratiometric measurement removes the necessity for carrying out on-board calibration tests prior to each measurement.

Thus, reagentless, fluorescently responsive glucose sensors present a number of advantages over enzyme-based biosensors, including elimination of chemical transformations, elimination of substrate requirements, and self-calibration, which together lead to rapid response times, continuous monitoring capabilities, simple sample-handling, and lower cost due to simplified manufacturing and distribution processes.

Glucose-Binding Proteins

Aspects of the present subject matter provide biosensors comprising a ligand-binding protein that binds glucose (i.e., a glucose-binding protein). Typically, a natural glucose-binding protein has a glucose dissociation constant ($K_d$) of about 10 μM or less at room temperature. However, glucose-binding proteins may be selected, designed, or engineered (e.g., via mutation) to have a different affinity for glucose (e.g., to detect higher or lower levels of glucose). In various embodiments, a glucose-binding protein has a $K_d$ for glucose in the millimolar, micromolar, or nanomolar range. For example, a glucose-binding protein may have a $K_d$ for glucose of at least about 0.00001 mM, 0.0001 mM, 0.001 mM, 0.1 mM, 0.2 mM, 0.3 mM, 0.4 mM, 0.5 mM, 0.6 mM, 0.7 mM, 0.8 mM, 0.9 mM, 1 mM, 1.1 mM, 1.2 mM, 1.3 mM, 1.4 mM, 1.5 mM, 1.6 mM, 1.7 mM, 1.8 mM, 1.9 mM, 2 mM, 2.5 mM, 3 mM, 3.5 mM, 4 mM, 4.5 mM, 5 mM, 5.5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 21 mM, 22 mM, 23 mM, 24 mM, 25 mM, 26 mM, 27 mM, 28 mM, 29 mM, 30 mM, 31 mM, 32 mM, 33 mM, 34 mM, 35 mM, 36 mM, 37 mM, 38 mM, 39 mM, 40 mM, 41 mM, 42 mM, 43 mM, 44 mM, 45 mM, 46 mM, 47 mM, 48 mM, 49 mM, 50 mM, 75 mM, 100 mM, 200 mM, 300 mM, 400 mM, or 500 mM, and/or less than about 0.00001 mM, 0.0001 mM, 0.001 mM, 0.1 mM, 0.2 mM, 0.3 mM, 0.4 mM, 0.5 mM, 0.6 mM, 0.7 mM, 0.8 mM, 0.9 mM, 1 mM, 1.1 mM, 1.2 mM, 1.3 mM, 1.4 mM, 1.5 mM, 1.6 mM, 1.7 mM, 1.8 mM, 1.9 mM, 2 mM, 2.5 mM, 3 mM, 3.5 mM, 4 mM, 4.5 mM, 5 mM, 5.5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 21 mM, 22 mM, 23 mM, 24 mM, 25 mM, 26 mM, 27 mM, 28 mM, 29 mM, 30 mM, 31 mM, 32 mM, 33 mM, 34 mM, 35 mM, 36 mM, 37 mM, 38 mM, 39 mM, 40 mM, 41 mM, 42 mM, 43 mM, 44 mM, 45 mM, 46 mM, 47 mM, 48 mM, 49 mM, 50 mM, 75 mM, 100 mM, 200 mM, 300 mM, 400 mM, or 500 mM. In some embodiments, a glucose-binding protein has a $K_d$ for glucose within the range of 0.5 mM to 3.9 mM (hypoglycemic), 4 mM to 7 mM (euglycemic), 7 mM to 30 mM (hyperglycemic), 30 mM to about 100 mM (hyperosmolar hyperglycemic) ranges in human blood.

With respect to the present subject matter, $K_d$ is the equilibrium dissociation constant between a ligand-binding protein and its ligand. $K_d$ decreases with increasing affinity, and $K_d$ may be used as an expression of affinity (the lower the value, the higher the affinity). The $K_d$ value relates to the concentration of ligand required for detectable ligand-binding to occur and so the lower the $K_d$ value (lower concentration required), the higher the affinity of the ligand-binding protein for the ligand. The $K_d$ value corresponds to the ligand concentration at which the binding protein is 50% saturated.

| $K_d$ value | Molar concentration |
| --- | --- |
| $10^{-1}$ to $10^{-3}$ | Millimolar (mM) |
| $10^{-4}$ to $10^{-6}$ | Micromolar (μM) |
| $10^{-7}$ to $10^{-9}$ | Nanomolar (nM) |

The glucose-binding proteins (as well as biosensors comprising the ligand-binding proteins) provided herein lack enzymatic activity and are not enzymes. As used herein, an "enzyme" is a protein that catalyzes a specific biochemical reaction. The glucose is not chemically altered (i.e., no chemical bond or atom of the glucose/analyte is added or removed) by the glucose-binding protein. Thus, when glucose dissociates from a glucose-binding protein described herein, the glucose contains the same chemical structure it had before it became bound to the glucose-binding protein. In various embodiments, the glucose-binding protein does not comprises a glucose oxidase or a derivative thereof.

The ligand-binding protein may comprise a naturally occurring protein or a protein that is modified compared to a naturally occurring protein. For example, the ligand-binding protein may comprise one or more mutations compared to a naturally occurring protein. In some embodiments, the naturally occurring protein is a naturally occurring counterpart of the ligand-binding protein (e.g., the ligand-binding protein is a mutant of the naturally occurring counterpart).

A "naturally occurring counterpart" of a mutant polypeptide is a polypeptide produced in nature from which the mutant polypeptide has been or may be derived (e.g., by one or more mutations). For example, the naturally occurring counterpart is an endogenous polypeptide produced by an organism in nature, wherein the endogenous polypeptide typically does not have one or more of the mutations present in the mutant polypeptide. For convenience and depending on context, a naturally occurring counterpart may be referred to herein for the purpose of comparison and to illustrate the location and/or presence of one or more mutations, binding activities, and/or structural features.

As used herein, a "mutation" is a difference between the amino acid sequence of a modified polypeptide/protein and a naturally occurring counterpart. A polypeptide having a mutation may be referred to as a "mutant." Non-limiting examples of mutations include insertions, deletions, and substitutions. However, the term "mutation" excludes (i) the addition of amino acids to the N-terminus or C-terminus of a polypeptide, and (ii) the omission/deletion/replacement of a polypeptide's signal peptide (e.g., replacement with another signal peptide or with a methionine).

The addition of amino acids to the N-terminus or C-terminus of a protein via a peptide bond may be referred to herein as a "fusion" of the amino acids to the protein. Similarly, an exogenous protein fused to amino acids (e.g., another protein, a fragment, a tag, or a polypeptide moiety) at its N-terminus or C-terminus may be referred to as a "fusion protein." The added amino acids may comprise a non-native polypeptide, e.g., a polypeptide reporter group such as a fluorescent protein, a moiety that facilitates the isolation or modification of a polypeptide, or a moiety that facilitates the attachment of a polypeptide to a substrate or surface. As used herein, "non-native" when referring to the added amino acids (e.g., a "polypeptide") of a fusion protein indicates that the polypeptide is not naturally part of the protein to which it is fused in the fusion protein. For example, the sequence of a non-native polypeptide ("added amino acids") that is fused to a protein is encoded by an organism other than the organism from which the protein is derived, is not known to be naturally encoded by any organism, or is encoded by a gene other than the wild-type gene that encodes an endogenous version of the protein.

As used herein the term "signal peptide" refers to a short (e.g., 5-30 or 10-100 amino acids long) stretch of amino acids at the N-terminus of a protein that directs the transport of the protein. In various embodiments, the signal peptide is cleaved off during the post-translational modification of a protein by a cell. Signal peptides may also be referred to as "targeting signals," "leader sequences," "signal sequences," "transit peptides," or "localization signals." In instances where a signal peptide is not defined for a glucose-binding protein discussed herein, the signal peptide may optionally be considered to be, e.g., the first 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids from the N-terminus of the translated protein (compared to a protein that has not had the signal peptide removed, e.g., compared to a naturally occurring protein).

In some embodiments, the ligand-binding protein comprises 1, 2, 3, 4, 5, 6, 7, 8, 9, 10, 15, 20, 25, 30, 40, 50, 60, 70, 80, 90, 100, 1-10, 1-15, 1-20, 5-15, 5-20, 10-25, 10-50, 20-50, 25-75, 25-100 or more mutations compared to a naturally occurring protein while retaining at least about 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 99.5%, or about 100% of the activity of the naturally occurring protein. Mutations include but are not limited to substitutions, insertions, and deletions. Non-limiting examples of ligand-binding proteins may have 1, 2, 3, 4, 5, 6, 7, 8, 9, 10, 15, 20, 25, 30, 40, 50, 60, 70, 80, 90, 100, 1-10, 1-15, 1-20, 5-15, 5-20, 10-25, 10-50, 20-50, 25-75, 25-100, or more substitution mutations compared to a naturally occurring protein while retaining at least about 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 99.5%, or about 100% of the activity of the naturally occurring protein. In embodiments, at least one amino acid of the ligand-binding protein has been substituted with a cysteine. Alternatively or in addition, a ligand-binding protein may include one or more mutations that remove a cysteine, e.g., 1, 2, 3, 4, 5, 6, 7, 8, 9, 10 or more substitutions or deletions of a cysteine compared to a naturally occurring protein.

In some embodiments, the reporter group is conjugated to an amino acid that is no more than about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids from the N-terminus or the C-terminus of the ligand-binding protein. In some embodiments, the reporter group is conjugated to an amino acid that is at least about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids from the N-terminus or the C-terminus of the ligand-binding protein. In some embodiments, about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids (including or not including the signal peptide) have been deleted (e.g. are absent) from the N-terminus of the protein compared to its naturally occurring counterpart. In some embodiments, less than 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids (including or not including the signal peptide) have been deleted (e.g. are absent) from the N-terminus of the protein compared to its naturally occurring counterpart. In some embodiments, about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids have been deleted (e.g. are absent) from the C-terminus of the protein compared to its naturally occurring counterpart. In some embodiments, less than 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids have been deleted (e.g. are absent) from the C-terminus of the protein compared to its naturally occurring counterpart.

Alternatively, the ligand-binding protein is not a mutant. For example, a reporter group is fused to the N-terminus or the C-terminus of the ligand-binding protein.

In various embodiments, a ligand-binding protein may comprise a stretch of amino acids (e.g., the entire length of the ligand-binding protein or a portion comprising at least about 50, 100, 200, 250, 300, or 350 amino acids) in a sequence that is at least about 90%, 91%, 92%, 93%, 94%, 95%, 96%, 97%, 98%, 99%, 99.1%, 99.2%, 99.3%, 99.4%, or 99.5% identical to an amino acid sequence of a naturally occurring protein.

In some embodiments, the mutations are conservative, and the present subject matter includes many ligand-binding proteins in which the only mutations are substitution mutations. In non-limiting examples, a ligand-binding protein has no deletions or insertions compared to a naturally occurring protein (e.g., a naturally occurring counterpart). In non-limiting examples, the glucose-binding protein does not comprise a deletion or insertion compared to ttGBP1, tsGBP2, dmGBP3, tnGBP4, koGBP5, bhGBP6, smGBP7, or asGBP8. Alternatively, a ligand-binding protein may have (i) less than about 5, 4, 3, 2, or 1 inserted amino acids, and/or (ii) less than about 5, 4, 3, 2, or 1 deleted amino acids compared to a naturally occurring protein.

In various embodiments, a naturally occurring protein to which a ligand-binding protein is compared or has been derived (e.g., by mutation, fusion, or other modification) from a prokaryotic ligand-binding protein such as a bacterial ligand-binding protein. For example, the prokaryotic ligand-binding protein is a mutant, fragment, or variant of a natural (i.e., wild-type) bacterial protein. In various embodiments, the bacterial ligand-binding protein is from a thermophilic, mesophilic, or cryophilic prokaryotic microorganism (e.g., a thermophilic, mesophilic, or cryophilic bacterium).

A microorganism is "thermophilic" if it is capable of surviving, growing, and reproducing at temperatures between 41 and 140° C. (106 and 284° F.), inclusive. In various embodiments, a thermophilic organism has an optimal growth temperature between 41 and 140° C., or that is at least about 45, 50, 55, 60, 65, 70, 75, 80, 85, 90, 95, 100, 105, 110, 115, 120, 125, 130, 135, or 140° C. Many thermophiles are archaea. Thermophilic eubacteria are suggested to have been among the earliest bacteria. Thermophiles are found in various geothermally heated regions of the Earth, such as hot springs and deep sea hydrothermal vents, as well as decaying plant matter, such as peat bogs and compost. Unlike other types of microorganisms, thermophiles can survive at much hotter temperatures, whereas other bacteria would be damaged and sometimes killed if exposed to the same temperatures. Thermophiles may be classified into three groups: (1) obligate thermophiles; (2) facultative thermophiles; and (3) hyperthermophiles. Obligate thermophiles (also called extreme thermophiles) require such high temperatures for growth, whereas facultative thermophiles (also called moderate thermophiles) can thrive at high temperatures, but also at lower temperatures (e.g. below 50° C.). Hyperthermophiles are particularly extreme thermophiles for which the optimal temperatures are above 80° C. Some microorganisms can live at temperatures higher than 100° C. at large depths in the ocean where water does not boil because of high pressure. Many hyperthermophiles are also able to withstand other environmental extremes such as high acidity or radiation levels. A compound (e.g., a protein or biosensor) is "thermotolerant" if it is capable of surviving exposure to temperatures above 41° C. For example, in some embodiments a thermotolerant biosensor retains its function and does not become denatured when exposed to a temperature of about 45, 50, 55, 60, 65, 70, 75, 80, 85, 90, 95, 100, 105, 110, 115, 120, 125, 130, 135, or 140° C. for at least about 1, 2, 3, 4, 5, 6, 7, 8, 9, 10, 15, 20, 25, 30 or more minutes. In some embodiments, the thermotolerant compound survives exposure to 45, 50, 55, 60, 65, 70, 75, 80, 85, 90, 95, 100, 105, 110, 115, 120, 125, 130, 135, or 140° C. under pressure.

A microorganism is "mesophilic" if it is capable of surviving, growing, and reproducing at temperatures between 20 and 40° C. (68 and 104° F.), inclusive. "Psychrophiles" or "cryophiles" are microorganisms that are capable of growth and reproduction in cold temperatures. In various embodiments, a psychrophile is capable of growth and reproduction at a temperature of 10° C. or less, e.g., between −20° C. and +10° C.

In some embodiments, the microbial protein is produced by a bacterial microorganism, an archaean microorganism, an algal microorganism, a protozoan microorganism, or a fungal microorganism. In non-limiting examples, the microbial protein is produced by a Gram-positive bacterium or a Gram-negative bacterium. In various embodiments, a biosensor comprises a modified (e.g., mutated, fused, and/or conjugated) periplasmic binding protein or a cytoplasmic binding protein.

Aspects of the present subject matter provide a ligand-binding protein with a mutation that alters the interaction of the ligand-binding protein with a ligand (i.e. glucose). For example, the ligand-binding protein comprises a mutation that alters the interaction of the ligand-binding protein with the ligand compared to a naturally occurring counterpart. In some embodiments, the ligand-binding protein comprises a mutation that alters the interaction of an amino acid of the ligand-binding protein with a water molecule compared to a naturally occurring counterpart.

In some embodiments, the ligand-binding protein does not comprise a signal peptide. For example, the signal peptide (e.g., that is present in a naturally occurring counterpart) may be replaced with a methionine.

Exemplary implementations relate to a ligand such as glucose, wherein the ligand-binding protein comprises a glucose-binding protein. For example, the glucose-binding protein may comprise a mutant of, a fragment of, or a fusion protein comprising a microbial glucose-binding protein. In embodiments, the glucose-binding protein is not a mutant or fragment to which a non-native polypeptide has been attached or added. In some embodiments, the ligand-binding protein has an affinity ($K_d$) for glucose within the concentration range of glucose in a subject. In certain embodiments, the ligand-binding protein has an affinity ($K_d$) for glucose in the range of about 0.2 mM to about 500 mM, about 0.2 mM to about 100 mM, about 0.1 mM to about 120 mM, or about 4 mM to about 33 mM. In various embodiments, the ligand-binding protein has an affinity ($K_d$) for glucose in the range of about 0.8 mM to about 100 mM or about 0.2 mM to about 400 mM. In some embodiments, the ligand-binding protein has an affinity (Kd) for galactose greater than 100 mM, 200 mM, 300 mM, 400 mM, 500 mM, 600 mM, 700 mM, 800 mM, 900 mM, or 1000 mM, or in the range of about 100 mM to about 400 mM, about 100 mM to about 1000 mM, about 200 mM or about 1000 mM, or about 500 mM to about 1000 mM. The biosensor is capable of detecting glucose in, e.g. the hypoglycemic, euglycemic, hyperglycemic, or hyperglycemic-hyperosmotic range. Thus, unlike previous glucose sensors, the ratiometric reagentless glucose biosensors produce precise measurements over an extended glucose concentration range from hypoglycemic, euglycemic, hyperglycemic, as well as the hyperglycemic-hyperosmotic range in sample volumes of less than about 10, 9, 8, 7, 6, 5, 4, 3, 2, or 1 μl. In some embodiments, the volume of sample that is applied to a biosensor or a device comprising a biosensor is less than 0.1, 0.5, 1, 2, 3, 4, 5, 6, 7, 8, 9, 10, 25, 50, 75, 100, 150, 300, 500, or 1000 μl. In some embodiments, the volume is about 0.1 μl to about 1000 μl, about 0.1 μl to about 100 μl, about 1 μl to about 1000 μl, about 1 μl to about 10 μl, about 1 μl to about 100 μl, about 1 μl to about 50 μl, about 10 μl to about 50 μl, or about 5 μl to about 50 μl. In some embodiments, the ligand-binding protein comprises a mutation that alters (e.g., increases or decreases) the interaction of the mutant with bound glucose compared to a naturally occurring protein (e.g., a microbial glucose-binding protein), wherein the interaction is with a portion of the glucose selected from the group consisting of 1-hydroxyl, 2-hydroxyl, 3-hydroxyl, 4-hydroxyl, 6-hydroxyl, pyranose ring, or any combination thereof. In non-limiting examples, the ligand-binding protein comprises a mutation that alters (e.g., increases or decreases) the mutant's affinity and/or specificity for glucose compared to a the unmutated glucose-binding protein (e.g., a microbial glucose-binding protein). In non-limiting examples, the mutant's $K_d$ for the ligand is at least 0.001, 0.01, 0.1, 1, 2, 3, 4, 5, 6, 7, 8, 9, 10, 20, 30, 40, 50, 60, 70, 80, 90, 100, 150, 200, 250, 300, 350, 400, or 500 mM higher or lower than the unmutated ligand-binding protein. In certain embodiments, the glucose-binding protein comprises a mutation that alters the interaction between the protein and bound glucose, a mutation that alters the equilibrium between the open and closed states of the ligand-binding protein, a mutation that alters the interaction between the glucose-binding protein and a reporter group (such as a fluorescent conjugate, e.g., the interaction with a carbonyl group or a naphthalene ring of a prodan-derived fluorophore such as Acrylodan or Badan), and/or a mutation that impacts indirect interactions that alter the geometry of the glucose binding site. In various embodiments, the mutation does not reduce, or negligibly impacts, the thermostability of the glucose-binding protein. In some embodiments, the mutation alters the thermostability of the glucose-binding protein by less than about 1, 2, 3, 4, 5, or 10° C. In some embodiments, the naturally occurring counterpart of the ligand-binding protein is from a Gram-positive bacterium or a Gram-negative bacterium. Non-limiting examples of Gram-negative bacteria include *Thermus* sp., *Thermotoga* sp., *Kosmotoga* sp., and *Staphylothermus* sp. Non-limiting examples of Gram-positive bacteria include *Deinococcus* sp., *Bacillus* sp., and *Arthrobacter* sp.

In various embodiments, the glucose-binding protein is purified.

The present subject matter provides a glucose-binding protein that is or is a mutant of: an *Thermus* sp. (e.g., *T. caldophilus, T. eggertssonii, T. kawarayensis, T. murrieta, T. nonproteolyticus, T. parvatiensis, T. rehai, T. yunnanensis, T. amyloliquefaciens, T. antranikianii, T. aquaticus, T. arciformis, T. brockianus, T. caliditerrae, T. chliarophilus, T. composti, T. filiformis, T. igniterrae, T. islandicus, T. oshimai, T. profundus, T. scotoductus, T. tengchongensis*, or *T. thermophilus*) glucose-binding protein; a *Deinococcus* sp. (e.g., *D. aquivivus, D. puniceus, D. soli, D. xibeiensis, D. aerius, D. aerolatus, D. aerophilus, D. aetherius, D. alpinitundrae, D. altitudinis, D. apachensis, D. aquaticus, D. aquatilis, D. aquiradiocola, D. caeni, D. cellulosilyticus, D. claudionis, D. daejeonensis, D. depolymerans, D. deserti, D. erythromyxa, D. ficus, D. frigens, D. geothermalis, D. gobiensis, D. grandis, D. hohokamensis, D. hopiensis, D. indicus, D. maricopensis, D. marmoris, D. metalli, D. misasensis, D. murrayi, D. navajonensis, D. papagonensis, D. peraridilitoris, D. pimensis, D. piscis, D. proteolyticus, D. radiodurans, D. radiomollis, D. radiophilus, D. radiopugnans, D. reticulitermitis, D. roseus, D. saxicola, D. sonorensis, D. wulumuqiensis, D. xibeiensis, D. xinjiangensis, D. yavapaiensis*, or *D. yunweiensis*) glucose-binding protein; a *Thermotoga* sp. (e.g., *T. caldifontis, T. elfii, T. hypogea, T. lettingae, T. maritima, T. naphthophila, T. neapolitana, T. petrophila, T. profunda, T. subterranea*, or *T. thermarum*) glucose-binding protein; a *Kosmotoga* sp. (e.g., *K. olearia, K. arenicorallina, K. pacifica*, or *K. shengliensis*) glucose-binding protein; a *Bacillus* sp. (e.g., *B. acidiceler, B. acidicola, B. acidiproducens, B. acidocaldarius, B. acidoterrestris, B. aeolius, B. aerius, B. aerophilus, B. agaradhaerens, B. agri, B. aidingensis, B. akibai, B. alcalophilus, B. algicola, B. alginolyticus, B. alkalidiazotrophicus, B. alkalinitrilicus, B. alkalisediminis, B. alkalitelluris, B. altitudinis, B. alveayuensis, B. alvei, B. amyloliquefaciens, B.* a. subsp. *amyloliquefaciens, B.* a. subsp. *plantarum, B. amylolyticus, B. andreesenii, B. aneurinilyticus, B. anthracis, B. aquimaris, B. arenosi, B. arseniciselenatis, B. arsenicus, B. aurantiacus, B. arvi, B. aryabhattai, B. asahii, B. atrophaeus, B. axarquiensis, B. azotofixans, B. azotoformans, B. badius, B. barbaricus, B. bataviensis, B. beijingensis, B. benzoevorans, B. beringensis, B. berkeleyi, B. beveridgei, B. bogoriensis, B. boroniphilus, B. borstelensis, B. brevis Migula, B. butanolivorans, B. canaveralius, B. carboniphilus, B. cecembensis, B. cellulosilyticus, B. centrosporus, B. cereus, B. chagannorensis, B. chitinolyticus, B. chondroitinus, B. choshinensis, B. chungangensis, B. cibi, B. circulans, B. clarkii, B. clausii, B. coagulans, B. coahuilensis, B. cohnii, B. composti, B. curdlanolyticus, B. cycloheptanicus, B. cytotoxicus, B. daliensis, B. decisifrondis, B. decolorationis, B. deserti, B. dipsosauri, B. drentensis, B. edaphicus, B. ehimensis, B. eiseniae, B. enclensis, B. endophyticus, B. endoradicis, B. farraginis, B. fastidiosus, B. fengqiuensis, B. firmus, B. Plexus, B. foraminis, B. fordii, B. formosus, B. fortis, B. fumarioli, B. funiculus, B. fusiformis, B. galactophilus, B. galactosidilyticus, B. galliciensis, B. gelatini, B. gibsonii, B. ginsengi, B. ginsengihumi, B. ginsengisoli, B. globisporus, B.* g. subsp. *globisporus, B.* g. subsp. *marinus, B. glucanolyticus, B. gordonae, B. gottheilii, B. graminis, B. halmapalus, B. haloalkaliphilus, B. halochares, B. halodenitrificans, B. halodurans, B. halophilus, B. halosaccharovorans, B. hemicellulosilyticus, B. hemicentroti, B. herbersteinensis, B. horikoshii, B. horneckiae, B. horti, B. huizhouensis, B. humi, B. hwajinpoensis, B. idriensis, B. indicus, B. infantis, B. infernus, B. insolitus, B. invictae, B. iranensis, B. isabeliae, B. isronensis, B. jeotgali, B. kaustophilus, B. kobensis, B. kochii, B. kokeshiiformis, B. koreensis, B. korlensis, B. kribbensis, B. krulwichiae, B. laevolacticus, B. larvae, B. laterosporus, B. lautus, B. lehensis, B. lentimorbus, B. lentus, B. licheniformis, B. ligniniphilus, B. litoralis, B. locisalis, B. luciferensis, B. luteolus, B. luteus, B. macauensis, B. macerans, B. macquariensis, B. macyae, B. malacitensis, B. mannanilyticus, B. marisflavi, B. marismortui, B. marmarensis, B. massiliensis, B. megaterium, B. mesonae, B. methanolicus, B. methylotrophicus, B. migulanus, B. mojavensis, B. mucilaginosus, B. muralis, B. murimartini, B. mycoides, B. naganoensis, B. nanhaiensis, B. nanhaiisediminis, B. nealsonii, B. neidei, B. neizhouensis, B. niabensis, B. niacini, B. novalis, B. oceanisediminis, B. odysseyi, B. okhensis, B. okuhidensis, B. oleronius, B. oryzaecorticis, B. oshimensis, B. pabuli, B. pakistanensis, B. pallidus, B. pallidus, B. panacisoli, B. panaciterrae, B. pantothenticus, B. parabrevis, B. paraflexus, B. pasteurii, B. patagoniensis, B. peoriae, B. persepolensis, B. persicus, B. pervagus, B. plakortidis, B. pocheonensis, B. polygoni, B. polymyxa, B. popilliae, B. pseudalcalophilus, B. pseudofirmus, B. pseudomycoides, B. psychrodurans, B. psychrophilus, B. psychrosaccharolyticus, B. psychrotolerans, B. pulvifaciens, B. pumilus, B. purgationiresistens, B. pycnus, B. qingdaonensis, B. qingshengii, B. reuszeri, B. rhizosphaerae, B. rigui, B. ruris, B. safensis, B. salarius, B. salexigens, B. saliphilus, B. schlegelii, B. sediminis, B. selenatarsenatis, B. selenitireducens, B. seohaeanensis, B. shacheensis, B. shackletonii, B. siamensis, B. silvestris, B. simplex, B. siralis, B. smithii, B. soli, B. solimangrovi, B. solisalsi, B. songklensis, B. sonorensis, B. sphaericus, B. sporothermodurans, B. stearothermophilus, B. stratosphericus, B. subterraneus, B. subtilis, B.* s. subsp. *inaquosorum, B.* s. subsp. *spizizenii, B.* s. subsp. *subtilis, B. taeanensis, B. tequilensis, B. thermantarcticus, B. thermoaerophilus, B. thermoamylovorans, B. thermocatenulatus, B. thermocloacae, B. thermocopriae, B. thermodenitrificans, B. thermoglucosidasius, B. thermolactis, B. thermoleovorans, B. thermophilus, B. thermoruber, B. thermosphaericus, B. thiaminolyticus, B. thioparans, B. thuringiensis, B. tianshenii, B. trypoxylicola, B. tusciae, B. validus, B. vallismortis, B. vedderi, B. velezensis, B. vietnamensis, B. vireti, B. vulcani, B. wakoensis, B. weihenstephanensis, B. xiamenensis, B. xiaoxiensis*, or *B. zhanjiangensis*) glucose-binding protein; a *Staphylothermus* sp. (e.g., *S. hellenicus* or *S. marinus*) glucose-binding protein; or an *Arthrobacter* sp. (e.g., *A. agilis, A. alkaliphilus, A. alpinus, A. antarcticus, A. aurescens, A. bambusae, A. cas-*

*telli*, *A. chlorophenolicus*, *A. citreus*, *A. cryoconiti*, *A. cryotolerans*, *A. crystallopoietes*, *A. cumminsii*, *A. cupressi*, *A. defluvii*, *A. enclensis*, *A. flavus*, *A. gandavensis*, *A. globiformis*, *A. gyeryongensis*, *A. halodurans*, *A. histidinolovorans*, *A. humicola*, *A. koreensis*, *A. liuii*, *A. livingstonensis*, *A. luteolus*, *A. methylotrophus*, *A. monumenti*, *A. nanjingensis*, *A. nasiphocae*, *A. nicotinovorans*, *A. nitroguajacolicus*, *A. oryzae*, *A. parietis*, *A. pascens*, *A. pigmenti*, *A. pityocampae*, *A. psychrochitiniphilus*, *A. psychrolactophilus*, *A. ramosus*, *A. rhombi*, *A. roseus*, *A. russicus*, *A. sanguinis*, *A. soli*, *A. stackebrandtii*, *A. subterraneus*, *A. tecti*, *A. tumbae*, *A. viscosus*, or *A. woluwensis*) glucose-binding protein.

In various embodiments, a biosensor comprises a glucose-binding protein that is or is a mutant of: a glucose-binding protein from *Thermus thermophilus* (ttGBP1; SEQ ID NO: 1, 9, or 109); a glucose-binding protein from *Thermus scotoductus* (tsGBP2; SEQ ID NO: 2, 10, or 110); a glucose-binding protein from *Deinococcus maricopensis* (dmGBP3; SEQ ID NO: 3, 11, or 111); a glucose-binding protein from *Thermotoga neapolitana* (tnGBP4; SEQ ID NO: 4, 12, or 112); a glucose-binding protein from *Kosmotoga olearia* (koGBP5; SEQ ID NO: 5, 13, or 113); a glucose-binding protein from *Bacillus halodurans* (bhGBP6; SEQ ID NO: 6, 14, or 114); a glucose-binding protein from *Staphylothermus marinus* (smGBP7; SEQ ID NO: 7, 15, or 115); or a glucose-binding protein from *Arthrobacter* sp. (asGBP8; SEQ ID NO: 8, 16, or 116).

Aspects of the present subject matter include a glucose-binding protein that is or is a mutant of a protein listed in Table 2, e.g., the protein numbered 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, or 140 in Table 2.

In various embodiments, the naturally-occurring counterpart of the glucose-binding protein does not bind galactose, i.e. the glucose-binding protein is not a glucose-galactose binding protein (GGBP). In embodiments, the naturally-occurring counterpart of the glucose-binding protein has a $K_d$ for galactose that is higher than about 100 mM, 500 mM, 1000 mM, 2000 mM, 3000 mM, 4000 mM, 5000 mM, or 10000 mM. In certain embodiments, the naturally occurring counterpart of the glucose-binding protein is other than an *Escherichia coli* GGBP (ecGGBP; SEQ ID NO: 117), a *Thermoanaerobacter thermosaccharolyticum* GGBP (ttGGBP; SEQ ID NO: 118), a *Salmonella typhimurium* GGBP (stGGBP; SEQ ID NO: 119), a *Caldicellulosiruptor hydrothermalis* GGBP (chyGGBP; SEQ ID NO: 120), a *Caldicellulosiruptor obsidiansis* GGBP (cobGGBP; SEQ ID NO: 121), a *Paenibacillus* sp. GGBP (pspGGBP; SEQ ID NO: 122); a *Clostridium saccharolyticum* GGBP (csaGGBP; SEQ ID NO: 123); a *Clostridium autoethanogenum* GGBP (cauGGBP; SEQ ID NO: 128); a *Clostridium ljungdahlii* GGBP (cljGGBP; SEQ ID NO: 127); a *Butyrivibrio proteoclasticus* GGBP (bprGGBP; SEQ ID NO: 124); a *Roseburia intestinalis* GGBP (rinGGBP_A; SEQ ID NO: 125 or rinGGBP_B; SEQ ID NO: 129); a *Faecalibacterium prausnitzii* GGBP (fprGGBP; SEQ ID NO: 126); a *Erysipelothrix rhusiopathiae* GGBP (erhGGBP; SEQ ID NO: 130); or a *Eubacterium rectale* GGBP (ereGGBP; SEQ ID NO: 131). In some embodiments, the amino acid sequence of the glucose-binding protein is less than about 100%, 99%, 98%, 97%, 96%, 95%, 90%, 85%, 80%, 75%, 70%, 65%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, or 5% identical to ecGGBP, ttGGBP, stGGBP, chyGGBP, cobGGBP, pspGGBP, csaGGBP, bprGGBP, rinGGBP_A, rinGGBP_B, fprGGBP, cljGGBP, cauGGBP, erhGGBP, ereGGBP, or chyGGBP, or any combination thereof.

With regard to a defined polypeptide, % identity figures higher or lower than those provided herein will encompass various embodiments. Thus, where applicable, in light of a minimum % identity figure, a polypeptide may comprise an amino acid sequence which is at least 60%, 65%, 70%, 75%, 76%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to the reference SEQ ID NO or to each of the reference SEQ ID NOs. In embodiments, the polypeptide comprises an amino acid sequence that is 100% identical to the reference SEQ ID NO. Where applicable, in light of a maximum % identity to a reference sequence, a polypeptide may comprise an amino acid sequence which is less than 75%, 70%, 65%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, or 15% identical to the reference SEQ ID NO or to each of the reference SEQ ID NOs. In certain embodiments, a polypeptide comprises amino acids in a sequence that is preferably at least about 10%, 11%, 12%, 13%, 14%, 15%, 16%, 17%, 18%, 19%, 20%, 21%, 22%, 23%, 24%, 25%, 26%, 27%, 28%, 29%, or 30% and less than about 75%, 70%, 65%, 60%, 55%, 50%, 45%, 44%, 43%, 42%, 41%, 40%, 39%, 38%, 37%, 36%, 35%, 34%, 33%, 32%, 31%, or 30% identical to the reference SEQ ID NO or to each of the reference SEQ ID NOs. In certain embodiments, a polypeptide comprises amino acids in a sequence that is between about 10% and about 60%, 11% and about 60%, 12% and about 60%, 13% and about 60%, 14% and about 60%, 15% and about 60%, 16% and about 60%, 17% and about 60%, 18% and about 60%, 19% and about 60%, 20% and about 60%, 21% and about 60%, 22% and about 60%, 23% and about 60%, 24% and about 60%, 25% and about 60%, 26% and about 60%, 27% and about 60%, 28% and about 60%, 29% and about 60%, 30% and about 60%, about 25% and about 100%, about 25% and about 95%, about 25% and about 85%, about 25% and about 75%, about 25% and about 70%, about 25% and about 65%, 60%, about 25% and about 55%, about 25% and about 50%, about 25% and about 45%, about 25% and about 44%, about 25% and about 43%, about 25% and about 42%, about 25% and about 41%, about 25% and about 40%, about 25% and about 39%, about 25% and about 38%, about 25% and about 37%, about 25% and about 36%, about 25% and about 35%, about 25% and about 34%, about 25% and about 33%, about 25% and about 32%, about 25% and about 31%, or about 25% and about 30% identical to the reference SEQ ID NO or to each of the reference SEQ ID NOs. Non-limiting examples of reference proteins and amino acid sequences disclosed herein include:

(i) a glucose-binding protein from *Thermus thermophilus* (ttGBP1; genome, NC_005835, protein, YP_004303.1 and WP_011172778; SEQ ID NO: 1);

(ii) a glucose-binding protein from *Thermus scotoductus* (tsGBP2; genome, NC_014974, protein, YP_004202647.1; SEQ ID NO: 2);

(iii) a glucose-binding protein from *Deinococcus maricopensis* (dmGBP3; genome, NC_014958, protein, YP_004171760.1; SEQ ID NO: 3);

(iv) a glucose-binding protein from *Thermotoga neapolitana* (tnGBP4; genome, NC_011978, protein, YP_002534202.1; SEQ ID NO: 4);

(v) a glucose-binding protein from *Kosmotoga olearia* (koGBP5; genome, NC_012785, protein, YP_002941687.1; SEQ ID NO: 5);

(vi) a glucose-binding protein from *Bacillus halodurans* (bhGBP6; genome, NC_002570, protein, NP_244712.1; SEQ ID NO: 6);

(vii) a glucose-binding protein from *Staphylothermus marinus* (smGBP7; genome, NC_009033, protein, YP_001041152.1; SEQ ID NO: 7); and (viii) a glucose-binding protein from *Arthrobacter* sp. (asGBP8; genome, NC_008541, protein, YP_831349.1; SEQ ID NO: 8).

In some embodiments, the glucose-binding protein comprises an amino acid sequence with at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100% identity to 1, 2, 3, 4, 5, 6, 7, 8, 9, 10 or more glucose-binding proteins disclosed herein.

The glucose-binding proteins disclosed herein may optionally be fused (e.g., at their N-terminal and/or C-terminal ends) to a motif comprising a stretch of amino acids that facilitates the isolation or other manipulation such as conjugation to a moiety or immobilization on a substrate such as a plastic, a cellulose product such as paper, polymer, metal, noble metal, semi-conductor, or quantum dot (e.g., a fluorescent quantum dot). A non-limiting example of such a stretch of amino acids has the sequence: GGSHHHHHH (SEQ ID NO: 132). This motif is not required for, is not believed to influence or affect ligand-binding activity or signal transduction, and may be omitted from any ligand-binding protein or biosensor disclosed herein. Additionally, for every sequence disclosed herein that includes GGSHHHHHH (SEQ ID NO: 132), a corresponding sequence that is identical except that it lacks GGSHHHHHH (SEQ ID NO: 132) is also provided and intended to be disclosed. For example, each of SEQ ID NOs: 9-56 (and the non-limiting examples of other proteins used in the experiments disclosed herein) comprises this motif (SEQ ID NO: 132). Alternatively or in addition, a ligand-binding protein may be fused to a non-native polypeptide or "added amino acids" that facilitates the attachment thereof to a surface, such as the surface of a device.

In some embodiments, a polypeptide comprises 1, 2, 3, 4, 5, or more substitutions or deletions of a cysteine compared to the naturally occurring counterpart of the polypeptide (i.e., 1, 2, 3, 4, 5, or more native cysteines have been removed), e.g., 1, 2, 3, 4, 5, or more cysteine to alanine substitutions compared to the naturally occurring counterpart of the polypeptide. In some embodiments, all of the cysteines of a polypeptide have been deleted and/or substituted compared to its natural counterpart. In some embodiments, one or more cysteines of a polypeptide have been substituted with an alanine, a serine, or a threonine.

In embodiments, the amino acid sequence of a protein comprises no more than 1, 2, 3, 4, 5, 6, 7, 8, 9, 10, 15, 20, 25, 30, 35, 40, 45, or 50 mutations compared to its naturally occurring counterpart. In some embodiments, less than 50, 45, 40, 35, 30, 25, 20, 15, 10, 9, 8, 7, 6, 5, 4, 3, or 2 of the mutations is a deletion or insertion of 1, 2, 3, 4, or 5 or no more than 1, 2, 3, 4, or 5 amino acids. In some embodiments, 1, 2, 3, 4, 5, 6, 7, 8, 9, 10, 15, 20, 25, 30, 35, 40, 45, 50 or more of the mutations is a substitution mutation. In certain embodiments, every mutation to a protein compared to its naturally occurring counterpart is a substitution mutation. In various embodiments, 1, 2, 3, 4, 5, 6, 7, 8, 9, 10, 15, 20, 25, 30, 35, 40, 45, 50 or more or all of the mutations to a protein compared to its naturally occurring counterpart is a conservative substitution mutation.

In various embodiments, a polypeptide does not have any insertion or deletion compared to its natural counterpart, other than (optionally) the removal of the signal peptide and/or the fusion of compounds such as another polypeptide at the N-terminus or C-terminus thereof.

Ligand-Binding Proteins Comprising a Primary Complementary Surface (PCS)

The following BLAST parameters are used to identify sequence homologues of a glucose-binding protein such as ttGBP1: (1) Expect threshold is 10.0; (2) Gap cost is Existence: 11 and Extension: 1; (3) The Matrix employed is BLOSUM62; (4) The filter for low complexity regions is "on." Such an alignment may be generated using the ProteinHunter program. The ProteinHunter package always executes BLAST searches, with the following command "blastall -p blastp -m 8 -b 50000 -d %s -i <INPUT FILE>-o <OUTPUT FILE>"

where <INPUT FILE> and <OUTPUT FILE> specify the input and output files, respectively for a given calculation. This command executes the BLAST alignment program for protein sequences with default parameters, intrinsically set by the program. The BLAST program version is 2.2.24.

Sequence homologues of ttGBP1 identified using BLAST may be aligned with ttGBP1 using ClustalW to identify homologues that share a PCS with ttGBP1 as discussed below.

Aspects of the present subject matter provide ligand-binding proteins that share a PCS with a ttGBP1 disclosed herein. In embodiments, the PCS comprises at least about 5, 6, 7, 8, 9, 10, or 11 amino acid positions used to identify a glucose-binding protein. For example, the PCS of ttGBP1 may comprise positions 8, 9, 13, 64, 66, 119, 224, 244, 278, 312, 348, wherein each position is counted as in ttGBP1 (SEQ ID NO: 9 or 109; in which the signal peptide has been replaced with a methionine). In various embodiments, a protein shares a PCS with ttGBP1 if the amino acid sequence of the protein has (i) W, H, N, or Q at the position that aligns with position 8 of ttGBP1;

(ii) W, F, or Y at the position that aligns with position 9 of ttGBP1;

(iii) E, D, N, or Q at the position that aligns with position 13 of ttGBP1;

(iv) Q or N at the position that aligns with position 64 of ttGBP1;

(v) H, N, Q, W, or K at the position that aligns with position 66 of ttGBP1;

(vi) H, N, Q, or W at the position that aligns with position 119 of ttGBP1;

(vii) W, F, or Y at the position that aligns with position 224 of ttGBP1;

(viii) W, F, or Y at the position that aligns with position 244 of ttGBP1;

(ix) D, E, N, or Q at the position that aligns with position 278 of ttGBP1;

(x) K or R at the position that aligns with position 312 of ttGBP1; and (xi) H, N, Q, or W at the position that aligns with position 348 of ttGBP1, wherein the alignment between ttGBP1 (SEQ ID NO: 9 or 109) and the protein is constructed using the ClustalW alignment program.

The ProteinHunter package always executes multiple sequence alignments with the following command "clustalwinfile=<INPUT FILE>-outfile=<OUTPUT-FILE>-align -quiet"

This command executes the CLUSTALW multi-sequence alignment program for protein sequences. There are no user-specified parameter settings that alter the alignment behavior of the program. The CLUSTALW program version is 2.1.

For convenience and depending on context, a position that aligns with a stated position of ttGBP1 may be referred to herein as "equivalent" to the stated position.

Exemplary Ligand-Binding Proteins

Various biosensors provided herein comprise glucose-binding proteins, such as glucose-binding proteins that have altered amino acid sequences compared to their naturally occurring counterparts. In embodiments, such proteins are conjugated to reporter groups. ttGBP1 is a non-limiting reference protein respect to glucose-binding proteins. An alignment of ttGBP1 with other polypeptides is provided in FIG. 4.

In various embodiments, a glucose-binding protein (or its naturally occurring counterpart) comprises (a) an amino acid sequence that is preferably (i) at least about 10%, 11%, 12%, 13%, 14%, 15%, 16%, 17%, 18%, 19%, 20%, 21%, 22%, 23%, 24%, 25%, 26%, 27%, 28%, 29%, or 30%, and (ii) less than about 75%, 70%, 65%, 60%, 55%, 50%, 45%, 44%, 43%, 42%, 41%, 40%, 39%, 38%, 37%, 36%, or 35% identical to ttGBP1;

(b) a cysteine substitution (compared to its naturally occurring counterpart) within a stretch of at least 5, 10, or 20 amino acids having at least about 50%, 55%, 60%, 65%, 75%, 80%, 85%, 90%, or 95% identity to a stretch of consecutive amino acids including position 8 or 9 of ttGBP1;

(c) a stretch of at least 4, 5, 6, 7, 8, 9, 10, 11, 12, 13, 14, 15, 20, 25, or 30 amino acids having at least about 50%, 55%, 60%, 65%, 75%, 80%, 85%, 90%, or 95% identity to a stretch of consecutive amino acids including position 8 or 9 of ttGBP1;

(d) a stretch of amino acids in the sequence $WWX_1X_2X_3X_4E$ (SEQ ID NO: 133) or $WWX_1X_2X_4E$ (SEQ ID NO: 134) (where $X_1$ is any amino acid, or where $X_1$ is A, S, or T; where $X_2$ is any amino acid, or where $X_2$ is A, G or S; where $X_3$ is any amino acid, or where $X_3$ is A or G; and where $X_4$ is any amino acid, or where $X_4$ is D or G), (e) a cysteine substitution (compared to its naturally occurring counterpart) within a stretch of at least 5, 10, or 20 amino acids having at least about 50%, 55%, 60%, 65%, 75%, 80%, 85%, 90%, or 95% identity to a stretch of consecutive amino acids including position 42 of ttGBP1;

(f) a stretch of at least 4, 5, 6, 7, 8, 9, 10, 11, 12, 13, 14, 15, 20, 25, or 30 amino acids having at least about 50%, 55%, 60%, 65%, 75%, 80%, 85%, 90%, or 95% identity to a stretch of consecutive amino acids including position 42 of ttGBP1;

(g) a stretch of amino acids in the sequence $X_1QVX_2H$ (SEQ ID NO: 135) (where $X_1$ is any amino acid, or where $X_1$ is F or W; and where $X_2$ is any amino acid, or where $X_2$ is V or A);

(h) a cysteine substitution (compared to its naturally occurring counterpart) within a stretch of at least 5, 10, or 20 amino acids having at least about 50%, 55%, 60%, 65%, 75%, 80%, 85%, 90%, or 95% identity to a stretch of consecutive amino acids including position 120 of ttGBP1;

(i) a stretch of at least 4, 5, 6, 7, 8, 9, 10, 11, 12, 13, 14, 15, 20, 25, or 30 amino acids having at least about 50%, 55%, 60%, 65%, 75%, 80%, 85%, 90%, or 95% identity to a stretch of consecutive amino acids including position 120 of ttGBP1;

(j) a stretch of amino acids in the sequence HRXNV (SEQ ID NO: 136) (where X is any amino acid, or where X is S or G);

(k) a cysteine substitution (compared to its naturally occurring counterpart) within a stretch of at least 5, 10, or 20 amino acids having at least about 50%, 55%, 60%, 65%, 75%, 80%, 85%, 90%, or 95% identity to a stretch of consecutive amino acids including position 245 of ttGBP1;

(l) a stretch of at least 4, 5, 6, 7, 8, 9, 10, 11, 12, 13, 14, 15, 20, 25, or 30 amino acids having at least about 50%, 55%, 60%, 65%, 75%, 80%, 85%, 90%, or 95% identity to a stretch of consecutive amino acids including position 245 of ttGBP1;

(m) a stretch of amino acids in the sequence GDWX (SEQ ID NO: 137) (where X is any amino acid, or where X is V or A);

(n) a cysteine substitution (compared to its naturally occurring counterpart) within a stretch of at least 5, 10, or 20 amino acids having at least about 50%, 55%, 60%, 65%, 75%, 80%, 85%, 90%, or 95% identity to a stretch of consecutive amino acids including position 278 of ttGBP1;

(o) a stretch of at least 4, 5, 6, 7, 8, 9, 10, 11, 12, 13, 14, 15, 20, 25, or 30 amino acids having at least about 50%, 55%, 60%, 65%, 75%, 80%, 85%, 90%, or 95% identity to a stretch of consecutive amino acids including position 278 of ttGBP1;

(p) a stretch of amino acids in the sequence $DX_1FX_2X_3P$ (SEQ ID NO: 138) (where $X_1$ is any amino acid, or where $X_1$ is S, T, A, or G; where $X_2$ is any amino acid, or where $X_2$ is G, E, or S; and where $X_3$ is any amino acid, or where $X_2$ is L or I);

(q) a cysteine substitution (compared to its naturally occurring counterpart) within a stretch of at least 5, 10, or 20 amino acids having at least about 50%, 55%, 60%, 65%, 75%, 80%, 85%, 90%, or 95% identity to a stretch of consecutive amino acids including position 312 of ttGBP1;

(r) a stretch of at least 4, 5, 6, 7, 8, 9, 10, 11, 12, 13, 14, 15, 20, 25, or 30 amino acids having at least about 50%, 55%, 60%, 65%, 75%, 80%, 85%, 90%, or 95% identity to a stretch of consecutive amino acids including position 312 of ttGBP1;

(s) a stretch of amino acids in the sequence KGSIXA (SEQ ID NO: 139) (where X is any amino acid, or where X is P or A; where $X_2$ is any amino acid, or where $X_2$ is G, E, or S; and where $X_3$ is any amino acid, or where $X_2$ is L or I);

(t) no more than 1, 2, 3, 4, 5, 6, 7, 8, 9, 10, or 15 deleted or inserted amino acids compared to ttGBP1, not including amino acids added to the N-terminus or C-terminus of the polypeptide compared to its natural counterpart, and including or not including the signal peptide of the natural counterpart of the polypeptide;

(u) at least 10, 11, 12, 13, or 14 α-helices, or exactly 10, 11, 12, 13, or 14 α-helices; and/or (v) at least 5, 6, or 7 β-strands or exactly 5, 6, or 7 β-strands.

In embodiments, two or more or each of features (b)-(s) above occurs in the polypeptide in the order listed above as the amino acid sequence of the polypeptide is viewed or read from the N-terminus to the C-terminus (with additional features and/or amino acid sequences therebetween). For example, the polypeptide may have an N-terminus, followed by feature (b), (c), or (d), followed by feature (e), (f), or (g), followed by feature (h), (i), or (j), followed by feature (k), (1), or (m), followed by feature (n), (o), or (p), followed by feature (q), (r), or (s), followed by the C-terminus.

As used herein when referring to the order of features in an amino acid read from the N terminus to the C-terminus, a first feature is "followed by" a second feature when the second feature occurs after the first feature in the amino acid sequence. The words "followed by" do not require that the second feature immediately follow or be close to the first feature. For example, the N-terminus is followed by the C-terminus.

The features listed above are not limiting and may be combined with any other relevant features disclosed herein, including those listed below.

In some embodiments the polypeptide comprises the following sequence:

```
MXLEIFSWWTXGGEXXALXALIXXFKXKYPXXX!X#AXVAGGAGXNAKAVL

XXR$XGGXPPDTFQVHAGX#LXXXYVXAGXMXPLXDLXXXXGWXXXFPKXL

XXXXSXXGXXYS!P!N!HRGNVLWYNPAILXEXGXXXXXXXPXTWXXDXFX

XXAXXXKXXGXXXXPLALGDXXXWXXXHLFEXXLXXXLGA#XYXKLWXGXX

XFXDPXXXXXXXVKXALEXXXXXLXXXXXNX#HXXLTW##AXXLVA#GKAA

XNXMGDWAXGYXXXXXXXKPGX#FXWAAXPGTXXIFXXXXDXFGLPXKNAP

HX#XAXXWLKXXGSXEGQDXFNPXKGSIPARXDADXSXYDXYXQEXAXDFX

SXXLXPSLXHGXAAXEXFXTXXXXXXXXFXTXXXXXXXXXXXX#XAXAXXX

QXXXXXGXXXXXXXXXXXXXXXXX
```

wherein each

X is, individually, any amino acid or is absent,

! is, individually, I or V, $ is, individually, L or M,

% is, individually, F or Y, and # is, individually, N, D, Q, E, B, or Z.

In a non-limiting example, the glucose-binding polypeptide comprises an N-terminal domain and a C-terminal domain connected by a flexible hinge, with the ligand-binding site (the ligand binding domain) located in the cleft between the N-terminal and the C-terminal domain.

In some embodiments, the glucose-binding protein comprises, from the N-terminus to the C-terminus, a first β-strand (β1), followed by a first α-helix (α1), followed by a second β-strand (β2), followed by a second α-helix (α2), followed by a third β-strand (β3), followed by a third α-helix (α3), followed by a fourth α-helix (α4), followed by a fifth α-helix (α5), followed by a fourth β-strand (β4), followed by a sixth α-helix (α6), followed by a seventh α-helix (α7), followed by an eighth α-helix (α8), followed by an ninth α-helix (α9), followed by a tenth α-helix (α10), followed by a fifth β-strand (β5), followed by an eleventh α-helix (α11), followed by a sixth β-strand (β6), followed by a seventh β-strand (β7), followed by a twelfth α-helix (α12), followed by a thirteenth α-helix (α13), followed by a fourteenth α-helix (α14). In some embodiments, the polypeptide comprises (i) 1, 2, or 3 amino acid substitutions between β1 and al; (ii) 1, 2, or 3 amino acid substitutions between α1 and β2; (iii) 1, 2, or 3 amino acid substitutions between β2 and α2; (iv) 1, 2, or 3 amino acid substitutions between α2 and β3; (v) 1, 2, or 3 amino acid substitutions between β3 and α3; (vi) 1, 2, or 3 amino acid substitutions between α3 and α4; (vii) 1, 2, or 3 amino acid substitutions between α4 and α5; (viii) 1, 2, or 3 amino acid substitutions between α5 and β4; (ix) 1, 2, or 3 amino acid substitutions between β4 and α6; (x) 1, 2, or 3 amino acid substitutions between α6 and α7; (xi) 1, 2, or 3 amino acid substitutions between α7 and α8; (xii) 1, 2, or 3 amino acid substitutions between α8 and α9; (xiii) 1, 2, or 3 amino acid substitutions between α9 and α10; (xiv) 1, 2, or 3 amino acid substitutions between α10 and β5; (xv) 1, 2, or 3 amino acid substitutions between β5 and all; (xvi) 1, 2, or 3 amino acid substitutions between all and β6; (xvii) 1, 2, or 3 amino acid substitutions between β6 and β7; (xviii) 1, 2, or 3 amino acid substitutions between β7 and α12; (ix) 1, 2, or 3 amino acid substitutions between α12 and α13; (x) 1, 2, or 3 amino acid substitutions between α13 and α14; (xi) 1, 2, or 3 amino acid substitutions in β1, β2, β3, β4, β5, β6, β7; and/or (xii) 1, 2, or 3 amino acid substitutions in α1, α2, α3, α4, α5, α6, α7, α8, α9, α10, all, α12, α13, or α14. In some embodiments, the substitution(s) is a conservative substitution. In some embodiments, the substitution(s) is a substitution with cysteine. In various embodiments, the polypeptide comprises a cysteine substitution within β1, β2, β3, β4, or β7, and/or in all, α12, or α14, and/or between β1 and α1, or between α13 and α14.

Beta sheets consist of beta strands (also β-strand) connected laterally by at least two or three backbone hydrogen bonds, forming a generally twisted, pleated sheet. A β-strand is a stretch of polypeptide chain, e.g. 3 to 20 amino acids long, with backbone in an extended conformation.

Alpha-helical and β-strand segments assignments are calculated from a three-dimensional protein structure as follows, and as described in C. A. F. Andersen, B. Rost, 2003, *Structural Bioinformatics,* 341-363, P. E. Bourne, ed., Wiley, the entire content of which is incorporated herein by reference. First for a given residue, i, the backbone trace angle, τ, is calculated, defined as the dihedral angle between the four successive $C_\alpha$ atom positions of residues in the linear protein sequence i, i+1, i+2, i+3. These values are calculated for all residues. Second, the residues that form backbone hydrogen bonds with each other are recorded. A hydrogen bond is scored if the distance between the backbone amide nitrogen and carbonyl oxygen of two different residues in the protein is calculated to be 2.5 Å or less, and if the calculated angle between the nitrogen, its amide proton, and the carbonyl is greater than 120°. A residue is deemed to be in an α-helix, if $35 \leq \tau \leq 65$, and it makes a backbone hydrogen bond with its $i+4^{th}$ neighbor in the linear amino acid sequence. It is deemed to be in a β-strand, if the absolute t value falls in the interval $120 \leq |\tau| \leq 180$ and if it makes at least one hydrogen bond with another residue with the same τ value range. Alpha-helical segments comprise at least four residues; β-strand residues comprise at least three residues.

In some embodiments, the glucose-binding polypeptide does not comprise a $Ca^{2+}$ binding site. In some embodiments, the glucose-binding polypeptide comprises a $Ca^{2+}$ binding site.

In various embodiments, the $C_\alpha$ root-mean-square deviation (RMSD) between the backbone of the glucose-binding polypeptide and ttGBP1, tsGBP2, dmGBP3, tnGBP4, koGBP5, bhGBP6, smGBP7, and/or asGBP8 is, e.g., between about 0-3 Å, 0-1 Å, 0-1.5 Å, 0-2 Å, 0.1-3 Å, 0.5-1 Å, 0.5-1.5 Å, or 0.5-2 Å, or less than about 0.1 Å, 0.2 Å, 0.3 Å, 0.4 Å, 0.5 Å, 0.6 Å, 0.7 Å, 0.8 Å, 0.9 Å, 1.0 Å, 1.5 Å, 1.6 Å, 1.7 Å, 1.8 Å, 1.9 Å, 2.0 Å, 2.5 Å, or 3 Å. In some embodiments, the $C_\alpha$ RMSD between the N-terminal domain (i.e., the portion of the protein at the N-terminal side of the binding domain hinge) backbone of the glucose-binding polypeptide and the corresponding domain of ttGBP1, tsGBP2, dmGBP3, tnGBP4, koGBP5, bhGBP6, smGBP7, and/or asGBP8 is, e.g., between about 0-3 Å, 0-1 Å, 0-1.5 Å, 0-2 Å, 0.1-3 Å, 0.5-1 Å, 0.5-1.5 Å, or 0.5-2 Å, or less than about 0.1 Å, 0.2 Å, 0.3 Å, 0.4 Å, 0.5 Å, 0.6 Å, 0.7 Å, 0.8 Å, 0.9 Å, 1.0 Å, 1.5 Å, 1.6 Å, 1.7 Å, 1.8 Å, 1.9 Å, 2.0 Å, 2.5 Å, or 3 Å. In certain embodiments, the $C_\alpha$ RMSD between the C-terminal domain (i.e., the portion of the protein at the C-terminal side of the binding domain hinge) backbone of the glucose-binding polypeptide and the corresponding domain of ttGBP1, tsGBP2, dmGBP3, tnGBP4, koGBP5, bhGBP6, smGBP7, and/or asGBP8 is, e.g., between about 0-3 Å, 0-1 Å, 0-1.5 Å, 0-2 Å, 0.1-3 Å, 0.5-1 Å, 0.5-1.5 Å, or 0.5-2 Å, or less than about 0.1 Å, 0.2 Å, 0.3 Å, 0.4 Å, 0.5 Å, 0.6 Å, 0.7 Å, 0.8 Å, 0.9 Å, 1.0 Å, 1.5 Å, 1.6 Å, 1.7 Å, 1.8 Å, 1.9 Å, 2.0 Å, 2.5 Å, or 3 Å. Non-limiting considerations relating to the sequence and structural differences between homologous proteins are discussed in Chothia and Lesk (1986) *The EMBO Journal*, 5(4):823-826, the entire content of which is incorporated herein by reference.

Non-limiting examples of glucose-binding polypeptides that are useful in biosensors provided herein ttGGP1, tsGBP2, dmGBP3, tnGBP4, koGBP5, bhGBP6, smGBP7, and asGBP8. In embodiments, a biosensor comprises a modified ttGBP1, tsGBP2, dmGBP3, tnGBP4, koGBP5, bhGBP6, smGBP7, or asGBP8 polypeptide having an amino acid substitution compared to its naturally occurring counterpart, such that the polypeptide has a cysteine at position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 270, 271, 272, 273, 274, 275, 276, 277, 278, 279, 280, 281, 282, 283, 284, 285, 286, 287, 288, 289, 290, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, or 425 or any combination of 1, 2, 3, 4, or 5 thereof, wherein the position corresponds a SEQ ID NO disclosed herein for ttGBP1, tsGBP2, dmGBP3, tnGBP4, koGBP5, bhGBP6, smGBP7, or asGBP8. In embodiments, the cysteine is conjugated to a reporter group.

In various embodiments, a biosensor comprises a modified ttGBP1. In non-limiting examples, the modified ttGBP1 may comprise one or more, or any combination of the following substitutions compared to its naturally occurring counterpart: W8X, W9X, D12X, E13X, G41X, A42X, Q64X, H66X, H119X, W167X, S223X, W224X, Q225X, W244X, S277X, D278X, K312X, W337X, H348X, and M357C, where X is any amino acid, an amino acid that results in a conservative substitution, or a cysteine, and where each position is counted in ttGBP1 with the signal peptide replaced with a methionine (SEQ ID NO: 9 or 109). In some embodiments, the modified ttGBP1 comprises 1, 2, 3, 4, 5, 6, 7, 8, 9, 10, 11, 12, 13, 14, 15, 16, 17, 18, 19, or 20 of the following substitutions: W8C, W8F, W8M, W8Y, W9F, W9M, W9Y, W9C, D12C, E13C, G41C, A42C, Q64C, Q64N, Q64E, Q64M, H66C, H66Q, H119C, W167C, S223C, W224C, Q225C, W244C, W244M, W244F, W244Y, S277C, D278C, D278N, D278S, D278L, K312C, K312M, W337C, H348, and M357C.

In various embodiments, a biosensor comprises a modified tsGBP2. In non-limiting examples, the modified tsGBP2 may comprise one or more, or any combination of the following substitutions compared to its naturally occurring counterpart: W8X, W9X, D12X, E13X, G41X, A42X, Q64X, H66X, H119X, W167X, S223X, W224X, Q225X, W244X, S277X, D278X, K312X, W337X, H348X, and M357C, where X is any amino acid, an amino acid that results in a conservative substitution, or a cysteine, and where each position is counted in tsGBP2 with the signal peptide replaced with a methionine (SEQ ID NO: 10 or 110). In some embodiments, the modified tsGBP2 comprises 1, 2, 3, 4, 5, 6, 7, 8, 9, 10, 11, 12, 13, 14, 15, 16, 17, 18, 19, or 20 of the following substitutions: W8C, W8F, W8M, W8Y, W9F, W9M, W9Y, W9C, D12C, E13C, G41C, A42C, Q64C, Q64N, Q64E, Q64M, H66C, H66Q, H119C, W167C, S223C, W224C, Q225C, W244C, W244M, W244F, W244Y, S277C, D278C, D278N, D278S, D278L, K312C, K312M, W337C, H348C, and M357C.

In various embodiments, a biosensor comprises a modified dmGBP3. In non-limiting examples, the modified dmGBP3 may comprise one or more, or any combination of the following substitutions compared to its naturally occurring counterpart: W8X, W9X, D12X, E13X, G41X, A42X, Q64X, H66X, H119X, W166X, S223X, W224X, Q225X, W243X, A276X, D277X, K311X, W336X, H347X, and T356X, where X is any amino acid, an amino acid that results in a conservative substitution, or a cysteine, and where each position is counted in dmGBP3 with the signal peptide replaced with a methionine (SEQ ID NO: 11 or 111). In some embodiments, the modified dmGBP3 comprises 1, 2, 3, 4, 5, 6, 7, 8, 9, 10, 11, 12, 13, 14, 15, 16, 17, 18, 19, or 20 of the following substitutions: W8C, W8F, W8M, W8Y, W9F, W9M, W9Y, W9C, D12C, E13C, G41C, A42C, Q64C, Q64N, Q64E, Q64M, H66C, H66Q, H119C, W166C, S223C, W224C, Q225C, W243C, W243M, W243F, W243Y, A276C, D277C, D277N, D277S, D277L, K311C, K311M, W336C, H347C, and T356C.

In various embodiments, a biosensor comprises a modified tnGBP4. In non-limiting examples, the modified tnGBP4 may comprise one or more, or any combination of the following substitutions compared to its naturally occurring counterpart: W7X, W8X, G12X, E13X, G41X, A42X, Q64X, H66X, H119X, W169X, A225X, W226X, Q227X, W246X, S278X, D279X, K313X, F338X, H349X, and F357X, where X is any amino acid, an amino acid that results in a conservative substitution, or a cysteine, and where each position is counted in tnGBP4 with the signal peptide replaced with a methionine (SEQ ID NO: 12 or 112). In some embodiments, the modified tnGBP4 comprises 1, 2, 3, 4, 5, 6, 7, 8, 9, 10, 11, 12, 13, 14, 15, 16, 17, 18, 19, or 20 of the following substitutions: W7C, W7F, W7M, W7Y, W8F, W8M, W8Y, W8C, G12C, E13C, G41C, A42C, Q64C, Q64N, Q64E, Q64M, H66C, H66Q, H119C, W169C, A225C, W226C, Q227C, W246C, W246M, W246F, W246Y, S278C, D279C, D279N, D279S, D279L, K313C, K313M, F338C, H349C, and F357C.

In various embodiments, a biosensor comprises a modified koGBP5. In non-limiting examples, the modified koGBP5 may comprise one or more, or any combination of the following substitutions compared to its naturally occurring counterpart: W7X, W8X, G12X, E13X, G41X, A42X, Q64X, H66X, H119X, W169X, T225X, W226X, Q227X, W246X, T278X, D279X, K313X, F338X, H349X, and V358X, where X is any amino acid, an amino acid that results in a conservative substitution, or a cysteine, and where each position is counted in koGBP5 with the signal peptide replaced with a methionine (SEQ ID NO: 13 or 113). In some embodiments, the modified koGBP5 comprises 1, 2, 3, 4, 5, 6, 7, 8, 9, 10, 11, 12, 13, 14, 15, 16, 17, 18, 19, or 20 of the following substitutions: W7C, W7F, W7M, W7Y, W8F, W8M, W8Y, W8C, G12C, E13C, G41C, A42C, Q64C, Q64N, Q64E, Q64M, H66C, H66Q, H119C, W169C, T225C, W226C, Q227C, W246C, W246M, W246F, W246Y, T278C, D279C, D279N, D279S, D279L, K313C, K313M, F338C, H349C, and V358C.

In various embodiments, a biosensor comprises a modified bhGBP6. In non-limiting examples, the modified bhGBP6 may comprise one or more, or any combination of the following substitutions compared to its naturally occurring counterpart: W7X, W8X, G12X, E13X, G41X, A42X, Q64X, H66X, H119X, W168X, N224X, W225X, Q226X, W245X, T278X, D279X, K313X, F338X, H349X, and L358X, where X is any amino acid, an amino acid that results in a conservative substitution, or a cysteine, and where each position is counted in bhGBP6 with the signal peptide replaced with a methionine (SEQ ID NO: 14 or 114). In some embodiments, the modified bhGBP6 comprises 1, 2, 3, 4, 5, 6, 7, 8, 9, 10, 11, 12, 13, 14, 15, 16, 17, 18, 19, or 20 of the following substitutions: W7C, W7F, W7M, W7Y, W8F, W8M, W8Y, W8C, G12C, E13C, G41C, A42C, Q64C, Q64N, Q64E, Q64M, H66C, H66Q, H119C, W168C, N224C, W225C, Q226C, W245C, W245M, W245F, W245Y, T278C, D279C, D279N, D279S, D279L, K313C, K313M, F338C, H349C, and L358C.

In various embodiments, a biosensor comprises a modified smGBP7. In non-limiting examples, the modified smGBP7 may comprise one or more, or any combination of the following substitutions compared to its naturally occurring counterpart: W8X, W9X, G13X, E14X, G42X, A43X, Q65X, H67X, H119X, W176X, W241X, D242X, Q243X, W261X, S291X, D292X, K327X, F351X, H362X, and M371X, where X is any amino acid, an amino acid that results in a conservative substitution, or a cysteine, and where each position is counted in smGBP7 with the signal peptide replaced with a methionine (SEQ ID NO: 15 or 115). In some embodiments, the modified smGBP7 comprises 1, 2, 3, 4, 5, 6, 7, 8, 9, 10, 11, 12, 13, 14, 15, 16, 17, 18, 19, or 20 of the following substitutions: W8C, W8F, W8M, W8Y, W9F, W9M, W9Y, W9C, G13C, E14C, G42C, A43C, Q65C, Q64N, Q65E, Q65M, H67C, H67Q, H119C, W176C, W241C, D242C, Q243C, W261C, W261M, W261F, W261Y, S291C, D292C, D292N, D292S, D292L, K327C, K327M, F351C, H362C, and M371C.

In various embodiments, a biosensor comprises a modified asGBP8. In non-limiting examples, the modified asGBP8 may comprise one or more, or any combination of the following substitutions compared to its naturally occurring counterpart: W8X, W9X, S13X, E14X, G42X, G43X, Q65X, H67X, H119X, F170X, T226X, W227X, D228X, W247X, G279X, D280X, K315X, F340X, H351X, and A360X, where X is any amino acid, an amino acid that results in a conservative substitution, or a cysteine, and where each position is counted in asGBP8 with the signal peptide replaced with a methionine (SEQ ID NO: 16 or 116). In some embodiments, the modified asGBP8 comprises 1, 2, 3, 4, 5, 6, 7, 8, 9, 10, 11, 12, 13, 14, 15, 16, 17, 18, 19, or 20 of the following substitutions: W8C, W8F, W8M, W8Y, W9F, W9M, W9Y, W9C, S13C, E14C, G42C, G43C, Q65C, Q64N, Q65E, Q65M, H67C, H67Q, H119C, F170C, T226C, W227C, D228C, W247C, W247M, W247F, W247Y, G279C, D280C, D280N, D280S, D280L, K315C, K315M, F340C, H351C, and A360C.

In various embodiments, the disassociation constant of the mutant glucose-binding polypeptide differs by at least about 1 μM, 5 μM, 10μM, 20 μM, 25 μM, 30 μM, 35 μM, 40 μM, 45 μM, 50 μM, 75 μM, 100 μM, 200 μM, 300 μM, 400 μM, 500 μM, 600 μM, 700 μM, 800 μM, 900 μM, 1 mM, 2 mM, 3 mM, 4 mM, 5 mM, 6 mM, 7 mM, 8 mM, 9 mM, 10 mM, 20 mM, 30 mM, 40 mM, 50 mM, 60 mM, 70 mM, 80 mM, 90 mM, 100 mM, 150 mM, 200 mM, 250 mM, 300 mM, 350 mM, 400 mM, 450 mM, or 500 mM (increase or decrease) compared to its naturally occurring counterpart.

The biosensors and ligand-binding proteins provided herein are robust and useful at a wide range of physical conditions, e.g., pressure, temperature, salinity, osmolality, and pH conditions. For example, biosensors and ligand-binding proteins provided herein may survive substantial periods of time after being dried or exposed to high temperatures. In some embodiments, the biosensor maintains at least about 75%, 80%, 85%, 90%, 95%, 96%, 97%, 98%, 99%, 99.5%, 99.9%, or more of its signal transduction activity after exposure to a temperature of about 40, 45, 50, 55, 60, 65, 70, 75, 80, 85, 90, 95, 100, 105, 110, 115, 120, or 125, or 40-125° C. for about 1, 2, 3, 4, 5, 6, 15, 30, 60, 120, 180, 240, or 360 minutes. In certain embodiments, the biosensor maintains at least about 75%, 80%, 85%, 90%, 95%, 96%, 97%, 98%, 99%, 99.5%, 99.9%, or more of its signal transduction activity after 1, 2, 3, 4, or 5 freeze-thaw cycles in an aqueous solution. In various embodiments, the biosensor maintains at least about 75%, 80%, 85%, 90%, 95%, 96%, 97%, 98%, 99%, 99.5%, 99.9%, or more of its signal transduction activity after storage at a temperature of between 20-37° C. for about 1, 2, 3, 4, 5, 6, 7, 8, 9, 10, 11, 12, 18, 24, or 1-24 months in dry form. In some embodiments, the optimal functional temperature of the biosensor is between 41 and 122° C., between 20 and 40° C., or less than about 10° C. (e.g., between −20 and +10° C.). Devices, compositions, and biosensors provided herein may be stored, e.g., with or without protection from exposure to light. In some embodiments, the devices, compositions, and biosensors are stored in the dark, e.g., with protection from light.

Reporter Group Attachment

Aspects of the present subject matter provide a biosensor that comprises a one or more reporter groups attached to a ligand-binding protein, wherein binding of a ligand to a ligand-binding domain of the ligand-binding protein causes a change in signaling by the reporter group. In various embodiments, the reporter group is attached to an endosteric site, an allosteric site, or a peristeric site of the ligand-binding protein. In embodiments, the reporter group is covalently or noncovalently attached to the ligand-binding protein.

As used herein, "signaling" refers to the emission of energy (which may be referred to as a "signal") by one or more reporter groups. In various implementations, the signal comprises electromagnetic radiation such as a light. In some embodiments, the signal is detected as a complete emission spectrum (or spectrums) or a portion (or portions) thereof. For example, a signal may comprise emitted light at a particular wavelength or wavelengths, or range(s) of wavelengths. In some embodiments, a change in signaling comprises a spectral change (e.g., a spectral shift and/or change in intensity). In some embodiments, a change in signaling comprises a dichromatic shift or a monochromatic fluorescence intensity change.

For convenience and depending on context, a reporter group may be referred to by a name of an unattached form of the reporter group regardless of whether the reporter group is attached to a ligand-binding protein. For example, a compound known as "Compound A" when in an unconjugated form may be referred to herein as "Compound A" when in a form that is attached to a ligand-binding protein. In a specific example, the term "Acrylodan" is used to refer to unreacted/unconjugated Acrylodan, as well as Acrylodan that is conjugated to a ligand-binding protein.

In certain embodiments, a biosensor comprises a reporter group that is conjugated to a ligand-binding protein, and the reporter group is conjugated to an amino acid of the protein that is at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 angstroms (Å) from the ligand when the ligand is bound to the protein. In embodiments, the reporter group is conjugated to an amino acid of the protein that is about 0.1 Å to about 100 Å, about 0.1 Å to about 5 Å, about 5 Å to about 10 Å, about 10 Å to about 20 Å, about 20 Å to about 50 Å, about 50 Å to about 75 Å, or about 75 Å to about 100 Å from the ligand when the ligand is bound to the protein. In some embodiments, the reporter group is conjugated to an amino acid of the protein that is within an α-helix or a β-strand. In some embodiments, the reporter group is conjugated to an amino acid that (i) is not within an α-helix or a β-strand, but is within about 10, 9, 8, 7, 6, 5, 4, 3, 2, or 1 amino acids of an amino acid of the protein's amino acid sequence that is within an α-helix or a β-strand. In some embodiments, the reporter group is conjugated to an amino acid that is in an inter-domain hinge amino acid region between two domains of a protein. In some embodiments, the reporter group is conjugated to an amino acid that is between (i) an α-helix and a β-strand; (ii) two α-helixes; or (iii) two β-strands of a protein. In some embodiments, the reporter group is conjugated to an amino acid (e.g., a cysteine such as a cysteine added by substitution compared to a naturally corresponding polypeptide) between positions 1-25, 25-50, 50-75, 75-100, 100-125, 125-150, 150-175, 175-200, 200-225, 225-250, 250-275, 275-350, 275-300, 275-325, 300-325, 300-350, 300-400, 350-425, or 375-425 (inclusive) of a polypeptide (e.g., not including N-terminal fusion proteins compared to the polypeptide's naturally occurring counterpart).

Periplasmic binding proteins are characterized by two lobes connected by a hinge region; ligand bind at a location at the interface between the two domains. Such proteins or engineered versions thereof (as described herein) can adopt two different conformations: a ligand-free open form and a ligand-bound closed form, which interconvert through a relatively large bending motion around the hinge (FIG. 1A; Dwyer et al., 2004, Current Opinion in Structural Biology 12:495-504).

The remarkable adaptability of this superfamily of ligand-binding proteins is likely to have arisen from positioning the location of binding of the ligand at the interface between the lobes and from the large ligand-mediated conformational change. In this arrangement, ligands are placed within an environment that resembles a protein interior, but the residues forming the contact points or contact sites with the ligand are positioned at the surface of the lobes.

Direct signaling relationships between proteins and reporter groups are readily designed by replacing a residue known to form a ligand contact with a cysteine to which the fluorophore is attached ("endosteric" attachment site). Other, indirect signaling relationships can be established in two ways. The first relies on visual inspection of the ligand complex structure, and identifying residues that are located in the vicinity of the binding site, but do not interact directly with the ligand, and that are likely to be involved in conformational changes. Typically, such "peristeric" sites are located adjacent to the residues that form direct contacts with the bound ligand. In the case of the bPBPs, such residues are located at the perimeter of the inter-domain cleft that forms the ligand binding site location. The environment of these peristeric sites changes significantly upon formation of the closed state. These are examples of positions which are proximal to the ligand-binding pocket/domain. The second, most general, approach identifies sites in the protein structure that are located anywhere in the protein, including locations at some distance away from the ligand-binding site (i.e., distal to the ligand-binding pocket/domain), and undergo a local conformational change in concert with ligand binding. If the structures of both the open and closed states are known, then such "allosteric" sites can be identified using a computational method that analyzes the conformational changes that accompany ligand binding (Marvin et al., Proc. Natl. Acad. Sci. USA, 94:4366-4371, 1997). Alternatively, once allosteric sites have been identified in one bPBP, modeling and structural homology arguments can be invoked to identify such sites in other bPBPs in which only one state has been characterized (Marvin & Hellinga, J. Am. Chem. Soc., 120:7-11, 1998). This generalized conformational analysis also may identify peristeric and endosteric sites, which were identified and classified by visual inspection.

In non-limiting implementations, the reporter group is attached to the ligand-binding protein via a biotin-avidin interaction. The reporter group may be, e.g., conjugated to biotin and the ligand-binding protein is conjugated to avidin. In an example, the avidin is bound to four biotin molecules wherein each biotin molecule is individually conjugated to a reporter group. Alternatively, the reporter group is conjugated to avidin and the ligand-binding protein is conjugated to biotin. For example, the avidin is bound to four biotin molecules, wherein each biotin molecule is individually conjugated to a ligand-binding protein.

As used herein, "conjugated" means covalently attached. One compound may be directly conjugated to another compound, or indirectly conjugated, e.g., via a linker.

In some embodiments, the reporter group is directly attached to the ligand-binding protein. In various embodiments, the reporter group is attached to an amino acid of the ligand-binding protein that is at least about 2, 4, 6, 8, 10, 11, 12, 13, 14, 15, 16, 17, 18, 19, 20, 25, 30, 35, 40, 45, 50, 55, 60, 65, 70, 75, 80, 85, 90, 95, or 100 angstroms (Å) from the ligand when the ligand is bound to the ligand-binding protein. In certain embodiments, the reporter group is conjugated to an amino acid having a position within positions 1-25, 25-50, 50-75, 75-100, 100-125, 125-150, 150-175, 175-200, 200-225, 225-250, 250-275, or 275-300 of the ligand-binding protein, wherein position 1 is the N-terminal amino acid of the ligand-binding protein. In non-limiting examples, the reporter group is conjugated to an amino acid of the ligand-binding protein that is (a) within an α-helix or a β-strand of the ligand-binding protein; (b) not within an α-helix; (c) not within a β-strand; (d) within about 5 or 10 amino acids of an amino acid that is within an α-helix or β-strand; (e) within a stretch of consecutive amino acids that links two domains of the ligand-binding protein; (f) within a stretch of consecutive amino acids that links an α-helix and a β-strand; (g) within a stretch of consecutive amino acids that links two α-helices; or (h) within a stretch of consecutive amino acids that links two β-strands. In some embodiments, the reporter group is directly attached to the N-terminus or the C-terminus of the ligand-binding protein.

The reporter group may be conjugated to the ligand-binding protein a variety of linkers or bonds, including (but not limited to) a disulfide bond, an ester bond, a thioester bond, an amide bond, or a bond that has been formed by a click reaction. In some embodiments, the click reaction is a reaction between (a) an azide and an alkyne; (b) an azide and an alkyne in the presence of Cu(I); (c) an azide and a strained cyclooctyne; (d) an azide and a dibenzylcyclooctyne, a difluorooctyne, or a biarylazacyclooctynone; (e) a diaryl-strained-cyclooctyne and a 1,3-nitrone; (f) an azide, a tetrazine, or a tetrazole and a strained alkene; (g) an azide, a tetrazine, or a tretrazole and a oxanorbomadiene, a cyclooctene, or a trans-cycloalkene; (h) a tetrazole and an alkene; or (i) a tetrazole with an amino or styryl group that is activated by ultraviolet light and an alkene. These exemplary click chemistry reactions have high specificity, efficient kinetics, and occur in vivo under physiological conditions. See, e.g., Baskin et al. Proc. Natl. Acad. Sci. USA 104(2007):16793; Oneto et al. Acta biomaterilia (2014); Neves et al. Bioconjugate chemistry 24(2013):934; Koo et al. Angewandte Chemie 51(2012):11836; Rossin et al. Angewandte Chemie 49(2010):3375, and U.S. Patent Application Publication No. 20160220686, published Aug. 4, 2016, the entire content of each of which is incorporated herein by reference. For a review of a wide variety of click chemistry reactions and their methodologies, see e.g., Nwe K and Brechbiel M W, 2009, Cancer Biotherapy and Radiopharmaceuticals, 24(3): 289-302; Kolb H C et al., 2001 Angew. Chem. Int. Ed. 40: 2004-2021. The entire contents of each of the foregoing references are incorporated herein by reference.

As used herein, the term "linker" refers to a molecule or sequence (such as an amino acid sequence), that attaches, as in a bridge, one molecule or sequence to another molecule or sequence. "Linked" means attached or bound by covalent bonds, or non-covalent bonds, or other bonds, such as van der Waals forces. In some embodiments, a linker comprises a chemical structure that has resulted from a reaction used to attach one molecule to another.

In various implementations of the present subject matter, the reporter group is conjugated to a cysteine of the ligand-binding protein. The cysteine may be present in the amino acid sequence of a natural counterpart or version of the ligand-binding protein or added to the ligand-binding protein by a substitution mutation in a coding sequence or by altering the sequence synthetically using known chemical means. In some embodiments, the cysteine is at the N-terminus or the C-terminus of the ligand-binding protein. In some embodiments, the cysteine is no more than about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids from the N-terminus or the C-terminus of the ligand-binding protein. In some embodiments, the cysteine is at least about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids from the N-terminus or the C-terminus of the ligand-binding protein.

Non-limiting examples relate to the conjugation of a reporter group to a primary amine of the ligand-binding protein. In certain embodiments, the primary amine is present in a lysine of the ligand-binding protein. The lysine may be present in the amino acid sequence of a natural counterpart or version of the ligand-binding protein or added to the ligand-binding protein by a substitution mutation in a coding sequence or by altering the sequence synthetically using known chemical means. In some embodiments, the lysine is at the N-terminus or the C-terminus of the ligand-binding protein. In some embodiments, the lysine is no more than about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids from the N-terminus or the C-terminus of the ligand-binding protein. In some embodiments, the lysine is at least about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids from the N-terminus or the C-terminus of the ligand-binding protein.

Aspects of the present subject matter provide a biosensor in which the reporter group is attached to the ligand-binding protein via a linker. In some embodiments, the linker comprises an organic compound that is less than about 30, 20, 15, or 10 Å long. Non-limiting examples of linkers include O, S, NH, PH, and alkyl linkers.

"Alkyl," as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., $C_1$-$C_{30}$ for straight chain, $C_3$-$C_{30}$ for branched chain), more preferably 20 or fewer carbon atoms, more preferably 12 or fewer carbon atoms, and most preferably 8 or fewer carbon atoms. Likewise, preferred cycloalkyls have from 3-10 carbon atoms in their ring structure, and more preferably have 5, 6 or 7 carbons in the ring structure. The ranges provided above are inclusive of all values between the minimum value and the maximum value. The term "alkyl" includes both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety. Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. The alkyl groups may also contain one or more heteroatoms within the carbon backbone. Preferably the heteroatoms incorporated into the carbon backbone are oxygen, nitrogen, sulfur, and combinations thereof. In certain embodiments, the alkyl group contains between one and four heteroatoms.

In some embodiments, the linker comprises a bond formed by a chemical reaction involving a reactive group such as a maleimide group. Alternatively or in addition, the linker comprises a stretch of amino acids. In a non-limiting example, the linker comprises a polyglycine linker. In embodiments, the polyglycine linker comprises 2, 3, 4, 5, or more glycines. Optionally, the polyglycine linker further comprises a serine.

In various implementations, the reporter group is attached to a linker via a covalent bond and the linker is attached to a ligand-binding protein via a covalent bond. In embodiments, the covalent bond between the linker and the reporter group and/or the covalent bond between the linker and the ligand-binding protein is a disulfide bond, an ester bond, a thioester bond, an amide bond, a carbamate bond, or a bond that has been formed by a click reaction. Non-limiting examples of click reactions include reactions between an azide and an alkyne; an azide and an alkyne in the presence of Cu(I); an azide and a strained cyclooctyne; an azide and a dibenzylcyclooctyne, a difluorooctyne, or a biarylazacyclooctynone; a diaryl-strained-cyclooctyne and a 1,3-nitrone; an azide, a tetrazine, or a tetrazole and a strained alkene; an azide, a tetrazine, or a tretrazole and a oxanorbornadiene, a cyclooctene, or a trans-cycloalkene; a tetrazole and an alkene; or a tetrazole with an amino or styryl group that is activated by ultraviolet light and an alkene.

Reporter Groups

Various types of reporter groups may be used in embodiments of the present subject matter. For example, the reporter group may comprise a fluorophore that produces a fluorescent signal. Biosensors comprising a fluorophore may be referred to herein as fluorescently responsive sensors (FRSs).

Preferably, the binding of ligand to an FRS results in a change in ratiometric AR in the signal from a reporter group. A ratiometric signal ($R_{1,2}$) is defined as the quotient of two intensities, $I_{\lambda 1}$ and $I_{\lambda 2}$, measured at two independent wavelengths, $\lambda_1$ and $\lambda_2$ and may be calculated according to the following equation:

$$R_{1,2}=I_{\lambda 1}/I_{\lambda 2}$$

In some embodiments, intensities are, e.g., integrated, filtered, assessed, detected, or evaluated over a range of wavelengths. In some embodiments, intensities are integrated over a range of wavelengths in a recorded emission spectrum. In some embodiments, a range of wavelengths is selected using a filter. In some embodiments, $\lambda_1$ is the intensity over a 1 nm to 60 nm interval centered between 400 and 1000 nm, and $\lambda_2$ is the intensity over a 1 nm to 60 nm interval centered between 400 nm and 1000 nm. In some embodiments, intensities are integrated, filtered, assessed, detected, or evaluated over a 1 nm, 2 nm, 10 nm, 15 nm, 20 nm, 25 nm, 30 nm, 35 nm, 40 nm, 45 nm, 50 nm, 55 nm, 60 nm, 75 nm, 100 nm, 10-40 nm, 10-50 nm, 20-50 nm, or 10-100 nm regions, centered between 400-1000 nm, e.g. between 420 nm and 520 nm for $\lambda_1$, and 400-1000 nm, e.g. between 500 nm to 600 nm for $\lambda_2$. In some embodiments, intensities are recorded through a bandpass filter. A non-limiting example of a bandpass filter is a 10 nm, 15 nm, 20 nm, 25 nm, 30 nm, 35 nm, 40 nm, 45 nm, 50 nm, 75 nm, 100 nm, 10-40 nm, 10-50 nm, 20-50 nm, or 10-100 nm bandpass filter, centered between 400-1000 nm, e.g. at 452 nm for $\lambda_1$ and at 400-1000 nm, e.g. at 528 nm ($\lambda_2$).

Aspects of the present subject matter provide FRSs whose emission spectra change (e.g., the shape of the emission spectra change) in response to ligand binding. In various embodiments, the ratio of intensities at two chosen wavelengths of an FRS's emission spectrum changes upon ligand binding. In some embodiments, the spectral shape and/or intensity of the fluorophore changes when the position of atoms within the fluorophore changes with respect to each other (e.g., due to the rotation of bound atoms with respect to each other or a change in the angle of a bond). In non-limiting examples, the spectral shape and/or intensity of the fluorophore changes when (i) one portion of the fluorophore rotates around a bond axis compared to another portion of the fluorophore and/or (ii) when the angle of a bond between two atoms of the fluorophore changes. In a non-limiting example, the fluorophore is a prodan-derived fluorophore (e.g., Acrylodan or Badan) and binding of ligand alters the orientation of a dimethylamino group, a naphthalene ring, and/or a carbonyl with respect to the ligand-binding protein and/or each other. In a non-limiting example, the degree of polarization of a dipole on the fluorophore changes in response to ligand binding. In various embodiments, the spectral shape and/or intensity of the fluorophore changes when an atom electrostatically interacts with the fluorophore. For example, the spectral shape and/or intensity of the fluorophore changes when the source of a positive or negative charge changes its distance with respect to the fluorophore within about 1, 2, 3, 4, 5, or 10 Å of the fluorophore. In certain embodiments, the fluorophore has an emission spectrum comprising radiation with a wavelength (e.g., a peak emission wavelength) of about 400 nm, 410 nm, 420 nm, 430 nm, 440 nm, 450 nm, 460 nm, 470 nm, 480 nm, 490 nm, 500 nm, 510 nm, 520 nm, 530 nm, 540 nm, 550 nm, 560 nm, 570 nm, 580 nm, 590 nm, 600 nm, 610 nm, 620 nm, 630 nm, 640 nm, 650 nm, 660 nm, 670 nm, 680 nm, 690 nm, 700 nm, 710 nm, 720 nm, 730 nm, 740 nm, 750 nm, 760 nm, 770 nm, 780 nm, 790 nm, 800 nm, 850 nm, 900 nm, 950 nm, or 1000 nm, or about 400 nm to about 450 nm, about 450 nm to about 500 nm, about 500 nm to about 550 nm, about 550 nm to about 600 nm, about 600 nm to about 650 nm, about 650 to about 700 nm, about 700 nm to about 750 nm, about 750 nm to about 800 nm, or about 800 nm to about 1000 nm.

In some embodiments, the signal comprises the emission intensity of the fluorophore recorded at a single wavelength or range of wavelengths. The change in signal may be a shift in the single wavelength or range of wavelengths. In some embodiments, the shift in the wavelength is at least about 1 nm, at least about 2 nm, at least about 3 nm, at least about 4 nm, at least about 5 nm, at least about 6 nm, at least about 7 nm, at least about 8 nm, at least about 9 nm, at least about 10 nm, at least about 11 nm, at least about 12 nm, at least about 13 nm, at least about 14 nm, at least about 15 nm, at least about 16 nm, at least about 17 nm, at least about 18 nm, at least about 19 nm, at least about 20 nm, at least about 25 nm, at least about 30 nm, at least about 35 nm, at least about 40 nm, at least about 45 nm, at least about 50 nm, at least about 55 nm, at least about 60 nm, at least about 65 nm, at least about 70 nm, at least about 75 nm, at least about 80 nm, at least about 85 nm, at least about 90 nm, at least about 95 nm, at least about 100 nm, at least about 105 nm, at least about 110 nm, at least about 115 nm, at least about 120 nm, at least about 125 nm, or at least about 130 nm. In some embodiments, the shift in the wavelength is about 1 nm to about 20 nm, about 2 nm to about 20 nm, about 3 nm to about 20 nm, about 4 nm to about 20 nm, about 5 nm to about 20 nm, about 1 nm to about 19 nm, about 1 nm to about 18 nm, about 1 nm to about 17 nm, 1 nm to about 16 nm, about 1 nm to about 15 nm, about 1 nm to about 14 nm, about 1 nm to about 13 nm, about 1 nm to about 12 nm, about 1 nm to about 11 nm, or about 1 nm to about 10 nm. In some embodiments, the shift in the wavelength is about 1 nm to about 20 nm. In some embodiments, the shift in the wavelength is about 1 nm to about 130 nm.

In certain embodiments, the signal comprises the ratio or quotient of the emission intensities recorded at two distinct wavelengths or ranges of wavelengths, i.e., a ratiometric signal. For example, as shown in FIGS. 1A-D, ligand binding may be determined by measuring the ratio of blue to green emission intensities. The change in signal may be decreased emission intensity at one wavelength, and no change in emission intensity at the other wavelength. The change in signal may be increased emission intensity at one wavelength, and no change in emission intensity at the other wavelength. The change in signal may be increased emission intensity at one wavelength, and increased emission intensity at the other wavelength. The change in signal may be decreased emission intensity at one wavelength, and decreased emission intensity at the other wavelength. The change in signal may be increased emission intensity at one wavelength, and decreased emission intensity at the other wavelength. In some embodiments, the change in ratio of the emission intensities recorded at two distinct wavelengths or ranges of wavelengths may be at least about 1.1-fold, at least about 1.2-fold, at least about 1.4-fold, at least about 1.6-fold, at least about 1.8-fold, at least about 2.0-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, at least about 10-fold, at least about 12-fold, at least about 14-fold, at least about 16-fold, at least about 18-fold, at least about 20-fold, at least about 25-fold, at least about 30-fold, at least about 35-fold, at least about 40-fold, at least about 45-fold, at least about 50-fold, at least about 55-fold, at least about 60-fold, at least about 65-fold, at least about 70-fold, at least about 75-fold, at least about 80-fold, at least about 85-fold, at least about 90-fold, at least about 95-fold, or at least about 100-fold. In some embodiments, the change in ratio of the emission intensities recorded at two distinct wavelengths or ranges of wavelengths may be a decrease of at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%, or of 5-25%, 25-50%, 25-75%, 50-75%, 50-90%, or 75-99% or the reciprocal thereof.

The change in signal may be a change in the ratio of the two distinct wavelengths or ranges of wavelengths. The change in signal may be a shift in the two distinct wavelengths or ranges of wavelengths. In some embodiments, one wavelength shifts. In some embodiments, both wavelengths shift. In some embodiments, the shift in the wavelength is at least about 1 nm, at least about 2 nm, at least about 3 nm, at least about 4 nm, at least about 5 nm, at least about 6 nm, at least about 7 nm, at least about 8 nm, at least about 9 nm, at least about 10 nm, at least about 11 nm, at least about 12 nm, at least about 13 nm, at least about 14 nm, at least about 15 nm, at least about 16 nm, at least about 17 nm, at least about 18 nm, at least about 19 nm, at least about 20 nm, at least about 25 nm, at least about 30 nm, at least about 35 nm, at least about 40 nm, at least about 45 nm, at least about 50 nm, at least about 55 nm, at least about 60 nm, at least about 65 nm, at least about 70 nm, at least about 75 nm, at least about 80 nm, at least about 85 nm, at least about 90 nm, at least about 95 nm, at least about 100 nm, at least about 105 nm, at least about 110 nm, at least about 115 nm, at least about 120 nm, at least about 125 nm, or at least about 130 nm. In some embodiments, the shift in the wavelength is about 1 nm to about 20 nm, about 2 nm to about 20 nm, about 3 nm to about 20 nm, about 4 nm to about 20 nm, about 5 nm to about 20 nm, about 1 nm to about 19 nm, about 1 nm to about 18 nm, about 1 nm to about 17 nm, 1 nm to about 16 nm, about 1 nm to about 15 nm, about 1 nm to about 14 nm, about 1 nm to about 13 nm, about 1 nm to about 12 nm, about 1 nm to about 11 nm, or about 1 nm to about 10 nm. In some embodiments, the shift in the wavelength is about 1 nm to about 20 nm. In some embodiments, the shift in the wavelength is about 1 nm to about 130 nm.

A fluorophore may comprise, e.g., a fluorescent protein or an organic compound having a molecular weight less than about 2000 Daltons (Da). Non-limiting examples of commercially available fluorophores include such as 5-iodoacetamidofluorescein (5-IAF) or 6-iodoacetamidofluorescein (6-IAF), rhodamine, Oregon Green, eosin, Texas Red, indocarbocyanine, oxacarbocyanine, thiacarbocyanine, merocyanine, Badan, Acrylodan, IAEDANS, comprising 3-cyano-7-hydroxycoumarin, 7-hydroxycoumarin-3-carboxylic acid, 6,8-difluoro-7-hydroxy-4-methylcoumarin, or 7-amino-4-methylcoumarin, pyridyloxazole, nitrobenzoxadiazole, benzoxadiazole, DRAQ5, DRAQ7, or CyTRAK Orange, cascade blue, Nile red, Nile blue, cresyl violet, oxazine 170, proflavin, acridine orange, acridine yellow, auramine, crystal violet, malachite green, porphin, phthalocyanine, bilirubin, pyrene, N,N'-dimethyl-N-(iodoacetyl)-N'-(7-nitrobenz-2-ox-a-1,3-diazol-4-yl)ethylenediamide (NBD), N-((2-(iodoacetoxy)ethyl)-N-methy-Damino-7-nitrobenz-2-oxa-1,3-diazole (NBDE), JPW4039, JPW4042, JPW4045, Pacific Blue, CPM, N,N'-Dimethyl-N-(Iodoacetyl)-N'-(7-Nitrobenz-2-Oxa-1,3-Diazol-4-yl)Ethylenediamine (IANBD), 7-diethylamino-3-(4'-maleimidylphenyl)-4-methylcoumarin (CPM), BODIPY 499, BODIPY 507/545, BODIPY 499/508, Alexa 432, Alexa488, Alexa532, Alexa546, Cy5, or 1-(2-maleimidylethyl)-4-(5-(4-methoxyphenyl)oxazol-2-yl)pyridinium methanesulfonate (PyMPO maleimide) (PyMPO).

In various embodiments, the reporter group was thiol-reactive prior to being conjugated to a polypeptide disclosed herein. In embodiments, the reporter group is linked to a polypeptide disclosed herein via a disulfide bond. Additional non-limiting examples of commercially available fluorophores include fluorescent proteins such as Blue Fluorescent Protein (BFP), TagBFP, mTagBFP2, Azurite, Enhanced Blue Florescent Protein 2 (EBFP2), mKalamal, Sirius, Sapphire, T-Sapphire, Cyan Fluorescent Protein (CFP); Enhanced Cyan Fluorescent Protein (ECFP), Cerulean, SCFP3A, mTurquoise, mTurquoise2, monomeric Midoriishi-Cyan, TagCFP, mTFP1, AmCyanl, Green Fluorescent Protein (GFP), Enhanced Green Fluorescent Protein (EGFP), Emerald, Superfolder GFP, AcGFP1, ZsGreenl, Monomeric Azami Green, TagGFP2, mUKG, mWasabi, Clover, mNeon-Green, Yellow Fluorescent Protein (YFP), Enhanced Yellow Fluorescent Protein (EYFP), Citrine, Venus, Super Yellow Fluorescent Protein 2 (SYFP2), TagYFP, ZsYellowl, mBanana, Orange Fluorescent Protein (OFP), Monomeric Kusabira-Orange (mKO), mKOκ, mKO2, mOrange, mOrange2, Red Fluorescent Protein (RFP), DsRed-Express, DsRed-Express2, DsRed2, AsRed2, mRaspberry, mCheny, mStrawberry, mTangerine, tdTomato, TagRFP, TagRFP-T, mApple, mRuby, mRuby2, mPlum, HcRed-Tandem, mKate2, mNeptune, HcRed1, E2-Crimson, NirFP, TagRFP657, 1FP1.4, or iRFP.

In some embodiments, the fluorophore comprises xanthene, a xanthene derivative, cyanine, a cyanine derivative, squaraine, a squaraine derivative, naphthalene, a naphthalene derivative, coumarin, a coumarin derivative, oxadiazole, an oxadiazole derivative, anthracene, an anthracene derivative, a boradiazaindacine (BODIPY) family fluorophore, pyrene, a pyrene derivative, acridine, an acridine derivative, arylmethine, an arylmethine derivative, tetrapyrrole, or a tetrapyrrole derivative. For example, the fluorophore may comprise a xanthene derivative comprising fluorescein or a fluorescein derivative, rhodamine, Oregon Green, eosin, or Texas Red. Non-limiting examples of fluorescein derivatives include 5-fluorescein, 6-carboxyfluorescein, 3'6-carboxyfluorescein, 5(6)-carboxyfluorescein, 6-hexachlorofluorescein, 6-tetrachlorofluorescein, or isothiocyanate. In some embodiments, the fluorophore comprises a cyanine derivative comprising indocarbocyanine, oxacarbocyanine, thiacarbocyanine, or merocyanine. In certain embodiments, the fluorophore comprises a squaraine derivative comprising a ring-substituted squaraine. In various embodiments, the fluorophore comprises a naphthalene derivative comprising a dansyl or prodan naphthalene derivative. In a non-limiting example, the fluorophore comprises prodan or a derivative thereof. In certain embodiments, the fluorophore comprises Badan, Acrylodan, or N-(Iodoacetaminoethyl)-1-naphthylamine-5-sulfonic acid (IAEDANS). In some embodiments, the fluorophore comprises a coumarin derivative such as 3-cyano-7-hydroxycoumarin, 7-hydroxycoumarin-3-carboxylic acid, 6,8-difluoro-7-hydroxy-4-methylcoumarin (DiFMU), or 7-amino-4-methylcoumarin. In various embodiments, the fluorophore comprises an oxadiazole derivative such as pyridyloxazole, nitrobenzoxadiazole, or benzoxadiazole. In certain embodiments, the fluorophore comprises an anthracene derivative comprising an anthraquinone such as DRAQ5, DRAQ7, or CyTRAK Orange. In various embodiments, the fluorophore comprises a pyrene derivative comprising cascade blue. In non-limiting examples the fluorophore comprises an oxazine derivative such as Nile red, Nile blue, cresyl violet, or oxazine 170. In some embodiments, the fluorophore comprises an acridine derivative such as proflavin, acridine orange, or acridine yellow. In certain embodiments, the fluorophore comprises an arylmethine derivative such as auramine, crystal violet, or malachite green. In various embodiments, the fluorophore comprises a tetrapyrrole derivative comprising porphin, phthalocyanine, or bilirubin.

Aspects of the present subject matter relate to the use of fluorophores that may readily be attached to a ligand-binding protein disclosed herein, e.g., at a cysteine residue. For example, a fluorophore may comprise a sulfhydryl group prior to attachment to a ligand-binding protein that is reacted with a moiety of the ligand-binding protein to attach the fluorophore to the ligand-binding protein. In some embodiments, the fluorophore comprised a thiol group prior to attachment to the ligand-binding protein. For example, the fluorophore was thiol reactive prior to attachment to the ligand-binding protein. Non-limiting examples of fluorophores that may readily be attached to ligand-binding proteins using thiol reactions include fluorescein, pyrene, NBD, NBDE, Acrylodan (6-acryloyl 1-2-dimethylaminonaphthalene), Badan (6-bromo-acetyl-2-dimethylamino-naphthalene), JPW4039, JPW4042, or JPW4045.

In certain embodiments, the fluorophore comprises a derivative of a Prodan-based fluorophore such as Acrylodan or Badan. The excitation and emission properties of the Prodan-based fluorophores Acrylodan and Badan can be altered by manipulating the fluorescent ring system, while preserving the dimethylamino donor group, and the twistable carbonyl acceptor (Klymchenko, 2013, *Progress in Molecular Biology and Translational Science,* 35-58). Replacement of the two-ring naphthalene with a three-ring anthracene (Lu 2006 *J. Org. Chem.,* 71, 9651-9657), fluorene (Kucherak, 2010, *J. Phys. Chem. Lett.,* 1, 616-620), pyrene (Niko, 2013, *Chem. Eur. J.,* 19, 9760-9765), or styrene (Benedetti, 2012, *J. Am. Chem. Soc.,* 134, 12418-12421) cores significantly red-shift the excitation and emission properties, and in the case of the latter two, improve brightness through improvements in their excitation peak extinction coefficients. The entire content of each of the references cited above (as well as all other references referred to herein including the contents of nucleic acid and amino acid sequence accession number references) are incorporated herein by reference. Non-limiting examples of prodan analogues include 2-cyano-6-dihexylaminoanthracene and 2-propionyl-6-dihexylaminoanthracene, as well as fluorophores comprising the following structures:

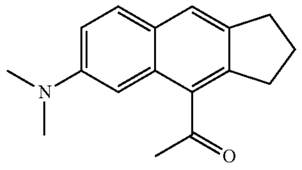
,
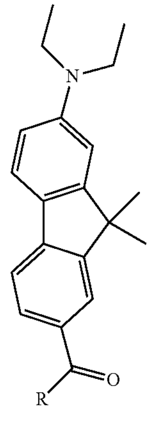
or

-continued

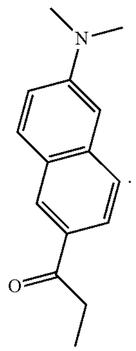

In some embodiments, the fluorophore comprises a fluorescent protein. Fluorescent proteins that emit blue, cyan, green, yellow, orange, red, far-red, or near infrared radiation when contacted with excitation radiation are known in the art and commercially available as proteins and via the expression of vectors that encode the fluorescent protein. Non-limiting examples of fluorescent proteins include Blue Fluorescent Protein (BFP), TagBFP, mTagBFP2, Azurite, Enhanced Blue Florescent Protein 2 (EBFP2), mKalamal, Sirius, Sapphire, T-Sapphire, Cyan Fluorescent Protein (CFP); Enhanced Cyan Fluorescent Protein (ECFP), Cerulean, SCFP3A, mTurquoise, mTurquoise2, monomeric Midoriishi-Cyan, TagCFP, mTFP1, AmCyanl, Green Fluorescent Protein (GFP), Enhanced Green Fluorescent Protein (EGFP), Emerald, Superfolder GFP, AcGFP1, ZsGreenl, Monomeric Azami Green, TagGFP2, mUKG, mWasabi, Clover, mNeonGreen, Yellow Fluorescent Protein (YFP), Enhanced Yellow Fluorescent Protein (EYFP), Citrine, Venus, Super Yellow Fluorescent Protein 2 (SYFP2), TagYFP, ZsYellowl, mBanana, Orange Fluorescent Protein (OFP), Monomeric Kusabira-Orange (mKO), mKOκ, mKO2, mOrange, mOrange2, Red Fluorescent Protein (RFP), DsRed-Express, DsRed-Express2, DsRed2, AsRed2, mRaspberry, mCherry, mStrawberry, mTangerine, tdTomato, TagRFP, TagRFP-T, mApple, mRuby, mRuby2, mPlum, HcRed-Tandem, mKate2, mNeptune, HcRedl, E2-Crimson, NirFP, TagRFP657, IFP1.4, or iRFP.

In some embodiments, the fluorophore comprises a quantum dot (Medintz et al. 2005) (Sapsford, Berti and Medintz 2006 Angew Chem Int Ed Engl, 45, 4562-89; Resch-Genger et al. 2008 Nat Methods, 5, 763-75). In some embodiments the emission properties of the conjugated protein are enhanced by immobilization on or near metallic nanoparticles (Zeng et al. 2014 *Chem Soc Rev,* 43, 3426-52; Shen et al. 2015 *Nanoscale,* 7, 20132-41).

In various embodiments, the peak emission wavelength and/or the emission intensity of the biosensor change when the ligand binds to the ligand-binding protein. In some embodiments, the biosensor exhibits a dichromatic signaling change when the ligand binds to the ligand-binding protein. In various embodiments, the peak emission wavelength of the biosensor shifts by at least about 5, 10, 15, 20, 30, 40, 50, or by about 5-50 nm when the biosensor binds to ligand. In certain embodiments, the emission intensity of the biosensor increases by at least about 5%, 10%, 20%, 30%, 40%, 50%, 60%, 70%, 80%, 90%, 100%, 150%, 200%, or 300% when the biosensor binds to ligand. In various embodiments, the signal produced by the reporter group persists for at least 1 nanoseconds (ns), 5 ns, 10 ns, 25 ns, 50 ns, 75 ns, 100 ns, 200 ns, 300 ns, 400 ns, 500 ns, 600 ns, 700 ns, 800 ns, 900 ns, 0.001 milliseconds (ms), 0.01 ms, 0.1 ms, 1 ms, 5 ms, 10 ms, 20 ms, 25 ms, 50 ms, 100 ms, or 500 ms when the ligand binds to the ligand-binding protein.

Ratiometric Sensing with Fluorescence Energy Transfer

The present subject matter provides methods for converting monochromatic responses into dichromatic responses that enable ratiometric sensing. If the fluorescence emission spectrum changes shape in response to analyte binding such that the ratio of emission intensities at two appropriately chosen wavelengths reports on analyte concentration (dichromatic response), then ratiometric measurements can be used to monitor analyte concentrations. In embodiments, these methods are based on establishing non-geometrically modulated Förster resonance energy transfer (ngmFRET) between a fluorophore (a directly responsive partner), and a second fluorophore that neither interacts directly with the ligand, nor is sensitive to ligand-mediated changes in its environment (an indirectly responsive partner). Biosensors that undergo ngmFRET (or altered ngmFRET) upon ligand binding are also provided herein, as well as compositions and devices comprising such biosensors.

Methods, compounds, and compositions provided herein overcome challenges regarding the design of biosensors that produce a ratiometric signal. For example, a biosensor that exhibits a monochromatic response (which does not produce a ratiometric signal) to ligand binding may be converted into a biosensor that produces a dichromatic/ratiometric signal. Moreover, the number of fluorophores that may be utilized in ratiometric biosensors is dramatically increased by the present subject matter. For example, fluorophores that typically do not show a dichromatic response to ligand binding (such as fluorescein and derivatives thereof) may be used together with an additional reporter group (such as another fluorophore) to produce a ratiometric signal. Also included are methods, compounds, and compositions relating to biosensors with multiple reporter groups that have improved ratiometric signals compared to other ratiometric biosensors (e.g., ratiometric biosensors having a single reporter group).

Traditional/conventional geometrically-modulated Fluorescence Resonance Energy Transfer (tgmFRET) is a physical phenomenon that was first described over 50 years ago. In tgmFRET, the transfer of excited state energy from a donor fluorophore to an acceptor fluorophore (i.e. energy transfer) is modulated by a ligand-binding event through changes in the distance and/or angle between the donor and acceptor fluorophores. tgmFRET is manifested by opposing changes in the fluorescence emission intensities of the donor and acceptor fluorophores, respectively, in response to ligand binding. For instance, a decrease in distance results in a decrease of the donor fluorescence emission intensity and an increase in the acceptor fluorescence intensity, as energy is transferred from the former to the latter. A ligand-mediated increase in the distance between the partners has the opposite effect (the fluorescence emission intensity of the donor increases, whereas that of the acceptor decreases). In tgmFRET, ligand-mediated modulation of fluorescence intensity arises from global changes in the entire system, and can occur only if both partners are present.

By contrast, in ngmFRET ligand-mediated modulation of fluorescence intensity arises from changes that are localized to the photophysics of the directly responsive fluorophore. Unlike tgmFRET, ligand-mediated changes in fluorescence therefore occur also if only the directly responsive partner is present in isolation by itself. Although the entire ngmFRET system comprising two partners is not required for evincing ligand-mediated changes in fluorescence emission intensity, the response of such a system is qualitatively changed or quantitatively enhanced over the responses of the isolated directly responsive partner (e.g. converting a monochromatic into a dichromatic response, thereby enabling ratiometry).

Furthermore, unlike tgmFRET, the pattern of fluorescence intensity changes manifested by ligand binding in ngmFRET systems are not limited to opposing changes only. Instead, in ngmFRET almost all combinations of emission intensity changes are possible: opposing changes in the two partners, both partners increase, both decrease, one partner remains unchanged whereas the other increases or decreases. The majority of these responses evince changes that are unequal in magnitude and/or direction (i.e. increase, decrease), and accordingly are manifested as ligand-mediated changes in the ratio of the two fluorescence emission intensities. This versatility of ngmFRET system response patterns has great utility in the field of fluorescent biosensors.

The ligand-mediated alteration of the photophysics of the directly responsive partner includes changes to its spectral properties such as the shape of the excitation or emission spectra, and the ratio of radiative to non-radiative emission rates. The fluorescence emission intensity of the indirectly responsive partner in isolation does not change in response to ligand binding; its intensity changes only in the presence of a directly responsive partner in the complete ngmFRET system. In the field fluorescence spectroscopy, the term "quenching" has often been used loosely to refer to a decrease fluorescence emission intensity. However, as used herein, the term "quenching" strictly means a "change in the ratio of radiative to non-radiative emission rates" of a fluorophore.

Aspects of the present subject matter provide biosensors in which ngmFRET occurs between two or more reporter groups (e.g., a donor fluorophore and an acceptor fluorophore) of the biosensor. For example, ngmFRET may change (e.g., increase or decrease) when ligand is bound to the biosensor and a donor fluorophore is contacted with radiation within its excitation wavelength. Effects from tgmFRET and ngmFRET may occur together and be combined into an overall ligand-mediated change in fluorescence emission intensity. In preferred embodiments, less than half or none of the change in overall ligand-mediated change in fluorescence emission intensity is due to tgmFRET. In embodiments, most of the overall ligand-mediated change in fluorescence emission intensity change is not due to a change in the distance between the donor and acceptor fluorophore or as a result of a change in the orientation between the donor and acceptor fluorophore. In non-limiting examples, less than about 25%, 20%, 15%, 10%, 5%, 4%, 3%, 2%, 1%, or 0.5% of the change in overall ligand-mediated change in fluorescence emission intensity is due to tgmFRET. In various embodiments, at least about 70%, 75%, 80%, 85%, 90%, 95%, 96%, 97%, 98%, 99%, 99.5%, 99.9%, or 99.99% of the ligand-mediated change in fluorescence emission intensity is due to ngmFRET. For example, the change in overall ligand-mediated change in fluorescence emission intensity comprises a spectral change (e.g., in the excitation or emission spectrum) and/or a change in the ratio of the radiative to non-radiative decay rates of one of the fluorophores (by itself and regardless of the presence of any other fluorophore/partner) upon ligand binding.

In some embodiments, ligand binding mediates spectral shifts in the absorption or emission spectrum of the directly responsive partner. In certain embodiments such changes are due at least in part to a switch between different excited states in the ligand-free and ligand-bound biosensor. The two excited states are associated with different transition dipoles. This class of changes is termed "dipole switching" herein.

In embodiments, the reporter groups include a directly responsive partner (which may be a donor fluorophore or an acceptor fluorophore) and an indirectly responsive partner (which may be a donor fluorophore or an acceptor fluorophore). Depending on context, a "directly responsive" partner is a fluorophore that responds to (i) ligand-induced protein conformational changes upon ligand binding to a ligand-binding protein; or (ii) ligand binding to the directly responsive partner itself. In some embodiments, the directly responsive partner comprises a fluorophore (i.e., it is a directly responsive fluorophore). In various embodiments, the directly responsive fluorophore exhibits a monochromatic or dichromatic spectral change, and/or a change in the ratio of radiative to non-radiative emission rates, upon ligand binding. In certain embodiments relating to ligand binding to the directly responsive partner itself, the directly responsive partner may be a fluorophore such as a fluorescent protein or a small molecule fluorescent compound. An "indirectly responsive" partner is a fluorophore for which no change in emission spectra, excitation spectra, or change in the ratio of radiative to non-radiative emission rates is caused by ligand binding in the absence of a directly responsive partner. In some embodiments, the indirectly responsive partner comprises a fluorophore (i.e., it is an indirectly responsive fluorophore). When paired with a directly responsive partner with which the indirectly responsive partner is a ngmFRET donor or acceptor, the emission fluorescence intensity of the indirectly responsive partner changes due to a change in energy flow in the ngmFRET pathway upon ligand binding. See, e.g., FIG. 56.

ngmFRET Biosensors

Provided herein are methods, compositions, biosensors, and devices comprising multiple reporter groups, e.g. a directly responsive fluorophore and an indirectly responsive fluorophore, between which ngmFRET occurs.

Aspects include a method of detecting a glucose in a sample, comprising contacting a biosensor with a glucose. The biosensor comprises a glucose-binding protein, a directly responsive fluorophore and an indirectly responsive fluorophore. The directly responsive and the indirectly responsive fluorophores are located at two distinct sites of the glucose-binding protein. In some embodiments, the directly responsive fluorophore is a donor fluorophore and the indirectly responsive fluorophore is an acceptor fluorophore. Alternatively, the directly responsive fluorophore is an acceptor fluorophore and the indirectly responsive fluorophore is a donor fluorophore. The method includes contacting the biosensor with radiation comprising a wavelength within the excitation spectrum of the donor fluorophore. When the biosensor is contacted with such radiation, a fluorescence property of the directly responsive fluorophore changes in response to glucose binding. This change in fluorescent property is independent of the indirectly responsive fluorophore, and occurs regardless of whether the indirectly responsive fluorophore is absent or present. The fluorescence properties of the indirectly responsive fluorophore do not change in response to glucose binding in the absence of the directly responsive fluorophore. When the biosensor is contacted with radiation comprising a wavelength within the excitation spectrum of the donor fluorophore, then (i) ngmFRET occurs between the directly responsive fluorophore and the indirectly responsive fluorophore; (ii) fluorescent light is emitted from the biosensor, and the light emitted from the biosensor comprises a combination of light emitted from the directly responsive fluorophore and light emitted from the indirectly responsive fluorophore; and (iii) the ratio of the fluorescence emission intensity emitted from the biosensor at each of two distinct wavelengths changes in response to glucose binding. In various embodiments, the method further comprises measuring fluorescent light that is emitted from the directly responsive fluorophore and the indirectly responsive fluorophore, and calculating a ratiometric signal to detect the glucose in the sample.

The ratiometric signal ($R_{1,2}$) comprises a quotient of two intensities, $I_{\lambda 1}$ and $I_{\lambda 2}$, measured at two independent wavelengths, $\lambda_1$ and $\lambda_2$ and is calculated according to the following equation:

$$R_{1,2}=I_{\lambda 1}/I_{\lambda 2}.$$

The two independent wavelengths $\lambda_1$ and $\lambda_2$ may be from a single fluorophore or from a combination of two or more fluorophores (e.g., a pair of fluorophores between which ngmFRET occurs). In some embodiments, $\lambda_1$ falls within the emission spectrum of a directly responsive fluorophore and $\lambda_2$ falls within the emission spectrum of an indirectly responsive fluorophore. In certain embodiments, $\lambda_1$ falls within the emission spectrum of an indirectly responsive fluorophore and $\lambda_2$ falls within the emission spectrum of a directly responsive fluorophore. In various embodiments, $\lambda_1$ falls within the emission spectrum of both a directly responsive fluorophore and an indirectly responsive fluorophore. In various embodiments, $\lambda_2$ falls within the emission spectrum of both a directly responsive fluorophore and an indirectly responsive fluorophore.

Aspects of the present subject matter provide FRSs whose emission spectra change (e.g., the shape of the emission spectra change) in response to glucose binding. In various embodiments, the ratio of intensities at two chosen wavelengths of an FRS's emission spectrum changes upon glucose binding.

In various embodiments, the emission spectra of two or more fluorophores contributes to $I_{\lambda 1}$ and/or $I_{\lambda 2}$. In some embodiments, the emission spectrum of a directly responsive fluorophore contributes to $I_{\lambda 1}$ and/or $I_{\lambda 2}$ and the emission spectrum of an indirectly responsive fluorophore contributes to $I_{\lambda 1}$ and/or $I_{\lambda 2}$. In certain embodiments, a directly responsive fluorophore contributes to $I_{\lambda 1}$ and the emission spectrum of an indirectly responsive fluorophore contributes to $I_{\lambda 2}$. In some embodiments, a directly responsive fluorophore contributes to $I_{\lambda 2}$ and the emission spectrum of an indirectly responsive fluorophore contributes to $I_{\lambda 1}$. In various embodiments, both the emission spectrum of a directly responsive fluorophore and the emission spectrum of an indirectly responsive fluorophore contributes to $I_{\lambda 1}$. In some embodiments, both the emission spectrum of a directly responsive fluorophore and the emission spectrum of an indirectly responsive fluorophore contributes to $I_{\lambda 2}$.

In some embodiments, the directly responsive fluorophore is Acrylodan and emission intensity is measured at a wavelength or range of wavelengths between about 400 nm and 1000 nm (e.g., including a wavelength of about 505, 506, 507, 508, 509, 510, 511, 512, 513, 514, 515, 516, 517, 518, 519, 520, 521, 522, 523, 524, or 525 nm), and wherein the indirectly responsive fluorophore is Alexa532 and emission intensity is measured at a wavelength or range of wavelengths between about 400 nm and 1000 nm (e.g., including a wavelength of about 540, 541, 542,543, 544, 545, 546, 547, 548, 549, 550, 551, 552, 553, 554, 555, 556, 557, 558, 559, or 560 nm). In certain embodiments, the directly responsive fluorophore is Acrylodan and emission intensity is measured at a wavelength or range of wavelengths between about 400 nm and 1000 nm (e.g., including a wavelength of about 480, 481, 482, 483, 484, 485, 486, 487, 488, 489, 490, 491, 492, 493, 494, 495, 496, 497, 498, 499, or 500 nm), and wherein the indirectly responsive fluorophore is Alexa555 and emission intensity is measured at a wavelength or range of wavelengths between about 400 nm and 1000 nm (e.g., including a wavelength of about 505, 506, 507, 508, 509, 510, 511, 512, 513, 514, 515, 516, 517, 518, 519, 520, 521, 522, 523, 524, or 525 nm). In various embodiments, the directly responsive fluorophore is Acrylodan and emission intensity is measured at a wavelength or range of wavelengths between about 400 nm and 1000 nm (e.g., including a wavelength of about 505, 506, 507, 508, 509, 510, 511, 512, 513, 514, 515, 516, 517, 518, 519, 520, 521, 522, 523, 524, or 525 nm), and wherein the indirectly responsive fluorophore is Texas Red and emission intensity is measured at a wavelength of wavelength or range of wavelengths between about 400 nm and 1000 nm (e.g., including a wavelength of about 605, 606, 607, 608, 609, 610, 611, 612, 613, 614, 615, 616, 617, 618, 619, 620, 621, 622, 623, 624, or 625 nm). In a non-limiting example, the glucose-binding protein comprises a cysteine at the position of its amino acid sequence that aligns with position 13 or 244 of tsGBP2 (SEQ ID NO: 10 or 110) when the amino acid sequence of the glucose-binding protein is aligned with the amino acid sequence of tsGBP2 using the ClustalW alignment program, and wherein the Acrylodan is covalently attached to the cysteine. In some embodiments, the Alexa532, the Alexa555, or the Texas Red is attached to the N-terminus or the C-terminus of the glucose-binding protein via a fluorophore attachment motif. In a non-limiting example, the glucose-binding protein comprises amino acids in the sequence of SEQ ID NO: 56.

In various embodiments, the change in the fluorescent property of the directly responsive fluorophore comprises (i) a bathochromic or hypsochromic shift in the emission or excitation spectrum thereof; and/or (ii) a change in the ratio of radiative to non-radiative emission rates thereof.

In embodiments, the directly responsive fluorophore comprises a donor fluorophore and the indirectly responsive fluorophore comprises an acceptor fluorophore. In some embodiments, the emission intensity of the donor fluorophore decreases and the emission intensity of the acceptor fluorophore increases upon glucose binding to the glucose-binding protein when the donor fluorophore is contacted with radiation within the excitation spectrum of the donor fluorophore. In some embodiments, the emission intensity of the donor fluorophore increases and the emission intensity of the acceptor fluorophore decreases upon glucose binding to the glucose-binding protein when the donor fluorophore is contacted with radiation within the excitation spectrum of the donor fluorophore. In some embodiments, the emission intensities of the donor fluorophore and the acceptor fluorophore both decrease upon glucose binding to the glucose-binding protein when the donor fluorophore is contacted with radiation within the excitation spectrum of the donor fluorophore. In some embodiments, the emission intensity of the donor fluorophore decreases and the emission intensity of the acceptor fluorophore increases, decreases, or remains about the same upon glucose binding to the glucose-binding protein when the donor fluorophore is contacted with radiation within the excitation spectrum of the donor fluorophore. In some embodiments, the emission intensity of the donor fluorophore increases, decreases, or remains about the same and the emission intensity of the acceptor fluorophore decreases upon glucose binding to the glucose-binding protein when the donor fluorophore is contacted with radiation within the excitation spectrum of the donor fluorophore. In some embodiments, the emission intensities of the donor fluorophore and the acceptor fluorophore both increase upon glucose binding to the glucose-binding protein when the donor fluorophore is contacted with radiation within the excitation spectrum of the donor fluorophore. In some embodiments, the emission intensity of the donor fluorophore increases, decreases, or remains about the same and the emission intensity of the acceptor fluorophore increases upon glucose binding to the glucose-binding protein when the donor fluorophore is contacted with radiation within the excitation spectrum of the donor fluorophore. In some embodiments, the emission intensity of the donor fluorophore increases and the emission intensity of the acceptor fluorophore increases, decreases, or remains about the same upon glucose binding to the glucose-binding protein when the donor fluorophore is contacted with radiation within the excitation spectrum of the donor fluorophore.

In embodiments the directly responsive fluorophore comprises an acceptor fluorophore and the indirectly responsive fluorophore comprises a donor fluorophore. In some embodiments, the emission intensity of the donor fluorophore decreases and the emission intensity of the acceptor fluorophore increases, decreases, or remains about the same upon glucose binding to the glucose-binding protein when the donor fluorophore is contacted with radiation within the excitation spectrum of the donor fluorophore. In some embodiments, the emission intensity of the donor fluorophore increases and the emission intensity of the acceptor fluorophore increases, decreases, or remains about the same upon glucose binding to the glucose-binding protein when the donor fluorophore is contacted with radiation within the excitation spectrum of the donor fluorophore. In some embodiments, the emission intensity of the donor fluorophore remains about the same and the emission intensity of the acceptor fluorophore decreases upon glucose binding to the glucose-binding protein when the donor fluorophore is contacted with radiation within the excitation spectrum of the donor fluorophore. In some embodiments, the emission intensity of the donor fluorophore decreases and the emission intensity of the acceptor fluorophore increases, decreases, or remains about the same upon glucose binding to the glucose-binding protein when the donor fluorophore is contacted with radiation within the excitation spectrum of the donor fluorophore. In some embodiments, the emission intensity of the donor fluorophore increases and the emission intensity of the acceptor fluorophore increases, decreases, or remains about the same upon glucose binding to the glucose-binding protein when the donor fluorophore is contacted with radiation within the excitation spectrum of the donor fluorophore. In some embodiments, the emission intensity of the donor fluorophore remains about the same and the emission intensity of the acceptor fluorophore increases upon glucose binding to the glucose-binding protein when the donor fluorophore is contacted with radiation within the excitation spectrum of the donor fluorophore. In some embodiments, the emission intensity of the donor fluorophore decreases and the emission intensity of the acceptor fluorophore increases upon glucose binding to the glucose-binding protein when the donor fluorophore is contacted with radiation within the excitation spectrum of the donor fluorophore. In some embodiments, the emission intensity of the donor fluorophore increases and the emission intensity of the acceptor fluorophore remains about the same, increases, or decreases upon glucose binding to the glucose-binding protein when the donor fluorophore is contacted with radiation within the excitation spectrum of the donor fluorophore.

In instances in which an emission intensity increases, the increase may be, e.g., between about 0.1% to 10%, 10% to 50%, or 50% to 100%, or at least about 0.1%, 0.5%, 1%, 2%, 3%, 4%, 5%, 10%, 15%, 20%, 25%, 50%, 75%, 100%, 2-fold, 3-fold, 4-fold, 5-fold, 6-fold, 7-fold, 8-fold, 9-fold, or 10-fold. In instances in which an emission intensity decreases, the decrease may be, e.g., a decrease of between about at least about 0.1% to 10%, 10% to 50%, or 50% to 00%, or at least about 0.1%, 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, or 90%. In various embodiments in which both the emission intensity of the donor fluorophore and the acceptor fluorophore increases, then the increases are not equal. In certain embodiments in which both the emission intensity of the donor fluorophore and the acceptor fluorophore decreases, then the decreases are not equal.

In certain embodiments, the indirectly responsive fluorophore is attached to the glucose-binding protein via a covalent bond. Various approaches for attaching reporter groups such as directly and indirectly responsive fluorophores to a polypeptide such as a glucose-binding protein are described herein. In some embodiments, the covalent bond comprises a disulfide bond, a thioester bond, a thioether bond, an ester bond, an amide bond, or a bond that has been formed by a click reaction.

In some embodiments, the indirectly responsive fluorophore is attached to the glucose-binding protein via a non-covalent bond. In certain embodiments, the indirectly responsive fluorophore is attached to a cysteine or a lysine of the glucose-binding protein.

In various embodiments, the indirectly responsive fluorophore is attached to the N-terminus or the C-terminus of the protein. In some embodiments, the indirectly responsive fluorophore is attached to the N-terminus or the C-terminus of the protein via a fluorophore attachment motif.

In some embodiments, fluorophore attachment motif comprises an amino acid or a polypeptide. Various embodiments may be used to link a fluorophore with a glucose-binding protein. In some embodiments, the amino acid or polypeptide comprises 1 amino acid, or a stretch of at least 1, 2, 3, 4, 5, 6, 7, 8, 9, 10, 20, 30, 40, 50, 60, 70, 80, 90, 100, 150, 200, 250, 500, 750, or 1000 amino acids. In a non-limiting example, the polypeptide comprises amino acids in the sequence of βZif (SEQ ID NO: 105). In another non-limiting example, the polypeptide comprises a stretch of at least 50, 60, 70, 80, 90, or 100 amino acids in a sequence that is at least about 85%, 90%, 95%, or 99% identical to the amino acid sequence of *E. coli* thioredoxin (ecTRX; SEQ ID NO: 140).

In some embodiments, the directly responsive fluorophore is attached to the glucose-binding protein via a covalent bond. In various embodiments, the covalent bond comprises a disulfide bond, a thioester bond, a thioether bond, an ester bond, an amide bond, or a bond that has been formed by a click reaction. In directly responsive fluorophore is attached to a cysteine or a lysine of the protein.

In some embodiments, an overlap of the emission spectrum of the donor fluorophore and the excitation spectrum of the acceptor fluorophore increases upon glucose binding. In certain embodiments, the directly responsive fluorophore comprises the donor fluorophore, and the increase results from a bathochromic shift in the emission spectrum of the donor fluorophore. Alternatively, the directly responsive fluorophore comprises the acceptor fluorophore, and the increase results from a hypsochromic shift in the excitation spectrum of the acceptor fluorophore.

In various embodiments, an overlap of the emission spectrum of the donor fluorophore and the excitation spectrum of the acceptor fluorophore decreases upon glucose binding. In some embodiments, the directly responsive fluorophore comprises the donor fluorophore, and the decrease results from a hypsochromic shift in the emission spectrum of the donor fluorophore. In certain embodiments, the directly responsive fluorophore comprises the acceptor fluorophore, and the decrease results from a bathochromic shift in the excitation spectrum of the acceptor fluorophore.

In some embodiments, the directly responsive fluorophore has a monochromatic spectral change upon glucose binding. Alternatively, the directly responsive fluorophore has a dichromatic spectral change upon glucose binding.

In certain embodiments, the emission intensity of the donor fluorophore and/or the acceptor fluorophore increases in two phases as glucose concentration increases.

In various embodiments, the ratio of radiative to non-radiative emission or intensity of the directly responsive fluorophore increases by at least about 0.1%, 0.5%, 1%, 2%, 3%, 4%, 5%, 10%, 15%, 20%, 25%, 50%, 75%, 100%, 2-fold, 3-fold, 4-fold, 5-fold, 6-fold, 7-fold, 8-fold, 9-fold, or 10-fold upon glucose binding to the glucose-binding protein. Alternatively, the ratio of radiative to non-radiative emission or intensity of the directly responsive fluorophore decreases by at least about 0.1%, 0.5%, 1%, 2%, 3%, 4%, 5%, 10%, 15%, 20%, 25%, 50%, 75%, 90%, 95%, or 99% upon glucose binding to the glucose-binding protein.

In embodiments, the directly responsive fluorophore and the indirectly responsive fluorophore are not a naphthalene derivative. In some embodiments, the directly responsive fluorophore and the indirectly responsive fluorophore are not Prodan, Acrylodan, or Badan. In certain embodiments, the directly responsive fluorophore is not a naphthalene derivative. In some embodiments, the directly responsive fluorophore is not Prodan, Acrylodan, or Badan.

In various embodiments, the directly responsive fluorophore comprises xanthene, a xanthene derivative, fluorescein, a fluorescein derivative, coumarin, a coumarin derivative, cyanine, a cyanine derivative, rhodamine, a rhodamine derivative, phenoxazine, a phenoxazine derivative, squaraine, a squaraine derivative, coumarin, a coumarin derivative, oxadiazole, an oxadiazole derivative, anthracene, an anthracene derivative, a boradiazaindacine (BODIPY) family fluorophore, pyrene, a pyrene derivative, acridine, an acridine derivative, arylmethine, an arylmethine derivative, tetrapyrrole, or a tetrapyrrole derivative. In some embodiments, the directly responsive fluorophore comprises fluorescein or a derivative thereof.

In some embodiments, the directly responsive fluorophore and/or the indirectly responsive fluorophore comprises a fluorescent protein. In various embodiments, the directly responsive fluorophore and/or the indirectly responsive fluorophore comprises an organic compound having a molecular weight less than about 2000 Da (e.g., 5-iodoacetamidofluorescein (5-IAF) or 6-iodoacetamidofluorescein (6-IAF), rhodamine, Oregon Green, eosin, Texas Red, indocarbocyanine, oxacarbocyanine, thiacarbocyanine, merocyanine, Badan, Acrylodan, IAEDANS, comprising 3-cyano-7-hydroxycoumarin, 7-hydroxycoumarin-3-carboxylic acid, 6,8-difluoro-7-hydroxy-4-methylcoumarin, or 7-amino-4-methylcoumarin, pyridyloxazole, nitrobenzoxadiazole, benzoxadiazole, DRAQ5, DRAQ7, or CyTRAK Orange, cascade blue, Nile red, Nile blue, cresyl violet, oxazine 170, proflavin, acridine orange, acridine yellow, auramine, crystal violet, malachite green, porphin, phthalocyanine, bilirubin, pyrene, N,N'-dimethyl-N-(iodoacetyl)-N'-(7-nitrobenz-2-ox-a-1,3-diazol-4-yl)ethylenediamide (NBD), N-((2-(iodoacetoxy)ethyl)-N-methy-Damino-7-nitrobenz-2-oxa-1,3-diazole (NBDE), JPW4039, JPW4042, JPW4045, Pacific Blue, CPM, N,N'-Dimethyl-N-(Iodoacetyl)-N'-(7-Nitrobenz-2-Oxa-1,3-Diazol-4-yl)Ethylenediamine (IANBD), 7-diethylamino-3-(4'-maleimidylphenyl)-4-methylcoumarin (CPM), BODIPY 499, BODIPY 507/545, BODIPY 499/508, Alexa 432, Alexa488, Alexa532, Alexa546, Cy5, or 1-(2-maleimidylethyl)-4-(5-(4-methoxyphenyl)oxazol-2-yl) pyridinium methanesulfonate (PyMPO maleimide) (PyMPO)). Numerous combinations of directly responsive fluorophores and indirectly responsive fluorophores are possible. For example, in various non-limiting examples, (a) the donor fluorophore comprises Pacific Blue and the acceptor fluorophore comprises 5-IAF or 6-iodoacetamidofluorescein (6-IAF); (b) the donor fluorophore comprises Pacific Blue and the acceptor fluorophore comprises Oregon Green; (c) the donor fluorophore comprises IAEDANS and the acceptor fluorophore comprises 5-IAF or 6-IAF; (d) the donor fluorophore comprises acrylodan and the acceptor fluorophore comprises Alexa532; (e) the donor fluorophore comprises acrylodan and the acceptor fluorophore comprises 5-IAF or 6-IAF; (f) the donor fluorophore comprises acrylodan and the acceptor fluorophore comprises Pacific Blue or YFP; (g) the donor fluorophore comprises 5-IAF or 6-IAF and the acceptor fluorophore comprises Pacific Blue; (h) the donor fluorophore comprises badan and the acceptor fluorophore comprises 5-IAF or 6-IAF; or (i) the donor fluorophore comprises badan and the acceptor fluorophore comprises Alexa532.

Aspects also include a biosensor for a glucose comprising a glucose-binding protein, a directly responsive fluorophore and an indirectly responsive fluorophore, the directly responsive and the indirectly responsive fluorophores being located at two distinct sites of the glucose-binding-protein, wherein (i) the directly responsive fluorophore is a donor fluorophore and the indirectly responsive fluorophore is an acceptor fluorophore; or (ii) the directly responsive fluorophore is an acceptor fluorophore and the indirectly responsive fluorophore is an donor fluorophore. In some embodiments, if the acceptor fluorophore comprises ruthenium or osmium, then the acceptor fluorophore is not attached to the amino group of the N-terminus of the glucose-binding protein.

Any of the glucose-binding proteins disclosed herein, as well as others, may be included in the biosensors and methods that are provided.

Aspects of the present subject matter also provide a method for constructing a biosensor, comprising: (a) providing a glucose-binding protein; (b) identifying at least one putative allosteric, endosteric, or peristeric site of the glucose-binding based a structure of the glucose-binding protein; (c) mutating the glucose-binding protein to substitute an amino acid at the at least one putative allosteric, endosteric, or peristeric site of the second protein with a cysteine; (d) conjugating a donor fluorophore or an acceptor fluorophore to the cysteine to produce single labeled biosensor; (e) detecting whether there is a spectral shift or change in emission intensity of the single labeled biosensor upon glucose binding when the donor fluorophore or the acceptor fluorophore is fully excited; and (f) if a spectral shift or change in emission intensity is detected in (e), attaching a donor fluorophore to the second protein if an acceptor fluorophore is attached to the cysteine, and attaching an acceptor fluorophore to the second protein if an acceptor fluorophore is attached to the cysteine.

In various embodiments, the glucose-binding protein has been identified by (i) selecting a first protein having a known amino acid sequence (seed sequence), wherein the first protein is known to bind a glucose; (ii) identifying a second protein having an amino acid sequence (hit sequence) with at least 15% sequence identity to the seed sequence; (iii) aligning the seed amino acid sequence and the hit sequence, and comparing the hit sequence with the seed sequence at positions of the seed sequence that correspond to at least 5 primary complementary surface (PCS) amino acids, wherein each of the at least 5 PCS amino acids has a hydrogen bond interaction or a van der Waals interaction with glucose when glucose is bound to the first protein; and (iv) identifying the second protein to be a glucose-binding protein if the hit sequence comprises at least 5 amino acids that are consistent with the PCS.

In some embodiments, the spectral shift comprises a monochromatic fluorescence intensity change or a dichromatic spectral shift.

Also provided is a method of converting a biosensor that shows a monochromatic response upon glucose binding into a biosensor with a dichromatic response upon glucose binding, the method comprising (a) selecting a biosensor that exhibits a monochromatic response upon glucose binding, wherein the biosensor comprises a glucose-binding protein and a first reporter group; and (b) attaching a second reporter group to the biosensor, wherein the second reporter group has (i) an excitation spectrum that overlaps with the emission spectrum of the first reporter group; or (ii) an emission spectrum that overlaps with the excitation spectrum of the first reporter group.

Also provided is a method of increasing a dichromatic response of a biosensor to glucose binding, the method comprising (a) selecting a biosensor that exhibits a dichromatic response upon glucose binding, wherein the biosensor comprises a glucose-binding protein and a first reporter group; and (b) attaching a second reporter group to the biosensor, wherein the second reporter group has (i) an excitation spectrum that overlaps with the emission spectrum of the first reporter group; or (ii) an emission spectrum that overlaps with the excitation spectrum of the first reporter group.

In some embodiments, the second reporter group is within about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 4, 6, 8, 10, 11, 12, 13, 14, 15, 16, 17, 18, 19, 20, 25, 30, 35, 40, 45, 50, 55, 60, 65, 70, 75, 80, 85, 90, 95, 100, 125, 150, or 200 angstroms (Å) of the first reporter group regardless of whether ligand is bound to the biosensor. Suitable distances may be determined in part by the distance-dependence of the energy transfer between a given donor-acceptor pair (see, e.g, J. R. Lakowicz, 2006, Principles of Fluorescence Spectroscopy, Springer, incorporated herein by reference). In some embodiments, when the glucose is bound to the biosensor, the average distance between the first reporter group and the second reporter group changes by less than about 5, 4, 3, 2, 1, 0.9, 0.8, 0.7, 0.6, 0.5, 0.4, 0.3, 0.2, 0.1, 0.05, or 0.01 angstroms (Å) compared to when glucose is not bound to the glucose-binding protein.

In various embodiments, if the acceptor fluorophore comprises palladium, platinum, ruthenium, or osmium, then the acceptor fluorophore is not attached to the amino group of the N-terminus of the ligand-binding protein. In some embodiments, the acceptor fluorophore does not comprise $[Ru(bpy)_3]^2$, $[Ru(Ph_2phen)_3]^{2+}$, $[Ru(bpy)_2(dcbpy)]^{2+}$, or $[Ru(bpy)_2(phen\text{-}ITC)]^{2+}$, where bpy is 2,2'-bipyridine, phen is 1,10-phenanthroline, dcbpy is 4,4'-dicarboxy-2,2'-bipyridine, and ITC is isothiocyanate. In certain embodiments, the biosensor does not comprise an *E. coli* glutamine-binding protein with Acrylodan attached to 179C. In some embodiments, the biosensor does not comprise *E. coli* glucose-binding protein with Acrylodan attached to 255C.

tgmFRET Biosensors

While ngmFRET is preferred to tgmFRET, tgmFRET may be used alternatively or in addition to ngmFRET in certain embodiments.

In various embodiments, the biosensor comprises multiple reporter groups, including a first reporter group and a second reporter group. For example, the first reporter group may comprise a donor fluorophore and the second reporter group may comprise an acceptor fluorophore. In certain embodiments, FRET is detectable by a change in the fluorescence of the acceptor fluorophore or by a decrease in of donor fluorophore fluorescence. In various embodiments, the donor fluorophore, and/or the acceptor fluorophore is fluorescent. In some embodiments, both the donor fluorophore and the acceptor fluorophore are fluorescent.

In various embodiments, the angle and/or distance between the donor fluorophore and the acceptor fluorophore changes upon glucose binding. In some embodiments, neither the donor fluorophore nor the acceptor fluorophore is directly responsive to glucose binding. In some embodiments the donor fluorophore and/or the acceptor fluorophore is attached to the N-terminus or the C-terminus of the glucose-binding protein (e.g., directly or via a fluorophore attachment motif). In certain embodiments, the donor fluorophore and/or the acceptor fluorophore is attached to a fluorophore attachment motif. For example, the fluorophore attachment motif may be conjugated to the N-terminus or the C-terminus of the glucose-binding protein.

In some embodiments, the donor fluorophore and/or the acceptor fluorophore comprises a fluorescent protein. In various embodiments, the donor fluorophore and/or the acceptor fluorophore comprises an organic compound having a molecular weight less than about 2000 Da (e.g., 5-iodoacetamidofluorescein (5-IAF) or 6-iodoacetamidofluorescein (6-IAF), rhodamine, Oregon Green, eosin, Texas Red, indocarbocyanine, oxacarbocyanine, thiacarbocyanine, merocyanine, Badan, Acrylodan, IAEDANS, comprising 3-cyano-7-hydroxycoumarin, 7-hydroxycoumarin-3-carboxylic acid, 6,8-difluoro-7-hydroxy-4-methylcoumarin, or 7-amino-4-methylcoumarin, pyridyloxazole, nitrobenzoxadiazole, benzoxadiazole, DRAQ5, DRAQ7, or CyTRAK Orange, cascade blue, Nile red, Nile blue, cresyl violet, oxazine 170, proflavin, acridine orange, acridine yellow, auramine, crystal violet, malachite green, porphin, phthalocyanine, bilirubin, pyrene, N,N'-dimethyl-N-(iodoacetyl)-N'-(7-nitrobenz-2-ox-a-1,3-diazol-4-yl)ethylenediamide (NBD), N-((2-(iodoacetoxy)ethyl)-N-methy-1)amino-7-nitrobenz-2-oxa-1,3-diazole (NBDE), Acrylodan, JPW4039, JPW4042, JPW4045, Oregon Green, Pacific Blue, CPM, N,N'-Dimethyl-N-(Iodoacetyl)-N'-(7-Nitrobenz-2-Oxa-1,3-Diazol-4-yl)Ethylenediamine (IANBD), 7-diethylamino-3-(4'-maleimidylphenyl)-4-methylcoumarin (CPM), BODIPY 499, BODIPY 507/545, BODIPY 499/508, Alexa 432, Alexa488, Alexa532, Alexa546, Cy5, or 1-(2-maleimidylethyl)-4-(5-(4-methoxyphenyl)oxazol-2-yl)pyridinium methanesulfonate (PyMPO maleimide) (PyMPO)). For example, the organic compound is a fluorophore. Numerous combinations of donor and acceptor fluorophores are possible.

Fluorophore Attachment Motifs

Aspects of the present subject matter include the use of one or more fluorophore attachment motifs to attach one or more reporter groups to a glucose-binding protein. For example, a reporter group may be attached to a fluorophore attachment motif that is attached to the N-terminus or the C-terminus of the glucose-binding protein.

In various implementations, the fluorophore attachment motif comprises an amino acid or a polypeptide. In some embodiments, the amino acid or polypeptide comprises 1 amino acid, or a stretch of at least 1, 2, 3, 4, 5, 6, 7, 8, 9, 10, 20, 30, 40, 50, 60, 70, 80, 90, 100, 150, 200, 250, 500, 750, or 1000 amino acids. In some embodiments, the polypeptide comprises amino acids in the βZif amino acid sequence (SEQ ID NO: 105).

In some embodiments, the polypeptide comprises a stretch of at least 50, 60, 70, 80, 90, or 100 amino acids in a sequence that is at least about 85%, 90%, 95%, or 99% identical to the amino acid sequence of *E. coli* thioredoxin (ecTRX; SEQ ID NO: 140). In some embodiments, the polypeptide is a mutant of ecTRX comprising a D3X, K4X, K19X, D27X, K37X, K53X, K58X, K70X, R74X, K83X, K91X, K97X, or K101X mutation, or any combination thereof, wherein X is any amino acid, and wherein each ecTRX amino acid position is numbered as in SEQ ID NO: 140. In certain embodiments, the polypeptide is a mutant of ecTRX comprising a D3A, K4R, K4Q, K19R, K19Q, D27A, K37R, K53M, K53R, K58M, K70R, R74C, K83R, K91R, K97R, or K101R mutation, or any combination thereof, wherein each ecTRX amino acid position is numbered as in SEQ ID NO: 140.

In non-limiting examples, the polypeptide comprises amino acids in the sequence set forth as any one of SEQ ID NOS: 140-158.

In certain embodiments, the polypeptide comprises (a) at least 1, 2, or 3 thiol groups; (b) at least 1, 2, or 3 cysteines that each comprise a sulfhydryl group; (c) at least 1, 2, or 3 primary amine groups; and/or (d) at least 1, 2, or 3 lysines that each comprise a primary amine. In some embodiments there is no disulfide bond between cysteines within the amino acid sequence of the polypeptide.

In some embodiments, the polypeptide comprises a hexahistidine tag. In some embodiments, the hexahistidine tag is attached to another portion of the polypeptide via a GGS linker.

Exemplary Methods of Using Biosensors Provided Herein

Aspects of the present subject matter provide a method of assaying for a ligand in a sample. The method may include contacting the sample with a biosensor disclosed herein under conditions such that the ligand-binding protein of the biosensor binds to the ligand if ligand is present in the sample. The method also comprises detecting (i) whether a signal is produced by a reporter group of the biosensor; and/or (ii) the a signal produced by a reporter group of the biosensor. In a non-limiting example, a reporter group of the biosensor is fluorescent, and the method further comprises contacting the reporter group with electromagnetic radiation having a wavelength that comprises a wavelength within the band of excitation wavelengths of the reporter group.

In various embodiments, the method further comprises (i) comparing a signal produced by a reporter group of the biosensor when the biosensor is contacted with the sample with a signal produced by a control sample containing a known quantity of ligand (e.g., ligand at a concentration of about 0.5, 1, 2, 3, 4, 5, 6, 7, 8, 9, 10, 15, 20, 25, 30, 35, 40, 45, 50, 75, 100, 125, 150, 200, 250, 300, 350, 400, 450, or 500 mM, or a series of control samples having concentrations within the range of about 0.5 mM to about 500 mM); and (ii) detecting the presence or absence of ligand in the sample based on this comparison. Alternatively or in addition, the method further comprises (i) comparing a signal produced by a reporter group of the biosensor when the biosensor is contacted with the sample with signals produced by a series of control samples containing known quantities of ligand; and (ii) determining the quantity of ligand in the sample based on this comparison. In some embodiments, the series of control samples comprises at least 2, 3, 4, 5, 6, 7, 8, 9, or 10 control samples, and wherein each control sample comprises a different quantity of ligand. Alternatively or in addition, the method further comprises determining the concentration of a ligand in a sample, wherein determining the concentration of the ligand in the sample comprises comparing the signal to a standard hyperbolic ligand binding curve to determine the concentration of the ligand in the test sample, wherein the standard hyperbolic ligand binding curve is prepared by measuring the signal produced by the reporter group of the biosensor when the biosensor is contacted with control samples containing known concentrations of ligand. In various embodiments, the method comprises (i) measuring a ratiometric change (ΔR) and/or an intensity change (ΔI) of a signal produced by the reporter group. In some embodiments, the method includes quantitating the level of ligand present in the sample.

In various embodiments, the ligand is glucose and the ligand-binding protein is a glucose-binding protein.

Aspects of the present subject matter also provide a method of assaying for multiple ligands in a sample, wherein the multiple ligands comprise a first ligand and a second ligand. Such a method may include contacting the sample with (i) a first biosensor a first ligand provided herein and (ii) a second biosensor for the second ligand, under conditions such that the ligand-binding protein of the first biosensor binds to the first ligand, if the first ligand is present in the sample, and detecting (i) a signal, e.g. magnitude of the signal, produced by a reporter group of the first biosensor, or (ii) whether a signal is produced by a reporter group of the first biosensor. In some embodiments, the second biosensor is also a biosensor provided herein, and the second biosensor is contacted with the second ligand under conditions such that the ligand-binding protein of the second biosensor binds to the second ligand it is present in the sample. The method may further comprise detecting (i) a signal, e.g. magnitude of the signal, produced by a reporter group of the second biosensor, or (ii) whether a signal is produced by a reporter group of the second biosensor.

In some embodiments, the signal produced by the reporter group of the first biosensor is different than the signal produced by the reporter group of the second biosensor. In a non-limiting example, the reporter group of the first biosensor and the reporter group of the second biosensor are each fluorescent, and the peak emission wavelength of the reporter group of the first biosensor is at least about 10, 25, 50, 75, or 100 nm greater or lower than the peak emission wavelength of the reporter group of the second biosensor.

Non-limiting examples of biosensors that may be used as the second biosensor include biosensors with ligand-binding proteins comprising a GGBP (e.g., an *E. coli* GGBP) or a derivative or mutant thereof; (ii) an *E. coli* arabinose binding protein (e.g., an *E. coli* arabinose binding protein) or a derivative or mutant thereof; (iii) a dipeptide binding protein (e.g., an *E. coli* dipeptide binding protein) or a derivative or mutant thereof; (iv) a histidine binding protein (e.g., an *E. coli*, histidine binding protein) or a derivative or mutant thereof; (v) a ribose binding protein (e.g., an *E. coli* ribose binding protein) or a derivative or mutant thereof; (vi) a sulfate binding protein (e.g., an *E. coli* sulfate binding protein) or a derivative or mutant thereof; (vii) a maltose binding protein (e.g., an *E. coli* maltose binding protein) or a derivative or mutant thereof; (viii) a glutamine binding protein (e.g., an *E. coli* glutamine binding protein) or a derivative or mutant thereof; (ix) a glutamate/aspartate binding protein (e.g., an *E. coli* glutamate/aspartate binding protein) or a derivative or mutant thereof; (x) a phosphate binding protein (e.g., an *E. coli* phosphate binding protein) or a derivative or mutant thereof; or (xi) an iron binding protein [e.g., a *Haemophilus influenza* (*H. influenzae*) iron binding protein] or a derivative or mutant thereof. For example, the second biosensor comprises an *E. coli* GGBP having a Y10C, Y10A, D14A, D14Q, D14N, D14S, D14T, D14E, D14H, D14L, D14Y, D14F, D14C, N15C, F16L, F16A, F16Y, F16C, N91A, K92C, E93C, S112A, S115A, E149C, E149K, E149Q, E149S, H152A, H152F, H152Q, H152N, H152C, D154A, D154C, D154N, A155S, A155H, A155L, A155F, A155Y, A155N, A155K, A155M, A155W, A155Q, A155C, R158A, R158K, R158C, M182C, M182W, W183C, W183A, N211F, N211W, N211K, N211Q, N211S, N211H, N211M, N211C, D212C, D236A, D236N, L238C, L255C, N256A, N256D, D257C, V293C, P294C, or V296C mutation (e.g., comprising 1, 2, 3, 4, 5 or more of these mutations), wherein each amino acid position is numbered as in (SEQ ID NO: 117); (ii) an *E. coli* arabinose binding protein having a D257C, F23C, K301C, L253C, or L298C mutation (e.g., comprising 1, 2, 3, 4, or 5 of these mutations) (see, e.g., U.S. Patent Application Publication No. 2004/0118681, the entire contents of which are incorporated herein by reference) (see, e.g., U.S. Patent Application Publication No. 2004/0118681, the entire contents of which are incorporated herein by reference); (iii) an *E. coli* dipeptide binding protein having a D450C, K394C, R141C, S111C, T44C, or W315C mutation (e.g., comprising 1, 2, 3, 4, 5 or 6 of these mutations) (see, e.g., U.S. Patent Application Publication No. 2004/0118681, the entire contents of which are incorporated herein by reference); (iv) an *E. coli*, histidine binding protein having a E167C, K229C, V163C, Y230C, F231C, Y88C mutation (e.g., comprising 1, 2, 3, 4, 5 or 6 of these mutations) (see, e.g., U.S. Patent Application Publication No. 2004/0118681, the entire contents of which are incorporated herein by reference); (v) an *E. coli* ribose binding protein having a T135C, D165C, E192C, A234C, L236C, or L265C mutation (e.g., comprising 1, 2, 3, 4, 5 or 6 of these mutations) (see, e.g., U.S. Patent Application Publication No. 2004/0118681, the entire contents of which are incorporated herein by reference); (vi) an *E. coli* sulfate binding protein having a L65C, N70C, Q294C, R134C, W290C, or Y67C mutation (e.g., comprising 1, 2, 3, 4, 5 or 6 of these mutations) (see, e.g., U.S. Patent Application Publication No. 2004/0118681 the entire content of which is incorporated herein by reference); (vii) an *E. coli* maltose binding protein having a D95C, F92C, E163C, G174C, I329C, or S233C mutation (e.g., comprising 1, 2, 3, 4, 5 or 6 of these mutations) (see, e.g., U.S. Patent Application Publication No. 2004/0118681 the entire content of which is incorporated herein by reference); (viii) an *E. coli* glutamine binding protein having a N160C, F221C, K219C, L162C, W220C, Y163C, or Y86C mutation (e.g., comprising 1, 2, 3, 4, 5 or more of these mutations) (see, e.g., U.S. Patent Application Publication No. 2004/0118681 the entire content of which is incorporated herein by reference); (ix) an *E. coli* glutamate/aspartate binding protein having a A207C, A210C, E119C, F126C, F131C, F270C, G211C, K268C, Q123C, or T129C mutation (e.g., comprising 1, 2, 3, 4, 5 or more of these mutations) (see, e.g., U.S. Patent Application Publication No. 2004/0118681 the entire content of which is incorporated herein by reference); (x) an *E. coli* phosphate binding protein having a A225C, N223C, N226C, S164C, or S39C mutation (e.g., comprising 1, 2, 3, 4, or 5 of these mutations) (see, e.g., U.S. Patent Application Publication No. 2004/0118681 the entire content of which is incorporated herein by reference); or (xi) a *Haemophilus influenza* (*H. influenzae*) iron binding protein having a E203C, K202C, K85C, or V287C mutation (e.g., comprising 1, 2, 3, or 4 of these mutations) (see, e.g., U.S. Patent Application Publication No. 2004/0118681 the entire content of which is incorporated herein by reference). In various embodiments, the sample is suspected of comprising glucose.

References and PDB[a] files for bPBP structures, genes, and ligand binding

| bPBP | crystal structure: open form | crystal structure: closed form | DNA sequence | ligand affinity |
|---|---|---|---|---|
| arabinose BP | | Quiocho and Vyas, 1984 1ABE | Scripture et al., 1987 | Clark et al., 1982; Miller et al., 1983 |
| dipeptide BP | Nickitenko et al., 1995 1DPE | Dunten & Mowbray, 1995 1DPP | Abouhamad et al., 1991 | Guyer et al., 1986; Smith et al., 1999 |
| Glu/Asp BP | | | | Barash Halpern, 1975; Willis Furlong, 1975 |
| Fe(III) BP | Bruns et al., 2001 1D9V | Bruns et al., 1997 1MRP | Sanders et al., 1994 | Adhikari et al., 1995 |
| glucose BP | | Vyas et al., 1988; Vyas et al., 1994 1GLG | Scholle et al., 1987 | Anraku, 1968 |
| histidine BP | | Yao et al., 1994 1HSL | Joshi & Ames 1996 | Miller et al., 1983 |
| maltose BP | Sharff et al., 1992 1OMP | Spurlino et al., 1991; Quiocho et al., 1997 1ANF | Duplay et al., 1984 | Schwartz et al., 1976 |
| phosphate BP | Ledvina et al., 1996 1OIB | Luecke & Quiocho, 1990 1IXH | Magota et al., 1984 | Medveczky & Rosenberg, 1969 |

-continued

| References and PDB[a] files for bPBP structures, genes, and ligand binding | | | | |
|---|---|---|---|---|
| | crystal structure | | | |
| bPBP | open form | closed form | DNA sequence | ligand affinity |
| glutamine BP | Hsiao et al., 1996 1GGG | Sun et al., 1998 1WDN | Nohno et al., 1986 | Weiner et al., 1971 |
| ribose BP | Bjorkman & Mowbray, 1998 1URP | Mowbray & Cole, 1992 2DRI | Groarke et al., 1983 | Willis & Furlong, 1974 |
| sulfate BP | | Pflugrath & Quiocho, 1985; He & Quiocho, 1993 1SBP | Hellinga & Evans, 1985 | Jacobson & Quiocho, 1988 |

[a]Protein Data Bank (Berman et al., 2000)

Abouhamad et al., Molec. Microbiol. 5: 1035-1047 (1991)
Adhikari et al., J. Biol. Chem. 270: 25142-25149 (1995)
Anraku, J. Biol. Chem. 243: 3116-3122 (1968)
Barash & Halpern, Biochim. Biophys. Acta 386: 168-180 (1975)
Bjorkman & Mowbray, J. Mol. Biol. 279: 651-664 (1998)
Bruns et al., Biochemistry 40: 15631-15637 (2001)
Bruns et al., Nat. Struct. Biol. 4: 919-924 (1997)
Clark et al., Biochemistry 21: 2227-2233 (1982)
Dunten & Mowbray, Protein Sci. 4: 2327-2334 (1995)
Duplay et al., J. Biol. Chem. 259: 10606-10613 (1984)
Groarke et al., J. Biol. Chem. 258: 12952-12956 (1983)
Guyer et al., J. Bacteriol. 168: 775-779 (1986)
He & Quiocho, Protein Sci. 2: 1643-1647 (1993)
Hellinga & Evans, Eur. J. Biochem. 149: 363-373 (1985)
Hsiao et al., J. Mol. Biol. 262: 225-242 (1996)
Jacobson & Quiocho, J. Mol. Biol. 204: 783-787 (1988)
Joshi & Ames, GenBank Accession Number U47027 (1996)
Ledvina et al., Proc. Natl. Acad. Sci. USA 93: 6786-6791 (1996)
Luecke & Quiocho, Nature 347: 402-406 (1990)
Magota et al., J. Bacteriol. 157: 909-917 (1984)
Medveczky & Rosenberg, Biochim. Biophys. Acta 192: 369-371 (1969)
Miller et al., J. Biol. Chem. 258: 13665-13672 (1983)
Mowbray & Cole, J. Mol. Biol. 225: 155-175 (1992)
Nickitenko et al., Biochemistry 34: 16585-16595 (1995)
Nohno et al., Molec. Gen. Genet. 205: 260-269 (1986)
Pflugrath & Quiocho, Nature 314: 257-260 (1985)
Quiocho et al., Structure 5: 997-1015 (1997)
Quiocho & Vyas, Nature 310: 381-386 (1984)
Sanders et al., Infect. Immun. 62: 4515-4515 (1994)
Scholle et al., Molec. Gen. Genet. 208: 247-253 (1987)
Scripture et al., J. Mol. Biol. 197: 37-46 (1987)
Schwartz et al., Eur. J. Biochem. 71: 167-170 (1976)
Sharff et al., Biochemistry 31: 10657-10663 (1992)
Smith et al., Microbiology 145: 2891-2901 (1999)
Spurlino et al., J. Biol. Chem. 266: 5202-5219 (1991)
Sun et al., J. Mol. Biol. 278: 219-229 (1998)
Vyas et al., Biochemistry 33: 4762-4768 (1994)
Vyas et al., Science 242: 1290-1295 (1988)
Weiner et al., Arch. Biochem. Biophys. 142: 715-717 (1971)
Willis & Furlong, J. Biol. Chem. 249: 6926-6929 (1974)
Willis & Furlong, J. Biol. Chem. 250: 2574-2580 (1975)
Yao et al., Biochemistry 33: 4769-4779 (1994)

Various types of samples may be used in methods provided herein. In non-limiting examples, a sample may comprise a reaction product, a buffer, and/or a solvent. In some embodiments, the solvent is an aqueous solvent. In some embodiments, the solvent comprises a non-polar solvent, a polar aprotic solvent, and/or a polar protic solvent. For example, a sample may comprise water, liquid ammonia, liquid sulfur dioxide, sulfuryl chloride, sulfuryl chloride fluoride, phosphoryl chloride, dinitrogen tetroxide, antimony trichloride, bromine pentafluoride, hydrogen fluoride, dimethyl sulfoxide, hexane, benzene, toluene, 1,4-dioxane, chloroform, diethyl ether, dichloromethane, N-methylpyrrolidone, tetrahydrofuran, ethyl acetate, acetone, dimethylformamide, acetonitrile, tormic acid, n-butanol, isopropanol, nitromethane, ethanol, methanol, and/or acetic acid.

In embodiments, a sample comprises a Newtonian liquid, a shear thickening liquid, a shear thinning liquid, a thixotropic liquid, a rheopectic liquid, or a Bingham plastic. In some implementations, a sample has a dynamic viscosity of at least about 0.5, 0.6, 0.7, 0.8, 0.9, 1, 1.1, 1.2, 1.3, 1.4, 1.5, or 2 pascal-seconds (Pa·s) or less than about 2, 1.5, 1.4, 1.3, 1.2, 1.1, 1, 0.9, 0.8, 0.7, 0.6, 0.5 Pa·s; and/or a kinematic viscosity of at least about 0.5, 0.6, 0.7, 0.8, 0.9, 1, 1.1, 1.2, 1.3, 1.4, 1.5, or 2 centistokes (cSt) or less than about 2, 1.5, 1.4, 1.3, 1.2, 1.1, 1, 0.9, 0.8, 0.7, 0.6, 0.5 cSt.

In various embodiments, the sample comprises a biological sample. The sample may comprise, e.g., a clinical sample (i.e., a sample collected in a clinical or veterinary setting, e.g., by or at the request or supervision or direction of a doctor, nurse, aid worker, or medic) and/or a physiological sample (a sample collected from an organism, e.g., a mammal such as a human). In certain embodiments, the biological sample comprises or has been provided or obtained from a skin surface or a mucosal surface. In some embodiments, the biological sample comprises a biological fluid. Non-limiting examples of biological fluids include sweat, tear fluid, blood, serum, plasma, interstitial fluid, amniotic fluid, sputum, gastric lavage, skin oil, milk, fecal matter, emesis, bile, saliva, urine, mucous, semen, lymph, spinal fluid, synovial fluid, a cell lysate, venom, hemolymph, and fluid obtained from plants such as the fluid transported in xylem cells or phloem sieve tube elements of a plant (e.g. sap).

The present subject matter also provides biosensors, methods, compositions, and devices useful for measuring the level of a ligand within a liquid solution or suspension or composition comprising cultured cells or tissue or a supernatant of such a solution or suspension, e.g., a sample of conditioned media or a sample of growth media in which a population of cells was cultured. In some embodiments, the sample is within a culture (e.g., inserted into a bioreactor) or provided from a media, culture, or reaction, e.g., in a bioreactor. For example, the sample may be within or provided from a fermenter such as a culture or culture supernatant from a fermentation reaction (e.g., an ongoing fermentation, such as during beer/wine production, the culture of cells in research settings, the production of a compound, etc.). Thus, the level of a ligand can be assayed at a timepoint of interest or at a series of timepoints over the duration of cell culture, e.g. continuously, in or from a reaction or culture. Bioreactors include devices or systems that support a biologically active environment. For example, a bioreactor may comprise a vessel in which a chemical process is carried out which involves organisms or biochemically active substances derived from such organisms. Such a process can either be aerobic or anaerobic. Organisms growing in bioreactors may be, e.g., submerged or suspended in liquid medium or may be attached to the surface of a solid medium. Submerged cultures may be suspended or immobilized. Suspension bioreactors can use a wider variety of organisms, since special attachment surfaces are not needed, and can operate at much larger scale than immobilized cultures. However, in a continuously operated process the organisms will be removed from the reactor with the effluent. Immobilization is a general term describing a wide variety of cell or particle attachment or entrapment. It can be applied to basically all types of biocatalysis including enzymes, cellular organelles, and cells (e.g., animal cells, plant cells, fungal cells, and bacterial cells). Immobilization is useful for continuously operated processes, since the organisms will not be removed with the reactor effluent, but is limited in scale because the cells are only present on the surfaces of the vessel. A bioreactor may also refer to a device or system meant to grow cells or tissues in the context of cell culture. The interrogation and/or monitoring of glucose levels in such samples permits the evaluation of the status of growth of the cells or production of secreted products by the cells to inform harvest or feeding or other modification of the culture.

Aspects of the present subject matter relate to the use of methods and biosensors provided herein to detect contamination.

In some embodiments, the sample comprises an environmental sample. Depending on context, there are instances in which a biological sample may also be, or may be within, an environmental sample. In certain embodiments, an environmental sample comprises a solute obtained from a biological composition, such as bone, nail, hair, shell, or cartilage. In various embodiments, an environmental sample comprises a solute obtained from an environmental substance and/or an environmental surface. For example, the solute may be dissolved/obtained from the environmental substance and/or an environmental surface using an aqueous or nonaqueous solution. In some embodiments, an aqueous may optionally comprise a nonaqueous solvent (e.g., mixed with an aqueous solvent). Non-limiting examples of environmental substances include rock, soil, clay, sand, meteorites, asteroids, dust, plastic, metal, mineral, fossils, sediment, and wood. Non-limiting examples of environmental surfaces include the surface of a vehicle such as a civilian vehicle (e.g., a satellite, a bike, a rocket, an automobile, a truck, a motorcycle, a yacht, a bus, or a plane) or a military vehicle (e.g., a tank, an armored personnel carrier, a transport truck, a jeep, a mobile artillery unit, a mobile antiaircraft unit, a minesweeper, a Mine-Resistant Ambush Protected (MRAP) vehicle, a lightweight tactical all-terrain vehicle, a high mobility multipurpose wheeled vehicle, a mobile multiple rocket launch system, an amphibious landing vehicle, a ship, a hovercraft, a submarine, a transport plane, a fighter jet, a helicopter, a rocket, or an Unmanned Arial Vehicle), a drone, a robot, a building, furniture, or an organism other than a human. In some embodiments, the sample comprises an environmental fluid. Non-limiting examples of environmental fluids include marine water, well water, drinking well water, water at the bottom of well dug for petroleum extraction or exploration, melted ice water, pond water, aquarium water, pool water, lake water, mud, stream water, river water, brook water, waste water, treated waste water, reservoir water, rain water, and ground water. In some embodiments, waste water comprises sewage water, septic tank water, agricultural runoff, water from an area in which chemical or oil spill has or is suspected of having occurred (e.g., an oil spill into a marine environment), water from an area where a radiation leak has or is suspected of having occurred (e.g., coolant from a nuclear reactor), water within the plumbing of a building, water within or exiting a research facility, and/or water within or exiting a manufacturing facility such as a factory.

As used herein, "suspected" with respect to an event means that there has been at least one test (e.g., a test other than a method or assay provided herein), occurrence (e.g., that is likely to or that may cause the event such as an emergency, leak, accident, flood, earthquake, storm, fire, malfunction, sunk vessel, or crash), or report (e.g., by a witness, informant, or observer) that is consistent with the event having occurred.

In certain embodiments, the sample comprises a food or beverage additive and/or a food or beverage composition. In some embodiments, the food or beverage composition comprises a fermented composition. In various embodiments, the sample comprises a fluid obtained from a food composition. Alternatively or in addition, the sample may comprise a solute dissolved from a food composition. In some examples, a solute is or has been dissolved from a food composition with an aqueous or nonaqueous solution. In various implementations, an aqueous solution may optionally comprise a nonaqueous solvent. In certain embodiments, a sample comprises a food composition in semisolid or liquid form. Non-limiting examples of such compositions include yogurt, soup, ice cream, a broth, a puree, a shake, a smoothie, a batter, a condiment, a sauce, and any combination thereof. In some implementations, a sample is a food engineering process (e.g., obtained from a food design, storage, transport, or production process or from equipment intended to process, transport, or store food). A food composition may comprise, e.g., a plant or a composition isolated from a plant, and/or an animal or a composition isolated from an animal. In various embodiments, a sample comprises a beverage composition. Non-limiting examples of beverage compositions include soft drinks, fountain beverages, water, coffee, tea, milk, dairy-based beverages, soy-based beverages (e.g., soy milk), almond-based beverages (e.g., almond milk), vegetable juice, fruit juice, fruit juice-flavored drinks, energy drinks, sports and fitness drinks, alcoholic products, and beverages comprising any combination thereof. Non-limiting examples of beverage compositions comprising water include purified water (e.g., filtered water, distilled water, or water purified by reverse osmosis), flavored water, mineral water, spring water, sparkling water, tonic water, and any combination thereof. In various embodiments, the sample comprises alcohol. Non-limiting examples of such samples include samples comprising or obtained/provided from beer, malt beverages, liqueur, wine, spirits, and any combination thereof.

In some embodiments, a sample comprises a nutritional or supplement composition. In certain implementations, the nutritional or supplement composition comprises an omega-3 fatty acid, a vitamin, a mineral, a protein powder, or a meal supplement.

In certain embodiments, a biosensor is implanted in a subject's body. For example, a biosensor may be implanted in a subject's blood vessel, vein, eye, natural or artificial pancreas, alimentary canal, stomach, intestine, esophagus, or skin (e.g., within the skin or under the skin). In various embodiments, the biosensor is configured within or on the surface of a contact lens. In some embodiments, the biosensor is configured to be implanted in or under the skin. In non-limiting examples, the biosensor is implanted in a subject with an optode and/or a microbead. In certain embodiments, the biosensor generates a signal transdermally.

Aspects of the present subject matter provide a method for assaying the level of glucose in a subject. The method may comprise contacting a biological sample from the subject with a biosensor for glucose under conditions such that the biosensor binds to glucose present in the biological sample. The biosensor comprises reporter group attached to a glucose-binding protein, and binding of glucose to a glucose-binding domain of the glucose-binding protein causes a change in signaling by the reporter group. In various embodiments, the subject has, has had, is suspected of having, or is undergoing routine testing (e.g., during a physical) for diabetes, such as Type I diabetes or Type II diabetes. In some embodiments, the biological sample comprises blood, plasma, serum, sweat, tear fluid, or urine. In certain embodiments, the biological sample is present in or on the surface of the subject. In various implementations, the biosensor is applied onto or inserted into the subject. For example, the biosensor may be tattooed into the subject or is in or on a device that is implanted into the subject. In some embodiments, the biosensor may be present in or on a contact lens that is worn by the subject. Methods for determining the level of glucose, e.g. in a subject who has or is suspected of having diabetes, may be performed without other testing related to diabetes performed as part of a battery of clinical testing.

As used herein, "suspected" with respect to a subject's condition (e.g., disease or injury) means that the subject has at least one symptom or test (e.g., a test other than an assay or method provided herein) that is consistent with the condition.

The present subject matter includes a method for monitoring the level of a ligand, comprising periodically or continuously detecting the level of the ligand, wherein detecting the level of the ligand comprises (a) providing or obtaining a sample; (b) contacting the sample with a biosensor for the ligand under conditions such that the ligand-binding protein of the biosensor binds to the ligand, and (c) detecting a signal produced by the biosensor.

Aspects of the present subject matter also provide a method for monitoring the level of a ligand (e.g., glucose) in a subject, comprising periodically detecting the level of the ligand in the subject. Detecting the level of the ligand in the subject may comprise (a) providing or obtaining a biological sample from the subject; (b) contacting the biological sample with a biosensor for the ligand provided herein under conditions such that the ligand-binding protein of the biosensor binds to the ligand, if the ligand is present in the biological sample, and (c) detecting (i) a signal produced by a reporter group of the biosensor, or (ii) whether a signal is produced by a reporter group of the biosensor. The level of the ligand may be detected, e.g., at least once every 1, 2, 3, 6, or 12 hours, at least once every 1, 2, 3, or 4 days, at least once every 1, 2, or three weeks, or at least once every 1, 2, 3, 4, 6, or 12 months.

The present subject matter also provides a method for monitoring the level of a ligand in a subject. The method comprises (a) administering a biosensor provided herein or a device comprising a biosensor provided herein to the subject, wherein after administration the biosensor is in contact with a bodily fluid or surface that typically comprises the ligand, and (b) detecting (i) a signal produced by a reporter group of the biosensor continuously or repeatedly at intervals less than about 30 minutes (m), 15 m, 10 m, 5 m, 1 m, 30 seconds (s), 15 s, 10 s, 5 s, 1 s, 0.1 s, 0.001 s, 0.0001 s, or 0.00001 apart, and/or (ii) whether a signal is produced by a reporter group of the biosensor continuously or repeatedly at intervals less than about 30 m, 15 m, 10 m, 5 m, 1 m, 30 s, 15 s, 10 s, 5 s, 1 s, 0.1 s, 0.001 s, 0.0001 s, or 0.00001 apart.

Non-limiting aspects of continuously monitoring ligand levels are described in Weidemaier et al. (2011) Biosensors and Bioelectronics 26, 4117-4123 and Judge et al. (2011) Diabetes Technology & Therapeutics, 13(3):309-317, the entire contents of each of which are hereby incorporated herein by reference.

Also within various implementations is a composition comprising a purified glucose-binding fluorescently-responsive sensor protein and a solid substrate, e.g., a particle, a bead such as a magnetic bead, or a planar surface such as a chip or slide, wherein the sensor protein is immobilized onto the solid substrate. In some embodiments, the biosensor is immobilized on a patch. In some embodiments, the patch comprises a polymer or copolymer comprising hydroxyethyl (meth)acrylate, a polyolefin, polyurethane, polystyrene, an ethylene/methacrylic acid copolymer, an ethylene/methyl methacrylate copolymer, a polyester, and/or a polyurethane. In some embodiments, the patch comprises a woven fabric, a knitted fabric, or a nonwoven fabric of a synthetic fiber and/or natural fiber. In certain embodiments, the patch has an adhesive layer. An exemplary solid substrate solid substrate comprises a cyclic olefin copolymer. In some embodiments, the glucose-binding protein is thermostable.

A thermostable glucose sensor protein is one in which the activity (glucose binding) is retained after exposure to relatively high temperatures. For example, the glucose sensor protein comprises a mid-point thermal melt transition greater than 30° C., greater than 40° C., greater than 50° C., greater than 60° C., greater than 70° C., greater than 80° C., greater than 90° C., or greater than 100° C., or about 30° C. to about 100° C., about 40° C. to about 100° C., about 50° C. to about 100° C., about 60° C. to about 100° C., about 70°

C. to about 100° C., about 80° C. to about 100° C., or about 90° C. to about 100° C. In some embodiments, the sensor protein contains a single cysteine residue. In some embodiments, the single cysteine residue is located in a site of the ligand-binding protein, where it responds to ligand binding. In some examples, the protein comprises the amino acid sequence of SEQ ID NO: 48 (tsGBP2.13C.W244F) or 56 (tsGBP2.13C_244F.bZif), and in some examples, the single cysteine is conjugated to Badan, Acrylodan, or a derivative thereof. For example, the derivative comprises a replacement of the two-ring naphthalene of Acrylodan or Badan with a three-ring anthracene, a fluorene, or a styrene. A reporter group is covalently bound to the single cysteine. In some situations, the solid substrate comprises a plurality of sensor proteins, each of which comprises a different dissociation constant ($K_d$) for glucose, e.g., for detecting and quantifying glucose levels across many ranges of concentrations.

The present subject matter also includes a composition comprising purified glucose sensor protein with less than 65% identity and greater than 27% identity (e.g., 44-48% sequence identity) to any one of SEQ ID NOS: 1-16 or 109-116, wherein the sensor protein comprises a single cysteine residue, and a solid substrate, such that the sensor protein is immobilized onto the solid substrate. As described above, a reporter group is covalently bound to the single cysteine. In some example, the solid substrate comprises a plurality of sensor proteins, each of which comprises a different dissociation constant ($K_d$) for glucose for sensing over a wide range or ranges of glucose concentrations.

In some embodiments, a method of detecting the presence of or the quantity of glucose in a test sample is carried out using the following steps: contacting the test sample with the biosensor or sensor protein/solid support construct to yield a complex of glucose and the ligand-binding protein or biosensor protein; contacting the complex with an excitation light; measuring an emission intensity of the reporter group from at least two wavelengths; computing a ratiometric signal from the two (or more) wavelengths; and comparing the signal to a known glucose binding curve of signals to identify the presence of or calculate the quantity of glucose in the test sample. The test sample may be obtained from a variety of sources. For example, the test sample may be selected from a bodily fluid, a food, a beverage, or a bioreactor culture broth. The testing method may be carried out in vivo, e.g., using an implantable device or dermal patch, or ex vivo.

In various embodiments, the subject to be tested is a mammal, e.g., a primate (such as a human, a monkey, a chimpanzee, or a gorilla), a fish, a bird, a reptile, an amphibian, or an arthropod. In some embodiments, the subject is a fish, a cow, a pig, a camel, a llama, a horse, a race horse, a work horse, a goat, a rabbit, a sheep, a hamster, a guinea pig, a cat, a wolf, a dog (e.g., a pet dog, a work dog, a police dog, or a military dog), a rat, a mouse, a seal, a whale, a manatee, a lizard, a snake, a chicken, a goose, a swan, a duck, or a penguin.

Exemplary Devices and Compositions Comprising Biosensors

Aspects of the present subject matter provide a device comprising one or more biosensors provided herein. Such devices may be, e.g., wearable, implantable, portable, or fixed.

In some embodiments, the device is a nanoparticle or a microparticle comprising the biosensor. Non-limiting examples of devices include devices comprising a test strip, patch, plate, bead, or chip comprising a biosensor provided herein. In certain embodiments, a device may comprise a desiccated biosensor.

The present subject matter also provides a contact lens or a skin patch comprising a biosensor provided herein. In some embodiments, the biosensor is throughout the contact lens or skin patch or within a particular region or zone of a contact lens or skin patch (e.g., in one or more shapes (e.g., a square, circle, or star), dots, lines, or zones, located at the periphery or a portion of the periphery of a contact lens or patch). In some embodiments, the skin patch comprises an adhesive that facilitates attachment of the patch to the surface of skin.

Devices provided herein may include a variety of structural compositions. For example, many polymers (including copolymers), and plastics may be used. Non-limiting examples of compositions useful in certain devices include glass, polystyrene, polypropylene, cyclic olefin copolymers, ethylene-norbornene copolymers, polyethylene, dextran, nylon, amylase, paper, a natural cellulose, a modified cellulose, a polyacrylamide, gabbros, gold, and magnetite (as well as combinations thereof). In some embodiments, the device comprises a hydrogel, a cryogel, or a soluble gel. For example, the biosensor may be incorporated into or onto the hydrogel, cryogel, or soluble gel. In various embodiments, the device comprises a matrix comprising nanopores, micropores, and/or macropores. In certain embodiments, the surface of a device comprises a polymer. In an embodiment, the surface comprises the surface of a particle or a bead having a diameter of about 0.001-1, 0.001-0.1, 0.01-0.1, 0.001-0.01, 0.1-1, 0.1-0.5, or 0.01-0.5 centimeters (cm). For example, the particle comprises a nanoparticle or a microparticle.

Non-limiting examples of polymers include cyclic olefin copolymers, ethylene-norbornene copolymers, polylactic acid, polyglycolic acid, agarose, alginate, poly(lactide-co-glycolide), gelatin, collagen, agarose, natural and synthetic polysaccharides, polyamino acids, poly(lysine), polyesters, polyhydroxybutyrates, polyanhydrides, polyphosphazines, polyvinyl alcohol, polyalkylene oxide, polyethylene oxide, polyallylamines, polyacrylates, modified styrene polymers, poly(4-aminomethylstyrene), pluronic polyols, polyoxamers, polyuronic acid, polyvinylpyrrolidone, hydroxyethyl (meth)acrylate, polyolefins, polyurethane, polystyrene, ethylene/methacrylic acid copolymers, ethylene/methyl methacrylate copolymers, polyester, and polyurethane. In some embodiments, the patch comprises a woven fabric, a knitted fabric, or a nonwoven fabric of a synthetic fiber and/or natural fiber.

Non-limiting examples of temporary tattoo compositions for application to a subject's skin are discussed in U.S. Patent Application Publication No. 20090325221, published Dec. 31, 2009, and U.S. Pat. No. 6,428,797, the entire contents of each of which are incorporated herein by reference. Biosensor disclosed herein may be incorporated into any temporary tattoo or other composition for application to the skin. For example, a temporary tattoo decal for application to a subject's skin and configured to detect the presence of a ligand may comprise, e.g., a base paper or plastic; a water-soluble slip layer applied to the base paper or plastic; a temporary tattoo applied to the water-soluble release layer on the base paper, wherein the temporary tattoo comprises a biosensor disclosed herein; an adhesive layer overlying the temporary tattoo; and a protective sheet overlying the adhesive layer.

In some embodiments, the device comprises a plastic polymer comprising cyclic olefin copolymer (COC), such as e.g. TOPAS® COC. Several types of cyclic olefin copolymers are available based on different types of cyclic monomers and polymerization methods. Cyclic olefin copolymers are produced by chain copolymerization of cyclic monomers such as 8,9,10-trinorbom-2-ene (norbornene) or 1,2,3,4,4a,5,8,8α-octahydro-1,4:5,8-dimethanonaphthalene (tetracyclododecene) with ethene (such as TOPAS Advanced Polymer's TOPAS, Mitsui Chemical's APEL), or by ring-opening metathesis polymerization of various cyclic monomers followed by hydrogenation (Japan Synthetic Rubber's ARTON, Zeon Chemical's Zeonex and Zeonor). See, e.g., International Union of Pure and Applied Chemistry (2005) *Purr. Appl. Chem.* 77(5):801-814. These later materials using a single type of monomer may be referred to as cyclic olefin polymers (COPs). A CAS Registry number for COC is 26007-43-2.

In some embodiments, the biosensor is covalently or noncovalently (e.g., electrostatically) attached to a surface of a device. In certain embodiments, the biosensor is attached to a surface of a device or is not attached to a surface of the device (e.g., the biosensor is physically present within the device as a component of a solution or powder but not chemically immobilized onto or into a device surface). For example, the biosensor may move within the confines of a device chamber.

A biosensor may be attached to a device via a variety or means, e.g., via attachment motif. In some embodiments, the attachment motif is attached to the N-terminus or the C-terminus of the biosensor. In certain embodiments, the biosensor is linked to an attachment motif via a covalent bond. In various embodiments, the biosensor is linked to the attachment motif via a linker. A non-limiting example of a linker is a polyglycine comprising 2, 3, 4, 5, or more glycines and optionally further comprising a serine. In some embodiments, the attachment motif comprises a polypeptide. Non-limiting examples of polypeptides useful in attachment moieties include hexahistidine peptides, hexalysine peptides, zinc-finger domains (ZF-QNKs), and disulfide-containing truncated zinc fingers (βZifs). An example of a hexalysine peptide comprises amino acids in the sequence of SEQ ID NO: 108, an example of a ZF-QNK comprises amino acids in the sequence of SEQ ID NO: 106, and an example of a βZif comprises amino acids in the sequence of SEQ ID NO: 105. In some embodiments, the attachment motif comprises a polypeptide that binds to plastic or cellulose.

The hexahistidine, hexalysine, βZif and QNK-ZF fusions enable FRSs to be immobilized onto chemically functionalized surfaces. Non-limiting aspects of chemically functionalized surfaces are discussed in Biju, V. (2014) *Chem Soc Rev,* 43, 744-64 and McDonagh (2008) *Chem Rev,* 108, 400-422, the entire contents of which are incorporated herein by reference. Directed evolution methods have been used to develop peptides that bind directly to non-functionalized surfaces (Care, Bergquist and Sunna 2015 *Trends Biotechnol,* 33, 259-68; Baneyx 2007 *Curr. Opin. Biotechnol.,* 18, 312-317; Gunay and Klok 2015 *Bioconjug* Chem, 26, 2002-15), including various plastics (Adey et al. 1995 *Gene,* 156, 27-31; Serizawa et al. 2005 J Am Chem Soc, 127, 13780-1; Serizawa, Sawada and Kitayama 2007a *Angew Chem Int Ed Engl,* 46, 723-6; Serizawa, Sawada and Matsuno 2007b *Langmuir,* 23, 11127-33; Serizawa, Techawanitchai and Matsuno 2007c *Chembiochem,* 8, 989-93; Matsuno et al. 2008 *Langmuir,* 24, 6399-403; Chen, Serizawa and Komiyama 2011 *J Pept Sci,* 17, 163-8; Kumada 2010 *J. Biosci. and BioEng.,* 109, 583-587; Date et al. 2011 *ACS Appl Mater Interfaces,* 3, 351-9; Kumada 2012, Vodnik, Strukelj and Lunder 2012 *J. Biotech.,* 160, 222-228; Kumada 2014 *Biochem. et Biophys. Acta,* 1844, 1960-1969; Ejima, Matsuno and Serizawa 2010 *Langmuir,* 26, 17278-85), inorganic materials (Hnilova 2012 *Soft Matter,* 8, 4327-4334; Care et al. 2015 *Trends Biotechnol,* 33, 259-68), nanoparticles (Avvakumova et al. 2014 *Trends Biotechnol,* 32, 11-20), and cellulosic paper (Guo et al. 2013 *Biomacromolecules,* 14, 1795-805). Such peptides, or natural material-binding domains (Oliveira et al. 2015 *Biotechnol Adv,* 33, 358-69), also can be fused to FRSs to direct site-specific, oriented immobilization on their target materials while preserving FRS function. For instance, plastic-binding peptides have been developed that direct immobilization on polystyrene (Adey et al. 1995 *Gene,* 156, 27-31; Serizawa et al. 2007c *Chembiochem,* 8, 989-93; Kumada 2010 *Biochem. et Biophys. Acta,* 1844, 1960-1969; Vodnik et al. 2012 *Anal Biochem,* 424, 83-6), polymethyl acrylate (Serizawa et al. 2005 *J Am Chem Soc,* 127, 13780-1; Serizawa et al. 2007a *Angew Chem Int Ed Engl,* 46, 723-6; Serizawa et al. 2007b *Langmuir,* 23, 11127-33; Kumada 2014 *Biochem. et Biophys. Acta,* 1844, 1960-1969), polycarbonate (Kumada 2012 *J. Biotech.,* 160, 222-228), polylactide (Matsuno et al. 2008 *Langmuir,* 24, 6399-403), and polyphenylene vinylene (Ejima et al. 2010 *Langmuir,* 26, 17278-85). Cellulose-binding peptides (Guo et al. 2013 *Biomacromolecules,* 14, 1795-805) and natural domains (Oliveira et al. 2015 *Biotechnol Adv,* 33, 358-69; Shoseyov, Shani and Levy 2006 *Microbiol Mol Biol Rev,* 70, 283-95) can be used to immobilize fusion proteins on paper. Inorganic material include noble metals (Hnilova 2012 *Soft Matter,* 8, 4327-4334), semi-conductors (Care et al. 2015 *Trends Biotechnol,* 33, 259-68), and fluorescent quantum dots (Medintz et al. 2005 *Nat Mater,* 4, 435-46; Lee et al. 2002 *Science,* 296, 892-5). The entire contents of each of the references above (and all other references herein) is incorporated herein by reference.

In some embodiments, the attachment motif is attached to a device surface and/or within a matrix of the device. In some embodiments, a biosensor is attached to an attachment motif via a covalent bond and the attachment motif is attached to a device via a covalent bond. Non-limiting examples of covalent bonds include disulfide bonds, ester bonds, thioester bonds, amide bonds, and bonds that have been formed by click reactions. Non-limiting examples of a click reaction include a reaction between an azide and an alkyne; an azide and an alkyne in the presence of Cu(I); an azide and a strained cyclooctyne; an azide and a dibenzylcyclooctyne, a difluorooctyne, or a biarylazacyclooctynone; a diaryl-strained-cyclooctyne and a 1,3-nitrone; an azide, a tetrazine, or a tetrazole and a strained alkene; an azide, a tetrazine, or a tretrazole and a oxanorbornadiene, a cyclooctene, or a trans-cycloalkene; a tetrazole and an alkene; or a tetrazole with an amino or styryl group that is activated by ultraviolet light and an alkene.

Alternatively or in addition, a surface of a device may be modified to contain a moiety (e.g. a reactive group) what facilitates the attachment of a biosensor and/or binds to the biosensor. In some embodiments, the biosensor is attached to a surface via a biotin-avidin interaction.

In various implementations, the device comprises a first region or chamber for receiving a sample and a second region or chamber that comprises the biosensor, wherein the first region or chamber is separated from the second region or chamber by a filter. In some examples, the filter is impermeable to compounds greater than about 1, 2, 3, 4, 5, 10, 50, 200, or 250 kiloDalton (kDa) in size. The sample may comprise, e.g., a tube, such as a tube that is configured for centrifugation. When sample is placed into the first region and the device is centrifuged, then a portion of the sample comprising a ligand flows through the filter into the second region where the biosensor is contacted.

Non-limiting examples of devices provided herein include endoscopy probes and colonoscopy probes.

In some embodiments, the device comprises an optode. In non-limiting examples, the optode comprises an optical fiber and a single biosensor or composite biosensor. In certain embodiments, the single biosensor or composite biosensor is immobilized on the surface or at an end of the optical fiber. In some embodiments, the optode is configured for implantation into a subject. Alternatively or in addition, the optode is configured for insertion into a sample.

The devices provided herein may optionally comprise a biosensor panel, a composite sensor, a sensor array, and/or a composition comprising a plurality of biosensors. In various embodiments, a device comprises multiple glucose biosensors that detect a range of different glucose concentrations in a single sample and/or assay run (i.e., each biosensor has a different affinity for glucose). Devices may provide spatial localization of multiple biosensors to provide the necessary addressability of different elements in a multisensor array comprising sensors that differ in their engineered affinities for coverage of a wide range of glucose concentrations, or sensors that each detects distinct analytes.

Aspects of the present subject matter provide a biosensor panel comprising a plurality of biosensors, wherein the plurality of biosensors comprises at least one biosensor disclosed herein. In some embodiments, the plurality comprises at least about 2, 3, 4, 5, 10, 20, 30, 40, 50, 60, 70, 80, 90, or 100 biosensors.

The present subject matter also provides a composite sensor. The composite sensor may comprise a sensor element, wherein the sensor element comprises 2 or more biosensors, wherein at least 1 of the 2 or more biosensors is a biosensor disclosed herein. In some embodiments, the biosensors are not spatially separated in the sensor element, e.g., the biosensors are mixed within a solution, or immobilized on a surface of the sensor element. Alternatively, a mixture of different biosensors is physically present, e.g., loose, within a region or chamber of a sensor device/structure. In various embodiments, the composite sensor comprises a plurality of sensor elements, wherein each sensor element of the plurality of sensor elements comprises 2 or more biosensors, wherein at least 1 of the 2 or more biosensors is a biosensor provided herein. In some embodiments, the plurality of sensor elements comprises at least about 2, 3, 4, 5, 10, 20, 30, 40, 50, 60, 70, 80, 90, or 100 sensor elements.

Also included herein is a sensor array comprising a plurality of biosensors of the present subject matter. The sensor array may include, e.g., multichannel array or a multiplexed array. In some embodiments, the biosensors of the plurality of biosensors are spatially separated from each other. In certain embodiments, the biosensors are arranged linearly or in a grid on a surface of the array.

The present subject matter provides a composition comprising a plurality of biosensors including at least one biosensor disclosed herein. Also provided is a non-human mammal comprising a biosensor or device disclosed herein.

Exemplary Polypeptides and Polynucleotides

The present subject matter provides polynucleotides encoding any one of the polypeptides disclosed herein. The polypeptides are also provided. In various embodiments, the polynucleotides are codon-optimized for expression in a desired host cell, such as bacterial cells (e.g., *E. coli*), yeast, insect cells, plant cells, algal cells, or mammalian cells. The polypeptides provided herein include polypeptides comprising the amino acid sequence of any one of SEQ ID NOS: 1-56 or 109-116. The polynucleotides provided herein include polynucleotides encoding a polypeptide comprising the amino acid sequence of any one of SEQ ID NOS: 1-56 or 109-116.

The polypeptides and biosensors provided herein may be in a variety of forms, e.g., purified in solution, dried (e.g. lyophilized) such as in the form of a powder, and in the form of a crystal (e.g., a crystal suitable for x-ray crystallography). Thus, aspects of the present subject matter provide crystal structures and crystalized forms of the ligand-binding proteins and biosensors disclosed herein. Such crystal structures and crystalized proteins are useful for designing and optimizing biosensors using principles and methods discussed herein.

Also provided are expression vectors comprising a polynucleotide of the present subject matter and/or encoding a polypeptide disclosed herein. Non-limiting examples of expression vectors include viral vectors and plasmid vectors. In some embodiments, an expression vector comprises nucleotides in the sequence set forth as any one of SEQ ID NOS: 57-104. In various embodiments, a polynucleotide encoding a ligand-binding protein and/or biosensor is operably linked to a promoter. The promoter may be expressed, e.g., in a prokaryotic and/or a eukaryotic cell.

The subject matter further includes an isolated cell comprising an expression vector provided herein. The isolated cell may be, e.g., a bacterial cell, a yeast cell, an algal cell, a plant cell, an insect cell, or a mammalian cell. Also included is a non-human multicellular organism such as a plant or an animal (e.g., an insect, a mammal, a worm, a fish, a bird, or a reptile) comprising an expression vector disclosed herein.

Exemplary Methods for Designing Biosensors

Aspects of the present subject matter provide method of identifying a candidate ligand-binding protein for use in a biosensor, comprising: (a) selecting a first protein having a known amino acid sequence (seed sequence), wherein the first protein is known to bind glucose; (b) identifying a second protein having an amino acid sequence (hit sequence) with at least 15% sequence identity to the seed sequence; (c) aligning the seed amino acid sequence and the hit sequence, and comparing the hit sequence with the seed sequence at positions of the seed sequence that correspond to at least 5 primary complementary surface (PCS) amino acids, wherein each of the at least 5 PCS amino acids has a hydrogen bond interaction or a van der Waals interaction with glucose when glucose is bound to the first protein; and (d) identifying the second protein to be a candidate ligand-binding protein if the hit sequence comprises at least 5 amino acids that are consistent with the PCS.

The present subject matter also includes a method for constructing a candidate biosensor, comprising: (a) providing a candidate ligand-binding protein; (b) generating a structure of the second protein; (c) identifying at least one putative allosteric, endosteric, or peristeric site of the second protein based on the structure; (d) mutating the second protein to substitute an amino acid at the at least one putative allosteric, endosteric, or peristeric site of the second protein with a cysteine; and (e) conjugating a fluorescent compound to the cysteine. In some embodiments, the structure comprises a homology model of the second protein generated using a structure of the first protein. In some embodiments, the structure comprises a structure experimentally determined by nuclear magnetic resonance spectroscopy or X-ray crystallography.

Aspects of the present subject matter further provide a method for constructing a biosensor comprising a desired dissociation constant ($K_d$) for glucose, comprising: (a) providing an initial biosensor that does not comprise the desired $K_d$ for glucose, wherein the initial biosensor is a biosensor provided herein; (b) mutating the initial biosensor to (i) alter a direct interaction in the PCS between the initial biosensor and bound glucose; (ii) manipulate the equilibrium between open and closed states of the initial biosensor; (iii) alter an interaction between the ligand-binding protein and the reporter group of the initial biosensor; or (iv) alter an indirect interaction that alters the geometry of the binding site of the biosensor, to produce a modified biosensor; and (c) selecting the modified biosensor if the modified biosensor comprises the desired $K_d$ for glucose. In some embodiments, the reporter group comprises Acrylodan, Badan, or a derivative thereof, and mutating the initial biosensor in (b) comprises altering an interaction between the ligand-binding protein and a carbonyl group of the Acrylodan, Badan, or derivative thereof. In some embodiments, the reporter group comprises Acrylodan, Badan, or a derivative thereof, and mutating the initial biosensor in (b) comprises altering an interaction between the ligand-binding protein and a naphthalene ring of the Acrylodan, Badan, or derivative thereof. In some embodiments, mutating the initial biosensor comprises introducing a substitution mutation into the initial biosensor. In some embodiments, the method further comprises immobilizing the affinity-tuned biosensor on a substrate.

In some embodiments, the second protein comprises (i) amino acids in the sequence of any one of SEQ ID NOS: 1-56 or 109-116; (ii) a stretch of amino acids in a sequence that is least about 95, 96, 97, 98, or 99% identical to the sequence of any one of SEQ ID NOS: 1-56 or 109-116; (iii) a stretch of at least about 50, 100, 150, 200, 250, 300, 350, 400, or 425 amino acids in a sequence that is at least about 95, 96, 97, 98, or 99% identical to a sequence within any one of SEQ ID NOS: 1-56 or 109-116; or (iv) a stretch of at least about 50, 100, 150, 200, 250, 300, 350, 400, or 425 amino acids in a sequence that is identical to a sequence within any one of SEQ ID NOS: 1-56 or 109-116. In various embodiments, attaching the reporter group to the putative allosteric, endosteric, or peristeric site of the first protein comprises substituting a cysteine at the site with a cysteine. For example, the reporter group is conjugated to the cysteine. Preferably, attaching a reporter group to the corresponding amino acid of the second protein produces a functional biosensor.

The selected first protein (e.g., the amino acid sequence thereof) may be novel or known. However, in many instances, the function of the first protein will not be known. In a non-limiting example, identifying a protein not previously known to have glucose binding activity may comprise a structurally assisted functional evaluation (SAFE) homolog search method comprising the following steps:

(1) Collecting a sequence homology set using a BLAST sequence alignment tool starting with a glucose-binding protein sequence disclosed herein or a homologue thereof (e.g., ttGBP1, tsGBP2, dmGBP3, tnGBP4, koGBP5, bhGBP6, smGBP7, or asGBP8) as a seed. Permissive settings are used, such that pairwise hits are required to have a minimum of only, e.g., 20%, 25%, 30%, 35% or 40% sequence identity with the seed sequence. The lengths of the hit and seed are mutually constrained such that the alignment covers at least, e.g., 60%, 65%, 70%, 85%, or 90% within each partner.

(2) Structure-based encoding of biological function: A primary complementary surface (PCS) comprising the protein residues that form hydrogen bonds and van der Waals contacts with a bound glucose is defined using computer-assisted, visual inspection of the three-dimensional structure of the protein-glucose complex. This definition specifies residue positions and their permitted amino acid identity. Multiple amino acid identities are permitted at each position to encode functionally equivalent residues. This definition establishes a search filter for the accurate prediction of glucose-binding proteins within the universe of sequence homologs collected in (1). For example, a candidate's residue corresponding to position 8 of ttGBP1 may be W, H, N, or Q, a candidate's residue corresponding to position 9 of ttGBP1 may be W, F, or Y, a candidate's residue corresponding to position 13 of ttGBP1 may be E, D, N, or Q, a candidate's residue corresponding to position 64 of ttGBP1 may be Q or N, a candidate's residue corresponding to position 66 of ttGBP1 may be H, N, Q, W, or K, a candidate's residue corresponding to position 119 of ttGBP1 may be H, N, Q, or W, a candidate's residue corresponding to position 224 of ttGBP1 may be W, F, or Y, a candidate's residue corresponding to position 244 of ttGBP1 may be W, F, or Y, a candidate's residue corresponding to position 278 of ttGBP1 may D, E, N, or Q, a candidate's residue corresponding to position 312 of ttGBP1 may be K or R, and a candidate's residue corresponding to position 348 of ttGBP1 may be H, N, Q, or W.

(3) Accurate sequence alignment: Tools such as ClustalW are used to construct an accurate alignment of all the sequence homologs. The seed sequence is included in the alignment. This multiple sequence alignment establishes the equivalent positions of the seed sequence (primary complementary surface) PCS in each sequence homolog.

(4) Function evaluation: The glucose-binding properties of each of the aligned sequence homologs is determined by measuring their compliance with the PCS sequence filter. A "Hamming distance", H, is assigned for each homolog, which specifies the degree of sequence identity of all the residues at the aligned PCS positions. A value of H=0 indicates that the identities of all the residues at the aligned PCS positions match the amino acid(s) allowed in the PCS search filter; H>0, indicates that one or more aligned positions have disallowed residues. Sequences for which H=0 are predicted to encode glucose-binding proteins.

(5) Selection of representative SAFE homologs: The sequence homologs are ordered by (a) identity with the seed PCS, as measured by the Hamming distance, (b) fractional overall sequence identity with the seed sequence. A subset for sequences with H=0, sampling the fractional overall sequence identity is selected for experimental verification.

In a non-limiting example, identifying a protein not previously known to have glucose binding activity may comprise the following steps:

(1) performing a computational search of sequence databases to define a broad group of simple sequence or structural homologs of any known, glucose-binding protein;

(2) using the list from step (1), deriving a search profile containing common sequence and/or structural motifs shared by the members of the list [e.g. by using computer programs such as MEME (Multiple Em for Motif Elicitation available at meme.sdsc.edu/meme/cgi-bin/meme.cgi) or BLAST];

(3) searching sequence/structural databases, using a derived search profile based on the common sequence or structural motif from step (2) as query (e.g., using computer programs such as BLAST, or MAST (Motif Alignment Search Tool available at meme.sdsc.edu/meme/cgi-bin/mast.cgi), and identifying a candidate sequence, wherein a sequence homology and/or structural similarity to a reference glucose binding protein is a predetermined percentage threshold;

(4) compiling a list of candidate sequences to generate a list of candidate glucose-binding proteins;

(5) expressing the candidate glucose-binding proteins in a host organism; and (6) testing for glucose binding activity, wherein detection of glucose binding in the organism (or the media thereof) indicates that the candidate sequence comprises a novel glucose-binding protein.

In non-limiting examples, the MEME suite of sequence analysis tools (meme.sdsc.edu/meme/cgi-bin/meme.cgi) can also be used as an alternative to BLAST. Sequence motifs are discovered using the program "MEME". These motifs can then be used to search sequence databases using the program "MAST." The BLAST search algorithm is well-known.

In various embodiments relating to alignments using a ClustalW alignment program, the ClustalW alignment program may be, e.g., ClustalW alignment program version 2.1.

Each embodiment disclosed herein is contemplated as being applicable to each of the other disclosed embodiments. Thus, all combinations of the various elements described herein are within the scope of the invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

DESCRIPTION OF THE DRAWINGS

FIG. 1A: FRSs can be constructed by site-specifically attaching a fluorophore to a protein that undergoes a conformational change upon binding ligand (triangle) in a location between the two lobes of the protein (periplasmic binding protein or engineered derivative thereof), such that the shape and intensities of the fluorescent conjugate emission spectra changes. FIG. 1B: In the absence of ligand, the emitted fluorescence color is predominantly blue, whereas the ligand complex fluoresces green. Arrows indicate the direction of change upon ligand addition. FIG. 1C: The ligand dependence of the absolute blue and green intensities. FIG. 1D: The ratio of the blue and green emission intensities enables ligand binding to be determined.

FIG. 2A: Class I, represented by *E. coli* glucose-galactose binding protein (PDB code 1GLG).

FIGS. 5A-C: Glucose response ($\lambda_1$=523 nm, $\lambda_2$=479 nm; ${}^{app}K_d$=3.8 mM; ${}^{true}K_d$=5.6 mM). FIGS. 5D-F: Galactose response ($\lambda_1$=519 nm, $\lambda_2$=475 nm; ${}^{app}K_d$=120 mM; ${}^{true}K_d$=140 mM).

FIG. 6A: Simplified Jablonski diagram illustrating radiative and non-radiative pathways in the donor and acceptor. The donor excited state (D*) is formed through illumination by the excitation source (wavy arrow) whereas the acceptor excited state (A*) is formed by resonance energy transfer (dashed arrow). The fluorescence intensity is determined by the ratio of radiative decay (gray arrows) of the excited states (gray lines) to the ground state (black line) relative to all non-radiative processes (black arrows), and the resonance energy transfer rate, $k_t$, from donor to acceptor. FIG. 6B: Inter-dipole geometry. Top, FRET efficiency ($f=Q_r/(Q_0-Q_\infty)$, where the $Q_r$, $Q_0$, $Q_\infty$ are the quantum efficiencies at distances r, closest approach, and infinity, respectively) varies as the $6^{th}$ power of the distance between two dipoles. Bottom, FRET efficiency varies as the square of the orientation factor κ, where $\kappa=\sin\theta_D \sin\theta_A \cos\chi-2\cos\theta_D\cos\theta_A$ with $\theta_D$ and $\theta_A$ the angles of the donor (blue) and acceptor (red) electronic transition dipoles with the line connecting them, and χ the angle between the planes within which they lie. FIG. 6C: Spectral overlap (grey area) between the donor fluorescence emission (${}^{D}I$, gray) and acceptor fluorescence excitation (${}^{A}A$, black) spectra. This overlap increases with bathochromic or hypsochromic shifts of the donor emission (red arrow) and acceptor excitation (dotted blue arrow) spectra, respectively. Shifts in the opposite directions decreases spectral overlap.

FIG. 7 shows the sequence of an exemplary ttGBP1 expression construct (SEQ ID NO: 57), optimized using OrfOpt.

FIG. 8 shows the sequence of an exemplary tsGBP2 expression construct (SEQ ID NO: 58), optimized using OrfOpt.

FIG. 9 shows the sequence of an exemplary dmGBP3 expression construct (SEQ ID NO: 59), optimized using OrfOpt.

FIG. 10 shows the sequence of an exemplary tnGBP4 expression construct (SEQ ID NO: 60), optimized using OrfOpt.

FIG. 11 shows the sequence of an exemplary koGBP5 expression construct (SEQ ID NO: 61), optimized using OrfOpt.

FIG. 12 shows the sequence of an exemplary bhGBP6 expression construct (SEQ ID NO: 62), optimized using OrfOpt.

FIG. 13 shows the sequence of an exemplary smGBP7 expression construct (SEQ ID NO: 63), optimized using OrfOpt.

FIG. 14 shows the sequence of an exemplary asGBP8 expression construct (SEQ ID NO: 64), optimized using OrfOpt.

FIG. 15 shows the sequence of an exemplary tsGBP2_C8 expression construct (SEQ ID NO: 65), optimized using OrfOpt.

FIG. 16 shows the sequence of an exemplary tsGBP2_C9 expression construct (SEQ ID NO: 66), optimized using OrfOpt.

FIG. 17 shows the sequence of an exemplary tsGBP2_C12 expression construct (SEQ ID NO: 67), optimized using OrfOpt.

FIG. 18 shows the sequence of an exemplary tsGBP2_C13 expression construct (SEQ ID NO: 68), optimized using OrfOpt.

FIG. 19 shows the sequence of an exemplary tsGBP2_C41 expression construct (SEQ ID NO: 69), optimized using OrfOpt.

FIG. 20 shows the sequence of an exemplary tsGBP2_C42 expression construct (SEQ ID NO: 70), optimized using OrfOpt.

FIG. 21 shows the sequence of an exemplary tsGBP2_C64 expression construct (SEQ ID NO: 71), optimized using OrfOpt.

FIG. 22 shows the sequence of an exemplary tsGBP2_C66 expression construct (SEQ ID NO: 72), optimized using OrfOpt.

FIG. 23 shows the sequence of an exemplary tsGBP2_C119 expression construct (SEQ ID NO: 73), optimized using OrfOpt.

FIG. 24 shows the sequence of an exemplary tsGBP2_C167 expression construct (SEQ ID NO: 74), optimized using OrfOpt.

FIG. 25 shows the sequence of an exemplary tsGBP2_C223 expression construct (SEQ ID NO: 75), optimized using OrfOpt.

FIG. 26 shows the sequence of an exemplary tsGBP2_C224 expression construct (SEQ ID NO: 76), optimized using OrfOpt.

FIG. 27 shows the sequence of an exemplary tsGBP2_C225 expression construct (SEQ ID NO: 77), optimized using OrfOpt.

FIG. 28 shows the sequence of an exemplary tsGBP2_C244 expression construct (SEQ ID NO: 78), optimized using OrfOpt.

FIG. 29 shows the sequence of an exemplary tsGBP2_C277 expression construct (SEQ ID NO: 79), optimized using OrfOpt.

FIG. 30 shows the sequence of an exemplary tsGBP2_C278 expression construct (SEQ ID NO: 80), optimized using OrfOpt.

FIG. 31 shows the sequence of an exemplary tsGBP2_C312 expression construct (SEQ ID NO: 81), optimized using OrfOpt.

FIG. 32 shows the sequence of an exemplary tsGBP2_C337 expression construct (SEQ ID NO: 82), optimized using OrfOpt.

FIG. 33 shows the sequence of an exemplary tsGBP2_C348 expression construct (SEQ ID NO: 83), optimized using OrfOpt.

FIG. 34 shows the sequence of an exemplary tsGBP2_C357 expression construct (SEQ ID NO: 84), optimized using OrfOpt.

FIG. 35 shows the sequence of an exemplary tsGBP2.13C.W8F expression construct (SEQ ID NO: 85), optimized using OrfOpt.

FIG. 36 shows the sequence of an exemplary tsGBP2.13C.W8M expression construct (SEQ ID NO: 86), optimized using OrfOpt.

FIG. 37 shows the sequence of an exemplary tsGBP2.13C.W8Y expression construct (SEQ ID NO: 87), optimized using OrfOpt.

FIG. 38 shows the sequence of an exemplary tsGBP2.13C.W9F expression construct (SEQ ID NO: 88), optimized using OrfOpt.

FIG. 39 shows the sequence of an exemplary tsGBP2.13C.W9M expression construct (SEQ ID NO: 89), optimized using OrfOpt.

FIG. 40 shows the sequence of an exemplary tsGBP2.13C.W9Y expression construct (SEQ ID NO: 90), optimized using OrfOpt.

FIG. 41 shows the sequence of an exemplary tsGBP2.13C.Q64N expression construct (SEQ ID NO: 91), optimized using OrfOpt.

FIG. 42 shows the sequence of an exemplary tsGBP2.13C.Q64E expression construct (SEQ ID NO: 92), optimized using OrfOpt.

FIG. 43 shows the sequence of an exemplary tsGBP2.13C.Q64M expression construct (SEQ ID NO: 93), optimized using OrfOpt.

FIG. 44 shows the sequence of an exemplary tsGBP2.13C.H66Q expression construct (SEQ ID NO: 94), optimized using OrfOpt.

FIG. 45 shows the sequence of an exemplary tsGBP2.13C.W244M expression construct (SEQ ID NO: 95), optimized using OrfOpt.

FIG. 46 shows the sequence of an exemplary tsGBP2.13C.W244F expression construct (SEQ ID NO: 96), optimized using OrfOpt.

FIG. 47 shows the sequence of an exemplary tsGBP2.13C.W244Y expression construct (SEQ ID NO: 97), optimized using OrfOpt.

FIG. 48 shows the sequence of an exemplary tsGBP2.13C.D278N expression construct (SEQ ID NO: 98), optimized using OrfOpt.

FIG. 49 shows the sequence of an exemplary tsGBP2.13C.D278S expression construct (SEQ ID NO: 99), optimized using OrfOpt.

FIG. 50 shows the sequence of an exemplary tsGBP2.13C.D278L expression construct (SEQ ID NO: 100), optimized using OrfOpt.

FIG. 51 shows the sequence of an exemplary tsGBP2.13C.K312M expression construct (SEQ ID NO: 101), optimized using OrfOpt.

FIG. 52 shows the sequence of an exemplary tsGBP2.13C.bZif expression construct (SEQ ID NO: 102), optimized using OrfOpt.

FIG. 53 shows the sequence of an exemplary tsGBP2.244C.bZif expression construct (SEQ ID NO: 103), optimized using OrfOpt.

FIG. 54 shows the sequence of an exemplary tsGBP2.13C_244F.bZif expression construct (SEQ ID NO: 104), optimized using OrfOpt.

FIG. 55A shows Acrylodan; FIG. 55P shows PyMPO.

FIG. 56 is a diagram relating to directly responsive partners and indirectly responsive partners in ngmFRET pathways.

DETAILED DESCRIPTION

Figure 1A:
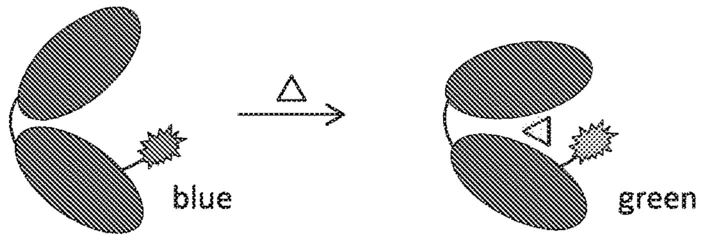
FIG. 1A is a cartoon and FIGS. 1B-D are graphs illustrating fluorescently responsive sensors.
Figure 1B:
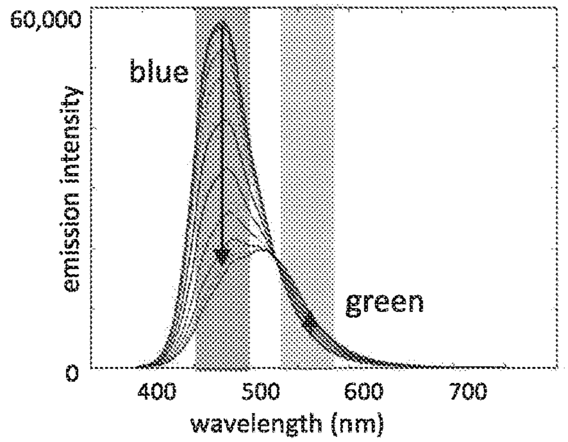
Figure 1C:
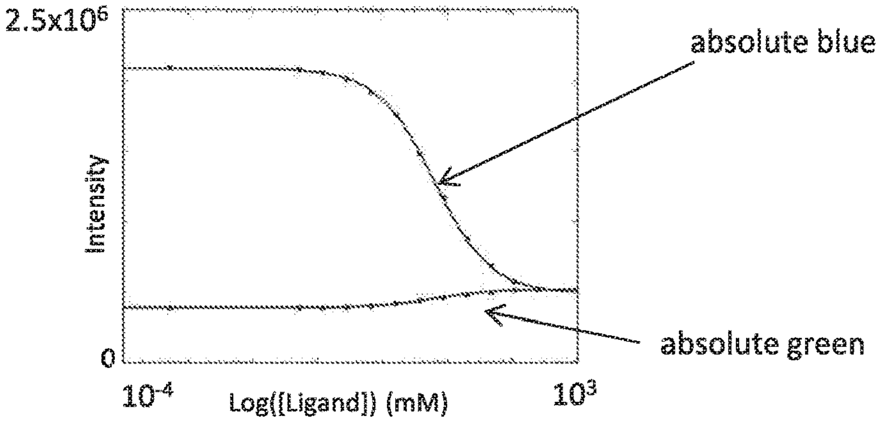
Figure 1D:
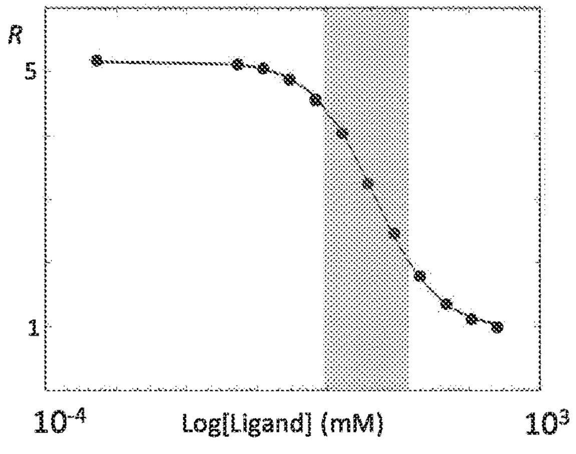
Figure 2A:
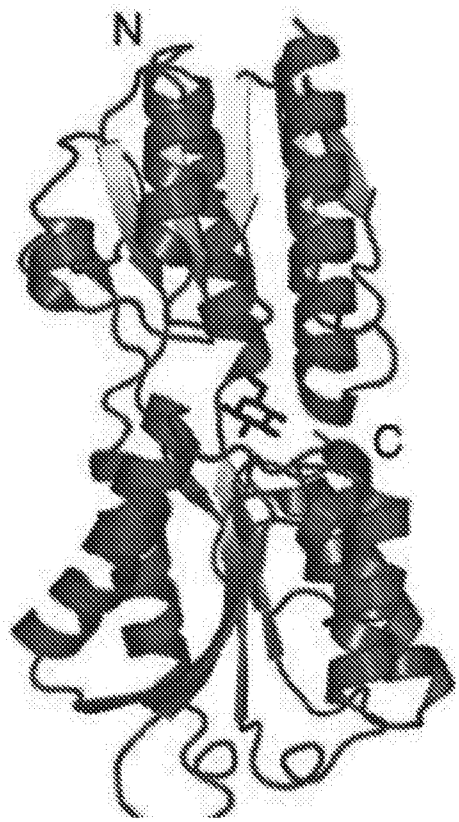
FIGS. 2A and B are exemplary structures of two classes of periplasmic binding proteins, which are distinguishable by the topology of their core β-strands.

Microbes have separately evolved different types of proteins that bind to glucose in what can be seen as an example of convergent evolution. Across these types of proteins, glucose-binding involves a large hinge-bending motion that transitions the proteins from an open to a closed state in which the glucose is enveloped within a cleft between two domains. Multiple structural classes of bacterial proteins that bind glucose have been categorized based on the ordering of β-strands within each domain (FIGS. 2A and B). The *E. coli* glucose-galactose binding protein (ecGGBP) and homologs thereof fall within one of these structural classes. The *Thermus thermophilus* glucose-binding protein (ttGBP1) and homologues thereof fall within another structural class. The glucose-binding interactions in ttGBP1 are different in composition and geometry from the ecGGBP homologs.

Fluorescently responsive sensors (FRSs) based on engineered (i.e., produced by artificial selection, design, mutation, conjugation, and/or other human-directed activity) proteins that couple ligand-binding events to changes in the emission properties of fluorophores (being fluorescent by themselves and regardless of the presence of any other fluorophore/partner) or semi-synthetically incorporated chromophores have wide-ranging applications in cell biology and analytical chemistry. If the fluorescence emission spectrum of an engineered FRS changes shape in response to ligand binding such that the ratio of intensities at two appropriately chosen wavelengths reports on ligand concentration (dichromatic response), then ratiometric measurements can be used to monitor analyte concentrations (FIGS. 1A-D). Ratiometry is essential for devices that rely on changes in fluorescence emission intensities, because it provides an internally consistent reference. The self-calibrating nature of a ratiometric measurement removes the necessity for carrying out on-board calibration tests prior to each measurement, obviating the need for multiple components and fluidic circuitry. Accordingly, reagentless, ratiometric fluorescent sensors have many uses in process engineering, environmental or clinical chemistry, including single-use point-of-care applications, wearable devices, or implanted "tattoos" that are interrogated transdermally.

The periplasmic binding protein (PBP) superfamily provide a rich source of FRSs, because PBPs combine a large diversity of ligand specificities with a common structural mechanism that is well suited to the construction of fluorescence signal transduction schemes. The three-dimensional PBP monomer structure comprises two α/β domains linked by a β-strand hinge. Different PBP structural classes have been categorized based on the ordering of β-strands within each domain (FIGS. 2A and B). Binding of ligand is accompanied by a large hinge-bending motion that transitions the protein from an open to a closed state in which the ligand is enveloped within a cleft between the two domains. Semi-synthetic FRSs can be engineered with PBPs by site-specifically attaching single, thiol-reactive, environmentally sensitive fluorophores that respond to the ligand-mediated conformational change. Semisynthetic, fluorescently labeled glucose-binding proteins in the periplasmic binding protein superfamily have been engineered successfully as reagentless, ratiometric glucose biosensors that can be used for point-of-care diagnostics and in vivo continuous glucose monitoring applications. These engineered proteins have been based on homologs of the *Escherichia coli* glucose-galactose (ecGGBP) and ribose-binding proteins (Class I). The ecGGBP protein comprises a classic "EF hand" motif that binds $Ca^{2+}$, which is located on the surface of its C-terminal domain, away from the glucose-binding site (Gifford, Walsh and Vogel, 2007, *Biochem J,* 405, 199-221). Although the two ligand-binding sites are separated, $Ca^{2+}$ binding influences glucose affinities (Snyder, Buoscio and Falke, 1990, *Biochemistry,* 29, 3937-43; Falke et al., 1991, *Biochemistry,* 30, 8690-7).

Figure 2B:
FIG. 2B: Class II, represented by *E. coli* maltose-maltotriose binding protein (PDB code 1ANF).

A glucose-binding protein has been identified in the hyperthermophilic bacterium *Thermus thermophilus* (ttGBP1) (Class II). This protein is homologous to a group of periplasmic-binding proteins that are adaptations of the *E. coli* maltose-binding protein and are structurally quite distinct from the ecGGBP proteins (FIG. 2). The glucose-binding interactions in ttGBP1 are different in composition and geometry from the ecGGBP homologs. For example, ttGBP1 may be distinguished from ecGGBP in that it: (i) has a different arrangement of α-helices and β-strands than ecGGBP; (ii) ttGBP1 lacks a $Ca^{2+}$ binding site; and (iii) ttGBP1 has a low sequence identity, e.g. no significant sequence identity, to ecGGBP.

Significance of a given alignment is an important question in constructing sets of sequence homologs has been addressed in the art (e.g., in D. W. Mount, 2001, "Bioinformatics", *Cold Spring Harbor Laboratory Press*, the entire content of which is incorporated herein by reference). One approach is to assess whether the alignment score of a particular sequence pair is significantly different from a random pair of sequences with the same amino composition and gap distribution. The BLAST program generates a list of possible pairs of aligned sequence fragments whose score cannot be improved upon by extending or trimming. For each such "high-scoring segment", HSP, its expectation value, E, that the match is random is reported. For values ≤0.01, the E value corresponds to the classical P value, the probability of the null hypothesis (i.e. probability of a random match). Small values of E (0.01 or less) correspond to significant matches: the closer to 0, the more significant the match (i.e. the probability that the match is random is close to 0).

In the case of aligning ecGGBP (Genbank Accession No. YP_003350022.1) with ttGPB1 (NCBI Accession No. YP_004303.1) the HSP has an E value greater than 1.6. In other words, the alignment of these two sequences shows that they are about as similar as two random and unrelated sequences, e.g., the alignments of these two sequences are indistinguishable from a random alignment.

Here we present the construction of semisynthetic, reagentless, ratiometric fluorescent glucose biosensors based on the hyperthermophilic glucose-binding protein homolog of ttGBP1 identified in *Thermus scotoductus* (tsGBP2). These engineered tsGBP conjugates respond to glucose concentrations in clinically relevant concentration ranges (from ~1 mM in extreme hypoglycemia, to ~100 mM for the hyperosmolar, hyperglycemic condition, with healthy, euglycemic levels at ~6 mM). The thermostability of these proteins exceeds 100° C. Furthermore, the selectivity of tsGBP2 has been engineered such that a sensor with a glucose affinity of about 5.6 mM, which is near-optimal for sensing in the euglycemic concentration range, has an affinity for galactose of about 140 mM (see, e.g., FIG. 5). Fluorescent glucose sensing based on tsGBP may therefore present significant advantages in the development of robust glucose sensors.

Glucose monitoring is essential for the management of diabetes mellitus, a disease that affects at least 366 million people world-wide and is increasing every year. The majority of current glucose-monitoring technologies rely on enzymes for which glucose is one of the substrates. Glucose concentration measurements are therefore subject to variations in second substrate concentrations consumed in the enzyme reaction, such as oxygen in the case of glucose oxidase. Additional complications arise in systems where reaction rates are measured for enzymes immobilized on electrodes. In such arrangements, accuracy is compromised by factors that alter the rate at which glucose arrives at the electrode surface interfere with accuracy, such as hematocrit levels, or surface "fouling" by deposition of proteins and cells in the foreign body response. Ratiometric fluorescent glucose sensors obviate these problems, and accordingly have been incorporated successfully in optodes for continuous glucose monitoring in animals and humans.

In FRS-based sensors, signals arise from reversible binding equilibria of the analyte (ligand) to a receptor. These signals are most precise at ligand concentrations that match the receptor ligand-disassociation constant. Precision is maintained to within ~80% of this maximal level over a concentration range approximately 3-fold above or below this point. Construction of effective FRS therefore requires matching of ligand-binding affinities to the relevant analyte concentrations. Arrays of multiple sensors may have to be used in concert to cover wide concentration ranges. Clinically relevant glucose levels vary approximately 100-fold (from ~1 mM in extreme hypoglycemia, to ~100 mM for the hyperosmolar, hyperglycemic condition, with healthy, euglycemic levels at ~6 mM (American Diabetes Association 2000 Clinical Diabetes, 18; Pasquel 2014 Diabetes Care, 37, 3124-3131), requiring an array of multiple FRS sensors with distinct glucose affinities to report directly on the full range of clinically relevant glucose concentrations with high precision. Here we report a set of appropriately tuned hyperthermostable, glucose-responsive FRSs, constructed by mutating their glucose-binding site.

Immobilization of FRSs on solid surfaces with minimal perturbation of the molecular sensing mechanism is an important step for incorporating biosensors into devices. Immobilization enables retention of the sensor within the sampling element (e.g. optode surface or implanted bead for in vivo sensing applications; or in a sample-handling cartridge for ex vivo sensing). Immobilization also may provide spatial localization to provide the necessary addressability of different elements in a multi-sensor array comprising sensors that differ in their engineered affinities for coverage of a wide range of glucose concentrations, or sensors that each detect distinct analytes.

Ex vivo clinical chemistries such as point-of-care applications require that the FRS is incorporated into a cartridge into which a sample is introduced at the time of measurement. Such "disposables" need to have a long shelf life that preferably does not require temperature control (e.g. refrigeration) for storage or distribution. It is preferable to incorporate immobilized protein in a stable, dried form in such disposables. The inherent resistance to denaturation of thermostable proteins minimizes the need for temperature control during manufacturing and storage, and may extend to the long-term stability of a desiccated state.

The spectral response and thermostability of the robust thermostable glucose FRSs reported here are conserved following site-specific immobilization on beads or other solid substrates. Furthermore, these properties are recovered rapidly upon reconstitution following drying and prolonged storage under accelerated aging conditions. These engineered proteins are therefore useful for the development of robust, high-precision, wide-dynamic range glucose sensing applications, including continuous monitoring, point-of-care, wearable sensor systems.

Biosensors

Biosensors are molecular recognition elements that transduce ligand-binding events into physical detectable signals. Biosensors as detailed herein bind at least one ligand and emit a detectable signal such as fluorescence. A ligand-bound biosensor results in a signal that is different from a signal from the corresponding unbound biosensor. This difference facilitates detection of the at least one ligand and/or determination of ligand concentration. The biosensors may be used without the presence or assistance of other reagents.

The present subject matter provides improved biosensors that rapidly, reliably, and accurately detect and quantify glucose with significant advantages over previous systems. Aspects include a biosensor for glucose, comprising a reporter group that is attached to a glucose-binding protein. The glucose comprises glucose, and the glucose-binding protein includes a domain or region(s) that binds the glucose. The domain or region involved in ligand binding is comprised of a plurality of residues, e.g., non-contiguous amino acids of the ligand-binding protein, which are contact points or sites of contact between the ligand and its cognate ligand-binding protein. The binding of a glucose to the glucose-binding domain of the glucose-binding protein causes a change in signaling by the reporter group. In various implementations, the biosensor may produce a signal when a glucose is bound to the glucose binding domain that is not produced (and/or that is different from a signal that is produced) when the glucose is absent from the glucose binding domain. These biosensors have widespread utility including in clinical, food and beverage, industrial, and environmental settings.

A reporter group that transduces or emits a detectable signal may be attached to the glucose-binding proteins (biosensors) described herein. As used herein, "transduce" means the conversion of ligand occupancy in the binding site of a ligand-binding protein to a detectable signal. Occupancy refers to the state of ligand being bound or not bound to a cognate ligand-binding protein. In embodiments, detectable signal comprises a fluorescent, electrochemical, nuclear magnetic resonance (NMR), or electron paramagnetic resonance (EPR) signal. The reporter group is attached to the glucose-binding protein so that a signal transduced by the reporter group when the glucose-binding protein is bound to glucose differs from a signal transduced by the reporter group when the glucose-binding protein is not bound to glucose. The proteins may be engineered to include a single cysteine to which the detectable label, e.g., a fluorophore is covalently attached. The biosensors are reagentless in that their monitoring mechanism requires neither additional substrates for a signal to develop, nor measurement of substrate consumption or product generation rates to determine glucose concentrations.

Binding of ligand mediates conformational changes in the biosensor, such as hinge-bending motions of the polypeptide. The conformational changes affect the environment of the reporter such that a change in the reporter-generated signal occurs. That is, without ligand bound, the biosensor results in signal generated from the reporter, and when ligand is bound, the signal generated from the reporter changes. The ligand-bound biosensor results in a reporter-generated signal that is different from the unbound biosensor. For example, the spectral shape of the tsGBP2 13C.Acrylodan W244F biosensor changes when the biosensor becomes bound to glucose (see FIGS. 5A-5C, which shows that the spectral shape of this biosensor changes as glucose concentration increases).

In some embodiments, the methods and compositions include a plurality of a single type of biosensor. The biosensors may be identical in structure and function. For example, the biosensors of a single type may have the same polypeptide, the same reporter, and the same ligand affinity.

In other embodiments, the methods and compositions include a plurality of different types of biosensors. A plurality of these different types of biosensors may be arranged or incorporated in a panel. As used herein, a "panel" refers to two or more biosensors. The two or more biosensors may be different from each other. The biosensors may differ in structure and/or function. Biosensors may differ in polypeptide sequence, reporter, ligand affinities, or a combination thereof. Accordingly, there may be different types of biosensors. In some embodiments, each biosensor in the panel comprises the same reporter group. In some embodiments, each biosensor in the panel comprises a different reporter group. The panel may include at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, or at least 100 biosensors.

The panel of biosensors includes at least one sensor element. "Sensor element" refers to a single spot, site, location, or well for the at least one biosensor, to which a sample or aliquot thereof may be applied. The panel may be a composite sensor or an array.

In some embodiments, the panel is a composite sensor. In a composite sensor, each sensor element includes a mixture of two or more different biosensors. In some embodiments, the composite sensor includes one sensor element. In some embodiments, the composite sensor includes two or more sensor elements. In some embodiments, signals are measured from a composite sensor in which the signals arise from one or more biosensors in the sensor element. For example, signals may be measured from a composite sensor in which the signals arise from a subset of the total number of biosensors in the sensor element. For example, signals may be measured from a composite sensor in which the signals arise from two of five biosensors in the sensor element.

In some embodiments, the panel is an array. In an array, each sensor element includes a single type of biosensor. An array comprises a plurality of individually and spatially localized sensor elements. Each sensor element includes a biosensor that is different than or the same as the biosensor of a different sensor element. In some embodiments, signals are measured from an array in which the signals arise separately from two or more selected biosensors in separate sensor elements. An array may comprise a plurality of sensor elements of a variety of sizes and configurations. An array may comprise a plurality of sensor elements arranged linearly. For example, an array may comprise a plurality of micrometer-sized sensor elements arranged in a single row. An array may comprise a plurality of sensor elements arranged in a grid. The grid may be two- or three-dimensional. In some embodiments, the grid is a spatially addressable grid. In some embodiments, the biosensors are incorporated into an array, such as a multichannel or multiplexed array.

The biosensors of the present disclosure can be used in any setting where glucose detection is required or desired, such a medical setting (e.g., determining the level of blood glucose in a subject), environmental setting (e.g., determining the level of glucose in an environmental sample), biological setting (e.g., determining the presence or amount of glucose in a reaction), or in process engineering, such as monitoring the amount of glucose in a fermentation reaction (e.g., a bacterial culture, a yeast culture, beer/wine production, etc.). Other examples include, but are not limited to, uses in the food industry (Suleiman et al, In: Biosensor Design and Application: Mathewson and Finley Eds; American Chemical Society, Washington, D.C. 1992, vol. 511); in clinical chemistry (Wilkins et al., Med. Eng. Phys. 1996, 18, 273-288; Pickup, Tr. Biotech. 1993, 11, 285-291; Meyerhoff et al., Endricon 1966, 6, 51-58; Riklin et al., Nature 1995, 376, 672-675); Willner et al., J. Am. Chem. Soc. 1996, 118, 10321-10322); as the basis for the construction of a fluorescent flow cell containing immobilized ligand binding protein-FAST conjugates (see, e.g., Wilkins et al., Med. Eng. Phys. 1966, 18, 273-288; Pickup, Tr. Biotech. 1993, 11, 285-291; Meyerhoff et al., Endricon. 1966, 6, 51; Group, New Engl. J. Med. 1993, 329, 977-986; Gough et al., Diabetes 1995, 44, 1005-1009); and in an implantable devices.

The biosensors as detailed herein may be administered in a variety of ways known by those of skill in the art, as appropriate for each application. Biosensors may be provided in a solution. The solution may be buffered. Biosensors may be provided in a solution and mixed directly with a sample. In some embodiments, a biosensor is immobilized onto a surface. Biosensors may be immobilized within a disposable cartridge into which a sample may be introduced or applied. Biosensors may be implanted or incorporated in a wearable device. The biosensor may be provided as an optode.

The biosensor may be attached to or incorporated in a wearable device. Wearable devices may include, for example, adhesive strips, patches, and contact lenses. The biosensor may be configured for placement in contact with a subject's skin or mucosal surface. In some embodiments, the biosensor is configured as an adhesive strip. In some embodiments, the biosensor is configured within or on the surface of a contact lens. In some embodiments, the contact lens is formed from a transparent substrate shaped to be worn directly over a subject's eye, as described in, for example, U.S. Pat. No. 8,608,310.

The biosensor may be implanted. The biosensor may be implanted in a subject's body. The biosensor may be implanted in a subject's blood vessel, vein, eye, natural or artificial pancreas, skin, or anywhere in the alimentary canal including the stomach, intestine and esophagus. The biosensor may be implanted in a subject with a microbead. In some embodiments, the biosensor is configured to be implanted in the skin. The biosensor may be implanted in a subject sub-dermally. The biosensor may generate the signal transdermally. In some embodiments, the biosensor may be implanted in a subject with transdermal microbeads, wherein the optical signals can be transmitted remotely between the biosensor and detecting device.

In some embodiments, the biosensor is administered as an optode. As used herein, "optode" refers to an optical fiber with a single biosensor, or a composite biosensor, immobilized at the surface or at the end. An "optode" may also be referred to as an "optrode." In some embodiments, the biosensor is implanted in a subject as an optode. The optode may be incorporated with or into a needle. The optode may be incorporated with a probe such as endoscopy or colonoscopy probes. The optode may be used in a tumor, near a tumor, or at the periphery of a tumor. In some embodiments, the biosensor may be implanted in a subject as an optode, wherein the optical signals can be transmitted between the biosensor and detecting device using physical links. In some embodiments, the biosensor is administered as an optode to a sample or reaction. The optode may be contacted with a sample or reaction. In some embodiments, an optode is used to continuously or episodically monitor a ligand in a sample or reaction.

Methods Of Detecting The Presence Of A Ligand

Provided herein is a method of detecting the presence of a ligand in a sample. The method may include contacting the biosensor with the sample; measuring a signal from the biosensor; and comparing the signal to a ligand-free control. A difference in signal indicates the presence of ligand in the sample.

Also provided herein is a method of detecting the presence of glucose in a sample. The method may include (a) providing a glucose biosensor disclosed herein in which the reporter group is attached the glucose-binding protein so that a signal transduced by the reporter group when the glucose-binding protein is bound to glucose differs from a signal transduced by the reporter group when the glucose-binding protein is not bound to glucose; (b) contacting the biosensor with the test sample under conditions such that the biosensor can bind to glucose present in the test sample; and (c) comparing the signal transduced by the reporter group when the biosensor is contacted with the test sample with the signal transduced by the reporter group when the biosensor is contacted with a glucose-free control sample, wherein a difference in the signal transduced by the reporter group when the biosensor is contacted with the test sample, as compared to when the biosensor is contacted with the control sample, indicates that the test sample contains glucose.

Methods Of Determining The Concentration Of A Ligand

Provided herein is a method of determining the concentration of a ligand in a sample. The method may include contacting the biosensor with the sample; measuring a signal from the biosensor; and comparing the signal to a standard hyperbolic ligand binding curve to determine the concentration of ligand in the test sample. The standard hyperbolic ligand binding curve may be prepared by measuring the signal transduced by the biosensor when contacted with control samples containing known concentrations of ligand.

Another aspect of the present disclosure provides a method of determining the concentration of glucose in a test sample comprising, consisting of, or consisting essentially of: (a) providing a glucose biosensor comprising a glucose biosensor as described herein in which the reporter group is attached the glucose-binding protein so that a signal transduced by the reporter group when the glucose-binding protein is bound to glucose differs from a signal transduced by the reporter group when the glucose-binding protein is not bound to glucose; (b) contacting the biosensor with the test sample under conditions such that the biosensor can bind to glucose present in the test sample; and (c) comparing the signal transduced by the reporter group when the biosensor is contacted with the test sample with a standard, e.g., hyperbolic glucose binding curve prepared by measuring the signal transduced by the reporter group when the biosensor is contacted with control samples containing known quantities of glucose to determine the concentration of glucose in the test sample.

Methods Of Monitoring The Presence Of A Ligand

The present invention is directed to a method of episodically or continuously monitoring the presence of a ligand in a reaction. In certain embodiments, the biosensors may be used in the continuous monitoring of glucose in a reaction. In certain embodiments, the glucose sensors may be used in episodic monitoring of sample aliquots.

The method of episodically or continuously monitoring the presence of a ligand in a reaction may include contacting the biosensor with the reaction; maintaining the reaction under conditions such that the polypeptide is capable of binding ligand present in the reaction; and episodically or continuously monitoring the signal from the biosensor in the reaction.

The method of episodically or continuously monitoring the presence of a ligand in a reaction may include contacting the biosensor with the reaction; maintaining the reaction under conditions such that the polypeptide is capable of binding ligand present in the reaction; episodically or continuously monitoring the signal from the biosensor in the reaction; and comparing the signal to a standard hyperbolic ligand binding curve to determine the concentration of ligand in the test sample. The standard hyperbolic ligand binding curve may be prepared by measuring the signal transduced by the biosensor when contacted with control samples containing known concentrations of ligand.

In some embodiments, the method further includes comparing the signal to a ligand-free control, wherein a difference in signal indicates the presence of ligand in the reaction.

In some embodiments, the method further includes comparing the signal to a standard hyperbolic ligand binding curve to determine the concentration of ligand in the test sample. The standard hyperbolic ligand binding curve may be prepared by measuring the signal transduced by the biosensor when contacted with control samples containing known concentrations of ligand.

Another aspect of the present disclosure provides a method of continuously monitoring the presence of glucose in a reaction comprising, consisting of, or consisting essentially of: (a) providing a glucose biosensor as described herein in which the reporter group is attached the glucose-binding protein so that a signal transduced by the reporter group when the glucose-binding protein is bound to glucose differs from a signal transduced by the reporter group when the glucose-binding protein is not bound to glucose; (b)

maintaining the biosensor within the reaction and under conditions such that the biosensor can bind to glucose present in the reaction; (c) continuously monitoring the signal transduced by the reporter group when the biosensor is contacted with the glucose present in the reaction; and optionally (d) comparing the signal transduced by the reporter group when the biosensor is contacted with the glucose present in the reaction with the signal transduced by the reporter group when the biosensor is contacted with a glucose-free control sample, wherein a difference in the signal transduced by the reporter group when the biosensor is contacted with the glucose present in the reaction, as compared to when the biosensor is contacted with the control sample, indicates glucose is present in the reaction.

Yet another aspect of the present disclosure provides a method of continuously monitoring the concentration of glucose in a reaction comprising, consisting of, or consisting essentially of: (a) providing a glucose biosensor comprising a glucose biosensor as described herein in which the reporter group is attached the glucose-binding protein so that a signal transduced by the reporter group when the glucose-binding protein is bound to glucose differs from a signal transduced by the reporter group when the glucose-binding protein is not bound to glucose; (b) maintaining the biosensor within the reaction under conditions such that the biosensor can bind to glucose present in the reaction; and (c) continuously monitoring the signal transduced by the reporter group when the biosensor is contacted with the glucose present in the reaction; and (d) comparing the signal transduced by the reporter group when the biosensor is contacted with the glucose present in the reaction with a standard hyperbolic glucose binding curve prepared by measuring the signal transduced by the reporter group when the biosensor is contacted with control samples containing known quantities of glucose to determine the concentration of glucose in the reaction.

General Definitions

Unless specifically defined otherwise, all technical and scientific terms used herein shall be taken to have the same meaning as commonly understood by one of ordinary skill in the art (e.g., in cell culture, molecular genetics, and biochemistry).

As used herein, the term "about" in the context of a numerical value or range means ±10% of the numerical value or range recited or claimed, unless the context requires a more limited range.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

A small molecule is a compound that is less than 2000 daltons in mass. The molecular mass of the small molecule is preferably less than 1000 daltons, more preferably less than 600 daltons, e.g., the compound is less than 500 daltons, 400 daltons, 300 daltons, 200 daltons, or 100 daltons.

As used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes/nucleic acids or sequences/amino acids that flank it in its naturally-occurring state. Purified also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

"Subject" as used herein refers to any organism from which a biological sample is obtained. For example, the sample is a biological fluid or tissue. For example, a subject is one who wants or is in need of detecting ligand or determining the concentration of ligand with the herein described biosensors. The subject may be a human or a non-human animal. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be of any age or stage of development, such as, for example, an adult, an adolescent, or an infant.

As used herein, an "expression vector" is a DNA or RNA vector that is capable of effecting expression of one or more polynucleotides. Preferably, the expression vector is also capable of replicating within the host cell. Expression vectors can be either prokaryotic or eukaryotic, and are typically include plasmids. Expression vectors of the present invention include any vectors that function (i.e., direct gene expression) in host cells of the present invention, including in one of the prokaryotic or eukaryotic cells described herein, e.g., gram-positive, gram-negative, pathogenic, non-pathogenic, commensal, cocci, *Bacillus*, or spiral-shaped bacterial cells; archaeal cells; or protozoan, algal, fungi, yeast, plant, animal, vertebrate, invertebrate, arthropod, mammalian, rodent, primate, or human cells. Expression vectors of the present invention contain regulatory sequences such as transcription control sequences, translation control sequences, origins of replication, and other regulatory sequences that are compatible with the host cell and that control the expression of a polynucleotide. In particular, expression vectors of the present invention include transcription control sequences. Transcription control sequences are sequences which control the initiation, elongation, and termination of transcription. Particularly important transcription control sequences are those which control transcription initiation such as promoter, enhancer, operator and repressor sequences. Suitable transcription control sequences include any transcription control sequence that can function in at least one of the cells of the present invention. A variety of such transcription control sequences are known to those skilled in the art.

As used herein, the singular forms "a," "an," and "the" include the plural reference unless the context clearly dictates otherwise. Thus, for example, a reference to "a disease," "a disease state", or "a nucleic acid" is a reference to one or more such embodiments, and includes equivalents thereof known to those skilled in the art and so forth.

As used herein, "pharmaceutically acceptable" carrier or excipient refers to a carrier or excipient that is suitable for use with humans and/or animals without undue adverse side effects (such as toxicity, irritation, and allergic response) commensurate with a reasonable benefit/risk ratio. It can be, e.g., a pharmaceutically acceptable solvent, suspending agent or vehicle, for delivering the instant compounds to the subject.

The term "diagnosis" refers to a determination that a disease is present in the subject. Similarly, the term "prognosis" refers to a relative probability that a certain future outcome may occur in the subject. For example, in the context of the present disclosure, prognosis can refer to the likelihood that an individual will develop a disease, or the likely severity of the disease (e.g., severity of symptoms, rate of functional decline, survival, etc.).

Unless required otherwise by context, the terms "polypeptide" and "protein" are used interchangeably.

A polypeptide or class of polypeptides may be defined by the extent of identity (% identity) of its amino acid sequence to a reference amino acid sequence, or by having a greater % identity to one reference amino acid sequence than to another. A variant of any of genes or gene products disclosed herein may have, e.g., 50%, 55%, 60%, 65%, 70%, 75%, 80%, 85%, 90%, 95%, 96%, 97%, 98%, or 99% sequence identity to the nucleic acid or amino acid sequences described herein. The term "% identity," in the context of two or more nucleic acid or polypeptide sequences, refers to two or more sequences or subsequences that are the same or have a specified percentage of amino acid residues or nucleotides that are the same, when compared and aligned for maximum correspondence, as measured using a sequence comparison algorithm or by visual inspection. For example, % identity is relative to the entire length of the coding regions of the sequences being compared, or the length of a particular fragment or functional domain thereof. Variants as disclosed herein also include homologs, orthologs, or paralogs of the genes or gene products described herein. In some embodiments, variants may demonstrate a percentage of homology or identity, for example, at least about 50%, 55%, 60%, 65%, 70%, 75%, 80%, 85%, 90%, 95%, 96%, 97%, 98%, or 99% identity conserved domains important for biological function, e.g., in a functional domain, e.g. a ligand-binding or catalytic domain.

For sequence comparison, one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Percent identity is determined using BLAST. For the BLAST searches, the following parameters were employed: (1) Expect threshold is 10; (2) Gap cost is Existence: 11 and Extension: 1; (3) The Matrix employed is BLOSUM62; (4) The filter for low complexity regions is "on."

The present invention also provides for functional fragments of the genes or gene products described herein. A fragment of a protein is characterized by a length (number of amino acids) that is less than the length of the full length mature form of the protein. A fragment, in the case of these sequences and all others provided herein, may be a part of the whole that is less than the whole. Moreover, a fragment ranges in size from a single nucleotide or amino acid within a polynucleotide or polypeptide sequence to one fewer nucleotide or amino acid than the entire polynucleotide or polypeptide sequence. Finally, a fragment is defined as any portion of a complete polynucleotide or polypeptide sequence that is intermediate between the extremes defined above.

For example, fragments of any of the proteins or enzymes disclosed herein or encoded by any of the genes disclosed herein can be 10 to 20 amino acids, 10 to 30 amino acids, 10 to 40 amino acids, 10 to 50 amino acids, 10 to 60 amino acids, 10 to 70 amino acids, 10 to 80 amino acids, 10 to 90 amino acids, 10 to 100 amino acids, 50 to 100 amino acids, 75 to 125 amino acids, 100 to 150 amino acids, 150 to 200 amino acids, 200 to 250 amino acids, 250 to 300 amino acids, 300 to 350, 350 to 400 amino acids, or 400 to 425 amino acids. The fragments encompassed in the present subject matter comprise fragments that retain functional fragments. As such, the fragments preferably retain the binding domains that are required or are important for functional activity. Fragments can be determined or generated by using the sequence information herein, and the fragments can be tested for functional activity using standard methods known in the art. For example, the encoded protein can be expressed by any recombinant technology known in the art and the binding activity of the protein can be determined.

As used herein a "biologically active" fragment is a portion of a polypeptide which maintains an activity of a full-length reference polypeptide. Biologically active fragments as used herein exclude the full-length polypeptide. Biologically active fragments can be any size as long as they maintain the defined activity. Preferably, the biologically active fragment maintains at least 10%, at least 50%, at least 75% or at least 90%, of the activity of the full length protein.

Amino acid sequence variants/mutants of the polypeptides of the defined herein can be prepared by introducing appropriate nucleotide changes into a nucleic acid defined herein, or by in vitro synthesis of the desired polypeptide. Such variants/mutants include, for example, deletions, insertions or substitutions of residues within the amino acid sequence. A combination of deletion, insertion and substitution can be made to arrive at the final construct, provided that the final peptide product possesses the desired activity and/or specificity.

Mutant (altered) peptides can be prepared using any technique known in the art. For example, a polynucleotide defined herein can be subjected to in vitro mutagenesis or DNA shuffling techniques as broadly described by Harayama (1998). Products derived from mutated/altered DNA can readily be screened using techniques described herein to determine if they possess, for example, glucose binding activity.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues. In some embodiments, a mutated or modified protein does not comprise any deletions or insertions. In various embodiments, a mutated or modified protein has less than about 10, 9, 8, 7, 6, 5, 4, 3, or 2 deleted or inserted amino acids.

Substitution mutants have at least one amino acid residue in the polypeptide molecule removed and a different residue inserted in its place. Sites may be substituted in a relatively conservative manner in order to maintain activity and/or specificity. Such conservative substitutions are shown in the table below under the heading of "exemplary substitutions."

In certain embodiments, a mutant/variant polypeptide has only, or not more than, one or two or three or four conservative amino acid changes when compared to a naturally occurring polypeptide. Details of conservative amino acid changes are provided in the table below. As the skilled person would be aware, such minor changes can reasonably be predicted not to alter the activity of the polypeptide when expressed in a recombinant cell.

Exemplary Substitutions

| Original Residue | Exemplary Substitutions |
|---|---|
| Alanine (Ala) | Val; Leu; Ile; Gly |
| Arginine (Arg) | Lys |
| Asparagine (Asn) | Gln; His |
| Cysteine (Cys) | Ser |
| Glutamine (Gln) | Asn; His |
| Glutamic Acid (Glu) | Asp |
| Glycine (Gly) | Pro; Ala |
| Histidine (His) | Asn; Gln |
| Isoleucine (Ile) | Leu; Val; Ala |
| Leucine (Leu) | Ile; Val; Met; Ala; Phe |
| Lysine (Lys) | Arg |
| Methionine (Met) | Leu; Phe |
| Phenylalanine (Phe) | Leu; Val; Ala |
| Proline (Pro) | Gly |
| Serine (Ser) | Thr |

-continued

| Original Residue | Exemplary Substitutions |
|---|---|
| Threonine (Thr) | Ser |
| Tryptophan (Trp) | Tyr |
| Tyrosine (Tyr) | Trp; Phe |
| Valine (Val) | Ile; Leu; Met; Phe; Ala |

Mutations can be introduced into a nucleic acid sequence such that the encoded amino acid sequence is altered by standard techniques, such as site-directed mutagenesis and PCR-mediated mutagenesis. Preferably, conservative amino acid substitutions are made at one or more predicted nonessential amino acid residues. A "conservative amino acid substitution" is one in which the amino acid residue is replaced with an amino acid residue having a similar side chain. Families of amino acid residues having similar side chains have been defined in the art. Certain amino acids have side chains with more than one classifiable characteristic. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, tryptophan, cysteine), nonpolar side chains (e.g., alanine, valine, leucine, isoleucine, proline, phenylalanine, methionine, tyrosine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a given polypeptide is replaced with another amino acid residue from the same side chain family. Alternatively, in another embodiment, mutations can be introduced randomly along all or part of a given coding sequence, such as by saturation mutagenesis, and the resultant mutants can be screened for given polypeptide biological activity to identify mutants that retain activity. Conversely, the invention also provides for variants with mutations that enhance or increase the endogenous biological activity. Following mutagenesis of the nucleic acid sequence, the encoded protein can be expressed by any recombinant technology known in the art and the activity/specificity of the protein can be determined. An increase, decrease, or elimination of a given biological activity of the variants disclosed herein can be readily measured by the ordinary person skilled in the art, i.e., by measuring the capability for binding a ligand and/or signal transduction.

In various embodiments, a polypeptide comprises mutations such that 1, 2, 3, 4, 5, 6, 7, 8, 9, or 10, or less than about 10, 9, 8, 7, 6, 5, 4, 3, or 2 amino acids is substituted with a cysteine and/or a lysine.

Polypeptides can be produced in a variety of ways, including production and recovery of natural polypeptides or recombinant polypeptides according to methods known in the art. In one embodiment, a recombinant polypeptide is produced by culturing a cell capable of expressing the polypeptide under conditions effective to produce the polypeptide, such as a host cell defined herein.

Key to the Sequence Listing

| SEQ ID NO | Sequence Name |
|---|---|
| 1 | ttGBP1 [U.S. National Center for Biotechnology Information (NCBI) Accession Nos. YP_004303.1 and WP_011172778.1] |
| 2 | tsGBP2 [U.S. National Center for Biotechnology Information (NCBI) Accession Nos. YP_004202647.1 and WP_015717367.1] |
| 3 | dmGBP3 [U.S. National Center for Biotechnology Information (NCBI) Accession Nos. YP_004171760.1 and WP_013557600.1] |
| 4 | tnGBP4 [U.S. National Center for Biotechnology Information (NCBI) Accession Nos. YP_002534202.1 and WP_015919155.1] |
| 5 | koGBP5 [U.S. National Center for Biotechnology Information (NCBI) Accession No. YP_002941687.1 and WP_015869326.1] |
| 6 | bhGBP6 [U.S. National Center for Biotechnology Information (NCBI) Accession Nos. NP_244712.1 and WP_010899970.1] |
| 7 | smGBP7 [U.S. National Center for Biotechnology Information (NCBI) Accession Nos. YP_001041152.1 and WP_011839435.1] |
| 8 | asGBP8 [U.S. National Center for Biotechnology Information (NCBI) Accession No. YP_831349.1 and WP_011691715.1] |
| 9 | ttGBP1 (with signal peptide replaced with M and a HHHHHH at C-terminus) |
| 10 | tsGBP2 (with signal peptide replaced with M and a GGSHHHHHH at C-terminus) |
| 11 | dmGBP3 (with signal peptide replaced with M and a GGSHHHHHH at C-terminus) |
| 12 | tnGBP4 (with signal peptide replaced with M and a GGSHHHHHH at C-terminus) |
| 13 | koGBP5 (with signal peptide replaced with M and a GGSHHHHHH at C-terminus) |
| 14 | bhGBP6 (with signal peptide replaced with M and a GGSHHHHHH at C-terminus) |
| 15 | smGBP7 (with signal peptide replaced with M and a GGSHHHHHH at C-terminus) |
| 16 | asGBP8 (with signal peptide replaced with M and a GGSHHHHHH at C-terminus) |
| 17 | tsGBP2_C8 (8C substitution mutant with signal peptide replaced with M and a GGSHHHHHH at C-terminus) |
| 18 | tsGBP2_C9 (9C substitution mutant with signal peptide replaced with M and a GGSHHHHHH at C-terminus) |
| 19 | tsGBP2_C12 (12C substitution mutant with signal peptide replaced with M and a GGSHHHHHH at C-terminus) |
| 20 | tsGBP2_C13 (13C substitution mutant with signal peptide replaced with M and a GGSHHHHHH at C-terminus) |
| 21 | tsGBP2_C41 (41C substitution mutant with signal peptide replaced with M and a GGSHHHHHH at C-terminus) |
| 22 | tsGBP2_C42 (42C substitution mutant with signal peptide replaced with M and a GGSHHHHHH at C-terminus) |
| 23 | tsGBP2_C64 (64C substitution mutant with signal peptide replaced with M and a GGSHHHHHH at C-terminus) |
| 24 | tsGBP2_C66 (66C substitution mutant with signal peptide replaced with M and a GGSHHHHHH at C-terminus) |
| 25 | tsGBP2_C119 (119C substitution mutant with signal peptide replaced with M and a GGSHHHHHH at C-terminus) |
| 26 | tsGBP2_C167 (167C substitution mutant with signal peptide replaced with M and a GGSHHHHHH at C-terminus) |
| 27 | tsGBP2_C223 (223C substitution mutant with signal peptide replaced with M and a GGSHHHHHH at C-terminus) |
| 28 | tsGBP2_C224 (224C substitution mutant with signal peptide replaced with M and a GGSHHHHHH at C-terminus) |
| 29 | tsGBP2_C225 (225C substitution mutant with signal peptide replaced with M and a GGSHHHHHH at C-terminus) |
| 30 | tsGBP2_C244 (244C substitution mutant with signal peptide replaced with M and a GGSHHHHHH at C-terminus) |
| 31 | tsGBP2_C277 (cysteine substitution mutant with signal peptide replaced with M and a GGSHHHHHH at C-terminus) |
| 32 | tsGBP2_C278 (278C substitution mutant with signal peptide replaced with M and a GGSHHHHHH at C-terminus) |
| 33 | tsGBP2_C312 (312C substitution mutant with signal peptide replaced with M and a GGSHHHHHH at C-terminus) |
| 34 | tsGBP2_C337 (337C substitution mutant with signal peptide replaced with M and a GGSHHHHHH at C-terminus) |
| 35 | tsGBP2_C348 (348C substitution mutant with signal peptide replaced with M and a GGSHHHHHH at C-terminus) |
| 36 | tsGBP2_C357 (357C substitution mutant with signal peptide replaced with M and a GGSHHHHHH at C-terminus) |
| 37 | tsGBP2.13C.W8F (13C, 8F double substitution mutant) |
| 38 | tsGBP2.13C.W8M (13C, 8M double substitution mutant with signal peptide replaced with M and a GGSHHHHHH at C-terminus) |
| 39 | tsGBP2.13C.W8Y (13C, 8Y double substitution mutant with signal peptide replaced with M and a GGSHHHHHH at C-terminus) |

-continued

| SEQ ID NO | Sequence Name |
|---|---|
| 40 | tsGBP2.13C.W9F (13C 9F double substitution mutant with signal peptide replaced with M and a GGSHHHHHH at C-terminus) |
| 41 | tsGBP2.13C.W9M (13C 9M double substitution mutant with signal peptide replaced with M and a GGSHHHHHH at C-terminus) |
| 42 | tsGBP2.13C.W9Y (13C, 9Y double substitution mutant with signal peptide replaced with M and a GGSHHHHHH at C-terminus) |
| 43 | tsGBP2.13C.Q64N (13C, 64N double substitution mutant with signal peptide replaced with M and a GGSHHHHHH at C-terminus) |
| 44 | tsGBP2.13C.Q64E (13C, 64E double substitution mutant with signal peptide replaced with M and a GGSHHHHHH at C-terminus) |
| 45 | tsGBP2.13C.Q64M (13C, 64M double substitution mutant with signal peptide replaced with M and a GGSHHHHHH at C-terminus) |
| 46 | tsGBP2.13C.H66Q (13C, 66Q double substitution mutant with signal peptide replaced with M and a GGSHHHHHH at C-terminus) |
| 47 | tsGBP2.13C.W244M (13C, 244M double substitution mutant with signal peptide replaced with M and a GGSHHHHHH at C-terminus) |
| 48 | tsGBP2.13C.W244F (13C, 244F double substitution mutant with signal peptide replaced with M and a GGSHHHHHH at C-terminus) |
| 49 | tsGBP2.13C.W244Y (13C, 244Y double substitution mutant with signal peptide replaced with M and a GGSHHHHHH at C-terminus) |
| 50 | tsGBP2.13C.D278N (13C, 278N double substitution mutant with signal peptide replaced with M and a GGSHHHHHH at C-terminus) |
| 51 | tsGBP2.13C.D278S (13C, 278S double substitution mutant with signal peptide replaced with M and a GGSHHHHHH at C-terminus) |
| 52 | tsGBP2.13C.D278L (13C, 278L double substitution mutant with signal peptide replaced with M and a GGSHHHHHH at C-terminus) |
| 53 | tsGBP2.13C.K312M (13C, 312M double substitution mutant with signal peptide replaced with M and a GGSHHHHHH at C-terminus) |
| 54 | tsGBP2.13C.bZif (13C substitution mutant, with bZif fusion, signal peptide replaced with M and a GGSHHHHHH at C-terminus) |
| 55 | tsGBP2.244C.bZif (244C substitution mutant, with bZif fusion with signal peptide replaced with M and a GGSHHHHHH at C-terminus) |
| 56 | tsGBP2.13C_244F.bZif (13C, 244F double substitution mutant, with bZif fusion, signal peptide replaced with M and a GGSHHHHHH at C-terminus) |
| 57 | Exemplary ttGBP1 expression sequence, optimized using OrfOpt |
| 58 | Exemplary tsGBP2 expression sequence, optimized using OrfOpt |
| 59 | Exemplary dmGBP3 expression sequence, optimized using OrfOpt |
| 60 | Exemplary tnGBP4 expression sequence, optimized using OrfOpt |
| 61 | Exemplary koGBP5 expression sequence, optimized using OrfOpt |
| 62 | Exemplary bhGBP6 expression sequence, optimized using OrfOpt |
| 63 | Exemplary smGBP7 expression sequence, optimized using OrfOpt |
| 64 | Exemplary asGBP8 expression sequence, optimized using OrfOpt |
| 65 | Exemplary tsGBP2_C8 expression sequence, optimized using OrfOpt |
| 66 | Exemplary tsGBP2_C9 expression sequence, optimized using OrfOpt |
| 67 | Exemplary tsGBP2_C12 expression sequence, optimized using OrfOpt |
| 68 | Exemplary tsGBP2_C13 expression sequence, optimized using OrfOpt |
| 69 | Exemplary tsGBP2_C41 expression sequence, optimized using OrfOpt |
| 70 | Exemplary tsGBP2_C42 expression sequence, optimized using OrfOpt |
| 71 | Exemplary tsGBP2_C64 expression sequence, optimized using OrfOpt |
| 72 | Exemplary tsGBP2_C66 expression sequence, optimized using OrfOpt |
| 73 | Exemplary tsGBP2_C119 expression sequence, optimized using OrfOpt |
| 74 | Exemplary tsGBP2_C167 expression sequence, optimized using OrfOpt |
| 75 | Exemplary tsGBP2_C223 expression sequence, optimized using OrfOpt |
| 76 | Exemplary tsGBP2_C224 expression sequence, optimized using OrfOpt |
| 77 | Exemplary tsGBP2_C225 expression sequence, optimized using OrfOpt |
| 78 | Exemplary tsGBP2_C244 expression sequence, optimized using OrfOpt |
| 79 | Exemplary tsGBP2_C277 expression sequence, optimized using OrfOpt |
| 80 | Exemplary tsGBP2_C278 expression sequence, optimized using OrfOpt |
| 81 | Exemplary tsGBP2_C312 expression sequence, optimized using OrfOpt |
| 82 | Exemplary tsGBP2_C337 expression sequence, optimized using OrfOpt |
| 83 | Exemplary tsGBP2_C348 expression sequence, optimized using OrfOpt |
| 84 | Exemplary tsGBP2_C357 expression sequence, optimized using OrfOpt |
| 85 | Exemplary tsGBP2.13C.W8F expression sequence, optimized using OrfOpt |
| 86 | Exemplary tsGBP2.13C.W8M expression sequence, optimized using OrfOpt |
| 87 | Exemplary tsGBP2.13C.W8Y expression sequence, optimized using OrfOpt |
| 88 | Exemplary tsGBP2.13C.W9F expression sequence, optimized using OrfOpt |
| 89 | Exemplary tsGBP2.13C.W9M expression sequence, optimized using OrfOpt |
| 90 | Exemplary tsGBP2.13C.W9Y expression sequence, optimized using OrfOpt |
| 91 | Exemplary tsGBP2.13C.Q64N expression sequence, optimized using OrfOpt |
| 92 | Exemplary tsGBP2.13C.Q64E expression sequence, optimized using OrfOpt |
| 93 | Exemplary tsGBP2.13C.Q64M expression sequence, optimized using OrfOpt |
| 94 | Exemplary tsGBP2.13C.H66Q expression sequence, optimized using OrfOpt |
| 95 | Exemplary tsGBP2.13C.W244M expression sequence, optimized using OrfOpt |
| 96 | Exemplary tsGBP2.13C.W244F expression sequence, optimized using OrfOpt |

-continued

| SEQ ID NO | Sequence Name |
|---|---|
| 97 | Exemplary tsGBP2.13C.W244Y expression sequence, optimized using OrfOpt |
| 98 | Exemplary tsGBP2.13C.D278N expression sequence, optimized using OrfOpt |
| 99 | Exemplary tsGBP2.13C.D278S expression sequence, optimized using OrfOpt |
| 100 | Exemplary tsGBP2.13C.D278L expression sequence, optimized using OrfOpt |
| 101 | Exemplary tsGBP2.13C.K312M expression sequence, optimized using OrfOpt |
| 102 | Exemplary tsGBP2.13C.bZif expression sequence, optimized using OrfOpt |
| 103 | Exemplary tsGBP2.244C.bZif expression sequence, optimized using OrfOpt |
| 104 | Exemplary tsGBP2.13C_244F.bZif expression sequence, optimized using OrfOpt |
| 105 | βZif |
| 106 | ZF-QNK |
| 107 | Hexahistidine Tag |
| 108 | Hexalysine Tag |
| 109 | ttGBP1 (with signal peptide replaced with M) |
| 110 | tsGBP2 (with signal peptide replaced with M) |
| 111 | dmGBP3 (with signal peptide replaced with M) |
| 112 | tnGBP4 (with signal peptide replaced with M) |
| 113 | koGBP5 (with signal peptide replaced with M) |
| 114 | bhGBP6 (with signal peptide replaced with M) |
| 115 | smGBP7 (with signal peptide replaced with M) |
| 116 | asGBP8 (with signal peptide replaced with M) |
| 117 | ecGGBP (with signal peptide removed) |
| 118 | ttGGBP (NCBI Accession Nos. YP_003852930.1 and WP_013298803.1) |
| 119 | stGGBP (NCBI Accession No. WP_001036943.1) |
| 120 | chyGGBP (NCBI Accession Nos. WP_013402088.1 and YP_003991244.1) |
| 121 | cobGGBP (NCBI Accession Nos. WP_013289482.1 and YP_003839461.1) |
| 122 | pspGGBP (NCBI Accession Nos. WP_015735911.1 and YP_003243743.1) |
| 123 | csaGGBP (NCBI Accession Nos. WP_013273028.1 and YP_003822565.1) |
| 124 | bprGGBP (NCBI Accession Nos. WP_013280279.1 and YP_003830205.1) |
| 125 | rinGGBP_A (NCBI Accession Nos. WP_006855636.1 and YP_007778116.1) |
| 126 | fprGGBP (NCBI Accession Nos. WP_015536639.1 and YP_007799070.1) |
| 127 | cljGGBP (NCBI Accession No. CLJU_c08950) |
| 128 | cauGGBP (NCBI Accession No. CAETHG_2989) |
| 129 | rinGGBP_B (NCBI Accession Nos. WP_006855628.1 and YP_007778124.1) |
| 130 | erhGGBP (NCBI Accession Nos. WP_003775352.1 and YP_004561181.1) |
| 131 | ereGGBP (NCBI Accession Nos. WP_012741392.1 and YP_002936409.1) |
| 132 | GGSHHHHHH |
| 133 | WWXXXXE (conserved sequence) |
| 134 | WWXXXE (conserved sequence) |
| 135 | XQVXH (conserved sequence) |
| 136 | HRXNV (conserved sequence) |
| 137 | GDWX (conserved sequence) |
| 138 | DXFXXP (conserved sequence) |
| 139 | KGSIXA (conserved sequence) |
| 140 | ecTrx |
| 141 | Adaptor0 |
| 142 | Adaptor1.0 |
| 143 | Adaptor2.0a |
| 144 | Adaptor2.0b |
| 145 | Adaptor3.0 |
| 146 | Adaptor4.0 |
| 147 | Adaptor5.0 |
| 148 | Adaptor6.0 |
| 149 | Adaptor7.0 |
| 150 | Adaptor8.0 |
| 151 | Adaptor9.0 |
| 152 | Adaptor10.0 |
| 153 | Adaptor11.0 |
| 154 | Adaptor12.0 |
| 155 | Adaptor13 .0 |
| 156 | Adaptor14.0 |
| 157 | Adaptor15.0 |
| 158 | Adaptor16.0 |

The terms "bZif" and "βZif" are used synonymously herein.

Exemplary amino acid sequences are listed below for convenience.

ttGBP1
(SEQ ID NO: 9)
MKLEIFSWWAGDEGPALEALIRLYKQKYPGVEVINATVTGGAGVNARAVL
KTRMLGGDPPDTFQVHAGMELIGTWVVANRMEDLSALFRQEGWLQAFPKG
LIDLISYKGGIWSVPVNIHRSNVMWYLPAKLKGWGVNPPRTWDKFLATAQ
TLKQKGLEAPLALGENWTQQHLWESVALAVLGPDDWNNLWNGKLKFTDPK
AVRAWEVFGRVLDAANKDAAGLSWQQAVDRVVQGKAAFNIMGDWAAGYMT
TTLKLKPGTDFAWAPSPGTQGVFMMLSDSFGLPKGAKNRQNAINWLRLVG
SKEGQDTSNPLKGSIAARLDSDPSKYNAYGQSAMRDWRSNRIVGSLVHGA
VAPESFMSQFGTVMEIFLQTRNPQAAANAAQAIADQVGLGRLGQHHHHHH
** tsGBP2
(SEQ ID NO: 10)
MKLEIFSWWAGDEGPALEALIRLYKQKYPGVEVINATVTGGAGVNAKAVL
KTRMLGGDPPDTFQVHAGQELIGTWVVADRMEDLTSLFRQEGWLQAFPKG
LIDLLSYKGGIWSVPVNIHRSNVMWYIPAKLKEWGVTPPKTWAEFLATAQ
TLKRKGLEAPLALGENWTQQHLWESVALATLGADGWNNLWSGKLKFTDPK
AVAVWETFGKVLDAANKDAAGLSWQQAVDRVVQGKAAFNIMGDWAAGYMS
TTLKLKPGTDFAWTPSPGTSGIFMMLSDSFGLPKGAKNRQNAINWLKLVG
SKEGQDTFNPLKGSIAARLDSDPAKYNAYGQSAMKDWKSNRIVGSLVHGA
VAPESFMSQFGTVMEIFLQSRNPQAAANAAQAIANQVGLGRGGSHHHHHH dmGBP3
(SEQ ID NO: 11)
MKLEIFSWWSGDEGPALEALVKLYKQKYPSVDVVNATVAGGAGTNAKAVL
KTRMLGGDPPDSFQAHAGQELIGTWVVANRMEDLSSLFKSEGWTTKFPKD
LLPLISSKGGIWSVPVNVHRSNVMWYIPANLKKWGVTAPKTWDQFLTTAK
TLKTKNVTPLALGENWTQQHLWESVAVGTLGAQGWQNLWSGKLKFTDPKV
VKVWDTFGKVLDATNKDASGLSWQQATDRVVNGQAAFNIMGDWAAGYLST
TKKLKPGTGFGWAPSPSTSGTFIFLADSFGLPKGAKDRAEALSWLKLLGS
KQGQDTFNPLKGSIAARVDSDLSKYSTYSQSAAKDWKSNKIVGSLTHGAV
APESFTSTFGTVIDAFVASRNAQVAAATTQQLADKAGLGKGGSHHHHHH tnGBP4
(SEQ ID NO: 12)
MLEIFSWWTAGGEAEALEALIKVFNKYYPDVEVINATVAGGAGTNAKAVL
KTRILGGNPPDSFQVHAGMELIDTYVIPGYMTPITNLLEQWGVMDKFPKG
ILEMASYEGEIYSIPVNVHRGNVVFYNKKIAEEIGMNEPPKTWDEFIMYL
QKAKEKGYVGLALGDKNKWTALHLFETILLGVLGPNDYNGLWKGEVSFND
PRIRRAFEIMNKLLDYVNEDHAALAWQDATRLVYEGKALANVMGDWAEGY
LKSVGWEPGKDFGWFAVPETQNAFMVVSDTFGLPKNAPHKENAVKWLKVV
ASVEGQDAFNPIKGSIPARLDADRSKYDIYLQWSMEDFATKALTPSIAHG
SAAPEGFVTTLNDIINRFVTTRDIDSALEELLMAAEDEGYLVEGGSHHHH
HH

-continued koGBP5
(SEQ ID NO: 13)
MLEIFSWWTGGGEEEGLLALFDVFHKYYPDVEIINATVAGGAGTNAKAVL
KTRMLGGNPPDSFQVHGGMELIDTYVVTGMMEPITDLLEEWGIIDKFPED
ILKIASYKGEVYSIPVNVHRGNVVFYNKAILEEVGIEKVPSTWPEFIEVL
KKIKKAGYIPLALGDKNKWTATHLFEDILLSTLGPYNYNGLWNGRTSFEH
QGVKEALEIFKELMNYVNPNHASLTWQDATLLVFEGKAAFNVMGDWAEGY
LKTLGWTPGKEFGWMVVPGTKGSFMVVTDTFGLPKNAPHRENAIKWLKII
SSVEGQDTFNPIKGSIPARIDADRSLYDDYLIWSMDDFATNALCPSIIHG
SAAPEAFVTALNDTINMFITRKDVKKALKEIIYAAEDYLEGGSHHHHHH bhGBP6
(SEQ ID NO: 14)
MLEIFSWWTGAGEEDGLLALIELFEEKHPEIEVDNAAVAGGAGTNAKAVL
TSRMQGNDPPGTFQVHGGAELNDSWVAAGQMDPLNDLFEAEGWADKFPEE
LIELVSKDGNIYSVPVNIHRGNVLWYNTEIFEEHGLEVPTTFEEFFDVAD
ALQEAGVTPLALGDREPWAATHLFETVLLGTLGADDYNKLWSGEVGMDDP
RVEEAAEIFIRMLDYVNEDHSSRNWQDASQLVAQGEAAMNVMGDWAKGYF
VNDLNLAVKEDFGWAATPGTEGTFMVITDTFGLPTGVENPEVVKSFLAVL
GSQEGQDAFNPLKGSIPARVDADVSKYDEYGQETIEDFKSAELSPSLAHG
SAANEGFLTQVNQAINIFVTQKDVDSFVDSLKQYQPGGSHHHHHH smGBP7
(SEQ ID NO: 15)
MELVIYHWWTAGGEREAINAVFQVFKQKYPNIQIVENPVAGGAGSVMKSV
IIGLLAAGTPPDTFQVHAGAELKEYVDAGYLAPIDDIWSKLGLDKVIPST
LQVMAKFNGHYYAVPIDVHRSNVLWYNPKIFNELGIINKFGDPRNWSVDT
LLQVARYIKQQRPDIAPIALASRNKWPVTHLFEVLLANAGGPETYVKFFT
GKFNYNDPNDPVVQTVKKVLTVMATMAKEGLFNSNHPELTWDQAAALVAE
GKAAMFIHGDWVAGYYIANNYKYGKDWAAAPFPKNIFILLSDAFELPKNA
PHPEAAKDWLMVVGSKEAQEKFNLIKGSIPARTDVSPKYPDPYRPETAED
FQKSTLIPSAVHGGIAKEAFMTDLHNILTSMLTAVSVGTPVDNAVNTALA
QILQSVKTSGLASFWKGYTIDYFITKRGGSHHHHHH asGBP8
(SEQ ID NO: 16)
MKLEITSWWTSGSEADALNVLIDGVKAAKPGLSVDNAAVSGGGGANARQA
LAARLQAGSPPDAWQVHPAGQLKSYVDGGQVADLTDLWTEGDWASQMPKD
VAEAQQVDGKYYTVPIGVHRGNVLWTNPAVLSKANVTIDADAGIDGLISS
LEQVQASGTTPLALGDKDIFASSQLLESLIMSRAGADNWTKLFTSEYSFD
APEVKQALEDYKTILSFANKDHSAITWDEAAKKMADGEAAVNLMGDWAYG
ELLNAGKKPGTDFAWVAFPGKEDIFDYVGDGFSIPANNIPHAEAARAWLK
TLMDPKIQTEFAAKKGSIPAVTSADISGLSEYQQEAAKSLASGAVVSSLA
HAQAAGAEFAQTYADAVSTFNGSGNTDAFIASMTQAQKTQLGGSHHHHHH tsGBP2 Cysteine Scans
tsGBP2_C8
(SEQ ID NO: 17)
MKLEIFSCWAGDEGPALEALIRLYKQKYPGVEVINATVTGGAGVNAKAVL
KTRMLGGDPPDTFQVHAGQELIGTWVVADRMEDLTSLFRQEGWLQAFPKG -continued LIDLLSYKGGIWSVPVNIHRSNVMWYIPAKLKEWGVTPPKTWAEFLATAQ
TLKRKGLEAPLALGENW’TQQHLWESVALATLGADGWNNLWSGKLKFTDPK
AVAVWETFGKVLDAANKDAAGLSWQQAVDRVVQGKAAFNIMGDWAAGYMS
TTLKLKPGTDFAWTPSPGTSGIFMMLSDSFGLPKGAKNRQNAINWLKLVG
SKEGQDTFNPLKGSIAARLDSDPAKYNAYGQSAMKDWKSNRIVGSLVHGA
VAPESFMSQFGTVMEIFLQSRNPQAAANAAQAIANQVGLGRGGSHHHHHH
** tsGBP2_C9

(SEQ ID NO: 18)
MKLEIFSWCAGDEGPALEALIRLYKQKYPGVEVINATVTGGAGVNAKAVL
KTRMLGGDPPDTFQVHAGQELIGTWVVADRMEDLTSLFRQEGWLQAFPKG
LIDLLSYKGGIWSVPVNIHRSNVMWYIPAKLKEWGVTPPKTWAEFLATAQ
TLKRKGLEAPLALGENWTQQHLWESVALATLGADGWNNLWSGKLKFTDPK
AVAVWETFGKVLDAANKDAAGLSWQQAVDRVVQGKAAFNIMGDWAAGYMS
TTLKLKPGTDFAWTPSPGTSGIFMMLSDSFGLPKGAKNRQNAINWLKLVG
SKEGQDTFNPLKGSIAARLDSDPAKYNAYGQSAMKDWKSNRIVGSLVHGA
VAPESFMSQFGTVMEIFLQSRNPQAAANAAQAIANQVGLGRGGSHHHHHH
** tsGBP2_C12

(SEQ ID NO: 19)
MKLEIFSWWAGCEGPALEALIRLYKQKYPGVEVINATVTGGAGVNAKAVL
KTRMLGGDPPDTFQVHAGQELIGTWVVADRMEDLTSLFRQEGWLQAFPKG
LIDLLSYKGGIWSVPVNIHRSNVMWYIPAKLKEWGVTPPKTWAEFLATAQ
TLKRKGLEAPLALGENWTQQHLWESVALATLGADGWNNLWSGKLKFTDPK
AVAVWETFGKVLDAANKDAAGLSWQQAVDRVVQGKAAFNIMGDWAAGYMS
TTLKLKPGTDFAWTPSPGTSGIFMMLSDSFGLPKGAKNRQNAINWLKLVG
SKEGQDTFNPLKGSIAARLDSDPAKYNAYGQSAMKDWKSNRIVGSLVHGA
VAPESFMSQFGTVMEIFLQSRNPQAAANAAQAIANQVGLGRGGSHHHHHH
** tsGBP2_C13

(SEQ ID NO: 20)
MKLEIFSWWAGDCGPALEALIRLYKQKYPGVEVINATVTGGAGVNAKAVL
KTRMLGGDPPDTFQVHAGQELIGTWVVADRMEDLTSLFRQEGWLQAFPKG
LIDLLSYKGGIWSVPVNIHRSNVMWYIPAKLKEWGVTPPKTWAEFLATAQ
TLKRKGLEAPLALGENWTQQHLWESVALATLGADGWNNLWSGKLKFTDPK
AVAVWETFGKVLDAANKDAAGLSWQQAVDRVVQGKAAFNIMGDWAAGYMS
TTLKLKPGTDFAWTPSPGTSGIFMMLSDSFGLPKGAKNRQNAINWLKLVG
SKEGQDTFNPLKGSIAARLDSDPAKYNAYGQSAMKDWKSNRIVGSLVHGA
VAPESFMSQFGTVMEIFLQSRNPQAAANAAQAIANQVGLGRGGSHHHHHH
** tsGBP2_C41

(SEQ ID NO: 21)
MKLEIFSWWAGDEGPALEALIRLYKQKYPGVEVINATVTGCAGVNAKAVL
KTRMLGGDPPDTFQVHAGQELIGTWVVADRMEDLTSLFRQEGWLQAFPKG

-continued

LIDLLSYKGGIWSVPVNIHRSNVMWYIPAKLKEWGVTPPKTWAEFLATAQ
TLKRKGLEAPLALGENWTQQHLWESVALATLGADGWNNLWSGKLKFTDPK
AVAVWETFGKVLDAANKDAAGLSWQQAVDRVVQGKAAFNIMGDWAAGYMS
TTLKLKPGTDFAWTPSPGTSGIFMMLSDSFGLPKGAKNRQNAINWLKLVG
SKEGQDTFNPLKGSIAARLDSDPAKYNAYGQSAMKDWKSNRIVGSLVHGA
VAPESFMSQFGTVMEIFLQSRNPQAAANAAQAIANQVGLGRGGSHHHHHH
** tsGBP2_C42

(SEQ ID NO: 22)
MKLEIFSWWAGDEGPALEALIRLYKQKYPGVEVINATVTGGCGVNAKAVL
KTRMLGGDPPDTFQVHAGQELIGTWVVADRMEDLTSLFRQEGWLQAFPKG
LIDLLSYKGGIWSVPVNIHRSNVMWYIPAKLKEWGVTPPKTWAEFLATAQ
TLKRKGLEAPLALGENWTQQHLWESVALATLGADGWNNLWSGKLKFTDPK
AVAVWETFGKVLDAANKDAAGLSWQQAVDRVVQGKAAFNIMGDWAAGYMS
TTLKLKPGTDFAWTPSPGTSGIFMMLSDSFGLPKGAKNRQNAINWLKLVG
SKEGQDTFNPLKGSIAARLDSDPAKYNAYGQSAMKDWKSNRIVGSLVHGA
VAPESFMSQFGTVMEIFLQSRNPQAAANAAQAIANQVGLGRGGSHHHHHH
** tsGBP2_C64

(SEQ ID NO: 23)
MKLEIFSWWAGDEGPALEALIRLYKQKYPGVEVINATVTGGAGVNAKAVL
KTRMLGGDPPDTFCVHAGQELIGTWVVADRMEDLTSLFRQEGWLQAFPKG
LIDLLSYKGGIWSVPVNIHRSNVMWYIPAKLKEWGVTPPKTWAEFLATAQ
TLKRKGLEAPLALGENWTQQHLWESVALATLGADGWNNLWSGKLKFTDPK
AVAVWETFGKVLDAANKDAAGLSWQQAVDRVVQGKAAFNIMGDWAAGYMS
TTLKLKPGTDFAWTPSPGTSGIFMMLSDSFGLPKGAKNRQNAINWLKLVG
SKEGQDTFNPLKGSIAARLDSDPAKYNAYGQSAMKDWKSNRIVGSLVHGA
VAPESFMSQFGTVMEIFLQSRNPQAAANAAQAIANQVGLGRGGSHHHHHH
** tsGBP2_C66

(SEQ ID NO: 24)
MKLEIFSWWAGDEGPALEALIRLYKQKYPGVEVINATVTGGAGVNAKAVL
KTRMLGGDPPDTFQVCAGQELIGTWVVADRMEDLTSLFRQEGWLQAFPKG
LIDLLSYKGGIWSVPVNIHRSNVMWYIPAKLKEWGVTPPKTWAEFLATAQ
TLKRKGLEAPLALGENWTQQHLWESVALATLGADGWNNLWSGKLKFTDPK
AVAVWETFGKVLDAANKDAAGLSWQQAVDRVVQGKAAFNIMGDWAAGYMS
TTLKLKPGTDFAWTPSPGTSGIFMMLSDSFGLPKGAKNRQNAINWLKLVG
SKEGQDTFNPLKGSIAARLDSDPAKYNAYGQSAMKDWKSNRIVGSLVHGA
VAPESFMSQFGTVMEIFLQSRNPQAAANAAQAIANQVGLGRGGSHHHHHH
** tsGBP2_C119

(SEQ ID NO: 25)
MKLEIFSWWAGDEGPALEALIRLYKQKYPGVEVINATVTGGAGVNAKAVL
KTRMLGGDPPDTFQVHAGQELIGTWVVADRMEDLTSLFRQEGWLQAFPKG
LIDLLSYKGGIWSVPVNICRSNVMWYIPAKLKEWGVTPPKTWAEFLATAQ

-continued

TLKRKGLEAPLALGENWTQQHLWESVALATLGADGWNNLWSGKLKFTDPK
AVAVWETFGKVLDAANKDAAGLSWQQAVDRVVQGKAAFNIMGDWAAGYMS
TTLKLKPGTDFAWTPSPGTSGIFMMLSDSFGLPKGAKNRQNAINWLKLVG
SKEGQDTFNPLKGSIAARLDSDPAKYNAYGQSAMKDWKSNRIVGSLVHGA
VAPESFMSQFGTVMEIFLQSRNPQAAANAAQAIANQVGLGRGGSHHHHHH
** tsGBP2_C167

(SEQ ID NO: 26)

MKLEIFSWWAGDEGPALEALIRLYKQKYPGVEVINATVTGGAGVNAKAVL
KTRMLGGDPPDTFQVHAGQELIGTWVVADRMEDLTSLFRQEGWLQAFPKG
LIDLLSYKGGIWSVPVNIHRSNVMWYIPAKLKEWGVTPPKTWAEFLATAQ
TLKRKGLEAPLALGENCTQQHLWESVALATLGADGWNNLWSGKLKFTDPK
AVAVWETFGKVLDAANKDAAGLSWQQAVDRVVQGKAAFNIMGDWAAGYMS
TTLKLKPGTDFAWTPSPGTSGIFMMLSDSFGLPKGAKNRQNAINWLKLVG
SKEGQDTFNPLKGSIAARLDSDPAKYNAYGQSAMKDWKSNRIVGSLVHGA
VAPESFMSQFGTVMEIFLQSRNPQAAANAAQAIANQVGLGRGGSHHHHHH
** tsGBP2_C223

(SEQ ID NO: 27)

MKLEIFSWWAGDEGPALEALIRLYKQKYPGVEVINATVTGGAGVNAKAVL
KTRMLGGDPPDTFQVHAGQELIGTWVVADRMEDLTSLFRQEGWLQAFPKG
LIDLLSYKGGIWSVPVNIHRSNVMWYIPAKLKEWGVTPPKTWAEFLATAQ
TLKRKGLEAPLALGENWTQQHLWESVALATLGADGWNNLWSGKLKFTDPK
AVAVWETFGKVLDAANKDAAGLCWQQAVDRVVQGKAAFNIMGDWAAGYMS
TTLKLKPGTDFAWTPSPGTSGIFMMLSDSFGLPKGAKNRQNAINWLKLVG
SKEGQDTFNPLKGSIAARLDSDPAKYNAYGQSAMKDWKSNRIVGSLVHGA
VAPESFMSQFGTVMEIFLQSRNPQAAANAAQAIANQVGLGRGGSHHHHHH
** tsGBP2_C224

(SEQ ID NO: 28)

MKLEIFSWWAGDEGPALEALIRLYKQKYPGVEVINATVTGGAGVNAKAVL
KTRMLGGDPPDTFQVHAGQELIGTWVVADRMEDLTSLFRQEGWLQAFPKG
LIDLLSYKGGIWSVPVNIHRSNVMWYIPAKLKEWGVTPPKTWAEFLATAQ
TLKRKGLEAPLALGENWTQQHLWESVALATLGADGWNNLWSGKLKFTDPK
AVAVWETFGKVLDAANKDAAGLSCQQAVDRVVQGKAAFNIMGDWAAGYMS
TTLKLKPGTDFAWTPSPGTSGIFMMLSDSFGLPKGAKNRQNAINWLKLVG
SKEGQDTFNPLKGSIAARLDSDPAKYNAYGQSAMKDWKSNRIVGSLVHGA
VAPESFMSQFGTVMEIFLQSRNPQAAANAAQAIANQVGLGRGGSHHHHHH
** tsGBP2_C225

(SEQ ID NO: 29)

MKLEIFSWWAGDEGPALEALIRLYKQKYPGVEVINATVTGGAGVNAKAVL
KTRMLGGDPPDTFQVHAGQELIGTWVVADRMEDLTSLFRQEGWLQAFPKG
LIDLLSYKGGIWSVPVNIHRSNVMWYIPAKLKEWGVTPPKTWAEFLATAQ

-continued

TLKRKGLEAPLALGENWTQQHLWESVALATLGADGWNNLWSGKLKFTDPK
AVAVWETFGKVLDAANKDAAGLSWCQAVDRVVQGKAAFNIMGDWAAGYMS
TTLKLKPGTDFAWTPSPGTSGIFMMLSDSFGLPKGAKNRQNAINWLKLVG
SKEGQDTFNPLKGSIAARLDSDPAKYNAYGQSAMKDWKSNRIVGSLVHGA
VAPESFMSQFGTVMEIFLQSRNPQAAANAAQAIANQVGLGRGGSHHHHHH
** tsGBP2_C244

(SEQ ID NO: 30)

MKLEIFSWWAGDEGPALEALIRLYKQKYPGVEVINATVTGGAGVNAKAVL
KTRMLGGDPPDTFQVHAGQELIGTWVVADRMEDLTSLFRQEGWLQAFPKG
LIDLLSYKGGIWSVPVNIHRSNVMWYIPAKLKEWGVTPPKTWAEFLATAQ
TLKRKGLEAPLALGENWTQQHLWESVALATLGADGWNNLWSGKLKFTDPK
AVAVWETFGKVLDAANKDAAGLSWQQAVDRVVQGKAAFNIMGDCAAGYMS
TTLKLKPGTDFAWTPSPGTSGIFMMLSDSFGLPKGAKNRQNAINWLKLVG
SKEGQDTFNPLKGSIAARLDSDPAKYNAYGQSAMKDWKSNRIVGSLVHGA
VAPESFMSQFGTVMEIFLQSRNPQAAANAAQAIANQVGLGRGGSHHHHHH
** tsGBP2_C277

(SEQ ID NO: 31)

MKLEIFSWWAGDEGPALEALIRLYKQKYPGVEVINATVTGGAGVNAKAVL
KTRMLGGDPPDTFQVHAGQELIGTWVVADRMEDLTSLFRQEGWLQAFPKG
LIDLLSYKGGIWSVPVNIHRSNVMWYIPAKLKEWGVTPPKTWAEFLATAQ
TLKRKGLEAPLALGENWTQQHLWESVALATLGADGWNNLWSGKLKFTDPK
AVAVWETFGKVLDAANKDAAGLSWQQAVDRVVQGKAAFNIMGDWAAGYMS
TTLKLKPGTDFAWTPSPGTSGIFMMLCDSFGLPKGAKNRQNAINWLKLVG
SKEGQDTFNPLKGSIAARLDSDPAKYNAYGQSAMKDWKSNRIVGSLVHGA
VAPESFMSQFGTVMEIFLQSRNPQAAANAAQAIANQVGLGRGGSHHHHHH
** tsGBP2_C278

(SEQ ID NO: 32)

MKLEIFSWWAGDEGPALEALIRLYKQKYPGVEVINATVTGGAGVNAKAVL
KTRMLGGDPPDTFQVHAGQELIGTWVVADRMEDLTSLFRQEGWLQAFPKG
LIDLLSYKGGIWSVPVNIHRSNVMWYIPAKLKEWGVTPPKTWAEFLATAQ
TLKRKGLEAPLALGENWTQQHLWESVALATLGADGWNNLWSGKLKFTDPK
AVAVWETFGKVLDAANKDAAGLSWQQAVDRVVQGKAAFNIMGDWAAGYMS
TTLKLKPGTDFAWTPSPGTSGIFMMLSCSFGLPKGAKNRQNAINWLKLVG
SKEGQDTFNPLKGSIAARLDSDPAKYNAYGQSAMKDWKSNRIVGSLVHGA
VAPESFMSQFGTVMEIFLQSRNPQAAANAAQAIANQVGLGRGGSHHHHHH
** tsGBP2_C312

(SEQ ID NO: 33)

MKLEIFSWWAGDEGPALEALIRLYKQKYPGVEVINATVTGGAGVNAKAVL
KTRMLGGDPPDTFQVHAGQELIGTWVVADRMEDLTSLFRQEGWLQAFPKG
LIDLLSYKGGIWSVPVNIHRSNVMWYIPAKLKEWGVTPPKTWAEFLATAQ
TLKRKGLEAPLALGENWTQQHLWESVALATLGADGWNNLWSGKLKFTDPK

-continued

AVAVWETFGKVLDAANKDAAGLSWQQAVDRVVQGKAAFNIMGDWAAGYMS

TTLKLKPGTDFAWTPSPGTSGIFMMLSDSFGLPKGAKNRQNAINWLKLVG

SKEGQDTFNPLCGSIAARLDSDPAKYNAYGQSAMKDWKSNRIVGSLVHGA

VAPESFMSQFGTVMEIFLQSRNPQAAANAAQAIANQVGLGRGGSHHHHHH

** tsGBP2 C337

(SEQ ID NO: 34)

MKLEIFSWWAGDEGPALEALIRLYKQKYPGVEVINATVTGGAGVNAKAVL

KTRMLGGDPPDTFQVHAGQELIGTWVVADRMEDLTSLFRQEGWLQAFPKG

LIDLLSYKGGIWSVPVNIHRSNVMWYIPAKLKEWGVTPPKTWAEFLATAQ

TLKRKGLEAPLALGENWTQQHLWESVALATLGADGWNNLWSGKLKFTDPK

AVAVWETFGKVLDAANKDAAGLSWQQAVDRVVQGKAAFNIMGDWAAGYMS

TTLKLKPGTDFAWTPSPGTSGIFMMLSDSFGLPKGAKNRQNAINWLKLVG

SKEGQDTFNPLKGSIAARLDSDPAKYNAYGQSAMKDCKSNRIVGSLVHGA

VAPESFMSQFGTVMEIFLQSRNPQAAANAAQAIANQVGLGRGGSHHHHHH

** tsGBP2_C348

(SEQ ID NO: 35)

MKLEIFSWWAGDEGPALEALIRLYKQKYPGVEVINATVTGGAGVNAKAVL

KTRMLGGDPPDTFQVHAGQELIGTWVVADRMEDLTSLFRQEGWLQAFPKG

LIDLLSYKGGIWSVPVNIHRSNVMWYIPAKLKEWGVTPPKTWAEFLATAQ

TLKRKGLEAPLALGENWTQQHLWESVALATLGADGWNNLWSGKLKFTDPK

AVAVWETFGKVLDAANKDAAGLSWQQAVDRVVQGKAAFNIMGDWAAGYMS

TTLKLKPGTDFAWTPSPGTSGIFMMLSDSFGLPKGAKNRQNAINWLKLVG

SKEGQDTFNPLKGSIAARLDSDPAKYNAYGQSAMKDWKSNRIVGSLVCGA

VAPESFMSQFGTVMEIFLQSRNPQAAANAAQAIANQVGLGRGGSHHHHHH

** tsGBP2_C357

(SEQ ID NO: 36)

MKLEIFSWWAGDEGPALEALIRLYKQKYPGVEVINATVTGGAGVNAKAVL

KTRMLGGDPPDTFQVHAGQELIGTWVVADRMEDLTSLFRQEGWLQAFPKG

LIDLLSYKGGIWSVPVNIHRSNVMWYIPAKLKEWGVTPPKTWAEFLATAQ

TLKRKGLEAPLALGENWTQQHLWESVALATLGADGWNNLWSGKLKFTDPK

AVAVWETFGKVLDAANKDAAGLSWQQAVDRVVQGKAAFNIMGDWAAGYMS

TTLKLKPGTDFAWTPSPGTSGIFMMLSDSFGLPKGAKNRQNAINWLKLVG

SKEGQDTFNPLKGSIAARLDSDPAKYNAYGQSAMKDWKSNRIVGSLVHGA

VAPESFCSQFGTVMEIFLQSRNPQAAANAAQAIANQVGLGRGGSHHHHHH

** tsGBP2 13C Affinity Mutants tsGBP2.13C.W8F (SEQ ID NO: 37)

MKLEIFSFWAGDCGPALEALIRLYKQKYPGVEVINATVTGGAGVNAKAVL

KTRMLGGDPPDTFQVHAGQELIGTWVVADRMEDLTSLFRQEGWLQAFPKG

LIDLLSYKGGIWSVPVNIHRSNVMWYIPAKLKEWGVTPPKTWAEFLATAQ

TLKRKGLEAPLALGENWTQQHLWESVALATLGADGWNNLWSGKLKFTDPK

-continued

AVAVWETFGKVLDAANKDAAGLSWQQAVDRVVQGKAAFNIMGDWAAGYMS

TTLKLKPGTDFAWTPSPGTSGIFMMLSDSFGLPKGAKNRQNAINWLKLVG

SKEGQDTFNPLKGSIAARLDSDPAKYNAYGQSAMKDWKSNRIVGSLVHGA

VAPESFMSQFGTVMEIFLQSRNPQAAANAAQAIANQVGLGRGGSHHHHHH

** sGBP2.13C.W8M (SEQ ID NO: 38)

MKLEIFSMWAGDCGPALEALIRLYKQKYPGVEVINATVTGGAGVNAKAVL

KTRMLGGDPPDTFQVHAGQELIGTWVVADRMEDLTSLFRQEGWLQAFPKG

LIDLLSYKGGIWSVPVNIHRSNVMWYIPAKLKEWGVTPPKTWAEFLATAQ

TLKRKGLEAPLALGENWTQQHLWESVALATLGADGWNNLWSGKLKFTDPK

AVAVWETFGKVLDAANKDAAGLSWQQAVDRVVQGKAAFNIMGDWAAGYMS

TTLKLKPGTDFAWTPSPGTSGIFMMLSDSFGLPKGAKNRQNAINWLKLVG

SKEGQDTFNPLKGSIAARLDSDPAKYNAYGQSAMKDWKSNRIVGSLVHGA

VAPESFMSQFGTVMEIFLQSRNPQAAANAAQAIANQVGLGRGGSHHHHHH

** tsGBP2.13C.W8Y (SEQ ID NO: 39)

MKLEIFSYWAGDCGPALEALIRLYKQKYPGVEVINATVTGGAGVNAKAVL

KTRMLGGDPPDTFQVHAGQELIGTWVVADRMEDLTSLFRQEGWLQAFPKG

LIDLLSYKGGIWSVPVNIHRSNVMWYIPAKLKEWGVTPPKTWAEFLATAQ

TLKRKGLEAPLALGENWTQQHLWESVALATLGADGWNNLWSGKLKFTDPK

AVAVWETFGKVLDAANKDAAGLSWQQAVDRVVQGKAAFNIMGDWAAGYMS

TTLKLKPGTDFAWTPSPGTSGIFMMLSDSFGLPKGAKNRQNAINWLKLVG

SKEGQDTFNPLKGSIAARLDSDPAKYNAYGQSAMKDWKSNRIVGSLVHGA

VAPESFMSQFGTVMEIFLQSRNPQAAANAAQAIANQVGLGRGGSHHHHHH

** tsGBP2.13C.W9F (SEQ ID NO: 40)

MKLEIFSWFAGDCGPALEALIRLYKQKYPGVEVINATVTGGAGVNAKAVL

KTRMLGGDPPDTFQVHAGQELIGTWVVADRMEDLTSLFRQEGWLQAFPKG

LIDLLSYKGGIWSVPVNIHRSNVMWYIPAKLKEWGVTPPKTWAEFLATAQ

TLKRKGLEAPLALGENWTQQHLWESVALATLGADGWNNLWSGKLKFTDPK

AVAVWETFGKVLDAANKDAAGLSWQQAVDRVVQGKAAFNIMGDWAAGYMS

TTLKLKPGTDFAWTPSPGTSGIFMMLSDSFGLPKGAKNRQNAINWLKLVG

SKEGQDTFNPLKGSIAARLDSDPAKYNAYGQSAMKDWKSNRIVGSLVHGA

VAPESFMSQFGTVMEIFLQSRNPQAAANAAQAIANQVGLGRGGSHHHHHH

** tsGBP2.13C.W9M (SEQ ID NO: 41)

MKLEIFSWMAGDCGPALEALIRLYKQKYPGVEVINATVTGGAGVNAKAVL

KTRMLGGDPPDTFQVHAGQELIGTWVVADRMEDLTSLFRQEGWLQAFPKG

LIDLLSYKGGIWSVPVNIHRSNVMWYIPAKLKEWGVTPPKTWAEFLATAQ

TLKRKGLEAPLALGENWTQQHLWESVALATLGADGWNNLWSGKLKFTDPK

-continued

AVAVWETFGKVLDAANKDAAGLSWQQAVDRVVQGKAAFNIMGDWAAGYMS

TTLKLKPGTDFAWTPSPGTSGIFMMLSDSFGLPKGAKNRQNAINWLKLVG

SKEGQDTFNPLKGSIAARLDSDPAKYNAYGQSAMKDWKSNRIVGSLVHGA

VAPESFMSQFGTVMEIFLQSRNPQAAANAAQAIANQVGLGRGGSHHHHHH

** tsGBP2.13C.W9Y (SEQ ID NO: 42)

MKLEIFSWYAGDCGPALEALIRLYKQKYPGVEVINATVTGGAGVNAKAVL

KTRMLGGDPPDTFQVHAGQELIGTWVVADRMEDLTSLFRQEGWLQAFPKG

LIDLLSYKGGIWSVPVNIHRSNVMWYIPAKLKEWGVTPPKTWAEFLATAQ

TLKRKGLEAPLALGENWTQQHLWESVALATLGADGWNNLWSGKLKFTDPK

AVAVWETFGKVLDAANKDAAGLSWQQAVDRVVQGKAAFNIMGDWAAGYMS

TTLKLKPGTDFAWTPSPGTSGIFMMLSDSFGLPKGAKNRQNAINWLKLVG

SKEGQDTFNPLKGSIAARLDSDPAKYNAYGQSAMKDWKSNRIVGSLVHGA

VAPESFMSQFGTVMEIFLQSRNPQAAANAAQAIANQVGLGRGGSHHHHHH

** tsGBP2.13C.Q64N (SEQ ID NO: 43)

MKLEIFSWWAGDCGPALEALIRLYKQKYPGVEVINATVTGGAGVNAKAVL

KTRMLGGDPPDTFNVHAGQELIGTWVVADRMEDLTSLFRQEGWLQAFPKG

LIDLLSYKGGIWSVPVNIHRSNVMWYIPAKLKEWGVTPPKTWAEFLATAQ

TLKRKGLEAPLALGENWTQQHLWESVALATLGADGWNNLWSGKLKFTDPK

AVAVWETFGKVLDAANKDAAGLSWQQAVDRVVQGKAAFNIMGDWAAGYMS

TTLKLKPGTDFAWTPSPGTSGIFMMLSDSFGLPKGAKNRQNAINWLKLVG

SKEGQDTFNPLKGSIAARLDSDPAKYNAYGQSAMKDWKSNRIVGSLVHGA

VAPESFMSQFGTVMEIFLQSRNPQAAANAAQAIANQVGLGRGGSHHHHHH

** tsGBP2.13C.Q64E (SEQ ID NO: 44)

MKLEIFSWWAGDCGPALEALIRLYKQKYPGVEVINATVTGGAGVNAKAVL

KTRMLGGDPPDTFEVHAGQELIGTWVVADRMEDLTSLFRQEGWLQAFPKG

LIDLLSYKGGIWSVPVNIHRSNVMWYIPAKLKEWGVTPPKTWAEFLATAQ

TLKRKGLEAPLALGENWTQQHLWESVALATLGADGWNNLWSGKLKFTDPK

AVAVWETFGKVLDAANKDAAGLSWQQAVDRVVQGKAAFNIMGDWAAGYMS

TTLKLKPGTDFAWTPSPGTSGIFMMLSDSFGLPKGAKNRQNAINWLKLVG

SKEGQDTFNPLKGSIAARLDSDPAKYNAYGQSAMKDWKSNRIVGSLVHGA

VAPESFMSQFGTVMEIFLQSRNPQAAANAAQAIANQVGLGRGGSHHHHHH

** tsGBP2.13C.Q64M (SEQ ID NO: 45)

MKLEIFSWWAGDCGPALEALIRLYKQKYPGVEVINATVTGGAGVNAKAVL

KTRMLGGDPPDTFMVHAGQELIGTWVVADRMEDLTSLFRQEGWLQAFPKG

LIDLLSYKGGIWSVPVNIHRSNVMWYIPAKLKEWGVTPPKTWAEFLATAQ

TLKRKGLEAPLALGENWTQQHLWESVALATLGADGWNNLWSGKLKFTDPK

AVAVWETFGKVLDAANKDAAGLSWQQAVDRVVQGKAAFNIMGDWAAGYMS

-continued

TTLKLKPGTDFAWTPSPGTSGIFMMLSDSFGLPKGAKNRQNAINWLKLVG

SKEGQDTFNPLKGSIAARLDSDPAKYNAYGQSAMKDWKSNRIVGSLVHGA

VAPESFMSQFGTVMEIFLQSRNPQAAANAAQAIANQVGLGRGGSHHHHHH

** tsGBP2.13C.H66Q (SEQ ID NO: 46)

MKLEIFSWWAGDCGPALEALIRLYKQKYPGVEVINATVTGGAGVNAKAVL

KTRMLGGDPPDTFQVQAGQELIGTWVVADRMEDLTSLFRQEGWLQAFPKG

LIDLLSYKGGIWSVPVNIHRSNVMWYIPAKLKEWGVTPPKTWAEFLATAQ

TLKRKGLEAPLALGENWTQQHLWESVALATLGADGWNNLWSGKLKFTDPK

AVAVWETFGKVLDAANKDAAGLSWQQAVDRVVQGKAAFNIMGDWAAGYMS

TTLKLKPGTDFAWTPSPGTSGIFMMLSDSFGLPKGAKNRQNAINWLKLVG

SKEGQDTFNPLKGSIAARLDSDPAKYNAYGQSAMKDWKSNRIVGSLVHGA

VAPESFMSQFGTVMEIFLQSRNPQAAANAAQAIANQVGLGRGGSHHHHHH

** tsGBP2.13C.W244M (SEQ ID NO: 47)

MKLEIFSWWAGDCGPALEALIRLYKQKYPGVEVINATVTGGAGVNAKAVL

KTRMLGGDPPDTFQVHAGQELIGTWVVADRMEDLTSLFRQEGWLQAFPKG

LIDLLSYKGGIWSVPVNIHRSNVMWYIPAKLKEWGVTPPKTWAEFLATAQ

TLKRKGLEAPLALGENWTQQHLWESVALATLGADGWNNLWSGKLKFTDPK

AVAVWETFGKVLDAANKDAAGLSWQQAVDRVVQGKAAFNIMGDMAAGYMS

TTLKLKPGTDFAWTPSPGTSGIFMMLSDSFGLPKGAKNRQNAINWLKLVG

SKEGQDTFNPLKGSIAARLDSDPAKYNAYGQSAMKDWKSNRIVGSLVHGA

VAPESFMSQFGTVMEIFLQSRNPQAAANAAQAIANQVGLGRGGSHHHHHH

** tsGBP2.13C.W244F (SEQ ID NO: 48)

MKLEIFSWWAGDCGPALEALIRLYKQKYPGVEVINATVTGGAGVNAKAVL

KTRMLGGDPPDTFQVHAGQELIGTWVVADRMEDLTSLFRQEGWLQAFPKG

LIDLLSYKGGIWSVPVNIHRSNVMWYIPAKLKEWGVTPPKTWAEFLATAQ

TLKRKGLEAPLALGENWTQQHLWESVALATLGADGWNNLWSGKLKFTDPK

AVAVWETFGKVLDAANKDAAGLSWQQAVDRVVQGKAAFNIMGDFAAGYMS

TTLKLKPGTDFAWTPSPGTSGIFMMLSDSFGLPKGAKNRQNAINWLKLVG

SKEGQDTFNPLKGSIAARLDSDPAKYNAYGQSAMKDWKSNRIVGSLVHGA

VAPESFMSQFGTVMEIFLQSRNPQAAANAAQAIANQVGLGRGGSHHHHHH

** tsGBP2.13C.W244Y (SEQ ID NO: 49)

MKLEIFSWWAGDCGPALEALIRLYKQKYPGVEVINATVTGGAGVNAKAVL

KTRMLGGDPPDTFQVHAGQELIGTWVVADRMEDLTSLFRQEGWLQAFPKG

LIDLLSYKGGIWSVPVNIHRSNVMWYIPAKLKEWGVTPPKTWAEFLATAQ

TLKRKGLEAPLALGENWTQQHLWESVALATLGADGWNNLWSGKLKFTDPK

AVAVWETFGKVLDAANKDAAGLSWQQAVDRVVQGKAAFNIMGDYAAGYMS

-continued

TTLKLKPGTDFAWTPSPGTSGIFMMLSDSFGLPKGAKNRQNAINWLKLVG

SKEGQDTFNPLKGSIAARLDSDPAKYNAYGQSAMKDWKSNRIVGSLVHGA

VAPESFMSQFGTVMEIFLQSRNPQAAANAAQAIANQVGLGRGGSHHHHHH

** tsGBP2.13C.D278N (SEQ ID NO: 50)

MKLEIFSWWAGDCGPALEALIRLYKQKYPGVEVINATVTGGAGVNAKAVL

KTRMLGGDPPDTFQVHAGQELIGTWVVADRMEDLTSLFRQEGWLQAFPKG

LIDLLSYKGGIWSVPVNIHRSNVMWYIPAKLKEWGVTPPKTWAEFLATAQ

TLKRKGLEAPLALGENWTQQHLWESVALATLGADGWNNLWSGKLKFTDPK

AVAVWETFGKVLDAANKDAAGLSWQQAVDRVVQGKAAFNIMGDWAAGYMS

TTLKLKPGTDFAWTPSPGTSGIFMMLSNSFGLPKGAKNRQNAINWLKLVG

SKEGQDTFNPLKGSIAARLDSDPAKYNAYGQSAMKDWKSNRIVGSLVHGA

VAPESFMSQFGTVMEIFLQSRNPQAAANAAQAIANQVGLGRGGSHHHHHH

** tsGBP2.13C.D278S (SEQ ID NO: 51)

MKLEIFSWWAGDCGPALEALIRLYKQKYPGVEVINATVTGGAGVNAKAVL

KTRMLGGDPPDTFQVHAGQELIGTWVVADRMEDLTSLFRQEGWLQAFPKG

LIDLLSYKGGIWSVPVNIHRSNVMWYIPAKLKEWGVTPPKTWAEFLATAQ

TLKRKGLEAPLALGENWTQQHLWESVALATLGADGWNNLWSGKLKFTDPK

AVAVWETFGKVLDAANKDAAGLSWQQAVDRVVQGKAAFNIMGDWAAGYMS

TTLKLKPGTDFAWTPSPGTSGIFMMLSSSFGLPKGAKNRQNAINWLKLVG

SKEGQDTFNPLKGSIAARLDSDPAKYNAYGQSAMKDWKSNRIVGSLVHGA

VAPESFMSQFGTVMEIFLQSRNPQAAANAAQAIANQVGLGRGGSHHHHHH

** tsGBP2.13C.D278L (SEQ ID NO: 52)

MKLEIFSWWAGDCGPALEALIRLYKQKYPGVEVINATVTGGAGVNAKAVL

KTRMLGGDPPDTFQVHAGQELIGTWVVADRMEDLTSLFRQEGWLQAFPKG

LIDLLSYKGGIWSVPVNIHRSNVMWYIPAKLKEWGVTPPKTWAEFLATAQ

TLKRKGLEAPLALGENWTQQHLWESVALATLGADGWNNLWSGKLKFTDPK

AVAVWETFGKVLDAANKDAAGLSWQQAVDRVVQGKAAFNIMGDWAAGYMS

TTLKLKPGTDFAWTPSPGTSGIFMMLSLSFGLPKGAKNRQNAINWLKLVG

SKEGQDTFNPLKGSIAARLDSDPAKYNAYGQSAMKDWKSNRIVGSLVHGA

VAPESFMSQFGTVMEIFLQSRNPQAAANAAQAIANQVGLGRGGSHHHHHH

** tsGBP2.13C.K312M (SEQ ID NO: 53)

MKLEIFSWWAGDCGPALEALIRLYKQKYPGVEVINATVTGGAGVNAKAVL

KTRMLGGDPPDTFQVHAGQELIGTWVVADRMEDLTSLFRQEGWLQAFPKG

LIDLLSYKGGIWSVPVNIHRSNVMWYIPAKLKEWGVTPPKTWAEFLATAQ

TLKRKGLEAPLALGENWTQQHLWESVALATLGADGWNNLWSGKLKFTDPK

AVAVWETFGKVLDAANKDAAGLSWQQAVDRVVQGKAAFNIMGDWAAGYMS

TTLKLKPGTDFAWTPSPGTSGIFMMLSDSFGLPKGAKNRQNAINWLKLVG

-continued

SKEGQDTFNPLMGSIAARLDSDPAKYNAYGQSAMKDWKSNRIVGSLVHGA

VAPESFMSQFGTVMEIFLQSRNPQAAANAAQAIANQVGLGRGGSHHHHHH

** bZif Fusions tsGBP2.13C.bZif (SEQ ID NO: 54)

MKLEIFSWWAGDCGPALEALIRLYKQKYPGVEVINATVTGGAGVNAKAVL

KTRMLGGDPPDTFQVHAGQELIGTWVVADRMEDLTSLFRQEGWLQAFPKG

LIDLLSYKGGIWSVPVNIHRSNVMWYIPAKLKEWGVTPPKTWAEFLATAQ

TLKRKGLEAPLALGENWTQQHLWESVALATLGADGWNNLWSGKLKFTDPK

AVAVWETFGKVLDAANKDAAGLSWQQAVDRVVQGKAAFNIMGDWAAGYMS

TTLKLKPGTDFAWTPSPGTSGIFMMLSDSFGLPKGAKNRQNAINWLKLVG

SKEGQDTFNPLKGSIAARLDSDPAKYNAYGQSAMKDWKSNRIVGSLVHGA

VAPESFMSQFGTVMEIFLQSRNPQAAANAAQAIANQVGLGRGGSGGSTGE

KPYKCPECGKSFSRSGGSHHHHHH** tsGBP2.244C.bZif (SEQ ID NO: 55)

MKLEIFSWWAGDEGPALEALIRLYKQKYPGVEVINATVTGGAGVNAKAVL

KTRMLGGDPPDTFQVHAGQELIGTWVVADRMEDLTSLFRQEGWLQAFPKG

LIDLLSYKGGIWSVPVNIHRSNVMWYIPAKLKEWGVTPPKTWAEFLATAQ

TLKRKGLEAPLALGENWTQQHLWESVALATLGADGWNNLWSGKLKFTDPK

AVAVWETFGKVLDAANKDAAGLSWQQAVDRVVQGKAAFNIMGDCAAGYMS

TTLKLKPGTDFAWTPSPGTSGIFMMLSDSFGLPKGAKNRQNAINWLKLVG

SKEGQDTFNPLKGSIAARLDSDPAKYNAYGQSAMKDWKSNRIVGSLVHGA

VAPESFMSQFGTVMEIFLQSRNPQAAANAAQAIANQVGLGRGGSGGSTGE

KPYKCPECGKSFSRSGGSHHHHHH** tsGBP2.13C_244F.bZif (SEQ ID NO: 56)

MKLEIFSWWAGDCGPALEALIRLYKQKYPGVEVINATVTGGAGVNAKAVL

KTRMLGGDPPDTFQVHAGQELIGTWVVADRMEDLTSLFRQEGWLQAFPKG

L1DLLSYKGGIWSVPVNIHRSNVMWYIPAKLKEWGVTPPKTWAEFLATAQ

TLKRKGLEAPLALGENWTQQHLWESVALATLGADGWNNLWSGKLKFTDPK

AVAVWETFGKVLDAANKDAAGLSWQQAVDRVVQGKAAFNIMGDFAAGYMS

TTLKLKPGTDFAWTPSPGTSG1FMMLSDSFGLPKGAKNRQNAINWLKLVG

SKEGQDTFNPLKGSIAARLDSDPAKYNAYGQSAMKDWKSNRIVGSLVHGA

VAPESFMSQFGTVME1FLQSRNPQAAANAAQAIANQVGLGRGGSGGSTGE

KPYKCPECGKSFSRSGGSHHHHHH**

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1

Fluorescently Responsive Sensor Engineering Phases

The engineering of FRSs can be divided into five phases:

1. Binding protein discovery. A set of glucose-binding protein sequence homologs is identified. Accurate assignment of their ligand-binding function requires application of a prediction method that incorporates information encoded in the experimentally determined three-dimensional structure of known periplasmic glucose-binding proteins.
2. Experimental lead validation. Synthetic genes are constructed, which are optimized for heterologous expression in *Escherichia coli* of one or more predicted glucose-binding protein sequences. The glucose-binding properties and thermostabilities of the corresponding expressed, purified proteins are evaluated.
3. Engineering of fluorescent responses. Semisynthetic fluorescent conjugates of the experimentally validated leads are constructed by first attaching single fluorophores to single cysteine mutants. The effect of glucose binding on the fluorescence emission properties of those conjugates is evaluated. The spectral properties of a subset of responsive fluorophores is improved using a double-labeling strategy in which a second fluorophore is site-specifically attached to a small domain fused to the N- or C-terminus to establish ngmFRET. Those singly or doubly labeled conjugates that evince strong, ratiometric responses are selected as FRSs for use in sensing applications.
4. Affinity tuning. Single or multiple mutations are introduced by site-directed mutagenesis to alter the glucose-binding affinities of glucose-responsive FRSs. A set of FRS variants is selected that together cover the clinical glucose concentration range with high accuracy.
5. Device integration. FRSs are immobilized in the sampling component of the analytical device in a manner that preserves their fluorescent response and glucose affinity. Long-term storage conditions are established.

Example 2

Sensor Engineering Phase 1: Identification of a Family of Periplasmic Glucose-Binding Proteins Homologs Using Structurally Assisted Function Evaluation As a first step in constructing robust glucose sensor candidates, we examined bacterial genomic sequences to identify periplasmic glucose-binding protein sequences in known (hyper)thermophiles. Homologs from such organisms are likely to encode thermostable proteins. Analysis of enzyme families has shown that overall sequence identity below ~60% is a weak predictor of function conservation (Todd, 2001, *J. Mol. Biol.,* 307, 1113-1143; Tian, 2003, *J. Mol. Biol.,* 333, 863-882). Furthermore, functional assignments based on sequence homology alone are known to be particularly problematic in the PBP superfamily. For instance, PBPs that by overall sequence identity are predicted to bind oligopeptides were found to bind oligosaccharides. Enzyme functional assignments are improved greatly if a sequence selection filter based on conservation of catalytic residues identified from protein structures is included. Such catalytic residues comprise a subset of all the residues that contact an enzyme substrate or inhibitor. In the case of the PBPs, functional selection filters need to take into account all the protein-ligand contacts that encode the ligand-binding function. Accordingly, we have developed a structurally assisted functional evaluation (SAFE) method to identify PBP sequence homologs with accurately predicted function. The SAFE homolog search method consists of five steps:

1. Sequence homolog set is collected using the BLAST sequence alignment tool (Altschul et al., 1990, *J Mol Biol,* 215, 403-10), starting with *Thermus thermophilus* periplasmic glucose-galactose binding protein (ttGBP1) sequence as a seed. The following BLAST parameters: (1) Expect threshold is 10.0; (2) Gap cost is Existence: 11 and Extension: 1; (3) The Matrix employed is BLOSUM62; (4) The filter for low complexity regions is "on." Permissive settings are used, such that pairwise hits are required to have a minimum of only 20% sequence identity with the seed sequence. The lengths of the hit and seed are mutually constrained such that the alignment covers at least 70% within each partner. This set of sequences defines a universe of possible glucose-binding proteins without accurately assigning function.
2. Structure-based encoding of biological function. A primary complementary surface comprising the protein residues that form hydrogen bonds and van der Waals contacts with the bound glucose is defined using computer-assisted, visual inspection of the three-dimensional structure of the *Thermus thermophilus*-glucose complex (Cuneo et al., 2006, *J Biol Chem,* 284, 33217-23). This definition specifies residue positions and their permitted amino acid identity. Multiple amino acid identities are permitted at each position to encode functionally equivalent residues. This definition establishes a search filter for the accurate prediction of glucose-binding proteins within the universe of sequence homologs collected in (1).
3. Accurate sequence alignment. Tools such as ClustalW (Chenna et al., 2003, *Nucleic Acids Res,* 31, 3497-500) are used to construct an accurate alignment of all the sequence homologs. The ttGBP1 seed sequence is included in this alignment. This multiple sequence alignment establishes the equivalent positions of the ttGBP1 PCS in each sequence homolog.
4. Function evaluation. The glucose-binding properties of each of the aligned sequence homologs is determined by measuring their compliance with the PCS sequence filter. A "Hamming distance", H, is assigned for each homolog, which specifies the degree of sequence identity of all the residues at the aligned PCS positions. A value of H=0 indicates that the identities of all the residues at the aligned PCS positions match the amino acid(s) allowed in the PCS search filter; H>0, indicates that one or more aligned positions have disallowed residues. Sequences for which H=0 are predicted to encode glucose-binding proteins.
5. Selection of representative SAFE homologs. The sequence homologs are ordered by (a) identity with the seed PCS, as measured by the Hamming distance, (b) fractional overall sequence identity with the seed sequence. A subset for sequences with H=0, sampling the fractional overall sequence identity is selected for experimental verification.

These steps are encoded in the ProteinHunter software tool, which encodes the flow of execution, applies the PCS search filter, and visualizes the results, and handles organism annotations such as thermophilicity, and Gram stain status.

The ProteinHunter package always executes BLAST searches, with the following command "blastall -p blastp -m 8 -b 50000 -d %s -i <INPUT FILE>-o <OUTPUT FILE>"

where <INPUT FILE> and <OUTPUT FILE> specify the input and output files, respectively for a given calculation. This command executes the BLAST alignment program for protein sequences with default parameters, intrinsically set by the program. The BLAST program version is 2.2.24.

The ProteinHunter package always executes multiple sequence alignments with the following command "clustalwinfile=<INPUTFILE>-outfile=<OUTPUTFILE>-align -quiet"

This command executes the CLUSTALW multi-sequence alignment program for protein sequences. There are no user-specified parameter settings that alter the alignment behavior of the program. The CLUSTALW program version is 2.1.

Annotated genomic and plasmid sequences of 5062 prokaryotes were obtained from the National Center of Biotechnology Information (ftp://ftp.ncbi.nih.gov/genomes/Bacteria/all.gbk.tar.gz). The protein sequence for the *Thermus thermophiles* glucose-galactose binding protein (ttGBP1) was extracted from the protein structure file 2b3b (Cuneo et al., 2006, J Biol Chem, 284, 33217-23), and used as the seed sequence for the BLAST search described above. A total of 1120 sequence homologs from 736 genomes were identified, of which 140 had PCS residues that satisfied the PCS filter.

Figures 3A, 3B:
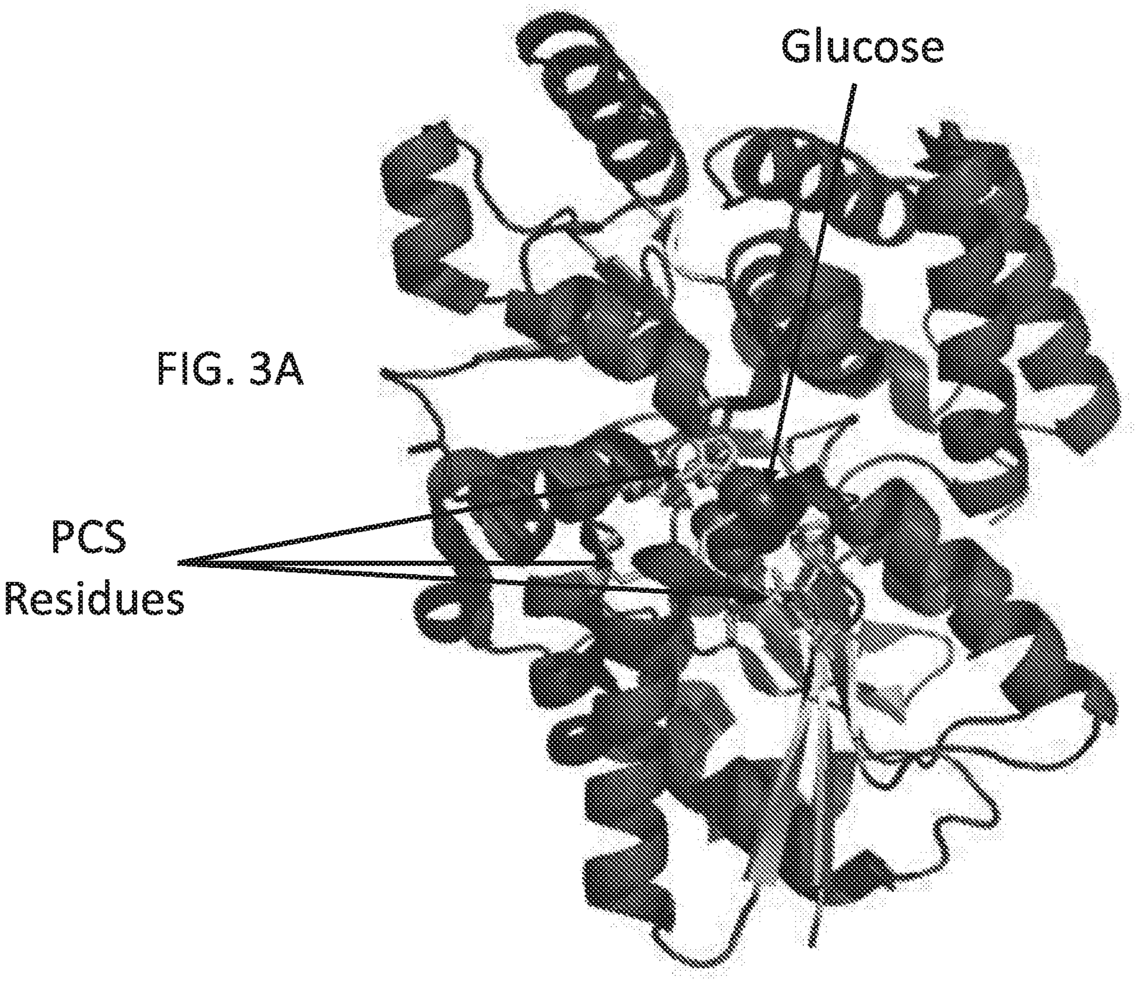
FIG. 3A is the structure of the *Thermus thermophilus* glucose-galactose binding protein (ttGBP1), including the glucose complex [PDB identifier 2b3b (Cuneo et al. 2006 J Biol Chem, 284, 33217-23, incorporated herein by reference)].
FIG. 3B is a table containing the PCS sequence filter used to identify the subset of glucose-binding proteins within a family of sequence ttGBP1 homologs. Note redundancies in the allowed residues at each position (the first amino acid listed corresponds to the wild-type ttGBP1 sequence). Positions are numbered as in ttGBP1 (SEQ ID NO: 9 or 109).

In ttGBP1, glucose binding is encoded by a PCS comprising eleven residues. This PCS consists of four tryptophan residues three of which form hydrogen bonds to either the hydroxyls (W9 and W224) or the pyranose ring (W8), the fourth tryptophan forms extensive van der Waals interactions with the pyranose ring (W244). The other seven residues (E13, Q64, H66, H119, D278, K312, and H348) form hydrogen bonds with all the glucose hydroxyls (FIGS. 3A and B; Table 1). A PCS filter specifying multiple amino acids at these 11 positions was used to predict glucose-binding proteins (FIG. 3B). A total of 140 homologs were predicted to encode glucose-binding proteins, on the basis of their Hamming distance scores (H=0). The overall sequence identities of these homologs relative to the ttGBP1 seed varied from 100% to 22% (Table 2). One of these hits (line 97, Table 2) is the glucose-binding protein that was identified originally in *Pseudomonas aeruginosa* (Adewoye and Worobec, 2000, *Gene,* 253, 323-30, incorporated herein by reference). This protein has a lysine at position 66, instead of the H66 in ttGBP1. Of the eleven PCS positions, residue 66 is the most diverse with three different hydrogen-bond donating amino acids occurring at the following frequencies: H, 47.9%; K, 42.1%; W, 8.6%; N, 1.4%. The only other position that exhibits diversity is 348: H, 98.6%; N, 1.4%. The amino acid identity at the other nine positions is unique.

TABLE 1

Residues in that form the primary complementary surface in ttGBP1[a].

| Residue | Interaction |
|---|---|
| W8 | Indole hydrogen bond to center of pyranose ring |
| W9 | Indole hydrogen bond with 3-OH |
| E13 | Hydrogen bonds with 4-OH and 6-OH |
| Q64 | Hydrogen bond with 3-OH |
| H66 | $N_{\varepsilon}$ forms hydrogen bond with 2-OH |
| H119 | Potential hydrogen bond with 3-OH and 4-OH |
| W224 | Indole hydrogen bond with 6-OH |
| W244 | Aromatic ring forms extensive van der Waals contacts with pyranose ring |
| D278 | Hydrogen bonds with 1-OH and 4-OH |
| K312 | Hydrogen bonds with 3-OH and 4-OH |
| H348 | No forms hydrogen bond with 1-OH |

[a]Single-letter amino acid code. Positions based on structure from PDB accession 2b3b.

TABLE 2

| # | Accession code | PCS position and sequence 8 | 9 | 13 | 64 | 66 | 119 | 224 | 244 | 278 | 312 | 348 | Identity | Thermophilicity | Gram | Organism |
|---|---|---|---|---|---|---|---|---|---|---|---|---|---|---|---|---|
| 1 | NC_005835\|YP_004303.1 | W | W | E | Q | H | H | W | W | D | K | H | 0.99 | Thermophilic | − | *Thermus thermophilus* |
| 2 | NC_017587\|YP_006059052.1 | W | W | E | Q | H | H | W | W | D | K | H | 0.98 | Thermophilic | − | *Thermus thermophilus* |
| 3 | NC_017272\|YP_005640237.1 | W | W | E | Q | H | H | W | W | D | K | H | 0.97 | Thermophilic | − | *Thermus thermophilus* |
| 4 | NC_014974\|YP_004202647.1 | W | W | E | Q | H | H | W | W | D | K | H | 0.91 | Thermophilic | − | *Thermus scotoductus* |
| 5 | NC_019386\|YP_006972235.1 | W | W | E | Q | H | H | W | W | D | K | H | 0.9 | Mesophilic | − | *Thermus oshimai* |
| 6 | NC_017278\|YP_005654113.1 | W | W | E | Q | H | H | W | W | D | K | H | 0.9 | Mesophilic | − | *Thermus* sp. |
| 7 | NC_014212\|YP_003685745.1 | W | W | E | Q | H | H | W | W | D | K | H | 0.82 | Thermophilic | + | *Meiothermus silvanus* |
| 8 | NC_013946\|YP_003505968.1 | W | W | E | Q | H | H | W | W | D | K | H | 0.82 | Thermophilic | + | *Meiothermus ruber* |
| 9 | NC_019793\|YP_007182364.1 | W | W | E | Q | H | H | W | W | D | K | H | 0.75 | Mesophilic | + | *Deinococcus peraridilitoris* |
| 10 | NC_014958\|YP_004171760.1 | W | W | E | Q | H | H | W | W | D | K | H | 0.73 | Mesophilic | + | *Deinococcus maricopensis* |
| 11 | NC_012526\|YP_002785095.1 | W | W | E | Q | H | H | W | W | D | K | H | 0.7 | Mesophilic | + | *Deinococcus deserti* |
| 12 | NC_008025\|YP_604376.1 | W | W | E | Q | H | H | W | W | D | K | H | 0.7 | Mesophilic | + | *Deinococcus geothermalis* |
| 13 | NC_017790\|YP_006260352.1 | W | W | E | Q | H | H | W | W | D | K | H | 0.69 | Mesophilic | + | *Deinococcus gobiensis* |
| 14 | NC_014221\|YP_003703981.1 | W | W | E | Q | H | H | W | W | D | K | H | 0.68 | Thermophilic | − | *Truepera radiovictrix* |
| 15 | NC_017790\|YP_006260037.1 | W | W | E | Q | H | H | W | W | D | K | H | 0.68 | Mesophilic | + | *Deinococcus gobiensis* |
| 16 | NC_014364\|YP_003805093.1 | W | W | E | Q | H | H | W | W | D | K | H | 0.65 | Mesophilic | − | *Spirochaeta smaragdinae* |
| 17 | NC_020409\|YP_007493932.1 | W | W | E | Q | H | H | W | W | D | K | H | 0.65 | Mesophilic | − | *Desulfovibrio piezophilus* |
| 18 | NC_016803\|YP_005168947.1 | W | W | E | Q | H | H | W | W | D | K | H | 0.65 | Mesophilic | − | *Desulfovibrio desulfuricans* |
| 19 | NC_012881\|YP_002990109.1 | W | W | E | Q | H | H | W | W | D | K | H | 0.64 | Mesophilic | − | *Desulfovibrio salexigens* |
| 20 | NC_007519\|YP_390145.1 | W | W | E | Q | H | H | W | W | D | K | H | 0.62 | Mesophilic | − | *Desulfovibrio alaskensis* |
| 21 | NC_016633\|YP_005062569.1 | W | W | E | Q | H | H | W | W | D | K | H | 0.62 | Mesophilic | + | *Sphaerochaeta pleomorpha* |
| 22 | NC_014484\|YP_003873938.1 | W | W | E | Q | H | H | W | W | D | K | H | 0.52 | Thermophilic | − | *Spirochaeta thermophila* |
| 23 | NC_017583\|YP_006045430.1 | W | W | E | Q | H | H | W | W | D | K | H | 0.51 | Thermophilic | − | *Spirochaeta thermophila* |
| 24 | NC_013525\|YP_003321952.1 | W | W | E | Q | H | H | W | W | D | K | H | 0.5 | Hyperthermophilic | + | *Thermobaculum terrenum* |

TABLE 2-continued

| # | Accession code | PCS position and sequence | | | | | | | | | | | Iden- | Thermo- | | |
|---|---|---|---|---|---|---|---|---|---|---|---|---|---|---|---|---|
| | | 8 | 9 | 13 | 64 | 66 | 119 | 224 | 244 | 278 | 312 | 348 | tity | philicity | Gram | Organism |
| 25 | NC_015707\|YP_004660650.1 | W | W | E | Q | H | H | W | W | D | K | H | 0.49 | Hyperthermo-philic | – | *Thermotoga thermarum* |
| 26 | NC_011961\|YP_002523752.1 | W | W | E | Q | H | H | W | W | D | K | H | 0.49 | Thermophilic | – | *Thermomicrobium roseum* |
| 27 | NC_011978\|YP_002534202.1 | W | W | E | Q | H | H | W | W | D | K | H | 0.49 | Hyperthermo-philic | – | *Thermotoga neapolitana* |
| 28 | NC_011661\|Dtur_1808 | W | W | E | Q | H | H | W | W | D | K | H | 0.48 | Thermophilic | + | *Dictyoglomus turgidum* |
| 29 | NC_014960\|YP_004172812.1 | W | W | E | Q | H | H | W | W | D | K | H | 0.48 | Thermophilic | – | *Anaerolinea thermophila* |
| 30 | NC_009328\|YP_001127216.1 | W | W | E | Q | H | H | W | W | D | K | H | 0.48 | Thermophilic | + | *Geobacillus thermodenitrifican* |
| 31 | NC_022080\|M493_16625 | W | W | E | Q | H | H | W | W | D | K | H | 0.48 | Thermophilic | + | *Geobacillus* sp. |
| 32 | NC_016593\|YP_004984007.1 | W | W | E | Q | H | H | W | W | D | K | H | 0.47 | Mesophilic | + | *Geobacillus thermoleovorans* |
| 33 | NC_006510\|YP_149060.1 | W | W | E | Q | H | H | W | W | D | K | H | 0.47 | Thermophilic | + | *Geobacillus kaustophilus* |
| 34 | NC_017934\|YP_006345378.1 | W | W | E | Q | H | H | W | W | D | K | H | 0.47 | Mesophilic | + | *Mesotoga prima* |
| 35 | NC_015387\|YP_004368987.1 | W | W | E | Q | H | H | W | W | D | K | H | 0.47 | Thermophilic | – | *Marinithermus hydrothermalis* |
| 36 | NC_013411\|YP_003254339.1 | W | W | E | Q | H | H | W | W | D | K | H | 0.47 | Thermophilic | + | *Geobacillus* sp. |
| 37 | NC_011653\|YP_002334739.1 | W | W | E | Q | H | H | W | W | D | K | H | 0.47 | Thermophilic | – | *Thermosipho africanus* |
| 38 | NC_009828\|YP_001470668.1 | W | W | E | Q | H | H | W | W | D | K | H | 0.47 | Hyperthermo-philic | – | *Thermotoga lettingae* |
| 39 | NC_009848\|YP_001488451.1 | W | W | E | Q | H | H | W | W | D | K | H | 0.47 | Mesophilic | + | *Bacillus pumilus* |
| 40 | NC_015660\|YP_004586376.1 | W | W | E | Q | H | H | W | W | D | K | H | 0.46 | Hyperthermo-philic | + | *Geobacillus thermoglucosidasiu* |
| 41 | NC_020210\|YP_007403540.1 | W | W | E | Q | H | H | W | W | D | K | H | 0.46 | Thermophilic | + | *Geobacillus* sp. |
| 42 | NC_009523\|RoseRS_0803 | W | W | E | Q | H | H | W | W | D | K | H | 0.46 | Thermophilic | – | *Roseiflexus* sp. |
| 43 | NC_009616\|YP_001306064.1 | W | W | E | Q | H | H | W | W | D | K | H | 0.46 | Thermophilic | – | *Thermosipho melanesiensis* |
| 44 | NC_002570\|NP_244712.1 | W | W | E | Q | H | H | W | W | D | K | H | 0.46 | Mesophilic | + | *Bacillus halodurans* |
| 45 | NC_009767\|Rcas_1174 | W | W | E | Q | H | H | W | W | D | K | H | 0.46 | Thermophilic | – | *Roseiflexus castenholzii* |
| 46 | NC_012785\|YP_002941687.1 | W | W | E | Q | H | H | W | W | D | K | H | 0.46 | Mesophilic | – | *Kosmotoga olearia* |
| 47 | NC_021171\|YP_007909332.1 | W | W | E | Q | H | H | W | W | D | K | H | 0.44 | Mesophilic | + | *Bacillus* sp. |
| 48 | NC_010003\|YP_001568934.1 | W | W | E | Q | H | H | W | W | D | K | H | 0.44 | Thermophilic | – | *Petrotoga mobilis* |
| 49 | NC_017455\|YP_005837174.1 | W | W | E | Q | H | H | W | W | D | K | H | 0.44 | Mesophilic | – | *Halanaerobium praevalens* |
| 50 | NC_016751\|YP_005097730.1 | W | W | E | Q | H | H | W | W | D | K | H | 0.44 | Mesophilic | + | *Marinitoga piezophila* |
| 51 | NC_013595\|YP_003343338.1 | W | W | E | Q | H | H | W | W | D | K | H | 0.44 | Mesophilic | + | *Streptosporangium roseum* |
| 52 | NC_019978\|YP_007315359.1 | W | W | E | Q | H | H | W | W | D | K | H | 0.43 | Mesophilic | + | *Halobacteroides halobius* |
| 53 | NC_018524\|YP_006643279.1 | W | W | E | Q | H | H | W | W | D | K | H | 0.43 | Mesophilic | + | *Nocardiopsis alba* |
| 54 | NC_017079\|YP_005442135.1 | W | W | E | Q | H | H | W | W | D | K | H | 0.42 | Mesophilic | + | *Caldilinea aerophila* |
| 55 | NC_009953\|YP_001538287.1 | W | W | E | Q | H | H | W | W | D | K | H | 0.39 | Mesophilic | + | *Salinispora arenicola* |
| 56 | NC_008699\|YP_922504.1 | W | W | E | Q | H | H | W | W | D | K | H | 0.38 | Mesophilic | + | *Nocardioides* sp. |
| 57 | NC_019395\|YP_006981831.1 | W | W | E | Q | H | H | W | W | D | K | H | 0.38 | Mesophilic | + | *Propionibacterium acidipropion* |
| 58 | NC_021064\|YP_007870224.1 | W | W | E | Q | H | H | W | W | D | K | H | 0.37 | Mesophilic | + | *Propionibacterium avidum* |
| 59 | NC_009380\|YP_001160076.1 | W | W | E | Q | H | H | W | W | D | K | H | 0.37 | Mesophilic | + | *Salinispora tropica* |
| 60 | NC_021085\|YP_007888188.1 | W | W | E | Q | H | H | W | W | D | K | H | 0.37 | Mesophilic | + | *Propionibacterium acnes* |
| 61 | NC_014830\|YP_004097363.1 | W | W | E | Q | H | H | W | W | D | K | H | 0.37 | Mesophilic | + | *Intrasporangium calvum* |
| 62 | NC_014039\|YP_003582156.1 | W | W | E | Q | H | H | W | W | D | K | H | 0.37 | Mesophilic | + | *Propionibacterium acnes* |
| 63 | NC_017803\|YP_006269831.1 | W | W | E | Q | H | H | W | W | D | K | H | 0.36 | Mesophilic | + | *Actinoplanes* sp. |
| 64 | NC_018707\|YP_006851986.1 | W | W | E | Q | H | H | W | W | D | K | H | 0.36 | Mesophilic | + | *Propionibacterium acnes* |
| 65 | NC_013172\|YP_003156024.1 | W | W | E | Q | H | H | W | W | D | K | H | 0.35 | Mesophilic | + | *Brachybacterium faecium* |
| 66 | NC_017093\|YP_005466360.1 | W | W | E | Q | H | H | W | W | D | K | H | 0.35 | Mesophilic | + | *Actinoplanes missouriensis* |
| 67 | NC_017550\|YP_005985051.1 | W | W | E | Q | H | H | W | W | D | K | H | 0.35 | Mesophilic | + | *Propionibacterium acnes* |
| 68 | NC_013729\|YP_003384633.1 | W | W | E | Q | H | H | W | W | D | K | H | 0.35 | Mesophilic | + | *Kribbella flavida* |
| 69 | NC_014246\|YP_003718075.1 | W | W | E | Q | H | H | W | W | D | K | H | 0.34 | Mesophilic | + | *Mobiluncus curtisii* |
| 70 | NC_013947\|YP_003509686.1 | W | W | E | Q | H | H | W | W | D | K | H | 0.34 | Mesophilic | + | *Stackebrandtia nassauensis* |
| 71 | NC_009033\|YP_001041152.1 | W | W | E | Q | H | H | W | W | D | K | H | 0.33 | Hyperthermo-philic | N/a | *Staphylothermus marinus* |
| 72 | NC_014205\|YP_003669472.1 | W | W | E | Q | H | H | W | W | D | K | H | 0.33 | Hyperthermo-philic | N/a | *Staphylothermus hellenicus* |
| 73 | NC_014804\|YP_004071798.1 | W | W | E | Q | H | H | W | W | D | K | H | 0.32 | Hyperthermo-philic | N/a | *Thermococcus barophilus* |
| 74 | NC_008541\|YP_831349.1 | W | W | E | Q | H | H | W | W | D | K | H | 0.32 | Mesophilic | + | *Arthrobacter* sp. |
| 75 | NC_000961\|NP_143109.1 | W | W | E | Q | H | H | W | W | D | K | H | 0.31 | Hyperthermo-philic | N/a | *Pyrococcus horikoshii* |
| 76 | NZ_CP006965\| WP_042682828.1 | W | W | E | Q | H | H | W | W | D | K | H | 0.3 | ? | N/a | *Methanobacterium* sp. |
| 77 | NC_009434\|PST_2440 | W | W | E | Q | K | H | W | W | D | K | H | 0.3 | Mesophilic | – | *Pseudomonas stutzeri* |
| 78 | NC_009439\|YP_001186649.1 | W | W | E | Q | K | H | W | W | D | K | H | 0.29 | Mesophilic | – | *Pseudomonas mendocina* |
| 79 | NC_021577\|M062_17030 | W | W | E | Q | K | H | W | W | D | K | H | 0.29 | Mesophilic | – | *Pseudomonas aeruginosa* |
| 80 | NC_017584\|YP_006046361.1 | W | W | E | Q | K | H | W | W | D | K | H | 0.28 | Mesophilic | – | *Rhodospirillum rubrum* |
| 81 | NC_006371\|YP_133554.1 | W | W | E | Q | K | H | W | W | D | K | Q | 0.28 | Psychrophilic | – | *Photobacterium profundum* |
| 82 | NC_017986\|YP_006387725.1 | W | W | E | Q | K | H | W | W | D | K | H | 0.28 | Mesophilic | – | *Pseudomonas putida* |
| 83 | NC_014532\|YP_003898163.1 | W | W | E | Q | N | H | W | W | D | K | H | 0.28 | Mesophilic | – | *Halomonas elongata* |
| 84 | NC_017506\|YP_005886650.1 | W | W | E | Q | K | H | W | W | D | K | H | 0.28 | ? | – | *Marinobacter adhaerens* |
| 85 | NC_007645\|YP_437156.1 | W | W | E | Q | K | H | W | W | D | K | H | 0.28 | Mesophilic | – | *Hahella chejuensis* |
| 86 | NC_018028\|YP_006458250.1 | W | W | E | Q | K | H | W | W | D | K | H | 0.28 | Mesophilic | – | *Pseudomonas stutzeri* |
| 87 | NC_010501\|YP_001751058.1 | W | W | E | Q | K | H | W | W | D | K | H | 0.27 | Mesophilic | – | *Pseudomonas putida* |
| 88 | NC_007963\|YP_574462.1 | W | W | E | Q | K | H | W | W | D | K | H | 0.27 | Mesophilic | – | *Chromohalobacter salexigens* |

TABLE 2-continued

| # | Accession code | PCS position and sequence | | | | | | | | | | | Identity | Thermophilicity | Gram | Organism |
|---|---|---|---|---|---|---|---|---|---|---|---|---|---|---|---|---|
| | | 8 | 9 | 13 | 64 | 66 | 119 | 224 | 244 | 278 | 312 | 348 | | | | |
| 89 | NC_014965\|YP_004189360.1 | W | W | E | Q | K | H | W | W | D | K | H | 0.27 | Mesophilic | − | *Vibrio vulnificus* |
| 90 | NC_015556\|YP_004474128.1 | W | W | E | Q | K | H | W | W | D | K | H | 0.27 | Mesophilic | − | *Pseudomonas fulva* |
| 91 | NC_023064\|U771_25180 | W | W | E | Q | K | H | W | W | D | K | H | 0.27 | Mesophilic | − | *Pseudomonas* sp. |
| 92 | NZ_AOIV00000000\| WP_008383305.1 | W | W | E | Q | W | H | W | W | D | K | H | 0.27 | Mesophilic | + | *Halogeometricum pallidum* |
| 93 | NC_012660\|YP_002874357.1 | W | W | E | Q | K | H | W | W | D | K | H | 0.26 | Mesophilic | − | *Pseudomonas fluorescens* |
| 94 | NC_014729\|YP_004036449.1 | W | W | E | Q | W | H | W | W | D | K | H | 0.26 | Mesophilic | + | *Halogeometricum borinquense* |
| 95 | NC_022223\|N175_10020 | W | W | E | Q | K | H | W | W | D | K | H | 0.26 | Mesophilic | + | *Listonella anguillarum* |
| 96 | NC_004578\|NP_791121.1 | W | W | E | Q | K | H | W | W | D | K | H | 0.26 | Mesophilic | − | *Pseudomonas syringae* |
| 97 | NC_018080\|YP_006481672.1 | W | W | E | Q | K | H | W | W | D | K | H | 0.26 | Mesophilic | − | *Pseudomonas aeruginosa* |
| 98 | NC_015733\|YP_004700499.1 | W | W | E | Q | K | H | W | W | D | K | H | 0.26 | Mesophilic | − | *Pseudomonas putida* |
| 99 | NC_016602\|YP_004993577.1 | W | W | E | Q | K | H | W | W | D | K | H | 0.26 | Mesophilic | − | *Vibrio furnissii* |
| 100 | NC_015276\|YP_004315089.1 | W | W | E | Q | K | H | W | W | D | K | H | 0.26 | Mesophilic | − | *Marinomonas mediterranea* |
| 101 | NZ_ALJD00000000\| WP_009367379.1 | W | W | E | Q | W | H | W | W | D | K | H | 0.25 | Mesophilic | + | *Halogranum salarium* |
| 102 | NC_021313\|YP_008055550.1 | W | W | E | Q | W | H | W | W | D | K | H | 0.25 | Mesophilic | + | *Salinarchaeum* sp. |
| 103 | NC_023076\|X970_03415 | W | W | E | Q | K | H | W | W | D | K | H | 0.25 | Mesophilic | − | *Pseudomonas monteilii* |
| 104 | NC_022738\|PVLB_20095 | W | W | E | Q | K | H | W | W | D | K | H | 0.25 | Mesophilic | − | *Pseudomonas* sp. |
| 105 | NC_021505\|YP_008115339.1 | W | W | E | Q | K | H | W | W | D | K | H | 0.25 | Mesophilic | − | *Pseudomonas putida* |
| 106 | NZ_AOLZ00000000\| WP_007142826.1 | W | W | E | Q | W | H | W | W | D | K | H | 0.25 | Mesophilic | + | *Halobiforma lacisalsi* |
| 107 | NZ_AOIL00000000\| WP_006827663.1 | W | W | E | Q | W | H | W | W | D | K | H | 0.25 | Mesophilic | + | *Natrialba taiwanensis* |
| 108 | NC_008027\|YP_609880.1 | W | W | E | Q | K | H | W | W | D | K | H | 0.25 | Mesophilic | − | *Pseudomonas entomophila* |
| 109 | NC_021884\|BDL_2837 | W | W | E | Q | K | H | W | W | D | K | H | 0.25 | Mesophilic | − | *Burkholderia pseudomallei* |
| 110 | NZ_AOJI00000000\| WP_008001569.1 | W | W | E | Q | W | H | W | W | D | K | H | 0.25 | Mesophilic | + | *Halorubrum aidingense* |
| 111 | NC_018643\|YP_006756306.1 | W | W | E | Q | K | H | W | W | D | K | H | 0.25 | Mesophilic | + | *alpha proteobacterium* |
| 112 | NC_009080\|YP_001081530.1 | W | W | E | Q | K | H | W | W | D | K | H | 0.25 | Mesophilic | − | *Burkholderia mallei* |
| 113 | NC_007908\|Rfer_1097 | W | W | E | Q | K | H | W | W | D | K | Q | 0.25 | Mesophilic | + | *Albidiferax ferrireducens* |
| 114 | NZ_AOIP00000000\| WP_006663935.1 | W | W | E | Q | W | H | W | W | D | K | H | 0.25 | Mesophilic | + | *Natrialba aegyptia* |
| 115 | NC_021173\|YP_007917520.1 | W | W | E | Q | K | H | W | W | D | K | H | 0.24 | Mesophilic | − | *Burkholderia thailandensis* |
| 116 | NC_010084\|YP_001580612.1 | W | W | E | Q | K | H | W | W | D | K | H | 0.24 | Mesophilic | − | *Burkholderia multivorans* |
| 117 | NZ_AOI000000000\| WP_006109396.1 | W | W | E | Q | W | H | W | W | D | K | H | 0.24 | Mesophilic | + | *Natrialba asiatica* |
| 118 | NC_011000\|YP_002232151.1 | W | W | E | Q | K | H | W | W | D | K | H | 0.24 | Mesophilic | − | *Burkholderia cenocepacia* |
| 119 | NC_017911\|YP_006325578.1 | W | W | E | Q | K | H | W | W | D | K | H | 0.24 | Mesophilic | − | *Pseudomonas fluorescens* |
| 120 | NC_019792\|YP_007179189.1 | W | W | E | Q | W | H | W | W | D | K | H | 0.24 | Mesophilic | + | *Natronobacterium gregoryi* |
| 121 | NC_010551\|YP_001807547.1 | W | W | E | Q | K | H | W | W | D | K | H | 0.24 | Mesophilic | − | *Burkholderia ambifaria* |
| 122 | NZ_AOIB00000000\| WP_005559649.1 | W | W | E | Q | W | H | W | W | D | K | H | 0.24 | Mesophilic | + | *Natronococcus amylolyticus* |
| 123 | NZ_AOHX00000000\| WP_008163842.1 | W | W | E | Q | W | H | W | W | D | K | H | 0.24 | Mesophilic | + | *Natronorubrum sulfidifaciens* |
| 124 | NC_017831\|YP_006273771.1 | W | W | E | Q | K | H | W | W | D | K | H | 0.24 | Mesophilic | − | *Burkholderia pseudomallei* |
| 125 | NC_004129\|YP_261701.1 | W | W | E | Q | K | H | W | W | D | K | H | 0.24 | Mesophilic | − | *Pseudomonas protegens* |
| 126 | NC_007005\|YP_234205.1 | W | W | E | Q | K | H | W | W | D | K | H | 0.24 | Mesophilic | − | *Pseudomonas syringae* |
| 127 | NC_006348\|YP_103699.1 | W | W | E | Q | K | H | W | W | D | K | H | 0.24 | Mesophilic | − | *Burkholderia mallei* |
| 128 | NC_015379\|YP_004352396.1 | W | W | E | Q | K | H | W | W | D | K | H | 0.24 | Mesophilic | − | *Pseudomonas brassicacearum* |
| 129 | NC_017920\|YP_006331954.1 | W | W | E | Q | K | H | W | W | D | K | H | 0.24 | Mesophilic | − | *Burkholderia* sp. |
| 130 | NC_010681\|YP_001894671.1 | W | W | E | Q | K | H | W | W | D | K | H | 0.24 | Mesophilic | − | *Burkholderia phytofirmans* |
| 131 | NC_009256\|YP_001118730.1 | W | W | E | Q | K | H | W | W | D | K | H | 0.24 | Mesophilic | − | *Burkholderia vietnamiensis* |
| 132 | NC_007510\|YP_368312.1 | W | W | E | Q | K | H | W | W | D | K | H | 0.24 | Mesophilic | − | *Burkholderia lata* |
| 133 | NC_020209\|YP_007398595.1 | W | W | E | Q | K | H | W | W | D | K | H | 0.24 | Mesophilic | − | *Pseudomonas poae* |
| 134 | NC_008390\|YP_772721.1 | W | W | E | Q | K | H | W | W | D | K | H | 0.24 | Mesophilic | − | *Burkholderia ambifaria* |
| 135 | NC_010622\|YP_001856864.1 | W | W | E | Q | K | H | W | W | D | K | H | 0.23 | Mesophilic | − | *Burkholderia phymatum* |
| 136 | NC_016589\|YP_004976536.1 | W | W | E | Q | K | H | W | W | D | K | H | 0.23 | Mesophilic | − | *Burkholderia* sp. |
| 137 | NC_020802\|YP_007640421.1 | W | W | E | Q | K | H | W | W | D | K | Q | 0.23 | Mesophilic | + | *Psychromonas* sp. |
| 138 | NC_008687\|YP_917171.1 | W | W | E | Q | K | H | W | W | D | K | H | 0.23 | Mesophilic | − | *Paracoccus denitrificans* |
| 139 | NC_014323\|YP_003777923.1 | W | W | E | Q | N | H | W | W | D | K | H | 0.22 | Mesophilic | − | *Herbaspirillum seropedicae* |
| 140 | NZ_AOIN00000000\| WP_006167401.1 | W | W | E | Q | W | H | W | W | D | K | H | 0.22 | Mesophilic | + | *Natrialba chahannaoensis* |

Example 3

Figure 4:
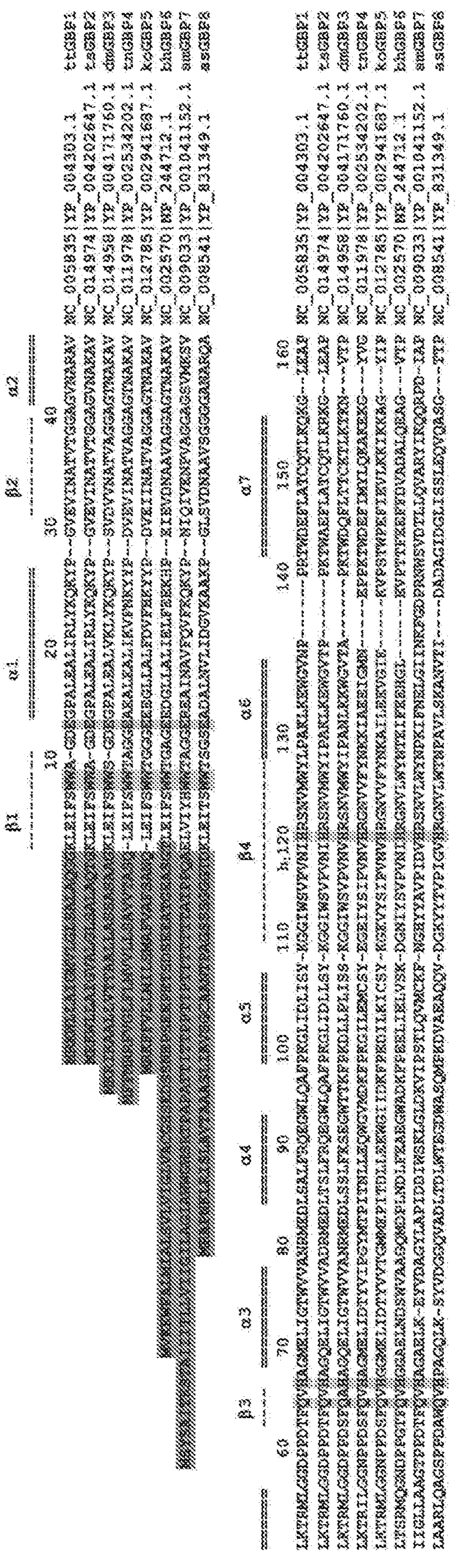
FIG. 4 is an alignment of the homologs predicted to be glucose-binding proteins (alignment generated by ClustalW; ordered by fractional sequence identity to the ttGBP1 seed sequence). Sequences taken from Table 2 (name, line number in Table 2, accession code, species, fractional identity to ttGBP1): Numbering according to ttGBP1. Dark gray: leader peptides; light gray, primary complementary surface (PCS) residues; –, position of insertions. Positions of the α helices ($\alpha_x$), and β sheets ($\beta_x$) observed in the ttGBP1 structure are indicated.
Figure 4:
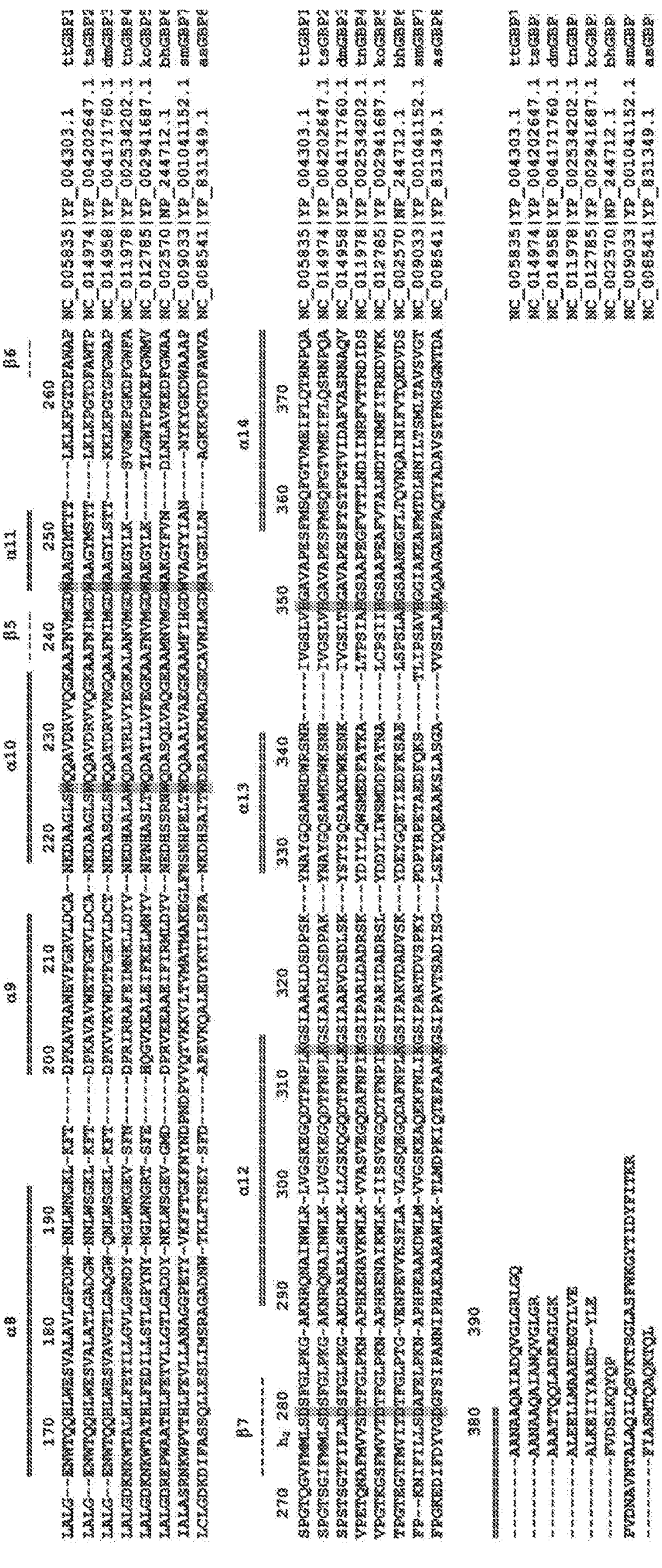
Figure 5A:
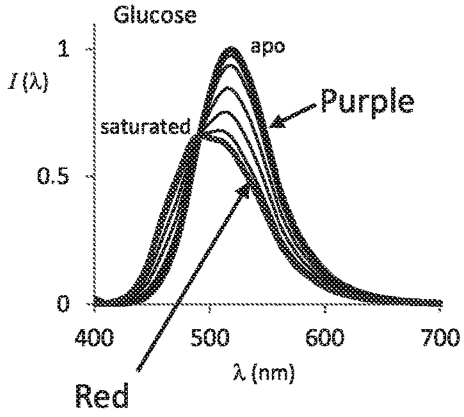
FIGS. 5A-F are graphs showing fluorescence responses of the tsGBP2 13C.Acrylodan W244F mutant to glucose and galactose. Left column, corrected emission spectra (see notes to Table 4; purple line, no ligand (apo); red line, saturating ligand; black lines, intermediate ligand concentrations). Middle column, dichromatic signal black circles, experimental data points; gray lines, fit to binding isotherm, yields ${}^{app}K_d$). Right column, Monochromatic signal (gray circles, $\lambda_1$ intensity data points and fit; black circles, $\lambda_2$ data points; lines, fits yield ${}^{true}K_d$).
Figure 5B:
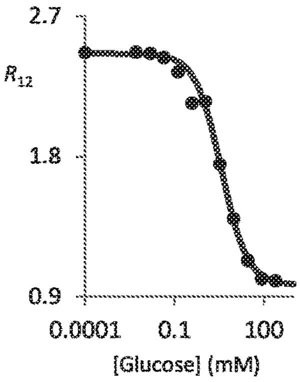
Figure 5C:
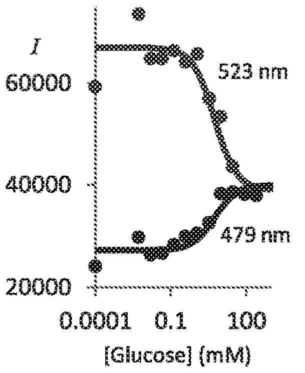
Figure 5D:
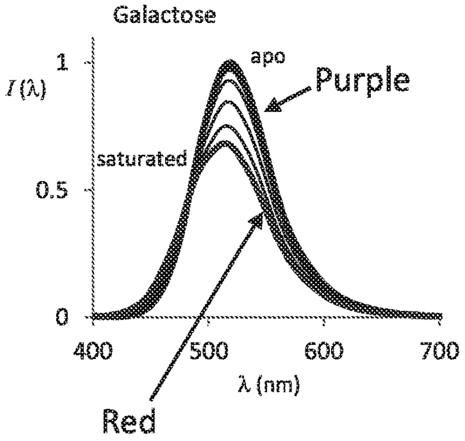
Figure 5E:
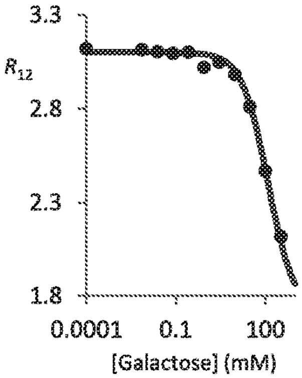
Figure 5F:
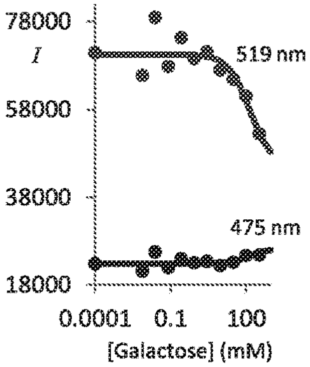

Sensor Engineering Phase 2: Lead Protein Validation Using Ligand-Mediated Thermostability Shifts Eight homologs that were predicted to be glucose-binding proteins (FIG. 4, Table 3) were selected to probe different degrees of sequence identity to the ttGBP1 seed, and their glucose-binding properties were determined experimentally. These experiments comprised four successive steps:

1. Synthetic gene construction. The amino acid sequence of the homology leads were backtranslated into DNA sequences. These were optimized for directing heterologous cytoplasmic expression of the protein homologues in *E. coli*, using either the OrfOpt or OrfMorph programs. These programs predict mRNA sequences that direct high-level protein expression in *E. coli*. The predicted gene sequences were assembled de novo from synthetic oligonucleotides.

2. Heterologous protein expression of the homologues in *E. coli*. Plasmids carrying the synthetic expression constructs (see above) were transformed into KRX competent cells (Promega). Protein production was induced in bacterial cultures of these cultures, as described in the Materials and Methods.
3. Purification of successfully expressed protein using immobilized metal affinity chromatography.
4. Verification of glucose binding. Determination of the glucose-binding properties of the purified proteins using a thermal stability shift assay.

All eight leads produced soluble protein in a T7 expression system in sufficient quantity for functional analysis. The glucose-binding properties of four of these were confirmed directly using the thermal shift assay (Table 3). Four of the GBP homologs exhibited mid-point thermal denaturation temperatures ($T_m$ values) over 100° C. Their glucose-binding properties were verified subsequently using a mutant, fluorescently labeled conjugate that responds to glucose binding (see below).

fluorophores that respond to ligand-mediated conformational changes. Identification of FRS candidates that can be used for sensing applications comprises three steps:

1. Cysteine scan. Mutant glucose-binding proteins containing single cysteines are constructed for site-specific attachment of thiol-reactive fluorophores. General structural principles have been established to identify positions in PBPs where attached single fluorophores are likely to exhibit ligand-dependent responses (de Lorimier et al., 2002, *Protein Sci,* 11, 2655-75). Candidate positions fall into three classes: endosteric, replacing a residue that contacts the ligand directly; peristeric, located at the rim of the binding site; allosteric (Marvin et al., 1997, *Proc Natl Acad Sci USA,* 94, 4366-71; Marvin, 1998, *J Am Chem Soc,* 120, 7-11), located outside the binding site at sites that undergo local structural changes in concert with the hinge-bending motion.
2. Fluorophore screening. Thiol-reactive, environmentally sensitive fluorophores are attached to each cysteine mutant prepared in step 1.
3. Evaluation of the glucose-mediated change of all the fluorescent conjugates prepared in step 2. Responses to ligand binding in which there is both a change in

TABLE 3

Ligand-binding and thermostability properties of ttGBP1 homologs.

| Name | Organism | NCBI Accession Codes: Genome | NCBI Accession Codes: Protein | Identity[a] | Gene Optimization Method[b] | Soluble Expression[c] | Thermostability[d] ${}^{apo}T_m$ (° C.) | Glucose Binding[e] |
|---|---|---|---|---|---|---|---|---|
| ttGBP1 | *Thermus thermophilus* | NC_005835 | YP_004303.1 | 1.0 | OrfMorph | y | >100 | y[f] |
| tsGBP2 | *Thermus scotoductus* | NC_014974 | YP_004202647.1 | 0.91 | OrfOpt | y | >100 | y[f] |
| dmGBP3 | *Deinococcus maricopensis* | NC_014958 | YP_004171760.1 | 0.73 | OrfOpt | y | 47 | y |
| tnGBP4 | *Thermotoga neapolitana* | NC_011978 | YP_002534202.1 | 0.49 | OrfOpt | y | >100 | y[f] |
| koGBP5 | *Kosmotoga olearia* | NC_012785 | YP_002941687.1 | 0.46 | OrfOpt | y | >100 | y[f] |
| bhGBP6 | *Bacillus halodurans* | NC_002570 | NP_244712.1 | 0.46 | OrfOpt | y | 53 | y |
| smGBP7 | *Staphylothermus marinus* | NC_009033 | YP_001041152.1 | 0.34 | OrfOpt | poor | 40[f] | y[f] |
| asGBP8 | *Arthrobacter* sp. | NC_008541 | YP_831349.1 | 0.32 | OrfOpt | y | 58 | y |

[a]Number of identical residues shared with the probe sequence.
[b]See materials and methods.
[c]Judged by SDS gel electrophoresis of the soluble fraction of a total lysate.
[d]Determined in a Roche LightCycler, using SYPRO Orange to monitor the appearance of unfolded protein.
[e]Determined by monitoring an increase in the thermostability of the protein in the presence of ligand.
[f]Determined using fluorescent Acrylodan and/or Badan conjugates (see text).

A majority of the sequence identity of these experimentally verified glucose-binding homologs relative the ttGBP1 seed were considerably below the 60% threshold with the sequences identity ranging from 91% to 32%. These results therefore demonstrate that biological function can be predicted accurately with the SAFE technique, even in sequence homologs with low fractional identities to the original seed.

The homolog from *Thermos scotoductus* (tsGBP2) was produced at the highest level by heterologous expression in *E. coli*. This protein was selected as the candidate for constructing robust glucose sensors.

Example 4

Sensor Engineering Phase 3: Cysteine Mutant Scans and Fluorophore Screening to Identify Fluorescently Responsive Glucose Sensors Semi-synthetic FRSs can be engineered by site-specifically attaching thiol-reactive, environmentally sensitive fluorescence emission intensity and spectral shape are essential for chemometric applications, because such changes enable ratiometric measurements. Changes in spectral shape typically are accompanied by a shift in the wavelength of the emission intensity maxima. Three classes of fluorescent responses are possible:

i. No response.
ii. Monochromatic response (emission intensity increases or decreases without a change in spectral shape)
iii. Dichromatic response (both intensity and spectral shape changes) which can be classified into two sub-classes:
   i. Hypsochromatic: emission intensity shifts to shorter wavelengths upon binding glucose ("blue shift").
   ii. Bathochromatic: emission intensity shifts to longer wavelengths upon binding glucose ("red shift").

4. Double labeling strategies to convert monochromatic responses into dichromatic signals, or to improve upon dichromatic responses.

Cysteine scans of tsGBP2. We constructed twenty single cysteine mutants in tsGBP2, exploring thirteen endosteric, five peristeric, and two allosteric positions. At each position we attached the Prodan-derived fluorophores Acrylodan and Badan, which differ by one methylene group in their thiol-reactive linker. The fluorescence emission intensities of twelve Acrylodan and four Badan conjugates responded to glucose at twelve attachment positions (Table 4). At only six attachment positions were the responses of both fluorophores qualitatively similar, and never quantitatively. We also tested for glucose binding by measuring ligand-mediated shifts in protein thermal stability (Table 3).

intensity spectral shapes arise from redistribution of populations of two emission states, 'blue' and 'green', corresponding to distinct excited state dipoles. Such a redistribution does not occur in monochromatic responses. The emission spectra of all the Acrylodan conjugates undergo a green→blue (hypsochromatic) shift upon ligand binding (Table 4), whereas the emission spectrum of Badan conjugate shifts in the opposite direction (bathochromatic). The Acrylodan conjugate attached to E13C exhibited the largest, wavelength-dependent changes in fluorescence emission intensities.

TABLE 4

Glucose response of Acrylodan and Badan conjugates in a cysteine scan of the Therm us scotoductus tsGBP2 scaffold.

| Cysteine position | Class[a] | Fluorophore Cysteine | Shape[b] | Emission wavelength (nm) λ1 | λ2 | $K_d$[c,d,e] (mM) $^{app}K_d$ | $^{true}K_d$ | Fluorophore Cysteine | Shape[b] | Emission wavelength (nm) λ1 | λ2 | $K_d$[c,d,e] (mM) $^{app}K_d$ | $^{true}K_d$ |
|---|---|---|---|---|---|---|---|---|---|---|---|---|---|
| W8C | e | Acrylodan | m | 462 | 550 | 0.008 | 0.007 | Badan | m | 488 | 448 | 70[d] | 113[d] |
| W9C | e | Acrylodan | m | 511 | 461 | 0.02 | 0.02 | Badan | m | | | ns | ns |
| D12C | p | Acrylodan | m | 513 | 478 | 0.005 | 0.003 | Badan | m | | | ns | ns |
| E13C | e | Acrylodan | d | 518 | 471 | 0.9 | 1.1 | Badan | m | 513 | 571 | 0.2 | 0.3 |
| G41C | e | Acrylodan | d | 519 | 474 | 0.009 | 0.01 | Badan | m | | | ns | ns |
| A42C | e | Acrylodan | 0 | | | ns | ns | Badan | m | | | ns | ns |
| Q64C | e | Acrylodan | 0 | | | ns | ns | Badan | m | | | ns | ns |
| H66C | e | Acrylodan | d | 486 | 446 | 73 | 155 | Badan | m | | | ns | ns |
| H119C | e | Acrylodan | m | 511 | 461 | 0.02 | 0.02 | Badan | m | | | ns | ns |
| W167C | p | Acrylodan | d | 492 | 552 | 0.02 | 0.02 | Badan | m | | | ns | ns |
| S223C | p | Acrylodan | 0 | | | ns | ns | Badan | m | | | ns | ns |
| W224C | e | Acrylodan | m | 483 | 515 | 0.7 | 0.9 | Badan | 0 | | | ns | ns |
| Q225C | p | Acrylodan | m | | | ns | ns | Badan | m | | | ns | ns |
| W244C | e | Acrylodan | m | 487 | 450 | 9.0 | 19 | Badan | m | 502 | 452 | 16 | 17 |
| S277C | a | Acrylodan | 0 | | | ns | ns | Badan | 0 | | | ns | ns |
| D278C | e | Acrylodan | m | | | ns | ns | Badan | 0 | | | ns | ns |
| K312C | e | Acrylodan | d | 515 | 465 | 0.009 | 0.01 | Badan | m | | | ns | ns |
| W337 | a | Acrylodan | m | | | ns | ns | Badan | 0 | | | ns | ns |
| H348 | e | Acrylodan | m | 487 | 515 | 1.3[d] | 1.6[d] | Badan | d | 523 | 515 | 4.3[d] | 5.2[d] |
| M357 | p | Acrylodan | 0 | | | ns | ns | Badan | m | | | ns | ns |

[a]a, allosteric e, endosteric; p, peristeric.
[b]m, monochromatic; d, dichromatic (i.e. spectral shape change); 0, no change.
[c]ns; no or minimal signal change up on glucose addition.
[d]Approximate values.
[e]Determined by fitting the ratiometric signal of the intensities measured at λ1 and λ2 to equation 1-5.

Endosteric attachment positions exhibited the most pronounced changes in fluorescence emissions in response to ligand binding. At least one of the two conjugates at all five peristeric positions were responsive to glucose. No allosteric conjugates exhibited fluorescence responses to glucose.

We observed ligand-dependent shifts in the wavelengths of emission intensity maxima at one peristeric (W167C) and five endosteric (E13C, G41C, H66C, K312C, H348) sites (Table 4), enabling dichromatic ratiometric measurements; the maximum intensity of other glucose-responsive conjugates remained the same (monochromatic responses). Five out of the six positions that enable dichromatic ratiometric measurements were labeled with Acrylodan and the sixth position with Badan. These two fluorophores differ only in their linker geometry, but this small difference determines whether dichromatic or monochromatic responses are observed for a particular conjugate. Changes in linker geometry and chromophore modifications give rise to significant differences in the detailed interactions of particular fluorophores with the protein, even within families of closely related molecules, thereby significantly impacting sensor characteristics, consistent with previous observations.

In these dichromatic responses of the Acrylodan and Badan conjugates, ligand-mediated changes in emission Conservation of signaling in glucose-binding protein homologs. The equivalent of the 13C mutation identified in tsGBP2 (see above) was installed in all the other seven ttGBP1 homologs and their Acrylodan and Badan conjugates tested for glucose binding (Table 5). Dichromatic responses were identified in all proteins. In all but one of the proteins, the response of the Acrylodan conjugate was dichromatic, as is the case in tsGBP 13C. The koGBP5 13C Acrylodan conjugate exhibited a monochromatic response, but its Badan conjugate was dichromatic. Both Acrylodan and Badan exhibited dichromatic responses in dmGBP3.

TABLE 5 ttGBP1 homologs labeled with Acrylodan or Badan[a].

| Protein | Mutation | Conjugate[b] | Shape[c] | Emission (nm) $\lambda_1$ | $\lambda_2$ | Affinity[a,d] (mM) $^{app}K_d$ | $^{true}K_d$ |
|---|---|---|---|---|---|---|---|
| ttGBP1 | E13C | A | d | 486 | 519 | 1.9 | 1.2 |
| | | B | m | 496 | 530 | 0.5 | 0.5 |
| tsGBP2 | E13C | A | d | 518 | 471 | 0.9 | 1.1 |
| | | B | m | 513 | 571 | 0.2 | 0.3 |

TABLE 5-continued ttGBP1 homologs labeled with Acrylodan or Badan[a].

| Protein | Mutation | Conjugate[b] | Shape[c] | Emission (nm) | | Affinity[a,d] (mM) | |
|---|---|---|---|---|---|---|---|
| | | | | $\lambda_1$ | $\lambda_2$ | $^{app}K_d$ | $^{true}K_d$ |
| dmGBP3 | E13C | A | d | 486 | 519 | 7.9 | 4.9 |
| | | B | d | 523 | 550 | 0.6[e] | 0.7[e] |
| tnGBP4 | E13C | A | d | 487 | 519 | 0.73 | 0.71 |
| | | B | m | 527 | 555 | 0.096 | 0.16 |
| koGBP5 | E13C | A | m | 491 | 517 | 2.4 | 1.6 |
| | | B | d | 535 | 503 | 0.2 | 0.2 |
| bhGBP6 | E13C | A | d | 486 | 515 | 0.49 | 0.48 |
| | | B | m | 515 | 490 | 1.8 | 1.5 |
| smGBP7 | E14C | A | d | 484 | 463 | 0.043 | 0.056 |
| | | B | m | 519 | 490 | 0.4 | 0.5 |

[a]Determined by fitting the ratiometric signal of the intensities measured at λ1 and λ2 to equation 1-5.
[b]A, Acrylodan; B, Badan.
[c]m, monochromatic; d, dichromatic (i.e. spectral shape change); 0, no change.
[d]nb, no binding.
[e]Approximate value.

These results demonstrate that the site of a cysteine mutation that exhibits dichromatic signaling is conserved among homologs. Identification of such a site in one homolog therefore is predictive throughout its protein family identified by the SAFE search method, even for family members that have low sequence identity (e.g. compare ttGBP1 and smGBP7).

Improving the fluorescence response to glucose in doubly labeled proteins. We tested whether fluorescence energy transfer (FRET) effects in doubly labeled proteins could improve ratiometric signaling. To this end, we fused a small, disulfide-containing domain, βZif (Smith et al., 2005, *Protein Sci*, 14, 64-73) to the C-terminus of several tsGBP2 cysteine mutants (Table 6). This arrangement enables independent, site-specific labeling with two different, thiol-reactive fluorophores by first reacting at the unprotected thiol in tsGBP2, followed by a reduction of the βZif disulfide to deprotect and label this second site with a second fluorophore. The first fluorophore, attached to tsGBP2 responds directly to glucose binding (directly responsive partner), whereas the second one, attached to the βZif fusion, does not (indirectly responsive partner). Indirectly responsive partners are selected according to their excitation and emission characteristics such that ngmFRET is established with the directly responsive partner. Under favorable circumstances, monochromatic responses of the directly responsive partner or weak dichromatic responses can be converted in to strong ratiometric signals, by exploiting ligand-induced modulation of non-geometrical factors affecting ngmFRET such as changes in spectral overlap between the two partnered fluorophores, and alteration of non-radiative decay rates in the directly responsive partner. Mechanisms for non-geometrically modulated FRET (ngmFRET) effects are detailed in Materials and Methods and PCT International Patent Application No. PCT/US16/62958, filed Nov. 19, 2016, the entire content of which is incorporated herein by reference.

TABLE 6

Glucose affinities of tsGBP2-βZif fusion proteins[a].

| Construct | Fluorophore (single cysteine) | Fluorophore (βZif) | Emission wavelength (nm) | | Kd (mM) | |
|---|---|---|---|---|---|---|
| | | | $\lambda 1$ | $\lambda 2$ | $^{app}K_d$ | $^{true}K_d$ |
| 13C.Acrylodan_βZif.Alexa532 | Acrylodan | Alexa532 | 515 | 548 | 0.5[b] | 0.7[b] |
| 13C.Acrylodan_βZif.Alexa555 | Acrylodan | Alexa555 | 491 | 556 | 1.1 | 1.0 |
| 13C.Acrylodan_βZif.TexasRed | Acrylodan | Texas Red | 515 | 615 | 0.9 | 1.2 |
| 244C.Acrylodan_βZif.Alexa532 | Acrylodan | Alexa532 | 491 | 545 | 42 | 52 |
| 244C.Acrylodan_βZif.Alexa555 | Acrylodan | Alexa555 | 491 | 565 | 17 | 22 |
| 244C.Acrylodan_βZif.TexasRed | Acrylodan | Texas Red | 491 | 613 | 14 | 18 |
| 13C 244F.Acrylodan_βZif.Alexa532 | Acrylodan | Alexa532 | 519 | 493 | 5.3 | 5.9 |
| 13C 244F.Acrylodan_βZif.Alexa555 | Acrylodan | Alexa532 | 515 | 493 | 4.5 | 4.8 |
| 13C 244F.Acrylodan_βZif.TexasRed | Acrylodan | Texas Red | 519 | 614 | 7.7 | 6.9 |

[a]Determined by fitting the ratiometric signal of the intensities measured at λ1 and λ2 to equations 1-5.
[b]Approximate value.

The Acrylodan conjugate attached to 244C elicits a strong monochromatic response (Table 4). To test whether this response could be converted into a dichromatic one, we partnered this conjugate with indirectly responsive acceptors Alexa532, Alexa555, and Texas Red, placed on the βZif domain (Table 6). In all cases ngmFRET was established between the two partners, and dichromatic responses were obtained. The wavelength interval for measuring the directly responsive donor intensity was centered near the Acrylodan emission peak, whereas that of the acceptors was placed at the emission maximum of each acceptor. For each of the three conjugates the intensities of both the directly responsive donor and the indirectly responsive acceptor increased with addition of glucose. This is consistent with a mechanism in which the glucose decreases the degree of quenching in the donor without a change in the shape of its emission spectrum, leading to increases in both the radiative emission and energy transfer rates (model d⁻φ⁰, Table 7). The unequal increases in donor and acceptor emission intensities results in dichromatic signals suitable for ratiometry. Alexa532 was the brightest of the three acceptors, and therefore well for glucose sensing.

TABLE 7

| Qualitative analysis of the patterns of donor and acceptor emission intensity changes in ngmFRET[a] | | | | |
|---|---|---|---|---|
| Directly responsive partner | Model | $Q_A/Q_D$ | $Q_D$ | $Q_A$ |
| Donor | $d^0\ \phi^+$ | ↑ | ↓ | ↑ |
| | $d^0\ \phi^-$ | ↓ | ↑ | ↓ |
| | $d^+\ \phi^0$ | ↓ | ↓ | ↓ |
| | $d^+\ \phi^+$ | * | ↓ | * |
| | $d^+\ \phi^-$ | ↓ | * | ↓ |
| | $d^-\ \phi^0$ | ↑ | ↑ | ↑ |
| | $d^-\ \phi^+$ | ↑ | * | ↑ |
| | $d^-\ \phi^-$ | * | ↑ | * |
| Acceptor | $a^0\ \phi^+$ | ↑ | ↓ | * |
| | $a^0\ \phi^-$ | ↓ | ↑ | * |
| | $a^+\ \phi^0$ | ↓ | 0 | ↓ |
| | $a^+\ \phi^+$ | * | ↓ | * |
| | $a^+\ \phi^-$ | ↓ | ↑ | * |
| | $a^-\ \phi^0$ | ↑ | 0 | ↑ |
| | $a^-\ \phi^+$ | ↑ | ↓ | ↑ |
| | $a^-\ \phi^-$ | * | ↑ | * |

[a]The effects of increasing or decreasing quenching in the directly responsive ngmFRET partner (d for donors, a for acceptors) or the energy transfer coupling (ϕ) between the donor and acceptor are tabulated. The consequences of using a directly responsive donor or acceptor are examined. Changes in quenching and energy transfer coupling parameters can occur singly or in combination, leading to 16 possible models. The models examine the effects of the direction of change in quenching parameters (no change, $d^0$ or $a^0$; increase $d^+$ or $a^+$; decrease, $d^-$ or $a^-$) and the energy transfer coupling factor (no change, $\phi^0$; increase, $\phi^+$; decrease, $\phi^-$) on the patterns in the direction of change of the donor, $Q_D$ (equation 30) or acceptor, $Q_A$ (equation 32) quantum yields, and their ratio, $Q_A/Q_D$ (equation 33): ↑, increase; ↓, decrease; 0, no change; *, response is dependent on precise quantitation rather than direction of change in the underlying parameter values.

We also tested whether the strong dichromatic response observed for the 13C.Acrylodan conjugate could be improved upon further by ngmFRET. This conjugate was paired with the three fluorophores described. Energy transfer was established in all three doubly labeled conjugates. The directly responsive donor emission intensity was measured for the blue state, and the three acceptor emissions were measured as described above. In all three cases, the ratio of the acceptor/donor intensities decreased with addition of glucose, as did the directly responsive donor intensities. The indirectly responsive acceptor intensity of the Alexa532 and Texas Red conjugates increased, whereas it decreased for Alexa555. These results are consistent with a mechanism in which the directly responsive Acrylodan donor switches from a green to a blue state, altering the energy transfer coupling factor, ϕ.

Example 5

Sensor Engineering Phase 4: Affinity Tuning

Blood glucose concentrations range from ~3 mM (hypoglycemia) to ~30 mM (hyperglycemia) and up to ~100 mM for the hyperosmolar hyperglycemic state (HHS) (Pasquel, 2014, *Diabetes Care,* 37, 3124-3131), with healthy levels at around 6 mM (euglycemia) (American Diabetes Association, 2000, *Clinical Diabetes,* 18). Measurements using reagentless sensors are most sensitive at analyte concentrations that match the dissociation constant (de Lorimier et al., 2002, *Protein Sci,* 11, 2655-75; Marvin et al., 1997, *Proc Natl Acad Sci USA,* 94, 4366-71). The glucose affinity of tsGBP13C.Acrylodan is too high and must therefore be "tuned" by raising the $K_d$ value.

The mutations that alter glucose affinities can fall into four classes:

1. Alteration of direct interactions in the PCS between the protein and the bound glucose.
2. Manipulation of the equilibrium between the open (ligand-free) and closed (ligand-bound) states.
3. Indirect interactions that alter the geometry of the binding site.
4. Alteration of interactions between the protein and the fluorescent conjugate.

Representatives of mutant class 1 were constructed in the tsGBP13C background, using Acrylodan and Badan conjugates to evaluate their effects on glucose binding (FIGS. 5A-F, Table 8). Both increases and decreases in affinity were observed, which together span four orders of magnitude (from ~0.1 mM to ~100 mM). This collection of mutants therefore can be used to construct fluorescent sensors covering the entire clinical range of glucose concentrations.

TABLE 8

| Glucose affinities of tsGBP 13C · Acrylodan and Badan conjugates. | | | | | | |
|---|---|---|---|---|---|---|
| | | | Emission wavelength (nm) | | Glucose affinity (mM)[c,d] | |
| Mutation | Fluorophore[a] | Change[b] | $\lambda_1$ | $\lambda_2$ | $^{app}K_d$ | $^{true}K_d$ |
| | A | d | 515 | 481 | 1.21 | 1.12 |
| | B | m/d | 513 | 571 | 0.23 | 0.29 |
| W8F | A | 0 | | | | |
| | B | 0 | | | | |
| W8M | A | d | 491 | 510 | 0.6[c] | 0.6[c] |
| | B | m | 546 | 491 | 0.27 | 0.38 |
| W8Y | A | m/d[c] | | | | |
| | B | 0 | | | | |
| W9F | A | m | 491 | 466 | 0.6[c] | 0.7[c] |
| | B | 0 | | | | |
| W9M | A | m | 491 | 515 | 0.4[c] | 0.4[c] |
| | B | m[c] | | | | |
| W9Y | A | d | 515 | 495 | 3.3 | 2.2 |
| | B | m | 532 | 487 | 0.65 | 1.2 |
| Q64N | A | d | 491 | 555 | 10 | 9.2 |
| | B | D | 515 | 560 | 1.3 | 1.2 |
| Q64E | A | d | 515 | 555 | 0.4[c] | 0.3[c] |
| | B | d | 519 | 555 | 2.1 | 2.9 |
| Q64M | A | m/d | 491 | 555 | 1.1 | 0.81 |
| | B | m | 519 | 492 | 0.1[c] | 0.1[c] |
| H66Q | A | d | 491 | 515 | 20[c] | 7[c] |
| | B | m | 485 | 540 | 0.1[c] | 0.09[c] |
| W244M | A | d | 515 | 490 | 40[c] | 20[c] |
| | B | d | 527 | 555 | 5[c] | 7[c] |
| W244F | A | d | 519 | 488 | 4.6 | 4.6 |
| | B | d | 523 | 555 | 2[c] | 2[c] |
| W244Y | A | d | 519 | 474 | 5.6 | 7.8 |
| | B | d | 519 | 555 | 4.1 | 3.8 |
| D278N | A | d | 515 | 470 | 100[c] | 100[c] |
| | B | m/d | 523 | 555 | 99 | 120 |
| D278S | A | m/d | 473 | 556 | 500[c] | 300[c] |
| | B | m/d | 527 | 555 | 81 | 91 |
| D278L | A | m | 459 | 549 | 800[c] | 400[c] |
| | B | 0 | | | | |
| K312M | A | d | 472 | 554 | 290 | 203 |
| | B | m | 527 | 555 | 26 | 39 |

[a]A, Acrylodan; B, Badan.
[b]m, monochromatic; d, dichromatic (i.e spectral shape change); 0, no-or very small change.
[c]Approximate value.
[d]Determined by fitting the ratiometric signal of the intensities measured at λ1 and λ2 to equations 1-5.

Example 6

Sensor Arrays for Detecting a Wide Range of Glucose Concentrations

The precision (reciprocal of the error) of individual sensor precision is maximal at the $K_d$ value, and decreases at lower or higher glucose concentrations (Marvin et al., 1997, *Proc Natl Acad Sci USA,* 94, 4366-71). Construction of a high-precision sensor capable of spanning the entire 100-fold clinical concentration range from extreme hypoglycemia to the HHS therefore requires combining several sensors together to maintain a high precision level. Candidates include (Tables 4 and 8): tsGBP13C.Acrylodan, tsGBP13C.Acrylodan 9Y, tsGBP13C.Acrylodan 64N, tsGBP13C.Acrylodan 66Q, tsGBP13C.Acrylodan 244F (Badan), tsGBP13C.Acrylodan 244Y (Badan), tsGBP13C.Acrylodan 244M (Badan), tsGBP13C.Acrylodan 278N. The βZif fusions also can used (Table 6).

Example 7

Sensor Engineering Phase 5: Device Integration

Protein immobilization on solid surfaces is an important step for incorporating biosensors into devices. Immobilization enables (i) spatial localization, (ii) control over the presentation of the sensors to the reader (e.g. by encoding geometries for optical readouts), (iii) selective retention in sample separation procedures. It is advantageous to control the geometry of the protein attachment to the solid surface, in order to minimize perturbation of the fluorescence sensing mechanism. Such constructs fuse an N- or C-terminal protein domain that can mediate site-specific attachment to an appropriately chemically activated surface. For instance, hexa-histidine peptide for metal-mediated immobilization. Here we show that site-specific attachment of a robust glucose sensor to suitably derivatized agarose beads conserves its emission fluorescence spectral response and thermostability.

The tsGBP13C_ 244F.Acrylodan protein was site-specifically immobilized through its C-terminal hexa-histidine tag on commercially available magnetic beads coated with Ni-NTA. The use of magnetic beads affords a straightforward means for holding the beads in place within their respective sensor patches in the sampling cartridge with a magnetic field. Site-specific immobilization is intended to minimize perturbation of the sensing mechanism. Comparison of protein thermostabilities determined in solution and on beads showed that protein stability was not perturbed by immobilization within the upper limit of the measured temperature (100° C.).

The magnetic beads coated with immobilized tsGBP13C_ 244F.Acrylodan were dried by incubation at 50° C. for 20 minutes, using an aqueous ammonium bicarbonate buffer. The stability properties of the sensor were recovered upon rehydration in the temperature, as determined up to 100° C. The dried beads were aged in situ inside fully assembled sample-handling cartridges by incubation for up to 7 days at 25° C., 37° C., and 50° C. in the dark. Fluorescence and glucose-responsive properties were tested in cartridges stored for 1, 2 and 7 days. For all drying conditions, the fluorescence ratio in the absence of glucose, and the glucose affinities of the immobilized sensors remained approximately unchanged. The tsGBP2-based FRSs therefore are sufficiently robust to be handled at ambient temperatures in a desiccated state, greatly simplifying manufacturing, distribution, and long-term storage conditions.

Example 8

Materials and Methods

Bioinformatic searches. Annotated genomic and plasmid sequences of 5062 prokaryotes were obtained from the National Center of Biotechnology Information (ftp://ftp.ncbi.nih.gov/genomes/Bacteria/all.gbk.tar.gz), together with annotations recording prokaryotic lifestyles ( . . . /ProkaryotesOrganismInfo.txt). The Protein Databank (PDB) was obtained from www.rcsb.org. The obtained genomic and structural data files were organized into pre-processed two databases (PG, prokaryotic genomes; PDB). The 'ProteinHunter' program provides an interface and methods for organizing, querying, and analyzing these databases. ProteinHunter comprises a graphical user interface, set of computer scripts, and a parallel computing environment. Together these set up the calculations, manage the flow of information and execution in each of the calculation phases, control other programs that carry out specific calculations such as BLAST (Altschul et al., 1990, *J Mol Biol,* 215, 403-10) and ClustalW (Chenna et al., 2003, *Nucleic Acids Res,* 31, 3497-500), and visualize the results.

To construct homolog sequence sets, single sequence seeds were extracted from either preprocessed PDB or PG databases. Homolog sets were then identified in the PDB or PG by using a seed sequence for a uni-directional BLAST search with the following parameters: expect threshold, 10.0; gap costs for existence, 11, and extension, 1; BLOSUM matrix; low complexity filter is on (the ProteinHunter package always executes BLAST searches with the following command "blastall -p blastp -m 8 -b 50000 -d <database file>-i <input file>-o <output file>, where <database file> specifies the name of the prebuilt search sequence file and <input file> and <output file> the seed sequence input and hit output files respectively. A pairwise BLAST alignment was scored in ProteinHunter as a homolog hit if it exceeded a minimum fraction of identical residues and if the alignment covered at least 70% of the probe and target sequences.

Function was inferred using the sequence of primary complementary surface (PCS) residues. A 11-residue, non-contiguous sequence comprising the PCS between the protein and the bound glucose in the ttGBP1 structure (PDB entry 2b3b) was identified using ProteinHunter (FIG. 3 and Table 2). PCS residues were selected as members of the PCS if the calculated distance between any of their atoms and any acetamide atom was less than 5 Å, and the distances between their backbone $C_\alpha$ and any atom in acetamide was greater than that of their $C_\beta$ atom and any atom in glucose. Secondary shell residues that do not form hydrogen bonds or van der Waals contacts were removed by inspection from the resulting set. To determine the PCS sequence of members in the ttGBP1 homolog set identified in ProteinHunter, their sequences were aligned using ClustalW (Chenna et al., 2003, *Nucleic Acids Res,* 31, 3497-500). This alignment identifies the positions of the PCS residues in each homolog, from which the corresponding PCS sequence in that homology is then read. For each homolog, the number of PCS mutations relative to the glucose-binding PCS (Hamming distance, $H_{PCS}$) was counted. Homologs with $H_{PCS}=0$ were inferred to be glucose-binding proteins. The PCS sequences were displayed sorted by their $H_{PCS}$ values, and within each $H_{PCS}$ value sorted by their fraction identical residues, indicating the replicon within which they reside (chromosome or plasmid), whether this replicon contains paralogs, and the temperature tolerance (hyperthermophile, thermophile, mesophile, psychrophile, unknown), their Gram stain classification (if known), and the percentage genomic AT content. Duplicate hits were removed automatically from this list if the organism name (genus and species), fractional identity and paralogs were the same. From this list representative, unique ttGBP1 homologs with $H_{PCS}=0$ were chosen by inspection (Table 2).

Gene synthesis and mutagenesis. The amino acid sequences for the predicted GBP homologs identified in the bioinformatic search (see above) were extracted from the PG database. The putative leader peptide that mediates anchoring of the periplasmic-binding protein on the outside of the membrane (Gram positive bacteria) or directs secretion into the periplasm (Gram negative bacteria) was deleted by examining the multiple sequence alignment and removing the sequences N-terminal to the start of the mature GBP amino acid sequence. Endogenous cysteines were changed to alanine. A hexahistidine tag was placed behind a GGS linker at the C-terminus of the mature protein to enable metal-mediated affinity purification (Hengen, 1995, *Adv Healthc Mater,* 2, 43-56). The final amino acid sequences were back-translated into a DNA sequence encoding the open reading frame (ORF), which was placed in a construct behind an efficient Shine-Dalgarno ribosome-binding site, and flanked by a T7 promoter and terminator at the 5' and 3' ends respectively, using the GeneFab program (Cox et al., 2007, *Protein Sci,* 16, 379-90). The resulting ORF sequences were optimized in context by OrfOpt or OrfMorph programs designed to predict highly expressed mRNA sequences in *E. coli* (see below). The resulting DNA sequences were synthesized by oligonucleotide assembly and cloned into pUC57 by GeneWiz, Inc. (South Plainfield, N.J.).

Subsequent single and multiple point mutations were designed by preparing mutant sequences of the synthetic ORF sequences using the GfMutagenesis program that introduces point mutations into an ORF using the most prevalent codon in *E. coli* for an amino acid. Constructs for site-specific double labeling were designed by inserting the βZif domain sequence (Smith et al., 2005, *Protein Sci,* 14, 64-73) before the hexa-histidine C-terminal purification tag. All variants also were constructed by total gene synthesis.

Synthetic gene optimization. The OrfOpt program (U.S. Patent Publication No. 2011/0171737, incorporated by reference) uses stochastic optimization algorithms that choose different codons within an ORF without altering the amino acid sequence to optimize a target function designed to identify mRNA sequences that express proteins at high levels in *E. coli*. The OrfOpt simultaneously imposes AU-rich nucleotide composition at the 5' and 3' ends of the ORF, low RNA secondary structure content and favorable codon usage (Allert et al., 2010, J Mol Biol, 402, 905-18). The OrfMorph program reproduces the pattern of codon usage and RNA secondary structure observed in the parent genome of a protein, but using *E. coli* codon preferences and nucleotide composition.

Codon usage is calculated using the codon adaptation index (CAI), as described for OrfOpt, using codon frequency tables calculated for the genome under examination. The mean CAI value for a genome, $\mu_c$, and its standard deviation, $\sigma_c$, are calculated over all the codons in a genome. A codon usage score, c, is calculated for each codon in an open reading frame (ORF) by averaging the CAI over a 9-codon window, centered on the codon for which this score is calculated. A normalized codon usage score, $z_c$, is calculated for each codon as Z-score: $z_c=(c-\mu_c)/\sigma_c$. A plot of $z_c$ along an ORF establishes the codon usage pattern of that ORF. Rare codons ($z_c<0$) are hypothesized to slow down the elongation rate of ribosome translation, introducing "pause" sites at extreme values. Such pause sites are hypothesized to direct kinetics of co-translational folding, allowing a newly synthesized segment to fold before more protein is made. An RNA secondary structure score, s, is determined for each nucleotide by summing its participation in all possible hairpins that can form in its vicinity (settings: minimum duplex length 4 basepairs; maximum loop length, 30 bases; vicinity length, 100 bases), as described for OrfOpt. The average secondary structure energy, $\mu_s$, and its standard deviations, $\sigma_s$, are calculated over all the nucleotides in a genome. A normalized secondary structure energy score, $z_s$, is calculated for codon as the Z-score: $z_s=(c-\mu_s)/\sigma_s$. A plot of $z_s$ along an ORF establishes the secondary structure pattern of that ORF. Regions of above-average secondary structure ($z_s>0$) are hypothesized to slow down the elongation rate of ribose translation, introducing "pause" sites at extremes. As with CAI-mediated pause sites, secondary structure-driven pause sites are hypothesized to direct the kinetics of co-translational folding.

To mimic these patterns for heterologous expression of an ORF in *E. coli*, first the $z_c$ and $z_s$ scores are calculated using the parent organism codon table, $\mu_c$, $\sigma_c$, $\mu_s$, and $\sigma_s$ values. Second, a stochastic search algorithm is used that randomly chooses between degenerate codons to construct trial mRNA nucleotide sequences, calculating $z_c$ and $z_s$ scores for each trial sequence, but using the *E. coli* codon table, and *E. coli* $\mu_c$, $\sigma_c$, $\mu_s$, and $\sigma_s$ values. For each trial, the absolute differences between the *E. coli* trial scores, and the wild-type scores are summed over the entire ORF. The OrfMorph program searches for a minimum of these differences. The stochastic search algorithm operates by first choosing a codon position, second choosing a degenerate codon within the allowed codons at that position. If the choice results in an improved score, the sequence is kept, otherwise it is rejected. After a position has been selected, it is removed from the pool of allowed positions, and the next is chosen from the remainder. The algorithm terminates when two successive sweeps do not yield further improvements in the score. The resulting RNA nucleotide sequence that has codon usage patterns and secondary structure patterns that closely match those of the wild-type mRNA sequence in its parental genomic context. The strategy is that such matching improves production of soluble protein by mimicking co-translational folding contributions that minimize mis-folded protein intermediate aggregation.

Protein expression, purification, and fluorescent conjugate preparation. Plasmids carrying the expression constructs (see above) were transformed into KRX competent cells (Promega), and grown overnight at 37° C. on LB agar plates (100 mg/mL ampicillin). A single colony was picked and grown overnight at 37° C. in Terrific Broth (TB; Research Products International). The overnight cultures were diluted 1:20 in 500 mL TB (100 mg/mL ampicillin), grown to an optical density of $A_{600}=0.5$ at 37° C. in vigorously aerated shaker flasks, induced by the addition of 2.5 mL rhamnose (20% w/v), and grown for a further 3-4 hrs. The cells were harvested by centrifugation (5,000 rpm, 10 min). After decanting the supernatant, the cell pellets were stored −80° C. The cell pellets were thawed, resuspended in 8 mL binding buffer (10 mM imadozole, 20 mM MOPS, 500 mM NaCl, pH 7.8). Following resuspension, 3 mL of BugBuster HT (EMD Millipore) was added. After incubation (20 mins, 25° C.), the cells were lysed on ice by sonication (2 minutes of one-second on/off pulses, 20-30% power). A clarified lysate was prepared by centrifugation (15,000 rpm, 20 min, 4° C.) from which recombinant protein was purified by batch immobilized metal affinity chromatography (IMAC). Resuspended IMAC agarose beads (5 mL; Sigma-Aldrich, P6611) were added to the lysate. After incubation at 4° C. in a Mini LabRoller (Labnet International) for 1 hr, the beads were washed at least five times with binding buffer. The immobilized protein beads were resuspended in labeling buffer (20 mM MOPS, 100 mM NaCl, pH 6.9) and labeled overnight (4° C., rotating end-over-end) with a thiol-reactive fluorophore (5-fold stoichiometric excess over protein). Following two rinses with labeling buffer to remove unincorporated label, the proteins were eluted from the beads. For double labeling of βZif fusions, a second thiol-reactive label was added following reduction of the disulfide with 5 mM TCEP. To elute labeled protein from the IMAC beads, 6 mL of elution buffer (400 mM imidazole, 500 mM NaCl, 20 mM MOPS, pH 7.8) was added, incubated for 30 min (4° C., rotating end-over-end), and the beads removed by centrifugation. Following dialysis of the eluate against three changes of assay buffer (20 mM MOPS, 20 mM KC1, pH 7.4), using 10 kDa semi-permeable membrane (Snakeskin tubing, Thermo Scientific), the fluorescent conjugates were concentrated in a 10 kDa cutoff spin concentrator (Vivaspin, GE Healthcare). Protein purity was assessed by SDS/PAGE. Protein concentrations were determined by (Nanodrop1000) at 280 nm (using extinction coefficients calculated from their sequence (Gill and von Hippel, 1989, *Anal Biochem,* 182, 319-26; Artimo et al. 2012, *Nucleic Acids Res,* 40, W597-603), or at the fluorophore absorbance peak (Acrylodan, 391 nm and Badan, 387 nm).

Determination of temperature- and ligand-dependent fluorescence landscapes. 12-, 24-, or 48-point logarithmic titration series were prepared on a Tecan Freedom liquid-handling robot, using an in-house program, 'TitrationPlate', that compiles an abstract description of a multi-component titration series into machine instructions for operating the robot. Temperature-dependent fluorescence emission intensities of 20 μL aliquots, each containing 10 μM protein, were measured in 384-well microtiter plates in a LightCycler 480 II (Roche) using excitation and emission wavelengths available for this instrument that most closely matched the optical characteristics of the fluorescent conjugate. Temperatures were advanced in 1K steps. At each temperature, data was collected at 1-second intervals for 60 seconds at which point the signal had relaxed to a steady value associated with the new temperature. Under these experimental photobleaching was not observed. The in-house program 'TitrationMeltPlate' was used to convert these observations into time-independent datasets that record fluorescence as a function of temperature for each well and associate wells with their concentration of titrant and additive. Management tools were developed to maintain a database of titrations and their analyses.

Determination of emission intensity spectra. Ligand- and wavelength-dependent emission intensities were recorded on a Nanodrop3300 (Thermo Scientific) at room temperature. Using the LED closest to the optimal excitation wavelength of the fluorophore (UV, 365 nm; blue, 470 nm; 'white', 460-550 nm).

Ratiometric analysis of glucose binding. Isothermal glucose titrations were extracted from the fluorescent landscape or emission spectra datasets obtained as described above. Monochromatic emission intensities $I_\lambda$ (these intensities correspond to a bandpass intensity, recorded either with a physical filter in the case of the Roche LightCycler, or by integrating in the interval λ−δ, λ+δ in the case of an emission spectrum), were fit to $$I_\lambda = {}^{apo}\beta_\lambda(1-\bar{y}_{true}) + {}^{sat}\beta_\lambda\bar{y}_{true} \quad 1$$

where ${}^{apo}\beta_\lambda$ and ${}^{sat}\beta_\lambda$ are the fluorescence baselines associated with the ligand-free and ligand-bound states of the protein, respectively, and $\bar{y}_{true}$ the fractional saturation of the protein (Layton and Hellinga, 2010, *Biochemistry,* 49, 10831-41). Baseline functions can be constant, linear, or a second-order polynomial. For the ligand- and temperature-dependent fluorescence landscapes, we use a constant value for ${}^{apo}\beta_x$, but ${}^{sat}\beta_x$ is described by a linear dependence on glucose concentration, [L]:

$${}^{sat}\beta_x = a_x + b_x[L] \quad 2$$

For a single glucose-binding site, the fractional saturation is given by $$\bar{y} = \frac{[L]}{[L]+K_d} \quad 3$$

where [L] is the ligand (glucose) concentration and $K_d$ the dissociation constant, ${}^{true}K_d$ for $\bar{y}_{true}$.

A ratiometric signal at a given point in a titration series, $R_{12}(t)$, is given by the ratio of intensities at two wavelengths, ${}^{obs}I(\lambda_1,t)$, ${}^{obs}I(\lambda_2,t)$ in the emission spectrum measured at that point:

$$R_{12}(t) = \frac{a_t^{obs}I(\lambda_1,t)}{a_t^{obs}I(\lambda_2,t)} \quad 4$$

where $a_t$ is an attenuation factor that describes the effect of variations in sample size (i.e. the amount of observable fluorophore) in the $t^{th}$ sample on the wavelength-independent intensity of the entire emission spectrum. This signal removes wavelength-independent emission intensity attenuation effects due to variations in conjugate concentration, photobleaching, fluctuations in excitation source intensities, and detection efficiency (Demchenko, 2010, *J Fluoresc,* 20, 1099-128; Demchenko, 2014, *Journal of Molecular Structure,* 1077, 51-67). It is a key aspect for high-precision sensing using the reagentless fluorescently-responsive sensors described here. The ratiometric signal also can be fit to a binding isotherm:

$$R_{1,2} = {}^{apo}\beta_R(1-\bar{y}_R) + {}^{sat}\beta_R\bar{y}_R \quad 5$$

where ${}^{apo}\beta_R$ and ${}^{sat}\beta_R$ are the baselines, and $\bar{y}_R$ the apparent fractional saturation of the protein (with ${}^{app}K_d$). In general, ${}^{true}K_d \neq {}^{app}K_d$; if both baselines are constant, a simple relationship can be derived relating ${}^{app}K_d$ to ${}^{true}K_d$ (Grimley et al., 2013, *J Neurosci,* 33, 16297-309):

$${}^{app}K_d = {}^{true}K_d\frac{{}^{apo}I_{\lambda 2}}{{}^{sat}I_{\lambda 2}} \quad 6$$

where ${}^{apo}I_{\lambda 2}$ and ${}^{sat}I_{\lambda 2}$ are the emission intensities of the monochromatic signal at wavelength $\lambda_2$ of the ligand-free and ligand-bound protein, respectively.

Following a fit of the titration series using equations 4 and 5, $a_t$ values can be recovered by taking the average comparison of the observed and calculated intensities at the two wavelengths:

$$a_t = \frac{1}{2}\left(\frac{{}^{calc}I(\lambda_1,t)}{{}^{obs}I(\lambda_1,t)} + \frac{{}^{calc}I(\lambda_2,t)}{{}^{obs}I(\lambda_2,t)}\right) \quad 7$$

The $a_t$ value can then be applied to all wavelengths to obtain an emission spectrum or integrated intensity of the $t^{th}$ titration point corrected for variations in sample size:

$${}^{corr}I(\lambda) = a_t^{obs}I(\lambda) \quad 8$$

where ${}^{corr}I(\lambda)$ and ${}^{obs}I(\lambda)$ are the wavelength-dependent intensities of the corrected and observed emission spectra, respectively.

The fractional error in the chemometric concentration measurement, depends on the first derivative of the binding isotherm as follows (Marvin et al., 1997, *Proc Natl Acad Sci USA,* 94, 4366-71):

$$\frac{\partial S}{S} = \frac{\varepsilon_{1,2}}{S} \times \left(\frac{dR_{1,2}}{dS}\right)^{-1} \quad 9$$

Where $R_{1,2}$ is the ratiometric signal (equation 5), $\varepsilon_{1,2}$ its experimental error, and $\delta S$ is the resulting chemometric error in the concentration. We can then define a relative precision function $$P(S) = \frac{S}{\delta S} \times \frac{1}{P_{max}} \quad 10$$

where P(S) is the relative precision at concentration S, which reaches a maximum value (i.e. lowest error), $P_{max}$, at the $K_d$.

For a given isothermal titration, values for ${}^{app}K_d$ and ${}^{true}K_d$ were obtained using a non-linear fitting algorithm in which these two parameters were simultaneously fit to the three experimental binding isotherms using equations 1 and 5, with the two monochromatic isotherms sharing the same ${}^{true}K_d$ value. Three separate pairs of ${}^{apo}\beta$ and ${}^{sat}\beta$ were fit in this procedure, corresponding to the two monochromatic and the ratiometric signals, respectively. Two distinct ratiometric response models can be used: coupled (both wavelengths respond to ligand); uncoupled (the second wavelength is non-responsive; i.e. remains constant). Optionally, an attenuation vector, a(t) containing $a_t$ values for each titration point (equation 7), can be refined by iterative fit cycles in which the a(t) vector of a previous cycle is used to adjust the integrated intensities of the next cycle. Programs 'Nanodrop3300' and 'TitrationMeltAnalysis' were developed to analyze wavelength- or temperature-dependent ligand-binding datasets respectively.

Analysis of glucose-binding properties using thermal melts. The thermal stability of purified GBP candidate proteins was determined by measuring the temperature-dependence of the fluorescence signal of an extrinsically added dye, SYPRO, using a Roche LightCycler (Layton and Hellinga, 2010, *Biochemistry,* 49, 10831-41). The total fluorescence intensity, S, is given by $$S=\beta_F f_F+\beta_U f_U \quad 11$$

where $f_F$ and $f_U$ are the fractions of protein in the folded and unfolded states, respectively, and $\beta_F$ and $\beta_U$ the fluorescence baselines of these two states. To get the fractions of the two states, we have $$f_N = \frac{1}{1+K_U(T)} \text{ and } f_U = 1 - f_N \quad 12$$

where $K_U(T)$ is the temperature-dependent unfolding equilibrium constant, which by the van't Hoff approximation is given by $$K_U = e^{-\Delta H_U\left(\frac{1}{T}-\frac{1}{T_m}\right)/R} \quad 13$$

Where T is the temperature, $T_m$, the unfolding reaction transition mid-point temperature, and $\Delta H_U$ the enthalpy of unfolding.

To obtain the temperature dependence of the binding reaction, the $K_d$ values of all the individually determined isotherms were fit the Gibbs-Hemholtz equation (Layton and Hellinga, 2010, *Biochemistry,* 49, 10831-41):

$$\Delta G_b^{\bullet}(T) = \Delta^{ref} H_b^{\bullet} + \Delta C_{p,b}(T - T_{ref}) - T\left(\Delta^{ref} S_b^{\bullet} + \Delta C_{p,b} \ln\frac{T}{T_{ref}}\right) \quad 14$$

where $\Delta G_b^{\bullet}(T)$ is the standard free energy of binding at 1 M ligand at temperature T, $$\Delta G_b^{\bullet}(T) = -RT \ln\left(1 + \frac{1}{K_d(T)}\right) \quad 15$$

$\Delta^{ref}H_b^{\bullet}$ and $\Delta^{ref}S_b^{\bullet}$ the molar enthalpy and entropy of binding, respectively, at the reference temperature, $T_{ref}$, and $\Delta C_{p,b}$ the heat capacity of the binding reaction. This data analysis was carried out using 'TitrationMeltAnalysis'.

Mechanisms for Ligand Sensing using Non-Geometric Modulation of FRET.

The subject matter disclosed herein is not limited to or bound by any particular scientific theory. However, discussions regarding ngmFRET are provided to facilitate the understanding of possible mechanisms involved with ngmFRET signaling in various embodiments described herein. Equations for calculating various values mentioned herein are also provided.

The total signal, S, of a fluorescent sensor (either single-wavelength emission intensities, $I_\lambda$, or ratios of intensities at two wavelengths, $R_{12}$) is the sum of the fluorescence due to the ligand-free (apo) and ligand-bound states:

$$S=\alpha(1-\bar{y})+\beta\bar{y} \quad 16$$

where $\alpha$ and $\beta$ are the fluorescent baselines in the ligand-free and -bound states, respectively, and $\bar{y}$ is the fractional occupancy of the binding sites (equation 3).

Fluorescence quantum yields are the fractions of photons emitted by the excited state relative to the total absorbed, and correspond to the ratio of the radiative decay rate relative to the sum of the rates of all possible decay pathways (FIG. 6). For a single flurophore:

$$Q = \frac{k_r}{k_r + k_{nr}} \quad 17$$

where $k_r$ and $k_{nr}$ are the radiative and non-radiative decay rates of the excited state, respectively. If we define q as the ratio between the radiative and non-radiative decay rates, $$q = \frac{k_{nr}}{k_r} \quad 18$$

then the quantum yield can be written as $$Q = \frac{1}{q+1} \quad 19$$

Chemical sensors exploit the ligand-mediated shift of a fluorescent system between the ligand-free and ligand-bound states which each exhibit distinct quantum yields:

$$Q_{obs}=Q_{apo}(1-\bar{y})+Q_{sat}\bar{y} \quad 20$$

where $Q_{obs}$, $Q_{apo}$ and $Q_{sat}$ are the quantum yield of the total system, the apo-protein, and the ligand-bound complex, respectively. In a system involving energy transfer between a donor and acceptor fluorophore, the $Q_{apo}$ and $Q_{sat}$ quantum yields each are combinations of their respective donor and acceptor quantum yields:

$$Q_{apo}={}^{D}Q_{apo}+{}^{A}Q_{apo} \text{ and } Q_{sat}={}^{D}Q_{sat}+{}^{A}Q_{sat} \quad 21$$

where the superscripts D and A indicate donor and acceptor fluorophores respectively. To understand ngmFRET-based sensors, we therefore need to examine the factors that affect each of these four quantum yields.

Figure 6A:
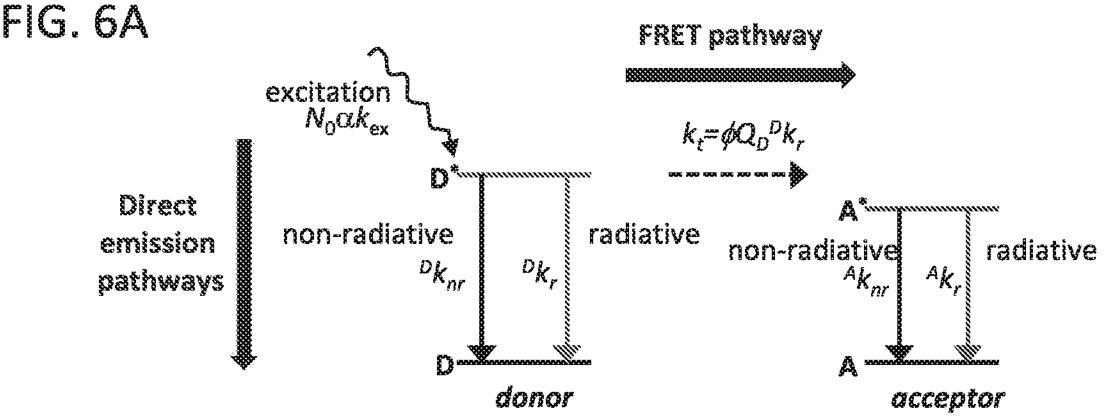
FIGS. 6A-D are diagrams illustrating three dominant factors that affect FRET between donor and acceptors in which one partner responds to ligand binding.
Figure 6B:
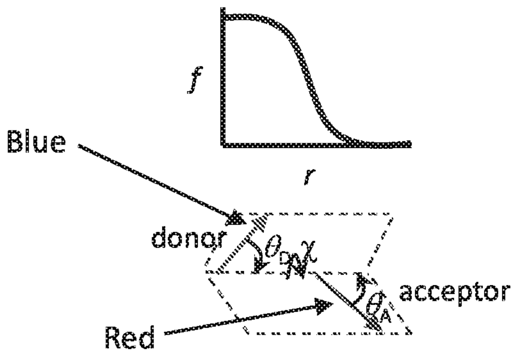
Figure 6C:
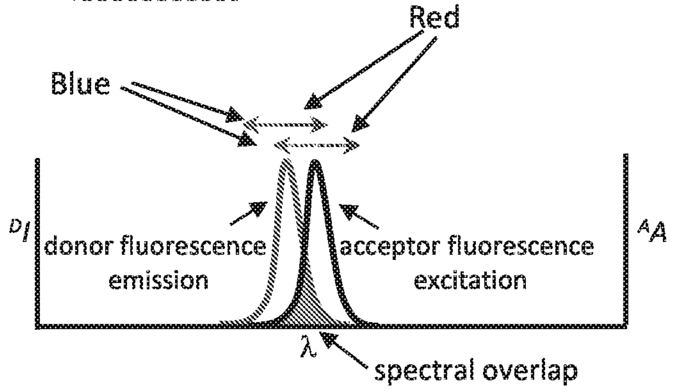
Figure 6D:
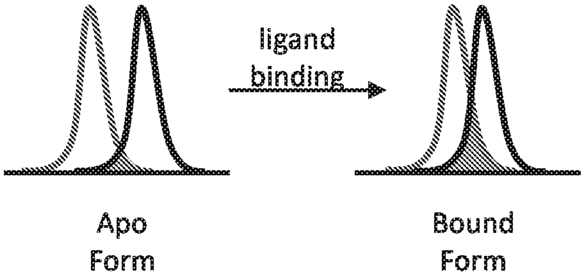
Figure 55A:
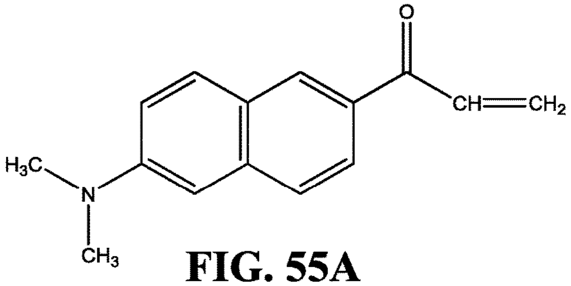
FIG. 55A-P are illustrations of fluorophore structures. Naphthalene family (arrows indicate known or potential internal twists)
Figure 55B:
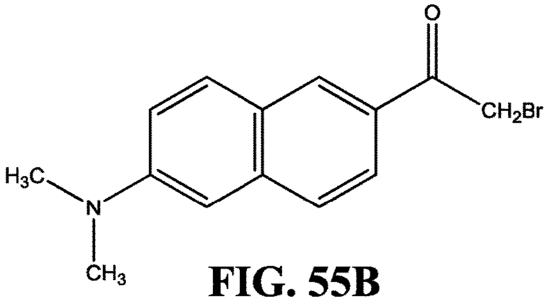
FIG. 55B shows Badan.
Figure 55C:
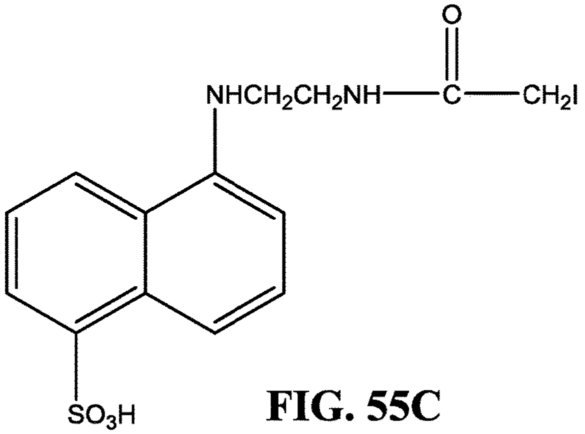
FIG. 55C shows IAEDANS. Xanthene family.
Figure 55D:
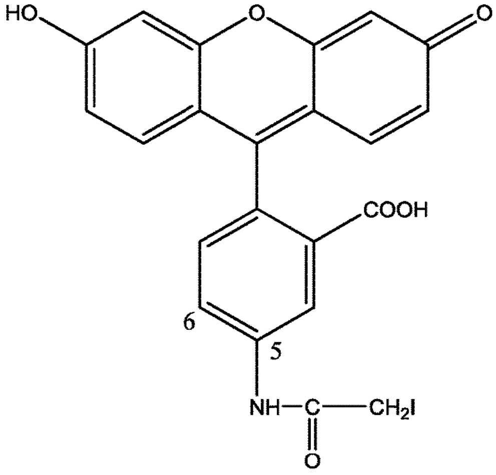
FIG. 55D shows Fluorescein (5-IAF and 6-IAF)
Figure 55E:
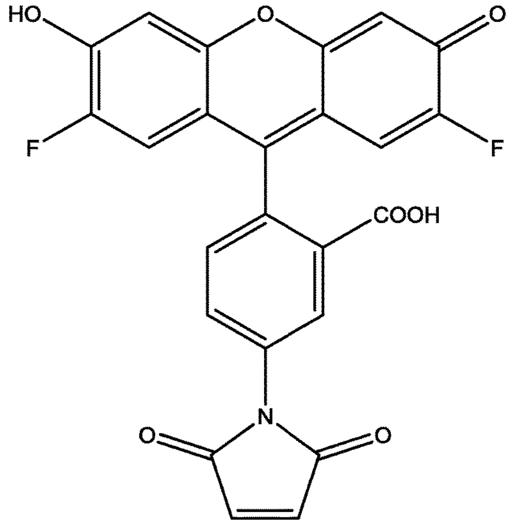
FIG. 55E shows Oregon Green.
Figure 55F:
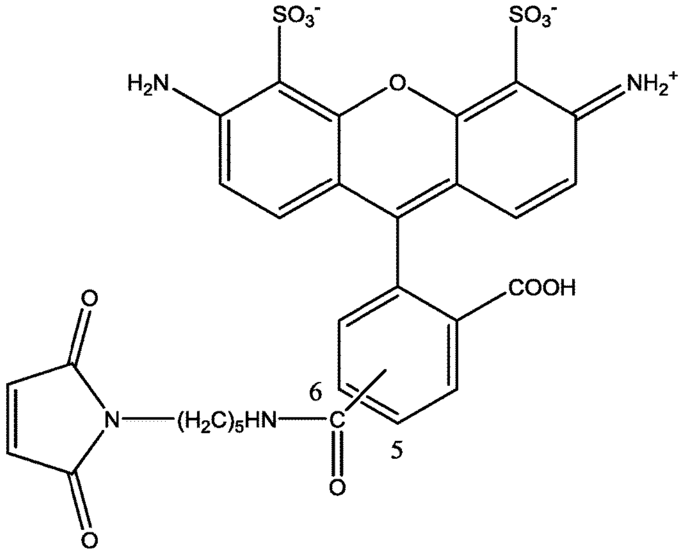
FIG. 55F shows Alexa 432.
Figure 55G:
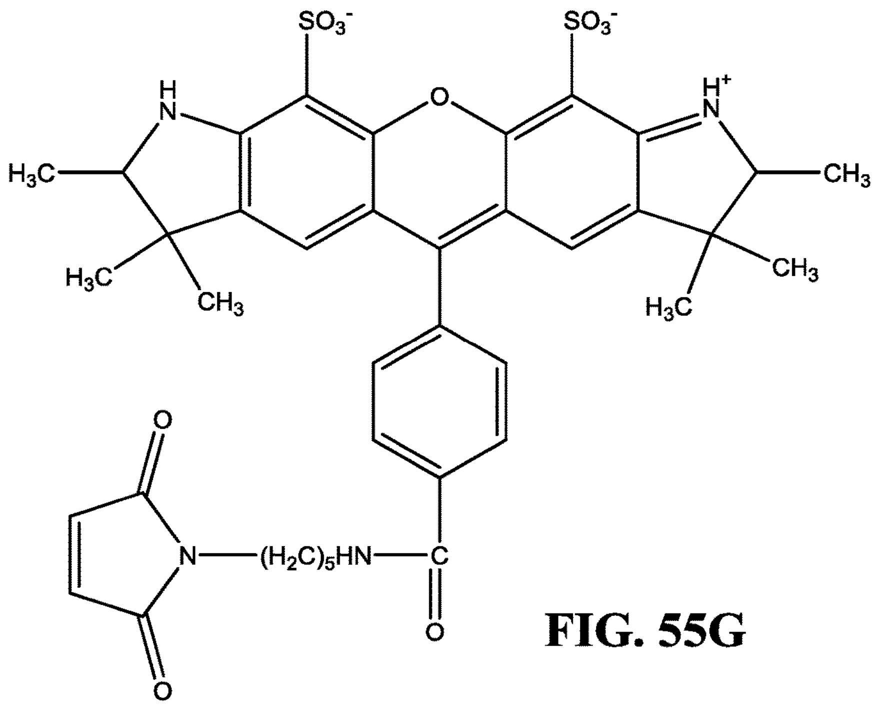
FIG. 55G shows Alexa532.
Figure 55H:
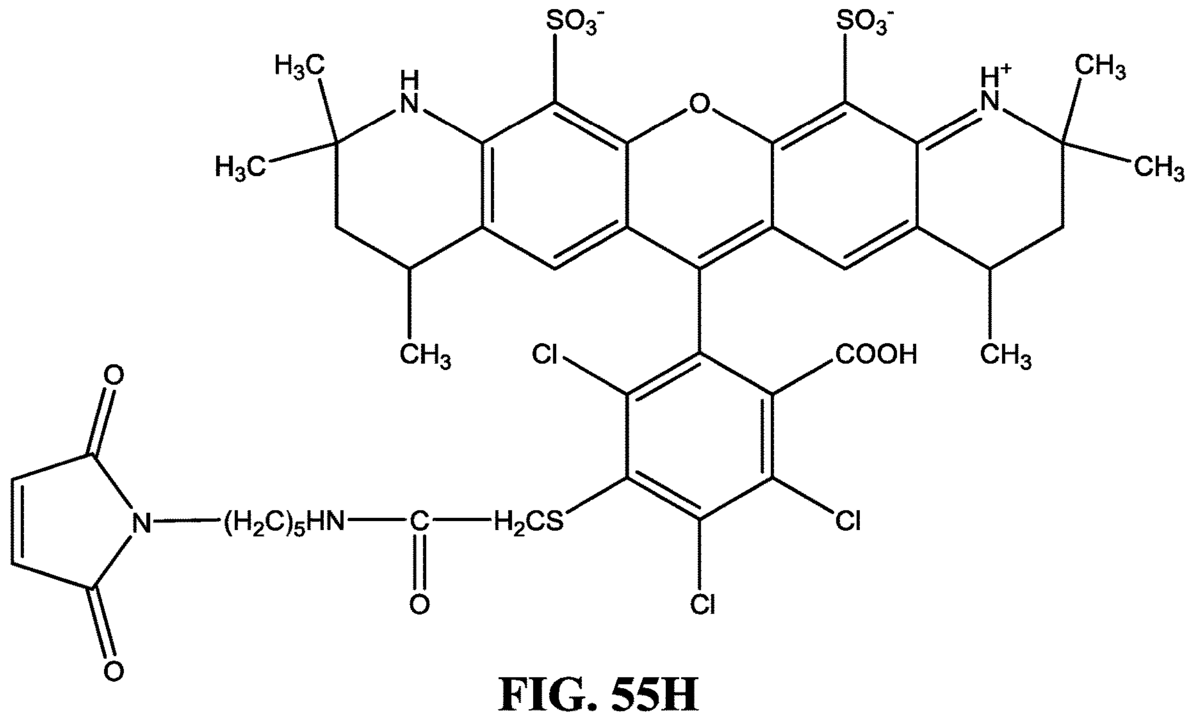
FIG. 55H shows Alexa 546.
Figure 55I:
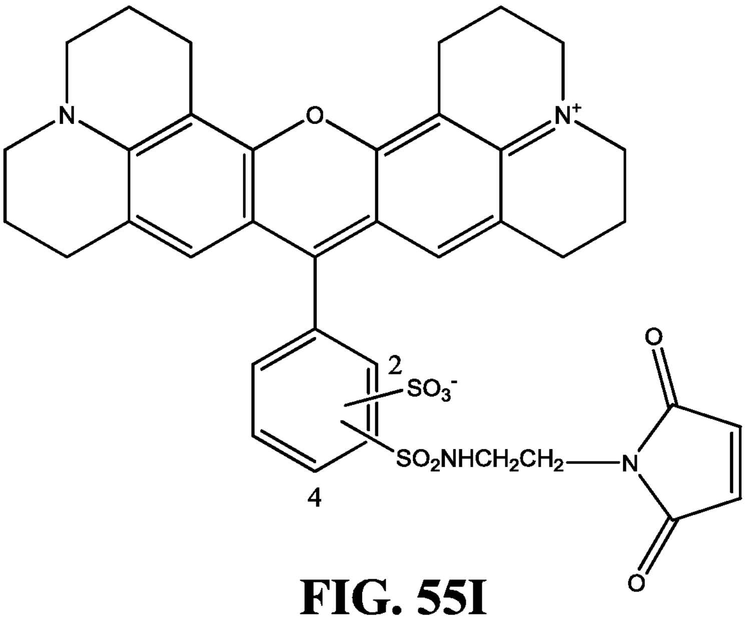
FIG. 55I shows Texas Red. Coumarin family.
Figure 55J:
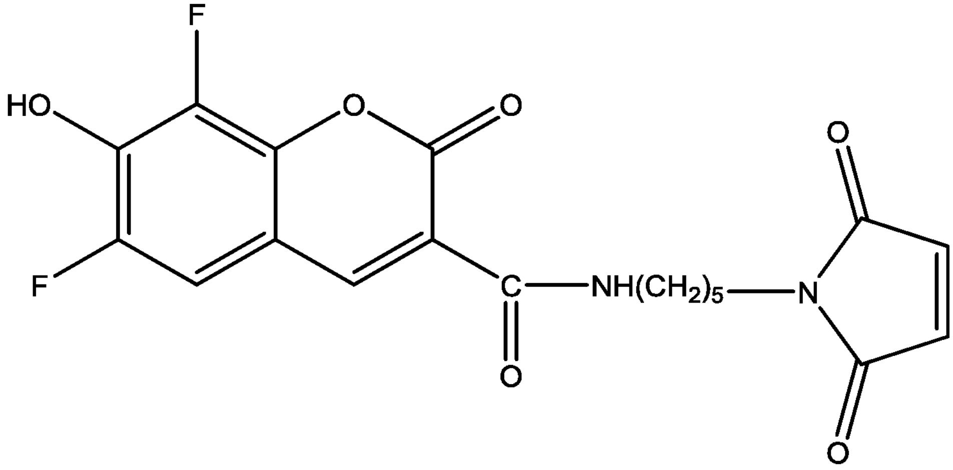
FIG. 55J shows Pacific Blue.
Figure 55K:
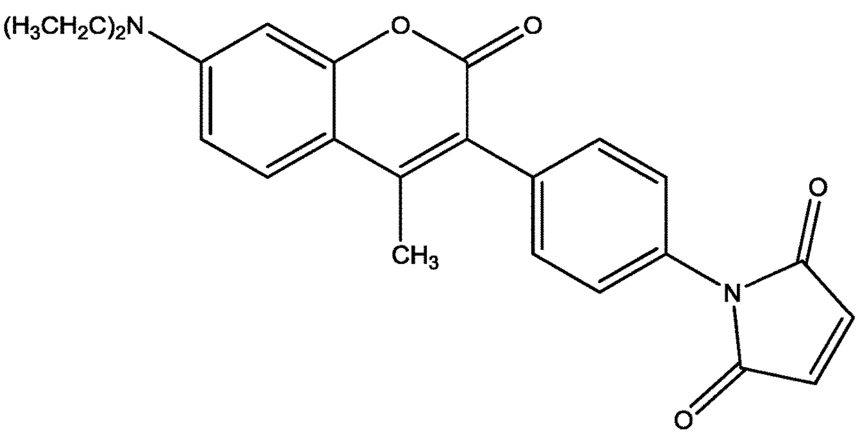
FIG. 55K shows CPM. Benzoxadiazole family.
Figure 55L:
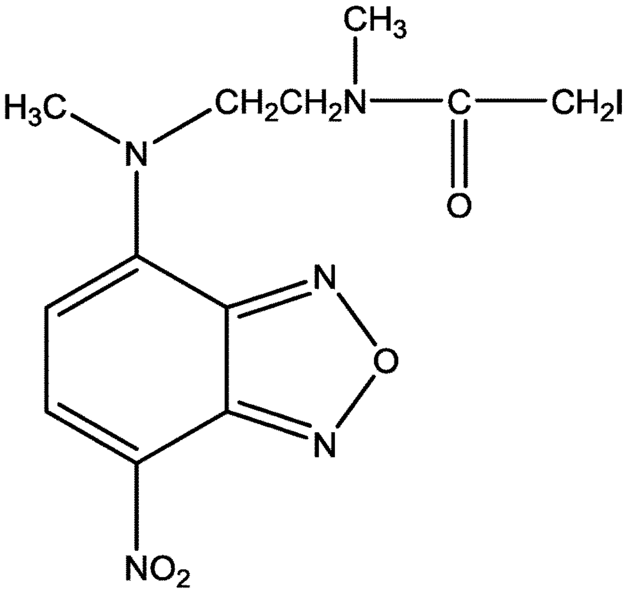
FIG. 55L shows IANBD. Boradiazaindacine (BODIPY) family.
Figure 55M:
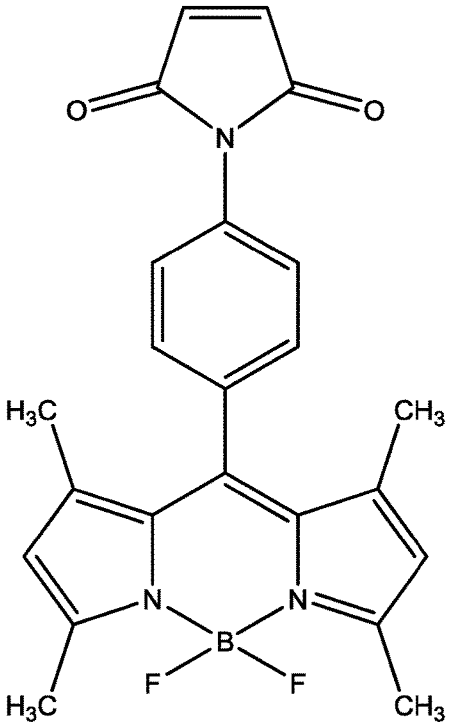
FIG. 55M shows BODIPY 499/508.
Figure 55N:
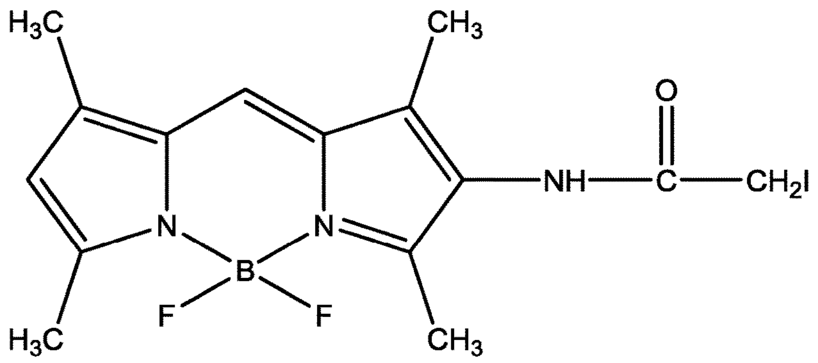
FIG. 55N shows BODIPY 507/545. Cyanine family.
Figure 55O:
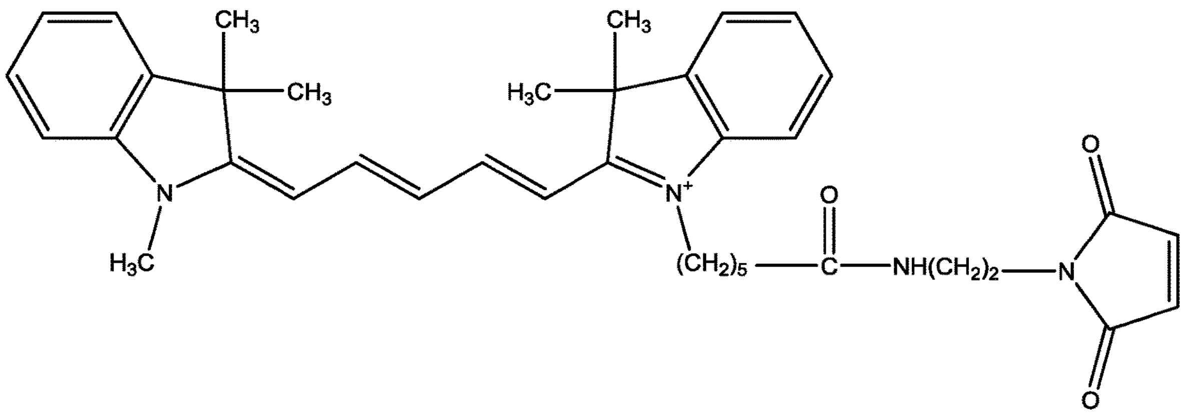
FIG. 55O shows Cy5. Miscellaneous.
Figure 55P:
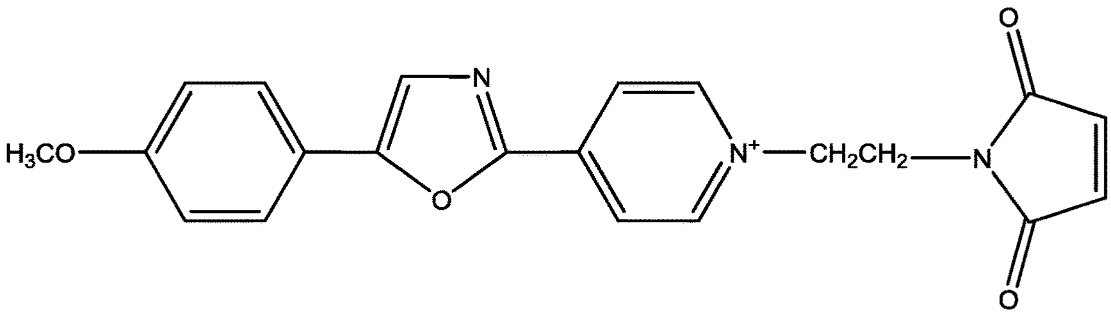

The intensity of the light emitted by a donor or its acceptor is determined by the rate of photon emission from their respective excited states (FIG. 6A). The excited state of a donor is formed by the incident light from the excitation source, and there are three pathways by which this state decays: radiative and non-radiative decay and resonance transfer (by itself and regardless of the presence of any other fluorophore/parter). By contrast, the rate of formation of the acceptor excited state is determined by the resonance transfer rate from the donor, and there are only two processes that determine its decay rate: the radiative and non-radiative pathways (by itself and regardless of the presence of any other fluorophore/parter). In an ngmFRET system, the patterns of ligand-mediated fluorescence intensity changes therefore depend on whether the fluorophore that responds directly to ligand binding functions as a donor or acceptor. To understand these relationships, we analyze the factors that determine the rates of formation and decay of the donor and acceptor excited states.

The rate of resonance energy transfer, $k_t$, along a non-radiative pathway between donor and acceptor (FIG. 6*a*) is a fraction of the intrinsic radiative emission pathway rate (by itself and regardless of the presence of any other fluorophore/parter), ${}^{D}k_r$ (the emission rate in the absence of an acceptor) multiplied by the energy transfer coupling factor, ϕ, (Lakowicz, 2006, Principles of fluorescence spectroscopy. Springer, New York; Valeur, 2012, Molecular Fluorescence. Principles and Applications. Weinheim: Wiley):

$$k_t=\varphi Q_D{}^{D}k_r \quad 22$$

where $Q_D$ is the donor quantum yield in the absence of an acceptor.

According to the Förster model of weakly coupled oscillators (Lakowicz, 2006, Principles of fluorescence spectroscopy. Springer, New York; Valeur, 2012, Molecular Fluorescence. Principles and Applications. Weinheim: Wiley), the energy transfer coupling factor is dependent on the spectral overlap, J, of the donor emission, ${}^{D}\lambda_{em}$, and acceptor excitation spectrum, ${}^{A}\lambda_{ex}$, and the variation of the geometry, G, between the donor and acceptor excited state transition dipoles with distance, r, and orientation factor, κ:

$$\varphi = G(r,\kappa)J({}^{D}\lambda_{em},{}^{A}\lambda_{ex})\frac{9000\ \ln 10}{128\pi^5 N_A n^4} \quad 23$$

where $$G(r,\kappa)=\frac{\kappa^2}{r^6} \quad 24$$

and

-continued $$J({}^{D}\lambda_{em},{}^{A}\lambda_{ex})=\int F({}^{D}\lambda_{em})\varepsilon({}^{A}\lambda_{ex})\lambda^4 d\lambda \quad 25$$

with n the refractive index of medium, $N_A$ Avogrado's number, $F({}^{D}\lambda_{em})$ the normalized donor emission spectrum, and $\varepsilon({}^{A}\lambda_{ex})$ the absorption coefficient of the acceptor excitation spectrum [this analysis is a re-arrangement of the traditional presentation of the equations describing tgmFRET, separating the different contributions (geometry, spectral overlap, quenching)]. Ligand-mediated modulation of r, κ and J therefore affects $k_t$ (FIG. 6B-D), leading to changes in donor and acceptor emission intensities (see below).

At steady state, the concentration of the donor excited state, [D*], is given by the following rate balance equation (see FIG. 6A):

$$N_0\alpha k_{ex}-[D^*]({}^{D}k_{nr}+{}^{D}k_r+k_t)=0 \quad 26$$

where $N_0$ is the population of ground state fluorophores, $k_{ex}$ the rate of excitation photon absorption, α the effective illumination, $k_t$, the resonance energy transfer rate, ${}^{D}k_{nr}$ and ${}^{D}k_r$ the radiative and non-radiative decay rates of the donor (by itself and regardless of the presence of any other fluorophore/parter) in the absence of acceptor, respectively. Substituting ${}^{D}k_r(d+1)$ for ${}^{D}k_r+{}^{D}k_{nr}$ (using equation 18, with d=q, the ratio of non-radiative to radiative decay rates in the donor), and replacing $k_t$ with equation 22 (with $Q_D=1/(1+d)$, according to equation 23), we obtain $$N_0\alpha k_{ex}-[D^*]{}^{D}k_r\left(1+d+\frac{\varphi}{1+d}\right)=0 \quad 27$$

Hence $$[D^*]=\frac{N_0\alpha k_{ex}}{{}^{D}k_r\left(1+d+\frac{\varphi}{1+d}\right)} \quad 28$$

The intensity of the emitted donor light, $I_D$, is $$I_D=[D^*]{}^{D}k_r=\frac{N_0\alpha k_{ex}}{\left(1+d+\frac{\varphi}{1+d}\right)} \quad 29$$

The donor quantum yield, $Q_D$, is this emission intensity relative to the intensity of the excitation, $k_{ex}\alpha N_0$ $$Q_D=\frac{1}{\left(1+d+\frac{\varphi}{1+d}\right)} \quad 30$$

The rate balance equation for the acceptor excited state concentration, [A*], is given by $$[D^*]k_t-[A^*]({}^{A}k_r+{}^{A}k_{nr}) \quad 31$$

Consequently, by applying equations 19, 22 and 30, the acceptor quantum yield, $Q_A$, is $$Q_A = \frac{\varphi}{(1+a)(1+d)\left(1+d+\frac{\varphi}{1+d}\right)} \quad 32$$

where a is the ratio of the radiative and non-radiative pathways in the acceptor.

The ratio of the acceptor and donor quantum yields therefore is $$\frac{Q_A}{Q_B} = \frac{\varphi}{(1+d)(1+a)} \quad 33$$

This equation clearly shows that any ligand-mediated change in energy transfer (ϕ) or quenching of either the donor (d) or acceptor (a) leads to a change in the ratio of donor and acceptor emission intensities, thereby enabling ratiometry.

Classical ligand-mediated modulation of tgmFRET is concerned only with ligand-mediated changes in the distance between the donor and acceptor (Clegg, 1995, *Curr. Opin. Biotechnol.,* 6, 103-110; Cheung, 1991, *Topics in Fluorescence Spectroscopy,* 2, 127-176), and does not take advantage of effects that alter the photophysics of individual chromophores. By contrast, in ngmFRET systems, the directly responsive partner (DRP) responds to ligand binding through ligand mediated changes that alter the ratio of its radiative and non-radiative pathways (quenching, d or a) or its spectral properties (J), whereas the indirectly responsive partner (IRP) changes only as a consequence of the effect that such change have on the resonance energy transfer rate ($k_t$). It is important to realize that the DRP can function either as a ngmFRET donor an acceptor, depending on how the spectral overlap is set up with the IRP. Regardless of whether the DRP is a donor or acceptor, ligand-mediated alteration of its non-radiative to radiative decay rate ratio (parameter d for a DRP donor; a for an acceptor; by itself and regardless of the presence of any other fluorophore/parter) changes its emission intensity. In DRP donors quenching also alters the ngmFRET transfer rate (see equations 22 and 27), thereby changing the emission intensities of not only itself but also its IRP. By contrast, in DPR acceptors quenching does not alter ngmFRET, and hence do not affect its IRP donor intensity. A DRP acceptor therefore can alter intensities of its donor IRP only if ligand binding changes ϕ. If the DRP is a donor, then manipulation of the ngmFRET coupling factor, ϕ, changes the rate of excited state decay; if it is an acceptor, the rate of excited state formation is altered.

Regardless of whether the DRP is a donor or acceptor, a change in any of the two parameters (ϕ and d or a) alters the ratio of the donor and acceptor quantum yields (equation 33), thereby enabling ratiometry. Ligand-mediated donor DRP quenching affects the quantum yields of both the donor, $Q_D$, and acceptor, $Q_A$, quantum yields (equations 30, 32). Quenching of an acceptor DRP alters only $Q_A$ (equation 30). Changes in ϕ affect quantum yields of both fluorophores, regardless whether the DRP functions as the donor or acceptor (equations 23-25, 30, 32). For systems in which there is no ligand-mediated change in the (average) distance between the two fluorophores, ϕ changes only if the DRP switches between two different excited state populations ("dipole switching") in response to ligand binding and if the two excited states differ in their spectral properties (emission for donor DRPs; absorption for acceptor DRPs). Excited state dipoles usually also differ in their dipole orientations, so it is likely that changes in spectral overlap involve (re-)orientation effects. They are also likely to differ in the relative rates of their radiative and non-radiative decay rates. Dipole switching therefore is likely to involve a combination of changes in ngmFRET and quenching effects.

There are eight possible combinations of ligand-mediated changes in quenching and ngmFRET parameters, which have different outcomes on the two emission intensities and their ratio, depending on whether the DRP is the donor or acceptor. The qualitative behavior of the resulting sixteen possibilities in ngmFRET systems are shown in Table 7. Twelve of these have a predictable outcome on the direction of change in the ratio of the two emission intensities. The effect on the direction of change for both donor and acceptor emission intensities can be predicted for seven models. For the other models, the direction of change of one or both peaks depends on the size of the change in the underlying parameters. Purely geometric effects (changes in inter-dipole distance or orientation) always result in anti-correlated changes in emission intensity changes (i.e. one increases and the other decreases, or vice versa). Correlated (i.e both intensities increase or decrease) or uncorrelated (one changes, the other remains constant) intensity changes therefore are prima facie evidence for an ngmFRET effect.

Example 9

Glucose Biosensors and Uses Thereof

We report the construction of a robust, thermostable, reagentless, fluorescently responsive glucose biosensor and its variants derived from *Thermus scotoductus* (tsGBP2). These engineered proteins can be used for high-precision chemometric measurements that span the entire clinical glucose concentration range, using fluorescence ratiometry measured with straightforward, inexpensive instrumentation.

Thermostable homologs of the *Thermus thermophilus* glucose-galactose binding protein (ttGBP1) were identified using a bioinformatics search strategy that applied a structure-based sequence filter to identify the subset of sequences that retain the original function within the larger collection of aligned sequence homologs. The homologs tested appeared at sequence identities from 32% to 91% of the ttGBP1 probe. At levels below 60%, overall identities are weak predictors of biological function (Todd, 2001, *J. Mol. Biol.,* 307, 1113-1143; Tian, 2003, *J. Mol. Biol.,* 333, 863-882; George, 2005, *Proc Natl Acad Sci USA,* 102, 12299-12304), application of the structure-based filter therefore was essential for accurate identification. The glucose-binding properties of the predicted hits were tested experimentally by constructing synthetic genes optimized for heterologous protein expression in *E. coli* (Allert, Cox and Hellinga, 2010, *J Mol Biol,* 402, 905-18) and determining the glucose-binding properties of the expressed proteins. This search resulted in the identification of a homolog from *Thermus scotoductus* (tsGBP2) as a suitable candidate for glucose sensor engineering.

Endosterically placed Acrylodan fluorescent conjugates were found to be highly effective ratiometric glucose sensors. The strongest dichromatic response was observed for the 13C.Acrylodan conjugate. We demonstrated that the signaling properties of conjugates attached to this position can be conserved throughout the family of ttGBP1 homologs. We also showed that signaling properties can be manipulated using site-specific double labeling to set up ngmFRET systems in which one partner is directly responsive to glucose binding.

A series of additional mutations were introduced to manipulate glucose affinities. Variants spanning four orders of magnitude (0.1-100 mM) were identified. Within these, a subset of mutants covers the entire pathophysiological glucose concentration range with responses that remain within 90% of the maximally achievable precision.

The tsGBP2-based FRSs can be immobilized site-specifically on magnetic beads without affecting protein stability or fluorescence responses. They can be dried, and aged aggressively (incubation at 50° C. for 7 days) without adversely affecting sensor performance. These results demonstrate some of the advantages of using hyperthermostable proteins.

Reagentless, fluorescently responsive sensors present a number of advantages over enzyme-based biosensors, including self-calibration, elimination of chemical transformations and multiple substrates, which together lead to simple sample-handling fluidic circuitry and rapid response times. FRSs can be used for one-time, episodic, and continuous monitoring measurements. Additionally, the use of robust engineered glucose sensors based on (hyper)thermophilic proteins is likely to simplify manufacturing and distribution processes. Combinations of mutant glucose sensors reported here into multiplexed arrays or composites can determine glucose concentrations from hypoglycemic to the hyperosmolar hyperglycemic state samples with high precision in one measurement. Such systems have significant potential for the development of next-generation high-accuracy, wide dynamic range sensing applications in continuous monitoring, point-of-care, or wearable systems.

The glucose sensors can be incorporated into point-of-care clinical devices to measure glucose concentrations accurately, and rapidly at the patient bedside. In such a device, a small blood sample (<10 μL) is obtained by means of a finger stick using a lancet. This sample droplet is then placed on the aperture of a disposable cartridge containing desiccated, immobilized glucose sensors inside a small measurement chamber. The sample enters the chamber by virtue of passive capillary action, wetting the sensors upon contact. As soon as the sensors have been wetted, they bind glucose, and report on its concentration by virtue of the engineered fluorescent sensor mechanism. The cartridge is placed inside a small reader (handheld or on a desktop), and their fluorescence signal is measured by the (inexpensive) optoelectronic components of the reader. Excitation light is provided by a light-emitting diode (LED). In the case of Acrylodan or Badan, a commercially available 400 nm blue LED is used, and the emitted light is measured through two bandpass filters. Cartridges can contain multiple sensors, spanning the entire clinical range of possible glucose concentrations. Each sensor is immobilized at a particular, known location inside the cartridge, providing "spatial addressability". The intensity at a particular wavelength is then recorded by imagining these sensors using an inexpensive camera, such as a Complementary metal-oxide semiconductor (CMOS) device commonly found in consumer electronics such as cell phones. Each pixel in the camera records the emitted light on a gray scale. Integration of that signal imaged through the two signals, is analyzed by an on-board computer to calculate the ratiometric signal for each immobilized sensor. Pre-recorded hyperbolic binding curves are then used to calculate the glucose concentration in the sample. Recording through multiple sensors, tuned for accurate detection at different glucose concentrations provides a high-accuracy reading. This process is completed in less than a minute.

Similar instrumentation can be used for any type of episodic measurements, for instance, using other bodily fluids, or samples obtained from animals, or non-biological samples such as foods and beverages.

The FRS glucose sensors also can be used to monitor glucose levels continuously. For instance, sensors can be immobilized at the tip of a thin optical fiber to construct a glucose-responsive optode. Such an optode can be introduced into the body subcutaneously, using a small needle. Excitation and emission light are passed to and from the immobilized sensor, respectively. The sensor is in continuous contact with the sample. Fluctuations in the glucose sample alter the dynamic equilibrium between the open and closed states of the glucose-binding protein, which is transduced into fluctuations of the fluorescent emission signal, by virtue of the sensing mechanism of the conjugated fluorophore. The emitted light intensities are read through filters by a reader connected to the optode. This reader continuously displays the change in signal, and the corresponding calculated glucose concentrations. Continuous glucose monitoring accomplished using a device containing the immobilized glucose biosensor(s), e.g., a fiber optic biosensor, introduced into the subject intradermally or subcutaneously (Judge et al., 2011, Diabetes Technology & Therapeutics 13 (3):309-317; Weidemaier et al., 2011, Biosensors and Bioelectronics 26:4117-4123; hereby incorporated by reference).

As was discussed above, the features that distinguish the described constructs, devices, and methods from earlier glucose assay systems include:

- Self-calibration
- Rapid response time
- Simple sample-handling fluidic circuitry
- No additional components/substrates ("reagentless")
- No incubation time to develop signal. Reading is near-instantaneous and continuous
- Stability (simplifies manufacturing, distribution, storage)
- Small sample volume (<10 μL).
- Capable of precise measurements over extended glucose concentration range (from the hypoglycemic to the hyperglycemic-hyperosmotic range)
- Multiple sensors also provides redundancy, lowering error
- Large scope of uses: episodic, continuous, ex vivo, in vivo, optodes, implants, dermal patches.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A biosensor for glucose, comprising a glucose-binding protein and a reporter group that transduces a detectable signal, wherein the reporter group is attached to the glucose-binding protein so that a signal transduced by the reporter group when the glucose-binding protein is bound to glucose differs from a signal transduced by the reporter group when the glucose-binding protein is not bound to glucose, wherein the glucose-binding protein does not comprise a $Ca^{2+}$ binding site, wherein the glucose-binding protein does not comprise an enzyme, and wherein the glucose-binding protein comprises a glucose-binding protein from *Thermus scotoductus* (tsGBP2; SEQ ID NO: 2, 10, or 110), wherein the glucose-binding protein comprises an E13C substitution and an W244X substitution, wherein X is any amino acid, an amino acid that results in a conservative substitution, or a cysteine, wherein each position is counted in tsGBP2 with the signal peptide replaced with a methionine (SEQ ID NO: 10 or 110), wherein the reporter group is attached to the substitute amino acid at position 13 or 244.

2. The biosensor of claim 1, wherein the *Thermus scotoductus* glucose-binding protein comprises amino acids in the sequence set forth as SEQ ID NO: 48 or 56, and wherein Acrylodan is attached to a cysteine of said glucose-binding protein.

3. The biosensor of claim 2, wherein the glucose-binding protein comprises the amino acid sequence of SEQ ID NO: 48.

4. The biosensor of claim 2, wherein the glucose-binding protein comprises the amino acid sequence of SEQ ID NO: 56.

5. The biosensor of claim 1, the X at position 244 is a cysteine.

6. The biosensor of claim 1, wherein the amino acid sequence of said glucose-binding protein is less than 20% identical to the amino acid sequence of *E. coli* glucose-galactose binding protein (ecGGBP; SEQ ID NO: 117).

7. The biosensor of claim 1, wherein the glucose-binding protein comprises an amino acid sequence that is between 90% and 100% identical to the amino acid sequence of tsGBP2.

8. The biosensor of claim 1, wherein the $C_{\alpha}$ root-mean-square deviation (RMSD) between the backbone of the glucose-binding polypeptide and tsGBP2 is between about 0-3 Å, 0-1 Å, 0-1.5 Å, 0-2 Å, 0.1-3 Å, 0.5-1 Å, 0.5-1.5 Å, or 0.5-2 Å, or less than about 0.1 Å, 0.2 Å, 0.3 Å, 0.4 Å, 0.5 Å, 0.6 Å, 0.7 Å, 0.8 Å, 0.9 Å, 1.0 Å, 1.5 Å, 1.6 Å, 1.7 Å, 1.8 Å, 1.9 Å, 2.0 Å, 2.5 Å, or 3 Å.

9. The biosensor of claim 1, wherein the reporter group is covalently attached to the glucose-binding protein.

10. The biosensor of claim 1, wherein the reporter group is conjugated to a cysteine of the glucose-binding protein.

11. The biosensor of claim 1, wherein the reporter group comprises a fluorophore.

12. The biosensor of claim 1, wherein Acrylodan or Badan is attached to the cysteine on position 13 of the glucose-binding protein.

13. The biosensor of claim 1, wherein X is phenylalanine.

14. The biosensor of claim 1, wherein the glucose-binding protein comprises an amino acid sequence having at least 90% identity to SEQ ID NO: 48.

15. The biosensor of claim 1, wherein the glucose-binding protein comprises an amino acid sequence having at least 90% identity to SEQ ID NO: 56.

16. A method of detecting the presence or concentration of glucose in a sample, the method comprising:

(a) contacting the biosensor of claim 1 with the sample;

(b) measuring a signal from the biosensor; and (c) comparing the signal to a glucose control value, wherein a difference in signal indicates the presence of glucose in the sample.

17. A method for monitoring the level of glucose in a subject, comprising (a) administering a biosensor according to claim 1 or a device comprising a biosensor according to claim 1 to the subject, wherein after administration the biosensor is in contact with a bodily fluid or surface of the subject, and (b) detecting (i) a signal produced by a reporter group of the biosensor continuously or repeatedly at intervals less than about 30 minutes apart, and/or (ii) whether a signal is produced by a reporter group of the biosensor continuously or repeatedly at intervals less than about 30 minutes apart.

* * * * *